US010253044B2

(12) United States Patent
Wang et al.

(10) Patent No.: US 10,253,044 B2
(45) Date of Patent: *Apr. 9, 2019

(54) 9H-PYRIMIDO [4,5-B]INDOLES AND RELATED ANALOGS AS BET BROMODOMAIN INHIBITORS

(71) Applicant: THE REGENTS OF THE UNIVERSITY OF MICHIGAN, Ann Arbor, MI (US)

(72) Inventors: Shaomeng Wang, Superior Township, MI (US); Yujun Zhao, Ann Arbor, MI (US); Bing Zhou, Ann Arbor, MI (US); Angelo Aguilar, Ann Arbor, MI (US); Liu Liu, Ann Arbor, MI (US); Longchuan Bai, Ann Arbor, MI (US); Donna McEachern, Ann Arbor, MI (US); Duxin Sun, Ann Arbor, MI (US); Bo Wen, Ann Arbor, MI (US); Ruijuan Luo, Ann Arbor, MI (US); Ting Zhao, Ann Arbor, MI (US); Arul Chinnaiyan, Ann Arbor, MI (US); Irfan A. Asangani, Ann Arbor, MI (US); Jeanne Stuckey, Fenton, MI (US); Jennifer Lynn Meagher, Ann Arbor, MI (US); Xu Ran, Ann Arbor, MI (US); Yang Hu, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 15/443,336

(22) Filed: Feb. 27, 2017

(65) Prior Publication Data

US 2017/0210761 A1  Jul. 27, 2017

Related U.S. Application Data

(62) Division of application No. 14/633,360, filed on Feb. 27, 2015, now Pat. No. 9,580,430.

(60) Provisional application No. 62/048,388, filed on Sep. 10, 2014, provisional application No. 62/031,640, filed on Jul. 31, 2014, provisional application No.
(Continued)

(51) Int. Cl.
A61K 31/519 (2006.01)
C07D 519/00 (2006.01)
C07D 487/04 (2006.01)
C07D 487/14 (2006.01)
A61K 31/437 (2006.01)
A61K 31/5377 (2006.01)
A61K 31/538 (2006.01)

(52) U.S. Cl.
CPC .......... C07D 519/00 (2013.01); A61K 31/437 (2013.01); A61K 31/519 (2013.01); A61K 31/538 (2013.01); A61K 31/5377 (2013.01); C07D 487/04 (2013.01); C07D 487/14 (2013.01)

(58) Field of Classification Search
CPC .................................................... A61K 31/519
USPC ........................................................ 514/267
See application file for complete search history.

(56) References Cited

U.S. PATENT DOCUMENTS 8,044,042 B2  10/2011  Adachi et al.
8,114,995 B2  2/2012  Hansen et al.
(Continued)

FOREIGN PATENT DOCUMENTS

EP  0989131  3/2000
WO  WO-2008/092231 A1  8/2008
(Continued)

OTHER PUBLICATIONS

Belkina et al., BET domain co-regulators in obesity, inflammation and cancer, Nat. Rev. Cancer, 12(7):465-77 (2012).
(Continued)

Primary Examiner — Jeffrey H Murray
(74) Attorney, Agent, or Firm — Marshall, Gerstein & Borun LLP

(57) ABSTRACT

The present disclosure provides substituted 9H-pyrimido[4,5-b]indoles and 5H-pyrido[4,3-b]indoles and related analogs represented by Formula I:

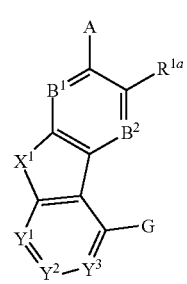

and the pharmaceutically acceptable salts, hydrates, and solvates thereof, wherein $R^{1a}$, A, $B^1$, $B^2$, G, $X^1$, $Y^1$, $Y^2$, and $Y^3$ are as defined as set forth in the specification. The present disclosure is also directed to the use of compounds of Formula I to treat a condition or disorder responsive to inhibition of BET bromodomains. Compounds of the present disclosure are especially useful for treating cancer.

14 Claims, 27 Drawing Sheets

Related U.S. Application Data

61/950,406, filed on Mar. 10, 2014, provisional application No. 61/946,501, filed on Feb. 28, 2014.

(56) References Cited

U.S. PATENT DOCUMENTS

| | | | |
|---|---|---|---|
| 8,476,260 | B2 | 7/2013 | Miyoshi et al. |
| 8,557,984 | B2 | 10/2013 | Bouillot et al. |
| 8,580,957 | B2 | 11/2013 | Demont et al. |
| 9,580,430 | B2* | 2/2017 | Wang .................. C07D 487/04 |
| 9,675,697 | B2* | 6/2017 | Wang .................. C07D 487/04 |
| 2010/0267709 | A1 | 10/2010 | Young et al. |
| 2010/0286127 | A1 | 11/2010 | Miyoshi et al. |
| 2012/0059002 | A1 | 3/2012 | Hansen et al. |
| 2012/0157428 | A1 | 6/2012 | Albrecht et al. |
| 2012/0202799 | A1 | 8/2012 | Crowe et al. |
| 2012/0208800 | A1 | 8/2012 | Chung et al. |
| 2012/0252781 | A1 | 10/2012 | Bailey et al. |
| 2013/0079335 | A1 | 3/2013 | Bailey |
| 2013/0184264 | A1 | 7/2013 | Bradner et al. |
| 2013/0252331 | A1 | 9/2013 | Bradner et al. |
| 2013/0281399 | A1 | 10/2013 | McLure et al. |
| 2013/0281450 | A1 | 10/2013 | Pratt et al. |
| 2013/0331382 | A1 | 12/2013 | Hubbard et al. |
| 2014/0005169 | A1 | 1/2014 | Albrecht et al. |
| 2014/0011862 | A1 | 1/2014 | Bradner et al. |
| 2014/0066410 | A1 | 3/2014 | Zhou et al. |
| 2014/0135316 | A1 | 5/2014 | Albrecht et al. |
| 2014/0142102 | A1 | 5/2014 | Fairfax et al. |
| 2014/0162971 | A1 | 6/2014 | Wang et al. |
| 2014/0256706 | A1 | 9/2014 | Wang et al. |

FOREIGN PATENT DOCUMENTS

| | | |
|---|---|---|
| WO | WO-2011/054856 A1 | 5/2011 |
| WO | WO-2011/143669 A2 | 11/2011 |
| WO | WO-2012/075383 | 6/2012 |
| WO | WO-2012/075456 A1 | 6/2012 |
| WO | WO-2012/174487 | 12/2012 |
| WO | WO-2013/024104 | 2/2013 |
| WO | WO-2013/027168 | 2/2013 |
| WO | WO-2013/030150 | 3/2013 |
| WO | WO-2013/033268 | 3/2013 |
| WO | WO2013/110198 * 8/2013 ........... C07D 487/04 |
| WO | WO-2013/110198 A1 | 8/2013 |
| WO | WO-2014/134232 A1 | 9/2014 |
| WO | WO-2014/134267 A1 | 9/2014 |
| WO | WO-2014/164596 A1 | 10/2014 |

OTHER PUBLICATIONS

Filippakopoulos et al., Histone recognition and large-scale structural analysis of the human bromodomain family, Cell, 149(1):214-31 (2012).

Garnier et al., BET bromodomain inhibitors: a patent review, Exp. Opin. Ther. Patents, 24:1-15 (2013).

Haynes et al., The bromodomain: a conserved sequence found in human, *Drosophila* and yeast proteins, Nucleic Acids Res., 20(10):2603 (1992).

Lim et al., Discovery of 1-amino-5H-pyrido[4,3-b]indol-4-carboxamide inhibitors of Janus kinase 2 (JAK2) for the treatment of myeloproliferative disorders, J. Med. Chem., 54(20):7334-49 (2011).

Muller et al., Bromodomains as therapeutic targets, Expert Rev. Mol. Med., 13:e29 (2011).

Sanchez et al., The role of human bromodomains in chromatin biology and gene transcription, Curr. Opin. Drug Discov. Devel., 12(5):659-65 (2009).

* cited by examiner

| Cell Line | AR-signaling | IC50 for JQ1 (nM) |
|---|---|---|
| VCaP | Positive | 50 |
| LNCaP | Positive | 160 |
| 22RV1 | Positive | 200 |
| RWPE | Negative | >5000 |
| PC3 | Negative | >5000 |
| DU145 | Negative | >5000 |

FIG. 1

9H-PYRIMIDO [4,5-B]INDOLES AND RELATED ANALOGS AS BET BROMODOMAIN INHIBITORS

This invention was made with government support under CA111275 and CA069568 awarded by the National Institutes of Health. The Government has certain rights in the invention.

BACKGROUND OF THE INVENTION

Field of the Invention

The present disclosure provides BET bromodomain inhibitors and therapeutic methods of treating conditions and diseases wherein inhibition of one or more BET bromodomains provides a benefit.

Background Art

The genomes of eukaryotic organisms are highly organized within the nucleus of the cell. The long strands of duplex DNA are wrapped around an octamer of histone proteins (usually comprising two copies of histones H2A, H2B, H3, and H4) to form a nucleosome, which then is further compressed to form a highly condensed chromatin structure. A range of different condensation states are possible, and the tightness of this structure varies during the cell cycle. The chromatin structure plays a critical role in regulating gene transcription, which cannot occur efficiently from highly condensed chromatin. The chromatin structure is controlled by a series of post translational modifications to histone proteins, notably histones H3 and H4. These modifications include acetylation, methylation, phosphorylation, ubiquitinylation, and SUMOylation.

Histone acetylation usually is associated with the activation of gene transcription, as the modification loosens the interaction of the DNA and the histone octamer by changing the electrostatics. In addition to this physical change, specific proteins bind to acetylated lysine residues within histones to read the epigenetic code. Bromodomains are small (about 110 amino acids) distinct domains within proteins that bind to acetylated lysine resides commonly, but not exclusively, in the context of histones. There is a family of about 50 proteins known to contain bromodomains, which have a range of functions within the cell.

The BET family of bromodomain-containing proteins ("BET bromodomains") includes four proteins, i.e., BRD2, BRD3, BRD4, and BRD-t, which contain tandem bromodomains capable of binding to two acetylated lysine residues in close proximity, thereby increasing the specificity of the interaction. BRD2 and BRD3 associate with histones along actively transcribed genes and may be involved in facilitating transcriptional elongation, while BRD4 may be involved in the recruitment of the pTEF-β complex to inducible genes, resulting in phosphorylation of RNA polymerase and increased transcriptional output. BRD4 or BRD3 also may fuse with NUT (nuclear protein in testis) forming novel fusion oncogenes, BRD4-NUT or BRD3-NUT, in a highly malignant form of epithelial neoplasia. Data suggests that BRD-NUT fusion proteins contribute to carcinogenesis. BRD-t is uniquely expressed in the testes and ovary. All family members have been reported to have some function in controlling or executing aspects of the cell cycle, and have been shown to remain in complex with chromosomes during cell division, which suggests a role in the maintenance of epigenetic memory. In addition, some viruses make use of these proteins to tether their genomes to the host cell chromatin as part of the process of viral replication.

A discussion of BET proteins can be found in WO 2012/075456, WO 2012/075383, and WO 2011/054864. A discussion of BET bromodomain inhibitors, e.g., I-BET-151 and I-BET-762, can be found in Delmore et al., *Cell* 146: 904-917 (2011) and Seal et al., *Bioorg. Med. Chem. Lett.* 22:2968-2972 (2012). Small molecule inhibitors of BET bromodomains have therapeutic potential for the treatment of many diseases and conditions in which BET bromodomains have a role, including cancer. BET bromodomain inhibitors are disclosed in the following U.S. Pat. Nos. 8,044,042, 8,476,260, 8,114,995, 8,557,984, and 8,580,957; the following U.S. patent application publications: US 20120059002, US 20120208800, US 2012202799, US 2012252781, US 20130252331, US 20140011862, US 20130184264, US 2013079335, US 20140011862, US 20140005169, US 20130331382, US 20130281450, US 20130281399, US 20120157428, and US 20100286127; and the following international applications: WO 1998011111, WO 2006129623, WO 2008092231, WO 2009084693, WO 2009158404, WO 2010123975, WO 2011054843, WO 2011054844, WO 2011054845, WO 2011054846, WO 2011054848, WO 2011143651, WO 2011143660, WO 2011143669, WO 2011161031, WO 2012075383, WO 2012116170, WO 2012151512, WO 2012174487, WO 2013024104, WO 2013027168, WO 2013030150, WO 2013033268, and WO 2013097601.

Men who develop metastatic castration-resistant prostate cancer (CRPC) invariably succumb to the disease. The development and progression to CRPC following androgen ablation therapy is predominantly driven by unregulated androgen receptor (AR) signaling (Taylor, B. S. et al., *Cancer Cell* 18:11-22 (2010); Chen, C. D. et al., *Nat Med* 10:33-39 (2004); Visakorpi, T. et al., *Nat Genet* 9:401-406 (1995)). Despite the success of recently approved therapies targeting AR signaling such as abiraterone (Stein, M. N., Goodin, S. and Dipaola, R. S., *Clin Cancer Res* 18:1848-1854 (2012); Reid, A. H. et al. *J Clin Oncol* 28: 1489-1495 (2010); de Bono, J. S. et al., *N Engl J Med* 364: 1995-2005 (2011)) and second generation anti-androgens MDV3100 (enzalutamide) (Mukherji, D. et al. *Expert Opin Investig Drugs* 21:227-233 (2012); Scher, H. I. et al., *N Engl J Med* 367:1187-1197 (2012)), durable responses are limited, presumably due to acquired resistance. Recently JQ1 and I-BET, two selective small molecule inhibitors that target the amino-terminal bromodomains of BRD4, have been shown to exhibit antiproliferative effects in a range of malignancies (Lockwood, W. W. et al., *Proc Natl Acad Sci USA* 109:19 408-19413 (2012); Dawson, M. A. et al., *Nature* 478: 529-533 (2011); Delmore, J. E. et al. *Cell* 146: 904-917 (2011); Puissant, A. et al. *Cancer Discov* 3:308-323 (2013)). BRD4 physically interacts with the N-terminal domain of AR and can be disrupted by JQ1 (Delmore, J. E. et al. *Cell* 146: 904-917 (2011); Puissant, A. et al. *Cancer Discov* 3:308-323 (2013); Filippakopoulos, P. et al. *Nature* 468: 1067-1073 (2010)).

The identification and therapeutic targeting of co-activators or mediators of AR transcriptional signaling should be considered as alternate strategies to treat CRPC (Attard, G. et al., *Clin Cancer Res* 17:1649-1657 (2011)). BRD4 is a conserved member of the bromodomain and extraterminal (BET) family of chromatin readers that include BRD2/3 and BRDT. BRD4 plays a critical role in transcription by RNA PolII, by facilitating recruitment of the positive transcription elongation factor P-TEFb (Jang, M. K. et al., *Mol Cell* 19:523-534 (2005); Yang, Z. et al., *Mol Cell* 19: 535-545 (2005). Similar to other BET-family proteins, BRD4 contains two conserved bromodomains, BD1 and BD2. Competitive binding of JQ1 or I-BET to the bromodomain pocket results in the displacement BRD4 from active chromatin and subsequent removal of RNA PolII from target genes (Dawson, M. A. et al., *Nature* 478: 529-533 (2011); Delmore, J. E. et al., *Cell* 146: 904-917 (2011); Puissant, A. et al., *Cancer Discov* 3:308-323 (2013); Filippakopoulos, P. et al., *Nature* 468:1067-1073 (2010); Loven, J. et al., 153:320-334 (2013)) Although most cancer cells express BET-family proteins, it is not clear why only a subset of cell lines from diverse cancers respond to BET-inhibitors (Lockwood, W. W. et al. *Proc Natl Acad Sci USA* 109:19408-19413 (2012); Mertz, J. A. et al., *Proc Natl Acad Sci USA* 108:16669-16674 (2011)). Recently, BRD4 was shown to interact with sequence-specific DNA-binding transcription factors in a gene-specific manner (Wu, S. Y. et al., *Mol Cell* 49:843-857 (2013)). As the genetic and epigenetic landscape differs between tumor types, it is possible that distinct transcriptional regulators that associate with BRD4 might influence the action of BET-inhibitors.

Breast cancer accounts for more than 20% of all cancers in women worldwide. The expression of androgen receptor (AR) is widespread both in ER (estrogen receptor)-positive and ER-negative breast cancers. In ER positive breast cancer adjuvant therapy with ER antagonist tamoxifen or aromatase inhibitors (AIs)—which block conversion of androgen to estrogens, has shown to be effective in inhibiting disease progression. Moreover, direct AR antagonist Enzalutamide (MDV3100) has recently been proposed as a therapeutic modality for AR positive breast cancers.

Despite research directed to BET bromodomains and BET bromodomain inhibitors, the design of potent, non-peptide inhibitors of BET bromodomains remains a significant challenge in modern drug discovery. Accordingly, a need still exists in the art for BET bromodomain inhibitors having physical and pharmacological properties that permit use of the inhibitors in therapeutic applications, especially in humans. The present disclosure provides compounds that bind to BET bromodomains and inhibit BET bromodomain activity.

BRIEF SUMMARY OF THE INVENTION

In one aspect, the present disclosure provides 9H-pyrimido[4,5-b]indoles, 5H-pyrido[4,3-b]indoles, and related analogs represented by Formulae I-VI and IX-XVII, below, and the pharmaceutically acceptable salts, hydrates, and solvates thereof, collectively referred to herein as "Compounds of the Disclosure." Compounds of the Disclosure are potent and specific inhibitors of BET bromodomains that bind to BET bromodomains and function as potent antagonists of BET bromodomains. Thus, Compounds of the Disclosure are useful in treating diseases or conditions wherein inhibition of BET bromodomains, e.g., BRD2, BRD3, BRD4, BRD-t, or an isoform or mutant thereof, provides a benefit.

In another aspect, the present disclosure provides methods of treating a condition or disease by administering a therapeutically effective amount of a Compound of the Disclosure to an individual, e.g., a human, in need thereof. The disease or condition of interest is treatable by inhibition of BET bromodomains, for example, a cancer, a chronic autoimmune disorder, an inflammatory condition, a proliferative disorder, sepsis, or a viral infection. Also provided are methods of preventing the proliferation of unwanted proliferating cells, such as cancer, in a subject, the methods comprising administering a therapeutically effective amount of a Compound of the Disclosure to a subject at risk of developing a condition characterized by unwanted proliferating cells. In some embodiments, the Compounds of the Disclosure reduce the proliferation of unwanted cells by inducing apoptosis in those cells.

In another aspect, the present disclosure provides a method of inhibiting BET bromodomains in an individual, comprising administering to the individual an effective amount of at least one Compound of the Disclosure.

In another aspect, the present disclosure provides a pharmaceutical composition comprising a Compound of the Disclosure and an excipient and/or pharmaceutically acceptable carrier.

In another aspect, the present disclosure provides a composition comprising a Compound of the Disclosure and an excipient and/or pharmaceutically acceptable carrier for use treating diseases or conditions wherein inhibition of BET bromodomains provides a benefit, e.g., cancer.

In another aspect, the present disclosure provides a composition comprising: (a) a Compound of the Disclosure; (b) a second therapeutically active agent; and (c) optionally an excipient and/or pharmaceutically acceptable carrier.

In another aspect, the present disclosure provides a Compound of the Disclosure for use in treatment of a disease or condition of interest, e.g., cancer.

In another aspect, the present disclosure provides a Compound of the Disclosure for use in treatment of breast cancer having active androgen receptor (AR) signaling.

In another aspect, the present disclosure provides a Compound of the Disclosure for use in treatment of prostate cancer, e.g., castration-resistant prostate cancer, having active AR signaling.

In another aspect, the present disclosure provides a use of a Compound of the Disclosure for the manufacture of a medicament for treating a disease or condition of interest, e.g., cancer.

In another aspect, the present disclosure provides a kit comprising a Compound of the Disclosure, and, optionally, a packaged composition comprising a second therapeutic agent useful in the treatment of a disease or condition of interest, and a package insert containing directions for use in the treatment of a disease or condition, e.g., cancer.

In another aspect, the present disclosure provides compounds as synthetic intermediates that can be used to prepare Compounds of the Disclosure.

In another aspect, the present disclosure provides methods of preparing Compounds of the Disclosure.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

BRIEF DESCRIPTION OF DRAWINGS

FIG. 1 is a table showing the $IC_{50}$ for JQ1 in each cell line is listed.

DETAILED DESCRIPTION OF THE INVENTION

Figure 2:
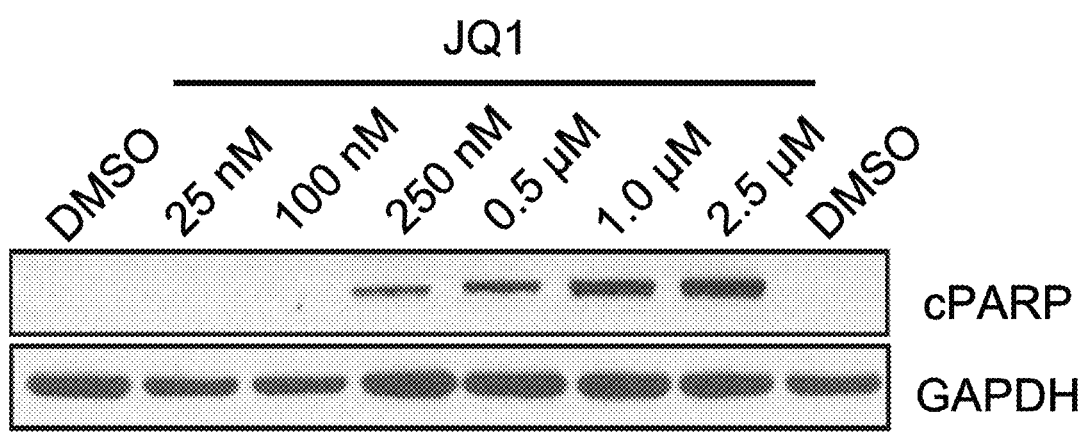
FIG. 2 is an illustration showing the induction of apoptosis in VCaP prostate cancer cells by JQ1. Cleaved PARP (cPARP) immunoblot analysis. GAPDH served as a loading control.

Compounds of the Disclosure are inhibitors of BET bromodomain proteins. In view of this property, Compounds of the Disclosure are useful for treating conditions or disorders responsive to BET bromodomain inhibition.

In one embodiment, Compounds of the Disclosure are compounds represented by Formula I:

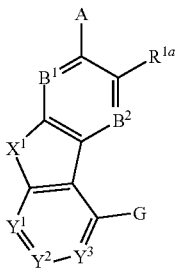

and the pharmaceutically acceptable salts, hydrates, and solvates thereof, wherein:

$B^1$ is —N= or —C($R^{1b}$)=;

$B^2$ is —N= or —C($R^{1c}$)=;

$Y^1$ is selected from the group consisting of —C($R^{2a}$)= and —N=;

$Y^2$ is selected from the group consisting of —C($R^{2b}$)= and —N=;

$Y^3$ is selected from the group consisting of —C($R^{2c}$)= and —N=;

G is selected from the group consisting of halo, hydroxy, cyano, optionally substituted cycloalkyl, optionally substituted heterocyclo, optionally substituted aryl, optionally substituted heteroaryl, aralkyl, (heteroaryl)alkyl, —OS(=O)$_2$CF$_3$, and —Z—$R^3$ $R^{1a}$ and $R^{1b}$ are each independently selected from the group consisting of hydrogen, hydroxy, alkyl, haloalkyl, alkoxy, alkylthio, amino, and halo;

$R^{1c}$ is selected from the group consisting of hydrogen, hydroxy, alkyl, haloalkyl, alkoxy, alkylthio, amino, carboxamido, and fluoro;

$R^{2a}$ and $R^{2c}$ are independently selected from the group consisting of hydrogen, halo, alkyl, and carboxamido;

$R^{2b}$ is selected from the group consisting of hydrogen, amino, optionally substituted alkyl, hydroxyalkyl, alkoxyalkyl, heteroalkyl, (heterocyclo)alkyl, (amino)alkyl, optionally substituted cycloalkyl, optionally substituted heterocyclo, and carboxamido;

$R^3$ is selected from the group consisting of optionally substituted cycloalkyl, optionally substituted aryl, optionally substituted heteroaryl, and optionally substituted heterocyclo;

A is optionally substituted 5-membered heteroaryl;

$X^1$ is selected from the group consisting of —O—, —S—, and —N($R^{5a1}$)—;

Z is selected from the group consisting of —C(=O)—, —O—, —S—, —SO$_2$—, and —N($R^{5b1}$)—;

$R^{5a1}$ is selected from the group consisting of hydrogen and alkyl, and $R^{5b1}$ is selected from the group consisting of hydrogen and alkyl, with the proviso that A is not 1,3-dimethyl-1H-pyrazol-4-yl, or:

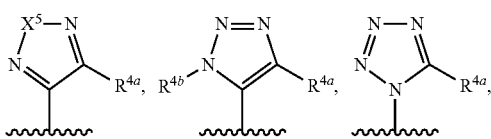

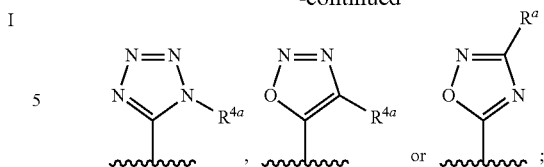

wherein:

$R^{4a}$ and $R^{4b}$ are each independently selected from the group consisting of hydrogen, halo, haloalkyl, and alkyl; and $X^5$ is selected from the group consisting of —O— and —S—.

In another embodiment, Compounds of the Disclosure are compounds represented by Formula I, and the pharmaceutically acceptable salts, hydrates, and solvates thereof, with the provisos that:

a) when G is halo, hydroxy, cyano, optionally substituted cycloalkyl, optionally substituted aryl, optionally substituted heteroaryl, aralkyl, (heteroaryl)alkyl, or —OS(=O)$_2$CF$_3$, then either $B^1$ or $B^2$, or both, is —N=; or b) when G is halo, hydroxy, cyano, optionally substituted cycloalkyl, optionally substituted aryl, optionally substituted heteroaryl, aralkyl, (heteroaryl)alkyl, or —OS(=O)$_2$CF$_3$, then either $R^{1b}$ or $R^{1c}$, or both, is hydroxy, alkyl, haloalkyl, alkoxy, alkylthio, amino, carboxamido, or fluoro.

In another embodiment, Compounds of the Disclosure are compounds represented by Formula I, and the pharmaceutically acceptable salts, hydrates, and solvates thereof, with the provisos that:

c) at least one of $Y^1$, $Y^2$, and $Y^3$ is —N=; and d) at least one of $Y^1$, $Y^2$, and $Y^3$ is not —N=.

In another embodiment, Compounds of the Disclosure are compounds represented by Formula II:

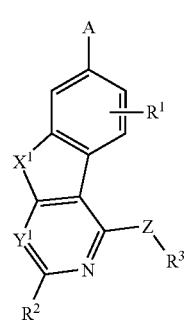

and the pharmaceutically acceptable salts, hydrates, and solvates thereof, wherein:

$R^1$ is selected from the group consisting of hydrogen, hydroxy, alkyl, haloalkyl, alkoxy, alkylthio, amino, and halo;

$R^2$ is selected from the group consisting of hydrogen, amino, alkyl, hydroxyalkyl, alkoxyalkyl, (heterocyclo)alkyl, (amino)alkyl, optionally substituted cycloalkyl, optionally substituted heterocyclo, and carboxamido;

$R^3$ is selected from the group consisting of optionally substituted cycloalkyl, optionally substituted aryl, optionally substituted heteroaryl, and optionally substituted heterocyclo;

A is optionally substituted 5-membered heteroaryl;

$X^1$ is selected from the group consisting of —O—, —S—, and —N($R^{5a1}$)—;

$Y^1$ is selected from the group consisting of —CH= and —N=;

$Z$ is selected from the group consisting of —O—, —S—, —SO$_2$—, and —N(R$^{5b1}$)—;

$R^{5a1}$ is selected from the group consisting of hydrogen and alkyl; and $R^{5b1}$ is selected from the group consisting of hydrogen and alkyl, with the proviso that A is not 1,3-dimethyl-1H-pyrazol-4-yl, or:

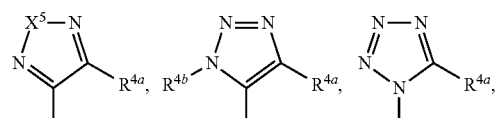

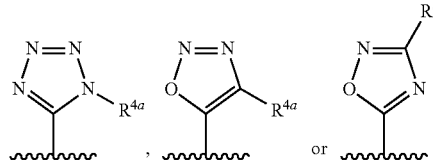

wherein:

$R^{4a}$ and $R^{4b}$ are each independently selected from the group consisting of hydrogen, halo, haloalkyl, and alkyl; and $X^5$ is selected from the group consisting of —O— and —S—.

In another embodiment, Compounds of the Disclosure are compounds represented by Formula II, and the pharmaceutically acceptable salts, hydrates, and solvates thereof, wherein:

$R^1$ is selected from the group consisting of hydrogen, hydroxy, alkyl, haloalkyl, alkoxy, alkylthio, amino, and halo;

$R^2$ is selected from the group consisting of hydrogen, alkyl, hydroxyalkyl, alkoxyalkyl, (heterocyclo)alkyl, (amino)alkyl, optionally substituted cycloalkyl, optionally substituted heterocyclo, and carboxamido;

$R^3$ is selected from the group consisting of optionally substituted aryl, optionally substituted heteroaryl, and optionally substituted heterocyclo;

A is optionally substituted 5-membered heteroaryl;

$X^1$ is selected from the group consisting of —O—, —S—, and —N(R$^{5a1}$)—;

$Y^1$ is selected from the group consisting of —CH= and —N=;

$Z$ is selected from the group consisting of —O—, —S—, —SO$_2$—, and —N(R$^{5b1}$)—;

$R^{5a1}$ is selected from the group consisting of hydrogen and alkyl; and $R^{5b1}$ is selected from the group consisting of hydrogen and alkyl.

In another embodiment, Compounds of the Disclosure are compounds represented by Formulae I and II, and the pharmaceutically acceptable salts, hydrates, and solvates thereof, wherein:

A is optionally substituted 5-membered heteroaryl selected from the group consisting of:

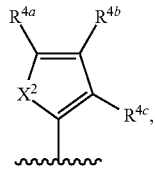
A-1

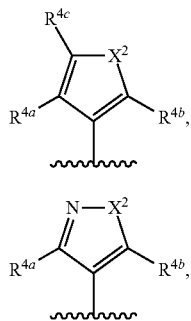
A-2

A-3

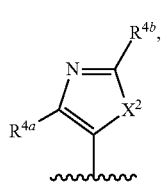
A-4

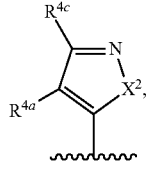
A-5

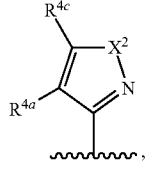
A-6

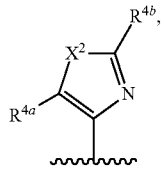
A-7

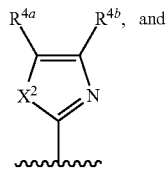
A-8

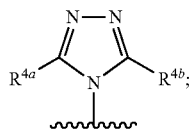
A-9

$R^{4a}$, $R^{4b}$, and $R^{4c}$ are each independently selected from the group consisting of hydrogen, halo, haloalkyl, and alkyl;

$X^2$ is selected from the group consisting of —O—, —S—, and —N($R^{5c1}$)—; and $R^{5c1}$ is selected from the group consisting of hydrogen and alkyl. In another embodiment, $R^{4a}$, $R^{4b}$, and $R^{4c}$ are each independently selected from the group consisting of hydrogen and alkyl, and X is selected from the group consisting of —O— and —N($R^{5c1}$)—.

In another embodiment, Compounds of the Disclosure are compounds represented by Formulae I and II, and the pharmaceutically acceptable salts, hydrates, and solvates thereof, wherein A is A-3 and $X^2$ is —N($R^{5c1}$)—.

In another embodiment, Compounds of the Disclosure are compounds represented by Formulae I and II, and the pharmaceutically acceptable salts, hydrates, and solvates thereof, wherein A is A-9, $R^{4a}$ is alkyl, and $R^{4b}$ is alkyl.

In another embodiment, Compounds of the Disclosure are compounds represented by Formula III:

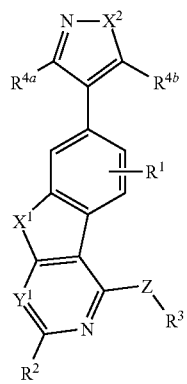

III and the pharmaceutically acceptable salts, hydrates, and solvates thereof, wherein $R^1$, $R^2$, $R^3$, $X^1$, $Y^1$, and Z are as defined above in connection with Formula II, and $R^{4a}$, $R^{4b}$, and $X^2$ is as defined above in connection with groups A-1 to A-9.

In another embodiment, Compounds of the Disclosure are compounds represented by Formula I, and the pharmaceutically acceptable salts, hydrates, and solvates thereof, wherein $R^{1a}$ is $C_{1-4}$ alkoxy.

In another embodiment, Compounds of the Disclosure are compounds represented by Formulae II and III, and the pharmaceutically acceptable salts, hydrates, and solvates thereof, wherein R is $C_{1-4}$ alkoxy.

In another embodiment, Compounds of the Disclosure are compounds represented by Formula III, and the pharmaceutically acceptable salts, hydrates, and solvates thereof, wherein $R^{4a}$ and $R^{4b}$ are each independently selected from the group consisting of hydrogen and $C_{1-4}$ alkyl.

In another embodiment, Compounds of the Disclosure are compounds represented by Formula III, and the pharmaceutically acceptable salts, hydrates, and solvates thereof, wherein $X^2$ is O.

In another embodiment, Compounds of the Disclosure are compounds represented by Formula I, and the pharmaceutically acceptable salts, hydrates, and solvates thereof, wherein $Y^2$ is —C($R^{2b}$)— and $R^{2b}$ is $C_{1-4}$ alkyl.

In another embodiment, Compounds of the Disclosure are compounds represented by Formulae II and III, and the pharmaceutically acceptable salts, hydrates, and solvates thereof, wherein $R^2$ is $C_{1-4}$ alkyl.

In another embodiment, Compounds of the Disclosure are compounds represented by Formulae I, II, and III, and the pharmaceutically acceptable salts, hydrates, and solvates thereof, wherein $X^1$ is —NH—.

In another embodiment, Compounds of the Disclosure are compounds represented by Formulae I, II, and III, and the pharmaceutically acceptable salts, hydrates, and solvates thereof, wherein X is —N($R^{5a1}$)—, wherein $R^{5a1}$ is $C_{1-4}$ alkyl.

In another embodiment, Compounds of the Disclosure are compounds represented by Formulae I, II, and III, and the pharmaceutically acceptable salts, hydrates, and solvates thereof, wherein $X^4$ is —N($CH_3$)—.

In another embodiment, Compounds of the Disclosure are compounds represented by Formulae I, II and III, and the pharmaceutically acceptable salts, hydrates, and solvates thereof, wherein Z is —NH—.

In another embodiment, Compounds of the Disclosure are compounds represented by Formula IV:

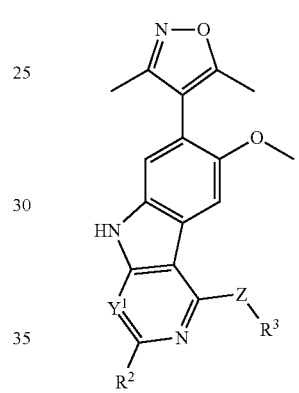

IV and the pharmaceutically acceptable salts, hydrates, and solvates thereof, wherein $R^2$, $R^3$, Z, and $Y^1$ are as defined above in connection with Formula II.

In another embodiment, Compounds of the Disclosure are compounds represented by Formula V:

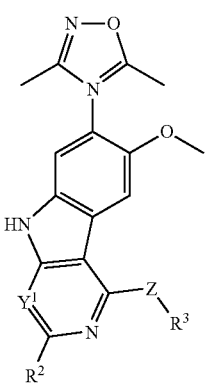

V and the pharmaceutically acceptable salts, hydrates, and solvates thereof, wherein $R^2$, $R^3$, $Y^1$, and Z are as defined above in connection with Formula II.

In another embodiment, Compounds of the Disclosure are compounds represented by Formula VI:

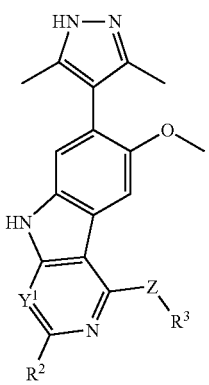

and the pharmaceutically acceptable salts, hydrates, and solvates thereof, wherein $R^2$, $R^3$, $Y^1$, and Z are as defined above in connection with Formula II.

In another embodiment, Compounds of the Disclosure are compounds represented by Formula I, and the pharmaceutically acceptable salts, hydrates, and solvates thereof, wherein G is selected from the group consisting of halo, hydroxy, optionally substituted cycloalkyl, optionally substituted aryl, optionally substituted heteroaryl, aralkyl, and (heteroaryl)alkyl.

In another embodiment, Compounds of the Disclosure are compounds represented by Formula I, and the pharmaceutically acceptable salts, hydrates, and solvates thereof, wherein G is —Z—$R^3$.

In another embodiment, Compounds of the Disclosure are compounds represented by any one of Formulae I-VI, and the pharmaceutically acceptable salts, hydrates, and solvates thereof, wherein Z is —NH—.

In another embodiment, Compounds of the Disclosure are compounds represented by any one of Formulae I-VI, and the pharmaceutically acceptable salts, hydrates, and solvates thereof, wherein Z is —O—.

In another embodiment, Compounds of the Disclosure are compounds represented by any one of Formulae I-VI, and the pharmaceutically acceptable salts, hydrates, and solvates thereof, wherein Z is —S—.

In another embodiment, Compounds of the Disclosure are compounds represented by any one of Formulae I-VI, and the pharmaceutically acceptable salts, hydrates, and solvates thereof, wherein Z is —SO$_2$—.

In another embodiment, Compounds of the Disclosure are compounds represented by Formula I, and the pharmaceutically acceptable salts, hydrates, and solvates thereof, wherein $Y^2$ is —C($R^{2b}$)— and $R^{2b}$ is hydrogen.

In another embodiment, Compounds of the Disclosure are compounds represented by any one of Formulae II-VI, and the pharmaceutically acceptable salts, hydrates, and solvates thereof, wherein R is hydrogen.

In another embodiment, Compounds of the Disclosure are compounds represented by Formula I, and the pharmaceutically acceptable salts, hydrates, and solvates thereof, wherein $Y^2$ is —C($R^{2b}$)— and $R^{2b}$ is $C_{1-4}$ alkyl.

In another embodiment, Compounds of the Disclosure are compounds represented by any one of Formulae II-VI, and the pharmaceutically acceptable salts, hydrates, and solvates thereof, wherein $R^2$ is alkyl. In another embodiment, $R^2$ is $C_{1-6}$ alkyl. In another embodiment, $R^2$ is $C_{1-4}$ alkyl.

In another embodiment, Compounds of the Disclosure are compounds represented by Formula I, and the pharmaceutically acceptable salts, hydrates, and solvates thereof, wherein $Y^2$ is —C($R^{2b}$)— and $R^{2b}$ is optionally substituted heterocyclo.

In another embodiment, Compounds of the Disclosure are compounds represented by any one of Formulae II-VI, and the pharmaceutically acceptable salts, hydrates, and solvates thereof, wherein R is optionally substituted heterocyclo.

In another embodiment, Compounds of the Disclosure are compounds represented by any one of Formulae I-VI, and the pharmaceutically acceptable salts, hydrates, and solvates thereof, wherein $Y^1$ is —CH=.

In another embodiment, Compounds of the Disclosure are compounds represented by any one of Formulae I-VI, and the pharmaceutically acceptable salts, hydrates, and solvates thereof, wherein $Y^1$ is —N=.

In another embodiment, Compounds of the Disclosure are compounds represented by any one of Formulae I-VI, and the pharmaceutically acceptable salts, hydrates, and solvates thereof, wherein G or $R^3$ is optionally substituted aryl.

In another embodiment, Compounds of the Disclosure are compounds represented by any one of Formulae I-VI, and the pharmaceutically acceptable salts, hydrates, and solvates thereof, wherein G or $R^3$ is optionally substituted aryl selected from the group consisting of optionally substituted phenyl and optionally substituted naphthyl.

In another embodiment, Compounds of the Disclosure are compounds represented by any one of Formulae I-VI, and the pharmaceutically acceptable salts, hydrates, and solvates thereof, wherein G or $R^3$ is optionally substituted phenyl selected from the group consisting of:

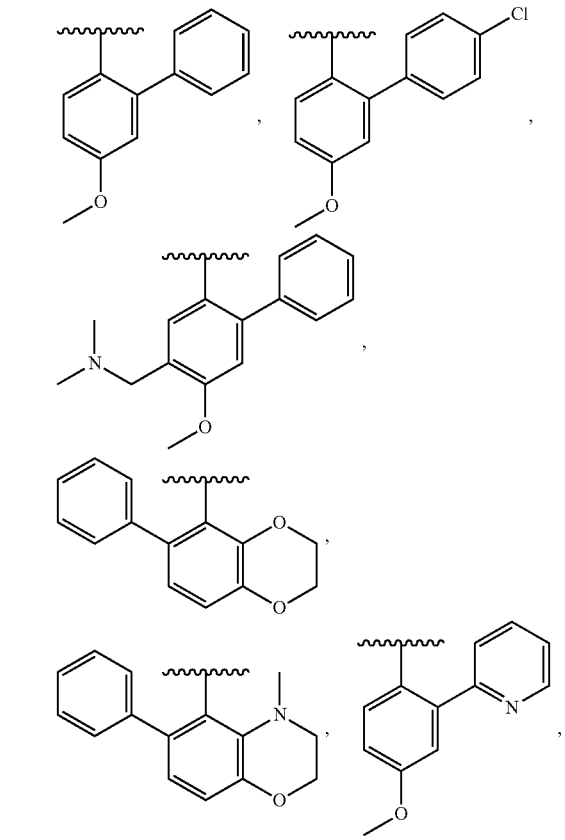

-continued

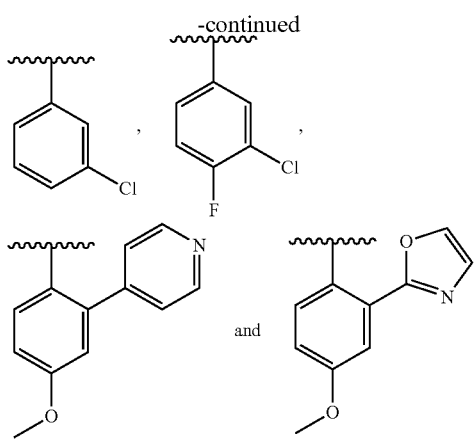

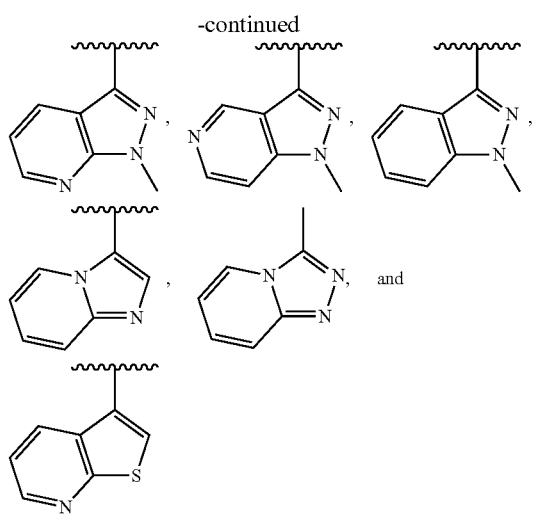

In another embodiment, Compounds of the Disclosure are compounds represented by any one of Formulae I-VI, and the pharmaceutically acceptable salts, hydrates, and solvates thereof, wherein G or $R^3$ is optionally substituted naphthyl selected from the group consisting of:

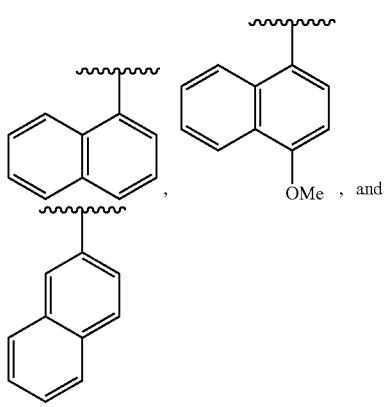

In another embodiment, the optionally substituted heteroaryl is selected from the group consisting of:

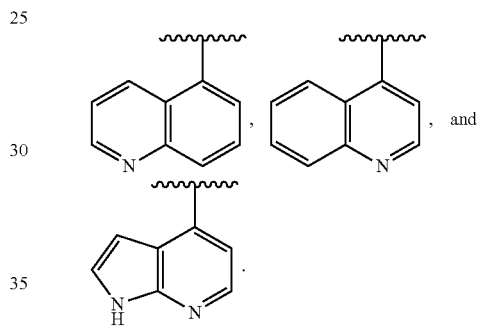

In another embodiment, Compounds of the Disclosure are compounds represented by any one of Formulae I-VI, and the pharmaceutically acceptable salts, hydrates, and solvates thereof, wherein G or $R^3$ is optionally substituted heteroaryl. In one embodiment, the optionally substituted heteroaryl is selected from the group consisting of:

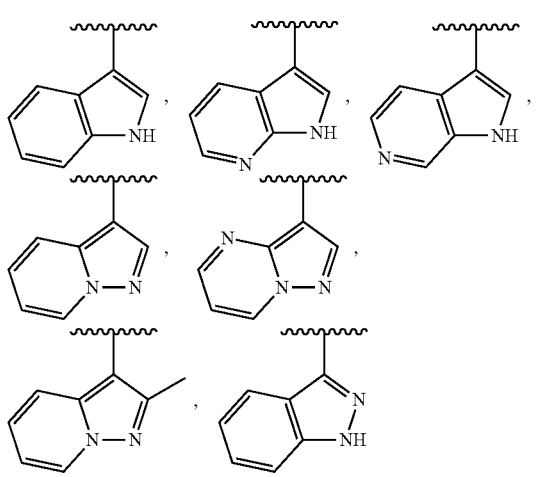

In another embodiment, Compounds of the Disclosure are compounds represented by any one of Formulae I-VI, and the pharmaceutically acceptable salts, hydrates, and solvates thereof, wherein G or $R^3$ is optionally substituted 6-membered heteroaryl. In one embodiment, the optionally substituted 6-membered heteroaryl is selected from the group consisting of:

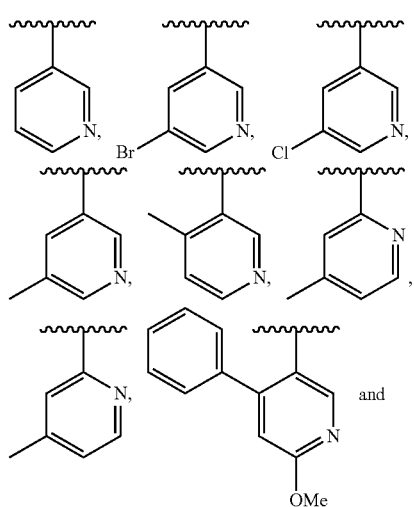

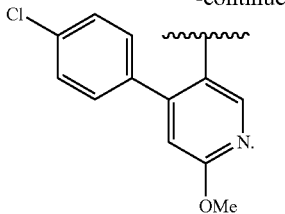

In another embodiment, Compounds of the Disclosure are compounds represented by any one of Formulae I-VI, and the pharmaceutically acceptable salts, hydrates, and solvates thereof, wherein G or $R^3$ is optionally substituted 5-membered heteroaryl.

In another embodiment, Compounds of the Disclosure are compounds represented by Formula I-VI, and the pharmaceutically acceptable salts, hydrates, and solvates thereof, wherein:

G or $R^3$ is optionally substituted 5-membered heteroaryl selected from the group consisting of:

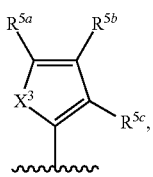

R3-1

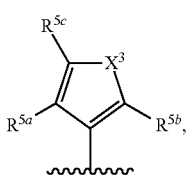

R3-2

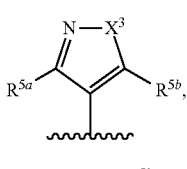

R3-3

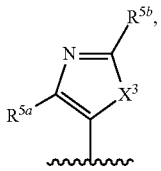

R3-4

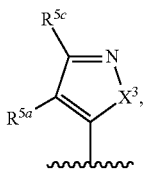

R3-5

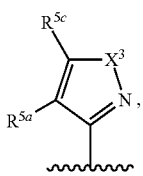

R3-6

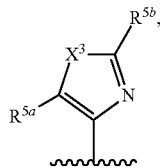

R3-7

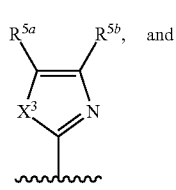

R3-8

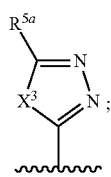

R3-9

$R^{5a}$, $R^{5b}$, and $R^5$ are each independently selected from the group consisting of hydrogen, halo, cyano, alkylcarbonyl, alkoxycarbonyl, haloalkyl, optionally substituted alkyl, hydroxyalkyl, alkoxyalkyl, alkenyl, aralkyl, optionally substituted cycloalkyl, optionally substituted heterocyclo, optionally substituted aryl, optionally substituted heteroaryl, and carboxamido;

$X^3$ is selected from the group consisting of —O—, —S—, and —N($R^{5d}$)—;

$R^{5d}$ is selected from the group consisting of hydrogen, optionally substituted alkyl, haloalkyl, hydroxyalkyl, alkoxyalkyl, (amino)alkyl, aralkyl, (heterocyclo)alkyl, optionally substituted cycloalkyl, optionally substituted heterocyclo, optionally substituted aryl, optionally substituted heteroaryl, carboxamido, (carboxamido)alkyl, and —C(=O)$R^{5e}$; and $R^{5e}$ is selected from the group consisting of alkyl and alkoxy.

In another embodiment, Compounds of the Disclosure are compounds represented by any one of Formulae I-VI, and the pharmaceutically acceptable salts, hydrates, and solvates thereof, wherein:

G or $R^3$ is optionally substituted 5-membered heteroaryl selected from the group consisting of:

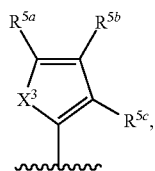

R3-1

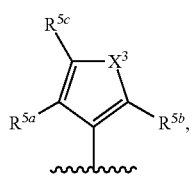

R3-2

-continued

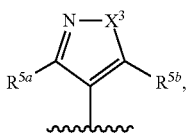
R3-3

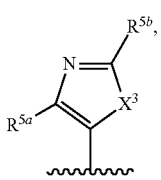
R3-4

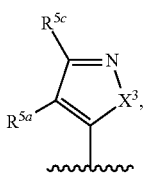
R3-5

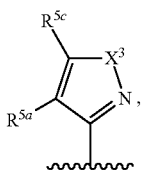
R3-6

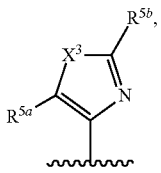
R3-7

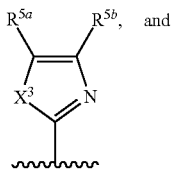
R3-8

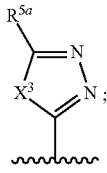
R3-9

$R^{5a}$, $R^{5b}$, and $R^{5c}$ are each independently selected from the group consisting of hydrogen, halo, cyano, alkylcarbonyl, alkoxycarbonyl, haloalkyl, optionally substituted alkyl, hydroxyalkyl, alkoxyalkyl, alkenyl, aralkyl, optionally substituted cycloalkyl, optionally substituted heterocyclo, optionally substituted aryl, optionally substituted heteroaryl, and carboxamido;

$X^3$ is selected from the group consisting of —O—, —S—, and —N($R^{5d}$)—;

$R^{5d}$ is selected from the group consisting of hydrogen, alkyl, haloalkyl, hydroxyalkyl, alkoxyalkyl, (amino)alkyl, aralkyl, optionally substituted cycloalkyl, optionally substituted heterocyclo, optionally substituted aryl, optionally substituted heteroaryl, carboxamido, (carboxamido)alkyl, and —C(=O)$R^{5e}$; and $R^{5e}$ is selected from the group consisting of alkyl and alkoxy.

In another embodiment, Compounds of the Disclosure are compounds represented by any one of Formulae I-VI, and the pharmaceutically acceptable salts, hydrates, and solvates thereof, wherein:

G or $R^3$ is optionally substituted heteroaryl selected from the group consisting of:

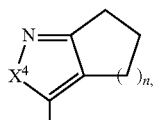
R3-10

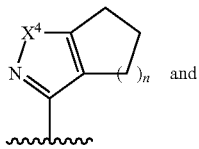
R3-11 and

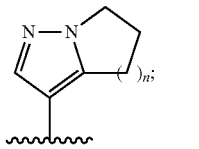
R3-12

$X^4$ is selected from the group consisting of —O—, —S—, and —N($R^f$)—;

$R^{5f}$ is selected from the group consisting of hydrogen, alkyl, haloalkyl, hydroxyalkyl, aralkyl, optionally substituted cycloalkyl, optionally substituted aryl, optionally substituted heteroaryl, and carboxamido; and n is 1, 2, or 3. In another embodiment, $X^4$ is —N($R^{5f}$)— and n is 1 or 2.

In another embodiment, Compounds of the Disclosure are compounds represented by any one of Formulae I-VI, and the pharmaceutically acceptable salts, hydrates, and solvates thereof, wherein G or $R^3$ is R3-1.

In another embodiment, Compounds of the Disclosure are compounds represented by any one of Formulae I-VI, and the pharmaceutically acceptable salts, hydrates, and solvates thereof, wherein G or $R^3$ is R3-2.

In another embodiment, Compounds of the Disclosure are compounds represented by any one of Formulae I-VI, and the pharmaceutically acceptable salts, hydrates, and solvates thereof, wherein G or $R^3$ is R3-3.

In another embodiment, Compounds of the Disclosure are compounds represented by any one of Formulae I-VI, and the pharmaceutically acceptable salts, hydrates, and solvates thereof, wherein G or $R^3$ is R3-4.

In another embodiment, Compounds of the Disclosure are compounds represented by any one of Formulae I-VI, and the pharmaceutically acceptable salts, hydrates, and solvates thereof, wherein G or $R^3$ is R3-5.

In another embodiment, Compounds of the Disclosure are compounds represented by any one of Formulae I-VI, and the pharmaceutically acceptable salts, hydrates, and solvates thereof, wherein G or $R^3$ is R3-6.

In another embodiment, Compounds of the Disclosure are compounds represented by any one of Formulae I-VI, and the pharmaceutically acceptable salts, hydrates, and solvates thereof, wherein G or $R^3$ is R3-7.

In another embodiment, Compounds of the Disclosure are compounds represented by any one of Formulae I-VI, and the pharmaceutically acceptable salts, hydrates, and solvates thereof, wherein G or R³ is R3-8.

In another embodiment, Compounds of the Disclosure are compounds represented by any one of Formulae I-VI, and the pharmaceutically acceptable salts, hydrates, and solvates thereof, wherein G or R³ is R3-9.

In another embodiment, Compounds of the Disclosure are compounds represented by any one of Formulae I-VI, and the pharmaceutically acceptable salts, hydrates, and solvates thereof, wherein R³ is R3-10.

In another embodiment, Compounds of the Disclosure are compounds represented by any one of Formulae I-VI, and the pharmaceutically acceptable salts, hydrates, and solvates thereof, wherein G or R³ is R3-11.

In another embodiment, Compounds of the Disclosure are compounds represented by any one of Formulae I-VI, and the pharmaceutically acceptable salts, hydrates, and solvates thereof, wherein G or R³ is R3-12.

In another embodiment, Compounds of the Disclosure are compounds represented by any one of Formulae I-VI, and the pharmaceutically acceptable salts, hydrates, and solvates thereof, wherein G or R³ is optionally substituted 5-membered heteroaryl selected from the group consisting of:

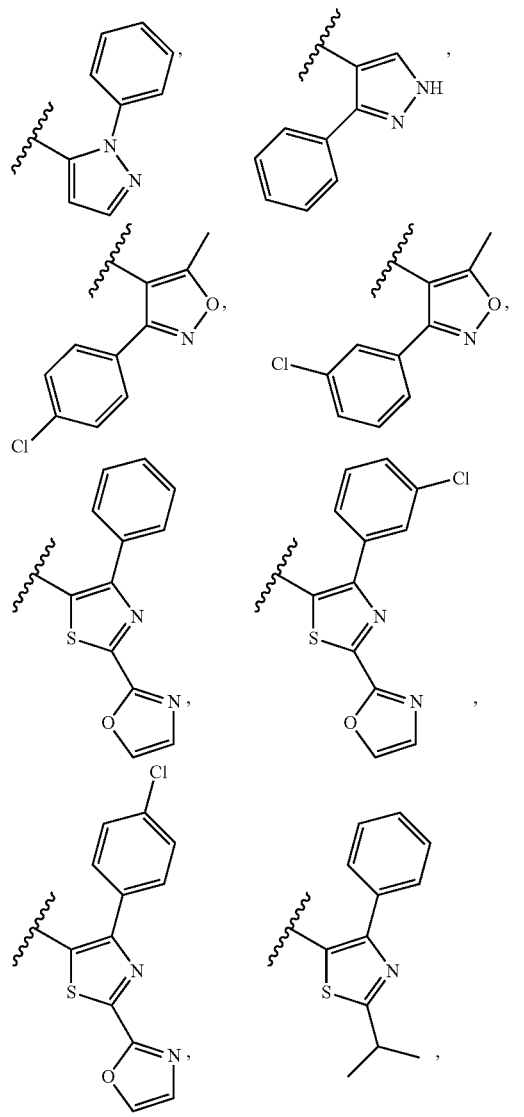

-continued

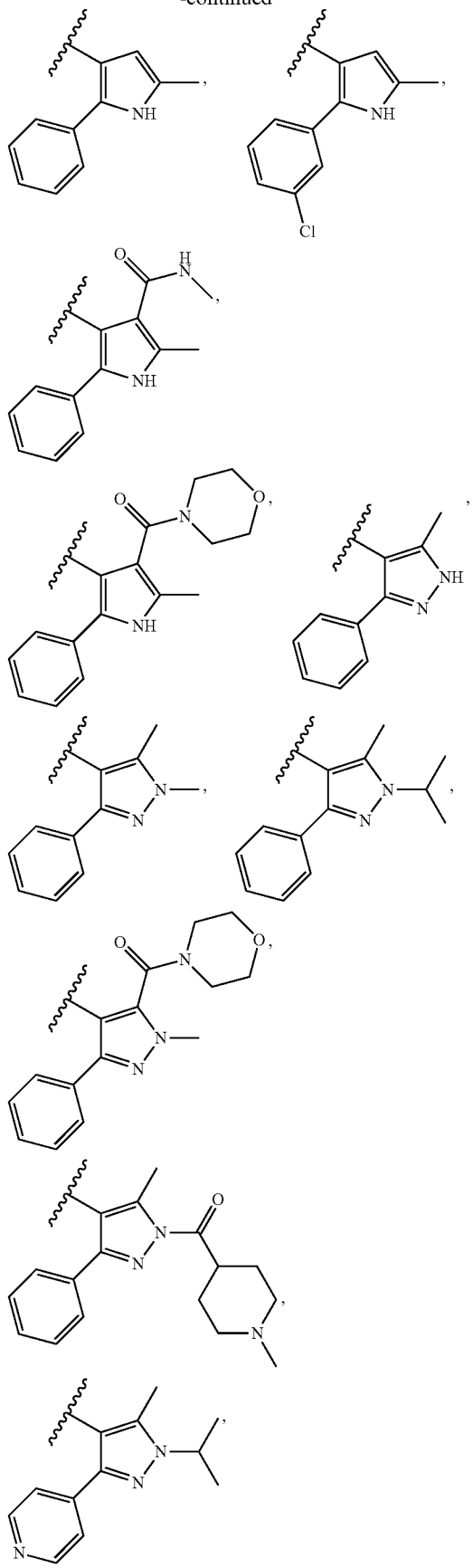

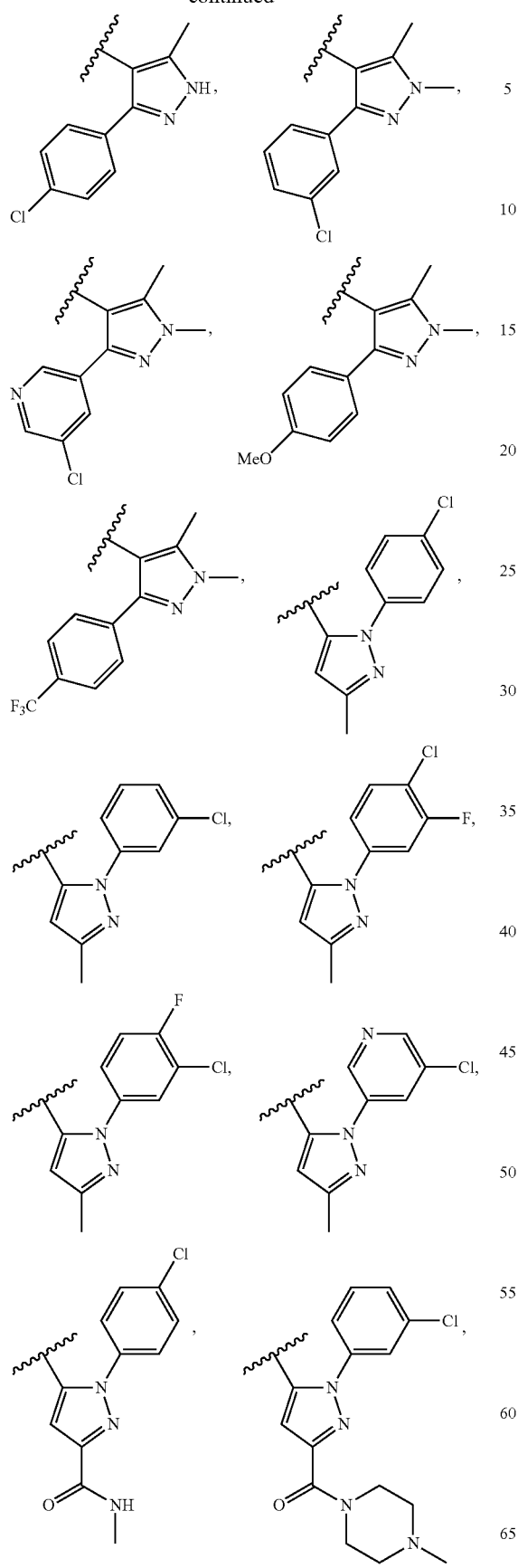
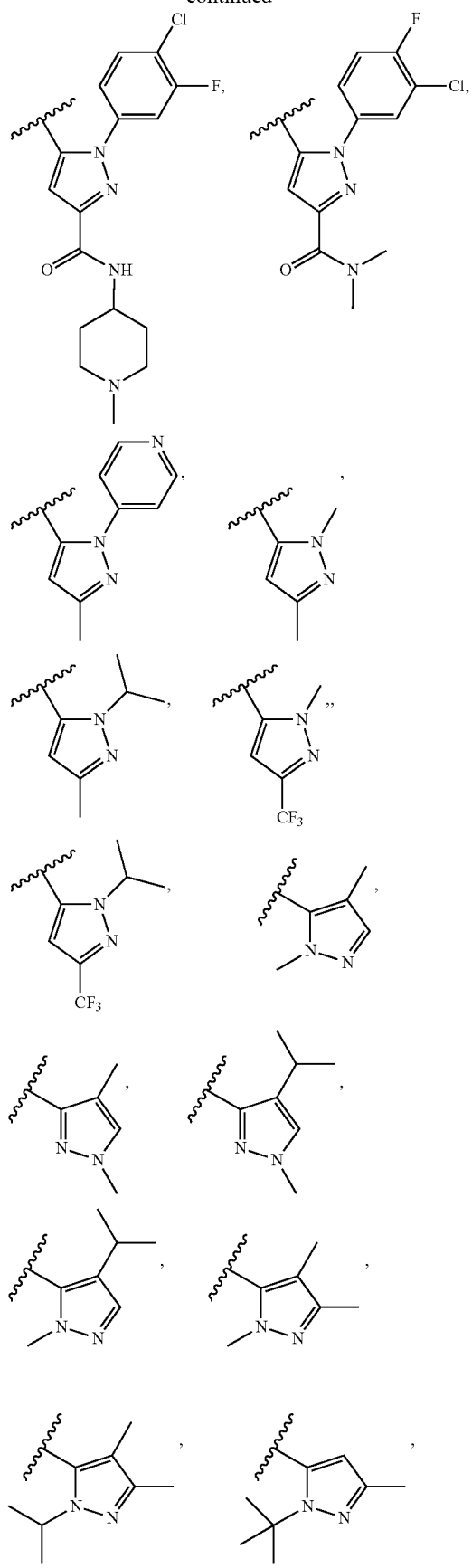

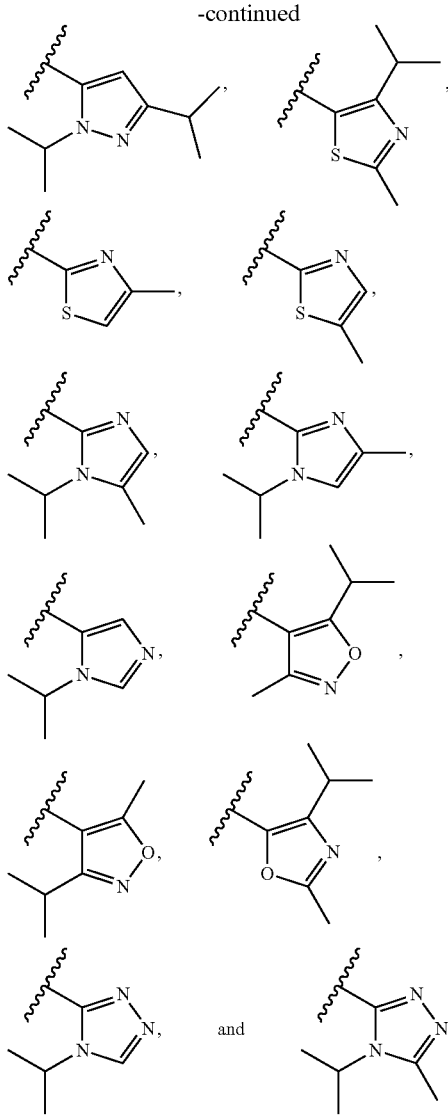

In another embodiment, Compounds of the Disclosure are compounds represented by any one of Formulae I-V, and the pharmaceutically acceptable salts, hydrates, and solvates thereof, wherein G or $R^3$ is selected from the group consisting of:

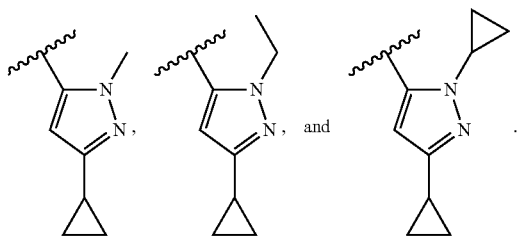

In another embodiment, Compounds of the Disclosure are compounds represented by any one of Formulae I-VI, and the pharmaceutically acceptable salts, hydrates, and solvates thereof, wherein R is optionally substituted cycloalkyl. In another embodiment, $R^3$ is selected from the group consisting of cyclopentyl and cyclohexyl.

In another embodiment, Compounds of the Disclosure are compounds represented Formula I, and the pharmaceutically acceptable salts, hydrates, and solvates thereof, wherein $R^{1a}$ is selected from the group consisting of hydroxy, alkyl, haloalkyl, alkoxy, alkylthio, amino, and halo; $R^{1b}$ is halo; and $R^{1c}$ is hydrogen.

In another embodiment, Compounds of the Disclosure are compounds represented Formula I, and the pharmaceutically acceptable salts, hydrates, and solvates thereof, wherein $R^{1a}$ is selected from the group consisting of hydroxy, alkyl, haloalkyl, alkoxy, alkylthio, amino, and halo; $R^{1b}$ is hydrogen; and $R^{1c}$ is fluoro.

In another embodiment, Compounds of the Disclosure are compounds represented by Formula IX:

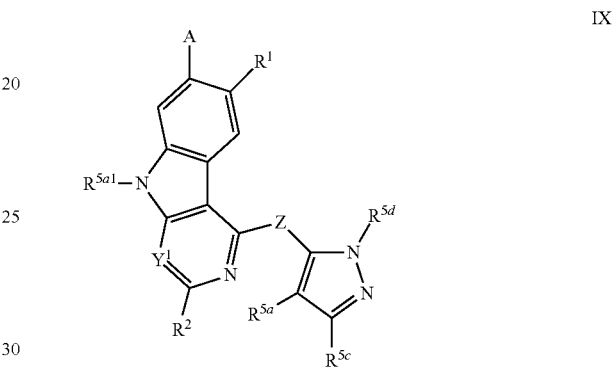

IX and the pharmaceutically acceptable salts, hydrates, and solvates thereof, wherein $R^1$, $R^2$, $R^{5a1}$, $R^{5a}$, $R^{5c}$, $R^{5d}$, A, Z, and $Y^1$ are as defined above in connection with Formula II, with the proviso that A is not 1,3-dimethyl-1H-pyrazol-4-yl, or:

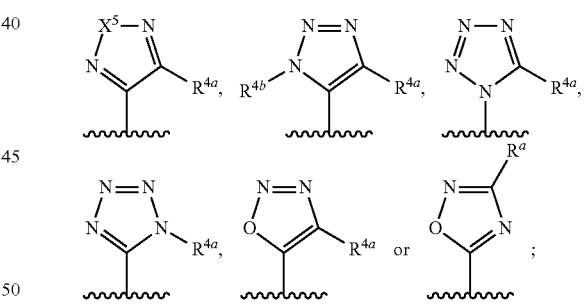

wherein:
$R^{4a}$ and $R^{4b}$ are each independently selected from the group consisting of hydrogen, halo, haloalkyl, and alkyl; and
$X^5$ is selected from the group consisting of —O— and —S—.

In another embodiment, Compounds of the Disclosure are compounds represented by Formula IX, and the pharmaceutically acceptable salts, hydrates, and solvates thereof, wherein $R^{5a1}$ is hydrogen. In another embodiment, $R^{5a1}$ is $C_{1-4}$ alkyl.

In another embodiment, Compounds of the Disclosure are compounds represented by Formula IX, and the pharmaceutically acceptable salts, hydrates, and solvates thereof, wherein $R^1$ is alkoxy. In another embodiment, $R^1$ is methoxy.

In another embodiment, Compounds of the Disclosure are compounds represented by Formula IX, and the pharmaceutically acceptable salts, hydrates, and solvates thereof, wherein A is selected from the group consisting of A-3 and A-9. In another embodiment, A is A-3. In another embodiment, X is —O—, and $R^{4a}$ and $R^{4b}$ are independently $C_{1-4}$ alkyl. In another embodiment, $R^{4a}$ and $R^{4b}$ are methyl.

In another embodiment, Compounds of the Disclosure are compounds represented by Formula IX, and the pharmaceutically acceptable salts, hydrates, and solvates thereof, wherein, Z is —NH—.

In another embodiment, Compounds of the Disclosure are compounds represented by Formula IX, and the pharmaceutically acceptable salts, hydrates, and solvates thereof, wherein, $Y^1$ is —N=.

In another embodiment, Compounds of the Disclosure are compounds represented by Formula IX, and the pharmaceutically acceptable salts, hydrates, and solvates thereof, wherein $R^{5a}$, $R^{5c}$, and $R^{5d}$ are independently selected from the group consisting of hydrogen, $C_{1-6}$ alkyl, and $C_{3-6}$ cycloalkyl.

In another embodiment, Compounds of the Disclosure are compounds represented by Formula X:

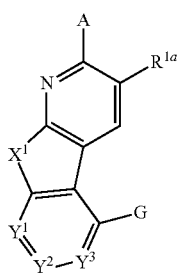

X and the pharmaceutically acceptable salts, hydrates, and solvates thereof, wherein $R^{1a}$, A, G, $X^1$, $Y^1$, $Y^2$, and $Y^3$ are as defined above in connection with Formula I, with the proviso that A is not 1,3-dimethyl-1H-pyrazol-4-yl, or:

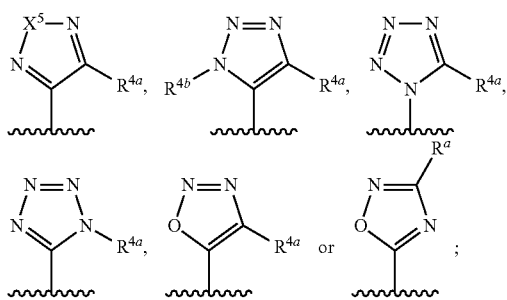

wherein:

$R^{4a}$ and $R^{4b}$ are each independently selected from the group consisting of hydrogen, halo, haloalkyl, and alkyl; and $X^5$ is selected from the group consisting of —O— and —S—. In another embodiment, G is selected from the group consisting of halo, hydroxy, optionally substituted heterocyclo, optionally substituted aryl, optionally substituted heteroaryl, aralkyl, and (heteroaryl)alkyl. In another embodiment, G is selected from the group consisting of optionally substituted aryl, optionally substituted heteroaryl, aralkyl, and (heteroaryl)alkyl. In another embodiment, G is —Z—$R^3$. In another embodiment, $Y^1$ is —N=; $Y^2$ is —C($R^{2b}$)=; and $Y^3$ is —C($R^{2c}$)=. In another embodiment, $Y^1$ is —C($R^{2a}$)=; $Y^2$ is —N=; and $Y^3$ is —C($R^2$)=. In another embodiment, $Y^1$ is —C($R^{2a}$)=; $Y^2$ is —C($R^{2b}$)=; and $Y^3$ is —N=. In another embodiment, $Y^1$ is —N=; $Y^2$ is —C($R^{2b}$)=; and $Y^3$ is —N=.

In another embodiment, Compounds of the Disclosure are compounds represented by Formula XI:

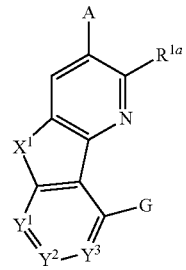

XI and the pharmaceutically acceptable salts, hydrates, and solvates thereof, wherein $R^{1a}$, A, G, $X^1$, $Y^1$, $Y^2$, and $Y^3$ are as defined above in connection with Formula I, with the proviso that A is not 1,3-dimethyl-1H-pyrazol-4-yl, or:

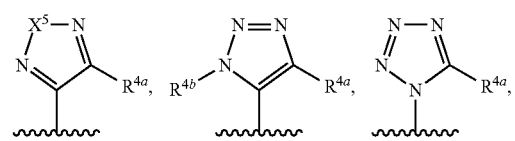

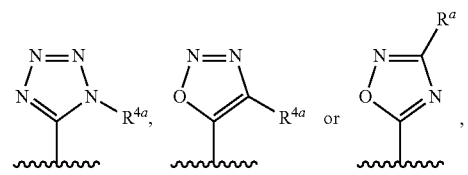

wherein:

$R^{4a}$ and $R^{4b}$ are each independently selected from the group consisting of hydrogen, halo, haloalkyl, and alkyl; and $X^5$ is selected from the group consisting of —O— and —S—. In another embodiment, G is selected from the group consisting of halo, hydroxy, optionally substituted heterocyclo, optionally substituted aryl, optionally substituted heteroaryl, aralkyl, and (heteroaryl)alkyl. In another embodiment, G is selected from the group consisting of optionally substituted aryl, optionally substituted heteroaryl, aralkyl, and (heteroaryl)alkyl. In another embodiment, G is —Z—R. In another embodiment, $Y^1$ is —N=; $Y^2$ is —C($R^{2b}$)=; and $Y^3$ is —C($R^{2c}$)=. In another embodiment, $Y^1$ is —C($R^{2a}$)=; $Y^2$ is —N=; and $Y^3$ is —C($R^{2c}$)=. In another embodiment, $Y^1$ is —C($R^{2a}$)=; $Y^2$ is —C($R^{2b}$)=; and $Y^3$ is —N=. In another embodiment, $Y^1$ is —N=; $Y^2$ is —C($R^{2b}$)=; and $Y^3$ is —N=.

In another embodiment, Compounds of the Disclosure are compounds represented by Formula XII:

XII

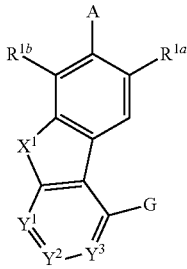

and the pharmaceutically acceptable salts, hydrates, and solvates thereof, wherein $R^{1a}$ and $R^{1b}$ are independently selected from the group consisting of hydroxy, alkyl, haloalkyl, alkoxy, alkylthio, amino, and halo; and A, G, $X^1$, $Y^1$, $Y^2$, and $Y^3$ are as defined above in connection with Formula I, with the proviso that A is not 1,3-dimethyl-1H-pyrazol-4-yl, or:

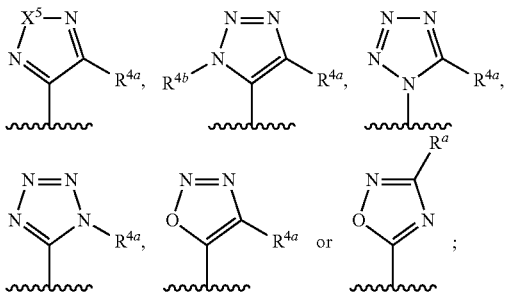

wherein:
$R^{4a}$ and $R^{4b}$ are each independently selected from the group consisting of hydrogen, halo, haloalkyl, and alkyl; and
$X^5$ is selected from the group consisting of —O— and —S—. In another embodiment, G is selected from the group consisting of halo, hydroxy, optionally substituted heterocyclo, optionally substituted aryl, optionally substituted heteroaryl, aralkyl, and (heteroaryl)alkyl. In another embodiment, G is selected from the group consisting of optionally substituted aryl, optionally substituted heteroaryl, aralkyl, and (heteroaryl)alkyl. In another embodiment, G is —Z—$R^3$. In another embodiment, $Y^1$ is —N=; $Y^2$ is —C($R^{2b}$)=; and $Y^3$ is —C($R^{2c}$)=. In another embodiment, $Y^1$ is —C($R^{2a}$)=; $Y^2$ is —N=; and $Y^3$ is —C($R^{2c}$)=. In another embodiment, $Y^1$ is —C($R^{2a}$)=; $Y^2$ is —C($R^{2b}$)=; and $Y^3$ is —N=. In another embodiment, $Y^1$ is —N=; $Y^2$ is —C($R^{2b}$)=; and $Y^3$ is —N=.

In another embodiment, Compounds of the Disclosure are compounds represented by Formula XIII:

XIII

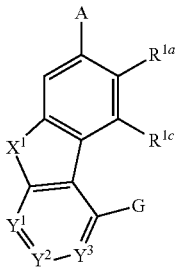

and the pharmaceutically acceptable salts, hydrates, and solvates thereof, wherein $R^{1a}$ and $R^{1c}$ are independently selected from the group consisting of hydroxy, optionally substituted heterocyclo, alkyl, haloalkyl, alkoxy, alkylthio, amino, and fluoro; and A, G, $X^1$, $Y^1$, $Y^2$, and $Y^3$ are as defined above in connection with Formula I, with the proviso that A is not 1,3-dimethyl-1H-pyrazol-4-yl, or:

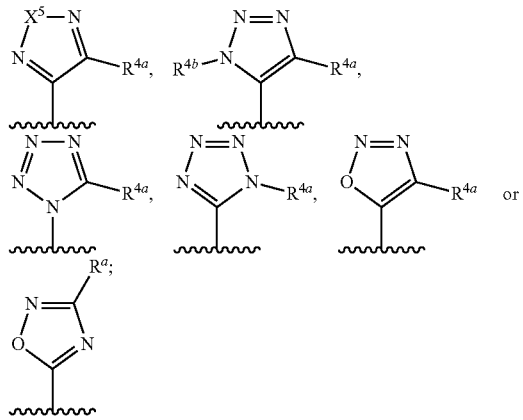

wherein:
$R^{4a}$ and $R^{4b}$ are each independently selected from the group consisting of hydrogen, halo, haloalkyl, and alkyl; and
$X^5$ is selected from the group consisting of —O— and —S—. In another embodiment, G is selected from the group consisting of halo, hydroxy, optionally substituted aryl, optionally substituted heteroaryl, aralkyl, and (heteroaryl)alkyl. In another embodiment, G is selected from the group consisting of optionally substituted aryl, optionally substituted heteroaryl, aralkyl, and (heteroaryl)alkyl. In another embodiment, G is —Z—$R^3$. In another embodiment, $Y^1$ is —N=; $Y^2$ is —C($R^{2b}$)=; and $Y^3$ is —C($R^{2c}$)=. In another embodiment, $Y^1$ is —C($R^{2a}$)=; $Y^2$ is —N=; and $Y^3$ is —C($R^{2c}$)=. In another embodiment, $Y^1$ is —C($R^{2a}$)=; $Y^2$ is —C($R^{2b}$)=; and $Y^3$ is —N=. In another embodiment, $Y^1$ is —N=; $Y^2$ is —C($R^{2b}$)=; and $Y^3$ is —N=.

In another embodiment, Compounds of the Disclosure are compounds represented by Formula XIV:

XIV

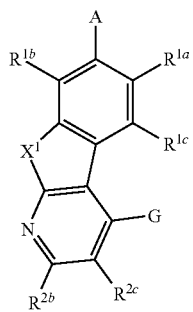

and the pharmaceutically acceptable salts, hydrates, and solvates thereof, wherein $R^{1a}$ is selected from the group consisting of hydroxy, alkyl, haloalkyl, alkoxy, alkylthio, amino, and halo; and $R^{1b}$, $R^{1c}$, $R^{2b}$, $R^{2c}$, A, G, and $X^1$ are as defined above in connection with Formula I, with the proviso that A is not 1,3-dimethyl-1H-pyrazol-4-yl, or:

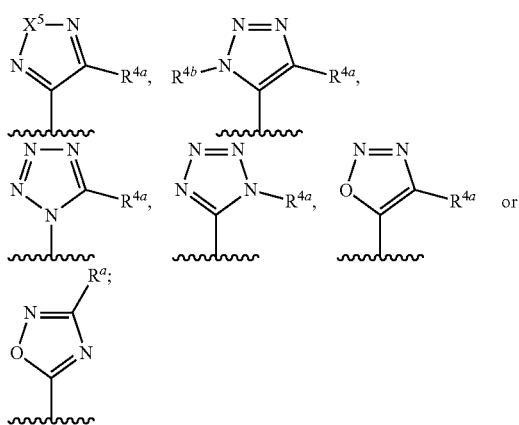

wherein:

$R^{4a}$ and $R^{4b}$ are each independently selected from the group consisting of hydrogen, halo, haloalkyl, and alkyl; and $X^5$ is selected from the group consisting of —O— and —S—. In another embodiment, G is selected from the group consisting of halo, hydroxy, optionally substituted aryl, optionally substituted heterocyclo, optionally substituted heteroaryl, aralkyl, and (heteroaryl)alkyl; and either $R^{1b}$ or $R^{1c}$, or both, is hydroxy, alkyl, haloalkyl, alkoxy, alkylthio, amino, or fluoro. In another embodiment, G is selected from the group consisting of optionally substituted aryl, optionally substituted heteroaryl, aralkyl, and (heteroaryl)alkyl; and either $R^{1b}$ or $R^{1c}$, or both, is hydroxy, alkyl, haloalkyl, alkoxy, alkylthio, amino, or fluoro. In another embodiment, G is —Z—$R^3$.

In another embodiment, Compounds of the Disclosure are compounds represented by Formula XV:

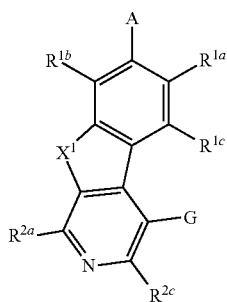

XV and the pharmaceutically acceptable salts, hydrates, and solvates thereof, wherein $R^{1a}$ is selected from the group consisting of hydroxy, alkyl, haloalkyl, alkoxy, alkylthio, amino, and halo; and $R^{1b}$, $R^{1c}$, $R^{2a}$, $R^{2c}$, A, G, and $X^1$ are as defined above in connection with Formula I, with the proviso that A is not 1,3-dimethyl-1H-pyrazol-4-yl, or:

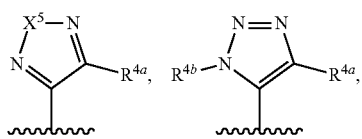

-continued

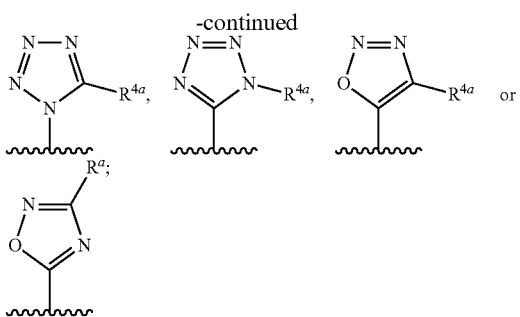

wherein:

$R^{4a}$ and $R^{4b}$ are each independently selected from the group consisting of hydrogen, halo, haloalkyl, and alkyl; and $X^5$ is selected from the group consisting of —O— and —S—. In another embodiment, G is selected from the group consisting of halo, hydroxy, optionally substituted heterocyclo, optionally substituted aryl, optionally substituted heteroaryl, aralkyl, and (heteroaryl)alkyl; and either $R^{1b}$ or $R^{1c}$, or both, is hydroxy, alkyl, haloalkyl, alkoxy, alkylthio, amino, or fluoro. In another embodiment, G is selected from the group consisting of optionally substituted aryl, optionally substituted heteroaryl, aralkyl, and (heteroaryl)alkyl; and either $R^{1b}$ or $R^{1c}$, or both, is hydroxy, alkyl, haloalkyl, alkoxy, alkylthio, amino, or fluoro. In another embodiment, G is —Z—$R^3$.

In another embodiment, Compounds of the Disclosure are compounds represented by Formula XVI:

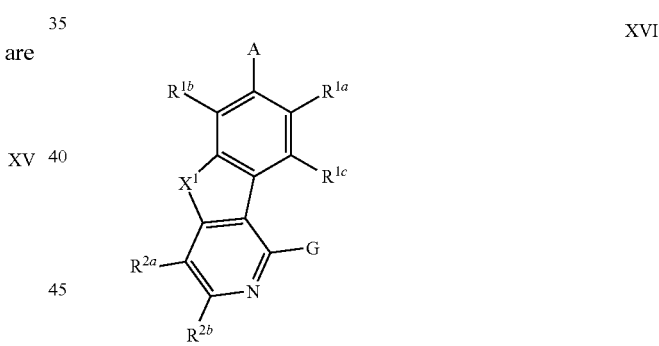

XVI and the pharmaceutically acceptable salts, hydrates, and solvates thereof, wherein $R^{1a}$ is selected from the group consisting of hydroxy, alkyl, haloalkyl, alkoxy, alkylthio, amino, and halo; and $R^{1b}$, $R^{1c}$, $R^{2a}$, $R^{2b}$, A, G, and $X^1$ are as defined above in connection with Formula I, with the proviso that A is not 1,3-dimethyl-1H-pyrazol-4-yl, or:

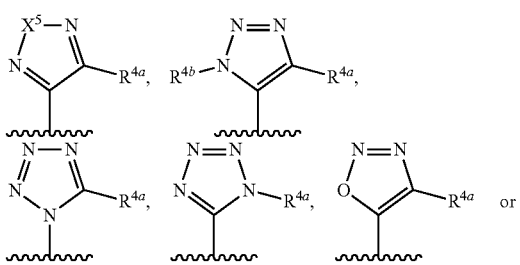

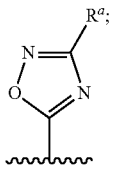

wherein:

$R^{4a}$ and $R^{4b}$ are each independently selected from the group consisting of hydrogen, halo, haloalkyl, and alkyl; and $X^5$ is selected from the group consisting of —O— and —S—. In another embodiment, G is selected from the group consisting of halo, hydroxy, optionally substituted heterocyclo, optionally substituted aryl, optionally substituted heteroaryl, aralkyl, and (heteroaryl)alkyl; and either $R^{1b}$ or $R^{1c}$, or both, is hydroxy, alkyl, haloalkyl, alkoxy, alkylthio, amino, or fluoro. In another embodiment, G is —Z—$R^3$.

In another embodiment, Compounds of the Disclosure are compounds represented by Formula XVII:

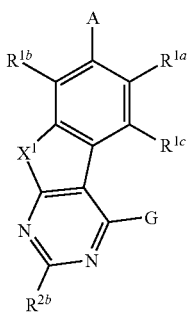

XVII and the pharmaceutically acceptable salts, hydrates, and solvates thereof, wherein $R^{1a}$ is selected from the group consisting of hydroxy, alkyl, haloalkyl, alkoxy, alkylthio, amino, and halo; and $R^{1b}$, $R^{1c}$, $R^{2b}$, A, G, and $X^1$ are as defined above in connection with Formula I, with the proviso that A is not 1,3-dimethyl-1H-pyrazol-4-yl, or:

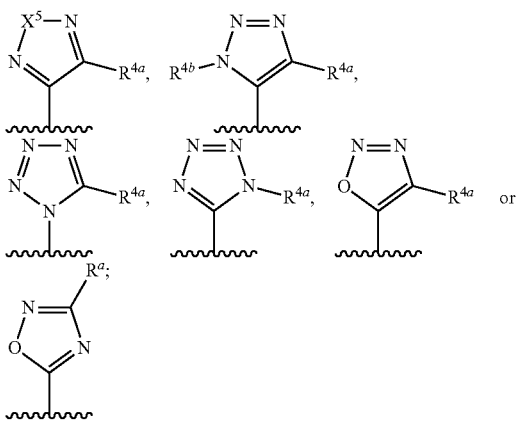

wherein:

$R^{4a}$ and $R^{4b}$ are each independently selected from the group consisting of hydrogen, halo, haloalkyl, and alkyl; and $X^5$ is selected from the group consisting of —O— and —S—. In another embodiment, G is selected from the group consisting of halo, hydroxy, optionally substituted heterocyclo, optionally substituted aryl, optionally substituted heteroaryl, aralkyl, and (heteroaryl)alkyl; and either $R^{1b}$ or $R^{1c}$, or both, is hydroxy, alkyl, haloalkyl, alkoxy, alkylthio, amino, or fluoro. In another embodiment, G is selected from the group consisting of optionally substituted aryl, optionally substituted heteroaryl, aralkyl, and (heteroaryl)alkyl; and either $R^{1b}$ or $R^{1c}$, or both, is hydroxy, alkyl, haloalkyl, alkoxy, alkylthio, amino, or fluoro. In another embodiment, G is —Z—$R^3$.

In another embodiment, Compounds of the Disclosure are compounds represented by Formula XVIII:

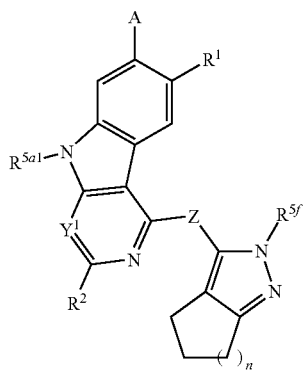

and the pharmaceutically acceptable salts, hydrates, and solvates thereof, wherein $R^1$, $R^2$, $R^{5a1}$, $R^{5a}$, $R^{5c}$, $R^{5d}$, A, Z, and $Y^1$ are as defined above in connection with Formula II, with the proviso that A is not 1,3-dimethyl-1H-pyrazol-4-yl, or:

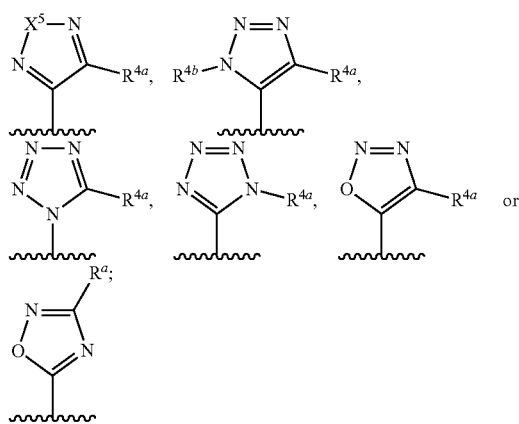

wherein:

$R^{4a}$ and $R^{4b}$ are each independently selected from the group consisting of hydrogen, halo, haloalkyl, and alkyl; and $X^5$ is selected from the group consisting of —O— and —S—.

In another embodiment, Compounds of the Disclosure are compounds represented by Formula XVIII, and the pharmaceutically acceptable salts, hydrates, and solvates thereof, wherein $R^{5a1}$ is hydrogen. In another embodiment, $R^{5a1}$ is $C_{1-4}$ alkyl.

In another embodiment, Compounds of the Disclosure are compounds represented by Formula XVIII, and the pharmaceutically acceptable salts, hydrates, and solvates thereof, wherein $R^1$ is alkoxy. In another embodiment, $R^1$ is methoxy.

In another embodiment, Compounds of the Disclosure are compounds represented by Formula XVIII, and the pharmaceutically acceptable salts, hydrates, and solvates thereof, wherein A is selected from the group consisting of A-3 and A-9. In another embodiment, A is A-3. In another embodiment, X is —O—, and $R^{4a}$ and $R^{4b}$ are independently $C_{1-4}$ alkyl. In another embodiment, $R^{4a}$ and $R^{4b}$ are methyl.

In another embodiment, Compounds of the Disclosure are compounds represented by Formula XVIII, and the pharmaceutically acceptable salts, hydrates, and solvates thereof, wherein, Z is —NH—.

In another embodiment, Compounds of the Disclosure are compounds represented by Formula XVIII, and the pharmaceutically acceptable salts, hydrates, and solvates thereof, wherein, $Y^1$ is —N=.

In another embodiment, Compounds of the Disclosure are compounds represented by Formula XVIII, and the pharmaceutically acceptable salts, hydrates, and solvates thereof, wherein $R^{5a}$, $R^{5c}$, and $R^{5d}$ are independently selected from the group consisting of hydrogen, $C_{1-6}$ alkyl, and $C_{3-6}$ cycloalkyl.

In another embodiment, Compounds of the Disclosure are compounds represented by Formula XVIII, and the pharmaceutically acceptable salts, hydrates, and solvates thereof, wherein $R^{5a1}$ is hydrogen, and $R^{5f}$ is selected from the group consisting of $C_{1-6}$ alkyl l and $C_{3-6}$ cycloalkyl.

In another embodiment, Compounds of the Disclosure are compounds represented by Formula XVIII, and the pharmaceutically acceptable salts, hydrates, and solvates thereof, wherein; $R^1$ is —$OCH_3$, $R^2$ is selected from the group consisting of —$CH_3$ and —$CH_2OCH_3$; and Z is —N(H)—.

In one aspect, the present disclosure provides the following specific embodiments:

Embodiment I

A method of treating a cancer selected from the group consisting of prostate cancer and breast cancer in a subject, the method comprising administering to the subject an effective amount of a compound that inhibits one or more BET bromodomain proteins.

Embodiment II

The method of Embodiment I, wherein the cancer is prostate cancer.

Embodiment III

The method of Embodiment II, wherein the prostate cancer has active AR signaling.

Embodiment IV

The method of Embodiments II or III, wherein the prostate cancer is castration resistant prostate cancer.

Embodiment V

The method of Embodiment I, wherein the cancer is breast cancer.

Embodiment VI

The method of Embodiment V, wherein the breast cancer has active AR signaling.

Embodiment VII

A method of identifying a patient sensitive to a compound that inhibits BET bromodomain proteins, the method comprising evaluating AR-signaling status in a patient having prostate cancer or breast cancer tumors.

Embodiment VIII

The method of any one of Embodiments I-VII, wherein the compound inhibits BRD2, BRD3, BRD4, and/or BRD-t.

Embodiment IX

The method of Embodiment VIII, wherein the compound inhibits BRD4.

Embodiment X

The method of any one of Embodiments I-IX, wherein the compound is:

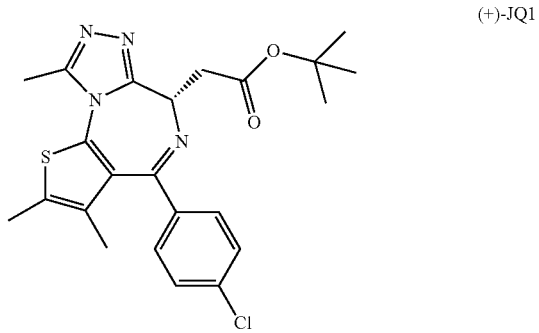
(+)-JQ1

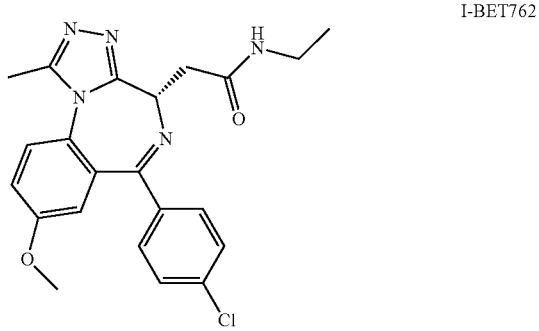
I-BET762

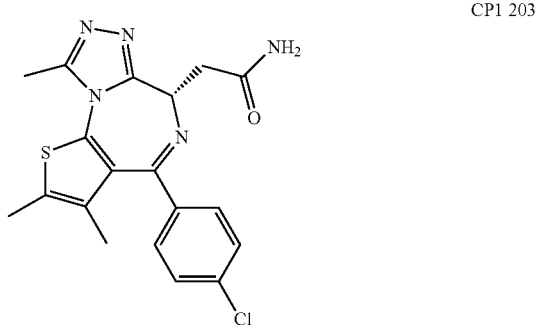
CPI 203

MS417
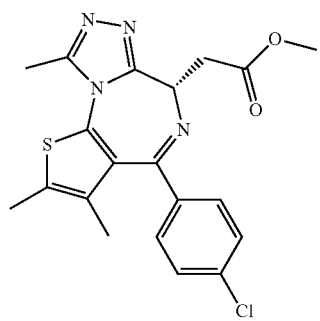
I-BET151
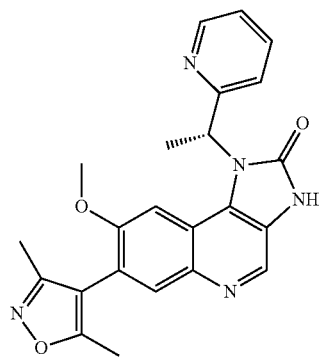
PFi-1
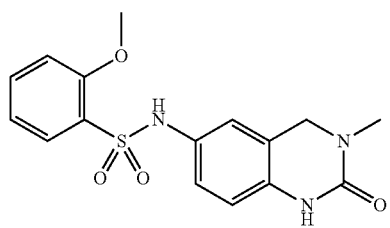
RVX-208
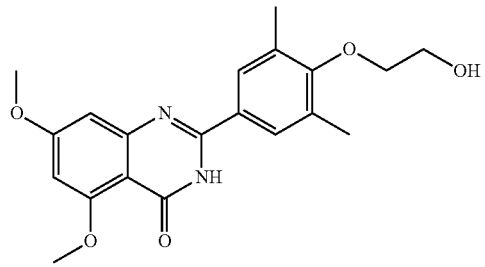
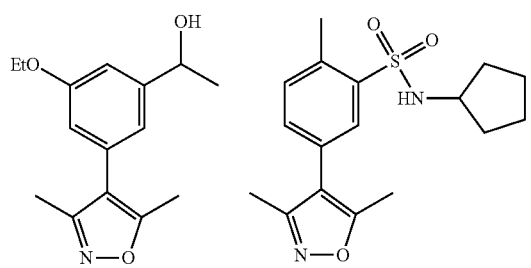
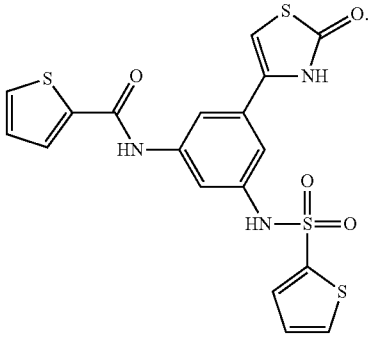
Embodiment XI
The method of any one of Embodiments I-IX, wherein the compound is:
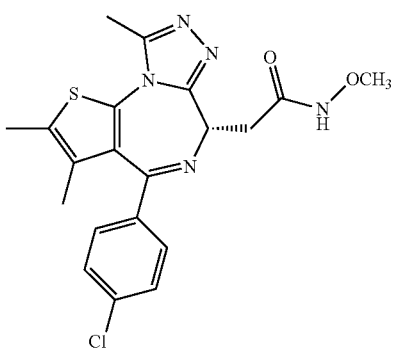
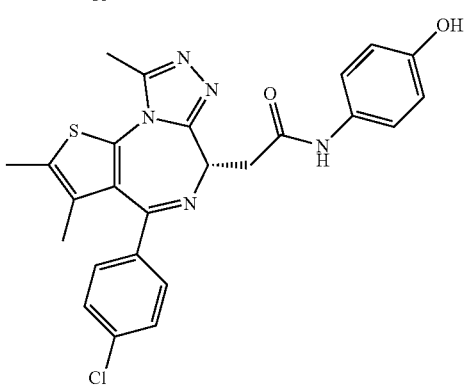
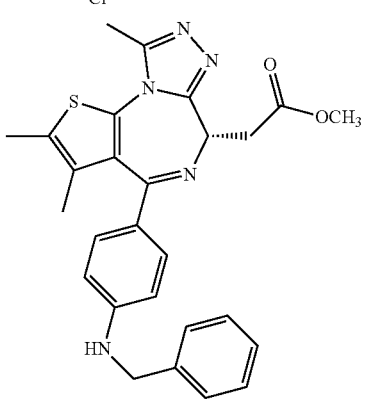

-continued
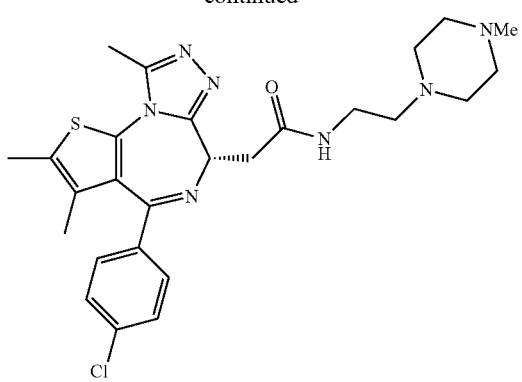
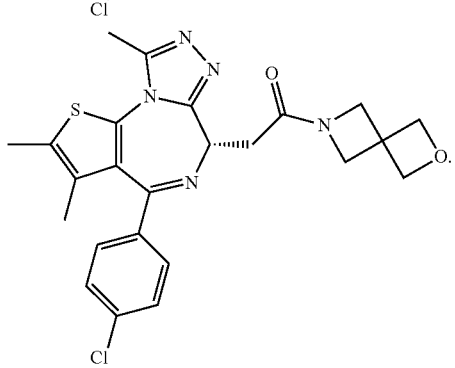
Embodiment XII
The method of any one of Embodiments I-IX, wherein the compound is:
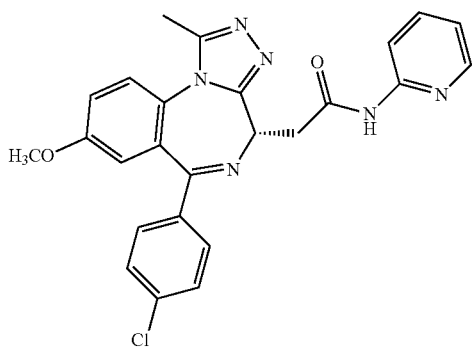
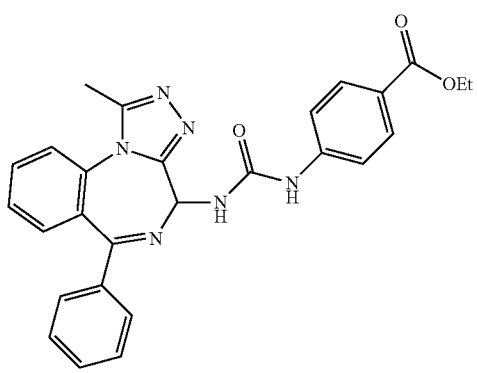
-continued
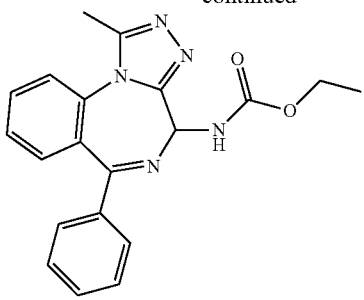
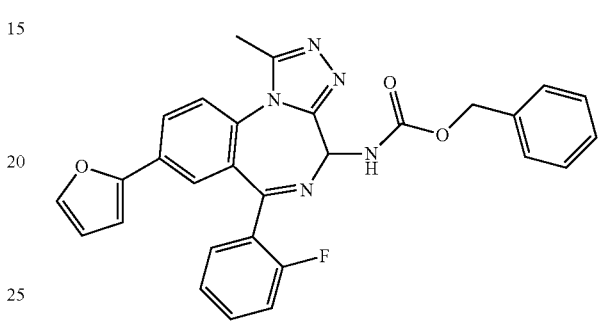
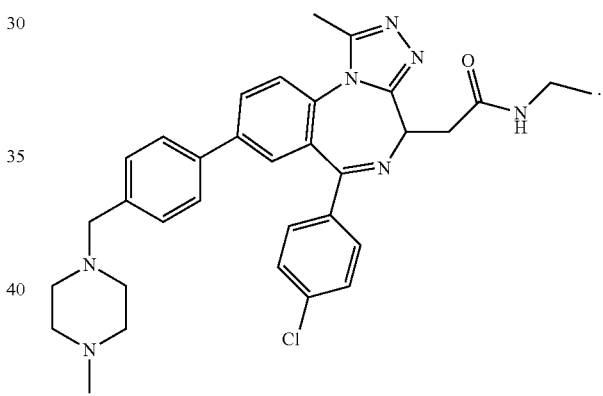
Embodiment XIII
The method of any one of Embodiments I-IX, wherein the compound is:
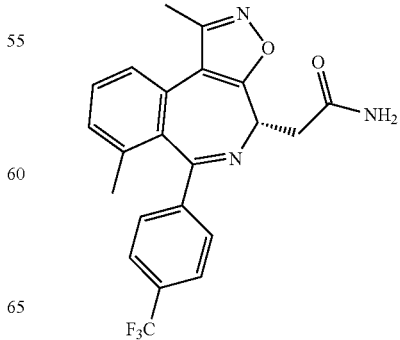

-continued
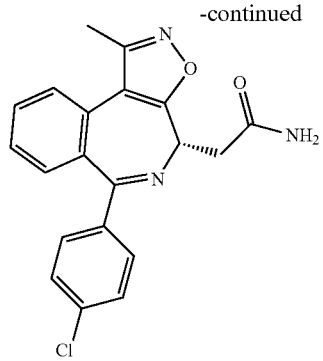
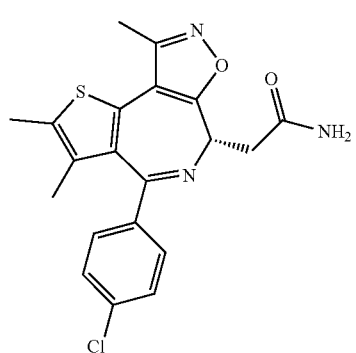
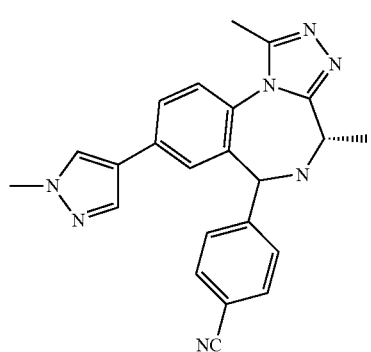
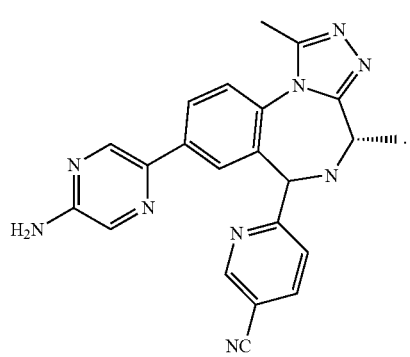
Embodiment XIV
The method of any one of Embodiments I-IX, wherein the compound is:
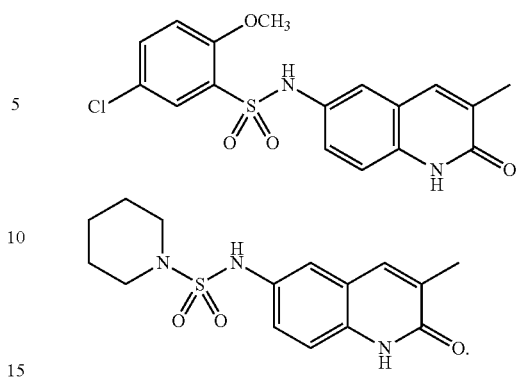
Embodiment XV
The method of any one of Embodiments I-IX, wherein the compound is:
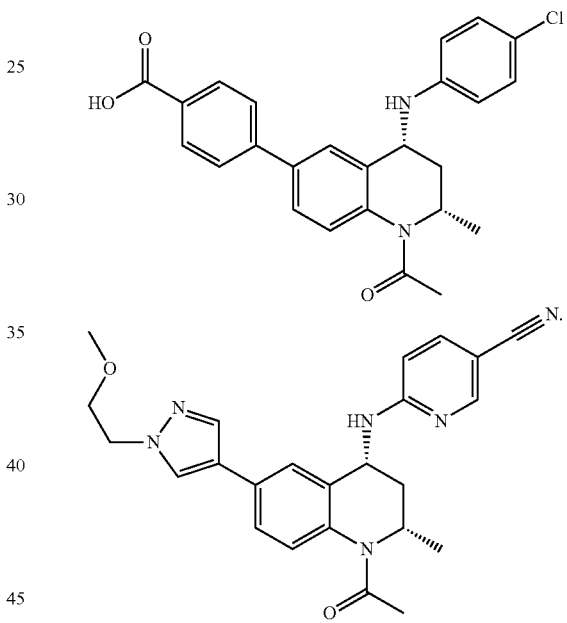
Embodiment XVI
The method of any one of Embodiments I-IX, wherein the compound is:
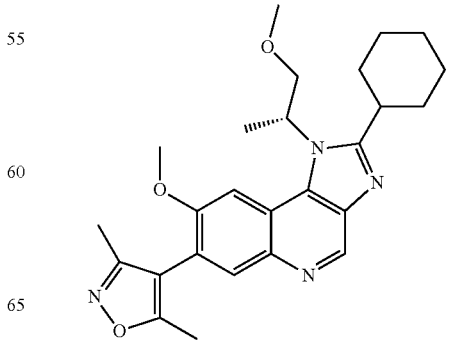

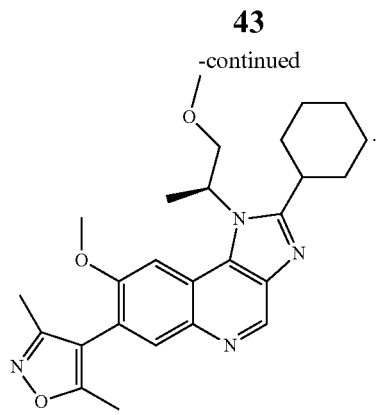

Embodiment XVII

The method of any one of Embodiments I-IX, wherein the compound is:

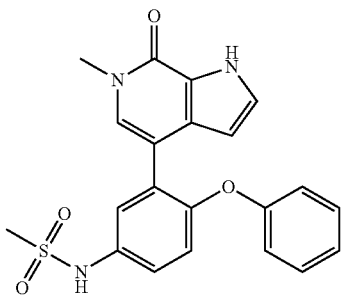

Embodiment XVIII

The method of any one of Embodiments I-IX, wherein the compound is:

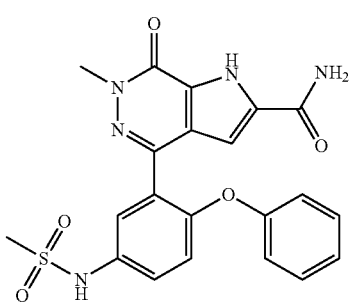

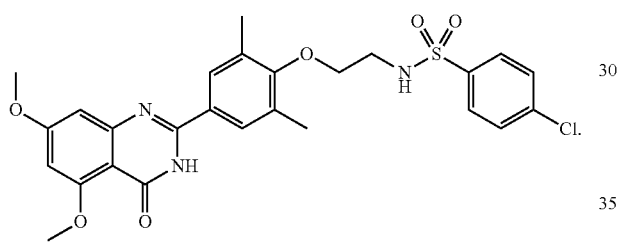

Embodiment XIX

The method of any one of Embodiments I-IX, wherein the compound is:

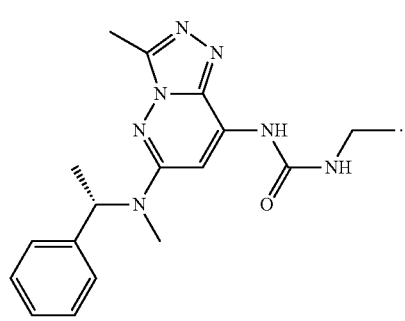 [SMILES: CCNC(=O)Nc1cc(N(C)[C@@H](C)c2ccccc2)nn2c(C)nnc12 ; "."]

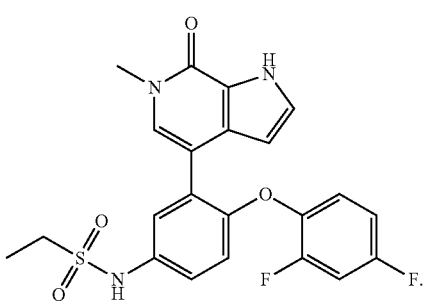

Embodiment XX

The method of any one of Embodiments I-IX, wherein the compound is:

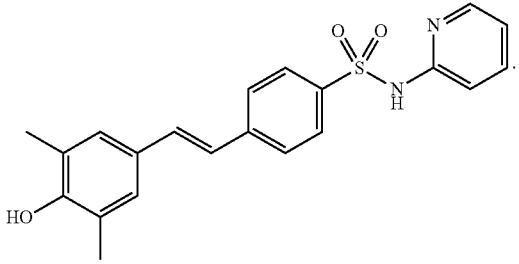 [SMILES: Cc1cc(/C=C/c2ccc(S(=O)(=O)Nc3ccccn3)cc2)cc(C)c1O ; "."]

Embodiment XXI

The method of any one of Embodiments I-IX, wherein the compound is:

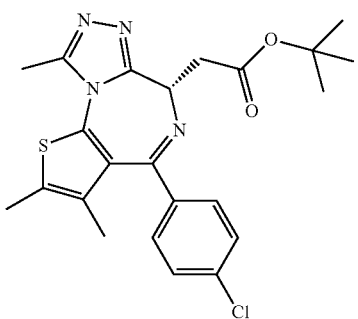

(+)-JQ1

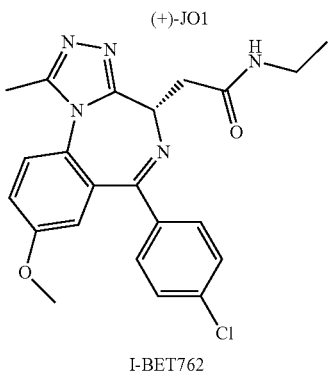

I-BET762

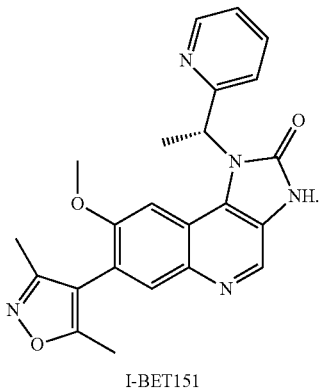

I-BET151

Embodiment XXII

The method of any one of Embodiments I-IV or VII-XXI, wherein the compound is administered as a single agent or in combination with standard therapy for prostate cancer.

Embodiment XXIII

The method of Embodiment XXII, wherein the standard therapy for prostate cancer is an inhibitor of AR signaling selected from the group consisting of biclutamide, abiraterone, and enzalutamide.

Embodiment XXIV

The method of any one of Embodiments I, V, 6VI, or VIII-XXI, wherein the compound is administered as a single agent or in combination with standard therapy for breast cancer.

Embodiment XXV

The method of Embodiment XXIV, wherein the standard therapy for breast cancer is selected from the group consisting of Herceptin, Taxol, Taxotere, Perjeta, Adriamycin, Cytoxan, Paraplatin, and Kadcyla.

Embodiment XXVII

The method of any one of Embodiments I-IX, wherein the compound any one of Formula I-XVII, or a pharmaceutically acceptable salt, hydrate, or solvates thereof.

Embodiment XXVIII

The method of any one of Embodiments I-IX, wherein the compound is any one of Cpd. Nos. 1-81, 83-113, 115-127, 129, 131-163, 166, 169-178, 181-183, 185-188, 190, 192-203, 205-207, 210-243, 247-274, 277-295, 304-331, or 333 of Table 1.

In another embodiment, Compounds of the Disclosure are compounds of Table 1, and the pharmaceutically acceptable salts, hydrates, and solvates thereof.

TABLE 1

| Cpd. No. | Structure | Name |
|---|---|---|
| 1 | 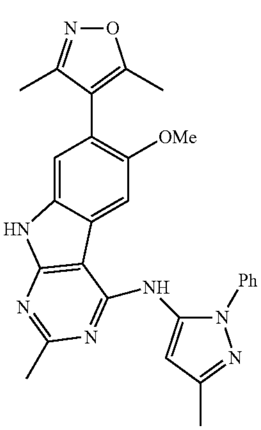 [SMILES: COc1cc2c(cc1-c1c(C)noc1C)[nH]c1nc(C)nc(Nc3cc(C)nn3-c3ccccc3)c12] | 7-(3,5-dimethylisoxazol-4-yl)-6-methoxy-2-methyl-N-(3-methyl-1-phenyl-1H-pyrazol-5-yl)-9H-pyrimido[4,5-b]indol-4-amine |

TABLE 1-continued

| Cpd. No. | Structure | Name |
|---|---|---|
| 2 | 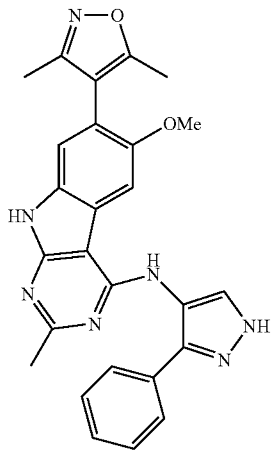 [SMILES: COc1cc2c(cc1-c1c(C)noc1C)[nH]c1nc(C)nc(Nc3c[nH]nc3-c3ccccc3)c12] | 7-(3,5-dimethylisoxazol-4-yl)-6-methoxy-2-methyl-N-(3-phenyl-1H-pyrazol-4-yl)-9H-pyrimido[4,5-b]indol-4-amine |
| 3 | 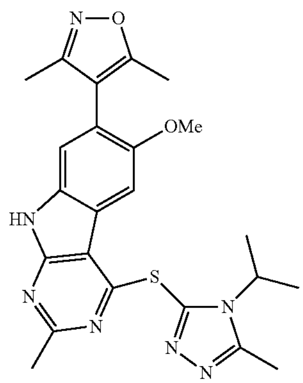 [SMILES: COc1cc2c(cc1-c1c(C)noc1C)[nH]c1nc(C)nc(Sc3nnc(C)n3C(C)C)c12] | 4-(4-((4-Isopropyl-5-methyl-4H-1,2,4-triazol-3-yl)thio)-6-methoxy-2-methyl-9H-pyrimido[4,5-b]indol-7-yl)-3,5-dimethylisoxazole |
| 4 | 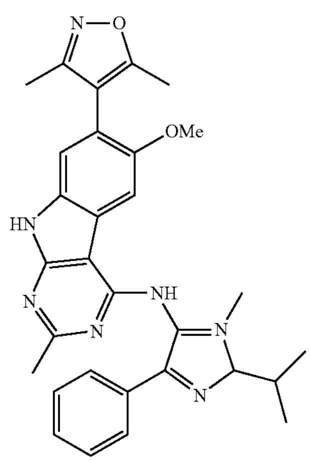 | 7-(3,5-Dimethylisoxazol-4-yl)-N-(1-isopropyl-5-methyl-3-phenyl-1H-pyrazol-4-yl)-6-methoxy-2-methyl-9H-pyrimido[4,5-b]indol-4-amine |

TABLE 1-continued

| Cpd. No. | Structure | Name |
|---|---|---|
| 5 | 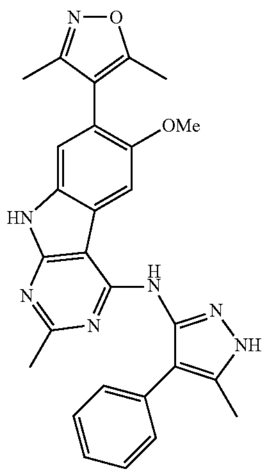 [SMILES: COc1cc2c(cc1-c1c(C)noc1C)[nH]c1nc(C)nc(Nc3n[nH]c(C)c3-c3ccccc3)c12] | 7-(3,5-Dimethylisoxazol-4-yl)-6-methoxy-2-methyl-N-(5-methyl-4-phenyl-1H-pyrazol-3-yl)-9H-pyrimido[4,5-b]indol-4-amine |
| 6 | 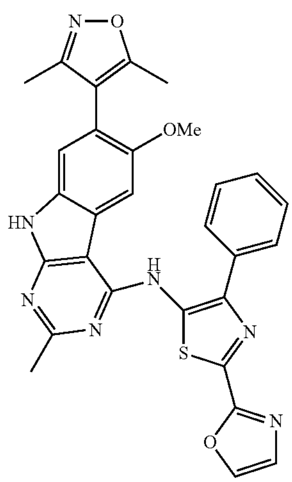 [SMILES: COc1cc2c(cc1-c1c(C)noc1C)[nH]c1nc(C)nc(Nc3sc(-c4ncco4)nc3-c3ccccc3)c12] | N-(7-(3,5-dimethylisoxazol-4-yl)-6-methoxy-2-methyl-9H-pyrimido[4,5-b]indol-4-yl)-2-(oxazol-2-yl)-4-phenylthiazol-5-amine |
| 7 | 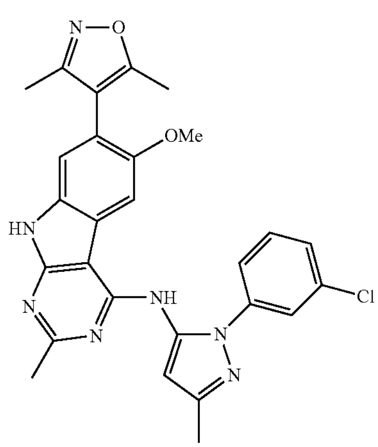 [SMILES: COc1cc2c(cc1-c1c(C)noc1C)[nH]c1nc(C)nc(Nc3cc(C)nn3-c3cccc(Cl)c3)c12] | N-(1-(3-Chlorophenyl)-3-methyl-1H-pyrazol-5-yl)-7-(3,5-dimethylisoxazol-4-yl)-6-methoxy-2-methyl-9H-pyrimido[4,5-b]indol-4-amine |

TABLE 1-continued

| Cpd. No. | Structure | Name |
| --- | --- | --- |
| 8 | 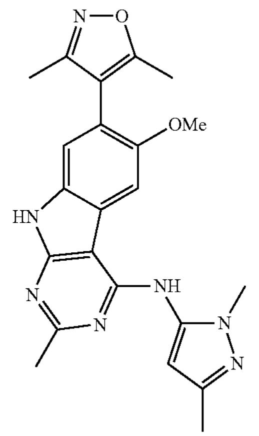 | N-(1,3-Dimethyl-1H-pyrazol-5-yl)-7-(3,5-dimethylisoxazol-4-yl)-6-methoxy-2-methyl-9H-pyrimido[4,5-b]indol-4-amine |
| 9 | 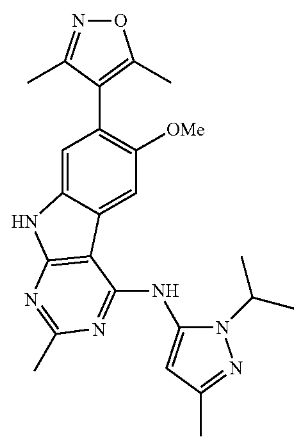 [SMILES: COc1cc2c(cc1-c1c(C)noc1C)[nH]c1nc(C)nc(Nc3cc(C)nn3C(C)C)c12] | 7-(3,5-Dimethylisoxazol-4-yl)-N-(1-isopropyl-3-methyl-1H-pyrazol-5-yl)-6-methoxy-2-methyl-9H-pyrimido[4,5-b]indol-4-amine |
| 10 | 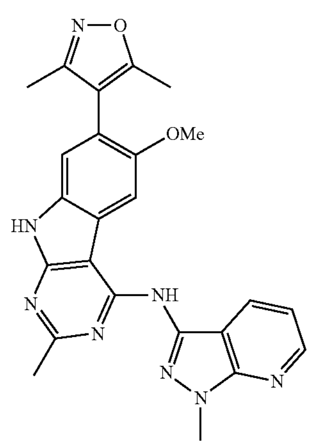 [SMILES: COc1cc2c(cc1-c1c(C)noc1C)[nH]c1nc(C)nc(Nc3nn(C)c4ncccc34)c12] | 7-(3,5-Dimethylisoxazol-4-yl)-6-methoxy-2-methyl-N-(1-methyl-1H-pyrazolo[3,4-b]pyridin-3-yl)-9H-pyrimido[4,5-b]indol-4-amine |

TABLE 1-continued

| Cpd. No. | Structure | Name |
| --- | --- | --- |
| 11 | 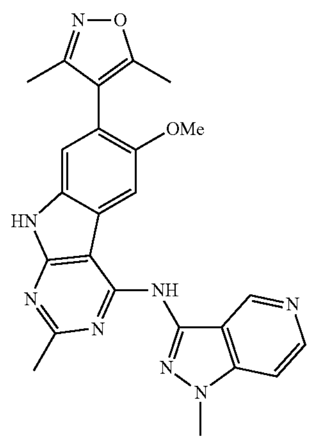 [SMILES: COc1cc2c(cc1-c1c(C)noc1C)[nH]c1nc(C)nc(Nc3nn(C)c4ccncc34)c12] | 7-(3,5-dimethylisoxazol-4-yl)-6-methoxy-2-methyl-N-(1-methyl-1H-pyrazolo[4,3-c]pyridin-3-yl)-9H-pyrimido[4,5-b]indol-4-amine |
| 12 | 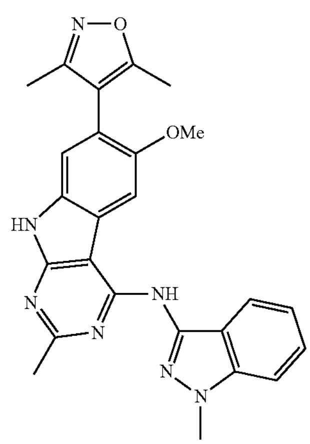 [SMILES: COc1cc2c(cc1-c1c(C)noc1C)[nH]c1nc(C)nc(Nc3nn(C)c4ccccc34)c12] | 7-(3,5-Dimethylisoxazol-4-yl)-6-methoxy-2-methyl-N-(1-methyl-1H-indazol-3-yl)-9H-pyrimido[4,5-b]indol-4-amine |
| 13 | 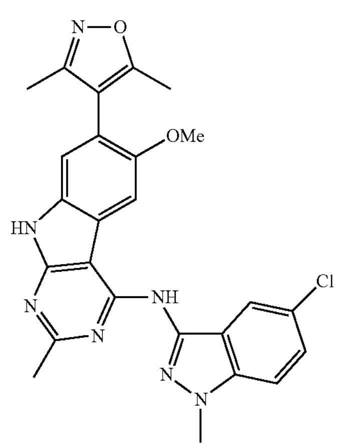 [SMILES: COc1cc2c(cc1-c1c(C)noc1C)[nH]c1nc(C)nc(Nc3nn(C)c4ccc(Cl)cc34)c12] | N-(5-Chloro-1-methyl-1H-indazol-3-yl)-7-(3,5-dimethylisoxazol-4-yl)-6-methoxy-2-methyl-9H-pyrimido[4,5-b]indol-4-amine |

TABLE 1-continued

| Cpd. No. | Structure | Name |
| --- | --- | --- |
| 14 | 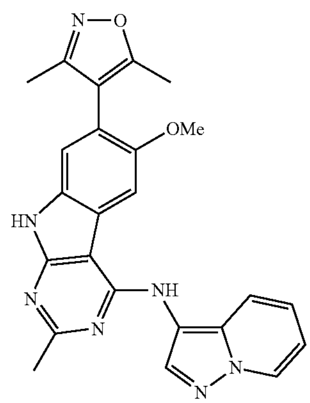 | 7-(3,5-Dimethylisoxazol-4-yl)-6-methoxy-2-methyl-N-(pyrazolo[1,5-a]pyridin-3-yl)-9H-pyrimido[4,5-b]indol-4-amine |
| 15 | 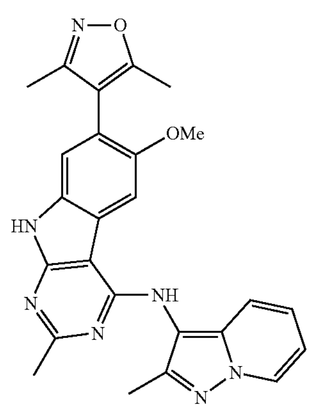 [SMILES: COc1cc2c(cc1-c1c(C)noc1C)[nH]c1nc(C)nc(Nc3c(C)nn4ccccc34)c12] | 7-(3,5-Dimethylisoxazol-4-yl)-6-methoxy-2-methyl-N-(2-methylpyrazolo[1,5-a]pyridin-3-yl)-9H-pyrimido[4,5-b]indol-4-amine |
| 16 | 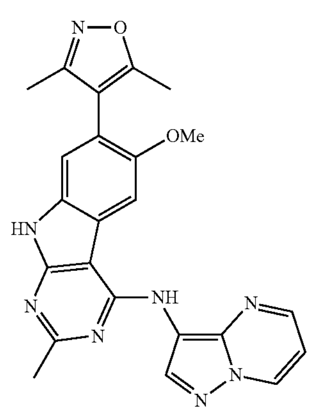 [SMILES: COc1cc2c(cc1-c1c(C)noc1C)[nH]c1nc(C)nc(Nc3cnn4cccnc34)c12] | 7-(3,5-Dimethylisoxazol-4-yl)-6-methoxy-2-methyl-N-(pyrazolo[1,5-a]pyrimidin-3-yl)-9H-pyrimido[4,5-b]indol-4-amine |

TABLE 1-continued

| Cpd. No. | Structure | Name |
| --- | --- | --- |
| 17 | 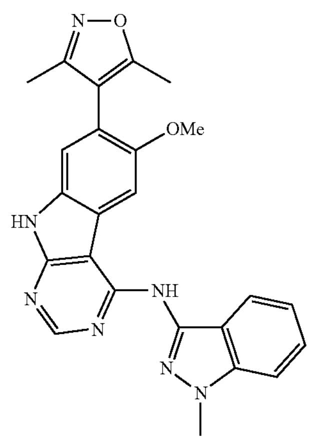 [SMILES: COc1cc2c(cc1-c1c(C)noc1C)[nH]c1ncnc(Nc3nn(C)c4ccccc34)c12] | 7-(3,5-Dimethylisoxazol-4-yl)-6-methoxy-N-(1-methyl-1H-indazol-3-yl)-9H-pyrimido[4,5-b]indol-4-amine |
| 18 | 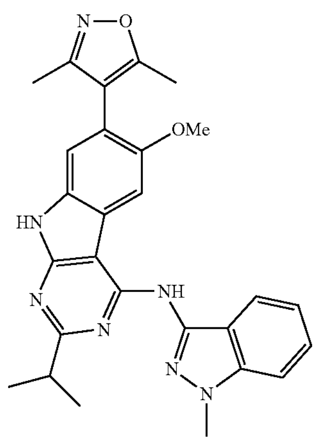 [SMILES: COc1cc2c(cc1-c1c(C)noc1C)[nH]c1nc(C(C)C)nc(Nc3nn(C)c4ccccc34)c12] | 7-(3,5-Dimethylisoxazol-4-yl)-2-isopropyl-6-methoxy-N-(1-methyl-1H-indazol-3-yl)-9H-pyrimido[4,5-b]indol-4-amine |
| 19 | 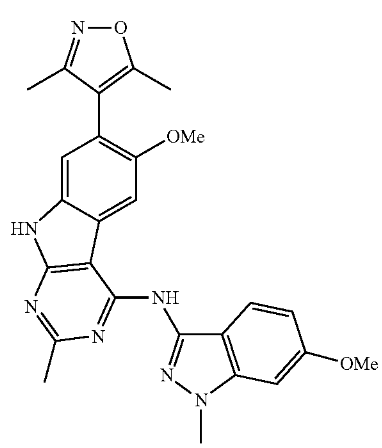 [SMILES: COc1ccc2c(Nc3nc(C)nc4[nH]c5cc(-c6c(C)noc6C)c(OC)cc5c34)nn(C)c2c1] | 7-(3,5-Dimethylisoxazol-4-yl)-6-methoxy-N-(6-methoxy-1-methyl-1H-indazol-3-yl)-2-methyl-9H-pyrimido[4,5-b]indol-4-amine |

TABLE 1-continued

| Cpd. No. | Structure | Name |
|---|---|---|
| 20 | 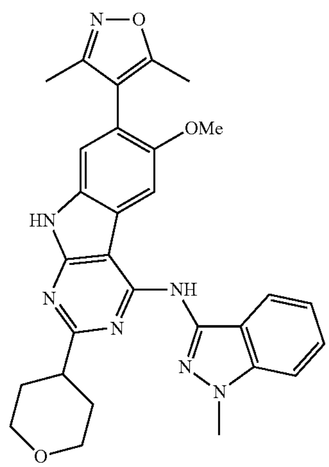 [SMILES: COc1cc2c(cc1-c1c(C)noc1C)[nH]c1nc(C3CCOCC3)nc(Nc3nn(C)c4ccccc34)c12] | 7-(3,5-Dimethylisoxazol-4-yl)-6-methoxy-N-(1-methyl-1H-indazol-3-yl)-2-(tetrahydro-2H-pyran-4-yl)-9H-pyrimido[4,5-b]indol-4-amine |
| 21 | 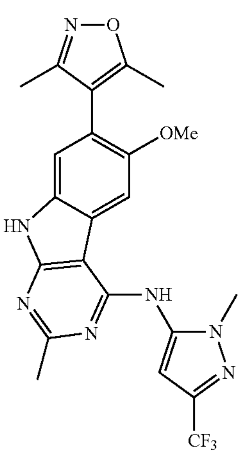 | 7-(3,5-Dimethylisoxazol-4-yl)-6-methoxy-2-methyl-N-(1-methyl-3-(trifluoromethyl)-1H-pyrazol-5-yl)-9H-pyrimido[4,5-b]indol-4-amine |
| 22 | 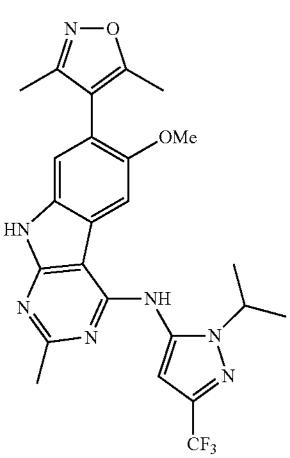 [SMILES: COc1cc2c(cc1-c1c(C)noc1C)[nH]c1nc(C)nc(Nc3cc(C(F)(F)F)nn3C(C)C)c12] | 7-(3,5-Dimethylisoxazol-4-yl)-N-(1-isopropyl-3-(trifluoromethyl)-1H-pyrazol-5-yl)-6-methoxy-2-methyl-9H-pyrimido[4,5-b]indol-4-amine |

TABLE 1-continued

| Cpd. No. | Structure | Name |
|---|---|---|
| 23 | 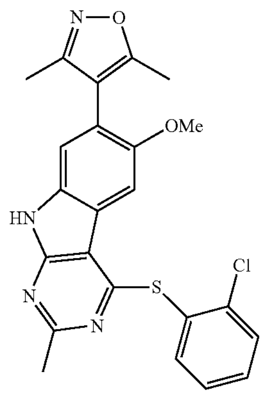 [SMILES: COc1cc2c(cc1-c1c(C)noc1C)[nH]c1nc(C)nc(Sc3ccccc3Cl)c12] | 4-(4-((2-chlorophenyl)thio)-6-methoxy-2-methyl-9H-pyrimido[4,5-b]indol-7-yl)-3,5-dimethylisoxazole |
| 24 | 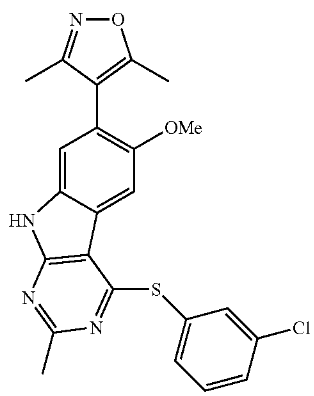 [SMILES: COc1cc2c(cc1-c1c(C)noc1C)[nH]c1nc(C)nc(Sc3cccc(Cl)c3)c12] | 4-(4-((3-chlorophenyl)thio)-6-methoxy-2-methyl-9H-pyrimido[4,5-b]indol-7-yl)-3,5-dimethylisoxazole |
| 25 | 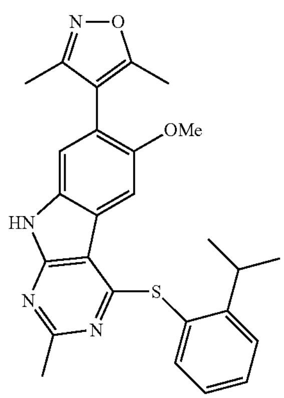 [SMILES: COc1cc2c(cc1-c1c(C)noc1C)[nH]c1nc(C)nc(Sc3ccccc3C(C)C)c12] | 4-(4-((2-isopropylphenyl)thio)-6-methoxy-2-methyl-9H-pyrimido[4,5-b]indol-7-yl)-3,5-dimethylisoxazole |
| 26 | 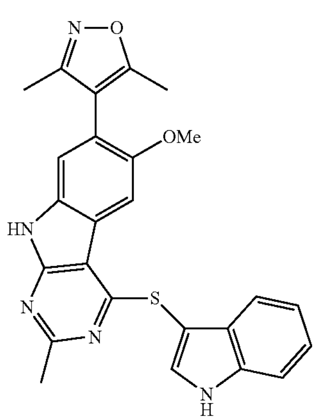 [SMILES: COc1cc2c(cc1-c1c(C)noc1C)[nH]c1nc(C)nc(Sc3c[nH]c4ccccc34)c12] | 4-(4-((1H-indol-3-yl)thio)-6-methoxy-2-methyl-9H-pyrimido[4,5-b]indol-7-yl)-3,5-dimethylisoxazole |

TABLE 1-continued

| Cpd. No. | Structure | Name |
|---|---|---|
| 27 | 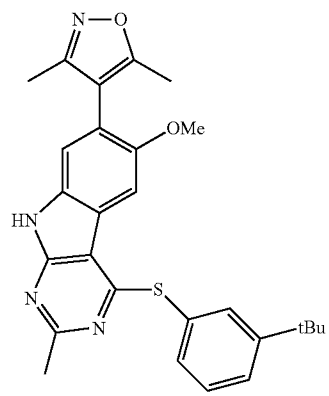 [SMILES: COc1cc2c(cc1-c1c(C)noc1C)[nH]c1nc(C)nc(Sc3cccc(C(C)(C)C)c3)c12] | 4-(4-((3-(tert-butyl)phenyl)thio)-6-methoxy-2-methyl-9H-pyrimido[4,5-b]indol-7-yl)-3,5-dimethylisoxazole |
| 28 | 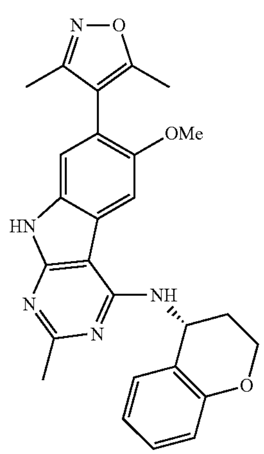 [SMILES: COc1cc2c(cc1-c1c(C)noc1C)[nH]c1nc(C)nc(N[C@@H]3CCOc4ccccc43)c12] | (R)-N-(chroman-4-yl)-7-(3,5-dimethylisoxazol-4-yl)-6-methoxy-2-methyl-9H-pyrimido[4,5-b]indol-4-amine |
| 29 | 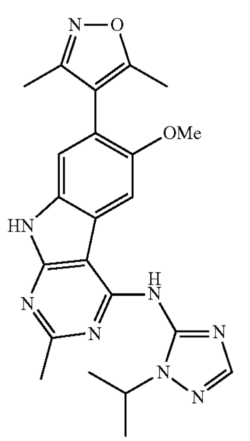 [SMILES: COc1cc2c(cc1-c1c(C)noc1C)[nH]c1nc(C)nc(Nc3ncnn3C(C)C)c12] | 7-(3,5-dimethylisoxazol-4-yl)-N-(1-isopropyl-1H-1,2,4-triazol-5-yl)-6-methoxy-2-methyl-9H-pyrimido[4,5-b]indol-4-amine |

TABLE 1-continued

| Cpd. No. | Structure | Name |
| --- | --- | --- |
| 30 | 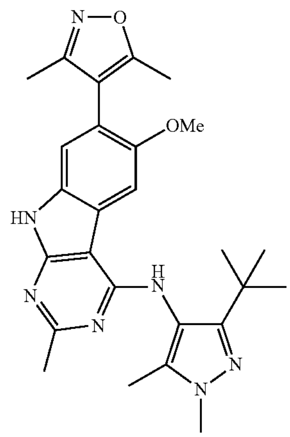 [SMILES: COc1cc2c(cc1-c1c(C)noc1C)[nH]c1nc(C)nc(Nc3c(C(C)(C)C)nn(C)c3C)c12] | N-(3-(tert-butyl)-1,5-dimethyl-1H-pyrazol-4-yl)-7-(3,5-dimethylisoxazol-4-yl)-6-methoxy-2-methyl-9H-pyrimido[4,5-b]indol-4-amine |
| 31 | 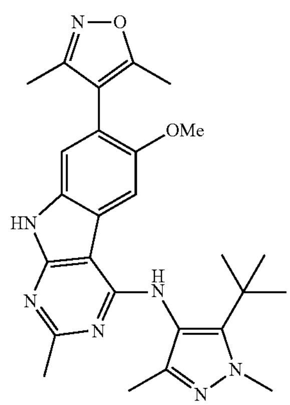 [SMILES: COc1cc2c(cc1-c1c(C)noc1C)[nH]c1nc(C)nc(Nc3c(C)nn(C)c3C(C)(C)C)c12] | N-(5-(tert-butyl)-1,3-dimethyl-1H-pyrazol-4-yl)-7-(3,5-dimethylisoxazol-4-yl)-6-methoxy-2-methyl-9H-pyrimido[4,5-b]indol-4-amine |
| 32 | 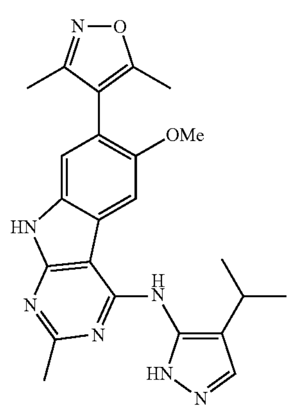 [SMILES: COc1cc2c(cc1-c1c(C)noc1C)[nH]c1nc(C)nc(Nc3[nH]ncc3C(C)C)c12] | 7-(3,5-dimethylisoxazol-4-yl)-N-(4-isopropyl-1H-pyrazol-5-yl)-6-methoxy-2-methyl-9H-pyrimido[4,5-b]indol-4-amine |

TABLE 1-continued

| Cpd. No. | Structure | Name |
|---|---|---|
| 33 | 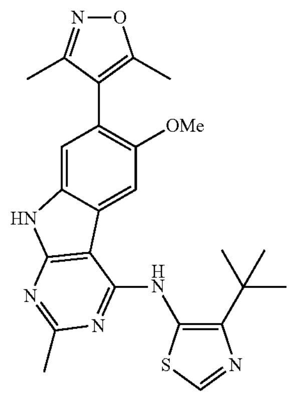 [SMILES: COc1cc2c(cc1-c1c(C)noc1C)[nH]c1nc(C)nc(Nc3scnc3C(C)(C)C)c12] | 4-(tert-butyl)-N-(7-(3,5-dimethylisoxazol-4-yl)-6-methoxy-2-methyl-9H-pyrimido[4,5-b]indol-4-yl)thiazol-5-amine |
| 34 | 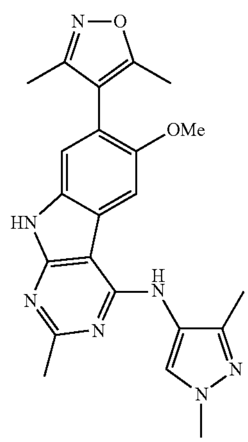 | N-(1,3-dimethyl-1H-pyrazol-4-yl)-7-(3,5-dimethylisoxazol-4-yl)-6-methoxy-2-methyl-9H-pyrimido[4,5-b]indol-4-amine |
| 35 | 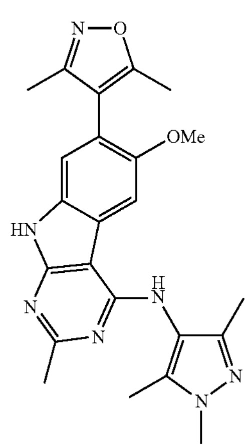 | 7-(3,5-dimethylisoxazol-4-yl)-6-methoxy-2-methyl-N-(1,3,5-trimethyl-1H-pyrazol-4-yl)-9H-pyrimido[4,5-b]indol-4-amine |

TABLE 1-continued

| Cpd. No. | Structure | Name |
| --- | --- | --- |
| 36 | 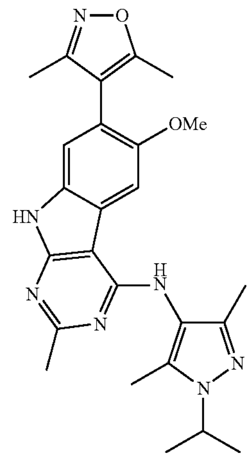 | 7-(3,5-dimethylisoxazol-4-yl)-N-(1-isopropyl-3,5-dimethyl-1H-pyrazol-4-yl)-6-methoxy-2-methyl-9H-pyrimido[4,5-b]indol-4-amine |
| 37 | 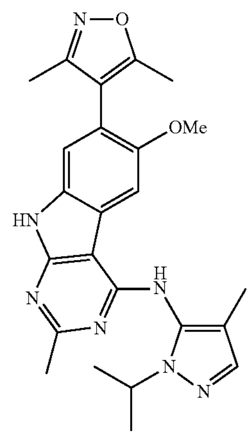 | 7-(3,5-dimethylisoxazol-4-yl)-N-(1-isopropyl-4-methyl-1H-pyrazol-5-yl)-6-methoxy-2-methyl-9H-pyrimido[4,5-b]indol-4-amine |
| 38 | 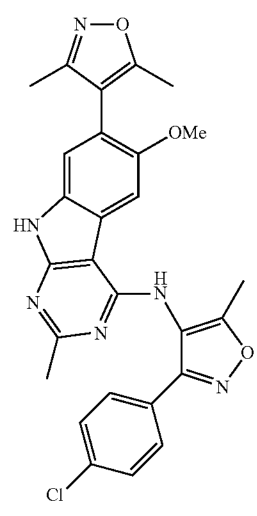 [SMILES: COc1cc2c(cc1-c1c(C)noc1C)[nH]c1nc(C)nc(Nc3c(-c4ccc(Cl)cc4)noc3C)c12] | 3-(4-chlorophenyl)-N-(7-(3,5-dimethylisoxazol-4-yl)-6-methoxy-2-methyl-9H-pyrimido[4,5-b]indol-4-yl)-5-methylisoxazol-4-amine |

TABLE 1-continued

| Cpd. No. | Structure | Name |
|---|---|---|
| 39 | 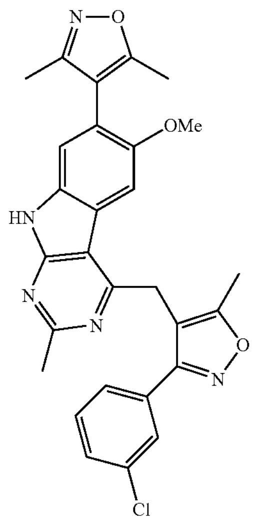 [SMILES: COc1cc2c(cc1-c1c(C)noc1C)[nH]c1nc(C)nc(Cc3c(-c4cccc(Cl)c4)noc3C)c12] | 3-(3-chlorophenyl)-N-(7-(3,5-dimethylisoxazol-4-yl)-6-methoxy-2-methyl-9H-pyrimido[4,5-b]indol-4-yl)-5-methylisoxazol-4-amine |
| 40 | 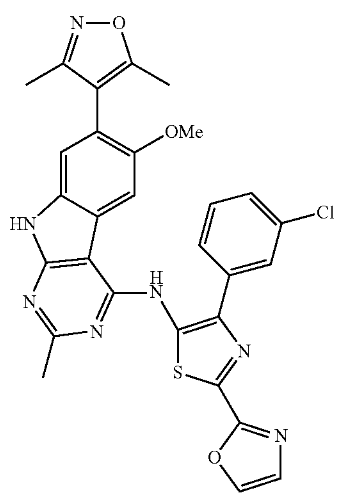 [SMILES: COc1cc2c(cc1-c1c(C)noc1C)[nH]c1nc(C)nc(Nc3sc(-c4ncco4)nc3-c3cccc(Cl)c3)c12] | 4-(3-chlorophenyl)-N-(7-(3,5-dimethylisoxazol-4-yl)-6-methoxy-2-methyl-9H-pyrimido[4,5-b]indol-4-yl)-2-(oxazol-2-yl)thiazol-5-amine |
| 41 | 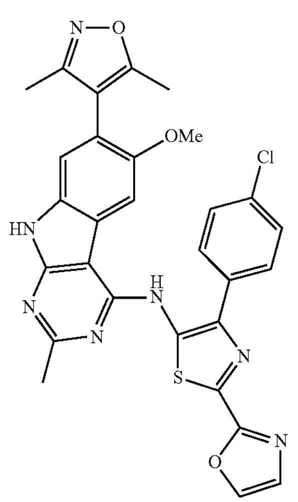 [SMILES: COc1cc2c(cc1-c1c(C)noc1C)[nH]c1nc(C)nc(Nc3sc(-c4ncco4)nc3-c3ccc(Cl)cc3)c12] | 4-(4-chlorophenyl)-N-(7-(3,5-dimethylisoxazol-4-yl)-6-methoxy-2-methyl-9H-pyrimido[4,5-b]indol-4-yl)-2-(oxazol-2-yl)thiazol-5-amine |

TABLE 1-continued

| Cpd. No. | Structure | Name |
| --- | --- | --- |
| 42 | 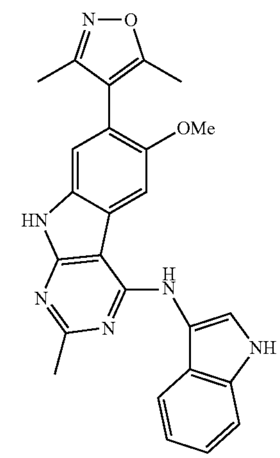 [SMILES: COc1cc2c(cc1-c1c(C)noc1C)[nH]c1nc(C)nc(Nc3c[nH]c4ccccc34)c12] | 7-(3,5-dimethylisoxazol-4-yl)-N-(1H-indol-3-yl)-6-methoxy-2-methyl-9H-pyrimido[4,5-b]indol-4-amine |
| 43 | 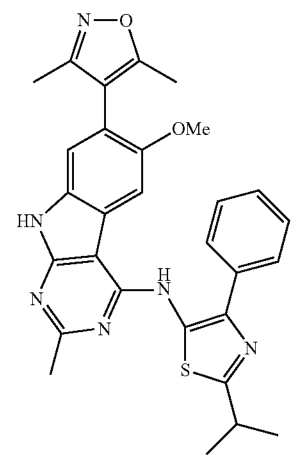 [SMILES: COc1cc2c(cc1-c1c(C)noc1C)[nH]c1nc(C)nc(Nc3sc(C(C)C)nc3-c3ccccc3)c12] | N-(7-(3,5-dimethylisoxazol-4-yl)-6-methoxy-2-methyl-9H-pyrimido[4,5-b]indol-4-yl)-2-isopropyl-4-phenylthiazol-5-amine |
| 44 | 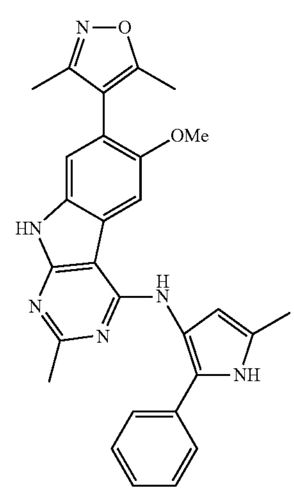 | 7-(3,5-dimethylisoxazol-4-yl)-6-methoxy-2-methyl-N-(5-methyl-2-phenyl-1H-pyrrol-3-yl)-9H-pyrimido[4,5-b]indol-4-amine |

TABLE 1-continued

| Cpd. No. | Structure | Name |
|---|---|---|
| 45 | 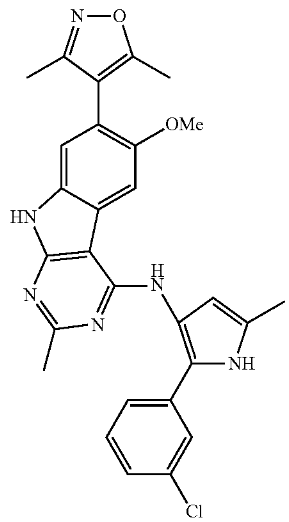 | N-(2-(3-chlorophenyl)-5-methyl-1H-pyrrol-3-yl)-7-(3,5-dimethylisoxazol-4-yl)-6-methoxy-2-methyl-9H-pyrimido[4,5-b]indol-4-amine |
| 46 | 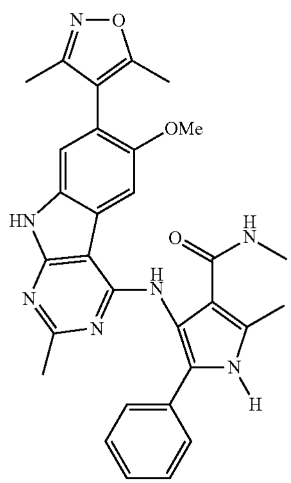 | 4-((7-(3,5-dimethylisoxazol-4-yl)-6-methoxy-2-methyl-9H-pyrimido[4,5-b]indol-4-yl)amino)-N,2-dimethyl-5-phenyl-1H-pyrrole-3-carboxamide |
| 47 | 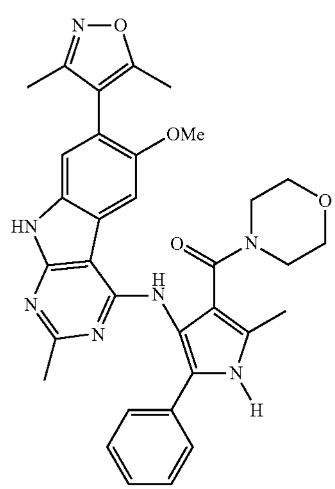 [SMILES: COc1cc2c(cc1-c1c(C)noc1C)[nH]c1nc(C)nc(Nc3c(-c4ccccc4)[nH]c(C)c3C(=O)N3CCOCC3)c12] | (4-((7-(3,5-dimethylisoxazol-4-yl)-6-methoxy-2-methyl-9H-pyrimido[4,5-b]indol-4-yl)amino)-2-methyl-5-phenyl-1H-pyrrol-3-yl)(morpholino)methanone |

TABLE 1-continued

| Cpd. No. | Structure | Name |
|---|---|---|
| 48 | 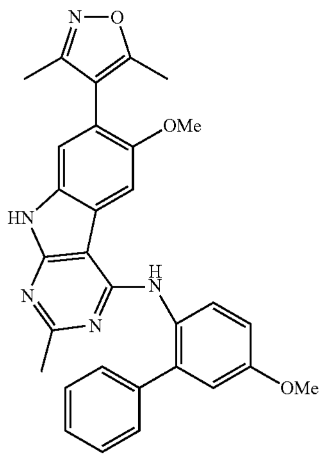 [SMILES: COc1ccc(Nc2nc(C)nc3[nH]c4cc(-c5c(C)noc5C)c(OC)cc4c23)c(-c2ccccc2)c1] | 7-(3,5-dimethylisoxazol-4-yl)-6-methoxy-N-(5-methoxy-[1,1'-biphenyl]-2-yl)-2-methyl-9H-pyrimido[4,5-b]indol-4-amine |
| 49 | 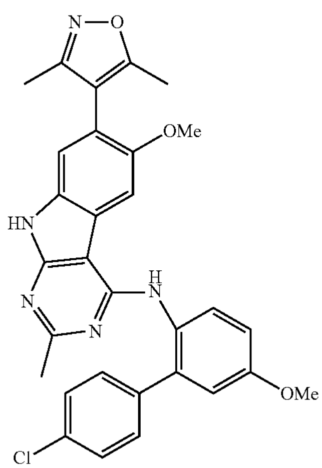 [SMILES: COc1ccc(Nc2nc(C)nc3[nH]c4cc(-c5c(C)noc5C)c(OC)cc4c23)c(-c2ccc(Cl)cc2)c1] | N-(4'-chloro-5-methoxy-[1,1'-biphenyl]-2-yl)-7-(3,5-dimethylisoxazol-4-yl)-6-methoxy-2-methyl-9H-pyrimido[4,5-b]indol-4-amine |
| 50 | 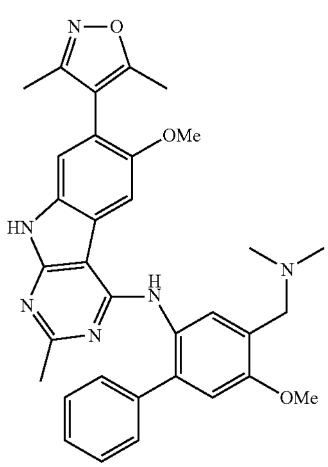 | N-(4-((dimethylamino)methyl)-5-methoxy-[1,1'-biphenyl]-2-yl)-7-(3,5-dimethylisoxazol-4-yl)-6-methoxy-2-methyl-9H-pyrimido[4,5-b]indol-4-amine |

TABLE 1-continued

| Cpd. No. | Structure | Name |
|---|---|---|
| 51 | 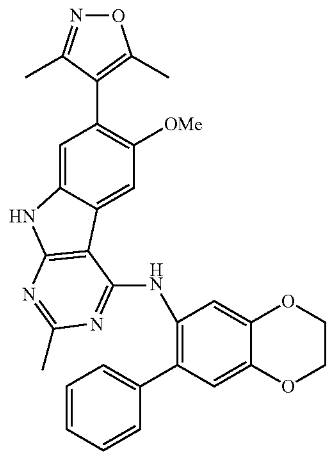 [SMILES: COc1cc2c(cc1-c1c(C)noc1C)[nH]c1nc(C)nc(Nc3cc4c(cc3-c3ccccc3)OCCO4)c12] | 7-(3,5-dimethylisoxazol-4-yl)-6-methoxy-2-methyl-N-(7-phenyl-2,3-dihydrobenzo[b][1,4]dioxin-6-yl)-9H-pyrimido[4,5-b]indol-4-amine |
| 52 | 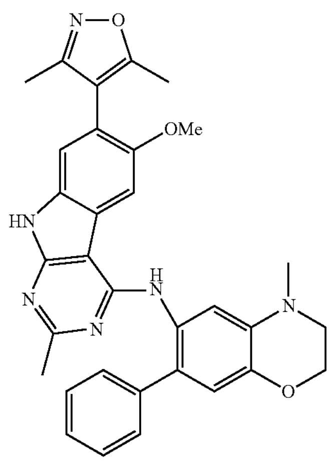 [SMILES: COc1cc2c(cc1-c1c(C)noc1C)[nH]c1nc(C)nc(Nc3cc4c(cc3-c3ccccc3)OCCN4C)c12] | N-(7-(3,5-dimethylisoxazol-4-yl)-6-methoxy-2-methyl-9H-pyrimido[4,5-b]indol-4-yl)-4-methyl-7-phenyl-3,4-dihydro-2H-benzo[b][1,4]oxazin-6-amine |
| 53 | 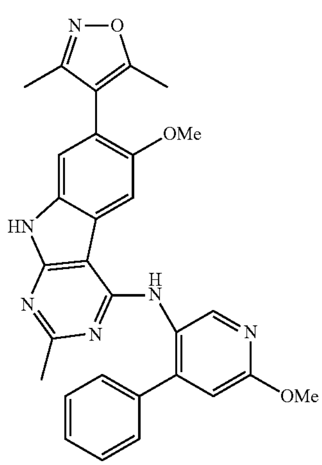 [SMILES: COc1cc(-c2ccccc2)c(Nc2nc(C)nc3[nH]c4cc(-c5c(C)noc5C)c(OC)cc4c23)cn1] | 7-(3,5-dimethylisoxazol-4-yl)-6-methoxy-N-(6-methoxy-4-phenylpyridin-3-yl)-2-methyl-9H-pyrimido[4,5-b]indol-4-amine |

TABLE 1-continued

| Cpd. No. | Structure | Name |
| --- | --- | --- |
| 54 | 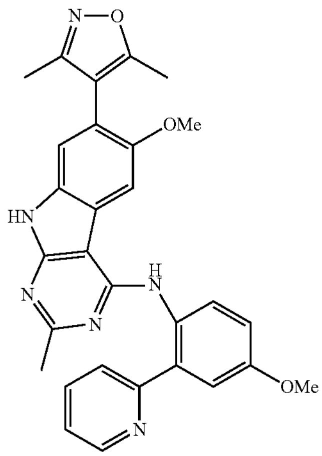 [SMILES: COc1ccc(Nc2nc(C)nc3[nH]c4cc(-c5c(C)noc5C)c(OC)cc4c23)c(-c2ccccn2)c1] | 7-(3,5-dimethylisoxazol-4-yl)-6-methoxy-N-(4-methoxy-2-(pyridin-2-yl)phenyl)-2-methyl-9H-pyrimido[4,5-b]indol-4-amine |
| 55 | 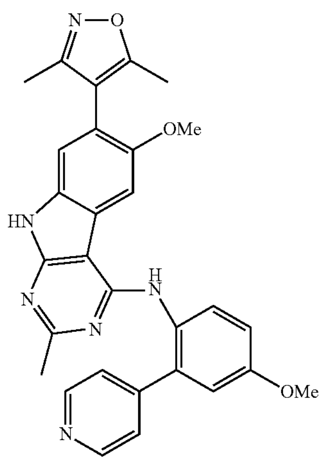 [SMILES: COc1ccc(Nc2nc(C)nc3[nH]c4cc(-c5c(C)noc5C)c(OC)cc4c23)c(-c2ccncc2)c1] | 7-(3,5-dimethylisoxazol-4-yl)-6-methoxy-N-(4-methoxy-2-(pyridin-4-yl)phenyl)-2-methyl-9H-pyrimido[4,5-b]indol-4-amine |
| 56 | 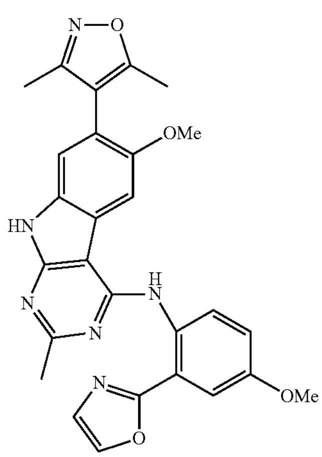 [SMILES: COc1ccc(Nc2nc(C)nc3[nH]c4cc(-c5c(C)noc5C)c(OC)cc4c23)c(-c2ncco2)c1] | 7-(3,5-dimethylisoxazol-4-yl)-6-methoxy-N-(4-methoxy-2-(oxazol-2-yl)phenyl)-2-methyl-9H-pyrimido[4,5-b]indol-4-amine |

TABLE 1-continued

| Cpd. No. | Structure | Name |
|---|---|---|
| 57 | 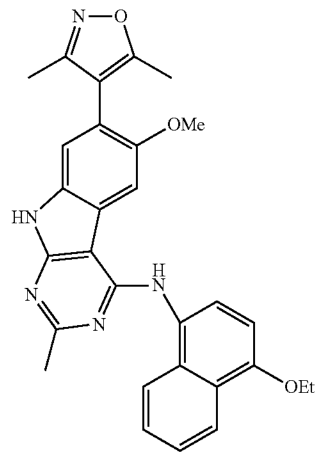 [SMILES: CCOc1ccc(Nc2nc(C)nc3[nH]c4cc(-c5c(C)noc5C)c(OC)cc4c23)c2ccccc12] | 7-(3,5-dimethylisoxazol-4-yl)-N-(4-ethoxynaphthalen-1-yl)-6-methoxy-2-methyl-9H-pyrimido[4,5-b]indol-4-amine |
| 58 | 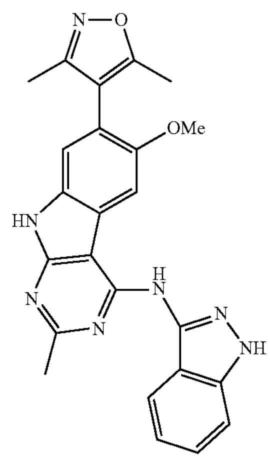 [SMILES: COc1cc2c(cc1-c1c(C)noc1C)[nH]c1nc(C)nc(Nc3n[nH]c4ccccc34)c12] | 7-(3,5-dimethylisoxazol-4-yl)-N-(1H-indazol-3-yl)-6-methoxy-2-methyl-9H-pyrimido[4,5-b]indol-4-amine |
| 59 | 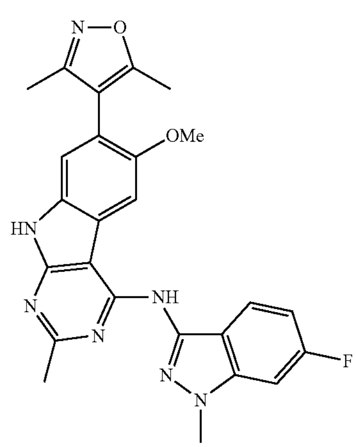 [SMILES: COc1cc2c(cc1-c1c(C)noc1C)[nH]c1nc(C)nc(Nc3nn(C)c4cc(F)ccc34)c12] | 7-(3,5-dimethylisoxazol-4-yl)-N-(6-fluoro-1-methyl-1H-indazol-3-yl)-6-methoxy-2-methyl-9H-pyrimido[4,5-b]indol-4-amine |

TABLE 1-continued
| Cpd. No. | Structure | Name |
|---|---|---|
| 60 | 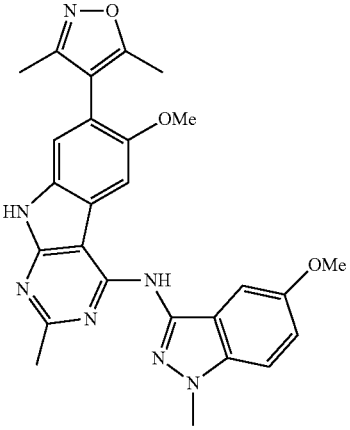 [SMILES: COc1ccc2c(c1)c(Nc1nc(C)nc3[nH]c4cc(-c5c(C)noc5C)c(OC)cc4c13)nn2C] | 7-(3,5-dimethylisoxazol-4-yl)-6-methoxy-N-(5-methoxy-1-methyl-1H-indazol-3-yl)-2-methyl-9H-pyrimido[4,5-b]indol-4-amine |
| 61 | 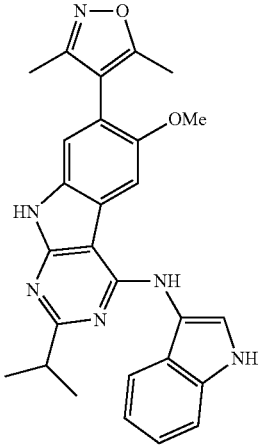 [SMILES: COc1cc2c(cc1-c1c(C)noc1C)[nH]c1nc(C(C)C)nc(Nc3c[nH]c4ccccc34)c12] | 7-(3,5-dimethylisoxazol-4-yl)-N-(1H-indol-3-yl)-2-isopropyl-6-methoxy-9H-pyrimido[4,5-b]indol-4-amine |
| 62 | 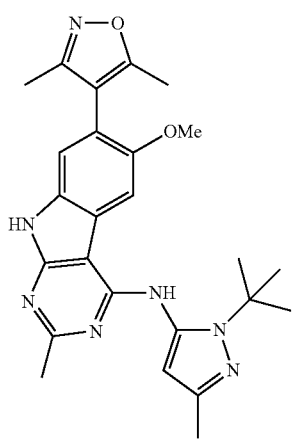 | N-(1-(tert-butyl)-3-methyl-1H-pyrazol-5-yl)-7-(3,5-dimethylisoxazol-4-yl)-6-methoxy-2-methyl-9H-pyrimido[4,5-b]indol-4-amine |

TABLE 1-continued
| Cpd. No. | Structure | Name |
|---|---|---|
| 64 | 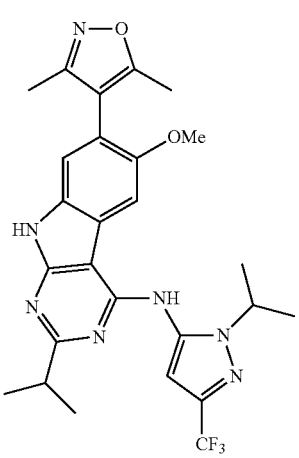 [SMILES: COc1cc2c(cc1-c1c(C)noc1C)[nH]c1nc(C(C)C)nc(Nc3cc(C(F)(F)F)nn3C(C)C)c12] | 7-(3,5-dimethylisoxazol-4-yl)-2-isopropyl-N-(1-isopropyl-3-(trifluoromethyl)-1H-pyrazol-5-yl)-6-methoxy-9H-pyrimido[4,5-b]indol-4-amine |
| 65 | 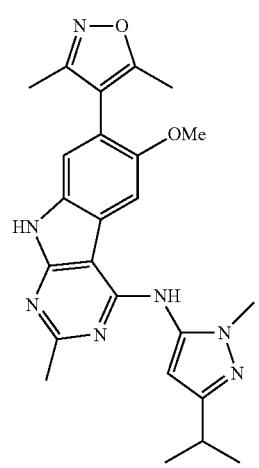 | 7-(3,5-dimethylisoxazol-4-yl)-N-(3-isopropyl-1-methyl-1H-pyrazol-5-yl)-6-methoxy-2-methyl-9H-pyrimido[4,5-b]indol-4-amine |
| 66 | 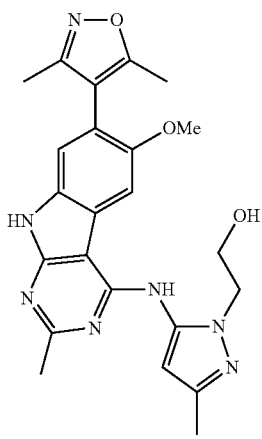 [SMILES: COc1cc2c(cc1-c1c(C)noc1C)[nH]c1nc(C)nc(Nc3cc(C)nn3CCO)c12] | 2-(5-((7-(3,5-dimethylisoxazol-4-yl)-6-methoxy-2-methyl-9H-pyrimido[4,5-b]indol-4-yl)amino)-3-methyl-1H-pyrazol-1-yl)ethan-1-ol |

TABLE 1-continued

| Cpd. No. | Structure | Name |
|---|---|---|
| 67 | 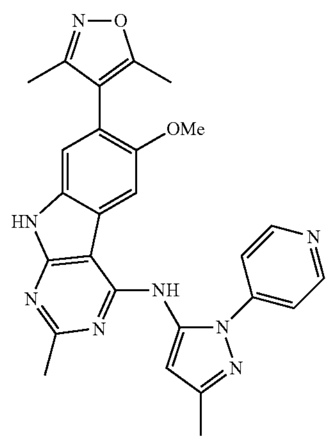 [SMILES: COc1cc2c(cc1-c1c(C)noc1C)[nH]c1nc(C)nc(Nc3cc(C)nn3-c3ccncc3)c12] | 7-(3,5-dimethylisoxazol-4-yl)-6-methoxy-2-methyl-N-(3-methyl-1-(pyridin-4-yl)-1H-pyrazol-5-yl)-9H-pyrimido[4,5-b]indol-4-amine |
| 68 | 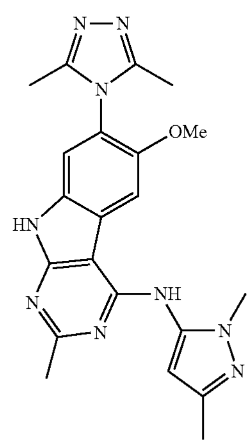 | N-(1,3-dimethyl-1H-pyrazol-5-yl)-7-(3,5-dimethyl-4H-1,2,4-triazol-4-yl)-6-methoxy-2-methyl-9H-pyrimido[4,5-b]indol-4-amine |
| 69 | 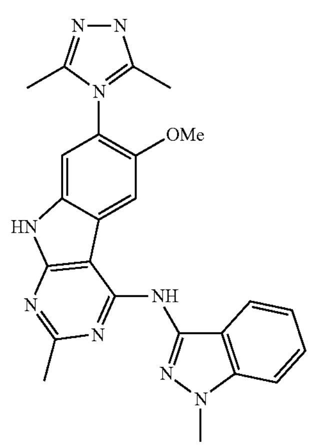 | 7-(3,5-dimethyl-4H-1,2,4-triazol-4-yl)-6-methoxy-2-methyl-N-(1-methyl-1H-indazol-3-yl)-9H-pyrimido[4,5-b]indol-4-amine |

TABLE 1-continued

| Cpd. No. | Structure | Name |
|---|---|---|
| 70 | 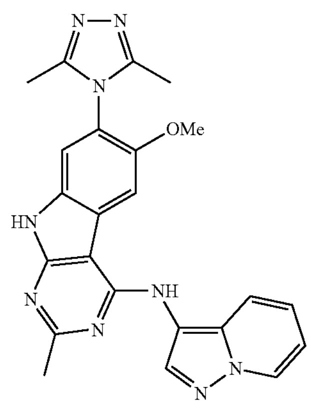 [SMILES: COc1cc2c(cc1-n1c(C)nnc1C)[nH]c1nc(C)nc(Nc3cnn4ccccc34)c12] | 7-(3,5-dimethyl-4H-1,2,4-triazol-4-yl)-6-methoxy-2-methyl-N-(pyrazolo[1,5-a]pyridin-3-yl)-9H-pyrimido[4,5-b]indol-4-amine |
| 71 | 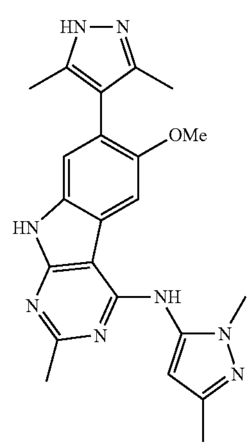 | 7-(3,5-dimethyl-1H-pyrazol-4-yl)-N-(1,3-dimethyl-1H-pyrazol-5-yl)-6-methoxy-2-methyl-9H-pyrimido[4,5-b]indol-4-amine |
| 72 | 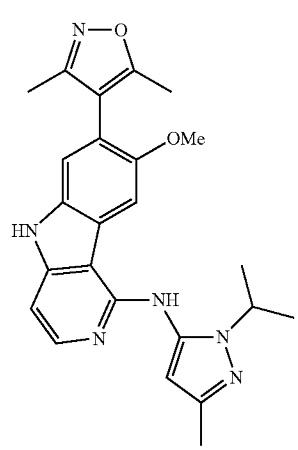 [SMILES: COc1cc2c(cc1-c1c(C)noc1C)[nH]c1ccnc(Nc3cc(C)nn3C(C)C)c12] | 7-(3,5-dimethylisoxazol-4-yl)-N-(1-isopropyl-3-methyl-1H-pyrazol-5-yl)-8-methoxy-5H-pyrido[4,3-b]indol-1-amine |

TABLE 1-continued

| Cpd. No. | Structure | Name |
|---|---|---|
| 73 | 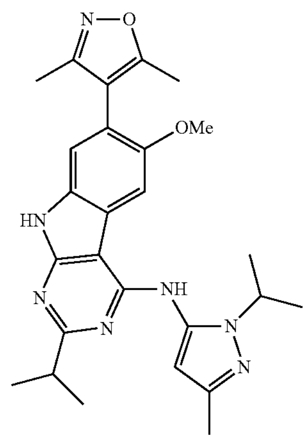 [SMILES: COc1cc2c(cc1-c1c(C)noc1C)[nH]c1nc(C(C)C)nc(Nc3cc(C)nn3C(C)C)c12] | 7-(3,5-dimethylisoxazol-4-yl)-2-isopropyl-N-(1-isopropyl-3-methyl-1H-pyrazol-5-yl)-6-methoxy-9H-pyrimido[4,5-b]indol-4-amine |
| 74 | 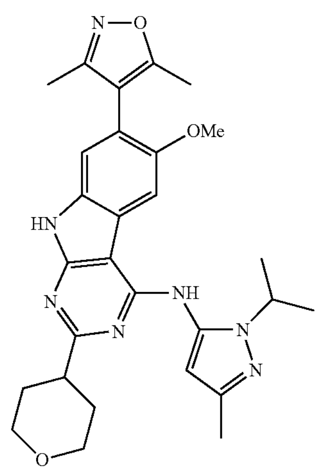 [SMILES: COc1cc2c(cc1-c1c(C)noc1C)[nH]c1nc(C3CCOCC3)nc(Nc3cc(C)nn3C(C)C)c12] | 7-(3,5-dimethylisoxazol-4-yl)-N-(1-isopropyl-3-methyl-1H-pyrazol-5-yl)-6-methoxy-2-(tetrahydro-2H-pyran-4-yl)-9H-pyrimido[4,5-b]indol-4-amine |
| 75 | 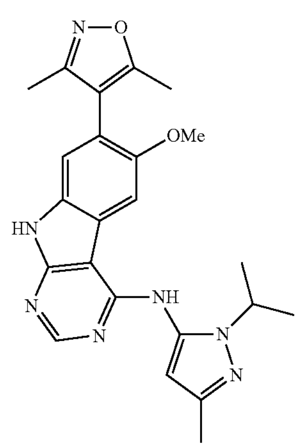 [SMILES: COc1cc2c(cc1-c1c(C)noc1C)[nH]c1ncnc(Nc3cc(C)nn3C(C)C)c12] | 7-(3,5-dimethylisoxazol-4-yl)-N-(1-isopropyl-3-methyl-1H-pyrazol-5-yl)-6-methoxy-9H-pyrimido[4,5-b]indol-4-amine |

TABLE 1-continued

| Cpd. No. | Structure | Name |
|---|---|---|
| 76 | 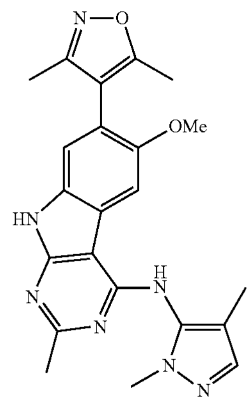 | N-(1,4-dimethyl-1H-pyrazol-5-yl)-7-(3,5-dimethylisoxazol-4-yl)-6-methoxy-2-methyl-9H-pyrimido[4,5-b]indol-4-amine |
| 77 | 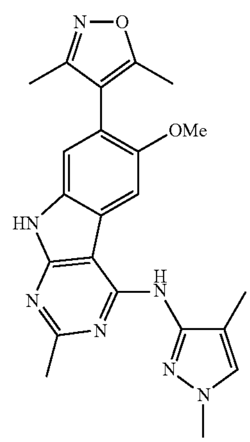 | N-(1,4-dimethyl-1H-pyrazol-3-yl)-7-(3,5-dimethylisoxazol-4-yl)-6-methoxy-2-methyl-9H-pyrimido[4,5-b]indol-4-amine |
| 78 | 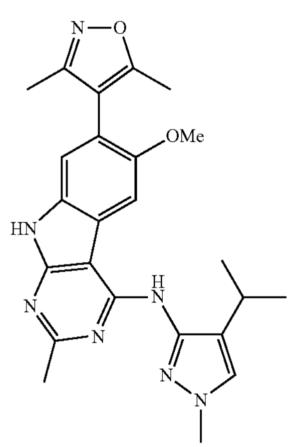 [SMILES: COc1cc2c(cc1-c1c(C)noc1C)[nH]c1nc(C)nc(Nc3nn(C)cc3C(C)C)c12] | 7-(3,5-dimethylisoxazol-4-yl)-N-(4-isopropyl-1-methyl-1H-pyrazol-3-yl)-6-methoxy-2-methyl-9H-pyrimido[4,5-b]indol-4-amine |

TABLE 1-continued

| Cpd. No. | Structure | Name |
| --- | --- | --- |
| 79 | 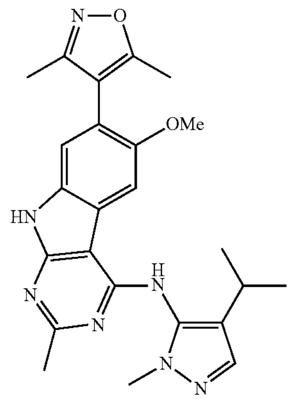 [SMILES: COc1cc2c(cc1-c1c(C)noc1C)[nH]c1nc(C)nc(Nc3c(C(C)C)cnn3C)c12] | 7-(3,5-dimethylisoxazol-4-yl)-N-(4-isopropyl-1-methyl-1H-pyrazol-5-yl)-6-methoxy-2-methyl-9H-pyrimido[4,5-b]indol-4-amine |
| 80 | 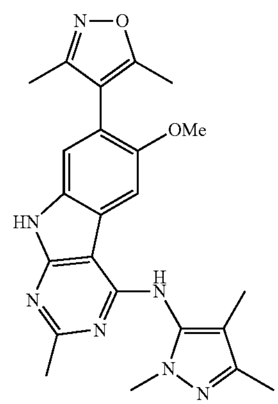 | 7-(3,5-dimethylisoxazol-4-yl)-6-methoxy-2-methyl-N-(1,3,4-trimethyl-1H-pyrazol-5-yl)-9H-pyrimido[4,5-b]indol-4-amine |
| 81 | 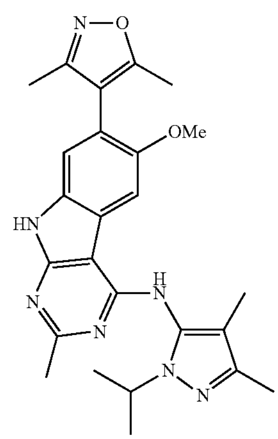 | 7-(3,5-dimethylisoxazol-4-yl)-N-(1-isopropyl-3,4-dimethyl-1H-pyrazol-5-yl)-6-methoxy-2-methyl-9H-pyrimido[4,5-b]indol-4-amine |

TABLE 1-continued

| Cpd. No. | Structure | Name |
|---|---|---|
| 83 | 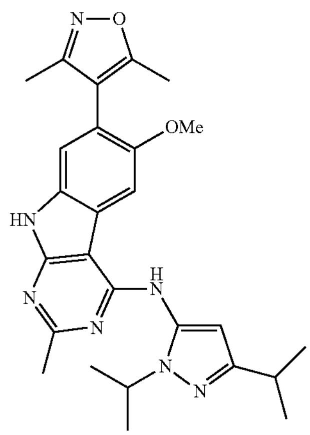 [SMILES: COc1cc2c(cc1-c1c(C)noc1C)[nH]c1nc(C)nc(Nc3cc(C(C)C)nn3C(C)C)c12] | N-(1,3-diisopropyl-1H-pyrazol-5-yl)-7-(3,5-dimethylisoxazol-4-yl)-6-methoxy-2-methyl-9H-pyrimido[4,5-b]indol-4-amine |
| 84 | 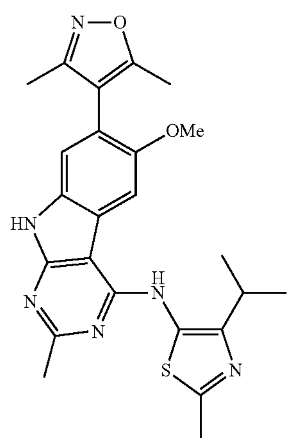 [SMILES: COc1cc2c(cc1-c1c(C)noc1C)[nH]c1nc(C)nc(Nc3sc(C)nc3C(C)C)c12] | N-(7-(3,5-dimethylisoxazol-4-yl)-6-methoxy-2-methyl-9H-pyrimido[4,5-b]indol-4-yl)-4-isopropyl-2-methylthiazol-5-amine |
| 85 | 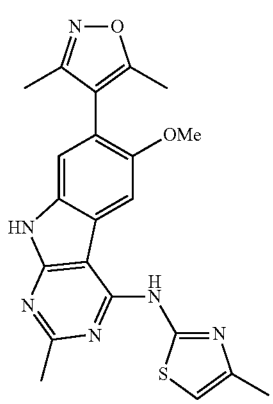 | N-(7-(3,5-dimethylisoxazol-4-yl)-6-methoxy-2-methyl-9H-pyrimido[4,5-b]indol-4-yl)-4-methylthiazol-2-amine |

TABLE 1-continued
| Cpd. No. | Structure | Name |
|---|---|---|
| 86 | 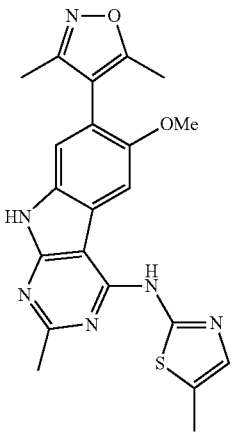 [SMILES: COc1cc2c(cc1-c1c(C)noc1C)[nH]c1nc(C)nc(Nc3ncc(C)s3)c12] | N-(7-(3,5-dimethylisoxazol-4-yl)-6-methoxy-2-methyl-9H-pyrimido[4,5-b]indol-4-yl)-5-methylthiazol-2-amine |
| 87 | 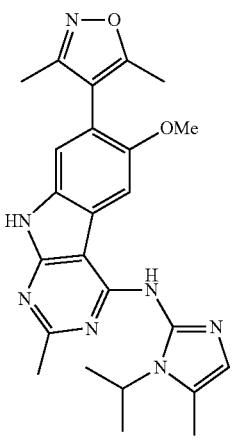 [SMILES: COc1cc2c(cc1-c1c(C)noc1C)[nH]c1nc(C)nc(Nc3ncc(C)n3C(C)C)c12] | 7-(3,5-dimethylisoxazol-4-yl)-N-(1-isopropyl-5-methyl-1H-imidazol-2-yl)-6-methoxy-2-methyl-9H-pyrimido[4,5-b]indol-4-amine |
| 88 | 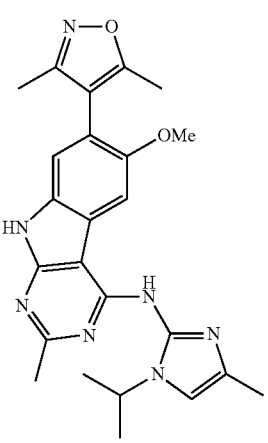 | 7-(3,5-dimethylisoxazol-4-yl)-N-(1-isopropyl-4-methyl-1H-imidazol-2-yl)-6-methoxy-2-methyl-9H-pyrimido[4,5-b]indol-4-amine |

TABLE 1-continued

| Cpd. No. | Structure | Name |
| --- | --- | --- |
| 89 | 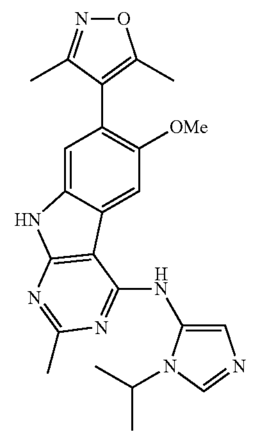 | 7-(3,5-dimethylisoxazol-4-yl)-N-(1-isopropyl-1H-imidazol-5-yl)-6-methoxy-2-methyl-9H-pyrimido[4,5-b]indol-4-amine |
| 90 | 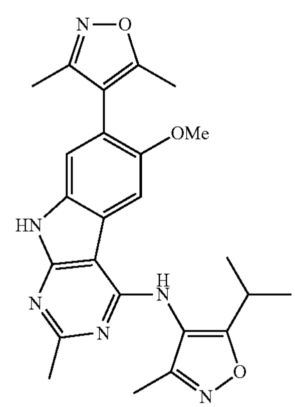 [SMILES: COc1cc2c(cc1-c1c(C)noc1C)[nH]c1nc(C)nc(Nc3c(C)noc3C(C)C)c12] | N-(7-(3,5-dimethylisoxazol-4-yl)-6-methoxy-2-methyl-9H-pyrimido[4,5-b]indol-4-yl)-5-isopropyl-3-methylisoxazol-4-amine |
| 91 | 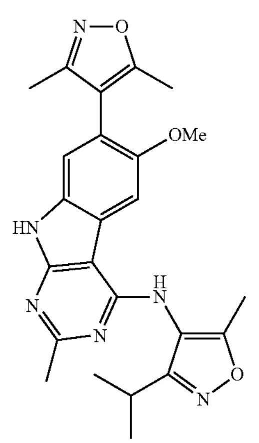 | N-(7-(3,5-dimethylisoxazol-4-yl)-6-methoxy-2-methyl-9H-pyrimido[4,5-b]indol-4-yl)-3-isopropyl-5-methylisoxazol-4-amine |

TABLE 1-continued
| Cpd. No. | Structure | Name |
|---|---|---|
| 92 | 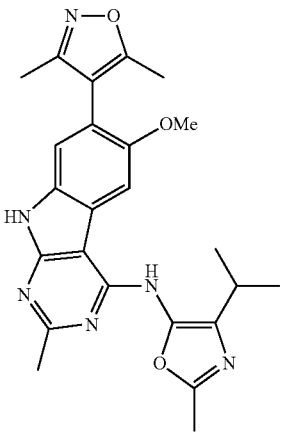 | N-(7-(3,5-dimethylisoxazol-4-yl)-6-methoxy-2-methyl-9H-pyrimido[4,5-b]indol-4-yl)-4-isopropyl-2-methyloxazol-5-amine |
| 93 | 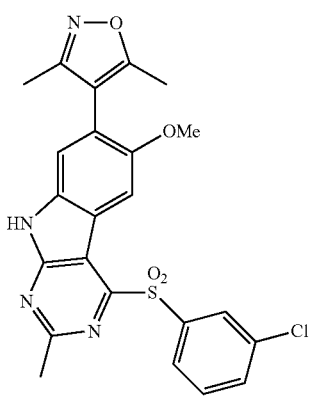 [SMILES: COc1cc2c(cc1-c1c(C)noc1C)[nH]c1nc(C)nc(S(=O)(=O)c3cccc(Cl)c3)c12] | 4-(4-((3-chlorophenyl)sulfonyl)-6-methoxy-2-methyl-9H-pyrimido[4,5-b]indol-7-yl)-3,5-dimethylisoxazole |
| 94 | 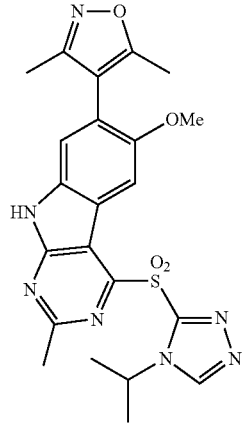 | 4-(4-((4-isopropyl-4H-1,2,4-triazol-3-yl)sulfonyl)-6-methoxy-2-methyl-9H-pyrimido[4,5-b]indol-7-yl)-3,5-dimethylisoxazole |

TABLE 1-continued
| Cpd. No. | Structure | Name |
|---|---|---|
| 95 | 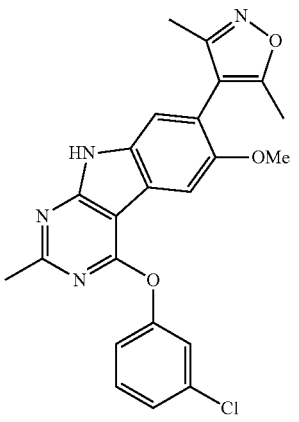 | 4-(4-(3-chlorophenoxy)-6-methoxy-2-methyl-9H-pyrimido[4,5-b]indol-7-yl)-3,5-dimethylisoxazole |
| 96 | 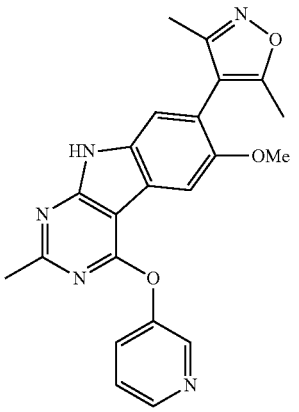 | 4-(6-methoxy-2-methyl-4-(pyridin-3-yloxy)-9H-pyrimido[4,5-b]indol-7-yl)-3,5-dimethylisoxazole |
| 97 | 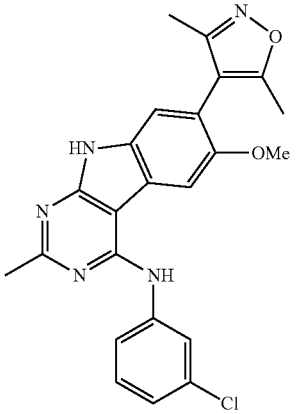 | N-(3-chlorophenyl)-7-(3,5-dimethylisoxazol-4-yl)-6-methoxy-2-methyl-9H-pyrimido[4,5-b]indol-4-amine |

TABLE 1-continued

| Cpd. No. | Structure | Name |
|---|---|---|
| 98 | 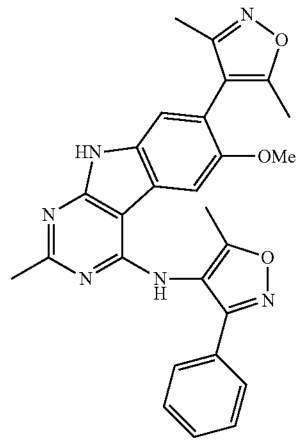 | N-(7-(3,5-dimethylisoxazol-4-yl)-6-methoxy-2-methyl-9H-pyrimido[4,5-b]indol-4-yl)-5-methyl-3-phenylisoxazol-4-amine |
| 99 | 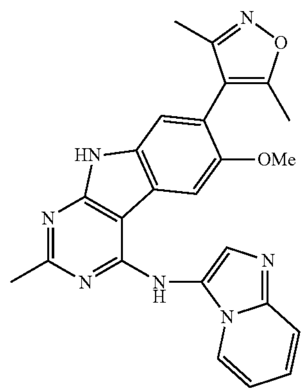 [SMILES: COc1cc2c(cc1-c1c(C)noc1C)[nH]c1nc(C)nc(Nc3cnc4ccccn34)c12] | 7-(3,5-dimethylisoxazol-4-yl)-N-(imidazo[1,2-a]pyridin-3-yl)-6-methoxy-2-methyl-9H-pyrimido[4,5-b]indol-4-amine |
| 100 | 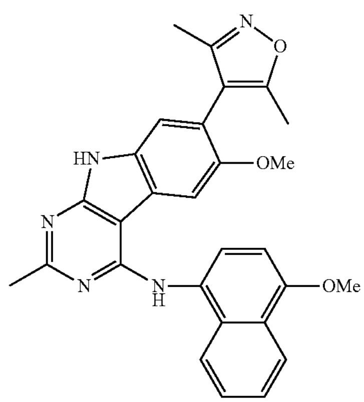 [SMILES: COc1cc2c(cc1-c1c(C)noc1C)[nH]c1nc(C)nc(Nc3ccc(OC)c4ccccc34)c12] | 7-(3,5-dimethylisoxazol-4-yl)-6-methoxy-N-(4-methoxynaphthalen-1-yl)-2-methyl-9H-pyrimido[4,5-b]indol-4-amine |
| 101 | 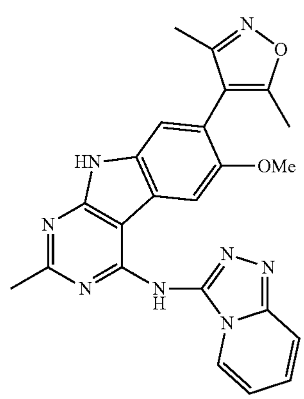 [SMILES: COc1cc2c(cc1-c1c(C)noc1C)[nH]c1nc(C)nc(Nc3nnc4ccccn34)c12] | N-([1,2,4]triazolo[4,3-a]pyridin-3-yl)-7-(3,5-dimethylisoxazol-4-yl)-6-methoxy-2-methyl-9H-pyrimido[4,5-b]indol-4-amine |

TABLE 1-continued

| Cpd. No. | Structure | Name |
|---|---|---|
| 102 | 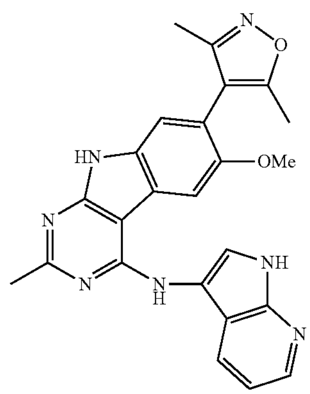 [SMILES: COc1cc2c(cc1-c1c(C)noc1C)[nH]c1nc(C)nc(Nc3c[nH]c4ncccc34)c12] | 7-(3,5-dimethylisoxazol-4-yl)-6-methoxy-2-methyl-N-(1H-pyrrolo[2,3-b]pyridin-3-yl)-9H-pyrimido[4,5-b]indol-4-amine |
| 103 | 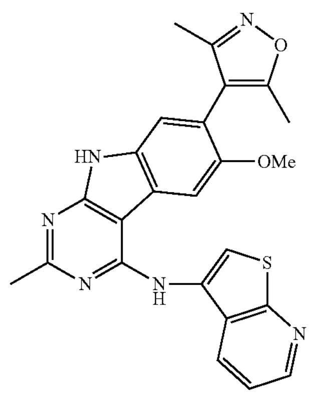 [SMILES: COc1cc2c(cc1-c1c(C)noc1C)[nH]c1nc(C)nc(Nc3csc4ncccc34)c12] | N-(7-(3,5-dimethylisoxazol-4-yl)-6-methoxy-2-methyl-9H-pyrimido[4,5-b]indol-4-yl)thieno[2,3-b]pyridin-3-amine |
| 104 | 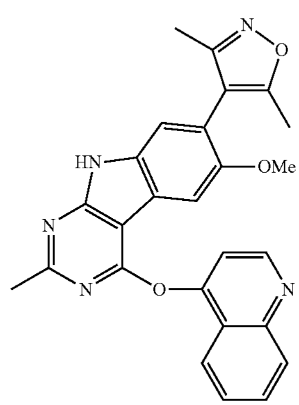 | 4-(6-methoxy-2-methyl-4-(quinolin-4-yloxy)-9H-pyrimido[4,5-b]indol-7-yl)-3,5-dimethylisoxazole |
| 105 | 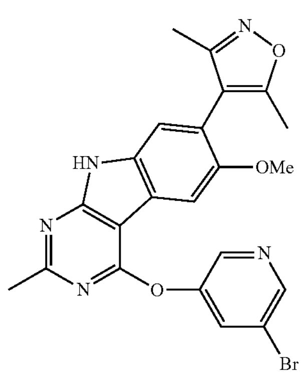 | 4-(4-(5-bromopyridin-3-yl)oxy)-6-methoxy-2-methyl-9H-pyrimido[4,5-b]indol-7-yl)-3,5-dimethylisoxazole |

TABLE 1-continued

| Cpd. No. | Structure | Name |
|---|---|---|
| 106 | 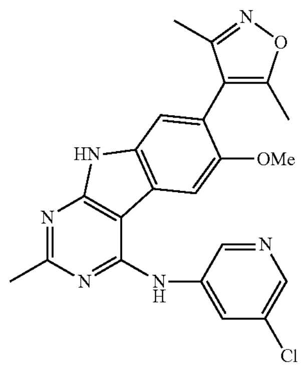 | N-(5-chloropyridin-3-yl)-7-(3,5-dimethylisoxazol-4-yl)-6-methoxy-2-methyl-9H-pyrimido[4,5-b]indol-4-amine |
| 107 | 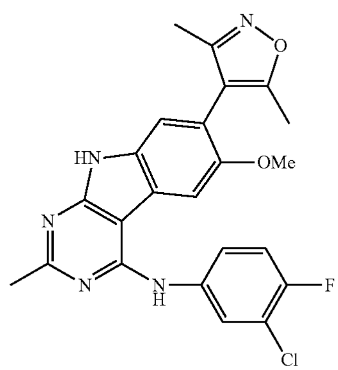 [SMILES: COc1cc2c(cc1-c1c(C)noc1C)[nH]c1nc(C)nc(Nc3ccc(F)c(Cl)c3)c12] | N-(3-chloro-4-fluorophenyl)-7-(3,5-dimethylisoxazol-4-yl)-6-methoxy-2-methyl-9H-pyrimido[4,5-b]indol-4-amine |
| 108 | 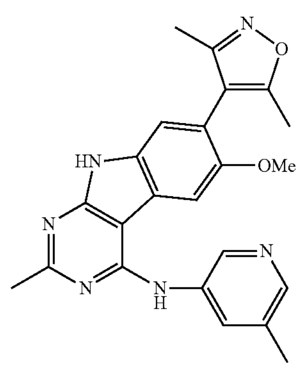 | 7-(3,5-dimethylisoxazol-4-yl)-6-methoxy-2-methyl-N-(5-methylpyridin-3-yl)-9H-pyrimido[4,5-b]indol-4-amine |
| 109 | 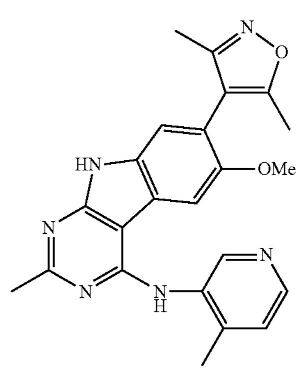 | 7-(3,5-dimethylisoxazol-4-yl)-6-methoxy-2-methyl-N-(4-methylpyridin-3-yl)-9H-pyrimido[4,5-b]indol-4-amine |

TABLE 1-continued

| Cpd. No. | Structure | Name |
|---|---|---|
| 110 | 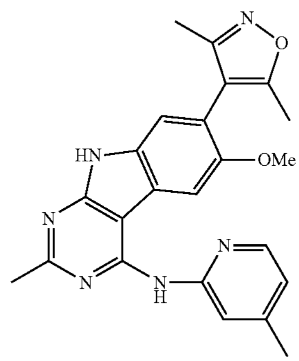 | 7-(3,5-dimethylisoxazol-4-yl)-6-methoxy-2-methyl-N-(4-methylpyridin-2-yl)-9H-pyrimido[4,5-b]indol-4-amine |
| 111 | 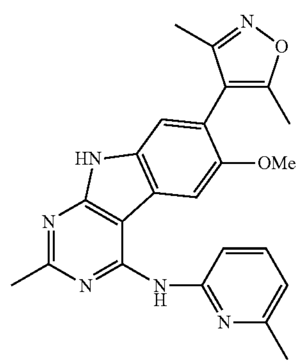 | 7-(3,5-dimethylisoxazol-4-yl)-6-methoxy-2-methyl-N-(6-methylpyridin-2-yl)-9H-pyrimido[4,5-b]indol-4-amine |
| 112 | 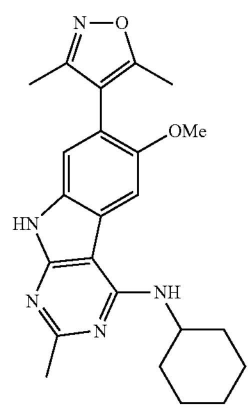 [SMILES: COc1cc2c(cc1-c1c(C)noc1C)[nH]c1nc(C)nc(NC3CCCCC3)c12] | N-cyclohexyl-7-(3,5-dimethylisoxazol-4-yl)-6-methoxy-2-methyl-9H-pyrimido[4,5-b]indol-4-amine |
| 113 | 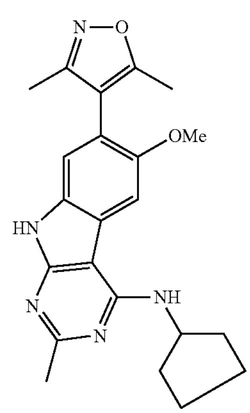 [SMILES: COc1cc2c(cc1-c1c(C)noc1C)[nH]c1nc(C)nc(NC3CCCC3)c12] | N-cyclopentyl-7-(3,5-dimethylisoxazol-4-yl)-6-methoxy-2-methyl-9H-pyrimido[4,5-b]indol-4-amine |

TABLE 1-continued

| Cpd. No. | Structure | Name |
| --- | --- | --- |
| 115 | 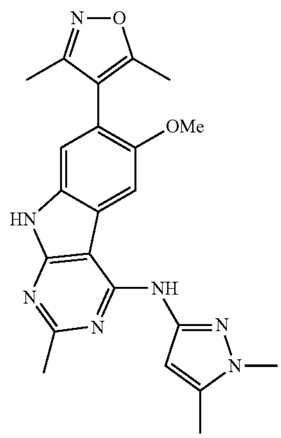 | N-(1,5-Dimethyl-1H-pyrazol-3-yl)-7-(3,5-dimethylisoxazol-4-yl)-6-methoxy-2-methyl-9H-pyrimido[4,5-b]indol-4-amine |
| 116 | 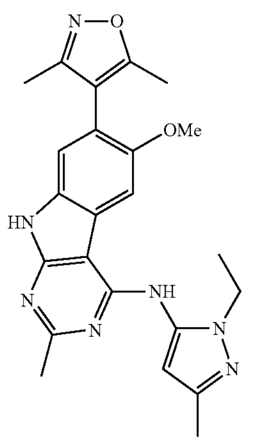 [SMILES: CCn1nc(C)cc1Nc1nc(C)nc2[nH]c3cc(-c4c(C)noc4C)c(OC)cc3c12] | 7-(3,5-Dimethylisoxazol-4-yl)-N-(1-ethyl-3-methyl-1H-pyrazol-5-yl)-6-methoxy-2-methyl-9H-pyrimido[4,5-b]indol-4-amine |
| 117 | 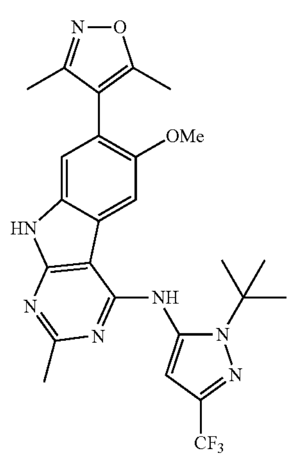 [SMILES: COc1cc2c(cc1-c1c(C)noc1C)[nH]c1nc(C)nc(Nc3cc(C(F)(F)F)nn3C(C)(C)C)c12] | N-(1-(tert-Butyl)-3-(trifluoromethyl)-1H-pyrazol-5-yl)-7-(3,5-dimethylisoxazol-4-yl)-6-methoxy-2-methyl-9H-pyrimido[4,5-b]indol-4-amine |

TABLE 1-continued

| Cpd. No. | Structure | Name |
| --- | --- | --- |
| 118 | 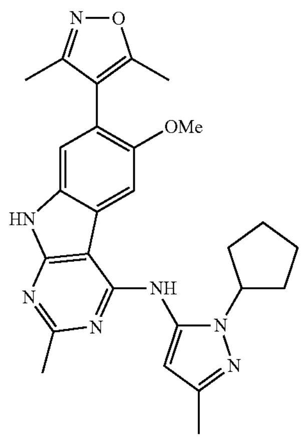 [SMILES: COc1cc2c(cc1-c1c(C)noc1C)[nH]c1nc(C)nc(Nc3cc(C)nn3C3CCCC3)c12] | N-(1-Cyclopentyl-3-methyl-1H-pyrazol-5-yl)-7-(3,5-dimethylisoxazol-4-yl)-6-methoxy-2-methyl-9H-pyrimido[4,5-b]indol-4-amine |
| 119 | 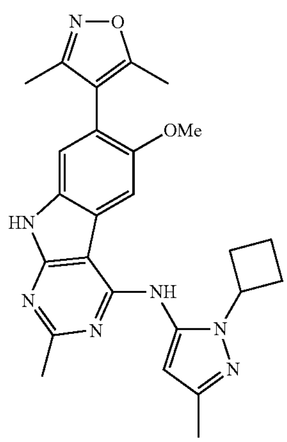 [SMILES: COc1cc2c(cc1-c1c(C)noc1C)[nH]c1nc(C)nc(Nc3cc(C)nn3C3CCC3)c12] | N-(1-Cyclobutyl-3-methyl-1H-pyrazol-5-yl)-7-(3,5-dimethylisoxazol-4-yl)-6-methoxy-2-methyl-9H-pyrimido[4,5-b]indol-4-amine |
| 120 | 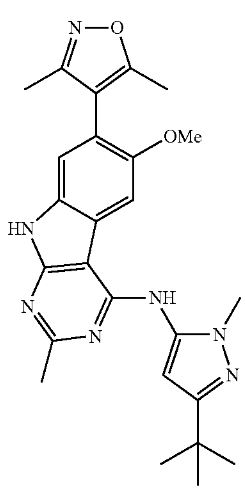 | N-(3-tert-Butyl-1-methyl-1H-pyrazol-5-yl)-7-(3,5-dimethylisoxazol-4-yl)-6-methoxy-2-methyl-9H-pyrimido[4,5-b]indol-4-amine |

TABLE 1-continued
| Cpd. No. | Structure | Name |
|---|---|---|
| 121 | 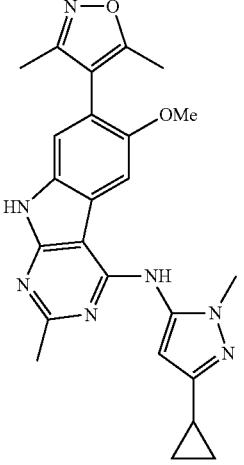 | N-(3-Cyclopropyl-1-methyl-1H-pyrazol-5-yl)-7-(3,5-dimethylisoxazol-4-yl)-6-methoxy-2-methyl-9H-pyrimido[4,5-b]indol-4-amine |
| 122 | 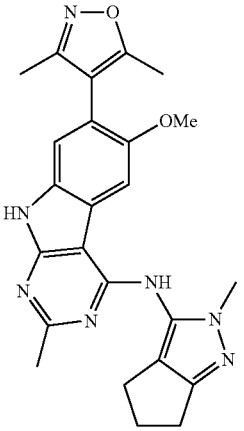 | 7-(3,5-Dimethylisoxazol-4-yl)-6-methoxy-2-methyl-N-(2-methyl-2,4,5,6-tetrahydrocyclopenta-[c]pyrazol-3-yl)-9H-pyrimido[4,5-b]indol-4-amine |
| 123 | 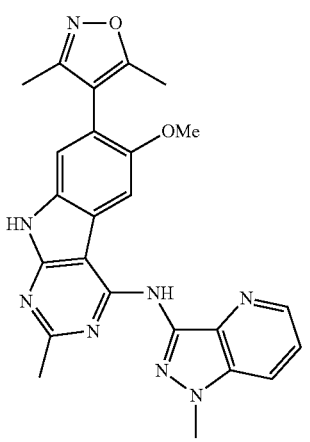 | 7-(3,5-Dimethylisoxazol-4-yl)-6-methoxy-2-methyl-N-(1-methyl-1H-pyrazolo[4,3-b]pyridin-3-yl)-9H-pyrimido[4,5-b]indol-4-amine |

TABLE 1-continued
| Cpd. No. | Structure | Name |
|---|---|---|
| 124 | 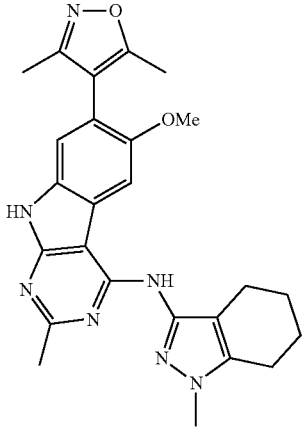 [SMILES: COc1cc2c(cc1-c1c(C)noc1C)[nH]c1nc(C)nc(Nc3nn(C)c4c3CCCC4)c12] | 7-(3,5-Dimethylisoxazol-4-yl)-6-methoxy-2-methyl-N-(1-methyl-4,5,6,7-tetrahydro-1H-indazol-3-yl)-9H-pyrimido[4,5-b]indol-4-amine |
| 125 | 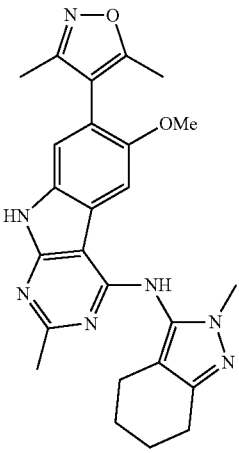 | 7-(3,5-Dimethylisoxazol-4-yl)-6-methoxy-2-methyl-N-(2-methyl-4,5,6,7-tetrahydro-2H-indazol-3-yl)-9H-pyrimido[4,5-b]indol-4-amine |
| 126 | 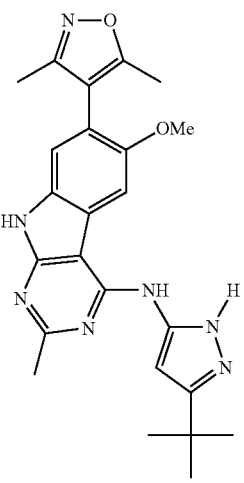 [SMILES: COc1cc2c(cc1-c1c(C)noc1C)[nH]c1nc(C)nc(Nc3cc(C(C)(C)C)n[nH]3)c12] | N-(3-(tert-Butyl)-1H-pyrazol-5-yl)-7-(3,5-dimethylisoxazol-4-yl)-6-methoxy-2-methyl-9H-pyrimido[4,5-b]indol-4-amine |

TABLE 1-continued

| Cpd. No. | Structure | Name |
| --- | --- | --- |
| 127 | 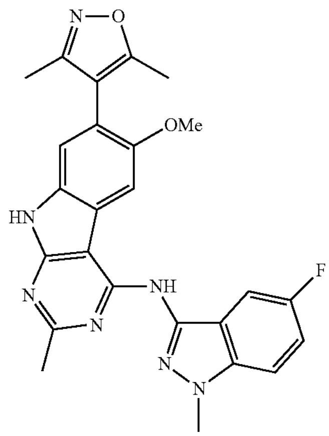 [SMILES: COc1cc2c(cc1-c1c(C)noc1C)[nH]c1nc(C)nc(Nc3nn(C)c4ccc(F)cc34)c12] | 7-(3,5-Dimethylisoxazol-4-yl)-N-(5-fluoro-1-methyl-1H-indazol-3-yl)-6-methoxy-2-methyl-9H-pyrimido[4,5-b]indol-4-amine |
| 129 | 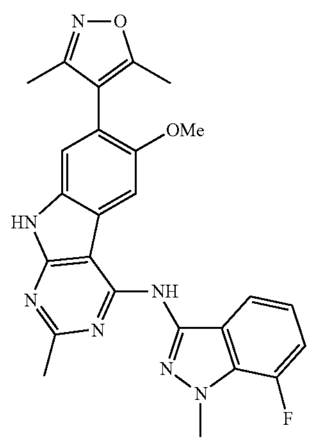 [SMILES: COc1cc2c(cc1-c1c(C)noc1C)[nH]c1nc(C)nc(Nc3nn(C)c4c(F)cccc34)c12] | 7-(3,5-Dimethylisoxazol-4-yl)-N-(7-fluoro-1-methyl-1H-indazol-3-yl)-6-methoxy-2-methyl-9H-pyrimido[4,5-b]indol-4-amine |
| 131 | 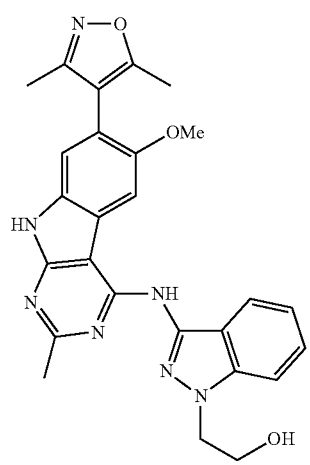 [SMILES: COc1cc2c(cc1-c1c(C)noc1C)[nH]c1nc(C)nc(Nc3nn(CCO)c4ccccc34)c12] | 2-(3-((7-(3,5-Dimethylisoxazol-4-yl)-6-methoxy-2-methyl-9H-pyrimido[4,5-b]indol-4-yl)amino)-1H-indazol-1-yl)ethanol |

TABLE 1-continued

| Cpd. No. | Structure | Name |
|---|---|---|
| 132 | 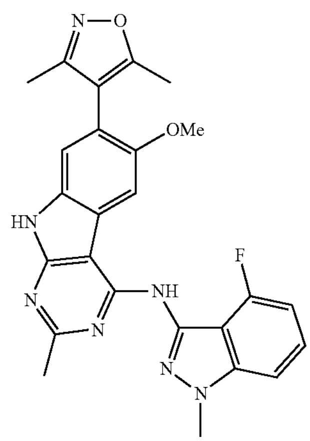 | 7-(3,5-Dimethylisoxazol-4-yl)-N-(4-fluoro-1-methyl-1H-indazol-3-yl)-6-methoxy-2-methyl-9H-pyrimido[4,5-b]indol-4-amine |
| 133 | 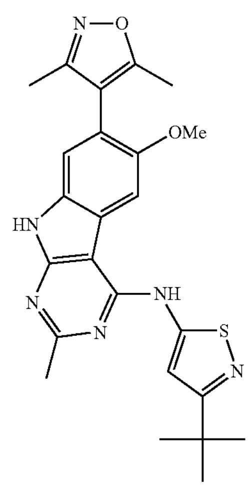 [SMILES: COc1cc2c(cc1-c1c(C)noc1C)[nH]c1nc(C)nc(Nc3cc(C(C)(C)C)ns3)c12] | 3-(tert-Butyl)-N-(7-(3,5-dimethylisoxazol-4-yl)-6-methoxy-2-methyl-9H-pyrimido[4,5-b]indol-4-yl)isothiazol-5-amine |
| 134 | 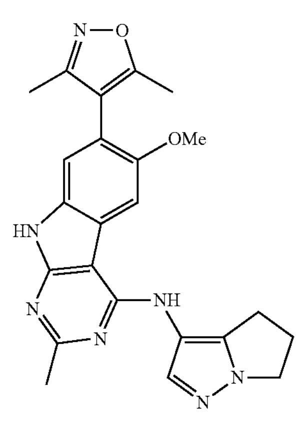 [SMILES: COc1cc2c(cc1-c1c(C)noc1C)[nH]c1nc(C)nc(Nc3cnn4c3CCC4)c12] | N-(5,6-Dihydro-4H-pyrrolo[1,2-b]pyrazol-3-yl)-7-(3,5-dimethylisoxazol-4-yl)-6-methoxy-2-methyl-9H-pyrimido[4,5-b]indol-4-amine |

TABLE 1-continued
| Cpd. No. | Structure | Name |
|---|---|---|
| 135 | 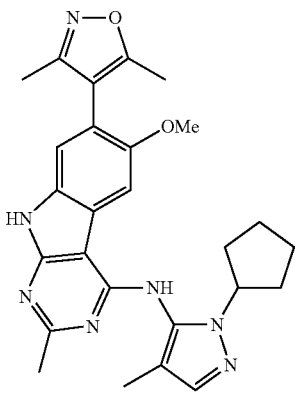 [SMILES: COc1cc2c(cc1-c1c(C)noc1C)[nH]c1nc(C)nc(Nc3c(C)cnn3C3CCCC3)c12] | N-(1-Cyclopentyl-4-methyl-1H-pyrazol-5-yl)-7-(3,5-dimethylisoxazol-4-yl)-6-methoxy-2-methyl-9H-pyrimido[4,5-b]indol-4-amine |
| 136 | 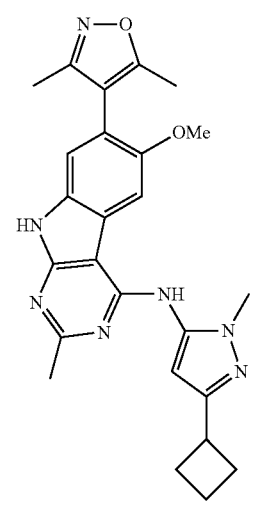 | N-(3-Cyclobutyl-1-methyl-1H-pyrazol-5-yl)-7-(3,5-dimethylisoxazol-4-yl)-6-methoxy-2-methyl-9H-pyrimido[4,5-b]indol-4-amine |
| 137 | 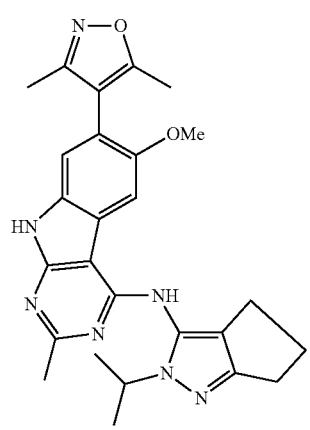 [SMILES: COc1cc2c(cc1-c1c(C)noc1C)[nH]c1nc(C)nc(Nc3c4c(nn3C(C)C)CCC4)c12] | 7-(3,5-Dimethylisoxazol-4-yl)-N-(2-isopropyl-2,4,5,6-tetrahydrocyclopenta[c]pyrazol-3-yl)-6-methoxy-2-methyl-9H-pyrimido[4,5-b]indol-4-amine |

TABLE 1-continued

| Cpd. No. | Structure | Name |
| --- | --- | --- |
| 138 | 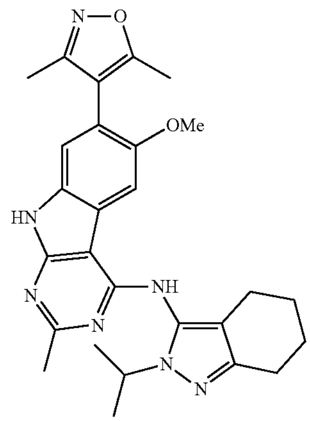 [SMILES: COc1cc2c(cc1-c1c(C)noc1C)[nH]c1nc(C)nc(Nc3c4c(nn3C(C)C)CCCC4)c12] | 7-(3,5-Dimethylisoxazol-4-yl)-N-(2-isopropyl-4,5,6,7-tetrahydro-2H-indazol-3-yl)-6-methoxy-2-methyl-9H-pyrimido[4,5-b]indol-4-amine |
| 139 | 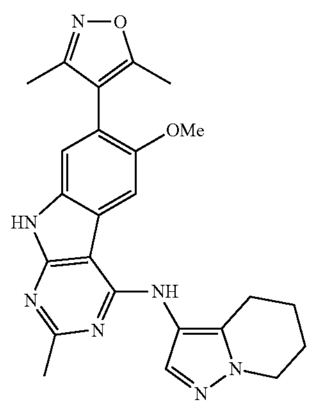 [SMILES: COc1cc2c(cc1-c1c(C)noc1C)[nH]c1nc(C)nc(Nc3cnn4c3CCCC4)c12] | 7-(3,5-Dimethylisoxazol-4-yl)-6-methoxy-2-methyl-N-(4,5,6,7-tetrahydropyrazolo[1,5-a]pyridin-3-yl)-9H-pyrimido[4,5-b]indol-4-amine |
| 140 | 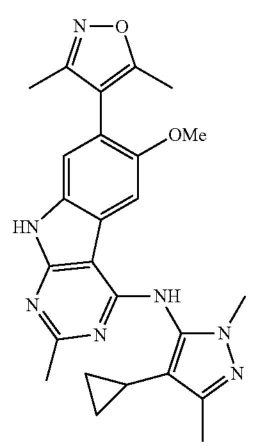 | N-(4-Cyclopropyl-1,3-dimethyl-1H-pyrazol-5-yl)-7-(3,5-dimethylisoxazol-4-yl)-6-methoxy-2-methyl-9H-pyrimido[4,5-b]indol-4-amine |

TABLE 1-continued
| Cpd. No. | Structure | Name |
|---|---|---|
| 141 | 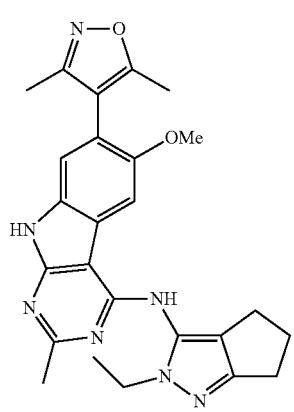 [SMILES: CCn1nc2c(c1Nc1nc(C)nc3[nH]c4cc(-c5c(C)noc5C)c(OC)cc4c13)CCC2] | 7-(3,5-Dimethylisoxazol-4-yl)-N-(2-ethyl-2,4,5,6-tetrahydrocyclopenta[c]pyrazol-3-yl)-6-methoxy-2-methyl-9H-pyrimido[4,5-b]indol-4-amine |
| 142 | 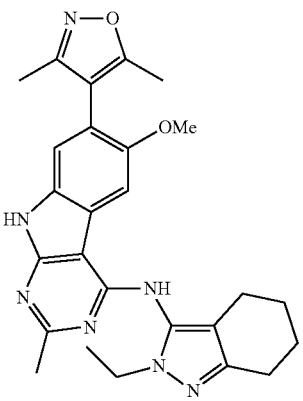 [SMILES: CCn1nc2c(c1Nc1nc(C)nc3[nH]c4cc(-c5c(C)noc5C)c(OC)cc4c13)CCCC2] | 7-(3,5-Dimethylisoxazol-4-yl)-N-(2-ethyl-4,5,6,7-tetrahydro-2H-indazol-3-yl)-6-methoxy-2-methyl-9H-pyrimido[4,5-b]indol-4-amine |
| 143 | 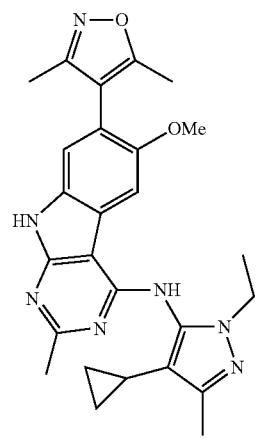 [SMILES: CCn1nc(C)c(C2CC2)c1Nc1nc(C)nc2[nH]c3cc(-c4c(C)noc4C)c(OC)cc3c12] | N-(4-Cyclopropyl-1-ethyl-3-methyl-1H-pyrazol-5-yl)-7-(3,5-dimethylisoxazol-4-yl)-6-methoxy-2-methyl-9H-pyrimido[4,5-b]indol-4-amine |

TABLE 1-continued
| Cpd. No. | Structure | Name |
|---|---|---|
| 144 | 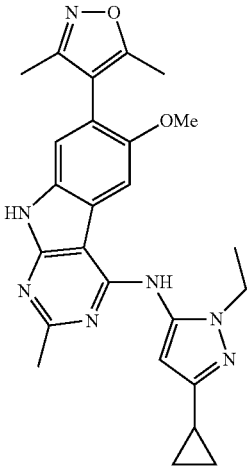 [SMILES: CCn1nc(C2CC2)cc1Nc1nc(C)nc2[nH]c3cc(-c4c(C)noc4C)c(OC)cc3c12] | N-(3-Cyclopropyl-1-ethyl-1H-pyrazol-5-yl)-7-(3,5-dimethylisoxazol-4-yl)-6-methoxy-2-methyl-9H-pyrimido[4,5-b]indol-4-amine |
| 145 | 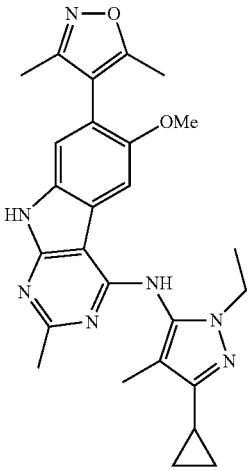 [SMILES: CCn1nc(C2CC2)c(C)c1Nc1nc(C)nc2[nH]c3cc(-c4c(C)noc4C)c(OC)cc3c12] | N-(3-Cyclopropyl-1-ethyl-4-methyl-1H-pyrazol-5-yl)-7-(3,5-dimethylisoxazol-4-yl)-6-methoxy-2-methyl-9H-pyrimido[4,5-b]indol-4-amine |
| 146 | 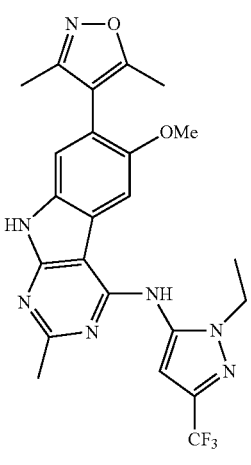 [SMILES: CCn1nc(C(F)(F)F)cc1Nc1nc(C)nc2[nH]c3cc(-c4c(C)noc4C)c(OC)cc3c12] | 7-(3,5-Dimethylisoxazol-4-yl)-N-(1-ethyl-3-(trifluoromethyl)-1H-pyrazol-5-yl)-6-methoxy-2-methyl-9H-pyrimido[4,5-b]indol-4-amine |

TABLE 1-continued

| Cpd. No. | Structure | Name |
|---|---|---|
| 147 | 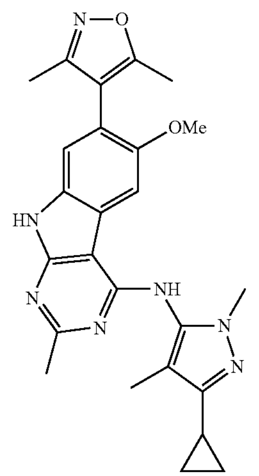 | N-(3-Cyclopropyl-1,4-dimethyl-1H-pyrazol-5-yl)-7-(3,5-dimethylisoxazol-4-yl)-6-methoxy-2-methyl-9H-pyrimido[4,5-b]indol-4-amine |
| 148 | 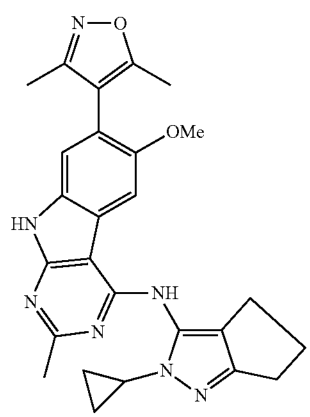 [SMILES: COc1cc2c(cc1-c1c(C)noc1C)[nH]c1nc(C)nc(Nc3c4c(nn3C3CC3)CCC4)c12] | N-(2-Cyclopropyl-2,4,5,6-tetrahydrocyclopenta[c]pyrazol-3-yl)-7-(3,5-dimethylisoxazol-4-yl)-6-methoxy-2-methyl-9H-pyrimido[4,5-b]indol-4-amine |
| 149 | 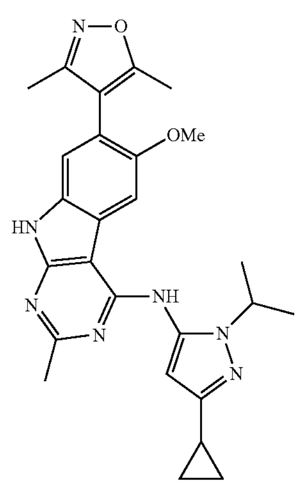 [SMILES: COc1cc2c(cc1-c1c(C)noc1C)[nH]c1nc(C)nc(Nc3cc(C4CC4)nn3C(C)C)c12] | N-(3-Cyclopropyl-1-isopropyl-1H-pyrazol-5-yl)-7-(3,5-dimethylisoxazol-4-yl)-6-methoxy-2-methyl-9H-pyrimido[4,5-b]indol-4-amine |

TABLE 1-continued
| Cpd. No. | Structure | Name |
|---|---|---|
| 150 | 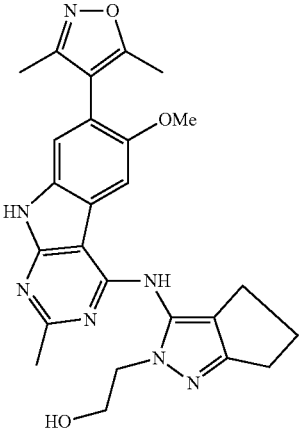 [SMILES: COc1cc2c(cc1-c1c(C)noc1C)[nH]c1nc(C)nc(Nc3c4c(nn3CCO)CCC4)c12] | 2-(3-((7-(3,5-Dimethylisoxazol-4-yl)-6-methoxy-2-methyl-9H-pyrimido[4,5-b]indol-4-yl)amino)-5,6-dihydrocyclopenta[c]pyrazol-2(4H)-yl)ethanol |
| 151 | 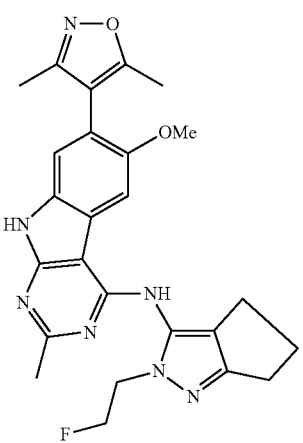 [SMILES: COc1cc2c(cc1-c1c(C)noc1C)[nH]c1nc(C)nc(Nc3c4c(nn3CCF)CCC4)c12] | 7-(3,5-Dimethylisoxazol-4-yl)-N-(2-(2-fluoroethyl)-2,4,5,6-tetrahydrocyclopenta[c]pyrazol-3-yl)-6-methoxy-2-methyl-9H-pyrimido[4,5-b]indol-4-amine |
| 152 | 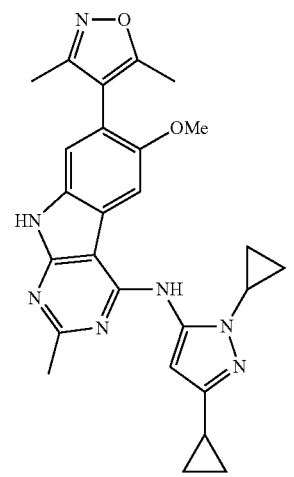 [SMILES: COc1cc2c(cc1-c1c(C)noc1C)[nH]c1nc(C)nc(Nc3cc(C4CC4)nn3C3CC3)c12] | N-(1,3-Dicyclopropyl-1H-pyrazol-5-yl)-7-(3,5-dimethylisoxazol-4-yl)-6-methoxy-2-methyl-9H-pyrimido[4,5-b]indol-4-amine |

TABLE 1-continued
| Cpd. No. | Structure | Name |
|---|---|---|
| 153 | 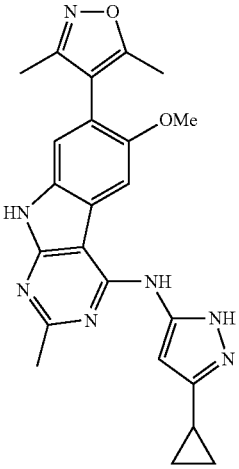 [SMILES: COc1cc2c(cc1-c1c(C)noc1C)[nH]c1nc(C)nc(Nc3cc(C4CC4)n[nH]3)c12] | N-(3-Cyclopropyl-1H-pyrazol-5-yl)-7-(3,5-dimethylisoxazol-4-yl)-6-methoxy-2-methyl-9H-pyrimido[4,5-b]indol-4-amine |
| 154 | 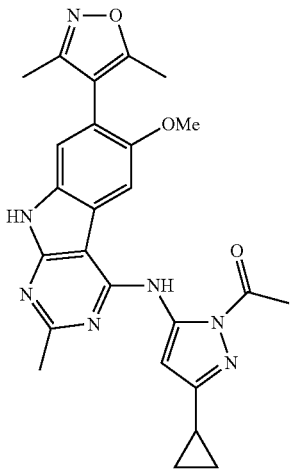 [SMILES: COc1cc2c(cc1-c1c(C)noc1C)[nH]c1nc(C)nc(Nc3cc(C4CC4)nn3C(C)=O)c12] | 1-(3-Cyclopropyl-5-((7-(3,5-dimethylisoxazol-4-yl)-6-methoxy-2-methyl-9H-pyrimido[4,5-b]indol-4-yl)amino)-1H-pyrazol-1-yl)ethanone |
| 155 | 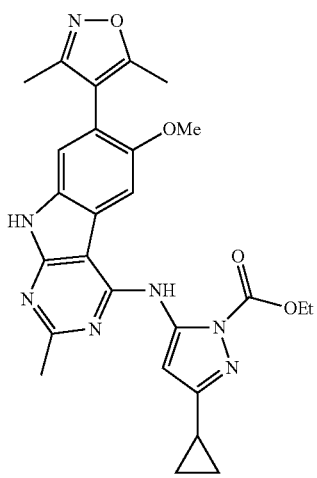 [SMILES: CCOC(=O)n1nc(C2CC2)cc1Nc1nc(C)nc2[nH]c3cc(-c4c(C)noc4C)c(OC)cc3c12] | Ethyl 3-cyclopropyl-5-((7-(3,5-dimethylisoxazol-4-yl)-6-methoxy-2-methyl-9H-pyrimido[4,5-b]indol-4-yl)amino)-1H-pyrazole-1-carboxylate |

TABLE 1-continued
| Cpd. No. | Structure | Name |
|---|---|---|
| 156 | 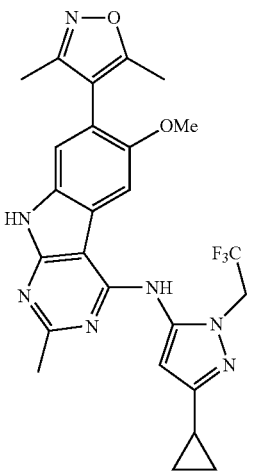 [SMILES: COc1cc2c(cc1-c1c(C)noc1C)[nH]c1nc(C)nc(Nc3cc(C4CC4)nn3CC(F)(F)F)c12] | N-(3-Cyclopropyl-1-(2,2,2-trifluoroethyl)-1H-pyrazol-5-yl)-7-(3,5-dimethylisoxazol-4-yl)-6-methoxy-2-methyl-9H-pyrimido[4,5-b]indol-4-amine |
| 157 | 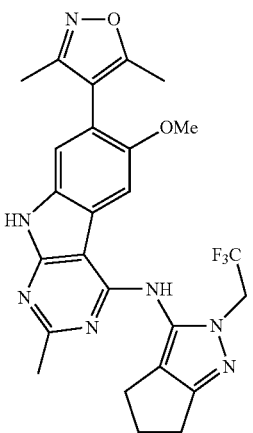 [SMILES: COc1cc2c(cc1-c1c(C)noc1C)[nH]c1nc(C)nc(Nc3c4c(nn3CC(F)(F)F)CCC4)c12] | 7-(3,5-Dimethylisoxazol-4-yl)-6-methoxy-2-methyl-N-(2-(2,2,2-trifluoroethyl)-2,4,5,6-tetrahydrocyclopenta[c]pyrazol-3-yl)-9H-pyrimido[4,5-b]indol-4-amine |
| 158 | 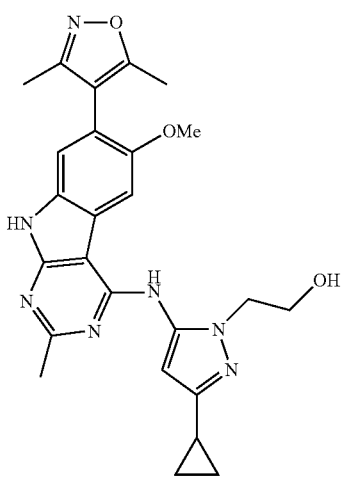 [SMILES: COc1cc2c(cc1-c1c(C)noc1C)[nH]c1nc(C)nc(Nc3cc(C4CC4)nn3CCO)c12] | 2-(3-Cyclopropyl-5-((7-(3,5-dimethylisoxazol-4-yl)-6-methoxy-2-methyl-9H-pyrimido[4,5-b]indol-4-yl)amino)-1H-pyrazol-1-yl)ethanol |

TABLE 1-continued
| Cpd. No. | Structure | Name |
| --- | --- | --- |
| 159 | 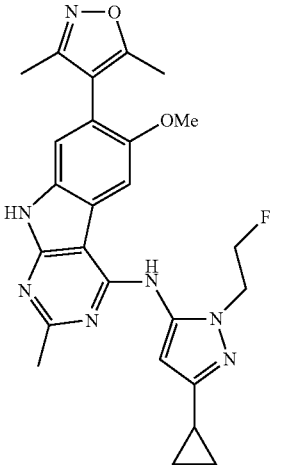 [SMILES: COc1cc2c(cc1-c1c(C)noc1C)[nH]c1nc(C)nc(Nc3cc(C4CC4)nn3CCF)c12] | N-(3-Cyclopropyl-1-(2-fluoroethyl)-1H-pyrazol-5-yl)-7-(3,5-dimethylisoxazol-4-yl)-6-methoxy-2-methyl-9H-pyrimido[4,5-b]indol-4-amine |
| 160 | 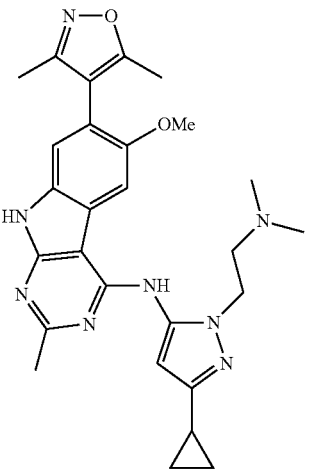 | N-(3-Cyclopropyl-1-(2-(dimethylamino)ethyl-1H-pyrazol-5-yl)-7-(3,5-dimethylisoxazol-4-yl)-6-methoxy-2-methyl-9H-pyrimido[4,5-b]indol-4-amine |
| 161 | 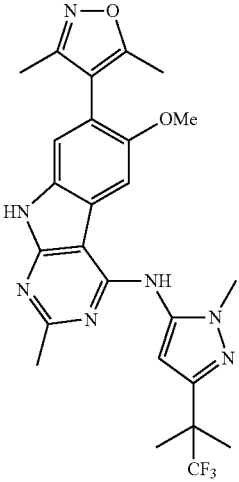 | 7-(3,5-Dimethylisoxazol-4-yl)-6-methoxy-2-methyl-N-(1-methyl-3-(1,1,1-trifluoro-2-methylpropan-2-yl)-1H-pyrazol-5-yl)-9H-pyrimido[4,5-b]indol-4-amine |

TABLE 1-continued
| Cpd. No. | Structure | Name |
|---|---|---|
| 162 | 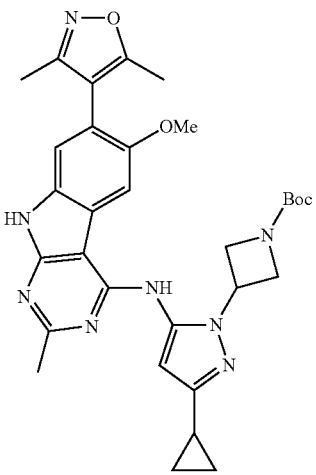 [SMILES: COc1cc2c(cc1-c1c(C)noc1C)[nH]c1nc(C)nc(Nc3cc(C4CC4)nn3C3CN(C(=O)OC(C)(C)C)C3)c12] | tert-butyl 3-(5-amino-3-cyclopropyl-1H-pyrazol-1-yl)azetidine-1-carboxylate |
| 163 | 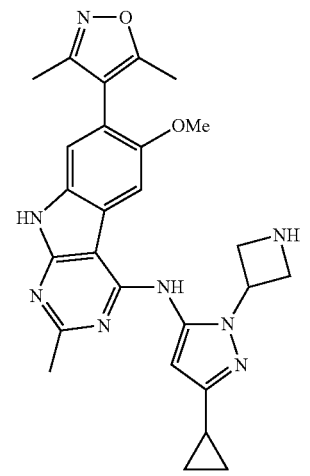 [SMILES: COc1cc2c(cc1-c1c(C)noc1C)[nH]c1nc(C)nc(Nc3cc(C4CC4)nn3C3CNC3)c12] | N-(1-(Azetidin-3-yl)-3-cyclopropyl-1H-pyrazol-5-yl)-7-(3,5-dimethylisoxazol-4-yl)-6-methoxy-2-methyl-9H-pyrimido[4,5-b]indol-4-amine |
| 166 | 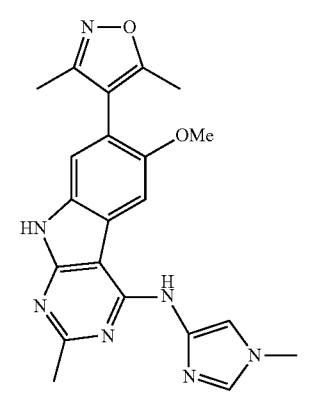 | 7-(3,5-dimethylisoxazol-4-yl)-6-methoxy-2-methyl-N-(1-methyl-1H-imidazol-4-yl)-9H-pyrimido[4,5-b]indol-4-amine |

TABLE 1-continued

| Cpd. No. | Structure | Name |
| --- | --- | --- |
| 169 | 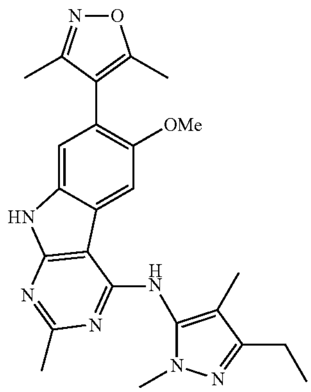 [SMILES: CCc1nn(C)c(Nc2nc(C)nc3[nH]c4cc(-c5c(C)noc5C)c(OC)cc4c23)c1C] | 7-(3,5-dimethylisoxazol-4-yl)-N-(3-ethyl-1,4-dimethyl-1H-pyrazol-5-yl)-6-methoxy-2-methyl-9H-pyrimido[4,5-b]indol-4-amine |
| 170 | 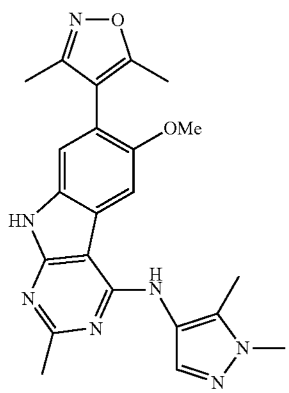 | N-(1,5-dimethyl-1H-pyrazol-4-yl)-7-(3,5-dimethylisoxazol-4-yl)-6-methoxy-2-methyl-9H-pyrimido[4,5-b]indol-4-amine |
| 171 | 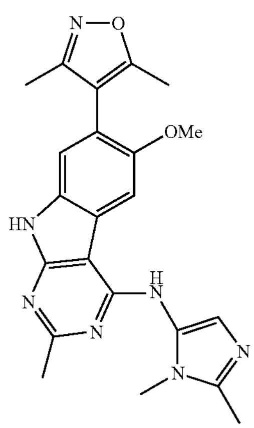 [SMILES: COc1cc2c(cc1-c1c(C)noc1C)[nH]c1nc(C)nc(Nc3cnc(C)n3C)c12] | N-(1,2-dimethyl-1H-imidazol-5-yl)-7-(3,5-dimethylisoxazol-4-yl)-6-methoxy-2-methyl-9H-pyrimido[4,5-b]indol-4-amine |
| 172 | 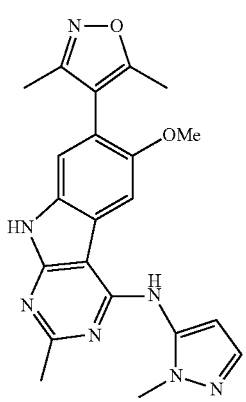 [SMILES: COc1cc2c(cc1-c1c(C)noc1C)[nH]c1nc(C)nc(Nc3ccnn3C)c12] | 7-(3,5-dimethylisoxazol-4-yl)-6-methoxy-2-methyl-N-(1-methyl-1H-pyrazol-5-yl)-9H-pyrimido[4,5-b]indol-4-amine |

TABLE 1-continued

| Cpd. No. | Structure | Name |
|---|---|---|
| 173 | 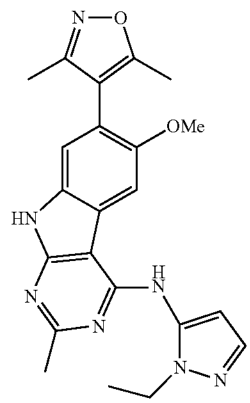 [SMILES: CCn1nccc1Nc1nc(C)nc2[nH]c3cc(-c4c(C)noc4C)c(OC)cc3c12] | 7-(3,5-dimethylisoxazol-4-yl)-N-(1-ethyl-1H-pyrazol-5-yl)-6-methoxy-2-methyl-9H-pyrimido[4,5-b]indol-4-amine |
| 174 | 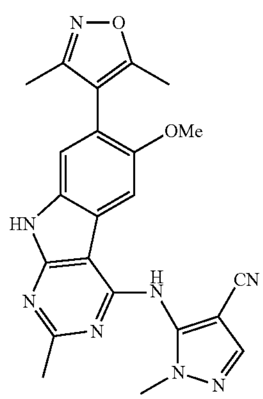 [SMILES: COc1cc2c(cc1-c1c(C)noc1C)[nH]c1nc(C)nc(Nc3c(C#N)cnn3C)c12] | 5-((7-(3,5-dimethylisoxazol-4-yl)-6-methoxy-2-methyl-9H-pyrimido[4,5-b]indol-4-yl)amino)-1-methyl-1H-pyrazole-4-carbonitrile |
| 175 | 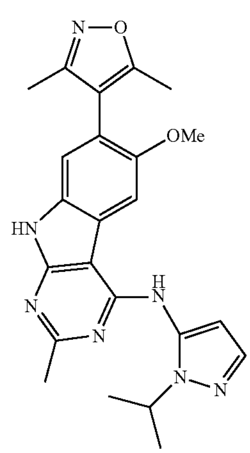 [SMILES: COc1cc2c(cc1-c1c(C)noc1C)[nH]c1nc(C)nc(Nc3ccnn3C(C)C)c12] | 7-(3,5-dimethylisoxazol-4-yl)-N-(1-isopropyl-1H-pyrazol-5-yl)-6-methoxy-2-methyl-9H-pyrimido[4,5-b]indol-4-amine |

TABLE 1-continued

| Cpd. No. | Structure | Name |
|---|---|---|
| 176 | 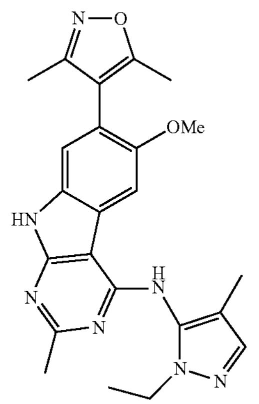 [SMILES: CCn1ncc(C)c1Nc1nc(C)nc2[nH]c3cc(-c4c(C)noc4C)c(OC)cc3c12] | 7-(3,5-dimethylisoxazol-4-yl)-N-(1-ethyl-4-methyl-1H-pyrazol-5-yl)-6-methoxy-2-methyl-9H-pyrimido[4,5-b]indol-4-amine |
| 177 | 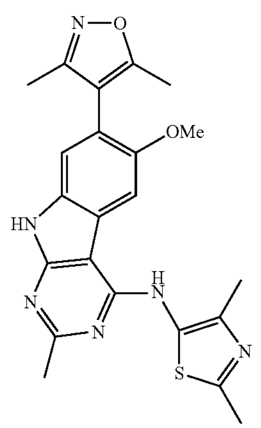 [SMILES: COc1cc2c(cc1-c1c(C)noc1C)[nH]c1nc(C)nc(Nc3sc(C)nc3C)c12] | N-(7-(3,5-dimethylisoxazol-4-yl)-6-methoxy-2-methyl-9H-pyrimido[4,5-b]indol-4-yl)-2,4-dimethylthiazol-5-amine |
| 178 | 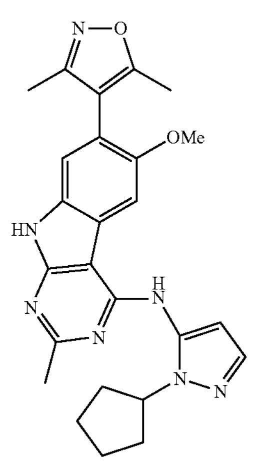 [SMILES: COc1cc2c(cc1-c1c(C)noc1C)[nH]c1nc(C)nc(Nc3ccnn3C3CCCC3)c12] | N-(1-cyclopentyl-1H-pyrazol-5-yl)-7-(3,5-dimethylisoxazol-4-yl)-6-methoxy-2-methyl-9H-pyrimido[4,5-b]indol-4-amine |

TABLE 1-continued

| Cpd. No. | Structure | Name |
| --- | --- | --- |
| 179 | 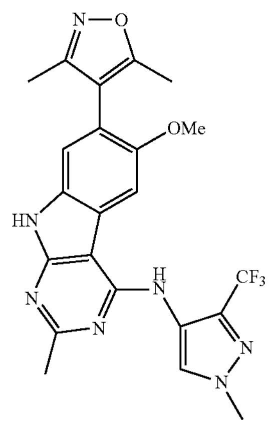 [SMILES: COc1cc2c(cc1-c1c(C)noc1C)[nH]c1nc(C)nc(Nc3cn(C)nc3C(F)(F)F)c12] | 7-(3,5-dimethylisoxazol-4-yl)-6-methoxy-2-methyl-N-(1-methyl-3-(trifluoromethyl)-1H-pyrazol-4-yl)-9H-pyrimido[4,5-b]indol-4-amine |
| 181 | 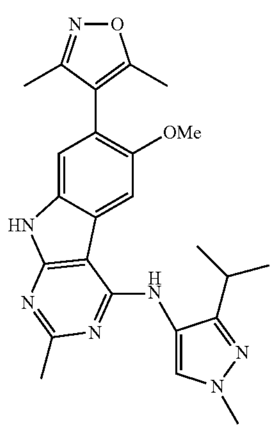 [SMILES: COc1cc2c(cc1-c1c(C)noc1C)[nH]c1nc(C)nc(Nc3cn(C)nc3C(C)C)c12] | 7-(3,5-dimethylisoxazol-4-yl)-N-(3-isopropyl-1-methyl-1H-pyrazol-4-yl)-6-methoxy-2-methyl-9H-pyrimido[4,5-b]indol-4-amine |
| 182 | 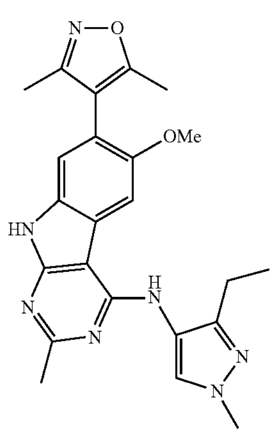 [SMILES: CCc1nn(C)cc1Nc1nc(C)nc2[nH]c3cc(-c4c(C)noc4C)c(OC)cc3c12] | 7-(3,5-dimethylisoxazol-4-yl)-N-(3-ethyl-1-methyl-1H-pyrazol-4-yl)-6-methoxy-2-methyl-9H-pyrimido[4,5-b]indol-4-amine |

TABLE 1-continued
| Cpd. No. | Structure | Name |
|---|---|---|
| 183 | 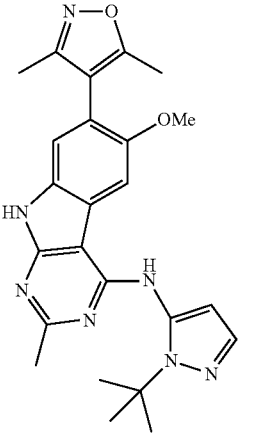 | N-(1-(tert-butyl)-1H-pyrazol-5-yl)-7-(3,5-dimethylisoxazol-4-yl)-6-methoxy-2-methyl-9H-pyrimido[4,5-b]indol-4-amine |
| 185 | 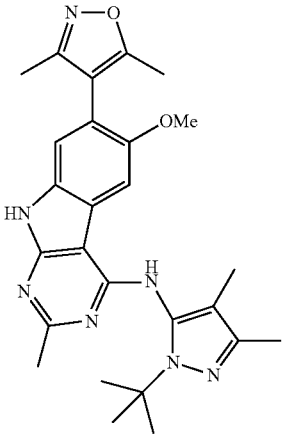 | N-(1-(tert-butyl)-3,4-dimethyl-1H-pyrazol-5-yl)-7-(3,5-dimethylisoxazol-4-yl)-6-methoxy-2-methyl-9H-pyrimido[4,5-b]indol-4-amine |
| 186 | 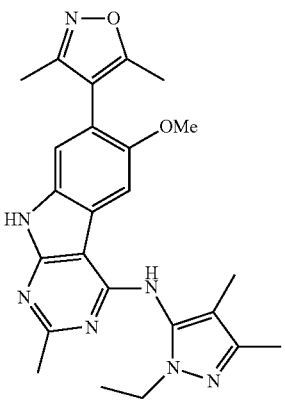 | 7-(3,5-dimethylisoxazol-4-yl)-N-(1-ethyl-3,4-dimethyl-1H-pyrazol-5-yl)-6-methoxy-2-methyl-9H-pyrimido[4,5-b]indol-4-amine |

TABLE 1-continued
| Cpd. No. | Structure | Name |
| --- | --- | --- |
| 187 | 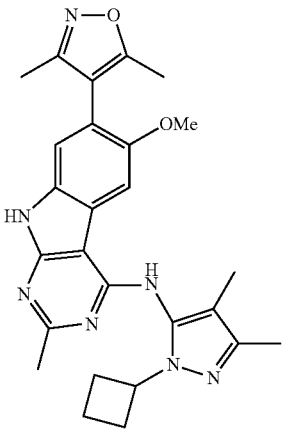 | N-(1-cyclobutyl-3,4-dimethyl-1H-pyrazol-5-yl)-7-(3,5-dimethylisoxazol-4-yl)-6-methoxy-2-methyl-9H-pyrimido[4,5-b]indol-4-amine |
| 188 | 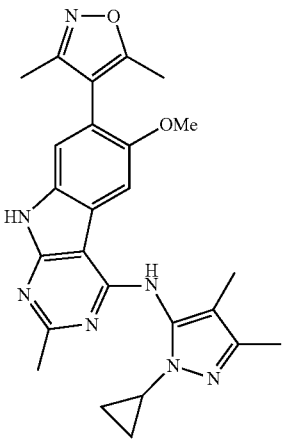 | N-(1-cyclopropyl-3,4-dimethyl-1H-pyrazol-5-yl)-7-(3,5-dimethylisoxazol-4-yl)-6-methoxy-2-methyl-9H-pyrimido[4,5-b]indol-4-amine |
| 190 | 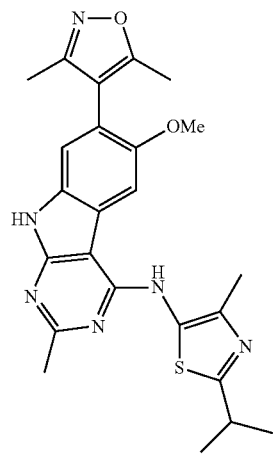 [SMILES: COc1cc2c(cc1-c1c(C)noc1C)[nH]c1nc(C)nc(Nc3sc(C(C)C)nc3C)c12] | N-(7-(3,5-dimethylisoxazol-4-yl)-6-methoxy-2-methyl-9H-pyrimido[4,5-b]indol-4-yl)-2-isopropyl-4-methylthiazol-5-amine |

| Cpd. No. | Structure | Name |
| --- | --- | --- |
| 192 | 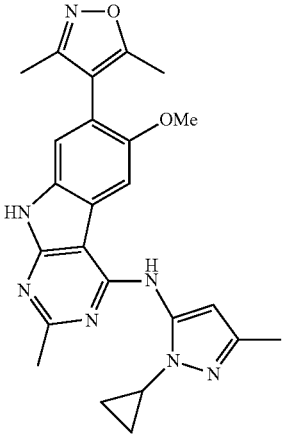 | N-(1-cyclopropyl-3-methyl-1H-pyrazol-5-yl)-7-(3,5-dimethylisoxazol-4-yl)-6-methoxy-2-methyl-9H-pyrimido[4,5-b]indol-4-amine |
| 193 | 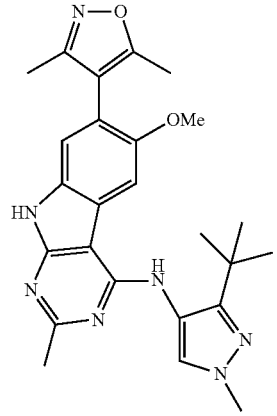 | N-(3-(tert-butyl)-1-methyl-1H-pyrazol-4-yl)-7-(3,5-dimethylisoxazol-4-yl)-6-methoxy-2-methyl-9H-pyrimido[4,5-b]indol-4-amine |
| 194 | 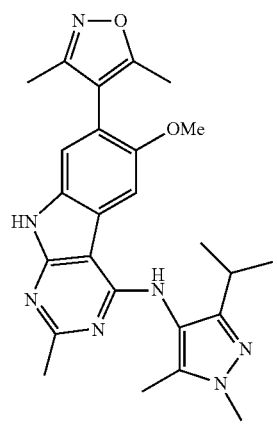 | 7-(3,5-dimethylisoxazol-4-yl)-N-(3-isopropyl-1,5-dimethyl-1H-pyrazol-4-yl)-6-methoxy-2-methyl-9H-pyrimido[4,5-b]indol-4-amine |

TABLE 1-continued
| Cpd. No. | Structure | Name |
|---|---|---|
| 195 | 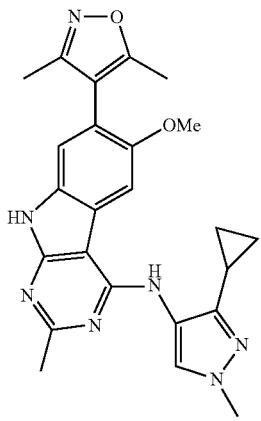 [SMILES: COc1cc2c(cc1-c1c(C)noc1C)[nH]c1nc(C)nc(Nc3cn(C)nc3C3CC3)c12] | N-(3-cyclopropyl-1-methyl-1H-pyrazol-4-yl)-7-(3,5-dimethylisoxazol-4-yl)-6-methoxy-2-methyl-9H-pyrimido[4,5-b]indol-4-amine |
| 196 | 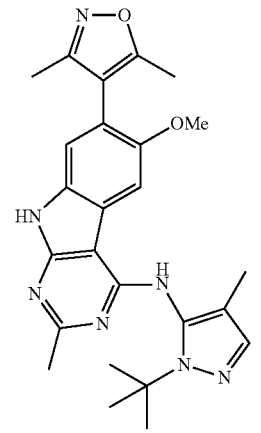 [SMILES: COc1cc2c(cc1-c1c(C)noc1C)[nH]c1nc(C)nc(Nc3c(C)cnn3C(C)(C)C)c12] | N-(1-(tert-butyl)-4-methyl-1H-pyrazol-5-yl)-7-(3,5-dimethylisoxazol-4-yl)-6-methoxy-2-methyl-9H-pyrimido[4,5-b]indol-4-amine |
| 197 | 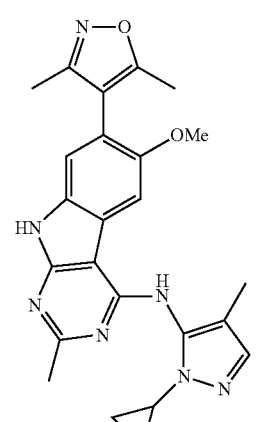 | N-(1-cyclopropyl-4-methyl-1H-pyrazol-5-yl)-7-(3,5-dimethylisoxazol-4-yl)-6-methoxy-2-methyl-9H-pyrimido[4,5-b]indol-4-amine |

TABLE 1-continued

| Cpd. No. | Structure | Name |
|---|---|---|
| 198 | 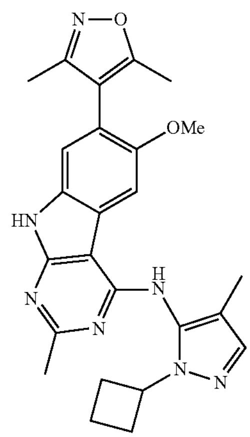 [SMILES: COc1cc2c(cc1-c1c(C)noc1C)[nH]c1nc(C)nc(Nc3c(C)cnn3C3CCC3)c12] | N-(1-cyclobutyl-4-methyl-1H-pyrazol-5-yl)-7-(3,5-dimethylisoxazol-4-yl)-6-methoxy-2-methyl-9H-pyrimido[4,5-b]indol-4-amine |
| 199 | 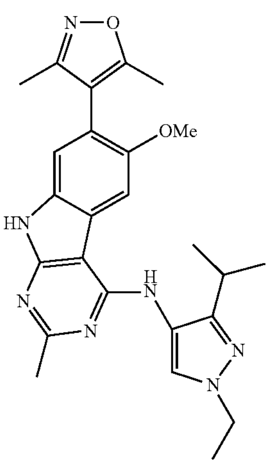 [SMILES: CCn1cc(Nc2nc(C)nc3[nH]c4cc(-c5c(C)noc5C)c(OC)cc4c23)c(C(C)C)n1] | 7-(3,5-dimethylisoxazol-4-yl)-N-(1-ethyl-3-isopropyl-1H-pyrazol-4-yl)-6-methoxy-2-methyl-9H-pyrimido[4,5-b]indol-4-amine |
| 200 | 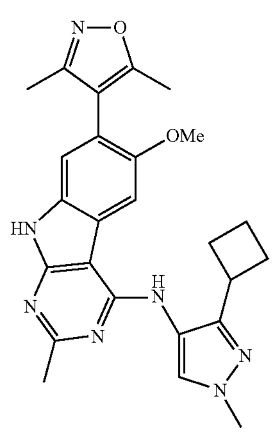 [SMILES: COc1cc2c(cc1-c1c(C)noc1C)[nH]c1nc(C)nc(Nc3cn(C)nc3C3CCC3)c12] | N-(3-cyclobutyl-1-methyl-1H-pyrazol-4-yl)-7-(3,5-dimethylisoxazol-4-yl)-6-methoxy-2-methyl-9H-pyrimido[4,5-b]indol-4-amine |

TABLE 1-continued
| Cpd. No. | Structure | Name |
|---|---|---|
| 201 | 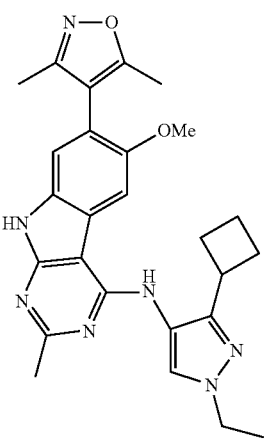 | N-(3-cyclobutyl-1-ethyl-1H-pyrazol-4-yl)-7-(3,5-dimethylisoxazol-4-yl)-6-methoxy-2-methyl-9H-pyrimido[4,5-b]indol-4-amine |
| 202 | 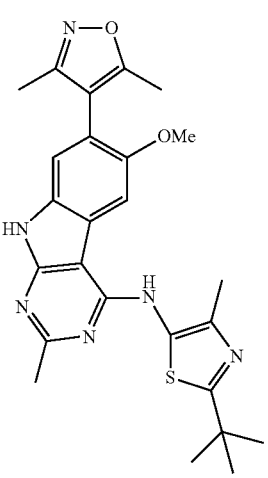 [SMILES: COc1cc2c(cc1-c1c(C)noc1C)[nH]c1nc(C)nc(Nc3sc(C(C)(C)C)nc3C)c12] | 2-(tert-butyl)-N-(7-(3,5-dimethylisoxazol-4-yl)-6-methoxy-2-methyl-9H-pyrimido[4,5-b]indol-4-yl)-4-methylthiazol-5-amine |
| 203 | 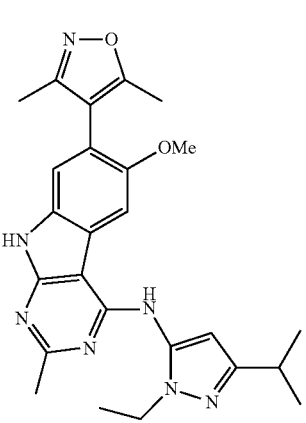 [SMILES: CCn1nc(C(C)C)cc1Nc1nc(C)nc2[nH]c3cc(-c4c(C)noc4C)c(OC)cc3c12] | 7-(3,5-dimethylisoxazol-4-yl)-N-(1-ethyl-3-isopropyl-1H-pyrazol-5-yl)-6-methoxy-2-methyl-9H-pyrimido[4,5-b]indol-4-amine |

TABLE 1-continued
| Cpd. No. | Structure | Name |
|---|---|---|
| 205 | 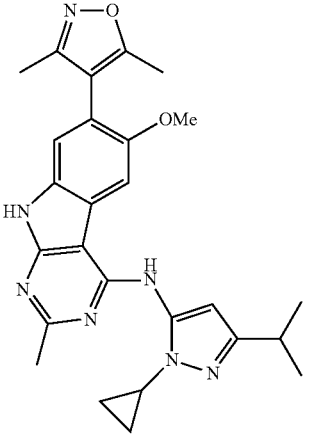 [SMILES: COc1cc2c(cc1-c1c(C)noc1C)[nH]c1nc(C)nc(Nc3cc(C(C)C)nn3C3CC3)c12] | N-(1-cyclopropyl-3-isopropyl-1H-pyrazol-5-yl)-7-(3,5-dimethylisoxazol-4-yl)-6-methoxy-2-methyl-9H-pyrimido[4,5-b]indol-4-amine |
| 206 | 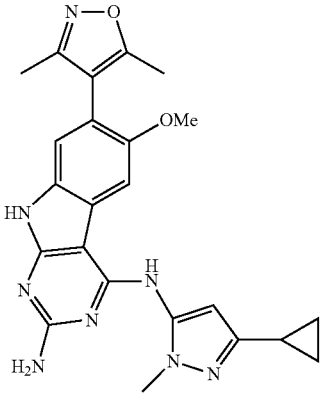 [SMILES: COc1cc2c(cc1-c1c(C)noc1C)[nH]c1nc(N)nc(Nc3cc(C4CC4)nn3C)c12] | N4-(3-cyclopropyl-1-methyl-1H-pyrazol-5-yl)-7-(3,5-dimethylisoxazol-4-yl)-6-methoxy-9H-pyrimido[4,5-b]indole-2,4-diamine |
| 207 | 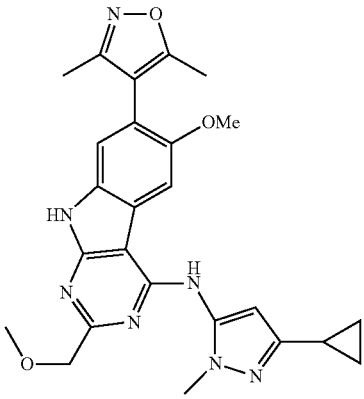 [SMILES: COCc1nc(Nc2cc(C3CC3)nn2C)c2c(n1)[nH]c1cc(-c3c(C)noc3C)c(OC)cc12] | N-(3-cyclopropyl-1-methyl-1H-pyrazol-5-yl)-7-(3,5-dimethylisoxazol-4-yl)-6-methoxy-2-(methoxymethyl)-9H-pyrimido[4,5-b]indol-4-amine |

TABLE 1-continued

| Cpd. No. | Structure | Name |
|---|---|---|
| 210 | 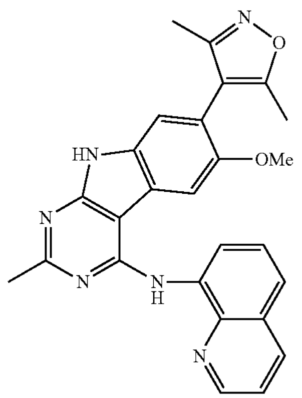 | 7-(3,5-dimethylisoxazol-4-yl)-6-methoxy-2-methyl-N-(quinolin-8-yl)-9H-pyrimido[4,5-b]indol-4-amine |
| 211 | 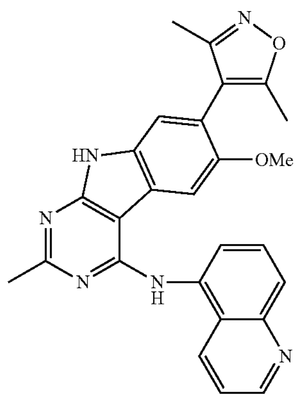 | 7-(3,5-dimethylisoxazol-4-yl)-6-methoxy-2-methyl-N-(quinolin-5-yl)-9H-pyrimido[4,5-b]indol-4-amine |
| 212 | 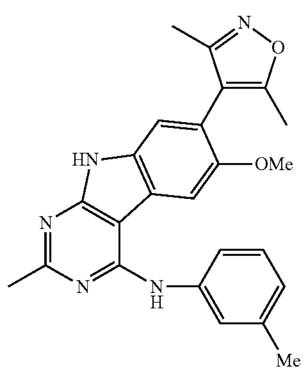 | 7-(3,5-dimethylisoxazol-4-yl)-6-methoxy-2-methyl-N-m-tolyl-9H-pyrimido[4,5-b]indol-4-amine |
| 213 | 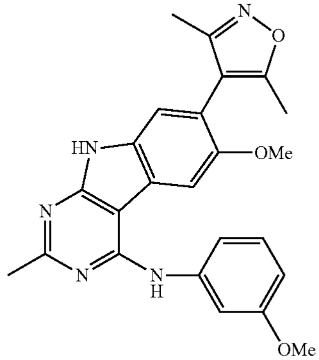 | 7-(3,5-dimethylisoxazol-4-yl)-6-methoxy-N-(3-methoxyphenyl)-2-methyl-9H-pyrimido[4,5-b]indol-4-amine |

TABLE 1-continued

| Cpd. No. | Structure | Name |
|---|---|---|
| 214 | 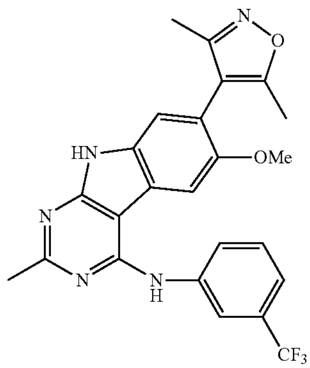 | 7-(3,5-dimethylisoxazol-4-yl)-6-methoxy-2-methyl-N-(3-(trifluoromethyl)phenyl)-9H-pyrimido[4,5-b]indol-4-amine |
| 215 | 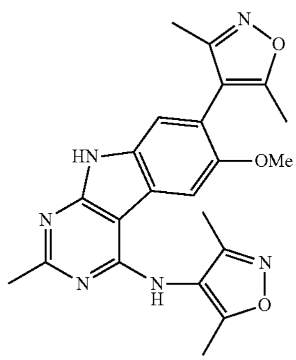 | N-(7-(3,5-dimethylisoxazol-4-yl)-6-methoxy-2-methyl-9H-pyrimido[4,5-b]indol-4-yl)-3,5-dimethylisoxazol-4-amine |
| 216 | 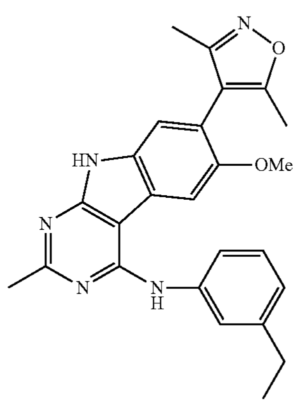 | 7-(3,5-dimethylisoxazol-4-yl)-N-(3-ethylphenyl)-6-methoxy-2-methyl-9H-pyrimido[4,5-b]indol-4-amine |
| 217 | 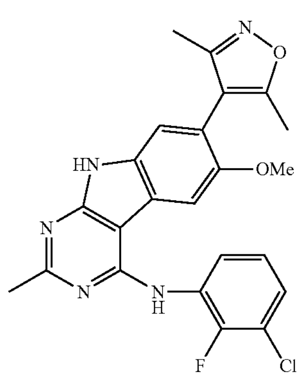 | N-(3-chloro-2-fluorophenyl)-7-(3,5-dimethylisoxazol-4-yl)-6-methoxy-2-methyl-9H-pyrimido[4,5-b]indol-4-amine |

TABLE 1-continued

| Cpd. No. | Structure | Name |
|---|---|---|
| 218 | 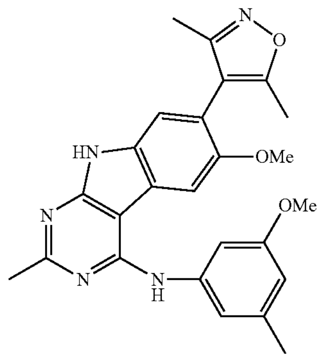 | 7-(3,5-dimethylisoxazol-4-yl)-6-methoxy-N-(3-methoxy-5-methylphenyl)-2-methyl-9H-pyrimido[4,5-b]indol-4-amine |
| 219 | 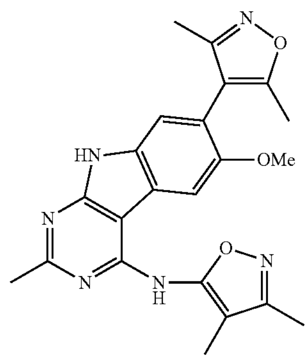 | N-(7-(3,5-dimethylisoxazol-4-yl)-6-methoxy-2-methyl-9H-pyrimido[4,5-b]indol-4-yl)-3,4-dimethylisoxazol-5-amine |
| 220 | 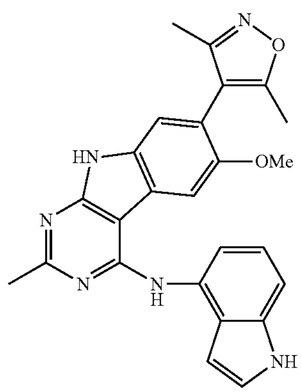 | 7-(3,5-dimethylisoxazol-4-yl)-N-(1H-indol-4-yl)-6-methoxy-2-methyl-9H-pyrimido[4,5-b]indol-4-amine |
| 221 | 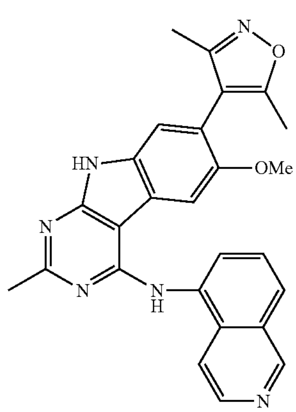 | 7-(3,5-dimethylisoxazol-4-yl)-N-(isoquinolin-5-yl)-6-methoxy-2-methyl-9H-pyrimido[4,5-b]indol-4-amine |

TABLE 1-continued

| Cpd. No. | Structure | Name |
|---|---|---|
| 222 | 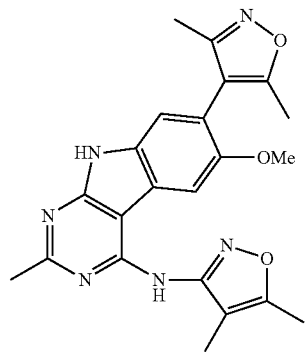 | N-(7-(3,5-dimethylisoxazol-4-yl)-6-methoxy-2-methyl-9H-pyrimido[4,5-b]indol-4-yl)-4,5-dimethylisoxazol-3-amine |
| 223 | 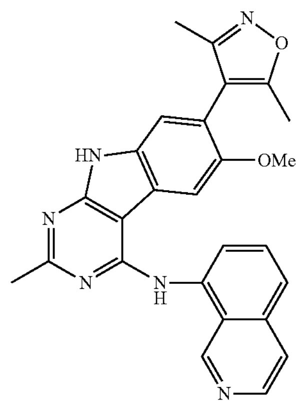 | 7-(3,5-dimethylisoxazol-4-yl)-N-(isoquinolin-8-yl)-6-methoxy-2-methyl-9H-pyrimido[4,5-b]indol-4-amine |
| 224 | 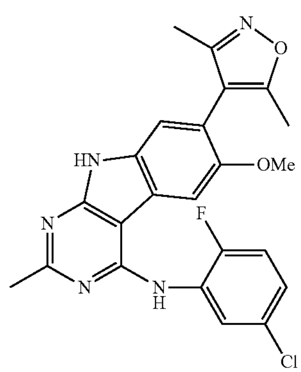 | N-(5-chloro-2-fluorophenyl)-7-(3,5-dimethylisoxazol-4-yl)-6-methoxy-2-methyl-9H-pyrimido[4,5-b]indol-4-amine |
| 225 | 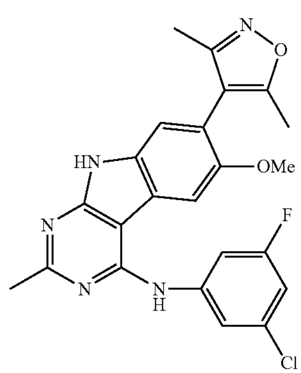 | N-(3-chloro-5-fluorophenyl)-7-(3,5-dimethylisoxazol-4-yl)-6-methoxy-2-methyl-9H-pyrimido[4,5-b]indol-4-amine |

TABLE 1-continued

| Cpd. No. | Structure | Name |
| --- | --- | --- |
| 226 | 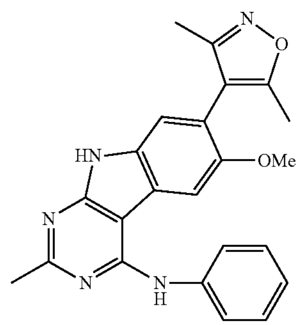 | 7-(3,5-dimethylisoxazol-4-yl)-6-methoxy-2-methyl-N-phenyl-9H-pyrimido[4,5-b]indol-4-amine |
| 227 | 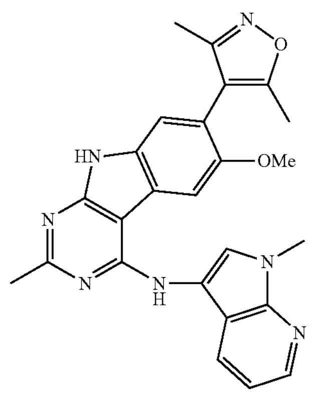 | 7-(3,5-dimethylisoxazol-4-yl)-6-methoxy-2-methyl-N-(1-methyl-1H-pyrrolo[2,3-b]pyridin-3-yl)-9H-pyrimido[4,5-b]indol-4-amine |
| 228 | 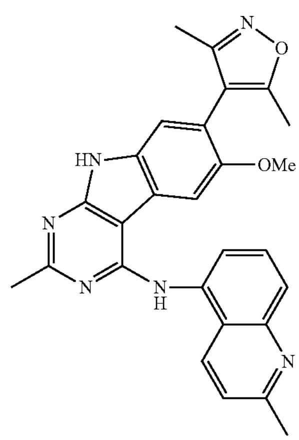 | 7-(3,5-dimethylisoxazol-4-yl)-6-methoxy-2-methyl-N-(2-methylquinolin-5-yl)-9H-pyrimido[4,5-b]indol-4-amine |
| 229 | 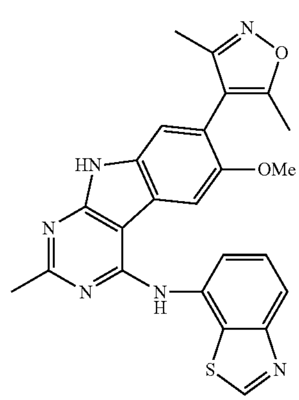 | N-(7-(3,5-dimethylisoxazol-4-yl)-6-methoxy-2-methyl-9H-pyrimido[4,5-b]indol-4-yl)benzo[d]thiazol-7-amine |

TABLE 1-continued

| Cpd. No. | Structure | Name |
|---|---|---|
| 230 | 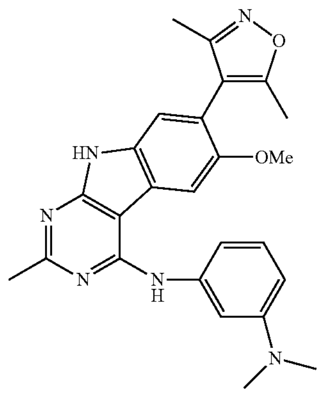 | N1-(7-(3,5-dimethylisoxazol-4-yl)-6-methoxy-2-methyl-9H-pyrimido[4,5-b]indol-4-yl)-N3,N3-dimethylbenzene-1,3-diamine |
| 231 | 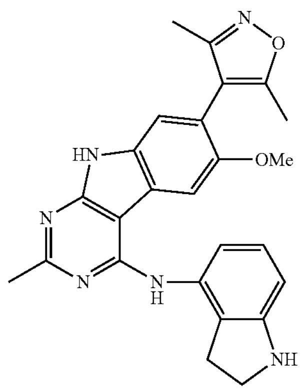 | 7-(3,5-dimethylisoxazol-4-yl)-N-(indolin-4-yl)-6-methoxy-2-methyl-9H-pyrimido[4,5-b]indol-4-amine |
| 232 | 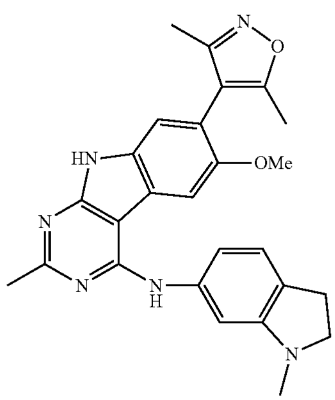 [SMILES: COc1cc2c(cc1-c1c(C)noc1C)[nH]c1nc(C)nc(Nc3ccc4c(c3)N(C)CC4)c12] | 7-(3,5-dimethylisoxazol-4-yl)-6-methoxy-2-methyl-N-(1-methylindolin-6-yl)-9H-pyrimido[4,5-b]indol-4-amine |
| 233 | 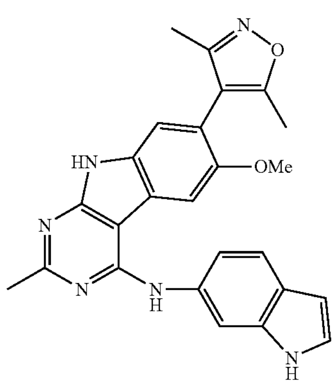 [SMILES: COc1cc2c(cc1-c1c(C)noc1C)[nH]c1nc(C)nc(Nc3ccc4cc[nH]c4c3)c12] | 7-(3,5-dimethylisoxazol-4-yl)-N-(1H-indol-6-yl)-6-methoxy-2-methyl-9H-pyrimido[4,5-b]indol-4-amine |

TABLE 1-continued

| Cpd. No. | Structure | Name |
|---|---|---|
| 234 | 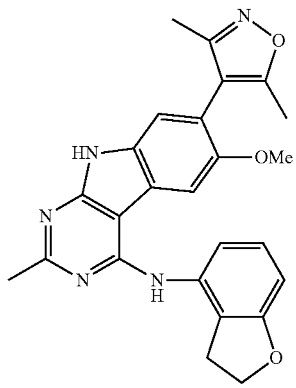 | N-(2,3-dihydrobenzofuran-4-yl)-7-(3,5-dimethylisoxazol-4-yl)-6-methoxy-2-methyl-9H-pyrimido[4,5-b]indol-4-amine |
| 235 | 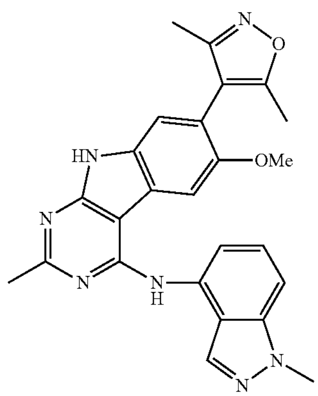 | 7-(3,5-dimethylisoxazol-4-yl)-6-methoxy-2-methyl-N-(1-methyl-1H-indazol-4-yl)-9H-pyrimido[4,5-b]indol-4-amine |
| 236 | 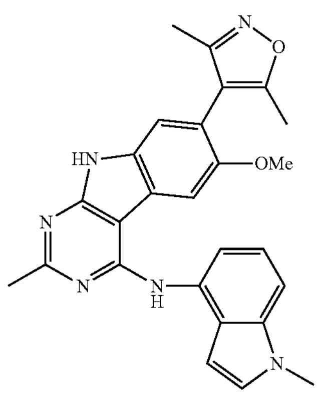 | 7-(3,5-dimethylisoxazol-4-yl)-6-methoxy-2-methyl-N-(1-methyl-1H-indol-4-yl)-9H-pyrimido[4,5-b]indol-4-amine |
| 237 | 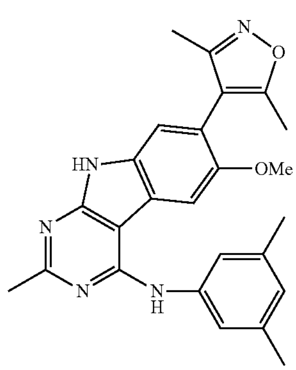 | 7-(3,5-dimethylisoxazol-4-yl)-N-(3,5-dimethylphenyl)-6-methoxy-2-methyl-9H-pyrimido[4,5-b]indol-4-amine |

TABLE 1-continued

| Cpd. No. | Structure | Name |
|---|---|---|
| 238 | 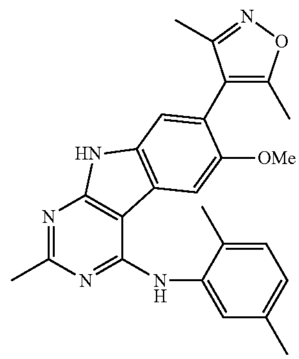 | 7-(3,5-dimethylisoxazol-4-yl)-N-(2,5-dimethylphenyl)-6-methoxy-2-methyl-9H-pyrimido[4,5-b]indol-4-amine |
| 239 | 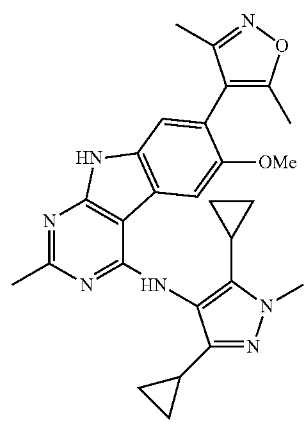 | N-(3,5-dicyclopropyl-1-methyl-1H-pyrazol-4-yl)-7-(3,5-dimethylisoxazol-4-yl)-6-methoxy-2-methyl-9H-pyrimido[4,5-b]indol-4-amine |
| 240 | 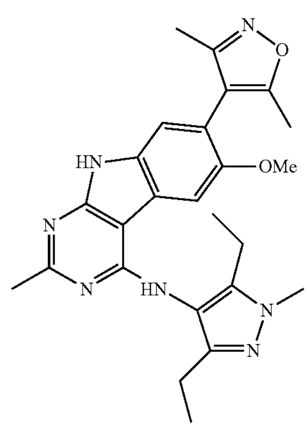 | N-(3,5-diethyl-1-methyl-1H-pyrazol-4-yl)-7-(3,5-dimethylisoxazol-4-yl)-6-methoxy-2-methyl-9H-pyrimido[4,5-b]indol-4-amine |
| 241 | 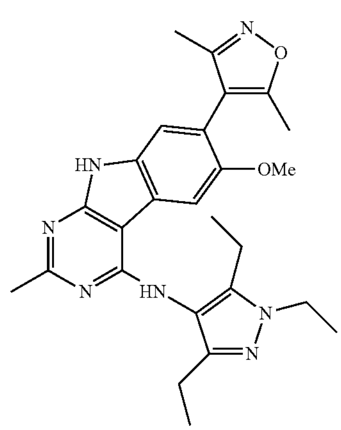 [SMILES: CCc1nn(CC)c(CC)c1Nc1nc(C)nc2[nH]c3cc(-c4c(C)noc4C)c(OC)cc3c12] | 7-(3,5-dimethylisoxazol-4-yl)-6-methoxy-2-methyl-N-(1,3,5-triethyl-1H-pyrazol-4-yl)-9H-pyrimido[4,5-b]indol-4-amine |

TABLE 1-continued

| Cpd. No. | Structure | Name |
|---|---|---|
| 242 | 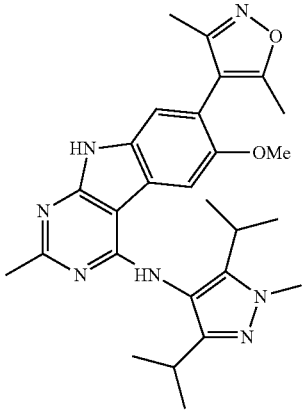 | N-(3,5-diisopropyl-1-methyl-1H-pyrazol-4-yl)-7-(3,5-dimethylisoxazol-4-yl)-6-methoxy-2-methyl-9H-pyrimido[4,5-b]indol-4-amine |
| 243 | 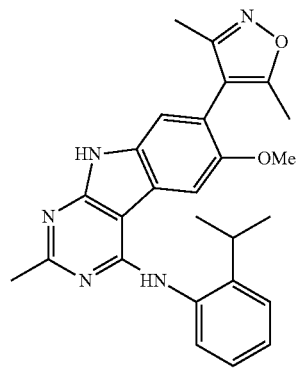 | 7-(3,5-dimethylisoxazol-4-yl)-N-(2-isopropylphenyl)-6-methoxy-2-methyl-9H-pyrimido[4,5-b]indol-4-amine |
| 247 | 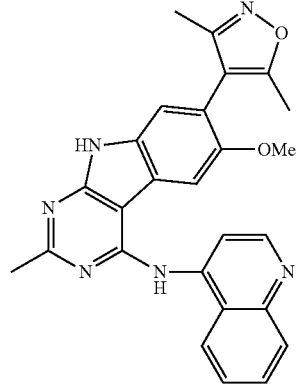 | 7-(3,5-dimethylisoxazol-4-yl)-6-methoxy-2-methyl-N-(quinolin-4-yl)-9H-pyrimido[4,5-b]indol-4-amine |
| 248 | 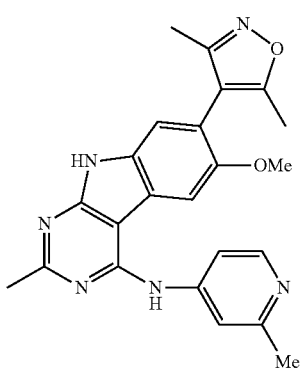 | 7-(3,5-dimethylisoxazol-4-yl)-6-methoxy-2-methyl-N-(2-methylpyridin-4-yl)-9H-pyrimido[4,5-b]indol-4-amine |

TABLE 1-continued

| Cpd. No. | Structure | Name |
|---|---|---|
| 249 | 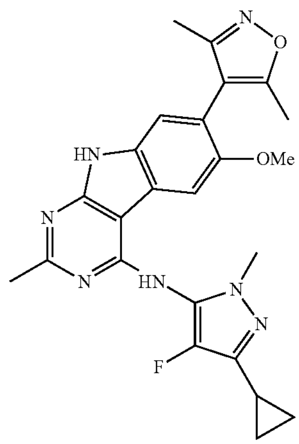 [SMILES: COc1cc2c(cc1-c1c(C)noc1C)[nH]c1nc(C)nc(Nc3c(F)c(C4CC4)nn3C)c12] | N-(3-cyclopropyl-4-fluoro-1-methyl-1H-pyrazol-5-yl)-7-(3,5-dimethylisoxazol-4-yl)-6-methoxy-2-methyl-9H-pyrimido[4,5-b]indol-4-amine |
| 250 | 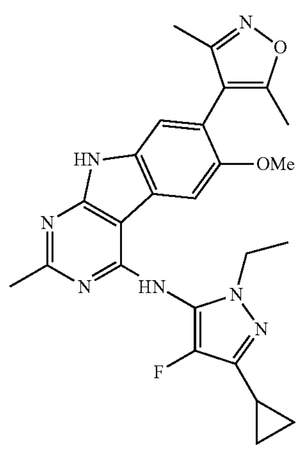 [SMILES: CCn1nc(C2CC2)c(F)c1Nc1nc(C)nc2[nH]c3cc(-c4c(C)noc4C)c(OC)cc3c12] | N-(3-cyclopropyl-1-ethyl-4-fluoro-1H-pyrazol-5-yl)-7-(3,5-dimethylisoxazol-4-yl)-6-methoxy-2-methyl-9H-pyrimido[4,5-b]indol-4-amine |
| 251 | 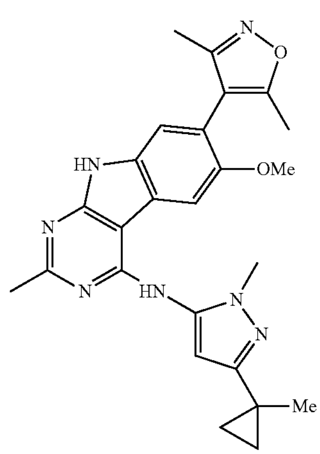 [SMILES: COc1cc2c(cc1-c1c(C)noc1C)[nH]c1nc(C)nc(Nc3cc(C4(C)CC4)nn3C)c12] | 7-(3,5-dimethylisoxazol-4-yl)-6-methoxy-2-methyl-N-(1-methyl-3-(1-methylcyclopropyl)-1H-pyrazol-5-yl)-9H-pyrimido[4,5-b]indol-4-amine |

TABLE 1-continued
| Cpd. No. | Structure | Name |
|---|---|---|
| 252 | 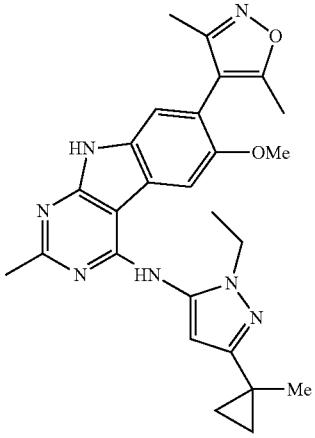 [SMILES: CCn1nc(C2(C)CC2)cc1Nc1nc(C)nc2[nH]c3cc(-c4c(C)noc4C)c(OC)cc3c12] | 7-(3,5-dimethylisoxazol-4-yl)-N-(1-ethyl-3-(1-methylcyclopropyl)-1H-pyrazol-5-yl)-6-methoxy-2-methyl-9H-pyrimido[4,5-b]indol-4-amine |
| 253 | 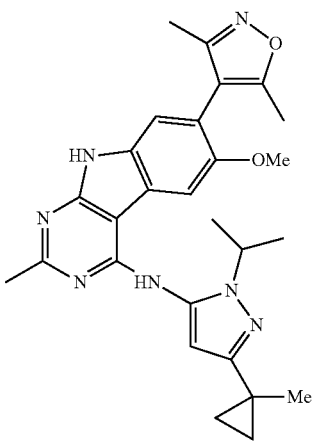 [SMILES: COc1cc2c(cc1-c1c(C)noc1C)[nH]c1nc(C)nc(Nc3cc(C4(C)CC4)nn3C(C)C)c12] | 7-(3,5-dimethylisoxazol-4-yl)-N-(1-isopropyl-3-(1-methylcyclopropyl)-1H-pyrazol-5-yl)-6-methoxy-2-methyl-9H-pyrimido[4,5-b]indol-4-amine |
| 254 | 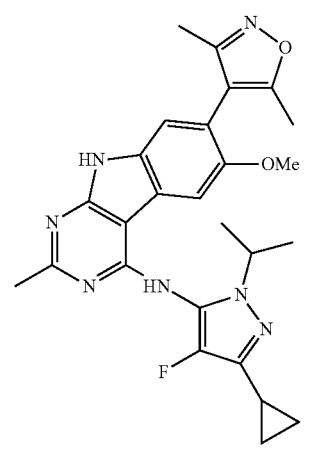 [SMILES: COc1cc2c(cc1-c1c(C)noc1C)[nH]c1nc(C)nc(Nc3c(F)c(C4CC4)nn3C(C)C)c12] | N-(3-cyclopropyl-4-fluoro-1-isopropyl-1H-pyrazol-5-yl)-7-(3,5-dimethylisoxazol-4-yl)-6-methoxy-2-methyl-9H-pyrimido[4,5-b]indol-4-amine |

TABLE 1-continued
| Cpd. No. | Structure | Name |
|---|---|---|
| 255 | 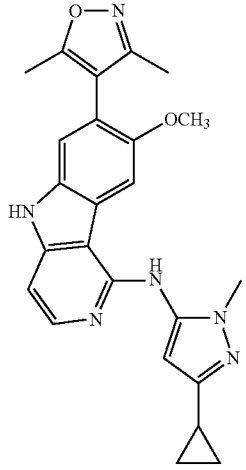 | N-(3-cyclopropyl-1-methyl-1H-pyrazol-5-yl)-7-(3,5-dimethylisoxazol-4-yl)-8-methoxy-5H-pyrido[4,3-b]indol-1-amine |
| 256 | 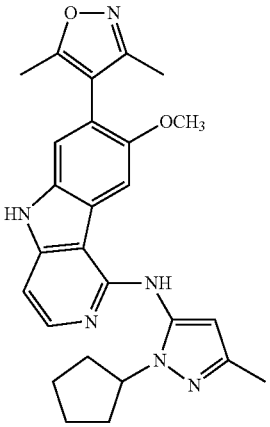 | N-(1-cyclopentyl-3-methyl-1H-pyrazol-5-yl)-7-(3,5-dimethylisoxazol-4-yl)-8-methoxy-5H-pyrido[4,3-b]indol-1-amine |
| 257 | 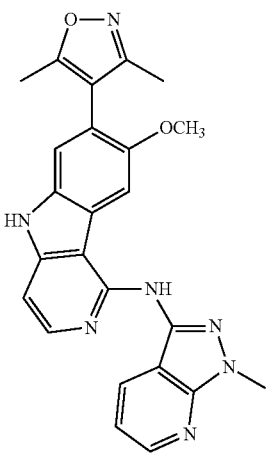 | 7-(3,5-dimethylisoxazol-4-yl)-8-methoxy-N-(1-methyl-1H-pyrazolo[3,4-b]pyridin-3-yl)-5H-pyrido[4,3-b]indol-1-amine |

TABLE 1-continued
| Cpd. No. | Structure | Name |
|---|---|---|
| 258 | 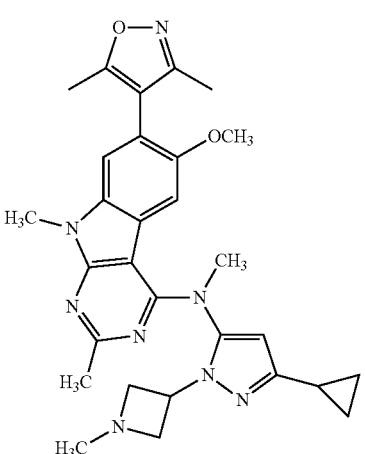 | N-(3-cyclopropyl-1-(1-methylazetidin-3-yl)-1H-pyrazol-5-yl)-7-(3,5-dimethylisoxazol-4-yl)-6-methoxy-N,2,9-trimethyl-9H-pyrimido[4,5-b]indol-4-amine |
| 259 | 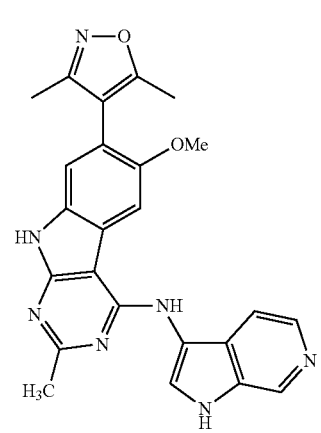 [SMILES: COc1cc2c(cc1-c1c(C)noc1C)[nH]c1nc(C)nc(Nc3c[nH]c4cnccc34)c12] | 7-(3,5-dimethylisoxazol-4-yl)-6-methoxy-2-methyl-N-(1H-pyrrolo[2,3-c]pyridin-3-yl)-9H-pyrimido[4,5-b]indol-4-amine |
| 260 | 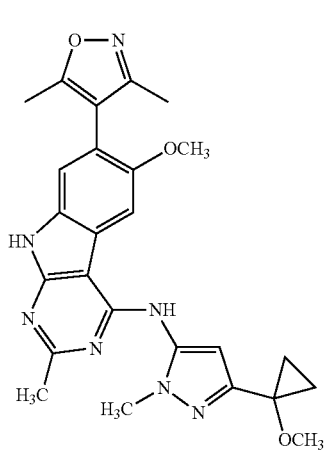 [SMILES: COc1cc2c(cc1-c1c(C)noc1C)[nH]c1nc(C)nc(Nc3cc(C4(OC)CC4)nn3C)c12] | 7-(3,5-dimethylisoxazol-4-yl)-6-methoxy-N-(3-(1-methoxycyclopropyl)-1-methyl-1H-pyrazol-5-yl)-2-methyl-9H-pyrimido[4,5-b]indol-4-amine |

TABLE 1-continued
| Cpd. No. | Structure | Name |
|---|---|---|
| 261 | 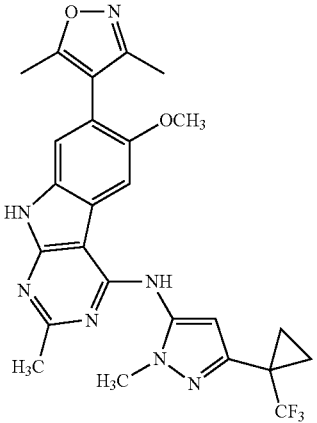 [SMILES: COc1cc2c(cc1-c1c(C)noc1C)[nH]c1nc(C)nc(Nc3cc(C4(C(F)(F)F)CC4)nn3C)c12] | 7-(3,5-dimethylisoxazol-4-yl)-6-methoxy-2-methyl-N-(1-methyl-3-(1-(trifluoromethyl)cyclopropyl)-1H-pyrazol-5-yl)-9H-pyrimido[4,5-b]indol-4-amine |
| 262 | 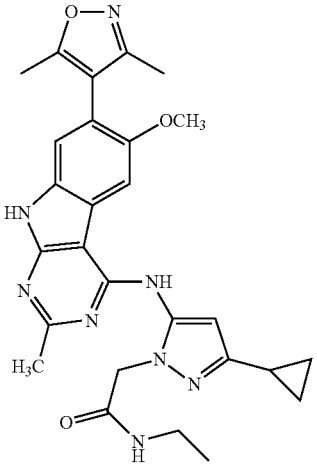 [SMILES: CCNC(=O)Cn1nc(C2CC2)cc1Nc1nc(C)nc2[nH]c3cc(-c4c(C)noc4C)c(OC)cc3c12] | 2-(3-cyclopropyl-5-((7-(3,5-dimethylisoxazol-4-yl)-6-methoxy-2-methyl-9H-pyrimido[4,5-b]indol-4-yl)amino)-1H-pyrazol-1-yl)-N-ethylacetamide |
| 263 | 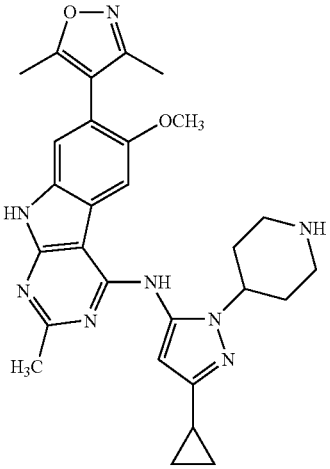 [SMILES: COc1cc2c(cc1-c1c(C)noc1C)[nH]c1nc(C)nc(Nc3cc(C4CC4)nn3C3CCNCC3)c12] | N-(3-cyclopropyl-1-(piperidin-4-yl)-1H-pyrazol-5-yl)-7-(3,5-dimethylisoxazol-4-yl)-6-methoxy-2-methyl-9H-pyrimido[4,5-b]indol-4-amine |

TABLE 1-continued

| Cpd. No. | Structure | Name |
|---|---|---|
| 264 | 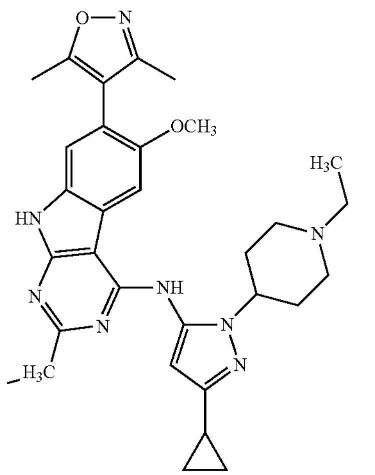 [SMILES: CCc1nc(Nc2cc(C3CC3)nn2C2CCN(CC)CC2)c2c(n1)[nH]c1cc(-c3c(C)noc3C)c(OC)cc12] | N-(3-cyclopropyl-1-(1-ethylpiperidin-4-yl)-1H-pyrazol-5-yl)-7-(3,5-dimethylisoxazol-4-yl)-6-methoxy-2-methyl-9H-pyrimido[4,5-b]indol-4-amine |
| 265 | 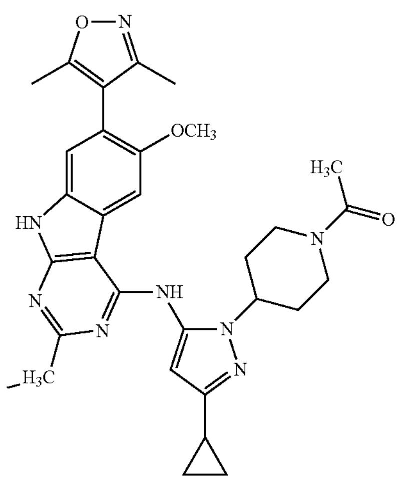 [SMILES: CCc1nc(Nc2cc(C3CC3)nn2C2CCN(C(C)=O)CC2)c2c(n1)[nH]c1cc(-c3c(C)noc3C)c(OC)cc12] | 1-(4-(3-cyclopropyl-5-(7-(3,5-dimethylisoxazol-4-yl)-6-methoxy-2-methyl-9H-pyrimido[4,5-b]indol-4-ylamino)-1H-pyrazol-1-yl)piperidin-1-yl)ethanone |
| 266 | 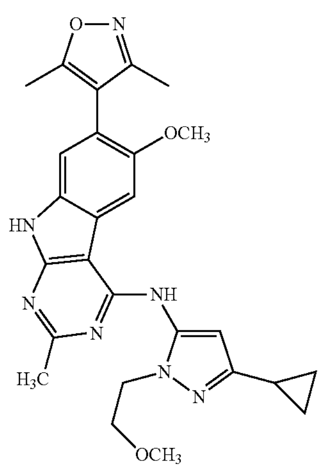 [SMILES: COCCn1nc(C2CC2)cc1Nc1nc(C)nc2[nH]c3cc(-c4c(C)noc4C)c(OC)cc3c12] | N-(3-cyclopropyl-1-(2-methoxyethyl)-1H-pyrazol-5-yl)-7-(3,5-dimethylisoxazol-4-yl)-6-methoxy-2-methyl-9H-pyrimido[4,5-b]indol-4-amine |

TABLE 1-continued
| Cpd. No. | Structure | Name |
|---|---|---|
| 267 | 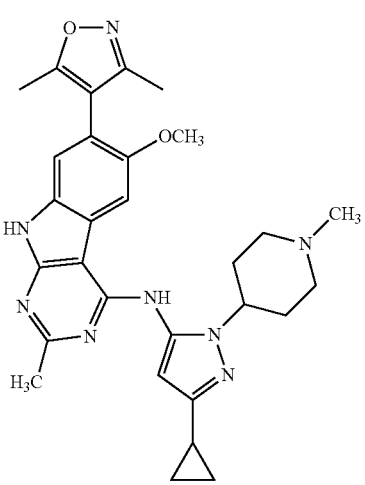 | N-(3-cyclopropyl-1-(1-methylpiperidin-4-yl)-1H-pyrazol-5-yl)-7-(3,5-dimethylisoxazol-4-yl)-6-methoxy-2-methyl-9H-pyrimido[4,5-b]indol-4-amine |
| 268 | 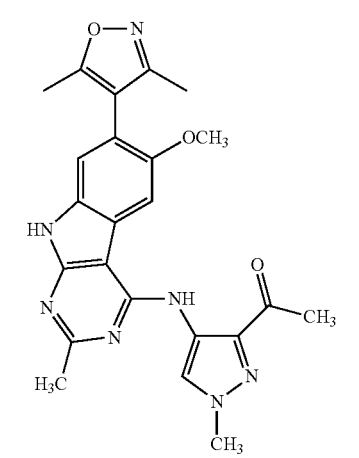 [SMILES: COc1cc2c(cc1-c1c(C)noc1C)[nH]c1nc(C)nc(Nc3cn(C)nc3C(C)=O)c12] | 1-(4-(7-(3,5-dimethylisoxazol-4-yl)-6-methoxy-2-methyl-9H-pyrimido[4,5-b]indol-4-ylamino)-1-methyl-1H-pyrazol-3-yl)ethanone |
| 269 | 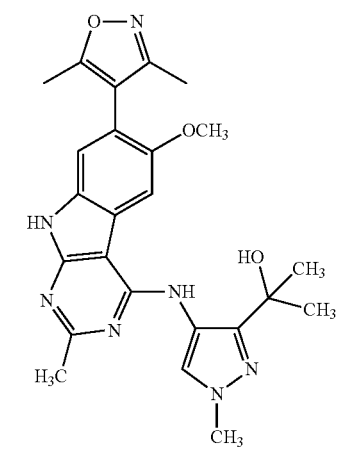 [SMILES: COc1cc2c(cc1-c1c(C)noc1C)[nH]c1nc(C)nc(Nc3cn(C)nc3C(C)(C)O)c12] | 2-(4-(7-(3,5-dimethylisoxazol-4-yl)-6-methoxy-2-methyl-9H-pyrimido[4,5-b]indol-4-ylamino)-1-methyl-1H-pyrazol-3-yl)propan-2-ol |

TABLE 1-continued

| Cpd. No. | Structure | Name |
|---|---|---|
| 270 | 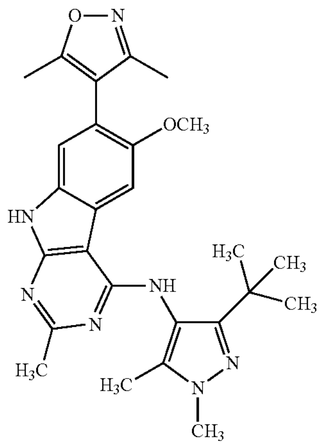 [SMILES: COc1cc2c(cc1-c1c(C)noc1C)[nH]c1nc(C)nc(Nc3c(C(C)(C)C)nn(C)c3C)c12] | N-(3-tert-butyl-1,5-dimethyl-1H-pyrazol-4-yl)-7-(3,5-dimethylisoxazol-4-yl)-6-methoxy-2-methyl-9H-pyrimido[4,5-b]indol-4-amine |
| 271 | 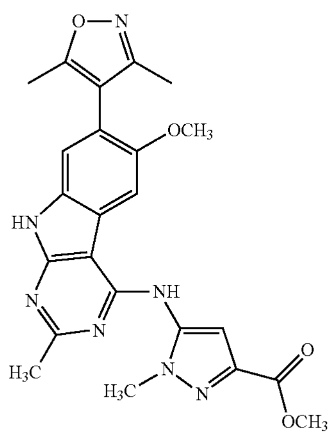 [SMILES: COC(=O)c1cc(Nc2nc(C)nc3[nH]c4cc(-c5c(C)noc5C)c(OC)cc4c23)n(C)n1] | methyl 5-(7-(3,5-dimethylisoxazol-4-yl)-6-methoxy-2-methyl-9H-pyrimido[4,5-b]indol-4-ylamino)-1-methyl-1H-pyrazole-3-carboxylate |
| 272 | 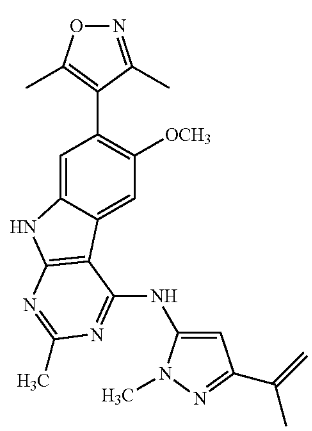 [SMILES: C=C(C)c1cc(Nc2nc(C)nc3[nH]c4cc(-c5c(C)noc5C)c(OC)cc4c23)n(C)n1] | 7-(3,5-dimethylisoxazol-4-yl)-6-methoxy-2-methyl-N-(1-methyl-3-(prop-1-en-2-yl)-1H-pyrazol-5-yl)-9H-pyrimido[4,5-b]indol-4-amine |

TABLE 1-continued

| Cpd. No. | Structure | Name |
|---|---|---|
| 273 | 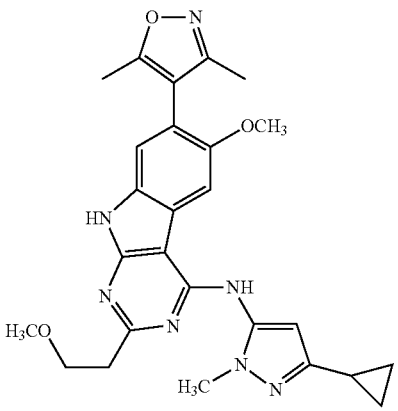 [SMILES: COCCc1nc(Nc2cc(C3CC3)nn2C)c2c(n1)[nH]c1cc(-c3c(C)noc3C)c(OC)cc12] | N-(3-cyclopropyl-1-methyl-1H-pyrazol-5-yl)-7-(3,5-dimethylisoxazol-4-yl)-6-methoxy-2-(2-methoxyethyl)-9H-pyrimido[4,5-b]indol-4-amine |
| 274 | 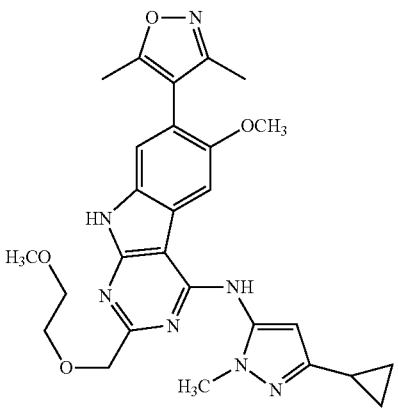 [SMILES: COCCOCc1nc(Nc2cc(C3CC3)nn2C)c2c(n1)[nH]c1cc(-c3c(C)noc3C)c(OC)cc12] | N-(3-cyclopropyl-1-methyl-1H-pyrazol-5-yl)-7-(3,5-dimethylisoxazol-4-yl)-6-methoxy-2-((2-methoxyethoxy)methyl)-9H-pyrimido[4,5-b]indol-4-amine |
| 277 | 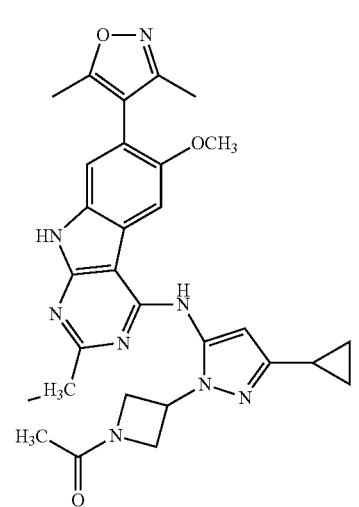 [SMILES: CCc1nc(Nc2cc(C3CC3)nn2C2CN(C(C)=O)C2)c2c(n1)[nH]c1cc(-c3c(C)noc3C)c(OC)cc12] | 1-(3-(3-cyclopropyl-5-(7-(3,5-dimethylisoxazol-4-yl)-6-methoxy-2-methyl-9H-pyrimido[4,5-b]indol-4-ylamino)-1H-pyrazol-1-yl)azetidin-1-yl)ethanone |

TABLE 1-continued

| Cpd. No. | Structure | Name |
|---|---|---|
| 278 | 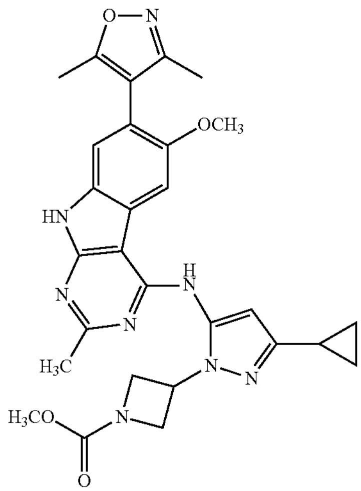 [SMILES: COC(=O)N1CC(n2nc(C3CC3)cc2Nc2nc(C)nc3[nH]c4cc(-c5c(C)noc5C)c(OC)cc4c23)C1] | methyl 3-(3-cyclopropyl-5-(7-(3,5-dimethylisoxazol-4-yl)-6-methoxy-2-methyl-9H-pyrimido[4,5-b]indol-4-ylamino)-1H-pyrazol-1-yl)azetidine-1-carboxylate |
| 279 | 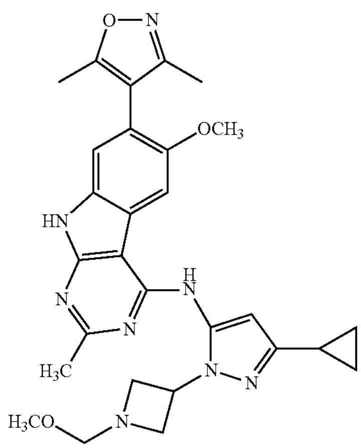 [SMILES: COCN1CC(n2nc(C3CC3)cc2Nc2nc(C)nc3[nH]c4cc(-c5c(C)noc5C)c(OC)cc4c23)C1] | N-(3-cyclopropyl-1-(1-ethylazetidin-3-yl)-1H-pyrazol-5-yl)-7-(3,5-dimethylisoxazol-4-yl)-6-methoxy-2-methyl-9H-pyrimido[4,5-b]indol-4-amine |
| 280 | 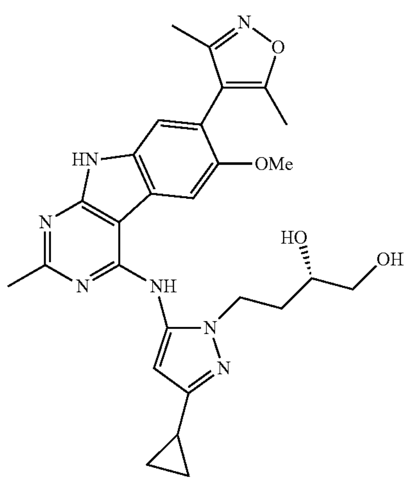 [SMILES: COc1cc2c(cc1-c1c(C)noc1C)[nH]c1nc(C)nc(Nc3cc(C4CC4)nn3CC[C@H](O)CO)c12] | (2S)-4-(3-cyclopropyl-5-(7-(3,5-dimethylisoxazol-4-yl)-6-methoxy-2-methyl-9H-pyrimido[4,5-b]indol-4-ylamino)-1H-pyrazol-1-yl)butane-1,2-diol |

TABLE 1-continued

| Cpd. No. | Structure | Name |
|---|---|---|
| 281 | 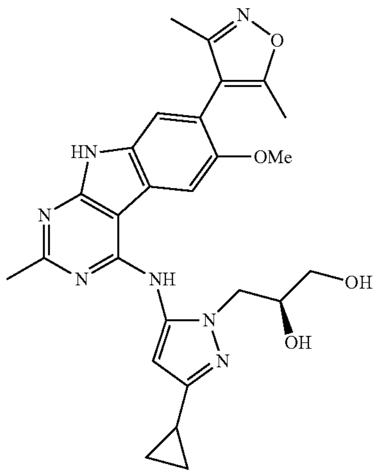 [SMILES: COc1cc2c(cc1-c1c(C)noc1C)[nH]c1nc(C)nc(Nc3cc(C4CC4)nn3C[C@H](O)CO)c12] | (S)-3-(3-cyclopropyl-5-((7-(3,5-dimethylisoxazol-4-yl)-6-methoxy-2-methyl-9H-pyrimido[4,5-b]indol-4-yl)amino)-1H-pyrazol-1-yl)propane-1,2-diol |
| 282 | 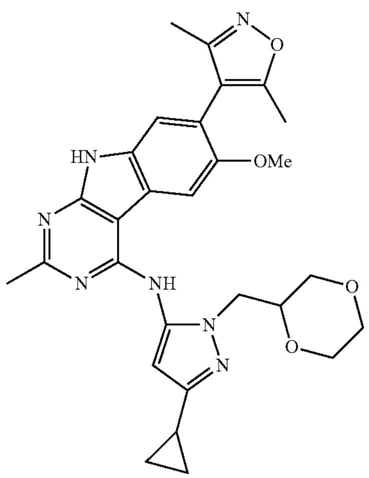 [SMILES: COc1cc2c(cc1-c1c(C)noc1C)[nH]c1nc(C)nc(Nc3cc(C4CC4)nn3CC3COCCO3)c12] | N-(1-((1,4-dioxan-2-yl)methyl)-3-cyclopropyl-1H-pyrazol-5-yl)-7-(3,5-dimethylisoxazol-4-yl)-6-methoxy-2-methyl-9H-pyrimido[4,5-b]indol-4-amine |
| 283 | 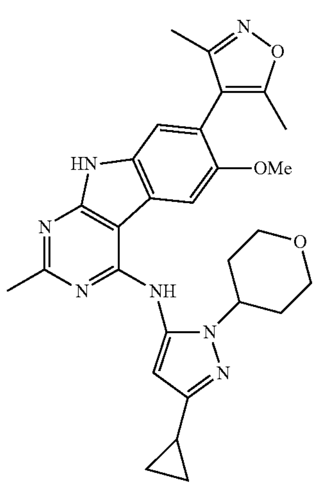 [SMILES: COc1cc2c(cc1-c1c(C)noc1C)[nH]c1nc(C)nc(Nc3cc(C4CC4)nn3C3CCOCC3)c12] | N-(3-cyclopropyl-1-(tetrahydro-2H-pyran-4-yl)-1H-pyrazol-5-yl)-7-(3,5-dimethylisoxazol-4-yl)-6-methoxy-2-methyl-9H-pyrimido[4,5-b]indol-4-amine |

TABLE 1-continued
| Cpd. No. | Structure | Name |
| --- | --- | --- |
| 284 | 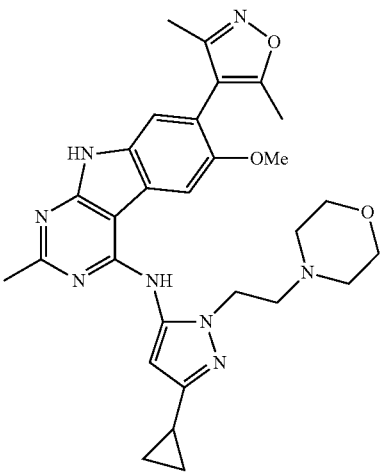 [SMILES: COc1cc2c(cc1-c1c(C)noc1C)[nH]c1nc(C)nc(Nc3cc(C4CC4)nn3CCN3CCOCC3)c12] | N-(3-cyclopropyl-1-(2-morpholinoethyl)-1H-pyrazol-5-yl)-7-(3,5-dimethylisoxazol-4-yl)-6-methoxy-2-methyl-9H-pyrimido[4,5-b]indol-4-amine |
| 285 | 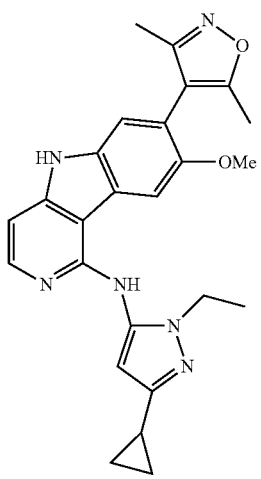 [SMILES: CCn1nc(C2CC2)cc1Nc1nccc2[nH]c3cc(-c4c(C)noc4C)c(OC)cc3c12] | N-(3-cyclopropyl-1-ethyl-1H-pyrazol-5-yl)-7-(3,5-dimethylisoxazol-4-yl)-8-methoxy-5H-pyrido[4,3-b]indol-1-amine |
| 286 | 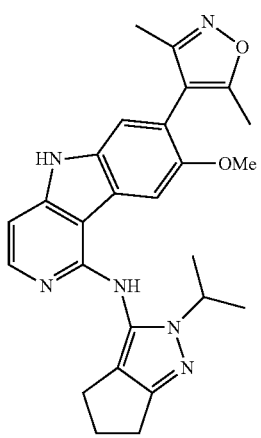 [SMILES: COc1cc2c(cc1-c1c(C)noc1C)[nH]c1ccnc(Nc3c4c(nn3C(C)C)CCC4)c12] | 7-(3,5-dimethylisoxazol-4-yl)-N-(2-isopropyl-2,4,5,6-tetrahydrocyclopenta[c]pyrazol-3-yl)-8-methoxy-5H-pyrido[4,3-b]indol-1-amine |

TABLE 1-continued

| Cpd. No. | Structure | Name |
|---|---|---|
| 287 | 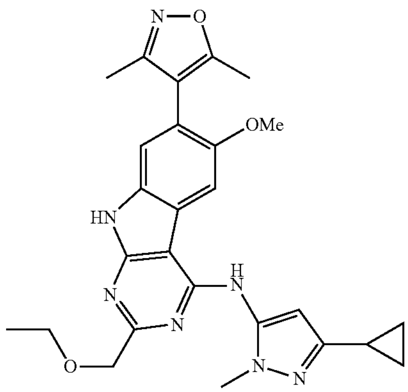 [SMILES: CCOCc1nc(Nc2cc(C3CC3)nn2C)c2c(n1)[nH]c1cc(-c3c(C)noc3C)c(OC)cc12] | N-(3-cyclopropyl-1-methyl-1H-pyrazol-5-yl)-7-(3,5-dimethylisoxazol-4-yl)-6-methoxy-2-(2-methoxyethyl)-9H-pyrimido[4,5-b]indol-4-amine |
| 288 | 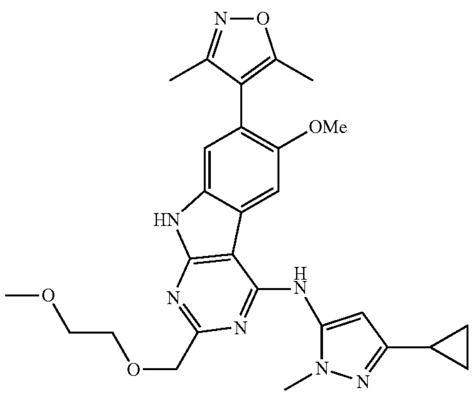 [SMILES: COCCOCc1nc(Nc2cc(C3CC3)nn2C)c2c(n1)[nH]c1cc(-c3c(C)noc3C)c(OC)cc12] | N-(3-cyclopropyl-1-methyl-1H-pyrazol-5-yl)-7-(3,5-dimethylisoxazol-4-yl)-6-methoxy-2-((2-methoxyethoxy)methyl)-9H-pyrimido[4,5-b]indol-4-amine |
| 289 | 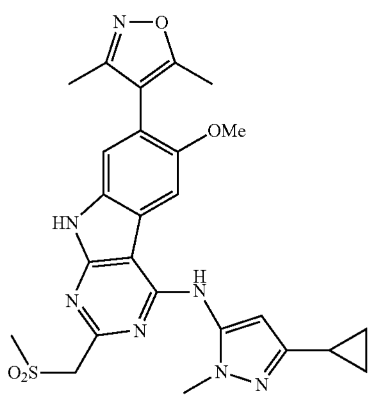 [SMILES: COc1cc2c(cc1-c1c(C)noc1C)[nH]c1nc(CS(C)(=O)=O)nc(Nc3cc(C4CC4)nn3C)c12] | N-(3-cyclopropyl-1-methyl-1H-pyrazol-5-yl)-7-(3,5-dimethylisoxazol-4-yl)-6-methoxy-2-((methylsulfonyl)methyl)-9H-pyrimido[4,5-b]indol-4-amine |
| 290 | 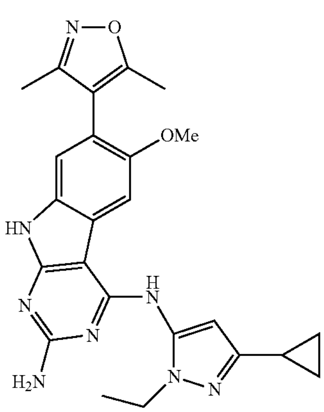 [SMILES: CCn1nc(C2CC2)cc1Nc1nc(N)nc2[nH]c3cc(-c4c(C)noc4C)c(OC)cc3c12] | N4-(3-cyclopropyl-1-ethyl-1H-pyrazol-5-yl)-7-(3,5-dimethylisoxazol-4-yl)-6-methoxy-9H-pyrimido[4,5-b]indole-2,4-diamine |

TABLE 1-continued
| Cpd. No. | Structure | Name |
|---|---|---|
| 291 | 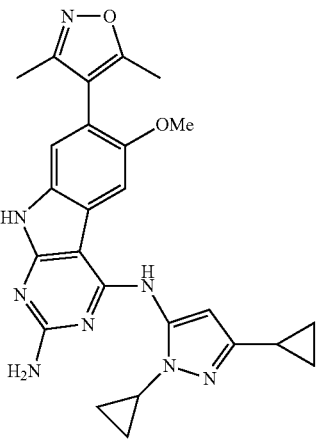 [SMILES: COc1cc2c(cc1-c1c(C)noc1C)[nH]c1nc(N)nc(Nc3cc(C4CC4)nn3C3CC3)c12] | N4-(1,3-dicyclopropyl-1H pyrazol-5-yl)-7-(3,5-dimethylisoxazol-4-yl)-6-methoxy-9H-pyrimido[4,5 b]indole-2,4-diamine |
| 292 | 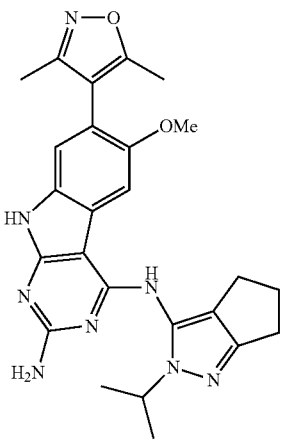 [SMILES: COc1cc2c(cc1-c1c(C)noc1C)[nH]c1nc(N)nc(Nc3c4c(nn3C(C)C)CCC4)c12] | 7-(3,5-dimethylisoxazol-4-yl)-N4-(2-isopropyl-2,4,5,6-tetrahydrocyclopenta[c]pyrazol-3-yl)-6-methoxy-9H-pyrimido[4,5-b]indole-2,4-diamine |
| 293 | 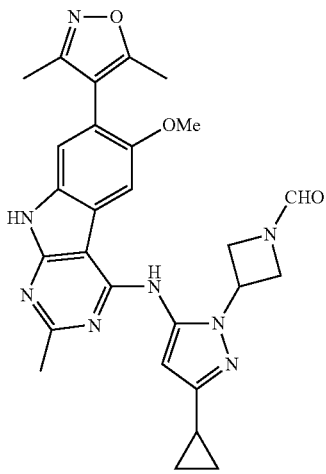 [SMILES: COc1cc2c(cc1-c1c(C)noc1C)[nH]c1nc(C)nc(Nc3cc(C4CC4)nn3C3CN(C=O)C3)c12] | 3-(3-cyclopropyl-5-((7-(3,5-dimethylisoxazol-4-yl)-6-methoxy-2-methyl-9H-pyrimido[4,5-b]indol-4-yl)amino)-1H-pyrazol-1-yl)azetidine-1-carbaldehyde |

TABLE 1-continued

| Cpd. No. | Structure | Name |
|---|---|---|
| 294 | 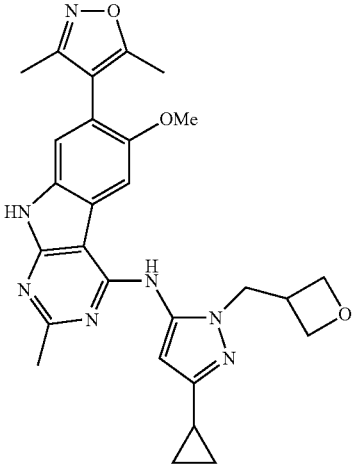 [SMILES: COc1cc2c(cc1-c1c(C)noc1C)[nH]c1nc(C)nc(Nc3cc(C4CC4)nn3CC3COC3)c12] | N-(3-cyclopropyl-1-(oxetan-3-ylmethyl)-1H-pyrazol-5-yl)-7-(3,5-dimethylisoxazol-4-yl)-6-methoxy-2-methyl-9H-pyrimido[4,5-b]indol-4-amine |
| 295 | 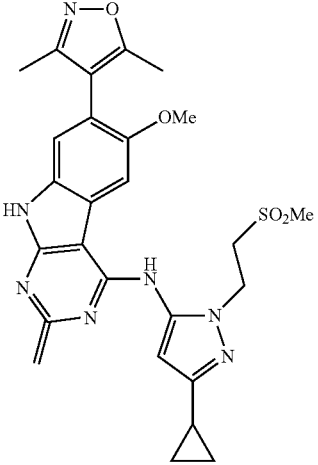 | N-(3-cyclopropyl-1-(2-(methylsulfonyl)ethyl)-1H-pyrazol-5-yl)-7-(3,5-dimethylisoxazol-4-yl)-6-methoxy-2-methyl-9H-pyrimido[4,5-b]indol-4-amine |
| 304 | 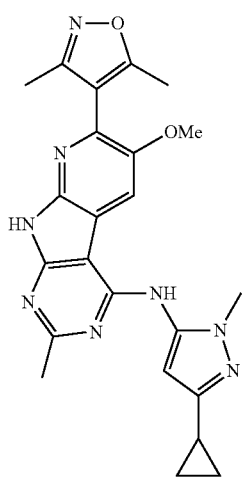 | N-(3-cyclopropyl-1-methyl-1H-pyrazol-5-yl)-7-(3,5-dimethylisoxazol-4-yl)-6-methoxy-2-methyl-9H-pyrido[3',2':4,5]pyrrolo[2,3-d]pyrimidin-4-amine |

TABLE 1-continued
| Cpd. No. | Structure | Name |
|---|---|---|
| 305 | 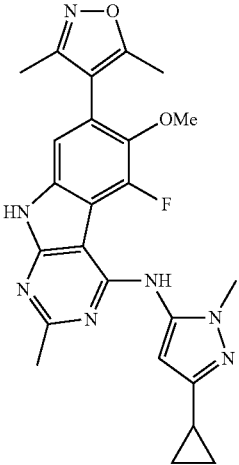 | N-(3-cyclopropyl-1-methyl-1H-pyrazol-5-yl)-7-(3,5-dimethylisoxazol-4-yl)-5-fluoro-6-methoxy-2-methyl-9H-pyrimido[4,5-b]indol-4-amine |
| 306 | 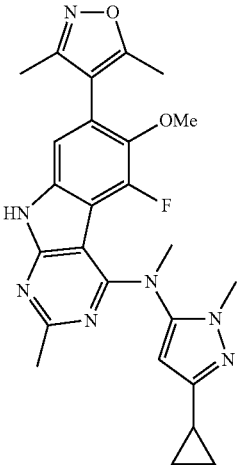 | N-(3-cyclopropyl-1-methyl-1H-pyrazol-5-yl)-7-(3,5-dimethylisoxazol-4-yl)-5-fluoro-6-methoxy-N,2-dimethyl-9H-pyrimido[4,5-b]indol-4-amine |
| 307 | 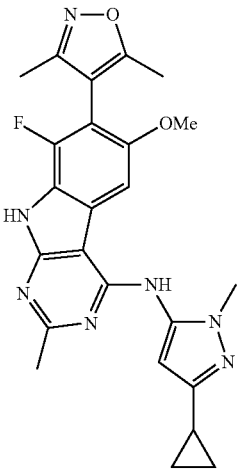 [SMILES: COc1cc2c([nH]c3nc(C)nc(Nc4cc(C5CC5)nn4C)c32)c(F)c1-c1c(C)noc1C] | N-(3-cyclopropyl-1-methyl-1H-pyrazol-5-yl)-7-(3,5-dimethylisoxazol-4-yl)-8-fluoro-6-methoxy-2-methyl-9H-pyrimido[4,5-b]indol-4-amine |

| Cpd. No. | Structure | Name |
|---|---|---|
| 308 | 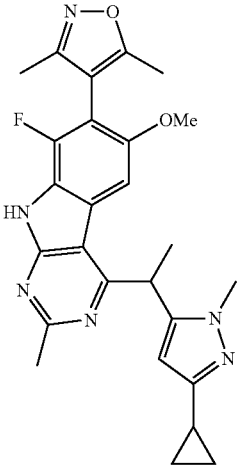 | N-(3-cyclopropyl-1-methyl-pyrazol-5-yl)-7-(3,5-dimethylisoxazol-4-yl)-8-fluoro-6-methoxy-N,2-dimethyl-9H-pyrimido[4,5-b]indol-4-amine |
| 309 | 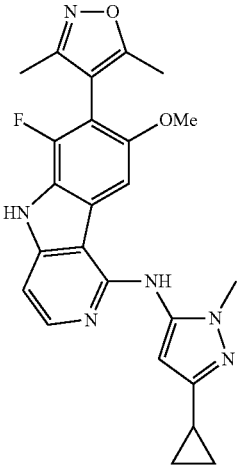 [SMILES: COc1cc2c([nH]c3ccnc(Nc4cc(C5CC5)nn4C)c32)c(F)c1-c1c(C)noc1C] | N-(3-cyclopropyl-1-methyl-1H-pyrazol-5-yl)-7-(3,5-dimethylisoxazol-4-yl)-6-fluoro-8-methoxy-5H-pyrido[4,3-b]indol-1-amine |
| 310 | 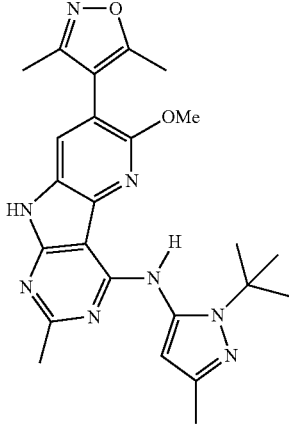 [SMILES: COc1nc2c(cc1-c1c(C)noc1C)[nH]c1nc(C)nc(Nc3cc(C)nn3C(C)(C)C)c12] | N-(1-(tert-butyl)-3-methyl-1H-pyrazol-5-yl)-7-(3,5-dimethylisoxazol-4-yl)-6-methoxy-2-methyl-9H-pyrido[2',3':4,5]pyrrolo[2,3-d]pyrimidin-4-amine |

TABLE 1-continued

| Cpd. No. | Structure | Name |
|---|---|---|
| 311 | 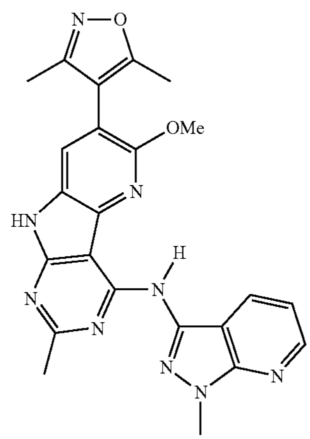 [SMILES: COc1nc2c(cc1-c1c(C)noc1C)[nH]c1nc(C)nc(Nc3nn(C)c4ncccc34)c12] | 7-(3,5-dimethylisoxazol-4-yl)-6-methoxy-2-methyl-N-(1-methyl-1H-pyrazolo[3,4-b]pyridin-3-yl)-9H-pyrido[2',3':4,5]pyrrolo[2,3-d]pyrimidin-4-amine |
| 312 | 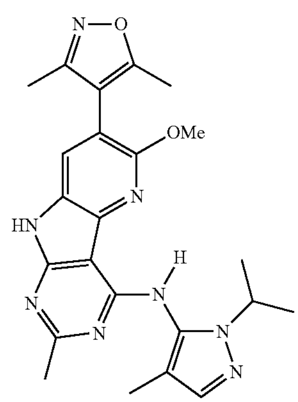 [SMILES: COc1nc2c(cc1-c1c(C)noc1C)[nH]c1nc(C)nc(Nc3c(C)cnn3C(C)C)c12] | 7-(3,5-dimethylisoxazol-4-yl)-N-(1-isopropyl-4-methyl-1H-pyrazol-5-yl)-6-methoxy-2-methyl-9H-pyrido[2',3':4,5]pyrrolo[2,3-d]pyrimidin-4-amine |
| 313 | 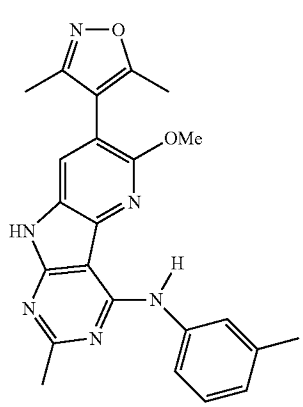 | 7-(3,5-dimethylisoxazol-4-yl)-6-methoxy-2-methyl-N-(m-tolyl)-9H-pyrido[2',3':4,5]pyrrolo[2,3-d]pyrimidin-4-amine |

TABLE 1-continued

| Cpd. No. | Structure | Name |
| --- | --- | --- |
| 314 | 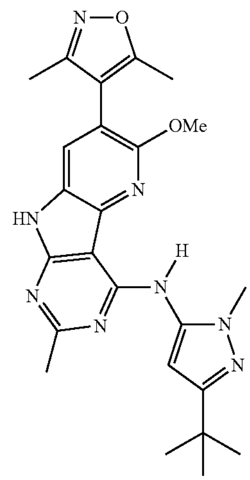 | N-(3-(tert-butyl)-1-methyl-1H-pyrazol-5-yl)-7-(3,5-dimethylisoxazol-4-yl)-6-methoxy-2-methyl-9H-pyrido[2',3':4,5]pyrrolo[2,3-d]pyrimidin-4-amine |
| 315 | 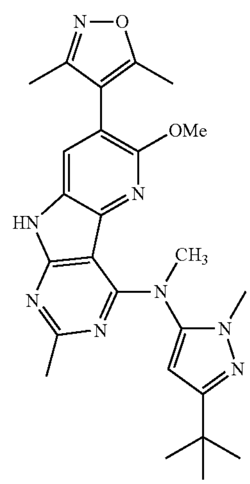 | N-(3-(tert-butyl)-1-methyl-1H-pyrazol-5-yl)-7-(3,5-dimethylisoxazol-4-yl)-6-methoxy-N,2-dimethyl-9H-pyrido[2',3':4,5]pyrrolo[2,3-d]pyrimidin-4-amine |
| 316 | 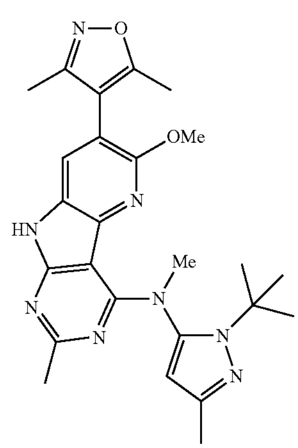 [SMILES: COc1nc2c(cc1-c1c(C)noc1C)[nH]c1nc(C)nc(N(C)c3cc(C)nn3C(C)(C)C)c12] | N-(1-(tert-butyl)-3-methyl-1H-pyrazol-5-yl)-7-(3,5-dimethylisoxazol-4-yl)-6-methoxy-N,2-dimethyl-9H-pyrido[2',3':4,5]pyrrolo[2,3-d]pyrimidin-4-amine |

TABLE 1-continued

| Cpd. No. | Structure | Name |
|---|---|---|
| 317 | 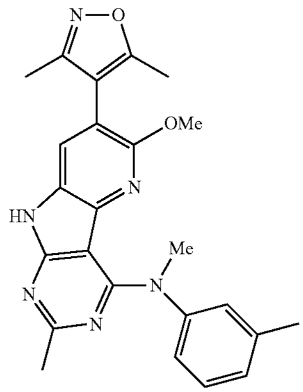 | 7-(3,5-dimethylisoxazol-4-yl)-6-methoxy-N,2-dimethyl-N-(m-tolyl)-9H-pyrido[2',3':4,5]pyrrolo[2,3-d]pyrimidin-4-amine |
| 318 | 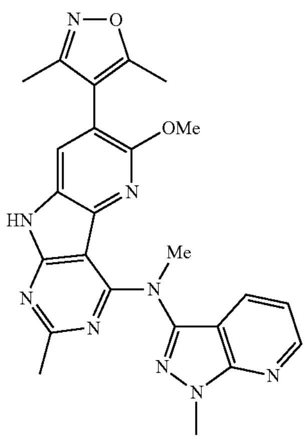 [SMILES: COc1nc2c(cc1-c1c(C)noc1C)[nH]c1nc(C)nc(N(C)c3nn(C)c4ncccc34)c12] | 7-(3,5-dimethylisoxazol-4-yl)-6-methoxy-N,2-dimethyl-N-(1-methyl-1H-pyrazolo[3,4-b]pyridin-3-yl)-9H-pyrido[2',3':4,5]pyrrolo[2,3-d]pyrimidin-4-amine |
| 319 | 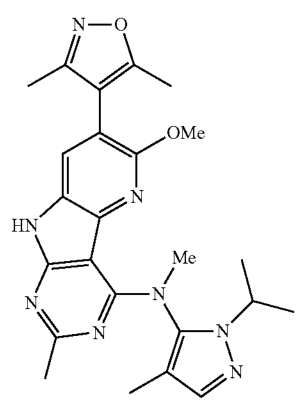 [SMILES: COc1nc2c(cc1-c1c(C)noc1C)[nH]c1nc(C)nc(N(C)c3c(C)cnn3C(C)C)c12] | 7-(3,5-dimethylisoxazol-4-yl)-N-(1-isopropyl-4-methyl-1H-pyrazol-5-yl)-6-methoxy-N,2-dimethyl-9H-pyrido[2',3':4,5]pyrrolo[2,3-d]pyrimidin-4-amine |

TABLE 1-continued
| Cpd. No. | Structure | Name |
|---|---|---|
| 320 | 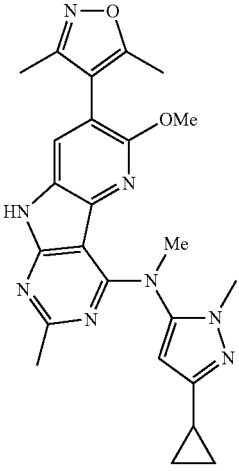 | N-(3-cyclopropyl-1-methyl-1H-pyrazol-5-yl)-7-(3,5-dimethylisoxazol-4-yl)-6-methoxy-N,2-dimethyl-9H-pyrido[2',3':4,5]pyrrolo[2,3-d]pyrimidin-4-amine |
| 321 | 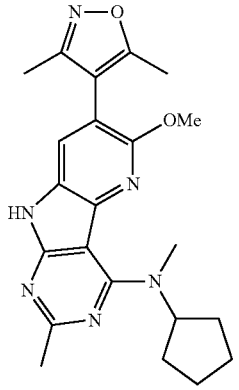 [SMILES: COc1nc2c(cc1-c1c(C)noc1C)[nH]c1nc(C)nc(N(C)C3CCCC3)c12] | N-cyclopentyl-7-(3,5-dimethylisoxazol-4-yl)-6-methoxy-N,2-dimethyl-9H-pyrido[2',3':4,5]pyrrolo[2,3-d]pyrimidin-4-amine |
| 322 | 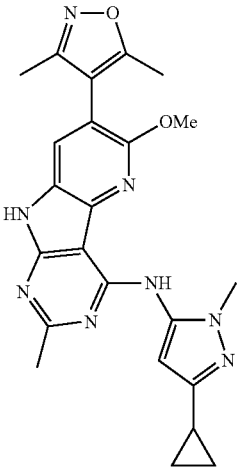 | N-(3-cyclopropyl-1-methyl-1H-pyrazol-5-yl)-7-(3,5-dimethylisoxazol-4-yl)-6-methoxy-2-methyl-9H-pyrido[2',3':4,5]pyrrolo[2,3-d]pyrimidin-4-amine |

TABLE 1-continued
| Cpd. No. | Structure | Name |
|---|---|---|
| 323 | 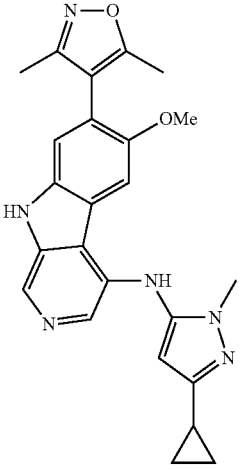 | N-(3-cyclopropyl-1-methyl-1H-pyrazol-5-yl)-7-(3,5-dimethylisoxazol-4-yl)-6-methoxy-9H-pyrido[3,4-b]indol-4-amine |
| 324 | 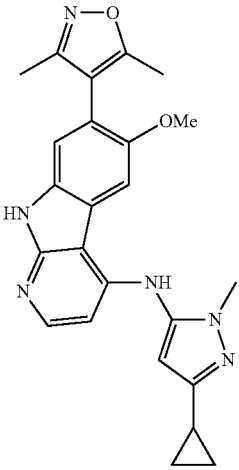 | N-(3-cyclopropyl-1-methyl-1H-pyrazol-5-yl)-7-(3,5-dimethylisoxazol-4-yl)-6-methoxy-9H-pyrido[2,3-b]indol-4-amine |
| 325 | 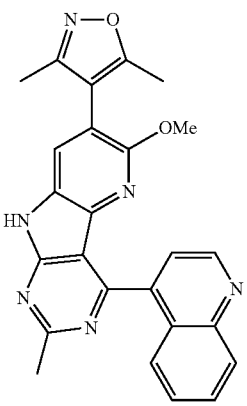 [SMILES: COc1nc2c(cc1-c1c(C)noc1C)[nH]c1nc(C)nc(-c3ccnc4ccccc34)c12] | 4-(6-methoxy-2-methyl-4-(quinolin-4-yl)-9H-pyrido[2',3':4,5]pyrrolo[2,3-d]pyrimidin-7-yl)-3,5-dimethylisoxazole |

TABLE 1-continued

| Cpd. No. | Structure | Name |
|---|---|---|
| 326 | 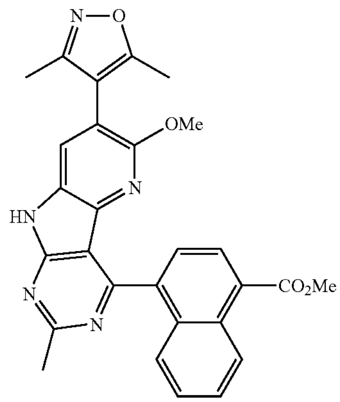 [SMILES: COC(=O)c1ccc(-c2nc(C)nc3[nH]c4cc(-c5c(C)noc5C)c(OC)nc4c23)c2ccccc12] | methyl 4-(7-(3,5-dimethylisoxazol-4-yl)-6-methoxy-2-methyl-9H-pyrido[2',3':4,5]pyrrolo[2,3-d]pyrimidin-4-yl)-1-naphthoate |
| 327 | 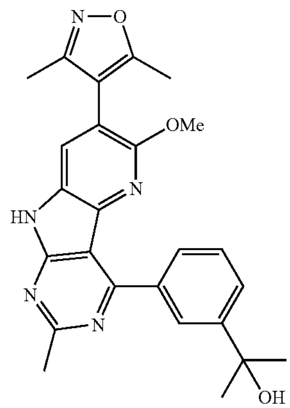 [SMILES: COc1nc2c(cc1-c1c(C)noc1C)[nH]c1nc(C)nc(-c3cccc(C(C)(C)O)c3)c12] | 2-(3-(7-(3,5-dimethylisoxazol-4-yl)-6-methoxy-2-methyl-9H-pyrido[2',3':4,5]pyrrolo[2,3-d]pyrimidin-4-yl)phenyl)propan-2-ol |
| 328 | 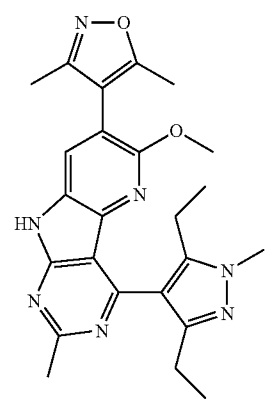 | 4-(4-(3,5-diethyl-1-methyl-1H-pyrazol-4-yl)-6-methoxy-2-methyl-9H-pyrido[2',3':4,5]pyrrolo[2,3-d]pyrimidin-7-yl)-3,5-dimethylisoxazole |
| 329 | 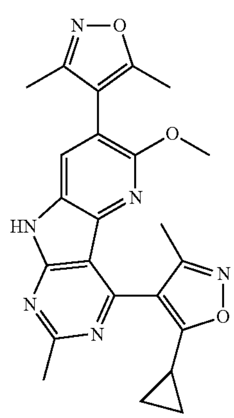 [SMILES: COc1nc2c(cc1-c1c(C)noc1C)[nH]c1nc(C)nc(-c3c(C)noc3C3CC3)c12] | 5-cyclopropyl-4-(7-(3,5-dimethylisoxazol-4-yl)-6-methoxy-2-methyl-9H-pyrido[2',3':4,5]pyrrolo[2,3-d]pyrimidin-4-yl)-3-methylisoxazole |

TABLE 1-continued

| Cpd. No. | Structure | Name |
|---|---|---|
| 330 | 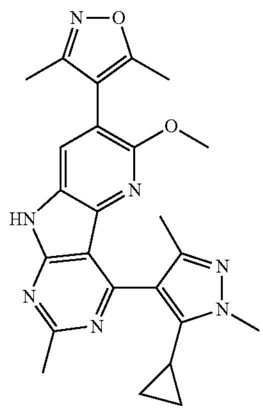 | 4-(4-(5-cyclopropyl-1,3-dimethyl-1H-pyrazol-4-yl)-6-methoxy-2-methyl-9H-pyrido[2',3':4,5]pyrrolo[2,3-d]pyrimidin-7-yl)-3,5-dimethylisoxazole |
| 331 | 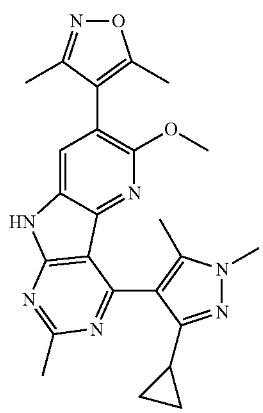 | 4-(4-(3-cyclopropyl-1,5-dimethyl-1H-pyrazol-4-yl)-6-methoxy-2-methyl-9H-pyrido[2',3':4,5]pyrrolo[2,3-d]pyrimidin-7-yl)-3,5-dimethylisoxazole |
| 333 | 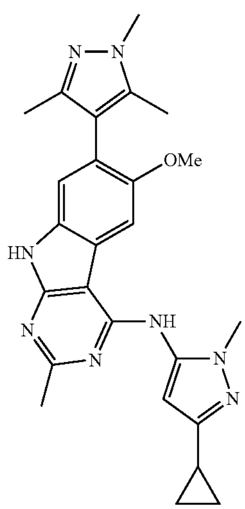 | N-(3-cyclopropyl-1-methyl-1H-pyrazol-5-yl)-6-methoxy-2-methyl-7-(1,3,5-trimethyl-1H-pyrazol-4-yl)-9H-pyrimido[4,5-b]indol-4-amine |

In another embodiment, Compounds of the Disclosure are compounds selected from the group consisting of:

N-(3-cyclopropyl-1-methyl-1H-pyrazol-5-yl)-7-(3,5-dimethylisoxazol-4-yl)-6-methoxy-2-methyl-9H-pyrimido[4,5-b]indol-4-amine;

N-(3-cyclopropyl-1-ethyl-1H-pyrazol-5-yl)-7-(3,5-dimethylisoxazol-4-yl)-6-methoxy-2-methyl-9H-pyrimido[4,5-b]indol-4-amine; and N-(1,3-dicyclopropyl-1H-pyrazol-5-yl)-7-(3,5-dimethylisoxazol-4-yl)-6-methoxy-2-methyl-9H-pyrimido[4,5-b]indol-4-amine, and the pharmaceutically acceptable salts, hydrates, and solvates thereof.

In another embodiment, Compounds of the Disclosure are compounds selected from the group consisting of:

N-(3-cyclopropyl-1-methyl-1H-pyrazol-5-yl)-7-(3,5-dimethylisoxazol-4-yl)-6-methoxy-2-methyl-9H-pyrimido[4,5-b]indol-4-amine;

N-(3-cyclopropyl-1-ethyl-1H-pyrazol-5-yl)-7-(3,5-dimethylisoxazol-4-yl)-6-methoxy-2-methyl-9H-pyrimido[4,5-b]indol-4-amine; and N-(3-cyclopropyl-1-methyl-1H-pyrazol-5-yl)-7-(3,5-dimethylisoxazol-4-yl)-6-methoxy-2-(methoxymethyl)-9H-pyrimido[4,5-b]indol-4-amine, and the pharmaceutically acceptable salts, hydrates, and solvates thereof.

In another embodiment, the present disclosure provides methods of preparing Compounds of the Disclosure. In one embodiment, the method of preparing Compounds of the Disclosure comprises reacting a compound of Formula VII:

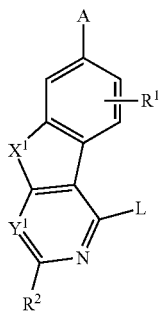

VII wherein:

L is a leaving group, e.g., Cl, I, Br, or $OSO_2R^6$, wherein $R^6$ is selected from the group consisting of alkyl, haloalkyl, and optionally substituted aryl;

$R^1$ is selected from the group consisting of hydrogen, hydroxy, alkyl, haloalkyl, alkoxy, alkylthio, amino, and halo;

$R^2$ is selected from the group consisting of hydrogen, amino, alkyl, hydroxyalkyl, alkoxyalkyl, (heterocyclo)alkyl, (amino)alkyl, optionally substituted cycloalkyl, optionally substituted heterocyclo, and carboxamido;

A is optionally substituted 5-membered heteroaryl;

$X^1$ is selected from the group consisting of —O—, —S—, and —N($R^{5a1}$)—;

$Y^1$ is selected from the group consisting of —CH= and —N=; and $R^{5a1}$ is selected from the group consisting of hydrogen and alkyl, with a compound having Formula VIII:

 H—Z—R³  VIII wherein:

Z is selected from the group consisting of —O—, —S—, and —N($R^{5b1}$)—;

$R^3$ is selected from the group consisting of optionally substituted cycloalkyl, optionally substituted aryl, optionally substituted heteroaryl, and optionally substituted heterocyclo; and $R^{5b1}$ is selected from the group consisting of hydrogen and alkyl.

In another embodiment, the method further comprises isolating the Compound of the Disclosure, e.g., free from starting materials, reagents, solvents, and/or reaction side-products. In another embodiment, the reaction is carried out in a solvent, e.g., one containing dimethylformamide, acetonitrile, dimethyl sulfoxide, and/or N-methyl-2-pyrrolidone. In another embodiment, the reaction is carried out at a temperature of about 50° C. to about 200° C., e.g., at about 50° C., about 60° C., about 70° C., about 80° C., about 90° C., about 100° C., about 110° C., about 120° C., about 130° C., about 140° C., about 150° C., about 160° C., about 170° C., about 180° C., about 190° C., or about 200° C.

Compounds of the Disclosure inhibit BET bromodomains and are useful in the treatment of a variety of diseases and conditions. In particular, Compounds of the Disclosure are useful in methods of treating a disease or condition wherein inhibition of BET bromodomains provides a benefit, for example, cancers and proliferative diseases. Methods of the disclosure comprise administering a therapeutically effective amount of a Compound of the Disclosure to an individual in need thereof. The present methods also encompass administering a second therapeutic agent to the individual in addition to the Compound of the Disclosure. The second therapeutic agent is selected from drugs known as useful in treating the disease or condition afflicting the individual in need thereof, e.g., a chemotherapeutic agent and/or radiation known as useful in treating a particular cancer.

Salts, hydrates, and solvates of the Compounds of the Disclosure can also be used in the methods disclosed herein. The present disclosure further includes all possible stereoisomers and geometric isomers of Compounds of the Disclosure to include both racemic compounds and optically active isomers. When a Compound of the Disclosure is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of the Compounds of the Disclosure are possible, the present disclosure is intended to include all tautomeric forms of the compounds.

The present disclosure encompasses the preparation and use of salts of Compounds of the Disclosure. As used herein, the pharmaceutical "pharmaceutically acceptable salt" refers to salts or zwitterionic forms of Compounds of the Disclosure. Salts of Compounds of the Disclosure can be prepared during the final isolation and purification of the compounds or separately by reacting the compound with an acid having a suitable cation. The pharmaceutically acceptable salts of Compounds of the Disclosure can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the disclosure include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulfonate, and p-toluenesulfonate salts. In addition, available amino groups present in the compounds of the disclosure can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference Compounds of the Disclosure appearing herein is intended to include compounds of Compounds of the Disclosure as well as pharmaceutically acceptable salts, hydrates, or solvates thereof.

The present disclosure encompasses the preparation and use of solvates of Compounds of the Disclosure. Solvates typically do not significantly alter the physiological activity or toxicity of the compounds, and as such may function as pharmacological equivalents. The term "solvate" as used herein is a combination, physical association and/or solvation of a compound of the present disclosure with a solvent molecule such as, e.g. a disolvate, monosolvate or hemisolvate, where the ratio of solvent molecule to compound of the present disclosure is about 2:1, about 1:1 or about 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Compounds of the Disclosure can be present as solvated forms with a pharmaceutically acceptable solvent, such as water, methanol, ethanol, and the like, and it is intended that the disclosure includes both solvated and unsolvated forms of Compounds of the Disclosure. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al., *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1):Article 12 (2004), and A. L. Bingham et al., *Chem. Commun.* 603-604 (2001). A typical, non-limiting, process of preparing a solvate would involve dissolving a Compound of the Disclosure in a desired solvent (organic, water, or a mixture thereof) at temperatures above 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The present disclosure provides Compounds of the Disclosure as BET bromodomain inhibitors for the treatment of a variety of diseases and conditions wherein inhibition of BET bromodomains has a beneficial effect. Compounds of the Disclosure typically have a binding affinity ($IC_{50}$) to BET bromodomains of less than 100 µM, e.g., less than 50 µM, less than 25 µM, and less than 5 µM, less than about 1 µM, less than about 0.5 µM, or less than about 0.1 µM. In one embodiment, the present disclosure relates to a method of treating an individual suffering from a disease or condition wherein inhibition of the BET bromodomains provides a benefit comprising administering a therapeutically effective amount of a Compound of the Disclosure to an individual in need thereof.

Since Compounds of the Disclosure are inhibitors of one or more BET bromodomains, a number of diseases and conditions mediated by BET bromodomain proteins can be treated by employing these compounds. The present disclosure is thus directed generally to a method for treating a condition or disorder responsive to inhibition of BRD2, BRD3, BRD4, BRD-t, or an isoform or mutant thereof, in an animal, e.g., a human, suffering from, or at risk of suffering from, the condition or disorder, the method comprising administering to the animal an effective amount of one or more Compounds of the Disclosure.

The present disclosure is further directed to a method of inhibiting BET bromodomains in an animal in need thereof, said method comprising administering to the animal an effective amount of at least one Compound of the Disclosure.

The methods of the present disclosure can be accomplished by administering a Compound of the Disclosure as the neat compound or as a pharmaceutical composition. Administration of a pharmaceutical composition, or neat compound of a Compound of the Disclosure, can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a Compound of the Disclosure and, optionally, a second therapeutic agent useful in the treatment of diseases and conditions wherein inhibition of BET bromodomains provides a benefit, packaged separately or together, and an insert having instructions for using these active agents.

In one embodiment, a Compound of the Disclosure is administered in conjunction with a second therapeutic agent useful in the treatment of a disease or condition wherein inhibition of BET bromodomains provides a benefit. The second therapeutic agent is different from the Compound of the Disclosure. A Compound of the Disclosure and the second therapeutic agent can be administered simultaneously or sequentially to achieve the desired effect. In addition, the Compound of the Disclosure and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A Compound of the Disclosure and the second therapeutic agent can be administered together as a single-unit dose or separately as multi-unit doses, wherein the Compound of the Disclosure is administered before the second therapeutic agent or vice versa. One or more doses of the Compound of the Disclosure and/or one or more dose of the second therapeutic agent can be administered. The Compound of the Disclosure therefore can be used in conjunction with one or more second therapeutic agents, for example, but not limited to, anticancer agents.

Diseases and conditions treatable by the methods of the present disclosure include, but are not limited to, cancer and other proliferative disorders, inflammatory diseases, sepsis, autoimmune disease, and viral infection. In one embodiment, a human patient is treated with a Compound of the Disclosure, or a pharmaceutical composition comprising a Compound of the Disclosure, wherein the compound is administered in an amount sufficient to inhibit BET bromodomain activity in the patient.

In one embodiment, the disease to be treated by the Compound of the Disclosure is cancer. Examples of treatable cancers include, but are not limited to, adrenal cancer, acinic cell carcinoma, acoustic neuroma, acral lentigious melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogeous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

In another embodiment, the cancer is a leukaemia, for example a leukaemia selected from acute monocytic leukemia, acute myelogenous leukemia, chronic myelogenous leukemia, chronic lymphocytic leukemia and mixed lineage leukaemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is colorectal cancer. In another embodiment, the cancer is prostate cancer. In another embodiment, the cancer is breast cancer.

In another embodiment, the present disclosure provides a method of treating a benign proliferative disorder, such as, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

Compounds of the Disclosure can also treat infectious and noninfectious inflammatory events and autoimmune and other inflammatory diseases by administration of an effective amount of a present compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendictitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituatarism, Guillain-Barre syndrome, Behcet's disease, scleracierma, mycosis fungoides, acute inflammatory responses (such as acute respiratory distress syndrome and ischemia/reperfusion injury), and Graves' disease.

In another embodiment, the present disclosure provides a method of treating systemic inflammatory response syndromes, such as LPS-induced endotoxic shock and/or bacteria-induced sepsis by administration of an effective amount of a Compound of the Disclosure to a mammal, in particular a human in need of such treatment.

In another embodiment, the present disclosure provides a method for treating viral infections and diseases. Examples of viral infections and diseases treated using the compounds and methods described herein include episome-based DNA viruses including, but not limited to, human papillomavirus, Herpesvirus, Epstein-Barr virus, human immunodeficiency virus, hepatis B virus, and hepatitis C virus.

In another embodiment, the present disclosure provides therapeutic method of modulating protein methylation, gene expression, cell proliferation, cell differentiation and/or apoptosis in vivo in diseases mentioned above, in particular cancer, inflammatory disease, and/or viral disease is provided by administering a therapeutically effective amount of a Compound of the Disclosure to a subject in need of such therapy.

In another embodiment, the present disclosure provides a method of regulating endogenous or heterologous promoter activity by contacting a cell with a Compound of the Disclosure.

In methods of the present disclosure, a therapeutically effective amount of a Compound of the Disclosure, typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A Compound of the Disclosure can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a Compound of the Disclosure is administered in an effective amount to achieve its intended purpose. The exact formulation, route of administration, and dosage is determined by an individual physician in view of the diagnosed condition or disease. Dosage amount and interval can be adjusted individually to provide levels of a Compound of the Disclosure that is sufficient to maintain therapeutic effects.

Toxicity and therapeutic efficacy of the Compounds of the Disclosure can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a Compound of the Disclosure required for use in therapy varies with the nature of the condition being treated, the length of time that activity is desired, and the age and the condition of the patient, and ultimately is determined by the attendant physician. Dosage amounts and intervals can be adjusted individually to provide plasma levels of the BET bromodomain inhibitor that are sufficient to maintain the desired therapeutic effects. The desired dose conveniently can be administered in a single dose, or as multiple doses administered at appropriate intervals, for example as one, two, three, four or more subdoses per day. Multiple doses often are desired, or required. For example, a Compound of the Disclosure can be administered at a frequency of: four doses delivered as one dose per day at four-day intervals (q4d×4); four doses delivered as one dose per day at three-day intervals (q3d×4); one dose delivered per day at five-day intervals (qd×5); one dose per week for three weeks (qwk3); five daily doses, with two days rest, and another five daily doses (5/2/5); or, any dose regimen determined to be appropriate for the circumstance.

A Compound of the Disclosure used in a method of the present disclosure can be administered in an amount of about 0.005 to about 500 milligrams per dose, about 0.05 to about 250 milligrams per dose, or about 0.5 to about 100 milligrams per dose. For example, a Compound of the Disclosure can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The dosage of a composition containing a Compound of the Disclosure, or a composition containing the same, can be from about 1 ng/kg to about 200 mg/kg, about 1 μg/kg to about 100 mg/kg, or about 1 mg/kg to about 50 mg/kg. The dosage of a composition can be at any dosage including, but not limited to, about 1 μg/kg. The dosage of a composition may be at any dosage including, but not limited to, about 1 μg/kg, about 10 μg/kg, about 25 μg/kg, about 50 μg/kg, about 75 μg/kg, about 100 μg/kg, about 125 μg/kg, about 150 μg/kg, about 175 μg/kg, about 200 μg/kg, about 225 μg/kg, about 250 μg/kg, about 275 μg/kg, about 300 μg/kg, about 325 μg/kg, about 350 μg/kg, about 375 μg/kg, about 400 μg/kg, about 425 μg/kg, about 450 μg/kg, about 475 μg/kg, about 500 μg/kg, about 525 μg/kg, about 550 μg/kg, about 575 μg/kg, about 600 μg/kg, about 625 μg/kg, about 650 μg/kg, about 675 μg/kg, about 700 μg/kg, about 725 μg/kg, about 750 μg/kg, about 775 μg/kg, about 800 μg/kg, about 825 μg/kg, about 850 μg/kg, about 875 μg/kg, about 900 μg/kg, about 925 μg/kg, about 950 μg/kg, about 975 μg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, about 125 mg/kg, about 150 mg/kg, about 175 mg/kg, about 200 mg/kg, or more. The above dosages are exemplary of the average case, but there can be individual instances in which higher or lower dosages are merited, and such are within the scope of this disclosure. In practice, the physician determines the actual dosing regimen that is most suitable for an individual patient, which can vary with the age, weight, and response of the particular patient.

As stated above, a Compound of the Disclosure can be administered in combination with a second therapeutically active agent. In some embodiments, the second therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

In another embodiment, chemotherapeutic agents or other anti-proliferative agents can be combined with Compound of the Disclosure to treat proliferative diseases and cancer. Examples of therapies and anticancer agents that can be used in combination with Compounds of the Disclosure include surgery, radiotherapy (e.g., gamma-radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effect (e.g., an antiemetic), and any other approved chemotherapeutic drug.

Examples of antiproliferative compounds include, but are not limited to, an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Nonlimiting exemplary aromatase inhibitors include, but are not limited to, steroids, such as atamestane, exemestane, and formestane, and non-steroids, such as aminoglutethimide, roglethimide, pyridoglutethimide, trilostane, testolactone, ketokonazole, vorozole, fadrozole, anastrozole, and letrozole.

Nonlimiting anti-estrogens include, but are not limited to, tamoxifen, fulvestrant, raloxifene, and raloxifene hydrochloride. Anti-androgens include, but are not limited to, bicalutamide. Gonadorelin agonists include, but are not limited to, abarelix, goserelin, and goserelin acetate.

Exemplary topoisomerase I inhibitors include, but are not limited to, topotecan, gimatecan, irinotecan, camptothecin and its analogues, 9-nitrocamptothecin, and the macromolecular camptothecin conjugate PNU-166148. Topoisomerase II inhibitors include, but are not limited to, anthracyclines, such as doxorubicin, daunorubicin, epirubicin, idarubicin, and nemorubicin; anthraquinones, such as mitoxantrone and losoxantrone; and podophillotoxines, such as etoposide and teniposide.

Microtubule active agents include microtubule stabilizing, microtubule destabilizing compounds, and microtubulin polymerization inhibitors including, but not limited to, taxanes, such as paclitaxel and docetaxel; vinca alkaloids, such as vinblastine, vinblastine sulfate, vincristine, and vincristine sulfate, and vinorelbine; discodermolides; cochicine and epothilones and derivatives thereof.

Exemplary nonlimiting alkylating agents include cyclophosphamide, ifosfamide, melphalan, and nitrosoureas, such as carmustine and lomustine.

Exemplary nonlimiting cyclooxygenase inhibitors include Cox-2 inhibitors, 5-alkyl substituted 2-arylaminophenylacetic acid and derivatives, such as celecoxib, rofecoxib, etoricoxib, valdecoxib, or a 5-alkyl-2-arylaminophenylacetic acid, such as lumiracoxib.

Exemplary nonlimiting matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Exemplary nonlimiting mTOR inhibitors include compounds that inhibit the mammalian target of rapamycin (mTOR) and possess antiproliferative activity such as sirolimus, everolimus, CCI-779, and ABT578.

Exemplary nonlimiting antimetabolites include 5-fluorouracil (5-FU), capecitabine, gemcitabine, DNA demethylating compounds, such as 5-azacytidine and decitabine, methotrexate and edatrexate, and folic acid antagonists, such as pemetrexed.

Exemplary nonlimiting platin compounds include carboplatin, cis-platin, cisplatinum, and oxaliplatin.

Exemplary nonlimiting methionine aminopeptidase inhibitors include bengamide or a derivative thereof and PPI-2458.

Exemplary nonlimiting bisphosphonates include etridonic acid, clodronic acid, tiludronic acid, pamidronic acid, alendronic acid, ibandronic acid, risedronic acid, and zoledronic acid.

Exemplary nonlimiting antiproliferative antibodies include trastuzumab, trastuzumab-DMI, cetuximab, bevacizumab, rituximab, PR064553, and 2C4. The term "antibody" is meant to include intact monoclonal antibodies, polyclonal antibodies, multispecific antibodies formed from at least two intact antibodies, and antibody fragments, so long as they exhibit the desired biological activity.

Exemplary nonlimiting heparanase inhibitors include compounds that target, decrease, or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras, for example, a farnesyl transferase inhibitor, such as L-744832, DK8G557, tipifarnib, and lonafarnib.

Exemplary nonlimiting telomerase inhibitors include compounds that target, decrease, or inhibit the activity of telomerase, such as compounds that inhibit the telomerase receptor, such as telomestatin.

Exemplary nonlimiting proteasome inhibitors include compounds that target, decrease, or inhibit the activity of the proteasome including, but not limited to, bortezomid.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, I-β-D-arabinofuransyl-cytosine (ara-c), and bisulfan; and ALK inhibitors, which are compounds which target, decrease, or inhibit anaplastic lymphoma kinase.

Exemplary nonlimiting Flt-3 inhibitors include PKC412, midostaurin, a staurosporine derivative, SU11248, and MLN518.

Exemplary nonlimiting HSP90 inhibitors include compounds targeting, decreasing, or inhibiting the intrinsic ATPase activity of HSP90; or degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins, or antibodies that inhibit the ATPase activity of HSP90, such as 17-allylamino, 17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing, or inhibiting the activity of the platelet-derived growth factor-receptors (PDGFR), such as a compound that targets, decreases, or inhibits the activity of PDGFR, such as an N-phenyl-2-pyrimidine-amine derivatives, such as imatinib, SU101, SU6668, and GFB-111; b) a compound targeting, decreasing, or inhibiting the activity of the fibroblast growth factor-receptors (FGFR); c) a compound targeting, decreasing, or inhibiting the activity of the insulin-like growth factor receptor I (IGF-IR), such as a compound that targets, decreases, or inhibits the activity of IGF-IR; d) a compound targeting, decreasing, or inhibiting the activity of the Trk receptor tyrosine kinase family, or ephrin B4 inhibitors; e) a compound targeting, decreasing, or inhibiting the activity of the Axl receptor tyrosine kinase family; f) a compound targeting, decreasing, or inhibiting the activity of the Ret receptor tyrosine kinase; g) a compound targeting, decreasing, or inhibiting the activity of the Kit/SCFR receptor tyrosine kinase, such as imatinib; h) a compound targeting, decreasing, or inhibiting the activity of the c-Kit receptor tyrosine kinases, such as imatinib; i) a compound targeting, decreasing, or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing, or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; Isis 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin, such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) a compound targeting, decreasing, or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, gefitinib, erlotinib, OSI-774, Cl-1033, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; and m) a compound targeting, decreasing, or inhibiting the activity of the c-Met receptor.

Exemplary compounds that target, decrease, or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g., thalidomide and TNP-470.

Additional, nonlimiting, exemplary chemotherapeutic compounds, one or more of which may be used in combination with a present BET bromodomain inhibitor, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl)phthalazine succinate, angiostatin, endostatin, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, bevacizumab, porfimer sodium, anecortave, triamcinolone, hydrocortisone, 11-a-epihydrocotisol, cortex olone, 17a-hydroxyprogesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA, and siRNA.

Other examples of second therapeutic agents, one or more of which a present BET bromodomain inhibitor also can be combined, include, but are not limited to: a treatment for Alzheimer's Disease, such as donepezil and rivastigmine; a treatment for Parkinson's Disease, such as L-DOPA/carbidopa, entacapone, ropinrole, pramipexole, bromocriptine, pergolide, trihexephendyl, and amantadine; an agent for treating multiple sclerosis (MS) such as beta interferon e.g., AVONEX® and REBIF®), glatiramer acetate, and mitoxantrone; a treatment for asthma, such as albuterol and montelukast; an agent for treating schizophrenia, such as zyprexa, risperdal, seroquel, and haloperidol; an anti-inflammatory agent, such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor, such as an acetylcholinesterase inhibitor, an MAO inhibitor, an interferon, an anti-convulsant, an ion channel blocker, riluzole, or an anti-Parkinson's agent; an agent for treating cardiovascular disease, such as a beta-blocker, an ACE inhibitor, a diuretic, a nitrate, a calcium channel blocker, or a statin; an agent for treating liver disease, such as a corticosteroid, cholestyramine, an interferon, and an anti-viral agent; an agent for treating blood disorders, such as a corticosteroid, an anti-leukemic agent, or a growth factor; or an agent for treating immunodeficiency disorders, such as gamma globulin.

The above-mentioned second therapeutically active agents, one or more of which can be used in combination with a Compound of the Disclosure, are prepared and administered as described in the art.

Compound of the Disclosure typically are administered in admixture with a pharmaceutical carrier selected with regard to the intended route of administration and standard pharmaceutical practice. Pharmaceutical compositions for use in accordance with the present disclosure are formulated in a conventional manner using one or more physiologically acceptable carriers comprising excipients and/or auxiliaries that facilitate processing of Compound of the Disclosure.

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the Compound of the Disclosure is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a Compound of the Disclosure. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a Compound of the Disclosure.

When a therapeutically effective amount of a Compound of the Disclosure is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of the Disclosure can be readily combined with pharmaceutically acceptable carriers well-known in the art. Standard pharmaceutical carriers are described in Remington's Pharmaceutical Sciences, Mack Publishing Co., Easton, Pa., 19th ed. 1995. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the Compound of the Disclosure to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

Compound of the Disclosure can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a Compound of the Disclosure can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

Compounds of the Disclosure also can be formulated in rectal compositions, such as suppositories or retention enemas, e.g., containing conventional suppository bases. In addition to the formulations described previously, the Compound of the Disclosure also can be formulated as a depot preparation. Such long-acting formulations can be administered by implantation (for example, subcutaneously or intramuscularly) or by intramuscular injection. Thus, for example, the Compound of the Disclosure can be formulated with suitable polymeric or hydrophobic materials (for example, as an emulsion in an acceptable oil) or ion exchange resins.

In particular, the Compounds of the Disclosure can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. Compound of the Disclosure also can be injected parenterally, for example, intravenously, intramuscularly, subcutaneously, or intracoronarily. For parenteral administration, the Compound of the Disclosure are typically used in the form of a sterile aqueous solution which can contain other substances, for example, salts or monosaccharides, such as mannitol or glucose, to make the solution isotonic with blood.

In another embodiment, the present disclosure provides kits which comprise a Compound of the Disclosure (or a composition comprising a Compound of the Disclosure) packaged in a manner that facilitates their use to practice methods of the present disclosure. In one embodiment, the kit includes a Compound of the Disclosure (or a composition comprising a Compound of the Disclosure) packaged in a container, such as a sealed bottle or vessel, with a label affixed to the container or included in the kit that describes use of the compound or composition to practice the method of the disclosure. In one embodiment, the compound or composition is packaged in a unit dosage form. The kit further can include a device suitable for administering the composition according to the intended route of administration.

The term "BET bromodomain" as used herein means one or more of BRD2, BRD3, BRD4, and BRD-t, or an isoform or mutant thereof.

The term "a disease or condition wherein inhibition of BET bromodomains provides a benefit" pertains to a condition in which at least one of BRD2, BRD3, BRD4, and BRD-t, and/or an action of at least one of BRD2, BRD3, BRD4, and BRD-t, is important or necessary, e.g., for the onset, progress, expression of that disease or condition, or a disease or a condition which is known to be treated by a BET bromodomain inhibitor. Examples of such conditions include, but are not limited to, a cancer, a chronic autoimmune disease, an inflammatory disease, a proliferative disease, sepsis, and a viral infection. One of ordinary skill in the art is readily able to determine whether a compound treats a disease or condition mediated by a BET bromodomain for any particular cell type, for example, by assays which conveniently can be used to assess the activity of particular compounds.

The term "second therapeutic agent" refers to a therapeutic agent different from a Compound of the Disclosure and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. As demonstrated below, a Compound of the Disclosure is a potent inhibitor of BET bromodomains and can be used in treating diseases and conditions wherein inhibition of BET bromodomains provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a Compound of the Disclosure to an individual in need of such treatment.

Within the meaning of the disclosure, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the disclosure, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce BET bromodomain signaling in the target cells; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefore suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a Compound of the Disclosure can be administered at the same time or sequentially in any order at different points in time as a second therapeutic agent. A Compound of the Disclosure and the second therapeutic agent can be administered separately, in any appropriate form and by any suitable route. When a Compound of the Disclosure and the second therapeutic agent are not administered concurrently, it is understood that they can be administered in any order to a subject in need thereof. For example, a Compound of the Disclosure can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a Compound of the Disclosure and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at about 1 minute to about 24 hours apart.

The use of the terms "a", "an", "the", and similar referents in the context of describing the disclosure (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure and is not a limitation on the scope of the disclosure unless otherwise claimed. No language in the specification should be construed as indicating any non-claimed element as essential to the practice of the disclosure.

The term "about," as used herein, includes the recited number ±10%. Thus, "about 10" means 9 to 11.

For the purpose of the present disclosure, the term "alkyl" as used by itself or as part of another group refers to a straight- or branched-chain aliphatic hydrocarbon containing one to twelve carbon atoms (i.e., $C_{1-12}$ alkyl) or the number of carbon atoms designated (i.e., a $C_1$ alkyl such as methyl, a C$_2$ alkyl such as ethyl, a C$_3$ alkyl such as propyl or isopropyl, etc.). In one embodiment, the alkyl group is chosen from a straight chain C$_{1-10}$ alkyl group. In another embodiment, the alkyl group is chosen from a branched chain C$_{3-10}$ alkyl group. In another embodiment, the alkyl group is chosen from a straight chain C$_{1-6}$ alkyl group. In another embodiment, the alkyl group is chosen from a branched chain C$_{3-6}$ alkyl group. In another embodiment, the alkyl group is chosen from a straight chain C$_{1-4}$ alkyl group. In another embodiment, the alkyl group is chosen from a branched chain C$_{3-4}$ alkyl group. In another embodiment, the alkyl group is chosen from a straight or branched chain C$_{3-4}$ alkyl group. Non-limiting exemplary C$_{1-10}$ alkyl groups include methyl, ethyl, propyl, isopropyl, butyl, sec-butyl, tert-butyl, iso-butyl, 3-pentyl, hexyl, heptyl, octyl, nonyl, decyl, and the like. Non-limiting exemplary C$_{1-4}$ alkyl groups include methyl, ethyl, propyl, isopropyl, butyl, sec-butyl, tert-butyl, and iso-butyl.

For the purpose of the present disclosure, the term "optionally substituted alkyl" as used by itself or as part of another group means that the alkyl as defined above is either unsubstituted or substituted with one, two, or three substituents independently chosen from nitro, haloalkoxy, aryloxy, aralkyloxy, alkylthio, sulfonamido, alkylcarbonyl, arylcarbonyl, alkylsulfonyl, arylsulfonyl, carboxy, carboxyalkyl, cycloalkyl, and the like. In one embodiment, the optionally substituted alkyl is substituted with two substituents. In another embodiment, the optionally substituted alkyl is substituted with one substituent. Non-limiting exemplary optionally substituted alkyl groups include —CH$_2$CH$_2$NO$_2$, —CH$_2$SO$_2$CH$_3$, CH$_2$CH$_2$CO$_2$H, —CH$_2$CH$_2$SO$_2$CH$_3$, —CH$_2$CH$_2$COPh, and —CH$_2$C$_6$H$_{11}$.

For the purpose of the present disclosure, the term "cycloalkyl" as used by itself or as part of another group refers to saturated and partially unsaturated (containing one or two double bonds) cyclic aliphatic hydrocarbons containing one to three rings having from three to twelve carbon atoms (i.e., C$_{3-12}$ cycloalkyl) or the number of carbons designated. In one embodiment, the cycloalkyl group has two rings. In one embodiment, the cycloalkyl group has one ring. In another embodiment, the cycloalkyl group is chosen from a C$_{3-8}$ cycloalkyl group. In another embodiment, the cycloalkyl group is chosen from a C$_{3-6}$ cycloalkyl group. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, and cyclopentenyl, cyclohexenyl.

For the purpose of the present disclosure, the term "optionally substituted cycloalkyl" as used by itself or as part of another group means that the cycloalkyl as defined above is either unsubstituted or substituted with one, two, or three substituents independently chosen from halo, nitro, cyano, hydroxy, amino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido) alkyl, mercaptoalkyl, and (heterocyclo)alkyl. In one embodiment, the optionally substituted cycloalkyl is substituted with two substituents. In another embodiment, the optionally substituted cycloalkyl is substituted with one substituent.

For the purpose of the present disclosure, the term "alkenyl" as used by itself or as part of another group refers to an alkyl group as defined above containing one, two or three carbon-to-carbon double bonds. In one embodiment, the alkenyl group is chosen from a C$_{2-6}$ alkenyl group. In another embodiment, the alkenyl group is chosen from a C$_{2-4}$ alkenyl group. Non-limiting exemplary alkenyl groups include ethenyl, propenyl, isopropenyl, butenyl, sec-butenyl, pentenyl, and hexenyl.

For the purpose of the present disclosure, the term "optionally substituted alkenyl" as used herein by itself or as part of another group means the alkenyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, aryl, heteroaryl, or heterocyclo.

For the purpose of the present disclosure, the term "alkynyl" as used by itself or as part of another group refers to an alkyl group as defined above containing one to three carbon-to-carbon triple bonds. In one embodiment, the alkynyl has one carbon-to-carbon triple bond. In one embodiment, the alkynyl group is chosen from a C$_{2-6}$ alkynyl group. In another embodiment, the alkynyl group is chosen from C$_{2-4}$ alkynyl group. Non-limiting exemplary alkynyl groups include ethynyl, propynyl, butynyl, 2-butynyl, pentynyl, and hexynyl groups.

For the purpose of the present disclosure, the term "optionally substituted alkynyl" as used herein by itself or as part of another group means the alkynyl as defined above is either unsubstituted or substituted with one, two or three substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, aryl, heteroaryl, or heterocyclo.

For the purpose of the present disclosure, the term "haloalkyl" as used by itself or as part of another group refers to an alkyl group substituted by one or more fluorine, chlorine, bromine and/or iodine atoms. In one embodiment, the alkyl group is substituted by one, two, or three fluorine and/or chlorine atoms. In another embodiment, the haloalkyl group is chosen from a C$_{1-4}$ haloalkyl group. Non-limiting exemplary haloalkyl groups include fluoromethyl, 2-fluoroethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

For the purpose of the present disclosure, the term "hydroxyalkyl" as used by itself or as part of another group refers to an alkyl group substituted with one or more, e.g., one, two, or three, hydroxy groups. In one embodiment, the hydroxyalkyl group is a monohydroxyalkyl group, i.e., substituted with one hydroxy group. In another embodiment, the hydroxyalkyl group is a dihydroxyalkyl group, i.e., substituted with two hydroxy groups, e.g.,

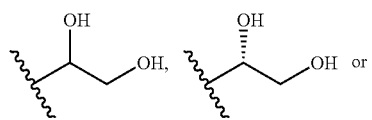

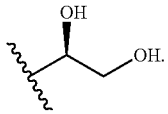

In another embodiment, the hydroxyalkyl group is chosen from a $C_{1-4}$ hydroxyalkyl group. Non-limiting exemplary hydroxyalkyl groups include hydroxymethyl, hydroxyethyl, hydroxypropyl and hydroxybutyl groups, such as 1-hydroxyethyl, 2-hydroxyethyl, 1,2-dihydroxyethyl, 2-hydroxypropyl, 3-hydroxypropyl, 3-hydroxybutyl, 4-hydroxybutyl, 2-hydroxy-1-methylpropyl, and 1,3-dihydroxyprop-2-yl.

For the purpose of the present disclosure, the term "alkoxy" as used by itself or as part of another group refers to an optionally substituted alkyl, optionally substituted cycloalkyl, optionally substituted alkenyl or optionally substituted alkynyl attached to a terminal oxygen atom. In one embodiment, the alkoxy group is chosen from a $C_{1-4}$ alkoxy group. In another embodiment, the alkoxy group is chosen from a $C_{1-4}$ alkyl attached to a terminal oxygen atom, e.g., methoxy, ethoxy, and tert-butoxy.

For the purpose of the present disclosure, the term "alkylthio" as used by itself or as part of another group refers to a sulfur atom substituted by an optionally substituted alkyl group. In one embodiment, the alkylthio group is chosen from a $C_{1-4}$ alkylthio group. Non-limiting exemplary alkylthio groups include —$SCH_3$, and —$SCH_2CH_3$.

For the purpose of the present disclosure, the term "alkoxyalkyl" as used by itself or as part of another group refers to an alkyl group substituted with an alkoxy group. Non-limiting exemplary alkoxyalkyl groups include methoxymethyl, methoxyethyl, methoxypropyl, methoxybutyl, ethoxymethyl, ethoxyethyl, ethoxypropyl, ethoxybutyl, propoxymethyl, iso-propoxymethyl, propoxyethyl, propoxypropyl, butoxymethyl, tert-butoxymethyl, isobutoxymethyl, sec-butoxymethyl, and pentyloxymethyl.

For the purpose of the present disclosure, the term "haloalkoxy" as used by itself or as part of another group refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

For the purpose of the present disclosure, the term "aryl" as used by itself or as part of another group refers to a monocyclic or bicyclic aromatic ring system having from six to fourteen carbon atoms (i.e., $C_6$-$C_{14}$ aryl). Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is chosen from phenyl or naphthyl.

For the purpose of the present disclosure, the term "optionally substituted aryl" as used herein by itself or as part of another group means that the aryl as defined above is either unsubstituted or substituted with one to five substituents independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino) alkyl, (carboxamido)alkyl, mercaptoalkyl, or (heterocyclo) alkyl.

In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, and 3-chloro-4-fluorophenyl. The term optionally substituted aryl is meant to include groups having fused optionally substituted cycloalkyl and fused optionally substituted heterocyclo rings. Non-limiting examples include:

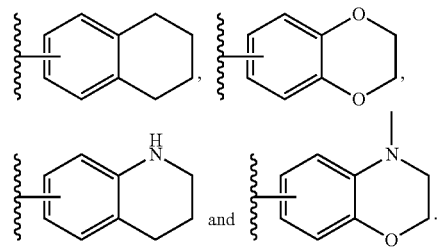

For the purpose of the present disclosure, the term "aryloxy" as used by itself or as part of another group refers to an optionally substituted aryl attached to a terminal oxygen atom. A non-limiting exemplary aryloxy group is PhO—.

For the purpose of the present disclosure, the term "aralkyloxy" as used by itself or as part of another group refers to an aralkyl group attached to a terminal oxygen atom. A non-limiting exemplary aralkyloxy group is $PhCH_2O$—.

For the purpose of the present disclosure, the term "heteroalkyl" as used by itself or part of another group refers to a stable straight or branched chain hydrocarbon radical containing 1 to 10 carbon atoms and at least two heteroatoms, which can be the same or different, selected from O, N, or S, wherein: 1) the nitrogen atom(s) and sulfur atom(s) can optionally be oxidized; and/or 2) the nitrogen atom(s) can optionally be quaternized. The heteroatoms can be placed at any interior position of the heteroalkyl group or at a position at which the heteroalkyl group is attached to the remainder of the molecule. In one embodiment, the heteroalkyl group contains two oxygen atoms. In one embodiment, the heteroalkyl contains one oxygen and one nitrogen atom. In one embodiment, the heteroalkyl contains two nitrogen atoms. Non-limiting exemplary heteroalkyl groups include —$CH_2OCH_2CH_2OCH_3$, —$OCH_2CH_2OCH_2CH_2OCH_3$, —$CH_2NHCH_2CH_2OCH_2$, —$OCH_2CH_2NH_2$, —$NHCH_2CH_2N(H)CH_3$, —$NHCH_2CH_2OCH_3$ and —$OCH_2CH_2OCH_3$.

For the purpose of the present disclosure, the term "heteroaryl" or "heteroaromatic" refers to monocyclic and bicyclic aromatic ring systems having 5 to 14 ring atoms (i.e., $C_5$-$C_{14}$ heteroaryl), wherein at least one carbon atom of one of the rings is replaced with a heteroatom independently selected from the group consisting of oxygen, nitrogen and sulfur. In one embodiment, the heteroaryl contains 1, 2, 3, or 4 heteroatoms independently selected from the group consisting of oxygen, nitrogen and sulfur. In one embodiment, the heteroaryl has three heteroatoms. In another embodiment, the heteroaryl has two heteroatoms. In another embodiment, the heteroaryl has one heteroatom. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is chosen from thienyl e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl e.g., 1H-pyrazol-3-yl, 1H-pyrazol-4-yl, and 1H-pyrazol-5-yl), pyridyl e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl e.g., oxazol-2-yl, oxazol-4-yl, and oxazol-5-yl), isoxazolyl (e.g., isoxazol-3-yl, isoxazol-4-yl, and isoxazol-5-yl), and indazolyl (e.g., 1H-indazol-3-yl). The term "heteroaryl" is also meant to include possible N-oxides. A non-limiting exemplary N-oxide is pyridyl N-oxide.

In one embodiment, the heteroaryl is a 5- or 6-membered heteroaryl. In one embodiment, the heteroaryl is a 5-membered heteroaryl, i.e., the heteroaryl is a monocyclic aromatic ring system having 5 ring atoms wherein at least one carbon atom of the ring is replaced with a heteroatom independently selected from nitrogen, oxygen, and sulfur. Non-limiting exemplary 5-membered heteroaryl groups include thienyl, furyl, pyrrolyl, oxazolyl, pyrazolyl, imidazolyl, thiazolyl, isothiazolyl, and isoxazolyl.

In another embodiment, the heteroaryl is a 6-membered heteroaryl, e.g., the heteroaryl is a monocyclic aromatic ring system having 6 ring atoms wherein at least one carbon atom of the ring is replaced with a nitrogen atom. Non-limiting exemplary 6-membered heteroaryl groups include pyridyl, pyrazinyl, pyrimidinyl, and pyridazinyl.

For the purpose of the present disclosure, the term "optionally substituted heteroaryl" as used by itself or as part of another group means that the heteroaryl as defined above is either unsubstituted or substituted with one to four substituents, e.g., one or two substituents, independently chosen from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, or (heterocyclo)alkyl. In one embodiment, the optionally substituted heteroaryl has one substituent. Any available carbon or nitrogen atom can be substituted. Non-limiting exemplary optionally substituted 5-membered heteroaryl groups include, but are not limited to:

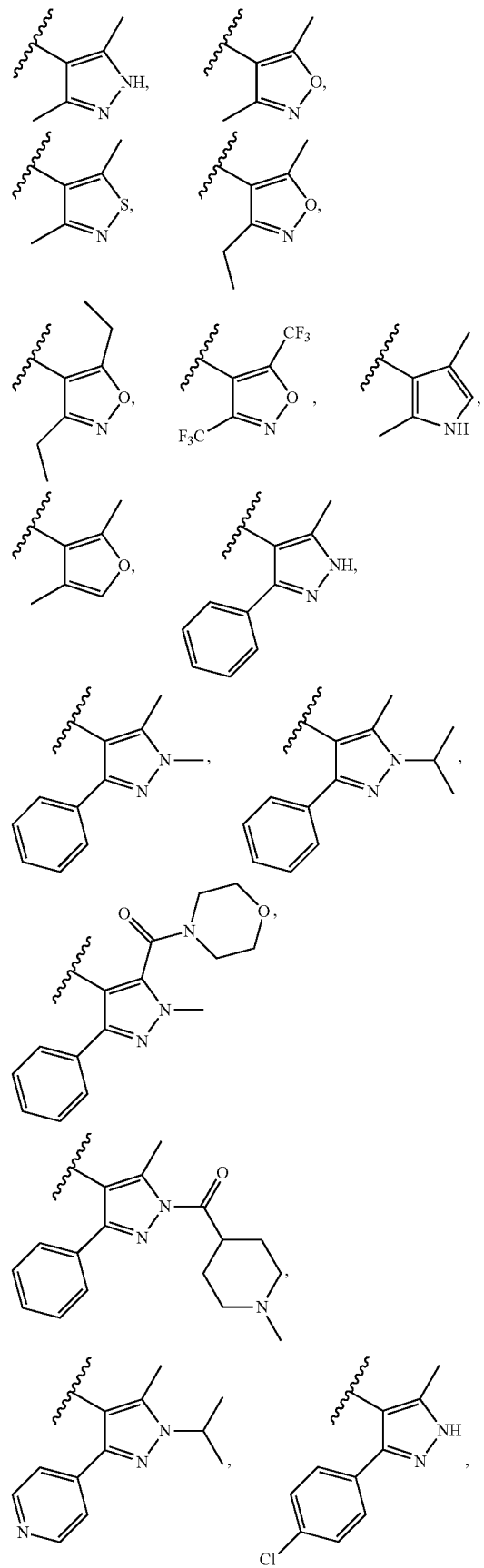

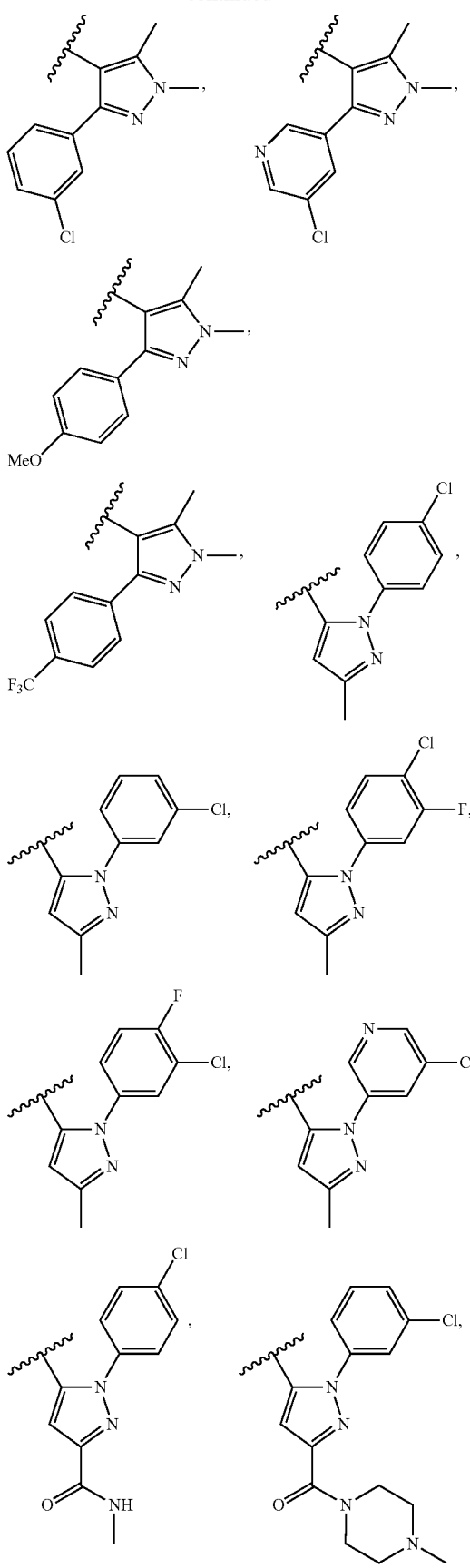
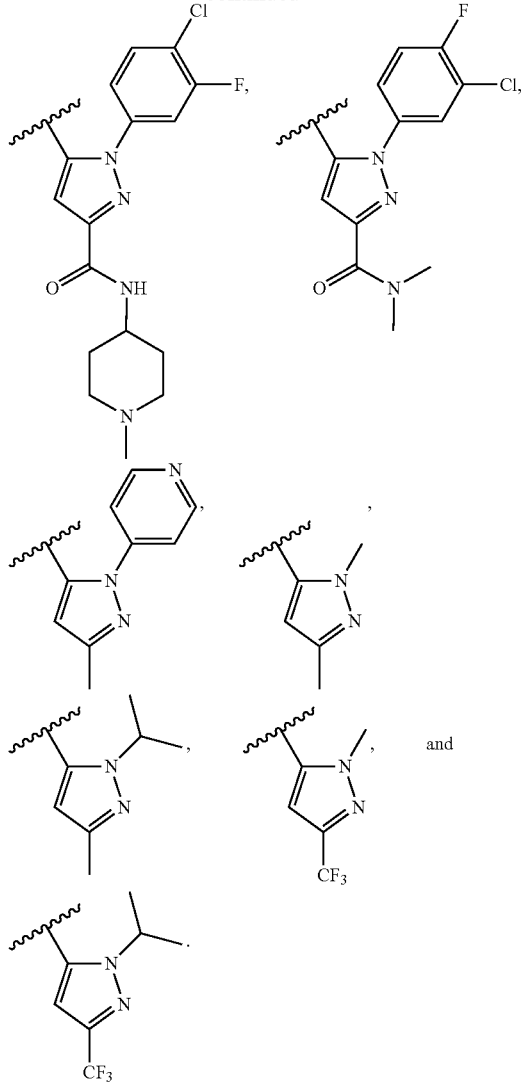

The term optionally substituted heteroaryl is also meant to include groups having fused optionally substituted cycloalkyl and fused optionally substituted heterocyclo rings. Non-limiting examples include:

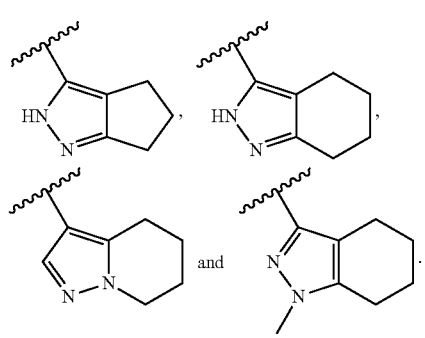

For the purpose of the present disclosure, the term "heterocycle" or "heterocyclo" as used by itself or as part of another group refers to saturated and partially unsaturated (e.g., containing one or two double bonds) cyclic groups containing one, two, or three rings having from three to fourteen ring members (i.e., a 3- to 14-membered heterocyclo) wherein at least one carbon atom of one of the rings is replaced with a heteroatom. Each heteroatom is independently selected from the group consisting of oxygen, sulfur, including sulfoxide and sulfone, and/or nitrogen atoms, which can be oxidized or quaternized. The term "heterocyclo" is meant to include groups wherein a ring —$CH_2$— is replaced with a —C(=O)—, for example, cyclic ureido groups such as 2-imidazolidinone and cyclic amide groups such as β-lactam, γ-lactam, δ-lactam, ε-lactam, and piperazin-2-one. The term "heterocyclo" is also meant to include groups having fused optionally substituted aryl groups, e.g., indolinyl, chroman-4-yl. In one embodiment, the heterocyclo group is chosen from a 5- or 6-membered cyclic group containing one ring and one or two oxygen and/or nitrogen atoms. The heterocyclo can be optionally linked to the rest of the molecule through any available carbon or nitrogen atom. Non-limiting exemplary heterocyclo groups include dioxanyl, tetrahydropyranyl, 2-oxopyrrolidin-3-yl, piperazin-2-one, piperazine-2,6-dione, 2-imidazolidinone, piperidinyl, morpholinyl, piperazinyl, pyrrolidinyl, and indolinyl.

For the purpose of the present disclosure, the term "optionally substituted heterocyclo" as used herein by itself or part of another group means the heterocyclo as defined above is either unsubstituted or substituted with one to four substituents independently selected from halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, alkoxycarbonyl, $CF_3C$(=O)—, arylcarbonyl, alkylsulfonyl, arylsulfonyl, carboxy, carboxyalkyl, alkyl, optionally substituted cycloalkyl, alkenyl, alkynyl, optionally substituted aryl, optionally substituted heteroaryl, optionally substituted heterocyclo, alkoxyalkyl, (amino)alkyl, (carboxamido)alkyl, mercaptoalkyl, or (heterocyclo)alkyl. Substitution may occur on any available carbon or nitrogen atom, or both. Non-limiting exemplary optionally substituted heterocyclo groups include:

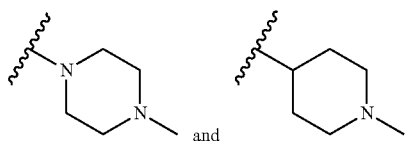

For the purpose of the present disclosure, the term "amino" as used by itself or as part of another group refers to —$NR^{7a}R^{7b}$, wherein $R^{7a}$ and $R^{7b}$ are each independently hydrogen, alkyl, hydroxyalkyl, optionally substituted cycloalkyl, optionally substituted aryl, optionally substituted heterocyclo, or optionally substituted heteroaryl, or $R^{7a}$ and $R^{7b}$ are taken together to form a 3- to 8-membered optionally substituted heterocyclo. Non-limiting exemplary amino groups include —$NH_2$ and —N(H)($CH_3$).

For the purpose of the present disclosure, the term "(amino)alkyl" as used by itself or as part of another group refers to an alkyl group substituted with an amino group. Non-limiting exemplary amino alkyl groups include —$CH_2CH_2NH_2$, and —$CH_2CH_2N(H)CH_3$, —$CH_2CH_2N(CH_3)_2$, and —$CH_2N(H)$cyclopropyl.

For the purpose of the present disclosure, the term "carboxamido" as used by itself or as part of another group refers to a radical of formula —C(=O)$NR^{9a}R^{9b}$, wherein $R^{9a}$ and $R^{9b}$ are each independently hydrogen, optionally substituted alkyl, hydroxyalkyl, optionally substituted cycloalkyl, optionally substituted aryl, optionally substituted heterocyclo, or optionally substituted heteroaryl, or $R^{9a}$ and $R^{9b}$ taken together with the nitrogen to which they are attached form a 3- to 8-membered optionally substituted heterocyclo group. In one embodiment, $R^{9a}$ and $R^{9b}$ are each independently hydrogen or optionally substituted alkyl. In one embodiment, $R^{9a}$ and $R^{9b}$ are taken together to taken together with the nitrogen to which they are attached form a 3- to 8-membered optionally substituted heterocyclo group. Non-limiting exemplary carboxamido groups include, but are not limited to, —$CONH_2$, —CON(H)$CH_3$, —CON($CH_3$)$_2$, —CON(H)Ph,

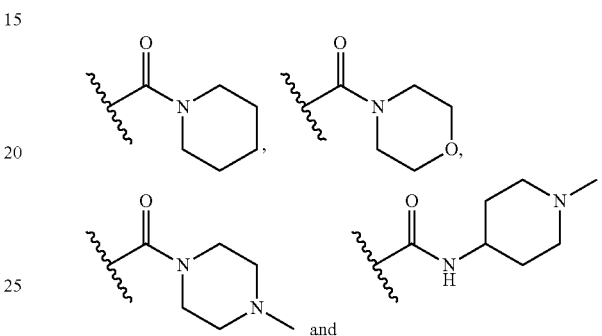

For the purpose of the present disclosure, the term "sulfonamido" as used by itself or as part of another group refers to a radical of the formula —$SO_2NR^{8a}R^{8b}$, wherein $R^{8a}$ and $R^{8b}$ are each independently hydrogen, optionally substituted alkyl, or optionally substituted aryl, or $R^{8a}$ and $R^{8b}$ taken together with the nitrogen to which they are attached from a 3- to 8-membered heterocyclo group. Non-limiting exemplary sulfonamido groups include —$SO_2NH_2$, —$SO_2N(H)CH_3$, and —$SO_2N(H)Ph$.

For the purpose of the present disclosure, the term "alkylcarbonyl" as used by itself or as part of another group refers to a carbonyl group, i.e., —C(=O)—, substituted by an alkyl group. A non-limiting exemplary alkylcarbonyl group is —$COCH_3$.

For the purpose of the present disclosure, the term "arylcarbonyl" as used by itself or as part of another group refers to a carbonyl group, i.e., —C(=O)—, substituted by an optionally substituted aryl group. A non-limiting exemplary arylcarbonyl group is —COPh.

For the purpose of the present disclosure, the term "alkoxycarbonyl" as used by itself or as part of another group refers to a carbonyl group, i.e., —C(=O)—, substituted by an alkoxy group. Non-limiting exemplary alkoxycarbonyl groups include —C(=O)OMe, —C(=O)OEt, and —C(=O)OtBu.

For the purpose of the present disclosure, the term "alkylsulfonyl" as used by itself or as part of another group refers to a sulfonyl group, i.e., —$SO_2$—, substituted by any of the above-mentioned optionally substituted alkyl groups. A non-limiting exemplary alkylsulfonyl group is —$SO_2CH_3$.

For the purpose of the present disclosure, the term "arylsulfonyl" as used by itself or as part of another group refers to a sulfonyl group, i.e., —$SO_2$—, substituted by any of the above-mentioned optionally substituted aryl groups. A non-limiting exemplary arylsulfonyl group is —$SO_2Ph$.

For the purpose of the present disclosure, the term "mercaptoalkyl" as used by itself or as part of another group refers to any of the above-mentioned alkyl groups substituted by a —SH group.

For the purpose of the present disclosure, the term "carboxy" as used by itself or as part of another group refers to a radical of the formula —COOH.

For the purpose of the present disclosure, the term "carboxyalkyl" as used by itself or as part of another group refers to any of the above-mentioned alkyl groups substituted with a —COOH. A non-limiting exemplary carboxyalkyl group is —CH$_2$CO$_2$H.

For the purpose of the present disclosure, the terms "aralkyl" or "arylalkyl" as used by themselves or as part of another group refers to an alkyl group substituted with one, two, or three optionally substituted aryl groups. In one embodiment, the optionally substituted aralkyl group is a C$_{1-4}$ alkyl substituted with one optionally substituted aryl group. In one embodiment, the optionally substituted aralkyl group is a C$_1$ or C$_2$ alkyl substituted with one optionally substituted aryl group. In one embodiment, the optionally substituted aralkyl group is a Q or C$_2$ alkyl substituted with one optionally substituted phenyl group. Non-limiting exemplary optionally substituted aralkyl groups include benzyl, phenethyl, —CHPh$_2$, —CH$_2$(4-F-Ph), —CH$_2$(4-Me-Ph), —CH$_2$(4-CF$_3$-Ph), and —CH(4-F-Ph)$_2$.

For the purpose of the present disclosure, the terms "(heterocyclo)alkyl" as used by itself or part of another group refers to an alkyl group substituted with an optionally substituted heterocyclo group. In one embodiment, the (heterocyclo)alkyl is a C$_{1-4}$ alkyl substituted with one optionally substituted heterocyclo group. Non-limiting exemplary (heterocyclo)alkyl groups include:

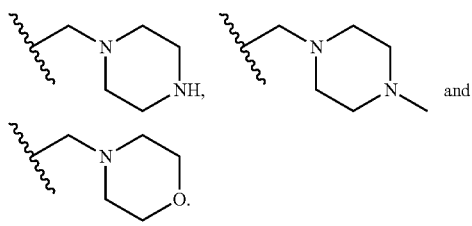

For the purpose of the present disclosure, the term "(carboxamido)alkyl" as used by itself or as part of another group refers to an alkyl group substituted with one or two carboxamido groups. In one embodiment, the (carboxamido)alkyl is a C$_{1-4}$ alkyl substituted with one carboxamido group. In another embodiment, the (carboxamido)alkyl is a C$_{1-4}$ alkyl substituted with two carboxamido groups. Non-limiting exemplary (carboxamido)alkyl groups include —CH$_2$CONH$_2$, —C(H)CH$_3$—CONH$_2$, —CH$_2$CON(H)CH$_3$, and —CH(CO$_2$NH$_2$)CH$_2$CH$_2$CO$_2$NH$_2$

EXAMPLES

Example 1

Synthesis of ethyl 2-amino-6-(3,5-dimethylisoxazol-4-yl)-5-methoxy-1H-indole-3-carboxylate (S6)

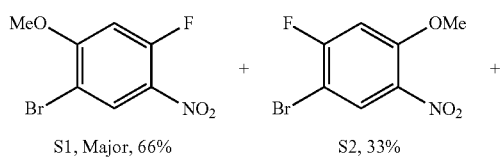

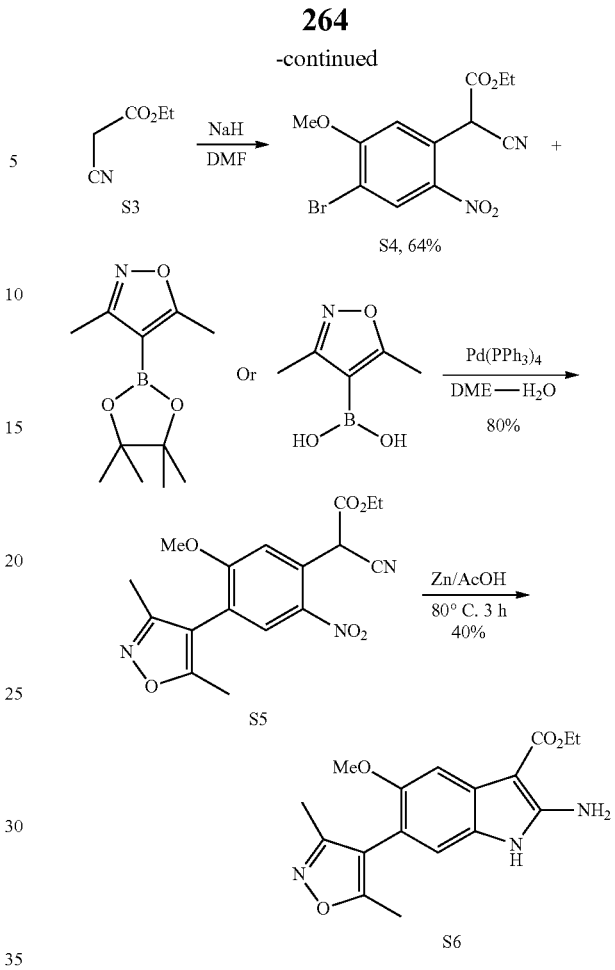

S3 (2.26 g, 20 mmol) was dissolved in anhydrous DMF (50 mL) and the solution was cooled to 0° C. NaH (1.2 g, 60% in mineral oil, 30 mmol) was added in small portions. The resulting reaction mixture was stirred for 0.5 h at 0° C. and an anhydrous DMF solution of known compounds S1 and S2 (20 mmol, J. Med. Chem. 55:449-464 (2012)) was added. The resulting solution was stirred at 0° C. for 3 h before quenching with 1 N HCl. The aqueous layer was extracted with ethyl acetate and combined organic layers were washed with brine and dried over anhydrous Na$_2$SO$_4$. The volatile components were removed on a rotary evaporator and the residue was purified by flash column chromatogram. The desired product S4 was isolated as colorless oil with impurity of the other regioisomer (4.17 g, 61% yield). $^1$H NMR (300 MHz, CDCl$_3$): 8.41 (s, 1H), 7.11 (s, 1H), 5.60 (s, 1H), 4.24 (q, J=7.03 Hz, 2H), 4.01 (s, 3H), 1.25 (t, J=7.14 Hz, 3H).

S4 (1.43 g, 4.2 mmol), 3,5-dimethyl-4-(4,4,5,5-tetramethyl-1,3,2-dioxaborolan-2-yl)isoxazole (2.34 g, 10.5 mmol), and K$_2$CO$_3$ (2.03 g, 14.7 mmol) were added to a round-bottom flask. DME (30 mL) and water (15 mL) were added at room temperature. The solution was degassed, then Pd(PPh$_3$)$_4$ (242 mg, 0.21 mmol) was added in one portion. The solution was again degassed, then heated at reflux for 14 h. The aqueous layer was extracted with ethyl acetate, the combined organic layers were washed with brine, then dried over anhydrous Na$_2$SO$_4$. The volatile components were removed on a rotary evaporator and the residue was purified by flash column chromatogram. The desired product S5 was isolated in >80% yield (1.47 g, contaminated with isomers and pinacol components). $^1$H NMR (CDCl$_3$, 300 MHz):

8.10 (s, 1H), 7.27 (s, 1H), 5.78 (s, 1H), 4.35 (q, J=7.12 Hz, 2H), 3.99 (s, 3H), 2.33 (s, 3H), 2.18 (s, 3H), 1.37 (t, J=7.14 Hz, 3H).

To an AcOH (30 mL) solution of S5 (1.47 g) at 80° C., 0.8 g Zn powder was added in small portions. The mixture was stirred at 80° C. for 1 h, another 0.8 g Zn powder was added, and the reaction was kept at the same temperature for 2 h. The reaction was cooled, filtered, and washed with AcOH. The AcOH solution was combined and the volatile components were removed on a rotary evaporator. Purification by flash column chromatogram furnished the desired product S6 (0.55 g, ca, 40% yield). $^1$H NMR (CDCl$_3$, 300 MHz): 8.01 (br, s, 1H), 7.44 (s, 1H), 6.78 (s, 1H), 5.73 (br, s, 2H), 4.40 (q, J=7.08 Hz, 2H), 3.82 (s, 3H), 2.29 (s, 3H), 2.15 (s, 3H), 1.45 (t, J=7.08 Hz, 3H). ESI-MS calculated for $C_{17}H_{20}N_3O_4$ [M+H]$^+$: 330.15, Obtained: 330.25.

Example 2

Synthesis of 4-(4-chloro-6-methoxy-9H-pyrimido[4,5-b]indol-7-yl)-3,5-dimethylisoxazole (S13)

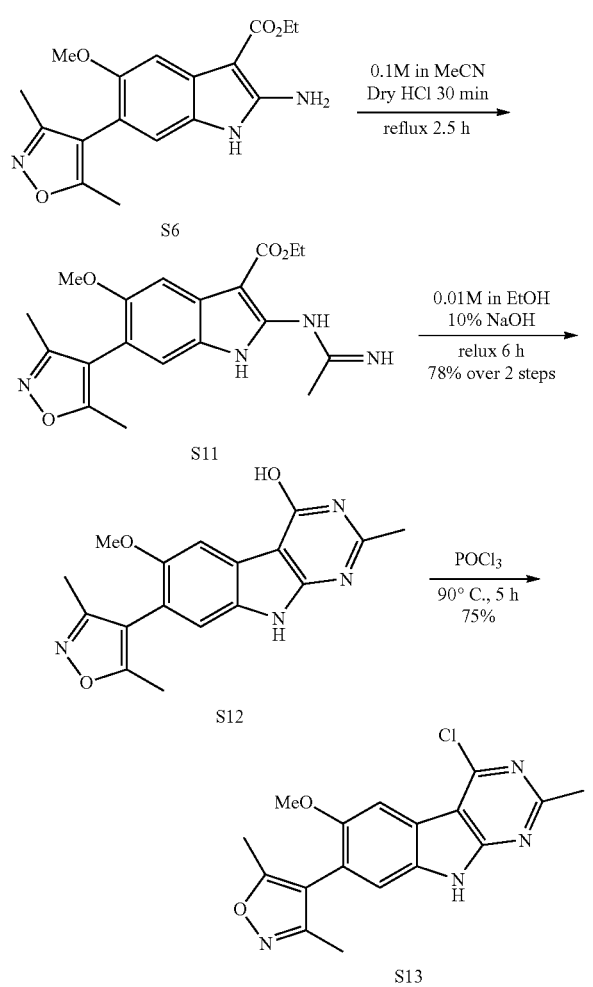

Step 1: To a round-bottom flask, S6 (0.37 g, 1.1 mmol) and MeCN (20 mL) were added at room temperature. Dry HCl was bubbled through MeCN for 30 min and the reaction mixture was warmed up to reflux (ca, 82° C.) for 2.5 h. The reaction was then cooled to room temperature and the volatile components were removed on a rotary evaporator. To this crude mixture, 10% NaOH aqueous solution (20 mL) and EtOH (50 mL) were added and the solution was heated at reflux for 6 h. The volatile components were then removed on a rotary evaporator and the aqueous residue was acidified with 2N HCl aqueous solution. The product S12 was allowed to precipitate at 0° C. Filtration of the mixture furnished pure S12 in 0.278 g (78% yield, 2 steps). $^1$H NMR (DMSO-d6, 300 MHz): 7.57 (s, 1H), 7.20 (s, 1H), 3.81 (s, 3H), 2.37 (s, 3H), 2.27 (s, 3H), 2.08 (s, 3H).

Step 2: To a round-bottom flask, S12 (0.278 g, 0.8 mmol) and POCl$_3$ (8 mL) were added. The mixture was heated at 90° C. for 6 h. The reaction mixture was cooled to room temperature and the volatile components were removed on a rotary evaporator. Water (20 mL) and ethyl acetate (20 mL) were added and the pH was adjusted to 8 using NaHCO$_3$ saturated aqueous solution. Filtration of the mixture furnished S13 as a brown solid in 0.208 g (75% yield). $^1$H NMR (DMSO-d6, 300 MHz): 7.81 (s, 1H), 7.43 (s, 1H), 3.89 (s, 3H), 2.69 (s, 3H), 2.31 (s, 3H), 2.11 (s, 3H).

Example 3

Synthesis of 4-(4-chloro-6-methoxy-9H-pyrimido[4,5-b]indol-7-yl)-3,5-dimethylisoxazole (CD54)

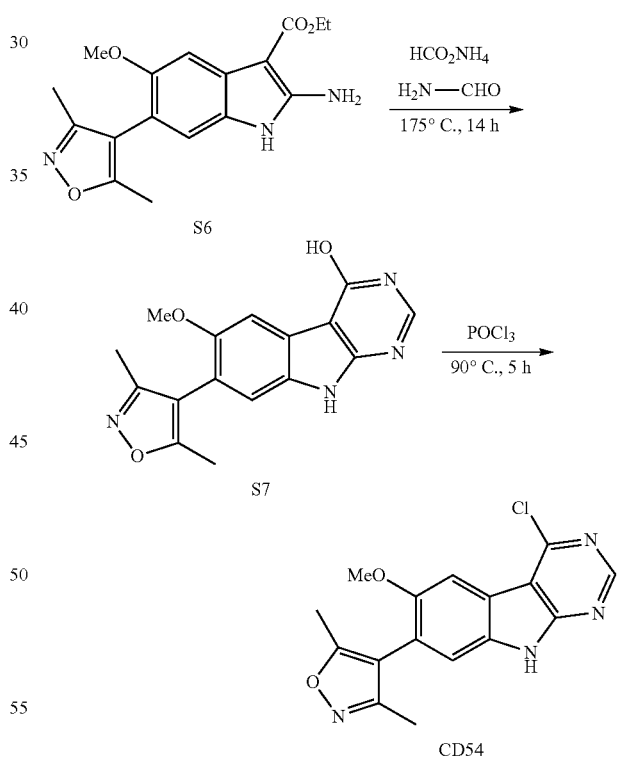

Step 1: S6 (0.45 g, 1.4 mmol), ammonium formate (1.06 g, 17 mmol), and formamide (16 mL) were heated at 175° C. for 14 h. The reaction was cooled to room temperature and water was added. Filtration of the mixture yielded S7 as a brown solid (0.24 g, 0.77 mmol, 55% yield). $^1$H NMR (DMSO-d6, 300 MHz): 8.09 (s, 1H), 7.57 (s, 1H), 7.24 (s, 1H), 3.81 (s, 3H), 3.30 (s, 1H), 2.62 (s, 3H), 2.06 (s, 3H), ESI-MS calculated for $C_{16}H_{15}N_4O_3$ [M+H]$^+$: 311.11, Obtained: 311.75

Step 2: S7 (0.24 g, 0.77 mmol) was dissolved in POCl$_3$ (10 mL) and the mixture was heated at 90° C. for 5 h. The mixture was cooled to room temperature and the volatile components were removed on a rotary evaporator. Ethyl acetate (20 mL) was added at 0° C., followed by NaHCO$_3$ (20 mL) and water (20 mL). The mixture was filtered and the desired CD54 product was collected as a brown solid (0.17 g). The aqueous layer was extracted with ethyl acetate and the combined organic layers were washed with brine and dried over anhydrous Na$_2$SO$_4$. The volatile components were removed on a rotary evaporator affording a brown solid (80 mg, 90 purity of CD54). $^1$H NMR (DMSO-d6, 300 MHz): 8.74 (s, 1H), 7.84 (s, 1H), 7.45 (s, 1H). 3.89 (s, 3H), 3.31 (br, s, 1H), 2.29 (s, 3H), 2.09 (s, 3H). $^{13}$C NMR (DMSO-d6, 75 MHz): 167.84, 161.17. 155.84, 122.24, 120.26, 116.96, 115.15, 113.11, 105.80, 57.84, 13.36, 12.39. ESI-MS calculated for C$_{16}$H$_{14}$$^{35}$ClN$_4$O$_2$[M+H]$^+$: 329.08, Obtained: 329.67

Example 4

Synthesis of 7-(3,5-Dimethylisoxazol-4-yl)-6-methoxy-N-(1-methyl-1H-indazol-3-yl)-9H-pyrimido[4,5-b]indol-4-amine (Cpd. No. 17)

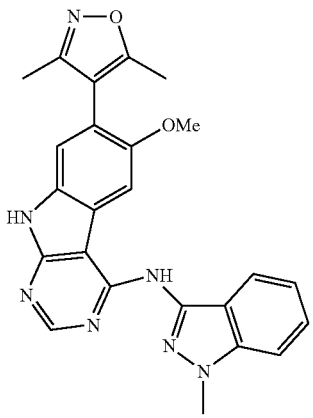 [SMILES: COc1cc2c(cc1-c1c(C)noc1C)[nH]c1ncnc(Nc3nn(C)c4ccccc34)c12]

4-(4-Chloro-6-methoxy-9H-pyrimido[4,5-b]indol-7-yl)-3,5-dimethylisoxazole (CD54, 56 mg) and 1-methyl-1H-indazol-3-amine (60 mg) were dissolved in isopropanol (5 mL). Five drops of concentrated HCl was added via a glass pipette. The mixture was heat at reflux for overnight. The reaction was then concentrated on a rotary evaporator and the remaining residues was purified by reverse phase HPLC to yield Cpd. No. 17 in 19 mg as a salt of CF$_3$CO$_2$H. $^1$H NMR (300 MHz, MeOD-d4): 8.57 (s, 1H), 8.17 (s, 1H), 7.91 (d, J=8.42 Hz, 1H), 7.70 (d, J=8.42 Hz, 1H), 7.62-7.54 (m, 1H), 7.54 (s, 1H), 7.32 (d, J=7.40 Hz, 1H), 4.20 (s, 3H), 3.98 (s, 3H), 2.35 (s, 3H), 2.18 (s, 3H). ESI-MS calculated for C$_{24}$H$_{22}$N$_7$O$_2$ [M+H]$^+$=440.18, Observed: 440.58

Example 5

Synthesis of 4-(4-chloro-2-isopropyl-6-methoxy-9H-pyrimido[4,5-b]indol-7-yl)-3,5-dimethylisoxazole (CD177)

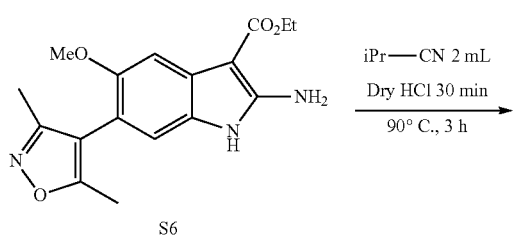

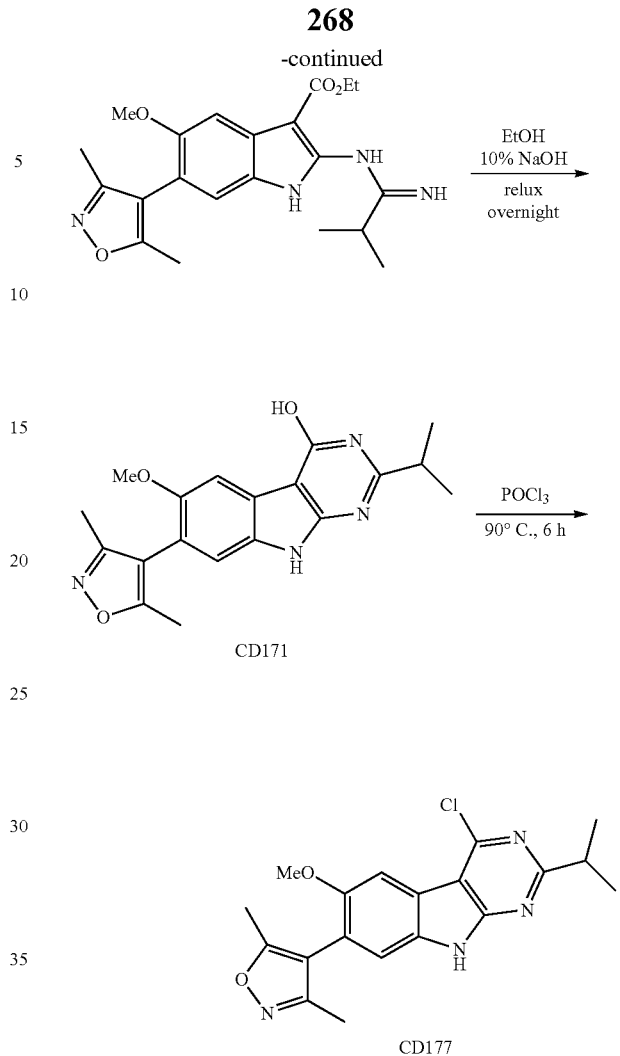

Step 1: S6 (400 mg) was dissolved in isobutyronitrile (2 mL). HCl gas was bubbled into the solution for 40 min and the solution was heated at 90° C. for 3 h. The solvent was concentrated in vacuum and the residue was dissolved in ethanol (40 mL). NaOH (10%, 30 mL) was added to the ethanol solution and the mixture was heated at reflux for overnight. The solution was cooled to room temperature and concentrated in vacuum. Ethyl acetate (20 mL) was added followed by aqueous HCl solution to set pH=4-5. The precipitate was collected by filtration and the residue was washed with diethyl ether to furnish CD171 in 0.26 g. $^1$H NMR (300 MHz, DMSO-d6): 12.05 (s, 1H), 12.00 (s, 1H), 7.54 (s, 1H), 7.18 (s, 1H), 3.81 (s, 3H), 2.97 (septet, J=6.75 Hz, 1H), 2.26 (s, 3H), 2.06 (s, 3H), 1.25 (d, J=6.80 Hz, 6H)

Step 2: CD171 (0.26 g) was mixed with phosphorus(V) oxychloride (5 mL) and heated at 90° C. for 6 h. The mixture was concentrated in vacuum and neutralized with excess aqueous NaHCO$_3$ saturated solution. Ethyl acetate (30 mL) was added and the precipitate was collected by filtration. The solid residue was washed with diethyl ether to furnish CD177 in 120 mg (43% yield). $^1$H NMR (300 MHz, DMSO-d6): 12.52 (s, 1H), 7.79 (s, 1H), 7.38 (s, 1H), 3.88 (s, 3H), 3.19 (septet, J=6.88 Hz, 1H), 2.28 (s, 3H), 2.09 (s, 3H), 1.33 (d, J=6.88 Hz, 6H).

Example 6

Synthesis of 7-(3,5-Dimethylisoxazol-4-yl)-2-isopropyl-6-methoxy-N-(1-methyl-1H-indazol-3-yl)-9H-pyrimido[4,5-b]indol-4-amine (Cpd. No. 18)

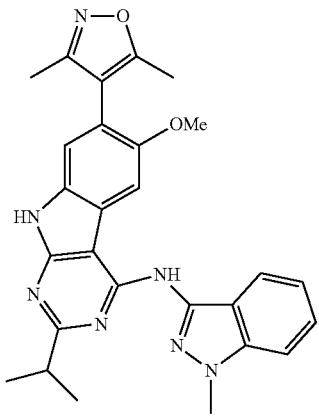 [SMILES: COc1cc2c(cc1-c1c(C)noc1C)[nH]c1nc(C(C)C)nc(Nc3nn(C)c4ccccc34)c12]

4-(4-Chloro-2-isopropyl-6-methoxy-9H-pyrimido[4,5-b]indol-7-yl)-3,5-dimethylisoxazole (CD177, 70 mg) and 1-methyl-1H-indazol-3-amine (60 mg) were dissolved in isopropanol (5 mL). Five drops of concentrated HCl was added via a glass pipette. The mixture was heat at reflux for overnight. The reaction was then concentrated on a rotary evaporator and the remaining residues was purified by reverse phase HPLC to yield Cpd. No. 18 in 40 mg as a salt of $CF_3CO_2H$. $^1H$ NMR (300 MHz, MeOD-d4): 7.97 (d, J=8.32 Hz, 1H), 7.90 (s, 1H), 7.67 (d, J=8.53 Hz, 1H), 7.62-7.55 (m, 1H), 7.49 (s, 1H), 7.31 (t, J=7.42 Hz, 1H), 4.16 (s, 3H), 3.89 (s, 3H), 3.36 (septet, J=6.78 Hz, 1H), 2.33 (s, 3H), 2.16 (s, 3H), 1.50 (d, J=6.90 Hz, 6H). ESI-MS calculated for $C_{27}H_{28}N_7O_2$ $[M+H]^+$=482.23, Observed: 482.42.

Example 7

Synthesis of 4-(4-chloro-6-methoxy-2-(tetrahydro-2H-pyran-4-yl)-9H-pyrimido[4,5-b]indol-7-yl)-3,5-dimethylisoxazole (CD197)

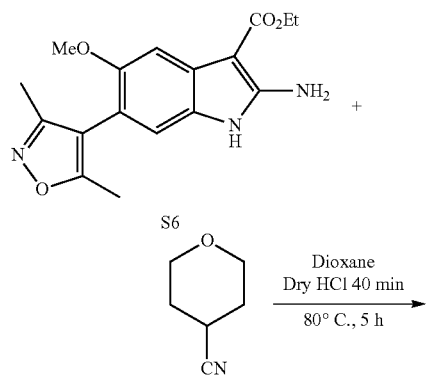

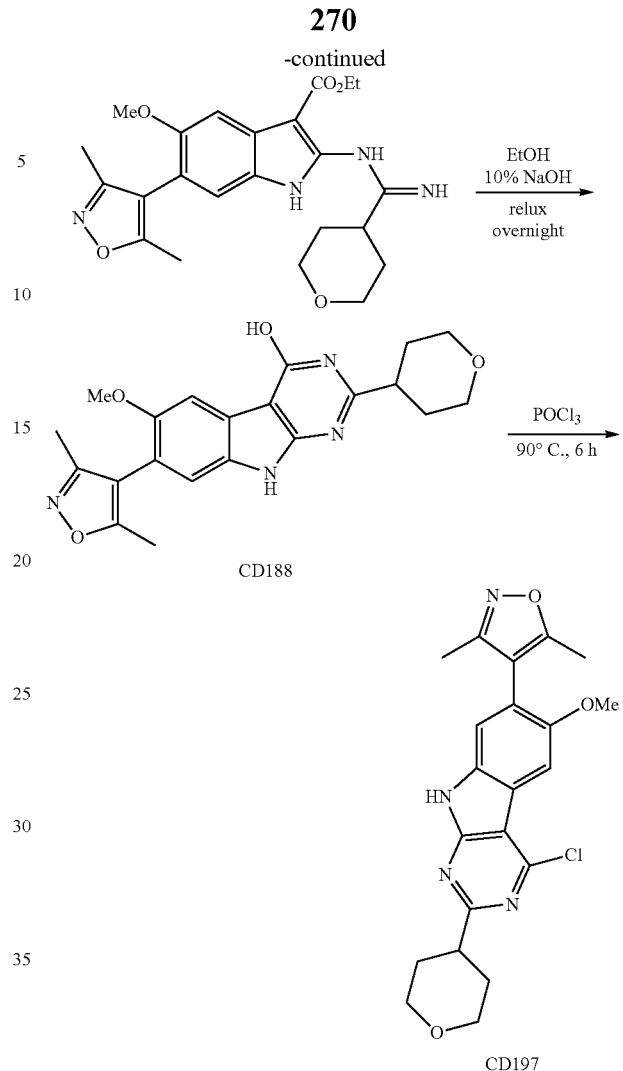

Step 1: S6 (300 mg), tetrahydropyranyl-4-carbonitrile (330 mg), and dioxane (10 mL) were placed in a round-bottom flask. HCl gas was bubbled into the solution for 40 min and the solution was heated at 80° C. for 5 h. The solvent was concentrated in vacuum and the residue was dissolved in ethanol (30 mL). NaOH (10%, 30 mL) was added to the ethanol solution and the mixture was heated at reflux for 12 h. The solution was cooled to room temperature and concentrated in vacuum. Ethyl acetate (20 mL) was added followed by addition of aqueous HCl solution to set pH=4-5. The precipitate was collected by filtration and the residue was washed with diethyl ether to furnish CD188 in 0.12 g (33% yield). ESI-MS calculated for $C_{21}H_{23}N_4O_4$ $[M+H]^+$=395.17, Obtained: 395.58.

Step 2: CD188 (0.12 g) was mixed with phosphorus(V) oxychloride (10 mL) and heated at 90° C. for 6 h. The mixture was concentrated in vacuum and neutralized with excess aqueous $NaHCO_3$ saturated solution. Ethyl acetate (20 mL) was added and the precipitate was collected by filtration. The solid residue was washed with diethyl ether to furnish CD197 in 80 mg (63% yield).

Example 8

Synthesis of 7-(3,5-Dimethylisoxazol-4-yl)-6-methoxy-N-(1-methyl-1H-indazol-3-yl)-2-(tetrahydro-2H-pyran-4-yl)-9H-pyrimido[4,5-b]indol-4-amine (Cpd. No. 20

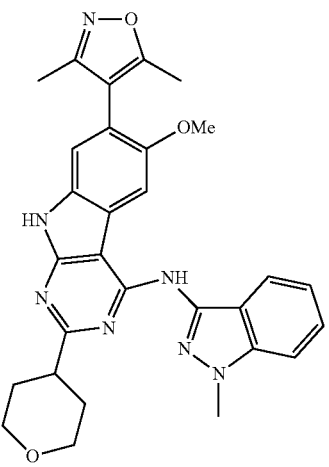 [SMILES: COc1cc2c(cc1-c1c(C)noc1C)[nH]c1nc(C3CCOCC3)nc(Nc3nn(C)c4ccccc34)c12]

4-(4-Chloro-6-methoxy-2-(tetrahydro-2H-pyran-4-yl)-9H-pyrimido[4,5-b]indol-7-yl)-3,5-dimethylisoxazole (CD197, 28 mg) and 1-methyl-1H-indazol-3-amine (60 mg) were dissolved in isopropanol (5 mL). Four drops of concentrated HCl was added via a glass pipette. The mixture was heat at reflux for overnight. The reaction was then concentrated on a rotary evaporator and the remaining residues was purified by reverse phase HPLC to yield Cpd. No. 21 in 13 mg as a salt of $CF_3CO_2H$. $^1H$ NMR (300 MHz, MeOD-d4): 7.93 (d, J=8.16 Hz, 1H), 7.88 (s, 1H), 7.68 (d, J=8.35 Hz, 1H), 7.64-7.54 (m, 1H), 7.49 (s, 1H), 7.34-7.24 (m, 1H), 4.17 (s, 3H), 4.08 (dt, J=6.13, 2.73 Hz, 2H), 3.88 (s, 3H), 3.70-3.45 (m, 2H), 2.33 (s, 3H), 2.16 (s, 3H), 2.10-1.98 (m, 5H). ESI-MS calculated for $C_{29}H_{30}N_7O_3$ $[M+H]^+$=524.24, Observed: 524.50.

Example 9

Synthesis of 7-(3,5-Dimethylisoxazol-4-yl)-6-methoxy-2-methyl-N-(3-methyl-1-phenyl-1H-pyrazol-5-yl)-9H-pyrimido[4,5-b]indol-4-amine (Cpd. No. 1)

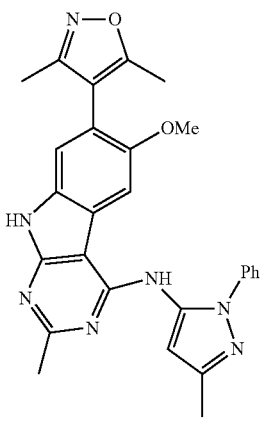 [SMILES: COc1cc2c(cc1-c1c(C)noc1C)[nH]c1nc(C)nc(Nc3cc(C)nn3-c3ccccc3)c12]

S13 (68 mg), 3-methyl-1-phenyl-1H-pyrazol-5-amine (80 mg), $NaHCO_3$ (100 mg) and anhydrous DMSO (3 mL) were heated at 130° C. for overnight. The mixture was then purified by reverse phase HPLC to yield Cpd. No. 1 as a $CF_3CO_2H$ salt in 5 mg (4% yield). $^1H$ NMR (300 MHz, MeOD-d4): 7.56-7.46 (m, 3H), 7.43 (s, 1H), 7.42-7.28 (m, 3H), 6.52 (s, 1H), 3.84 (s, 3H), 2.61 (s, 3H), 2.40 (s, 3H), 2.31 (s, 3H), 2.14 (s, 3H). ESI-MS calculated for $C_{27}H_{26}N_7O_2$ $[M+H]^+$=480.21; Observed: 480.67.

Example 10

Synthesis of 7-(3,5-Dimethylisoxazol-4-yl)-6-methoxy-2-methyl-N-(3-phenyl-1H-pyrazol-4-yl)-9H-pyrimido[4,5-b]indol-4-amine (Cpd. No. 2)

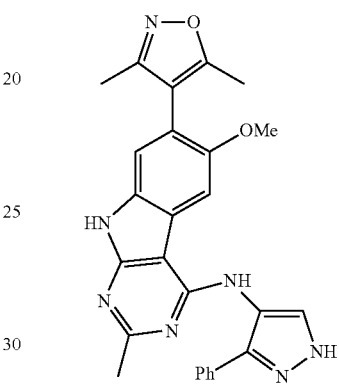

S13 (70 mg), 5-phenyl-1H-pyrazol-4-amine (70 mg), $NaHCO_3$ (100 mg) and anhydrous DMSO (3 mL) were heated at 130° C. for 16 h. The mixture was then purified by reverse phase HPLC to yield Cpd. No. 2 as a $CF_3CO_2H$ salt in 3 mg (3% yield). $^1H$ NMR (300 MHz, MeOD-d4): 8.01 (s, 1H), 7.72-7.66 (m, 2H), 7.44 (s, 3H), 7.42-7.32 (m, 3H), 3.87 (s, 3H), 2.57 (s, 3H), 2.32 (s, 3H), 2.15 (s, 3H). ESI-MS calculated for $C_{26}H_{24}N_7O_2$ $[M+H]^+$=466.20; observed: 466.75.

Example 11

Synthesis of 4-(4-((4-Isopropyl-5-methyl-4H-1,2,4-triazol-3-yl)thio)-6-methoxy-2-methyl-9H-pyrimido[4,5-b]indol-7-yl)-3,5-dimethylisoxazole (Cpd. No. 3)

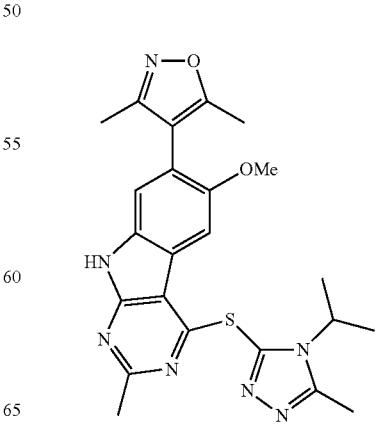

S13 (68 mg), 4-isopropyl-5-methyl-4H-1,2,4-triazole-3-thiol (64 mg), and $K_2CO_3$ (64 mg) were mixed in a round-bottom flask. Anhydrous DMSO (3 mL) was added and the reaction mixture was heated at 130° C. for overnight. The reaction was then cooled to ambient temperature and water (1 mL) was added. The mixture was purified on reverse phase HPLC to yield the desired product Cpd. No. 3 as a salt of trifluoroacetic acid in 45 mg (50% yield). $^1$H NMR (300 MHz, MeOD-d4): 7.70 (s, 1H), 7.42 (s, 1H), 5.00-4.90 (m, 1H), 3.96 (s, 3H), 2.86 (s, 3H), 2.54 (s, 3H), 2.34 (s, 3H), 2.17 (s, 3H), 1.62 (d, J=6.99 Hz, 6H). ESI-MS calculated for $G_3H_{26}N_7O_2S$ $[M+H]^+$=464.19; Observed: 464.33.

Example 12

Synthesis of 1-Isopropyl-5-methyl-3-phenyl-1H-pyrazol-4-amine (CE261 TFA salt)

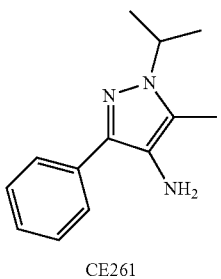 [SMILES: Cc1c(N)c(-c2ccccc2)nn1C(C)C]

CE261

Step 1: 2-(Hydroxyimino)-1-phenylbutane-1,3-dione (1.3 g) and isopropyl hydrazine (500 mg) were dissolved in ethanol. The solution was stirred at ambient temperature for overnight. The volatile components were removed a rotary evaporator. Ethyl acetate and water were added and the aqueous layer was extracted with ethyl acetate. The combined organic layers were dried and concentrated on a rotary evaporator.

Step 2: The previous remaining residue was dissolved in acetic acid (20 mL) followed by addition of zinc powder (1.8 g). The mixture was heat at 80° C. for overnight. The mixture was filtered and the filtrate was concentrated. The remaining residue was purified on preparative HPLC to yield the desired product CE261 in 96 mg as a salt of trifluoroacetic acid. $^1$H NMR (300 MHz, MeOD-d4): 7.65-7.57 (m, 2H), 7.54-7.38 (m, 3H), 5.40-5.10 (broad singlet, 2H), 4.61 (septet, J=6.63 Hz, 1H), 2.43 (s, 3H), 1.49 (d, J=6.63 Hz, 6H). $^{13}$C (75 MHz, MeOD-d4): 145.85, 135.02, 132.56, 130.13, 129.94, 129.17, 108.85, 52.08, 22.61, 8.92. ESI-MS calculated for $C_{13}H_{18}N_3$ $[M+H]^+$=216.15; Observed: 216.50.

Example 13

Synthesis of 7-(3,5-Dimethylisoxazol-4-yl)-N-(1-isopropyl-5-methyl-3-phenyl-1H-pyrazol-4-yl)-6-methoxy-2-methyl-9H-pyrimido[4,5-b]indol-4-amine (Cpd. No. 4)

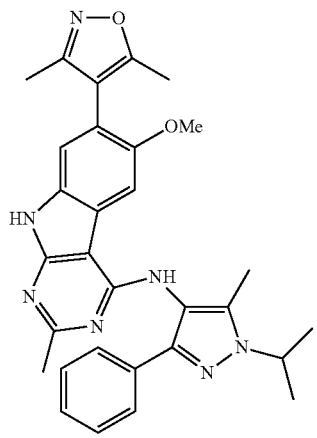 [SMILES: COc1cc2c(cc1-c1c(C)noc1C)[nH]c1nc(C)nc(Nc3c(-c4ccccc4)nn(C(C)C)c3C)c12]

S13 (70 mg) and 1-isopropyl-5-methyl-3-phenyl-1H-pyrazol-4-amine (70 mg) were dissolved in isopropanol (5 mL). Four drops of concentrated HCl was added via a glass pipette. The mixture was heated at reflux for overnight. The reaction mixture was concentrated on a rotary evaporator and the remaining residues were purified by HPLC to yield the desired product Cpd. No. 4 in 38 mg as a salt of trifluoroacetic acid. $^1$H NMR (300 MHz, MeOD-d4): 7.80-7.66 (m, 2H), 7.50-7.40 (m, 1H), 7.36-7.20 (m, 4H), 4.80-4.60 (m, 1H), 3.92 (s, 3H), 2.56 (s, 3H), 2.46-2.30 (m, 3H), 2.31 (s, 3H), 2.14 (s, 3H), 1.59 (d, J=5.75 Hz, 6H). ESI-MS calculated for $C_{30}H_{32}N_7O_2$ $[M+H]^+$=522.26; Observed: 522.58.

Example 14

Synthesis of 7-(3,5-Dimethylisoxazol-4-yl)-6-methoxy-2-methyl-N-(5-methyl-4-phenyl-1H-pyrazol-3-yl)-9H-pyrimido[4,5-b]indol-4-amine (Cpd. No. 5)

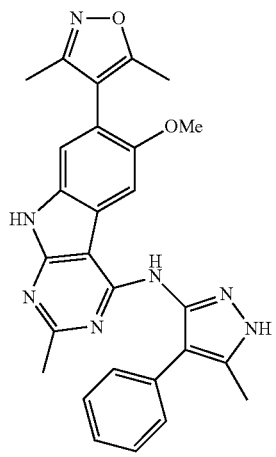 [SMILES: COc1cc2c(cc1-c1c(C)noc1C)[nH]c1nc(C)nc(Nc3n[nH]c(C)c3-c3ccccc3)c12]

S13 (70 mg) and 5-methyl-4-phenyl-1H-pyrazol-3-amine (68 mg) were dissolved in isopropanol (5 mL). Four drops of concentrated HCl was added via a glass pipette. The mixture was heated at reflux for overnight. The reaction was concentrated on a rotary evaporator and the remaining residues were purified by HPLC to yield the desired product Cpd. No 5 in 2 mg as a salt of trifluoroacetic acid. $^1$H NMR (300 MHz, MeOD-d4): 7.52 (s, 1H), 7.43-7.40 (m, 5H), 7.30 (s, 1H), 3.82 (s, 3H), 2.72 (s, 3H), 2.45 (s, 3H), 2.31 (s, 3H), 2.14 (s, 3H). ESI-MS calculated for $G_7H_{26}N_7O_2$ [M+H]$^+$=480.21; Observed: 480.17.

Example 15

Synthesis of 2-(Oxazol-2-yl)-4-phenylthiazol-5-amine (CE267)

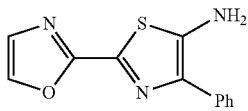

CE267

Oxazole-2-carbaldehyde (1 g), sulfur (352 mg), and 2-amino-2-phenylacetonitrile-HCl (1.69 g) were mixed in ethanol (50 mL). Triethyl amine (2.1 mL) was added and the mixture was heated at 50° C. for 1 h. The mixture was cooled to ambient temperature and aqueous hydroxylamine (hydroxylamine-HCl 1.90 g neutralized by sodium hydroxide) was added. The reaction was stirred at ambient temperature for overnight. The reaction mixture was filtered, concentrated, and partitioned between ethyl acetate and water. The aqueous layer was extracted with ethyl acetate. The combined organic layers were dried and concentrated on a rotary evaporator. The remaining residue was purified by flash column chromatography to yield CE267 in 260 mg. $^1$H NMR (300 MHz, DMSO-d6): 8.18 (d, J=0.77 Hz, 1H), 7.77-7.71 (m, 2H), 7.41 (t, J=7.65 Hz, 2H), 7.33 (d, J=0.76 Hz, 1H), 7.24 (t, J=7.35 Hz, 1H), 6.50 (s, 1H). $^{13}$C (75 MHz, DMSO-d6): 158.32, 150.83, 142.08, 136.92, 136.59, 134.41, 130.56, 130.45, 128.39, 128.23. ESI-MS calculated for $C_{12}H_{10}N_3OS$ [M+H]$^+$=244.05; Observed: 244.42.

Example 16

Synthesis of N-(7-(3,5-Dimethylisoxazol-4-yl)-6-methoxy-2-methyl-9H-pyrimido[4,5-b]indol-4-yl)-2-(oxazol-2-yl)-4-phenylthiazol-5-amine (Cpd. No. 6)

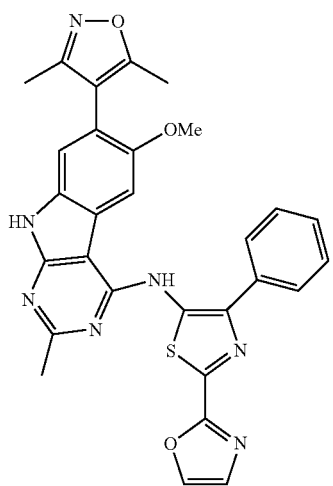 [SMILES: COc1cc2c(cc1-c1c(C)noc1C)[nH]c1nc(C)nc(Nc3sc(-c4ncco4)nc3-c3ccccc3)c12]

S13 (230 mg) and 2-(oxazol-2-yl)-4-phenylthiazol-5-amine (260 mg) were dissolved in isopropanol (20 mL). Eleven drops of concentrated HCl was added via a glass pipette. The mixture was heated at reflux for overnight. The reaction was concentrated on a rotary evaporator and the remaining residues were purified by HPLC to yield the desired product Cpd. No. 6 in 8 mg as a salt of trifluoroacetic acid. $^1$H NMR (300 MHz, DMSO-d6): 12.00 (s, 1H), 10.08 (s, 1H), 8.34 (s, 1H), 8.08 (d, J=7.80 Hz, 2H), 7.80 (s, 1H), 7.54 (t, J=7.62 Hz, 2H), 7.50 (s, 1H), 7.40 (t, J=7.33 Hz, 1H), 7.28 (s, 1H), 3.78 (s, 3H), 2.64 (s, 3H), 2.29 (s, 3H), 2.09 (s, 3H). ESI-MS calculated for $C_{29}H_{24}N_7O_3S$ [M+H]$^+$=550.17; Observed: 550.75.

Example 17

Synthesis of 1-(3-Chlorophenyl)-3-methyl-1H-pyrazol-5-amine (CE280)

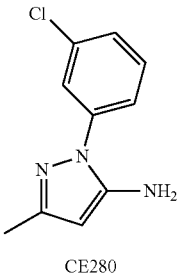

CE280

Step 1: (3-Chlorophenyl)hydrazine (415 mg), 3-oxobutanenitrile (895 mg), and sodium acetate (415 mg) were dissolved in ethanol (20 mL). The solution was heated at reflux for overnight. The reaction mixture was concentrated and partitioned between ethyl acetate and water. The aqueous layer was extracted with ethyl acetate. The combined organic layers were dried and concentrated on a rotary evaporator.

Step 2: The previous remaining residue was dissolved in methanol and trifluoroacetic acid (1 mL) was added. The mixture was left at ambient temperature for overnight. The reaction mixture was concentrated and neutralized by sodium bicarbonate saturated solution. The aqueous layer was extracted with ethyl acetate. The combined organic layers were dried and concentrated on a rotary evaporator. The remaining residue was purified by flash column chromatography to yield CE280 in 0.84 g. $^1$H NMR (300 MHz, CDCl$_3$): 7.67-7.61 (m, 1H), 7.52-7.45 (m, 1H), 7.42-7.34 (m, 1H), 7.32-7.25 (m, 1H), 7.26 (s, 1H), 5.47 (s, 1H), 3.77 (s, 2H), 2.22 (s, 3H). $^{13}$C (75 MHz, CDCl$_3$): 150.16, 145.46, 140.09, 135.27, 130.53, 127.07, 123.88, 121.48, 91.61, 14.11. ESI-MS calculated for $C_{10}H_{11}{}^{35}ClN_3$ [M+H]$^+$=208.06; Observed: 208.33.

Example 18

Synthesis of N-(1-(3-Chlorophenyl)-3-methyl-1H-pyrazol-5-yl)-7-(3,5-dimethylisoxazol-4-yl)-6-methoxy-2-methyl-9H-pyrimido[4,5-b]indol-4-amine (Cpd. No. 7)

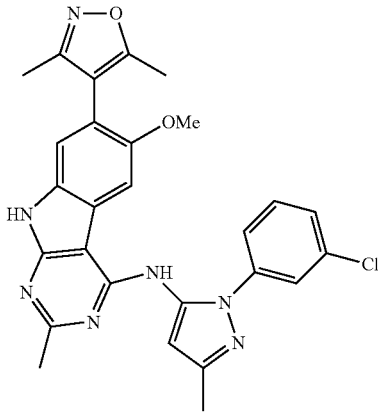 [SMILES: COc1cc2c(cc1-c1c(C)noc1C)[nH]c1nc(C)nc(Nc3cc(C)nn3-c3cccc(Cl)c3)c12]

Tris(dibenzylideneacetone)dipalladium(0) (18 mg) and 2,2'-bis(diphenylphosphino)-1,1'-binaphthyl (26 mg) were mixed in anhydrous toluene. And the mixture was heated at reflux for 3-4 minutes. This mixture was transferred into a round-bottom flask containing S13 (60 mg), 1-(3-chlorophenyl)-3-methyl-1H-pyrazol-5-amine (84 mg), $K_3PO_4$ (130 mg), and toluene (1 mL). The mixture was heated at reflux for overnight before quenching with methanol. The reaction mixture was filtered and the mixture was purified by HPLC to yield Cpd. No. 7 as a $CF_3CO_2H$ salt in 40 mg. $^1$H NMR (300 MHz, MeOD-d4): 7.54-7.49 (m, 1H), 7.45-7.42 (m, 1H), 7.43 (s, 1H), 7.42-3.80 (m, 1H), 7.34-2.25 (m, 1H), 7.27 (s, 1H), 6.52 (s, 1H), 3.84 (s, 3H), 2.61 (s, 3H), 2.39 (s, 3H), 2.30 (s, 3H), 2.13 (s, 3H). ESI-MS calculated for $C_{27}H_{25}^{35}ClN_7O_2$ [M+H]$^+$=514.18; Observed: 514.33.

Example 19

Synthesis of N-(1,3-Dimethyl-1H-pyrazol-5-yl)-7-(3,5-dimethylisoxazol-4-yl)-6-methoxy-2-methyl-9H-pyrimido[4,5-b]indol-4-amine (Cpd. No. 8)

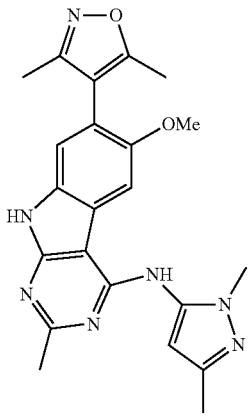

Cpd. No. 8 was prepared from S13 (68 mg) and 1,3-dimethyl-1H-pyrazol-5-amine (50 mg) following the same procedure for preparation of Cpd. No. 7. Cpd. No. 8 was isolated as a $CF_3CO_2H$ salt in 40 mg. $^1$H NMR (300 MHz, MeOD-d4): 7.46 (s, 1H), 7.43 (s, 1H), 6.25 (s, 1H), 3.87 (s, 3H), 3.76 (s, 3H), 2.70 (s, 3H), 2.31 (s, 3H), 2.30 (s, 3H), 2.14 (s, 3H). ESI-MS calculated for $C_{22}H_{24}N_7O_2$ [M+H]$^+$=418.20; Observed: 418.92.

Example 20

Synthesis of 7-(3,5-Dimethylisoxazol-4-yl)-N-(1-isopropyl-3-methyl-1H-pyrazol-5-yl)-6-methoxy-2-methyl-9H-pyrimido[4,5-b]indol-4-amine (Cpd. No. 9)

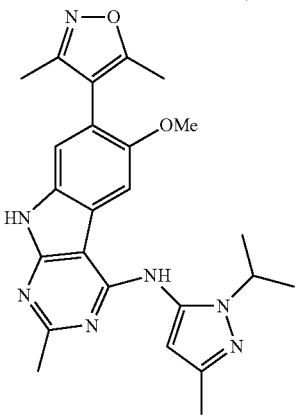

Cpd. No. 9 was prepared from S13 (70 mg) and 1-isopropyl-3-methyl-1H-pyrazol-5-amine (640 mg) following the same procedure for preparation of Cpd. No. 7. Cpd. No. 9 was isolated as a $CF_3CO_2H$ salt in 26 mg. $^1$H NMR (300 MHz, MeOD-d4): 7.45 (s, 1H), 7.18 (s, 1H), 6.18 (s, 1H), 4.59 (septet, J=6.68 Hz, 1H), 3.83 (s, 3H), 2.70 (s, 3H), 2.32 (s, 3H), 2.30 (s, 3H), 2.13 (s, 3H), 1.47 (d, J=6.66 Hz, 6H). ESI-MS calculated for $C_{24}H_{28}N_7O_2$ [M+H]$^+$=446.23; Observed: 446.67.

Example 21

Synthesis of 7-(3,5-Dimethylisoxazol-4-yl)-6-methoxy-2-methyl-N-(1-methyl-3-(trifluoromethyl)-1H-pyrazol-5-yl)-9H-pyrimido[4,5-b]indol-4-amine (Cpd. No. 21)

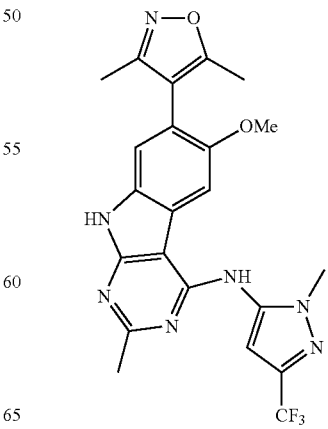

Cpd. No. 21 was prepared from S13 (102 mg) and 2-methyl-5-(trifluoromethyl)pyrazol-3-amine (100 mg) following the same procedure for preparation of Cpd. No. 7. Cpd. No. 21 was isolated as a salt of CF$_3$CO$_2$H in 29 mg. $^1$H NMR (300 MHz, MeOD-d4): 7.83 (s, 1H), 7.47 (s, 1H), 6.72 (s, 1H), 3.92 (s, 3H), 3.88 (s, 3H), 2.67 (s, 3H), 2.32 (s, 3H), 2.15 (s, 3H). ESI-MS calculated for C$_{22}$H$_{21}$F$_3$N$_7$O$_2$ [M+H]$^+$=472.17, Observed: 472.33.

Example 22

Synthesis of 1-Isopropyl-3-(trifluoromethyl)-1H-pyrazol-5-amine

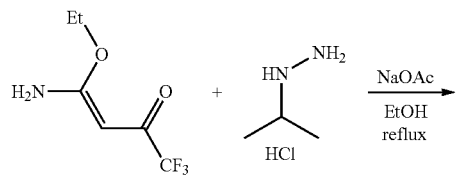

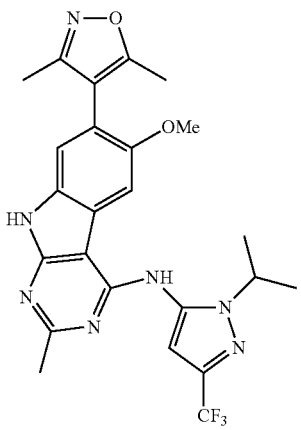 [SMILES: COc1cc2c(cc1-c1c(C)noc1C)[nH]c1nc(C)nc(Nc3cc(C(F)(F)F)nn3C(C)C)c12]

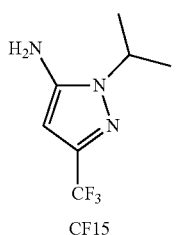

CF15

(E)-4-Amino-4-ethoxy-1,1,1-trifluoro-but-3-en-2-one (1.0 g) isopropylhydrazine-HCl (1.21 g), and sodium acetate (1.4 g) were mixed in a round-bottom flask. Ethanol (20 mL) was added and the mixture was heated at reflux for overnight. The reaction mixture was concentrated on rotary evaporator and the remaining residues were dissolved in ethyl acetate followed by extraction with water. The organic layer was collected and dried over anhydrous sodium sulfate. The solid was filtered off and the solvent was removed on a rotary evaporator. The remaining residue (1.12 g) was used without further purification. $^1$H NMR (300 MHz, CDCl$_3$): 5.79 (s, 1H), 4.37 (septet, J=6.67 Hz, 1H), 1.47 (d, J=6.67 Hz, 6H). ESI-MS calculated for C$_7$H$_{11}$F$_3$N$_3$ [M+H]$^+$=194.09, Observed: 194.17. Synthesis of 7-(3,5-Dimethylisoxazol-4-yl)-N-(1-isopropyl-3-(trifluoromethyl)-1H-pyrazol-5-yl)-6-methoxy-2-methyl-9H-pyrimido[4,5-b]indol-4-amine (Cpd. No. 22)

Cpd. No. 22 was prepared from S13 (102 mg) and 1-isopropyl-3-(trifluoromethyl)-1H-pyrazol-5-amine (174 mg) following the same procedure for preparation of Cpd. No. 7. Cpd. No. 22 was isolated as a salt of CF$_3$CO$_2$H in 60 mg. $^1$H NMR (300 MHz, MeOD-d4): 7.72 (s, 1H), 7.48 (s, 1H), 6.45 (s, 1H), 4.65 (septet, J=6.60 Hz, 1H), 3.90 (s, 1H), 2.67 (s, 1H), 2.31 (s, 1H), 2.14 (s, 1H), 1.51 (d, J=6.67 Hz, 6H). ESI-MS calculated for C$_{24}$H$_{25}$F$_3$N$_7$O$_2$ [M+H]$^+$=500.20, Observed: 500.42.

Example 23

Synthesis of 7-(3,5-Dimethylisoxazol-4-yl)-6-methoxy-2-methyl-N-(1-methyl-1H-pyrazolo[3,4-b]pyridin-3-yl)-9H-pyrimido[4,5-b]indol-4-amine (Cpd. No. 10)

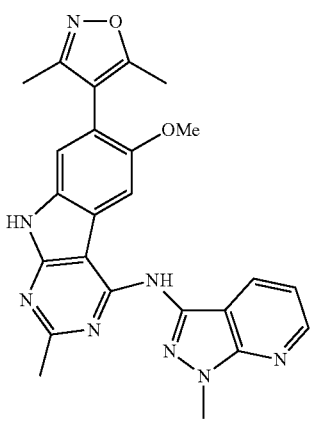 [SMILES: COc1cc2c(cc1-c1c(C)noc1C)[nH]c1nc(C)nc(Nc3nn(C)c4ncccc34)c12]

Cpd. No. 10 was prepared from S13 (68 mg) and 1-methyl-1H-pyrazolo[3,4-b]pyridin-3-amine (60 mg) following the same procedure for preparation of Cpd. No. 7. Cpd. No. 10 was isolated as a CF$_3$CO$_2$H salt in 32 mg. $^1$H NMR (300 MHz, MeOD-d4): 8.65 (d, J=3.99 Hz, 1H), 8.38 (d, J=8.15 Hz, 1H), 7.89, 7.48, 7.31 (dd, J=8.08, 4.55 Hz, 1H), 4.17 (s, 3H), 3.86 (s, 3H), 2.71 (s, 3H), 2.32 (s, 3H), 2.15 (s, 3H). ESI-MS calculated for C$_{24}$H$_{23}$N$_8$O$_2$ [M+H]$^+$=455.19; Observed: 455.50.

Example 24

Synthesis of 1-Methyl-1H-pyrazolo[4,3-c]pyridin-3-amine (CE311)

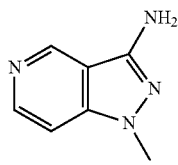

CE311

4-Chloronicotinonitrile (500 mg) and methyl hydrazine (828 mg) were dissolved in ethanol (20 mL). The mixture was heated at reflux for overnight. The reaction mixture was concentrated and partitioned between ethyl acetate and water. The aqueous layer was extracted with ethyl acetate. The combined organic layers were dried and concentrated on a rotary evaporator. The remaining residue (187 mg of CE311) was used directly for the next step. $^1$H NMR (300 MHz, CDCl$_3$): 8.85 (d, J=1.01 Hz, 1H), 8.31 (d, J=6.11 Hz, 1H), 7.05 (dd, J=6.12, 1.06 Hz, 1H), 4.50-4.20 (br, 2H), 3.81 (s, 3H). $^{13}$C (75 MHz, CDCl$_3$): 147.93, 144.54, 143.98, 143.70, 112.55, 103.50, 34.88. ESI-MS calculated for C$_7$H$_9$N$_4$ [M+H]$^+$=149.08; Observed: 149.50.

Example 25

Synthesis of 7-(3,5-dimethylisoxazol-4-yl)-6-methoxy-N-(1-methyl-1H-pyrazolo[4,3-c]pyridin-3-yl)-9H-pyrimido[4,5-b]indol-4-amine (Cpd. No. 11)

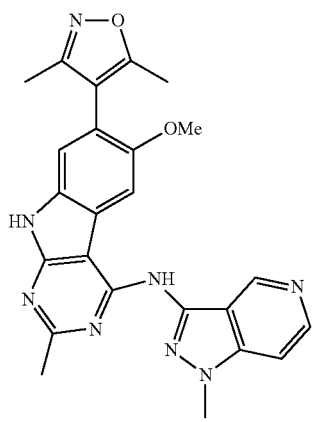 [SMILES: COc1cc2c(cc1-c1c(C)noc1C)[nH]c1nc(C)nc(Nc3nn(C)c4ccncc34)c12]

Cpd. No. 11 was prepared from S13 (70 mg) and 1-methyl-1H-pyrazolo[4,3-c]pyridin-3-amine (60 mg) following the same procedure for preparation of Cpd. No. 7. Cpd. No. 11 was isolated as a CF$_3$CO$_2$H salt in 47 mg. $^1$H NMR (300 MHz, CDCl$_3$): 9.71 (s, 1H), 8.46 (d, J=6.97 Hz, 1H), 8.12 (s, 1H), 8.08 (d, J=7.00 HZ, 1H), 7.38 (s, 1H), 4.23 (s, 3H), 3.98 (s, 3H), 2.65 (s, 3H), 2.34 (s, 3H), 2.18 (s, 3H). ESI-MS calculated for C$_{24}$H$_{23}$N$_8$O$_2$ [M+H]$^+$=455.19.

Example 26

Synthesis of 7-(3,5-Dimethylisoxazol-4-yl)-6-methoxy-2-methyl-N-(1-methyl-1H-indazol-3-yl)-9H-pyrimido[4,5-b]indol-4-amine (Cpd. No. 12)

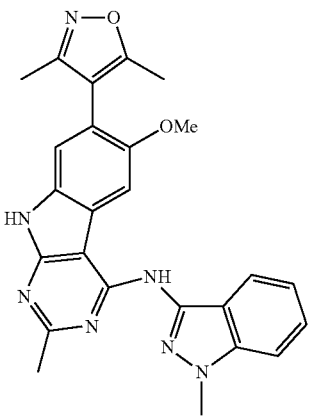 [SMILES: COc1cc2c(cc1-c1c(C)noc1C)[nH]c1nc(C)nc(Nc3nn(C)c4ccccc34)c12]

S13 (90 mg) and 1-methyl-1H-indazol-3-amine (90 mg) were dissolved in isopropanol (30 mL). Four drops of concentrated HCl was added via a glass pipette. The mixture was heated at reflux for overnight. The reaction was concentrated on a rotary evaporator and the remaining residues were purified by HPLC to yield the desired product Cpd. No. 12 in 60 mg as a salt of trifluoroacetic acid. $^1$H NMR (300 MHz, MeOD-d4): 8.44 (d, J=7.88 Hz, 1H), 7.84 (s, 1H), 7.68 (d, J=8.62 Hz, 1H), 7.57 (t, J=7.63 Hz, 1H), 7.47 (s, 1H), 7.30 (t, J=7.55 Hz, 1H), 4.16 (s, 3H), 3.86 (s, 3H), 2.73 (s, 3H), 2.33 (s, 3H), 2.16 (s, 3H). ESI-MS calculated for C$_{25}$H$_{24}$N$_7$O$_2$ [M+H]$^+$=454.20; Observed: 454.42.

Example 27

Synthesis of 5-Chloro-1-methyl-1H-indazol-3-amine (CE301)

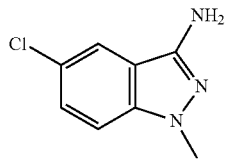

CE301

5-Chloro-2-fluorobenzonitrile (600 mg) and methyl hydrazine (1.1 mL) were dissolved in ethanol (20 mL). The mixture was heated at reflux for overnight. The reaction mixture was concentrated and partitioned between ethyl acetate and water. The aqueous layer was extracted with ethyl acetate. The combined organic layers were dried and concentrated on a rotary evaporator. The remaining residue (717 mg of CE301) was used directly for the next step. $^1$H NMR (300 MHz, CDCl$_3$): 7.48 (s, 1H), 7.26 (dd, J=8.86, 1.63 Hz, 1H), 7.11 (d, J=8.89 Hz, 1H), 4.20-3.90 (br, 2H), 3.82 (s, 3H). ESI-MS calculated for C$_8$H$_9$ClN$_3$ [M+H]$^+$=182.05; Observed: 182.67.

Example 28

Synthesis of N-(5-Chloro-1-methyl-1H-indazol-3-yl)-7-(3,5-dimethylisoxazol-4-yl)-6-methoxy-2-methyl-9H-pyrimido[4,5-b]indol-4-amine (Cpd. No. 13)

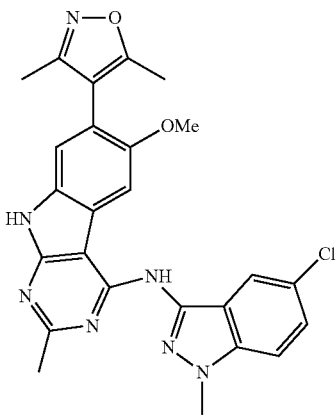 [SMILES: COc1cc2c(cc1-c1c(C)noc1C)[nH]c1nc(C)nc(Nc3nn(C)c4ccc(Cl)cc34)c12]

S13 (70 mg) and 5-chloro-1-methyl-1H-indazol-3-amine (100 mg) were dissolved in isopropanol (5 mL). Five drops of concentrated HCl was added via a glass pipette. The mixture was heated at reflux for overnight. The reaction was concentrated on a rotary evaporator and the remaining residues were purified by HPLC to yield the desired product Cpd. No. 13 in 18 mg as a salt of trifluoroacetic acid. $^1$H NMR (300 MHz, MeOD-d4): 7.92 (s, 2H), 7.69 (d, J=9.01 Hz, 1H), 7.52 (d, J=9.01 Hz, 1H), 7.48 (s, 1H), 4.15 (s, 3H), 3.89 (s, 3H), 2.71 (s, 3H), 2.34 (s, 3H), 2.16 (s, 3H). ESI-MS calculated for $C_{25}H_{23}{}^{35}ClN_7O_2$ $[M+H]^+$=488.16; Observed: 488.58.

Example 29

Synthesis of 7-(3,5-Dimethylisoxazol-4-yl)-6-methoxy-N-(6-methoxy-1-methyl-1H-indazol-3-yl)-2-methyl-9H-pyrimido[4,5-b]indol-4-amine (Cpd. No. 19)

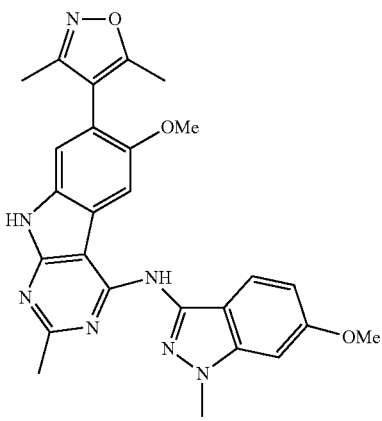 [SMILES: COc1ccc2c(Nc3nc(C)nc4[nH]c5cc(-c6c(C)noc6C)c(OC)cc5c34)nn(C)c2c1]

S13 (68 mg) and 1-methyl-6-methoxy-1H-indazol-3-amine (80 mg) were dissolved in isopropanol (5 mL). Six drops of concentrated HCl was added via a glass pipette. The mixture was heat at reflux for overnight. The reaction was then concentrated on a rotary evaporator and the remaining residues was purified by reverse phase HPLC to yield Cpd. No. 19 in 24 mg as a salt of $CF_3CO_2H$. $^1$H NMR (300 MHz, MeOD-d4): 7.89 (s, 1H), 7.75 (d, J=8.92 Hz, 1H), 7.47 (s, 1H), 7.07 (d, J=1.95 Hz, 1H), 6.92 (dd, J=8.86, 2.13 Hz, 1H), 4.11 (s, 3H), 3.95 (s, 3H), 3.90 (s, 3H), 2.77 (s, 3H), 2.33 (s, 3H), 2.16 (s, 3H). ESI-MS calculated for $C_{26}H_{26}N_7O_3$ $[M+H]^+$=484.21, Observed: 484.75.

Example 30

Synthesis of 7-(3,5-Dimethylisoxazol-4-yl)-6-methoxy-2-methyl-N-(pyrazolo[1,5-a]pyridin-3-yl)-9H-pyrimido[4,5-b]indol-4-amine (Cpd. No. 14)

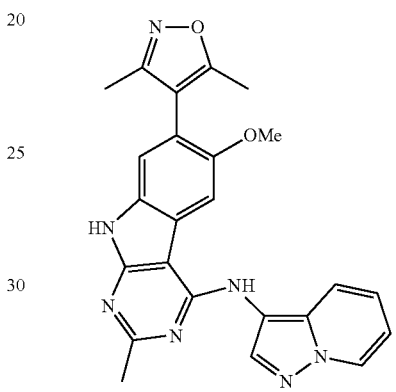

S13 (68 mg) and pyrazolo[1,5-a]pyridin-3-amine (84 mg) were dissolved in isopropanol (5 mL). Five drops of concentrated HCl was added via a glass pipette. The mixture was heated at reflux for overnight. The reaction was concentrated on a rotary evaporator and the remaining residues were purified by HPLC to yield the desired product Cpd. No. 14 in 55 mg as a salt of trifluoroacetic acid. $^1$H NMR (300 MHz, MeOD-d4): 8.67 (d, J=7.06 Hz, 1H), 8.22 (s, 1H), 8.10-7.80 (br, 1H), 7.68 (d, J=8.99 Hz, 1H), 7.47 (s, 1H), 7.43-7.33 (m, 1H), 7.06 (t, J=6.79 Hz, 1H), 3.89 (s, 3H), 2.60 (s, 3H), 2.33 (s, 3H), 2.15 (s, 3H). ESI-MS calculated for $C_{24}H_{22}N_7O_2$ $[M+H]^+$=440.18; Observed: 440.18.

Example 31

Synthesis of tert-Butyl (2-methylpyrazolo[1,5-a]pyridin-3-yl)carbamate (CE298)

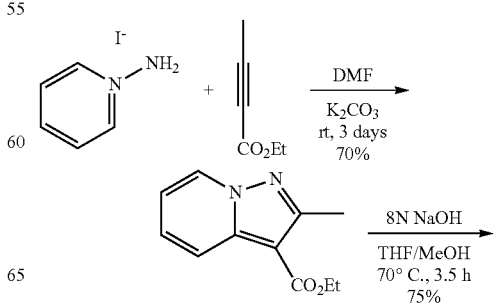

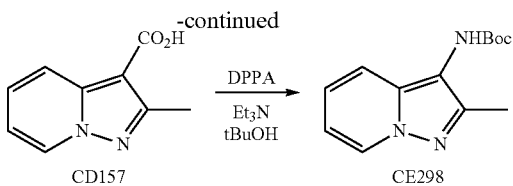

Step 1: 1-Aminopyridinium iodide (10 g), ethyl but-2-ynoate (6.05 g), potassium carbonate (7.45 g) were mixed in anhydrous DMF (50 mL). The reaction mixture was stirred at ambient temperature for 3 days. A mixture of water (100 mL), ethyl acetate (100 mL) and hexane (100 mL) was added and the product was collected by filtration. The filter cake was washed with a mixture of ethyl acetate:hexane=1:1, affording 6.4 g of ethyl 2-methylpyrazolo[1,5-a]pyridine-3-carboxylate (70% yield).

Step 2: 6.4 g of ethyl 2-methylpyrazolo[1,5-a]pyridine-3-carboxylate was dissolved in a mixture of methanol (40 mL) and THF (40 mL). To this mixture, 8 N NaOH (20 mL) was added and the mixture was heated at reflux for 70° C. for overnight. Acid-base work-up of the reaction mixture yielded CD157 in 4.1 g (75% yield), which was used without further purification.

Step 3: CD157 (350 mg) and triethylamine (0.5 mL) were dissolved in tert-butanol (5 mL). Diphenyl phosphoryl azide (DPPA, 0.65 mL) was added via a syringe. The reaction mixture was stirred at ambient temperature for overnight followed by heat-up at reflux for 24 hours. The reaction mixture was then filtered and washed with tert-butanol. The mixture was concentrated and purified by flash column chromatography to yield CE298 in 116 mg. $^1$H NMR (300 MHz, CDCl$_3$): 8.19 (d, J=6.77 Hz, 1H), 7.29 (d, J=7.99 Hz, 1H), 6.99 (t, J=7.68 Hz, 1H), 6.58 (t, J=6.68 Hz, 1H), 6.29 (s, 1H), 2.32 (s, 3H), 1.48 (s, 9H). ESI-MS calculated for C$_{13}$H$_{18}$N$_3$O$_2$ [M+H]$^+$=248.14; Observed: 248.00.

Example 32

Synthesis of 7-(3,5-Dimethylisoxazol-4-yl)-6-methoxy-2-methyl-N-(2-methylpyrazolo[1,5-a]pyridin-3-yl)-9H-pyrimido[4,5-b]indol-4-amine (Cpd. No. 15)

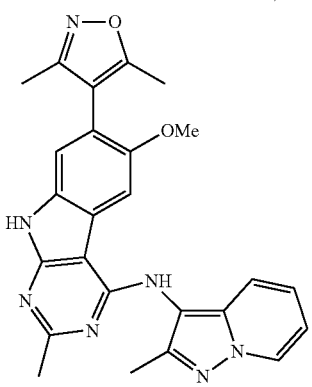 [SMILES: COc1cc2c(cc1-c1c(C)noc1C)[nH]c1nc(C)nc(Nc3c(C)nn4ccccc34)c12]

CE298 (116 mg) and triethylsilane (0.1 mL) were dissolved in dichloromethane (4 mL). Trifluoroacetic acid (6 mL) was added and the mixture was stirred at ambient temperature for 3 h. The volatile components were then removed on a rotary evaporator. S13 (70 mg) and isopropanol (5 mL) were added followed by addition of six drops of concentrated HCl. The mixture was heated at reflux for overnight. The reaction was concentrated on a rotary evaporator and the remaining residues were purified by HPLC to yield the desired product Cpd. No. 15 in 93 mg as a salt of trifluoroacetic acid. $^1$H NMR (300 MHz, MeOD-d4): 8.56 (d, J=6.96 Hz, 1H), 8.25 (broad singlet, 1H), 7.57 (d, J=8.80 Hz, 1H), 7.47 (s, 1H), 7.40-7.30 (m, 1H), 6.99 (t, J=6.74 Hz, 1H), 3.95 (s, 3H), 2.61 (s, 3H), 2.44 (s, 3H), 2.33 (s, 3H), 2.15 (s, 3H). ESI-MS calculated for C$_{25}$H$_{24}$N$_7$O$_2$ [M+H]$^+$=454.20; Observed: 454.42.

Example 33

Synthesis of 7-(3,5-Dimethylisoxazol-4-yl)-6-methoxy-2-methyl-N-(pyrazolo[1,5-a]pyrimidin-3-yl)-9H-pyrimido[4,5-b]indol-4-amine (Cpd. No. 16)

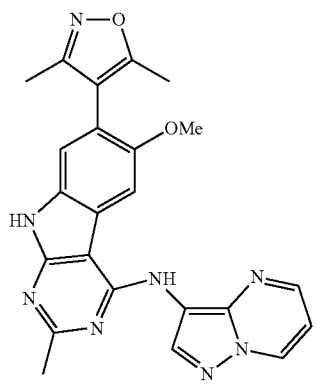 [SMILES: COc1cc2c(cc1-c1c(C)noc1C)[nH]c1nc(C)nc(Nc3cnn4cccnc34)c12]

S13 (120 mg) and pyrazolo[1,5-a]pyrimidin-3-amine (60 mg) were dissolved in isopropanol (5 mL). Six drops of concentrated HCl was added via a glass pipette. The mixture was heated at reflux for overnight. The reaction was concentrated on a rotary evaporator and the remaining residues were purified by HPLC to yield the desired product Cpd. No. 16 in 33 mg as a salt of trifluoroacetic acid. $^1$H NMR (300 MHz, MeOD-d4): 9.07 (dd, J=7.16, 1.64 Hz, 1H), 8.64 (dd, J=4.20, 1.69 Hz, 1H), 8.47 (s, 1H), 8.07 (s, 1H), 7.47 (s, 1H), 7.18 (dd, J=7.20, 4.17 Hz, 1H), 3.93 (s, 3H), 2.59 (s, 3H), 2.34 (s, 3H), 2.16 (s, 3H). ESI-MS calculated for C$_{23}$H$_{21}$N$_8$O$_2$ [M+H]$^+$=441.18; Observed: 441.67.

Example 34

Synthesis of 4-(4-((3-chlorophenyl)thio)-6-methoxy-2-methyl-9H-pyrimido[4,5-b]indol-7-yl)-3,5-dimethylisoxazole (Cpd. No. 23)

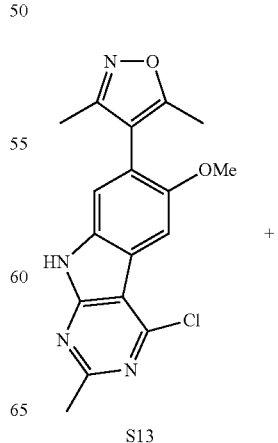

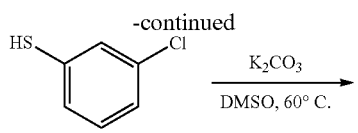

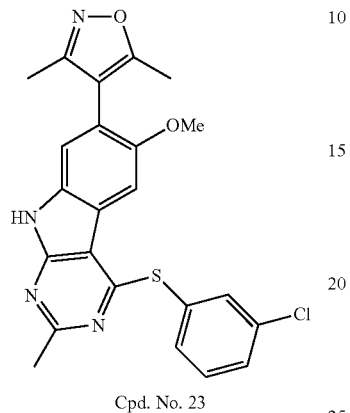

Cpd. No. 23

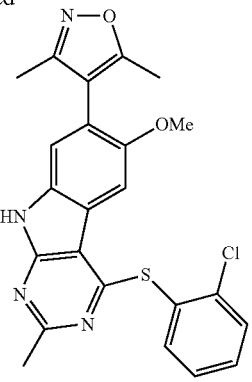

Cpd. No. 24

S13 (68 mg), 3-chlorobenzenethiol (85 mg), and K₂CO₃ (64 mg) were mixed in a round-bottom flask. Anhydrous DMSO (3 mL) was added and the reaction mixture was heated at 60° C. for overnight. The reaction was then cooled to ambient temperature and water (1 mL) was added. The mixture was purified on reverse phase HPLC to yield the desired product Cpd. No. 23 as a salt of trifluoroacetic acid in 38 mg. ESI-MS calculated for $C_{23}H_{20}ClN_4O_2S$ [M+H]⁺=451.09; Observed: 451.23. ¹H NMR (300 MHz, MeOD) δ 7.77-7.71 (m, 2H), 7.59 (d, J=6.9 Hz, 1H), 7.53-7.43 (m, 3H), 3.92 (s, 3H), 2.66 (s, 3H), 2.35 (s, 3H), 2.18 (s, 3H).

S13 (68 mg), 2-chlorobenzenethiol (85 mg), and K₂CO₃ (64 mg) were mixed in a round-bottom flask. Anhydrous DMSO (3 mL) was added and the reaction mixture was heated at 60° C. for overnight. The reaction was then cooled to ambient temperature and water (1 mL) was added. The mixture was purified on reverse phase HPLC to yield the desired product Cpd. No. 24 as a salt of trifluoroacetic acid in 44 mg. ESI-MS calculated for $C_{23}H_{20}ClN_4O_2S$ [M+H]⁺=451.09; Observed: 451.13. ¹H NMR (300 MHz, MeOD) δ 7.74 (s, 1H), 7.69 (dd, J=7.8, 1.6 Hz, 1H), 7.63 (dd, J=8.0, 1.3 Hz, 1H), 7.48 (td, J=7.7, 1.7 Hz, 1H), 7.42-7.35 (m, 2H), 3.93 (s, 3H), 2.56 (s, 3H), 2.36 (s, 3H), 2.19 (s, 3H).

Example 35

Synthesis of 4-(4-((2-chlorophenyl)thio)-6-methoxy-2-methyl-9H-pyrimido[4,5-b]indol-7-yl)-3,5-dimethylisoxazole (Cpd. No. 24)

Example 36

Synthesis of 4-(4-((2-isopropylphenyl)thio)-6-methoxy-2-methyl-9H-pyrimido[4,5-b]indol-7-yl)-3,5-dimethylisoxazole (Cpd. No. 25)

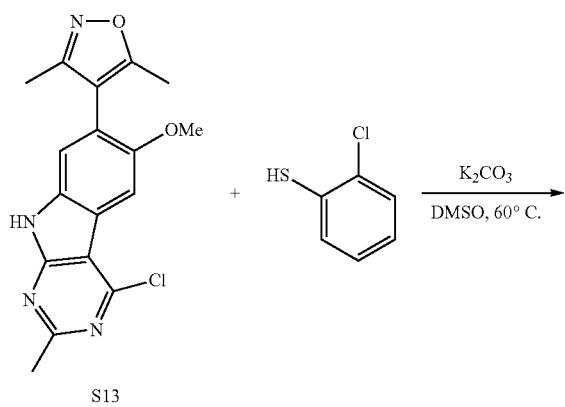

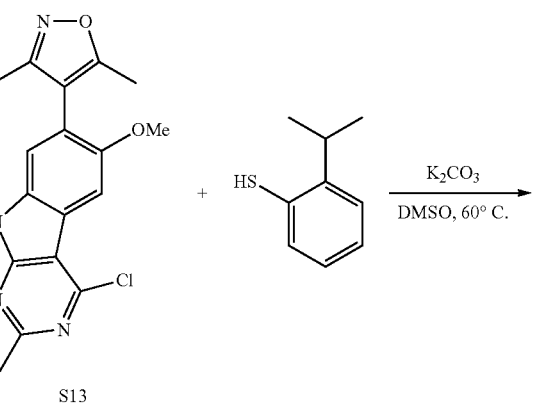

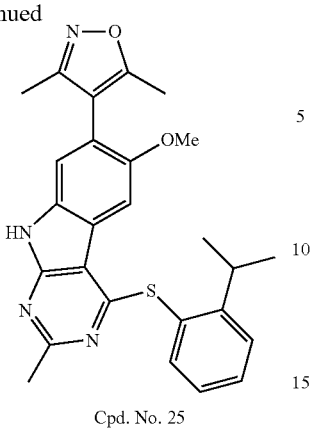

Cpd. No. 25

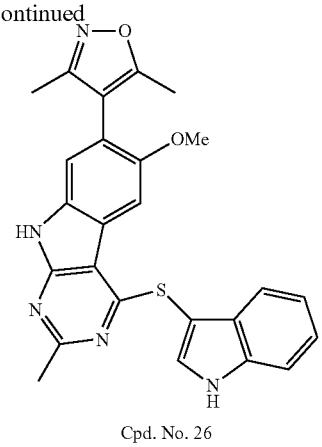

Cpd. No. 26

S13 (68 mg), 2-isopropylbenzenethiol (85 mg), and K$_2$CO$_3$ (64 mg) were mixed in a round-bottom flask. Anhydrous DMSO (3 mL) was added and the reaction mixture was heated at 60° C. for overnight. The reaction was then cooled to ambient temperature and water (1 mL) was added. The mixture was purified on reverse phase HPLC to yield the desired product Cpd. No. 25 as a salt of trifluoroacetic acid in 40 mg. ESI-MS calculated for C$_{26}$H$_{27}$N$_4$O$_2$S [M+H]$^+$=459.18; Observed: 459.25. $^1$H NMR (300 MHz, MeOD) δ 7.83 (s, 1H), 7.65-7.59 (m, 1H), 7.57-7.48 (m, 2H), 7.40 (s, 1H), 7.28 (ddd, J=7.8, 6.2, 2.7 Hz, 1H), 3.96 (s, 3H), 3.52 (dt, J=13.8, 6.8 Hz, 1H), 2.51 (s, 3H), 2.37 (s, 3H), 2.20 (s, 3H), 1.26 (d, J=6.9 Hz, 6H).

S13 (68 mg), 3-mercaptoindole (90 mg), and K$_2$CO$_3$ (64 mg) were mixed in a round-bottom flask. Anhydrous DMSO (3 mL) was added and the reaction mixture was heated at 60° C. for overnight. The reaction was then cooled to ambient temperature and water (1 mL) was added. The mixture was purified on reverse phase HPLC to yield the desired product Cpd. No. 26 as a salt of trifluoroacetic acid in 30 mg. ESI-MS calculated for C$_{25}$H$_{22}$N$_5$O$_2$S [M+H]$^+$=456.14; Observed: 456.25. $^1$H NMR (300 MHz, DMSO) δ 12.08 (s, 1H), 11.75 (s, 1H), 7.88-7.81 (m, 2H), 7.52 (d, J=8.1 Hz, 1H), 7.42 (d, J=7.9 Hz, 1H), 7.38 (s, 1H), 7.20 (t, J=7.6 Hz, 1H), 7.07 (t, J=7.5 Hz, 1H), 3.93 (s, 3H), 2.35 (s, 3H), 2.33 (s, 3H), 2.14 (s, 3H).

Example 38

Synthesis of 4-(4-((3-(tert-butyl)phenyl)thio)-6-methoxy-2-methyl-9H-pyrimido[4,5-b]indol-7-yl)-3,5-dimethylisoxazole (Cpd. No. 27)

Example 37

Synthesis of 4-(4-((1H-indol-3-yl)thio)-6-methoxy-2-methyl-9H-pyrimido[4,5-b]indol-7-yl)-3,5-dimethylisoxazole (Cpd. No. 26)

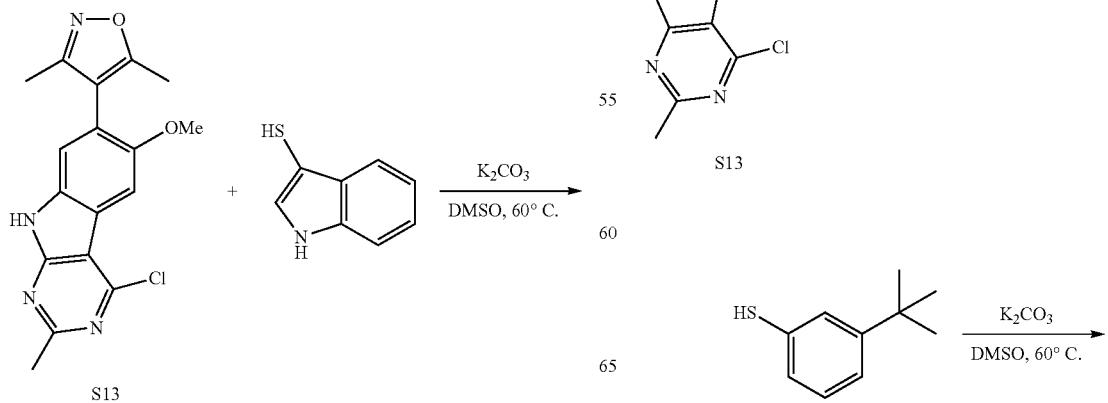

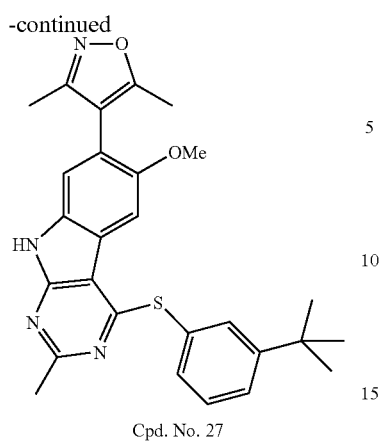

Cpd. No. 27

S13 (68 mg), 3-tert-butylthiophenol (90 mg), and K₂CO₃ (64 mg) were mixed in a round-bottom flask. Anhydrous DMSO (3 mL) was added and the reaction mixture was heated at 60° C. overnight. The reaction was then cooled to ambient temperature and water (1 mL) was added. The mixture was purified on reverse phase HPLC to yield the desired product Cpd. No. 27 as a salt of trifluoroacetic acid in 40 mg. ESI-MS calculated for $C_{27}H_{29}N_4O_2S$ [M+H]⁺=473.20; Observed: 473.44. ¹H NMR (300 MHz, DMSO) δ 12.17 (s, 1H), 7.84-7.29 (m, 6H), 3.88 (s, 3H), 2.51 (s, 3H), 2.32 (s, 3H), 2.12 (s, 3H), 1.31 (s, 9H).

Example 39

Synthesis of (R)—N-(chroman-4-yl)-7-(3,5-dimethylisoxazol-4-yl)-6-methoxy-2-methyl-9H-pyrimido[4,5-b]indol-4-amine (Cpd. No. 28)

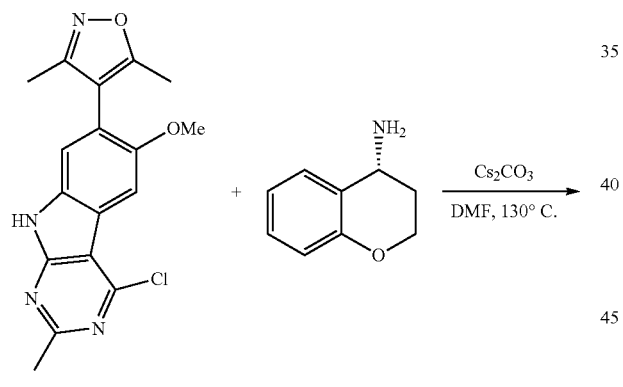

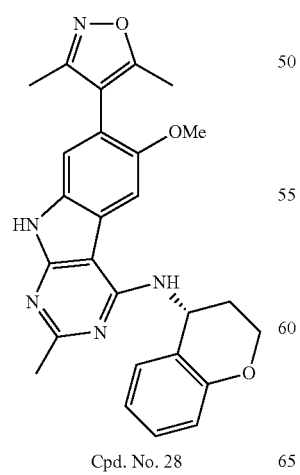

Cpd. No. 28

S13 (68 mg), (R)-chroman-4-ylamine (75 mg), and Cs₂CO₃ (244 mg) were mixed in a round-bottom flask. Anhydrous DMSO (3 mL) was added and the reaction mixture was heated at 60° C. overnight. The reaction was then cooled to ambient temperature and water (1 mL) was added. The mixture was purified on reverse phase HPLC to yield the desired product Cpd. No. 28 as a salt of trifluoroacetic acid in 1.5 mg. ESI-MS calculated for $C_{26}H_{26}N_5O_3$ [M+H]⁺=456.20; Observed: 456.44.

Example 40

Synthesis of 7-(3,5-dimethylisoxazol-4-yl)-N-(1-isopropyl-1H-1,2,4-triazol-5-yl)-6-methoxy-2-methyl-9H-pyrimido[4,5-b]indol-4-amine (Cpd. No. 29)

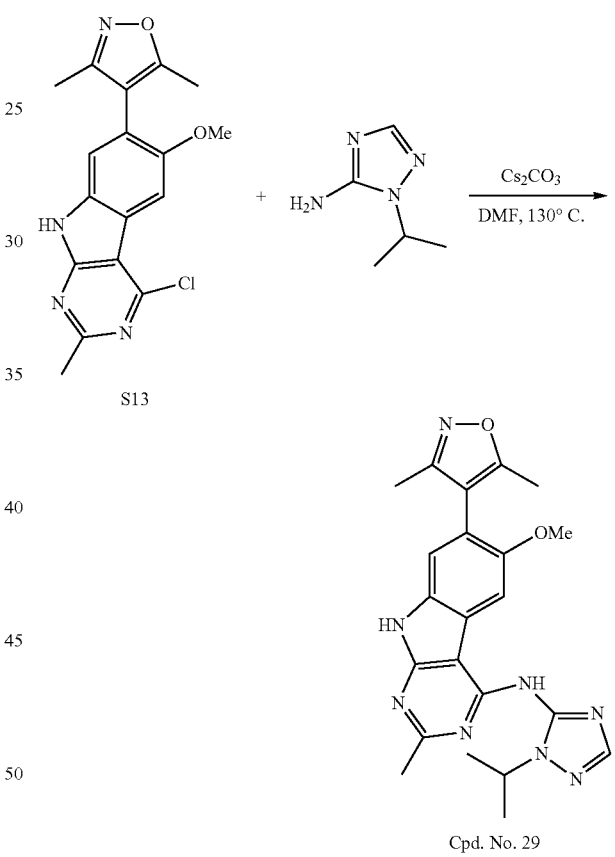

Cpd. No. 29

S13 (68 mg), 1-isopropyl-1H-1,2,4-triazol-5-amine (75 mg), and Cs₂CO₃ (244 mg) were mixed in a round-bottom flask. Anhydrous DMSO (3 mL) was added and the reaction mixture was heated at 60° C. overnight. The reaction was then cooled to ambient temperature and water (1 mL) was added. The mixture was purified on reverse phase HPLC to yield the desired product Cpd. No. 29 as a salt of trifluoroacetic acid in 4 mg. ESI-MS calculated for $C_{22}H_{25}N_8O_2$ [M+H]⁺=433.21; Observed: 433.32. ¹H NMR (300 MHz, MeOD) δ 8.24 (s, 1H), 7.50 (s, 1H), 7.39 (s, 1H), 5.07 (dt, J=13.3, 6.5 Hz, 1H), 3.86 (s, 3H), 2.71 (s, 3H), 2.34 (s, 3H), 2.17 (s, 3H), 1.61 (d, J=6.7 Hz, 6H).

Example 41

Synthesis of N-(3-(tert-butyl)-1,5-dimethyl-1H-pyrazol-4-yl)-7-(3,5-dimethylisoxazol-4-yl)-6-methoxy-2-methyl-9H-pyrimido[4,5-b]indol-4-amine (Cpd. No. 30)

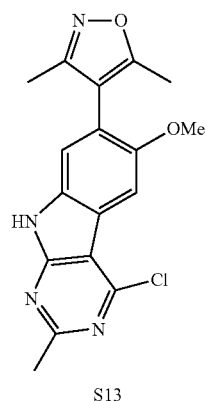
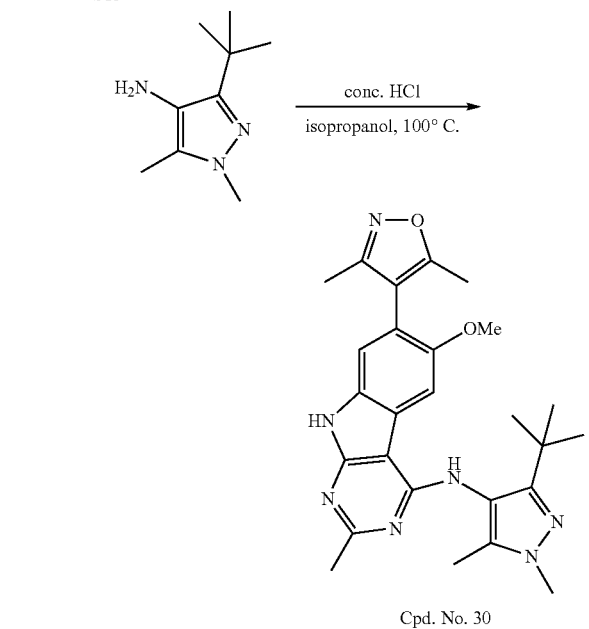

S13 (70 mg) and 3-tert-butyl-1,5-dimethylpyrazol-4-amine (68 mg) were dissolved in isopropanol (5 mL). Four drops of concentrated HCl was added via a glass pipette. The mixture was heated at reflux overnight. The reaction was concentrated on a rotary evaporator and the remaining residues were purified by HPLC to yield the desired product Cpd. No. 30 in 30 mg as a salt of trifluoroacetic acid. Aq. NaHCO$_3$ was added to the compound and the mixture was extracted by ethyl acetate. The combined organic layers were washed with brine and dried over anhydrous Na$_2$SO$_4$. The volatile components were removed on a rotary evaporator affording a solid. ESI-MS calculated for C$_{26}$H$_{32}$N$_7$O$_2$ [M+H]$^+$=474.26; Observed: 474.44. $^1$H NMR (300 MHz, MeOD) δ 7.97 (brs, 1H), 7.30 (s, 1H), 3.88 (brs, 3H), 3.80 (brs, 3H), 2.52 (s, 3H), 2.34 (s, 3H), 2.17 (s, 6H), 1.36 (s, 9H).

Example 42

Synthesis of N-(5-(tert-butyl)-1,3-dimethyl-1H-pyrazol-4-yl)-7-(3,5-dimethylisoxazol-4-yl)-6-methoxy-2-methyl-9H-pyrimido[4,5-b]indol-4-amine (Cpd. No. 31)

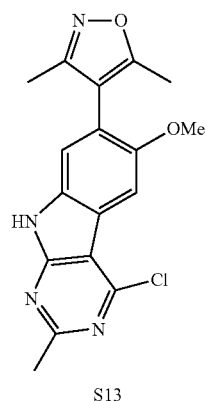
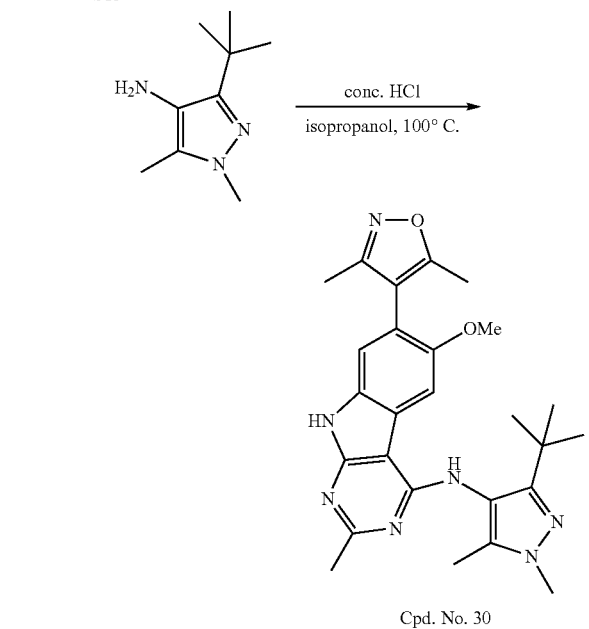

S13 (70 mg) and 5-tert-butyl-1,3-dimethylpyrazol-4-amine (68 mg) were dissolved in isopropanol (5 mL). Four drops of concentrated HCl was added via a glass pipette. The mixture was heated at reflux for overnight. The reaction was concentrated on a rotary evaporator and the remaining residues were purified by HPLC to yield the desired product Cpd. No. 31 in 30 mg as a salt of trifluoroacetic acid. ESI-MS calculated for C$_{26}$H$_{32}$N$_7$O$_2$ [M+H]$^+$=474.26; Observed: 474.34.

Example 43

Synthesis of 7-(3,5-dimethylisoxazol-4-yl)-N-(4-isopropyl-1H-pyrazol-5-yl)-6-methoxy-2-methyl-9H-pyrimido[4,5-b]indol-4-amine (Cpd. No. 32)

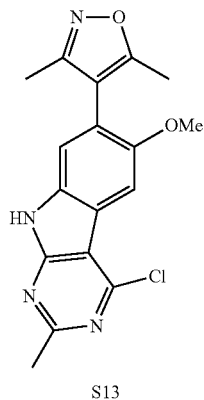

S13

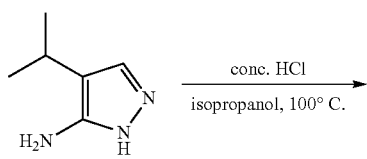

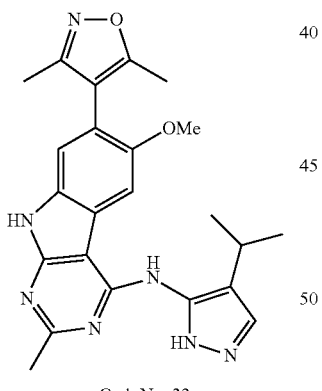

Cpd. No. 32

S13 (70 mg) and 4-isopropyl-1H-pyrazol-3-amine (88 mg) were dissolved in isopropanol (5 mL). Four drops of concentrated HCl was added via a glass pipette. The mixture was heated at reflux overnight. The reaction was concentrated on a rotary evaporator and the remaining residues were purified by HPLC to yield the desired product Cpd. No. 32 in 2 mg as a salt of trifluoroacetic acid. ESI-MS calculated for $C_{23}H_{26}N_7O_2$ $[M+H]^+$=432.21; Observed: 432.44. $^1$H NMR (300 MHz, MeOD) δ 7.76 (s, 1H), 7.46 (s, 1H), 7.28 (s, 1H), 3.87 (s, 3H), 3.04 (td, J=13.4, 6.6 Hz, 1H), 2.77 (s, 3H), 2.34 (s, 3H), 2.16 (s, 3H), 1.31 (d, J=6.9 Hz, 6H).

Example 44

Synthesis of 4-(tert-butyl)-N-(7-(3,5-dimethylisoxazol-4-yl)-6-methoxy-2-methyl-9H-pyrimido[4,5-b]indol-4-yl)thiazol-5-amine (Cpd. No. 33)

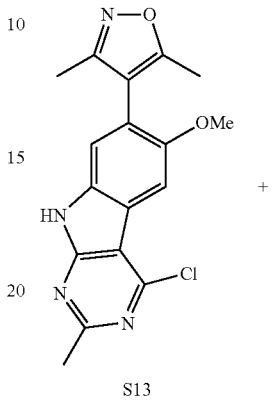

S13

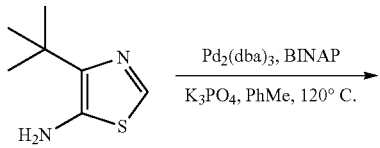

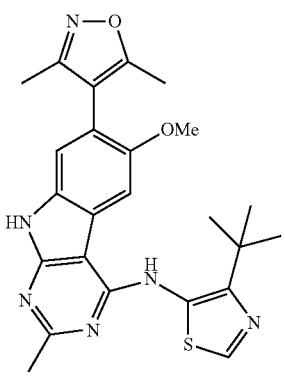

Cpd. No. 33

Pd$_2$(dba)$_3$ (18 mg) and BINAP (26 mg) were mixed in anhydrous toluene. And the mixture was heated at reflux for 3-4 minutes. This mixture was transferred into a round-bottom flask containing S13 (60 mg), 4-tert-butyl-1,3-thiazol-5-amine (84 mg), K$_3$PO$_4$ (130 mg), and toluene (1 mL). The mixture was heated at reflux for overnight before quenching with methanol. The reaction mixture was filtered and the mixture was purified by HPLC to yield Cpd. No. 33 as a CF$_3$CO$_2$H salt in 4 mg. ESI-MS calculated for $C_{24}H_{27}N_6O_2S$ $[M+H]^+$=463.19; Observed: 463.25. $^1$H NMR (300 MHz, MeOD) δ 9.02 (s, 1H), 7.76 (brs, 1H), 7.49 (s, 1H), 3.92 (s, 3H), 2.71 (s, 3H), 2.34 (s, 3H), 2.18 (s, 3H), 1.46 (s, 9H).

Example 45

Synthesis of N-(1,3-dimethyl-1H-pyrazol-4-yl)-7-(3,5-dimethylisoxazol-4-yl)-6-methoxy-2-methyl-9H-pyrimido[4,5-b]indol-4-amine (Cpd. No. 34)

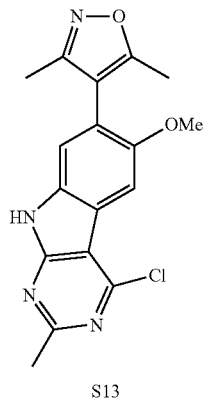

S13

+

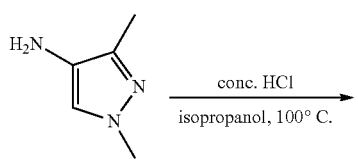

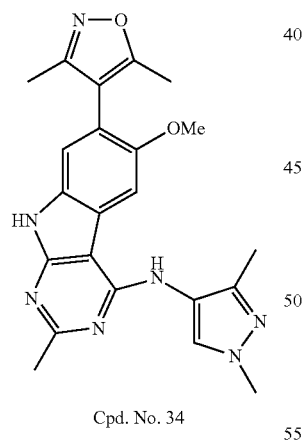

Cpd. No. 34

S13 (70 mg) and 1,3-dimethyl-1H-pyrazol-4-ylamine (88 mg) were dissolved in isopropanol (5 mL). Four drops of concentrated HCl was added via a glass pipette. The mixture was heated at reflux for overnight. The reaction was concentrated on a rotary evaporator and the remaining residues were purified by HPLC to yield the desired product Cpd. No. 34 in 30 mg as a salt of trifluoroacetic acid. ESI-MS calculated for $C_{22}H_{24}N_7O_2$ [M+H]$^+$=418.19; Observed: 418.45. $^1$H NMR (300 MHz, MeOD) δ 8.0-7.7 (m, 2H), 7.47 (s, 1H), 3.94 (s, 3H), 3.93 (s, 3H), 2.70 (s, 3H), 2.34 (s, 3H), 2.24 (s, 3H), 2.17 (s, 3H).

Example 46

Synthesis of 7-(3,5-dimethylisoxazol-4-yl)-6-methoxy-2-methyl-N-(1,3,5-trimethyl-1H-pyrazol-4-yl)-9H-pyrimido[4,5-b]indol-4-amine (Cpd. No. 35)

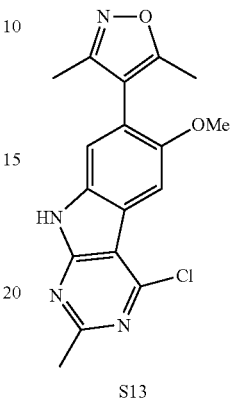

S13

+

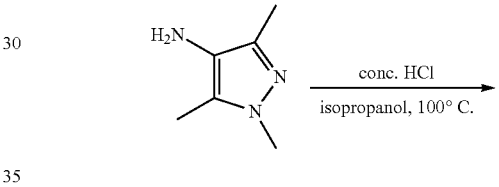

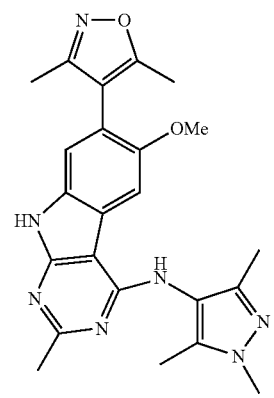

Cpd. No. 35

S13 (70 mg) and 1,3,5-trimethyl-1H-pyrazol-4-amine (88 mg) were dissolved in isopropanol (5 mL). Four drops of concentrated HCl was added via a glass pipette. The mixture was heated at reflux overnight. The reaction was concentrated on a rotary evaporator and the remaining residues were purified by HPLC to yield the desired product Cpd. No. 35 in 40 mg as a salt of trifluoroacetic acid. ESI-MS calculated for $C_{23}H_{26}N_7O_2$ [M+H]$^+$=432.21; Observed: 432.44. $^1$H NMR (300 MHz, MeOD) δ 8.20 (s, 1H), 7.48 (s, 1H), 3.97 (s, 3H), 3.85 (s, 3H), 2.70 (s, 3H), 2.34 (s, 3H), 2.28 (s, 3H), 2.20 (s, 3H), 2.16 (s, 3H).

Example 47

Synthesis of 7-(3,5-dimethylisoxazol-4-yl)-N-(1-isopropyl-3,5-dimethyl-1H-pyrazol-4-yl)-6-methoxy-2-methyl-9H-pyrimido[4,5-b]indol-4-amine (Cpd. No. 36)

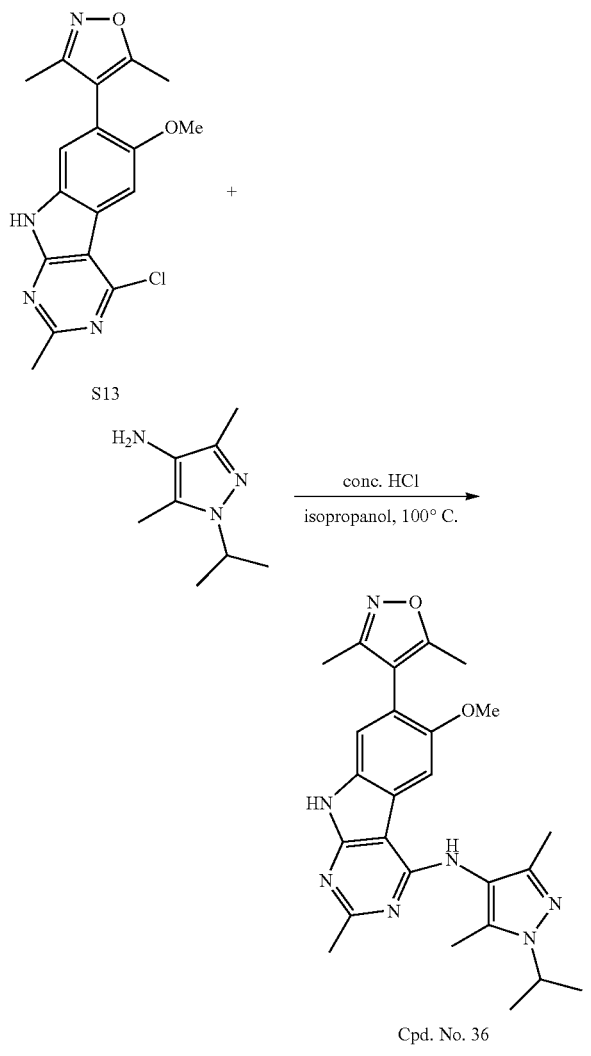

Cpd. No. 36

S13 (70 mg) and 1-isopropyl-3,5-dimethyl-1H-pyrazol-4-amine (88 mg) were dissolved in isopropanol (5 mL). Four drops of concentrated HCl was added via a glass pipette. The mixture was heated at reflux overnight. The reaction was concentrated on a rotary evaporator and the remaining residues were purified by HPLC to yield the desired product Cpd. No. 36 in 20 mg as a salt of trifluoroacetic acid. ESI-MS calculated for $C_{25}H_{30}N_7O_2$ [M+H]$^+$=460.24; Observed: 460.35. $^1$H NMR (300 MHz, MeOD) δ 8.20 (s, 1H), 7.49 (s, 1H), 4.70-4.52 (m, 1H), 3.97 (s, 3H), 2.70 (s, 3H), 2.33 (s, 3H), 2.31 (brs, 1H), 2.25 (s, 3H), 2.16 (s, 3H), 1.53 (d, J=6.4 Hz, 6H).

Example 48

Synthesis of 7-(3,5-dimethylisoxazol-4-yl)-N-(1-isopropyl-4-methyl-1H-pyrazol-5-yl)-6-methoxy-2-methyl-9H-pyrimido[4,5-b]indol-4-amine (Cpd. No. 37)

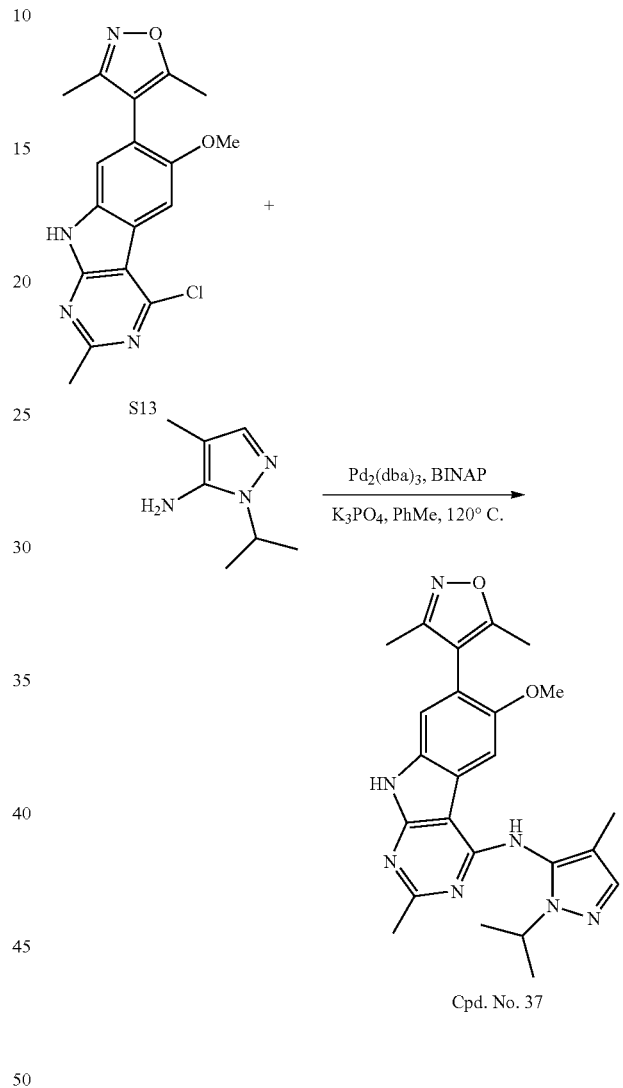

Cpd. No. 37

Pd$_2$(dba)$_3$ (18 mg) and BINAP (26 mg) were mixed in anhydrous toluene. And the mixture was heated at reflux for 3-4 minutes. This mixture was transferred into a round-bottom flask containing S13 (60 mg), 1-isopropyl-4-methyl-1H-pyrazol-5-amine (84 mg), K$_3$PO$_4$ (130 mg), and toluene (1 mL). The mixture was heated at reflux for overnight before quenching with methanol. The reaction mixture was filtered and the mixture was purified by HPLC to yield Cpd. No. 37 as a CF$_3$CO$_2$H salt in 2 mg. ESI-MS calculated for $C_{24}H_{28}N_7O_2$ [M+H]$^+$=446.23; Observed: 446.44. $^1$H NMR (300 MHz, MeOD) δ 7.57 (s, 1H), 7.48 (s, 1H), 7.07 (brs, 1H), 4.64 (dt, J=13.2, 6.7 Hz, 1H), 3.84 (s, 3H), 2.73 (s, 3H), 2.33 (s, 3H), 2.15 (s, 3H), 1.95 (s, 3H), 1.48 (d, J=6.7 Hz, 6H).

Example 49

Synthesis of 4-(4-(3-chlorophenoxy)-6-methoxy-2-methyl-9H-pyrimido[4,5-b]indol-7-yl)-3,5-dimethyl-isoxazole (Cpd. No. 95)

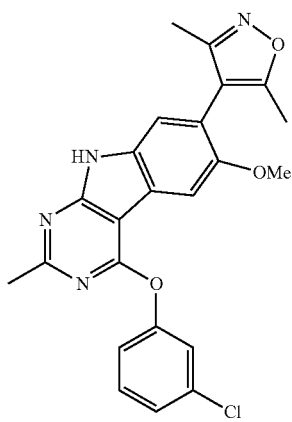

S13 (50 mg, 0.146 mmol), 3-chlorophenol (38 mg, 0.292 mmol), and potassium carbonate (61 mg, 0.438 mmol) were dissolved in DMSO (2 mL) and heated to 90° C. After overnight, the reaction was cooled to room temperature, brine was added and the resulting solution was extracted with ethyl acetate. The combined ethyl acetate extracts were washed twice with water, once with brine, and the ethyl acetate was removed by rotoevaporation. The resulting oil was purified by preparative HPLC and lyophilized to give the TFA salt of the title compound as a powder. $^1$H-NMR (300 MHz, CD$_3$OD) δ ppm 7.66 (s, 1H), 7.53-7.26 (m, 5H), 3.88 (s, 3H), 2.60 (s, 3H), 2.34 (s, 3H), 2.17 (s, 3H); ESI-MS m/z 435.25 (M+H)$^+$.

Example 50

Synthesis of 4-(6-methoxy-2-methyl-4-(pyridin-3-yloxy)-9H-pyrimido[4,5-b]indol-7-yl)-3,5-dimethyl-isoxazole (Cpd. No. 96)

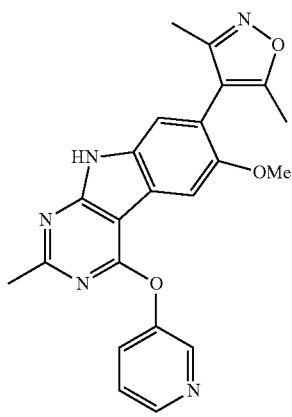

The title compound was prepared in a similar manner as described for the preparation of Cpd. No. 95. $^1$H-NMR (300 MHz, CD$_3$OD) δ ppm 8.93 (s, 1H), 8.67 (d, J=5.52 Hz, 1H), 8.31 (d, J=8.55 Hz, 1H), 7.89 (dd, J=5.12, 8.36 Hz, 1H), 7.77 (s, 1H), 7.41 (s, 1H), 3.91 (s, 3H), 2.58 (s, 3H), 2.34 (s, 3H), 2.18 (s, 3H); ESI-MS m/z 402.58 (M+H)$^+$.

Example 51

Synthesis of N-(3-chlorophenyl)-7-(3,5-dimethyl-isoxazol-4-yl)-6-methoxy-2-methyl-9H-pyrimido[4,5-b]indol-4-amine (Cpd. No. 97)

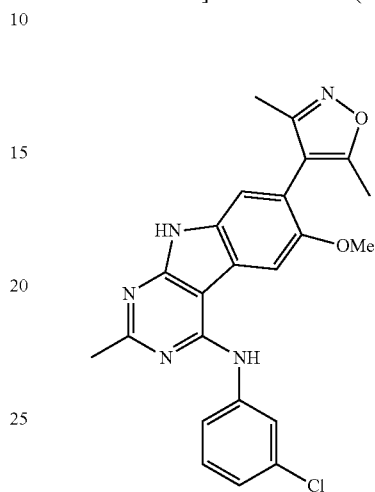

Concentrated hydrochloric acid (5 drops) was added to a solution of S13 (100 mg, 0.292 mmol) and 3-chloroaniline (82 mg, 0.642 mmol) in isopropanol (3 mL). After refluxing overnight, the reaction was cooled, the solvent was removed with a rotoevaporator and the crude was purified by preparative HPLC and lyophilized to give the TFA salt of the title compound as a powder. $^1$H-NMR (300 MHz, CD$_3$OD) δ ppm 7.69-7.66 (m, 1H), 7.65 (s, 1H), 7.56-7.46 (m, 2H), 7.43 (s, 1H), 7.38 (dt, J=1.92, 7.06 Hz, 1H), 3.84 (s, 3H), 2.69 (s, 3H), 2.33 (s, 3H), 2.15 (s, 3H); ESI-MS m/z 434.42 (M+H)$^+$.

Example 52

Synthesis of N-(7-(3,5-dimethylisoxazol-4-yl)-6-methoxy-2-methyl-9H-pyrimido[4,5-b]indol-4-yl)-5-methyl-3-phenylisoxazol-4-amine (Cpd. No. 98)

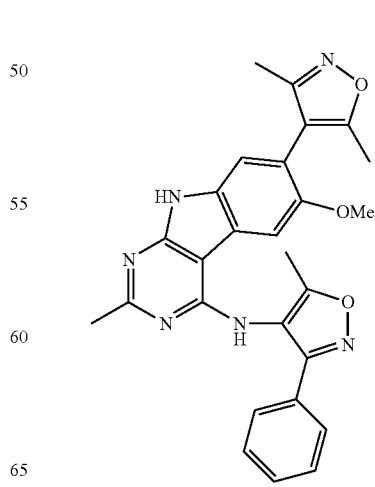

The title compound was prepared in a similar manner as described for the preparation of Cpd. No. 97. ¹H-NMR (300 MHz, CD₃OD) δ ppm 8.09-7.91 (m, 1H), 7.77-7.67 (m, 2H), 7.47 (s, 1H), 7.44-7.34 (m, 3H), 3.92 (s, 3H), 2.58 (s, 3H), 2.52 (s, 3H), 2.34 (s, 3H), 2.17 (s, 3H); ESI-MS m/z 481.50 (M+H)⁺.

Example 53

Synthesis of 7-(3,5-dimethylisoxazol-4-yl)-N-(imidazo[1,2-a]pyridin-3-yl)-6-methoxy-2-methyl-9H-pyrimido[4,5-b]indol-4-amine (Cpd. No. 99)

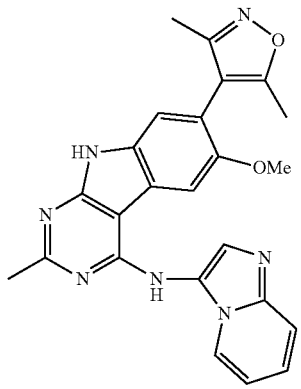 [SMILES: COc1cc2c(cc1-c1c(C)noc1C)[nH]c1nc(C)nc(Nc3cnc4ccccn34)c12]

The title compound was prepared in a similar manner as described for the preparation of Cpd, No. 97. ¹H-NMR (300 MHz, CD₃OD) δ ppm 8.58 (dt, J=0.95. 6.88 Hz, 1H), 8.21 (s, 1H), 8.13-8.02 (m, 3H), 7.53 (td, J=1.89, 6.40 Hz, 1H), 7.43 (s, 1H), 3.97 (s, 3H), 2.42 (s, 3H), 2.35 (s, 3H), 2.18 (s, 3H); ESI-MS m/z 440.67 (M+H)⁺.

Example 54

Synthesis of 7-(3,5-dimethylisoxazol-4-yl)-6-methoxy-N-(4-methoxynaphthalen-1-yl)-2-methyl-9H-pyrimido[4,5-b]indol-4-amine (Cpd. No. 100)

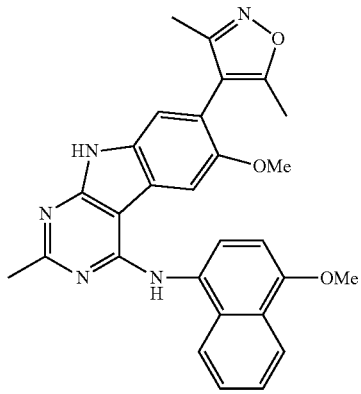 [SMILES: COc1cc2c(cc1-c1c(C)noc1C)[nH]c1nc(C)nc(Nc3ccc(OC)c4ccccc34)c12]

The title compound was prepared in a similar manner as described for the preparation of Cpd. No. 97. ¹H-NMR (300 MHz, CD₃OD) δ ppm 8.44-8.38 (m, 1H), 8.04-7.98 (m, 1H), 7.68-7.58 (m, 3H), 7.49-7.31 (m, 1H), 7.43 (s, 1H), 7.09 (d, J=8.26 Hz, 1H), 4.12 (s, 3H), 3.63 (s, 3H), 2.59 (s, 3H), 2.31 (s, 3H), 2.13 (s, 3H); ESI-MS m/z 480.58 (M+H)⁺.

Example 55

Synthesis of N-([1,2,4]triazolo[4,3-a]pyridin-3-yl)-7-(3,5-dimethylisoxazol-4-yl)-6-methoxy-2-methyl-9H-pyrimido[4,5-b]indol-4-amine (Cpd, No. 101)

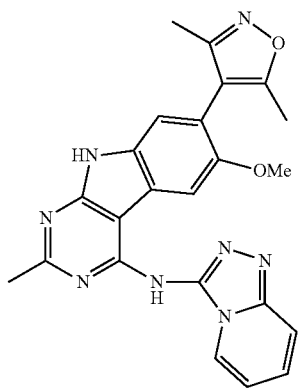 [SMILES: COc1cc2c(cc1-c1c(C)noc1C)[nH]c1nc(C)nc(Nc3nnc4ccccn34)c12]

The title compound was prepared in a similar manner as described for the preparation of Cpd. No. 95. ¹H-NMR (300 MHz, CD₃OD) δ ppm 8.73 (d, J=6.56 Hz, 1H), 8.05 (s, 1H), 7.97-7.82 (m, 2H), 7.45-7.36 (m, 2H), 4.02 (s, 3H), 2.74 (s, 3H), 2.35 (s, 3H), 2.19 (s, 3H); ESI-MS m/z 441.58 (M+H)⁺.

Example 56

Synthesis of 7-(3,5-dimethylisoxazol-4-yl)-6-methoxy-2-methyl-N-(1H-pyrrolo[2,3-b]pyridin-3-yl)-9H-pyrimido[4,5-b]indol-4-amine (Cpd. No. 102)

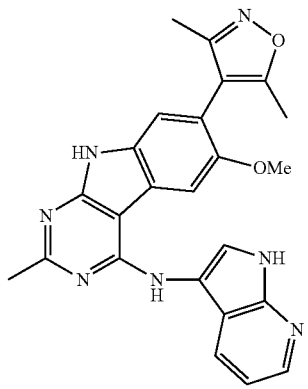 [SMILES: COc1cc2c(cc1-c1c(C)noc1C)[nH]c1nc(C)nc(Nc3c[nH]c4ncccc34)c12]

The title compound was prepared in a similar manner as described for the preparation of Cpd. No. 97. ¹H-NMR (300 MHz, CD₃OD) δ ppm 8.40 (d, J=4.31 Hz, 1H), 8.14 (dd, J=1.35, 7.94, 1H), 7.97-7.78 (m, 1H), 7.82 (s, 1H), 7.46 (s, 1H), 7.30 (dd, J=4.94, 7.95 Hz, 1H), 3.85 (s, 3H), 2.61 (s, 3H), 2.33 (s, 3H), 2.16 (s, 3H); ESI-MS m/z 440.33 (M+H)⁺.

Example 57

Synthesis of N-(7-(3,5-dimethylisoxazol-4-yl)-6-methoxy-2-methyl-9H-pyrimido[4,5-b]indol-4-yl)thieno[2,3-b]pyridin-3-amine (Cpd. No. 103)

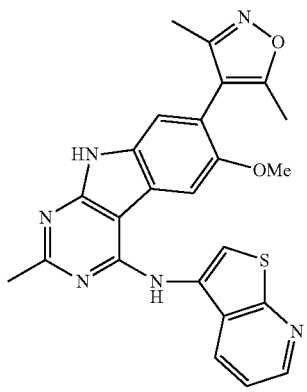 [SMILES: COc1cc2c(cc1-c1c(C)noc1C)[nH]c1nc(C)nc(Nc3csc4ncccc34)c12]

The title compound was prepared in a similar manner as described for the preparation of Cpd. No. 97. $^1$H-NMR (300 MHz, CD$_3$OD) δ ppm 8.68 (dd, J=1.44, 4.64 Hz, 1H), 8.22 (dd, J=1.50, 8.17 Hz, 1H), 8.01 (s, 1H), 7.91 (s, 1H), 7.52 (dd, J=4.67, 8.16 Hz, 1H), 7.48 (s, 1H), 3.86 (s, 3H), 2.60 (s, 3H), 2.34 (s, 3H), 2.16 (s, 3H); ESI-MS m/z 457.50 (M+H)$^+$.

Example 58

Synthesis of 4-(6-methoxy-2-methyl-4-(quinolin-4-yloxy)-9H-pyrimido[4,5-b]indol-7-yl)-3,5-dimethylisoxazole (Cpd. No. 104)

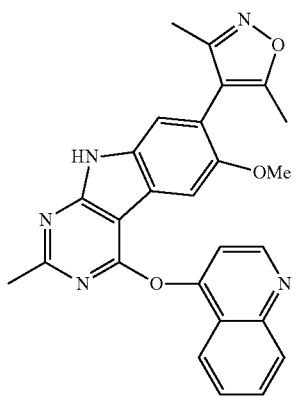

The title compound was prepared in a similar manner as described for the preparation of Cpd. No. 95. $^1$H-NMR (300 MHz, CD$_3$OD and 10% CDCl$_3$) δ ppm 9.12 (d, J=6.26 Hz, 1H), 8.69 (d, J=8.71 Hz, 1H), 8.27 (d, J=8.83 Hz, 1H), 8.23-8.14 (m, 1H), 8.04-7.96 (m, 2H), 7.65 (s, 1H), 7.45 (s, 1H), 3.78 (s, 3H), 2.68 (s, 3H), 2.34 (s, 3H), 2.17 (s, 3H); ESI-MS m/z 452.67 (M+H)$^+$.

Example 59

Synthesis of 4-(4-(5-bromopyridin-3-yloxy)-6-methoxy-2-methyl-9H-pyrimido[4,5-b]indol-7-yl)-3,5-dimethylisoxazole (Cpd. No. 105)

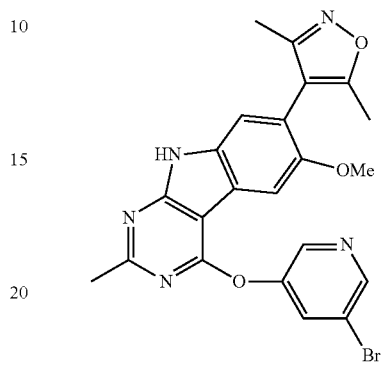

The title compound was prepared in a similar manner as described for the preparation of Cpd. No. 95. $^1$H-NMR (300 MHz, CD$_3$OD and 10% CDCl$_3$) δ ppm 8.64-8.60 (m, 2H), 8.13 (t, J=2.18 Hz, 1H), 7.72 (s, 1H), 7.38 (s, 1H), 3.91 (s, 3H), 2.59 (s, 3H), 2.34 (s, 3H), 2.18 (s, 3H); ESI-MS m/z 480.25 (M+H)$^+$.

Example 60

Synthesis of N-(5-chloropyridin-3-yl)-7-(3,5-dimethylisoxazol-4-yl)-6-methoxy-2-methyl-9H-pyrimido[4,5-b]indol-4-amine (Cpd. No. 106)

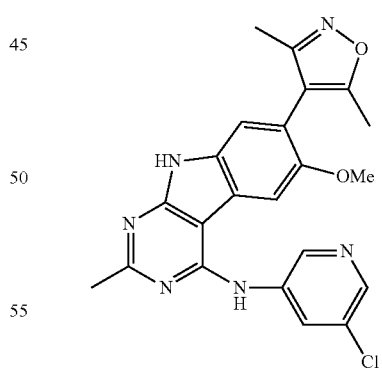

The title compound was prepared in a similar manner as described for the preparation of Cpd. No. 97. $^1$H-NMR (300 MHz, CD$_3$OD) δ ppm 8.86 (d, J=1.88 Hz, 1H), 8.52 (s, 1H), 8.31 (t, J=2.10 Hz, 1H), 8.04 (s, 1H), 7.47 (s, 1H), 3.96 (s, 3H), 2.71 (s, 3H), 2.34 (s, 3H), 2.17 (s, 3H); ESI-MS m/z 435.33 (M+H)$^+$.

Example 61

Synthesis of 4-(1-Chloro-8-methoxy-5H-pyrido[4,3-b]indol-7-yl)-3,5-dimethylisoxazole (RX3)

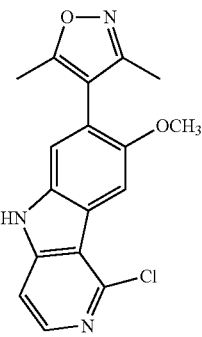 [SMILES: COc1cc2c(cc1-c1c(C)noc1C)[nH]c1ccnc(Cl)c12]

7-Bromo-1-chloro-8-methoxy-5H-pyrido[4,3-b]indole (157 mg, 0.5 mmol), 3,5-dimethylisoxazole-4-boronic acid pinacol ester (655 mg, 2.0 mmol), and K$_2$CO$_3$ (345 mg, 2.5 mmol) were dissolved in DME/H$_2$O (50 mL/25 mL) system. Then vacuumed, and refilled with N$_2$. After that, tetrakis(triphenylphosphine)palladium (0) was added, followed by vacuuming and refilling with N$_2$. The reaction mixture was heated to reflux for overnight, when cooled to room temperature, it was extracted with EtOAc, and the combined organic fractions were concentrated before purification in prep-HPLC. 57 mg (34.6%) of the titled compound was obtained after being lyophilized for 24 hours as a pale yellow powder. $^1$HNMR (300 MHz, MeOD-d$_4$) δ 8.26 (d, 1H, J=6.0 Hz), 8.09 (s, 1H), 7.60 (d, 1H, J=6.3 Hz), 7.49 (s, 1H), 3.98 (s, 3H), 2.63 (s, 3H), 2.20 (s, 3H). ESIMS m/z [M+H]$^+$ calculated=328.77; found=328.83.

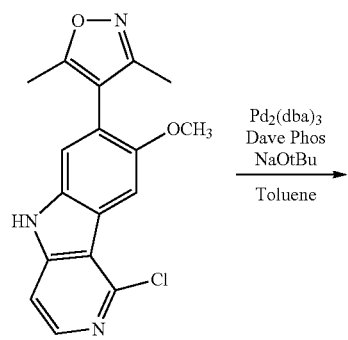

7-(3,5-dimethylisoxazol-4-yl)-8-methoxy-N-(1-methyl-1H-indazol-3-yl)-5H-pyrido[4,3-b]indol-1-amine can be synthesized from 4-(1-chloro-8-methoxy-5H-pyrido[4,3-b]indol-7-yl)-3,5-dimethylisoxazole and 1-methyl-1H-indazol-3-amine following the same method for the preparation of Cpd. No. 255.

Example 62

Synthesis of N-cyclohexyl-7-(3,5-dimethylisoxazol-4-yl)-6-methoxy-2-methyl-9H-pyrimido[4,5-b]indol-4-amine (Cpd. No. 112)

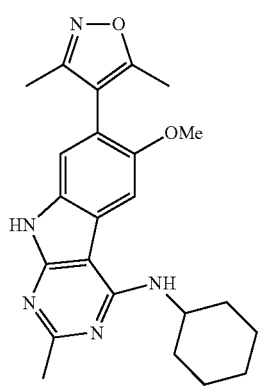 [SMILES: COc1cc2c(cc1-c1c(C)noc1C)[nH]c1nc(C)nc(NC3CCCCC3)c12]

In a round-bottomed flask, S13 (70 mg), NaHCO$_5$ (84 mg) and anhydrous DMSO (3 mL) were added. Cyclohexylamine (0.1 mL) was subsequently added via a syringe and the mixture was heated at 120° C. for overnight. The reaction mixture was then purified by reverse phase HPLC to yield the title product as a salt of trifluoroacetic acid in 32 mg. $^1$H NMR (300 MHz, MeOD-d4): 8.02 (s, 1H), 7.41 (s, 1H), 4.50-4.30 (m, 1H), 3.96 (s, 3H), 2.73 (s, 3H), 2.31 (s, 3H), 2.20-2.00 (m, 2H), 2.14 (s, 3H), 1.98-1.84 (m, 2H), 1.84-1.60 (m, 3H), 1.60-1.40 (m, 2H), 1.40-1.20 (m, 1H). ESI-MS calculated for C$_{23}$H$_{28}$N$_5$O$_2$ [M+H]$^+$=406.22; Observed: 406.42.

Example 63

Synthesis of N-cyclopentyl-7-(3,5-dimethylisoxazol-4-yl)-6-methoxy-2-methyl-9H-pyrimido[4,5-b]indol-4-amine (Cpd. No. 113)

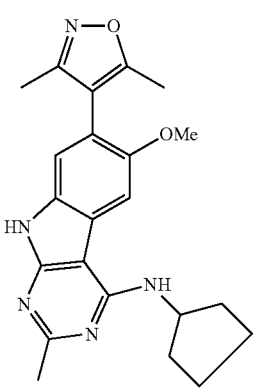 [SMILES: COc1cc2c(cc1-c1c(C)noc1C)[nH]c1nc(C)nc(NC3CCCC3)c12]

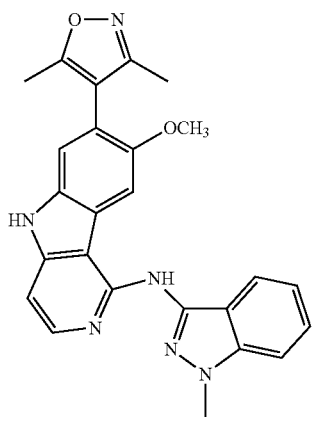

In a round-bottomed flask, S13 (68 mg), NaHCO₃ (100 mg) and anhydrous DMSO (3 mL) were added. Cyclopentylamine (0.1 mL) was subsequently added via a syringe and the mixture was heated at 120° C. for overnight. The reaction mixture was then purified by reverse phase HPLC to yield the title product as a salt of trifluoroacetic acid in 60 mg. ¹H NMR (300 MHz, MeOD-d4): 8.02 (s, 1H), 7.41 (s, 1H), 4.86-4.70 (m, 1H), 3.96 (s, 3H), 2.73 (s, 3H), 2.32 (s, 3H), 2.32-2.18 (m, 2H), 2.15 (s, 3H), 2.00-1.70 (m, 6H). ESI-MS calculated for $C_{22}H_{26}N_5O_2$ [M+H]⁺=392.21; Observed: 392.25.

Example 64

Synthesis of 3-Isopropyl-1-methyl-1H-pyrazol-5-amine (CF24)

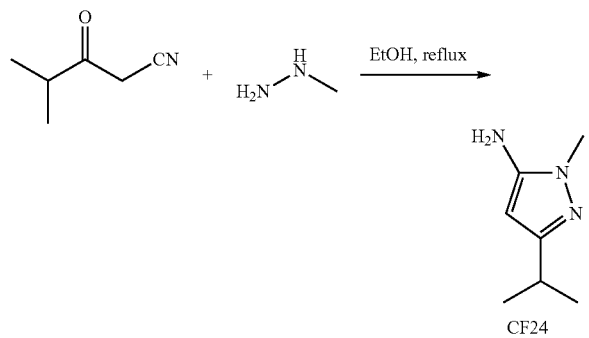

4-Methyl-3-oxopentanenitrile (1 g) was dissolved in ethanol (30 mL). Methyl hydrazine (26 mL) was added and the mixture was heated at reflux for overnight. The mixture was concentrated on a rotary evaporator followed by addition of ethyl acetate and water. The aqueous layer was extracted with ethyl acetate and the organic layers were combined, dried, and concentrated on a rotary evaporator. The remaining residue was purified by flash column chromatography and the desired product was obtained in 0.98 g. ¹H NMR (300 MHz, CDCl₃): 5.37 (s, 1H), 3.61 (s, 3H), 3.43 (br, s, 1H), 2.83 (septet, J=6.89 Hz, 1H), 1.21 (d, J=6.93 Hz, 6H). ¹³C NMR (75 MHz, CDCl₃): 158.17, 144.75, 88.24, 34.18, 28.35, 23.10. ESI-MS calculated for $C_7H_{14}N_3$[M+H]⁺=140.12, Observed: 140.33.

Synthesis of 7-(3,5-Dimethylisoxazol-4-yl)-N-(3-isopropyl-1-methyl-1H-pyrazol-5-yl)-6-methoxy-2-methyl-9H-pyrimido[4,5-b]indol-4-amine (Cpd. No. 65)

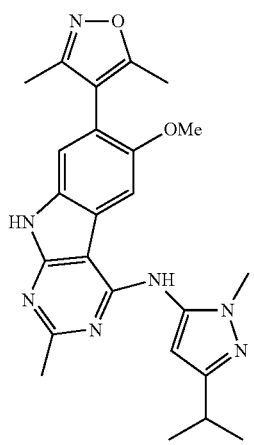

Pd₂(dba)₃ (27 mg, 0.03 mmol) and BINAP (37 mg, 0.06 mmol) were mixed in anhydrous toluene (5 mL). The mixture was heated at reflux for 3-4 minutes. This clear, orange-red color solution was transferred into a round-bottom flask containing S13 (102 mg, 0.3 mmol), 3-isopropyl-1-methyl-1H-pyrazol-5-amine (84 mg, 0.6 mmol), K₃PO₄ (212 mg, 1.0 mmol), and anhydrous toluene (5 mL). The mixture was heated at reflux for overnight before quenching with methanol. The reaction mixture was filtered through a pad of Celite® and the organic layer was collected, concentrated, and purified by HPLC to yield Cpd. No. 65 in 49 mg as a CF₃CO₂H salt. ¹H NMR (300 MHz, MeOD-d4): 7.46 (s, 1H), 7.42 (s, 1H), 6.25 (s, 1H), 3.87 (s, 3H), 3.81 (s, 3H), 2.97 (septet, J=6.92 Hz, 1H), 2.71 (s, 3H), 2.31 (s, 3H), 2.13 (s, 3H), 1.28 (d, J=6.95 Hz, 6H). ESI-MS calculated for $C_{24}H_{28}N_7O_2$ [M+H]⁺=446.23, Observed: 446.42.

Example 65

Synthesis of N-(1,5-Dimethyl-1H-pyrazol-3-yl)-7-(3,5-dimethylisoxazol-4-yl)-6-methoxy-2-methyl-9H-pyrimido[4,5-b]indol-4-amine (Cpd. No. 115)

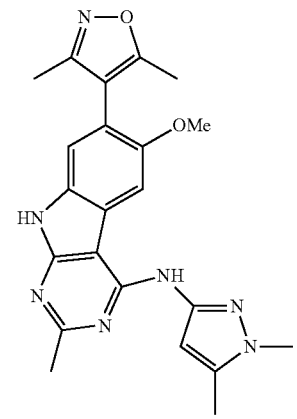

Pd₂(dba)₃ (27 mg, 0.03 mmol) and BINAP (37 mg, 0.06 mmol) were mixed in anhydrous toluene (5 mL). The mixture was heated at reflux for 3-4 minutes. This clear, orange-red color solution was transferred into a round-bottom flask containing S13 (102 mg, 0.3 mmol), 1,5-dimethyl-1H-pyrazol-3-amine (70 mg, 0.6 mmol), K₃PO₄ (212 mg, 1.0 mmol), and anhydrous toluene (5 mL). The mixture was heated at reflux for overnight before quenching with methanol. The reaction mixture was filtered through a pad of Celite® and the organic layer was collected, concentrated, and purified by HPLC to yield Cpd. No. 115 in 31 mg as a CF₃CO₂H salt. ¹H NMR (300 MHz, MeOD-d4): 8.24 (s, 1H), 7.46 (s, 1H), 6.25 (s, 1H), 3.98 (s, 3H), 3.90 (s, 3H), 2.84 (s, 3H), 2.39 (s, 3H), 2.33 (s, 3H), 2.16 (s, 3H). ESI-MS calculated for $C_{22}H_{24}N_7O_2$ [M+H]⁺=418.20, Observed: 418.50.

Example 66

Synthesis of 1-Ethyl-3-methyl-1H-pyrazol-5-amine (CF35)

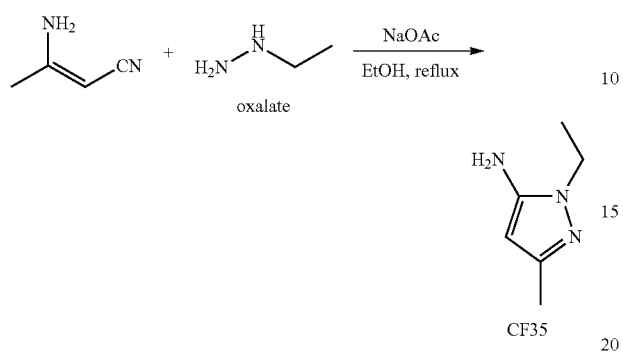

3-Aminocrotononitrile (2.0 g, 24.3 mmol) was dissolved in ethanol (40 mL). Ethyl hydrazine oxalate (5 g, 33.3 mmol) and sodium acetate (6 g, 73 mmol) were added and the mixture was heated at reflux for overnight. The mixture was concentrated on a rotary evaporator followed by addition of ethyl acetate and water. The aqueous layer was extracted with ethyl acetate and the organic layers were combined, dried, and concentrated on a rotary evaporator. The remaining residues were purified by flash column chromatography and the desired product was obtained in 1.277 g. $^1$H NMR (300 MHz, CDCl$_3$): 5.34 (s, 1H), 3.91 (q, J=7.26 Hz, 2H), 2.16 (s, 3H), 1.36 (t, J=7.26 Hz, 3H). ESI-MS calculated for $C_6H_{12}N_3[M+H]^+$=126.10, Observed: 126.33.

Synthesis of 7-(3,5-Dimethylisoxazol-4-yl)-N-(1-ethyl-3-methyl-1H-pyrazol-5-yl)-6-methoxy-2-methyl-9H-pyrimido[4,5-b]indol-4-amine (Cpd. No. 116)

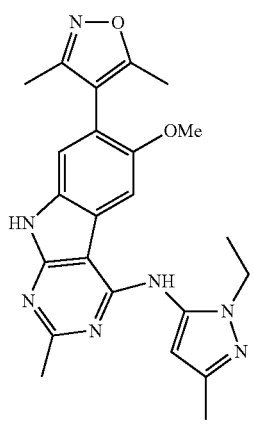 [SMILES: CCn1nc(C)cc1Nc1nc(C)nc2[nH]c3cc(-c4c(C)noc4C)c(OC)cc3c12]

Pd$_2$(dba)$_3$ (27 mg, 0.03 mmol) and BINAP (37 mg, 0.06 mmol) were mixed in anhydrous toluene (5 mL). The mixture was heated at reflux for 3-4 minutes. This clear, orange-red color solution was transferred into a round-bottom flask containing S13 (102 mg, 0.3 mmol), 1-ethyl-3-methyl-1H-pyrazol-5-amine (75 mg, 0.6 mmol), K$_3$PO$_4$ (212 mg, 1.0 mmol), and anhydrous toluene (5 mL). The mixture was heated at reflux for overnight before quenching with methanol. The reaction mixture was filtered through a pad of Celite® and the organic layer was collected, concentrated, and purified by HPLC to yield Cpd. No. 116 in 19 mg as a CF$_3$CO$_2$H salt. $^1$H NMR (300 MHz, MeOD-d4): 7.45 (s, 1H), 7.28 (s, 1H), 6.21 (s, 1H), 4.11 (q, J=7.22 Hz, 2H), 3.85 (s, 3H), 2.70 (s, 3H), 2.31 (s, 6H), 2.13 (s, 3H), 1.44 (t, J=7.23 Hz, 3H). ESI-MS calculated for $C_{23}H_{26}N_7O_2$ [M+H]$^+$=432.21, Observed: 432.92.

Example 67

Synthesis of 1-(tert-Butyl)-3-(trifluoromethyl)-1H-pyrazol-5-amine (CF39)

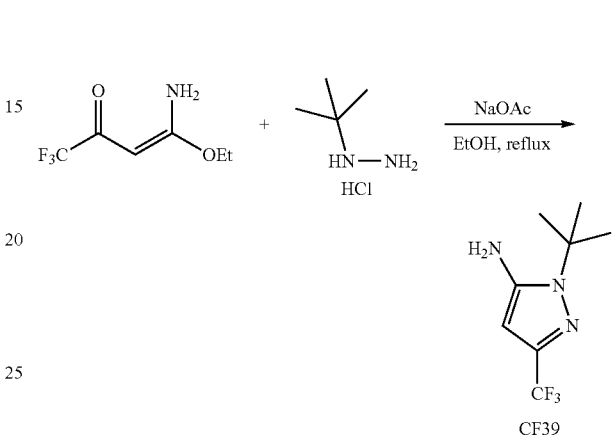

(E)-4-Amino-4-ethoxy-1,1,1-trifluorobut-3-en-2-one (2 g, 10.9 mmol) was dissolved in ethanol (40 mL). Tert-butyl hydrazine-HCl salt (2.74 g, 22 mmol) and sodium acetate (2.71 g, 33 mmol) were added and the mixture was heated at reflux for overnight. The mixture was concentrated on a rotary evaporator followed by addition of ethyl acetate and water. The aqueous layer was extracted with ethyl acetate and the organic layers were combined, dried, and concentrated on a rotary evaporator. The remaining residues were purified by flash column chromatography and the desired product was obtained in 1.0 g. $^1$H NMR (300 MHz, CDCl$_3$): 5.77 (s, 1H), 1.59 (s, 9H). ESI-MS calculated for $C_8H_{13}F_3N_3$ [M+H]$^+$=208.11, Observed: 208.42.

Synthesis of N-(1-(tert-Butyl)-3-(trifluoromethyl)-1H-pyrazol-5-yl)-7-(3,5-dimethylisoxazol-4-yl)-6-methoxy-2-methyl-9H-pyrimido[4,5-b]indol-4-amine (Cpd. No. 117)

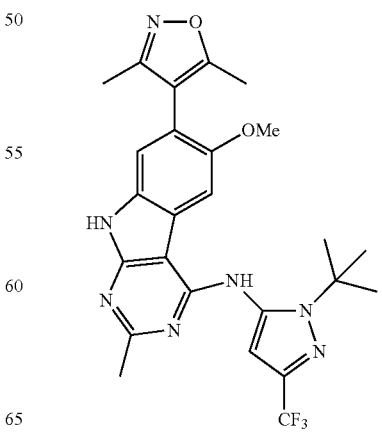

Pd$_2$(dba)$_3$ (27 mg, 0.03 mmol) and BINAP (37 mg, 0.06 mmol) were mixed in anhydrous toluene (5 mL). The mixture was heated at reflux for 3-4 minutes. This clear, orange-red color solution was transferred into a round-bottom flask containing S13 (102 mg, 0.3 mmol), 1-(tert-Butyl)-3-(trifluoromethyl)-1H-pyrazol-5-amine (120 mg, 0.6 mmol), K$_3$PO$_4$ (212 mg, 1.0 mmol), and anhydrous toluene (5 mL). The mixture was heated at reflux for overnight before quenching with methanol. The reaction mixture was filtered through a pad of Celite® and the organic layer was collected, concentrated, and purified by HPLC to yield Cpd. No. 117 in 10 mg as a CF$_3$CO$_2$H salt. $^1$H NMR (300 MHz, MeOD-d4): 7.44 (s, 2H), 6.70 (s, 1H), 3.87 (s, 3H), 2.66 (s, 3H), 2.32 (s, 3H), 2.15 (s, 3H), 1.71 (s, 3H). ESI-MS calculated for C$_{25}$H$_{27}$F$_3$N$_7$O$_2$ [M+H]$^+$=514.22, Observed: 514.17.

Example 68

Synthesis of N-(1-Cyclopentyl-3-methyl-1H-pyrazol-5-yl)-7-(3,5-dimethylisoxazol-4-yl)-6-methoxy-2-methyl-9H-pyrimido[4,5-b]indol-4-amine (Cpd. No. 118)

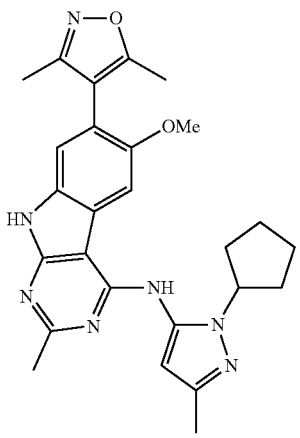 [SMILES: COc1cc2c(cc1-c1c(C)noc1C)[nH]c1nc(C)nc(Nc3cc(C)nn3C3CCCC3)c12]

Pd$_2$(dba)$_3$ (27 mg, 0.03 mmol) and BINAP (37 mg, 0.06 mmol) were mixed in anhydrous toluene (5 mL). The mixture was heated at reflux for 3-4 minutes. This clear, orange-red color solution was transferred into a round-bottom flask containing S13 (102 mg, 0.3 mmol), 1-cyclopentyl-3-methyl-1H-pyrazol-5-amine (100 mg, 0.6 mmol), K$_3$PO$_4$ (212 mg, 1.0 mmol), and anhydrous toluene (5 mL). The mixture was heated at reflux for overnight before quenching with methanol. The reaction mixture was filtered through a pad of Celite® and the organic layer was collected, concentrated, and purified by HPLC to yield Cpd. No. 118 in 60 mg as a CF$_3$CO$_2$H salt. $^1$H NMR (300 MHz, MeOD-d4): 7.44 (s, 1H), 7.19 (s, 1H), 6.18 (s, 1H), 4.69 (quintet, J=7.95 Hz, 1H), 3.83 (s, 3H), 2.70 (s, 3H), 2.31 (s, 3H), 2.13 (s, 3H), 2.10-2.00 (m, 4H), 2.00-1.80 (m, 2H), 1.70-1.50 (m, 2H). ESI-MS calculated for C$_{26}$H$_{30}$N$_7$O$_2$ [M+H]$^+$=472.25, Observed: 472.42.

Example 69

Synthesis of 1-Cyclobutyl-3-methyl-1H-pyrazol-5-amine (CF44)

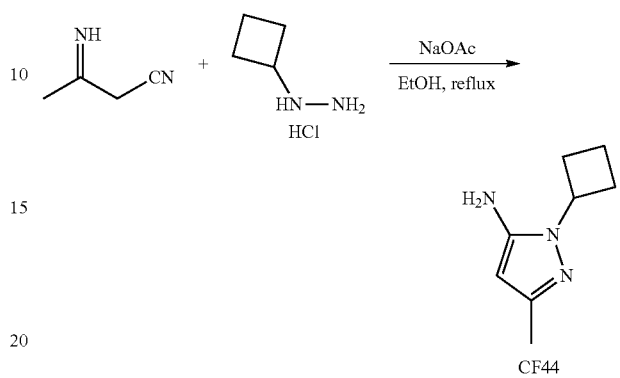

3-Aminocrotononitrile (670 mg, 8.16 mmol) was dissolved in ethanol (40 mL). Cyclobutyl hydrazine-HCl salt (1 g, 8.16 mmol) and sodium acetate (1.6 g, 20 mmol) were added and the mixture was heated at reflux for overnight. The mixture was concentrated on a rotary evaporator followed by addition of ethyl acetate and water. The aqueous layer was extracted with ethyl acetate and the organic layers were combined, dried, and concentrated on a rotary evaporator. The remaining residues were purified by flash column chromatography and the desired product was obtained in 100 mg. $^1$H NMR (300 MHz, CDCl$_3$): 5.31 (s, 1H), 4.60-4.40 (m, 1H), 3.50 (br, 2H, NH$_2$), 2.80-2.50 (m, 2H), 2.40-2.20 (m, 2H), 2.16 (s, 3H), 1.90-1.70 (m, 2H). ESI-MS calculated for C$_8$H$_{14}$N$_3$[M+H]$^+$=152.12, Observed: 152.08.

Synthesis of N-(1-Cyclobutyl-3-methyl-1H-pyrazol-5-yl)-7-(3,5-dimethylisoxazol-4-yl)-6-methoxy-2-methyl-9H-pyrimido[4,5-b]indol-4-amine (Cpd. No. 119)

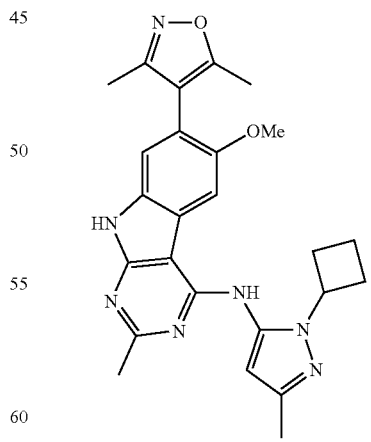

Pd$_2$(dba)$_3$ (27 mg, 0.03 mmol) and BINAP (37 mg, 0.06 mmol) were mixed in anhydrous toluene (5 mL). The mixture was heated at reflux for 3-4 minutes. This clear, orange-red color solution was transferred into a round-bottom flask containing S13 (102 mg, 0.3 mmol), 1-cyclobutyl-3-methyl-1H-pyrazol-5-amine (100 mg, 0.6 mmol), K₃PO₄ (212 mg, 1.0 mmol), and anhydrous toluene (5 mL). The mixture was heated at reflux for overnight before quenching with methanol. The reaction mixture was filtered through a pad of Celite® and the organic layer was collected, concentrated, and purified by HPLC to yield Cpd. No. 119 in 58 mg as a CF₃CO₂H salt. ¹H NMR (300 MHz, MeOD-d4): 7.45 (s, 1H), 7.22 (s, 1H), 6.20 (s, 1H), 4.90-4.70 (m, 1H), 3.84 (s, 3H), 2.70-2.50 (m, 2H), 2.69 (s, 3H), 2.40-2.20 (m, 2H), 2.34 (s, 3H), 2.31 (s, 3H), 2.13 (s, 3H), 1.90-1.60 (m, 2H). ESI-MS calculated for $C_{25}H_{28}N_7O_2$ [M+H]⁺=458.23, Observed: 548.58.

Example 70

Synthesis of N-(3-tert-Butyl-1-methyl-1H-pyrazol-5-yl)-7-(3,5-dimethylisoxazol-4-yl)-6-methoxy-2-methyl-9H-pyrimido[4,5-b]indol-4-amine (Cpd. No. 120)

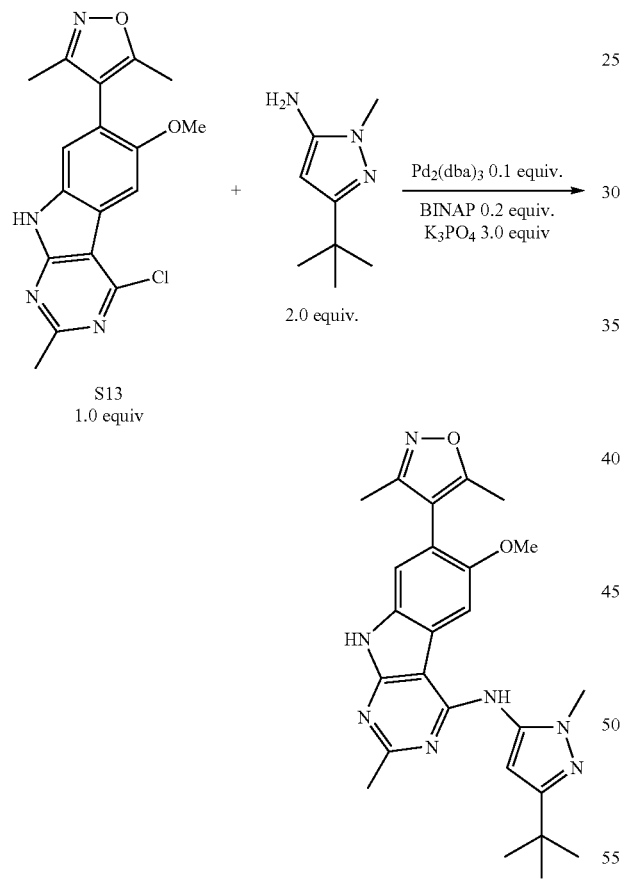

Pd₂(dba)₃ (27 mg, 0.03 mmol) and BINAP (37 mg, 0.06 mmol) were mixed in anhydrous toluene (5 mL). The mixture was heated at reflux for 3-4 minutes. This clear, orange-red color solution was transferred into a round-bottom flask containing S13 (102 mg, 0.3 mmol), 3-tert-butyl-1-methyl-1H-pyrazol-5-amine (100 mg, 0.6 mmol), K₃PO₄ (212 mg, 1.0 mmol), and anhydrous toluene (4 mL). The mixture was heated at reflux for overnight before quenching with methanol. The reaction mixture was filtered through a pad of Celite® and the organic layer was collected, concentrated, and purified by HPLC to yield Cpd. No. 120 as a CF₃CO₂H salt in 49 mg. ¹H NMR (300 MHz, MeOD-d4): 7.45 (s, 1H), 6.26 (s, 1H), 3.88 (s, 3H), 3.82 (s, 3H), 2.71 (s, 3H), 2.31 (s, 3H), 2.14 (s, 3H), 1.32 (s, 9H). ESI-MS calculated for $C_{25}H_{30}N_7O_2$ [M+H]⁺=460.25, Observed: 460.33.

Example 71

Synthesis of N-(3-Cyclopropyl-1-methyl-1H-pyrazol-5-yl)-7-(3,5-dimethylisoxazol-4-yl)-6-methoxy-2-methyl-9H-pyrimido[4,5-b]indol-4-amine (Cpd. No. 121)

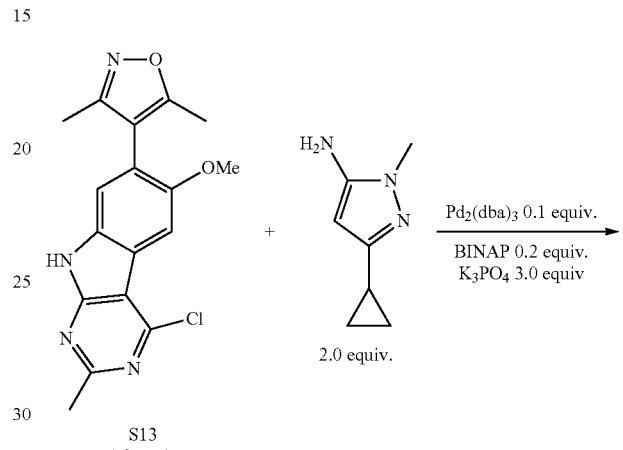

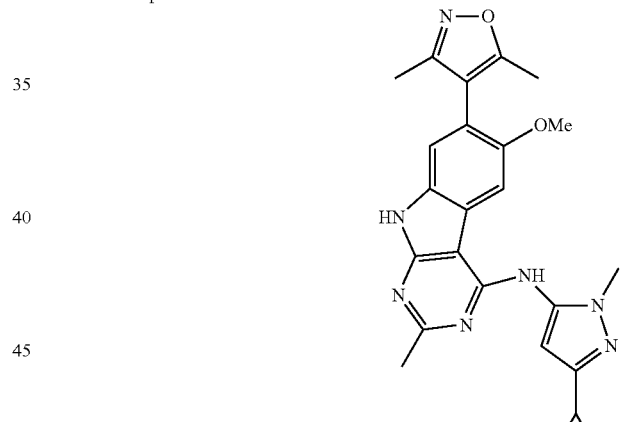

Pd₂(dba)₃ (27 mg, 0.03 mmol) and BINAP (37 mg, 0.06 mmol) were mixed in anhydrous toluene (5 mL). The mixture was heated at reflux for 3-4 minutes. This clear, orange-red color solution was transferred into a round-bottom flask containing S13 (102 mg, 0.3 mmol), 3-cyclopropyl-1-methyl-1H-pyrazol-5-amine (90 mg, 0.6 mmol), K₃PO₄ (212 mg, 1.0 mmol), and anhydrous toluene (4 mL). The mixture was heated at reflux for overnight before quenching with methanol. The reaction mixture was filtered through a pad of Celite® and the organic layer was collected, concentrated, and purified by HPLC to yield Cpd. No. 121 as a CF₃CO₂H salt in 49 mg. ¹H NMR (300 MHz, MeOD-d4): 7.45 (s, 1H), 7.25 (s, 1H), 6.09 (s, 1H), 3.86 (s, 3H), 3.75 (s, 3H), 2.71 (s, 3H), 2.31 (s, 3H), 2.14 (s, 3H), 2.00-1.80 (m, 1H), 1.00-0.90 (m, 2H), 0.76-0.68 (m, 2H). ESI-MS calculated for $C_{24}H_{26}N_7O_2$ [M+H]⁺=444.21, Observed: 444.33.

Example 72

Synthesis of 2-Methyl-2,4,5,6-tetrahydrocyclopenta[c]pyrazol-3-amine

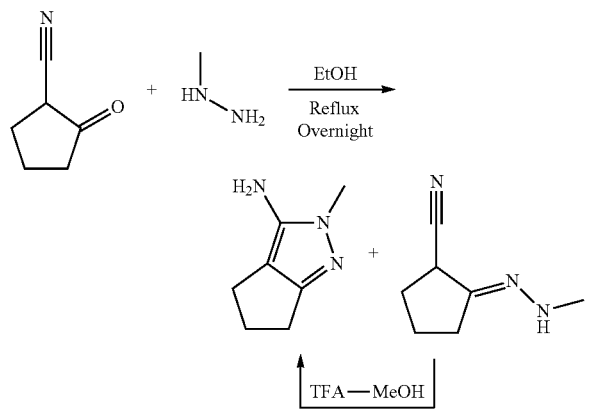

2-Oxocyclopentanecarbonitrile (1.5 g, 14 mmol) was dissolved in ethanol (30 mL). Methyl hydrazine (3.0 mL, 56 mmol) was added via a syringe and the reaction mixture was heated at reflux for overnight. The reaction mixture was cooled to ambient temperature and the solvent was removed on a rotary evaporator. Ethyl acetate and water was added and the aqueous layer was extracted with ethyl acetate. The organic layers were combined, dried, and concentrated on a rotary evaporator. The remaining residues were purified by flash column chromatography and the desired product was obtained in 0.64 g (the desired product was washed out at 40% methanol in ethyl acetate). At the eluent gradient of 80% ethyl acetate in hexane, we also isolated a hydrazone, partially condensed product, which was converted to 2-methyl-2,4,5,6-tetrahydrocyclo-penta[c]pyrazol-3-amine upon treatment of CF$_3$CO$_2$H in methanol for overnight. $^1$H NMR (300 MHz, CDCl$_3$): 3.70-3.50 (m, 2H, NH$_2$), 3.51 (s, 3H), 2.52 (t, J=7.13 Hz, 2H), 2.46-2.34 (m, 2H), 2.32-2.18 (m, 2H). ESI-MS calculated for C$_7$H$_{12}$N$_3$[M+H]$^+$=138.10, Observed: 138.08.

Synthesis of 7-(3,5-Dimethylisoxazol-4-yl)-6-methoxy-2-methyl-N-(2-methyl-2,4,5,6-tetrahydro-cyclopenta-[c]pyrazol-3-yl)-9H-pyrimido[4,5-b]indol-4-amine (Cpd. No. 122)

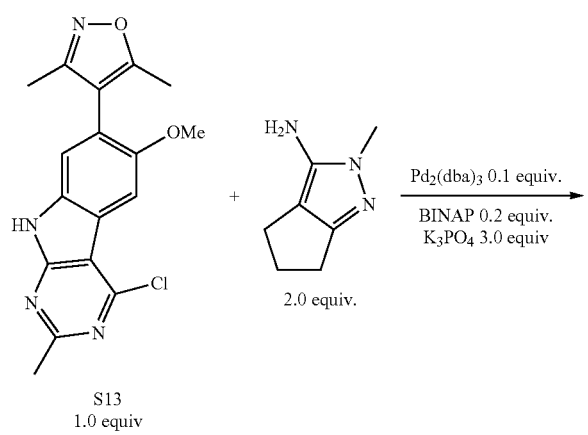

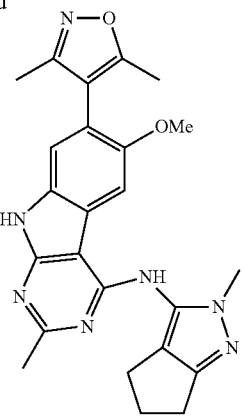

Pd$_2$(dba)$_3$ (27 mg, 0.03 mmol) and BINAP (37 mg, 0.06 mmol) were mixed in anhydrous toluene (5 mL). The mixture was heated at reflux for 3-4 minutes. This clear, orange-red color solution was transferred into a round-bottom flask containing S13 (102 mg, 0.3 mmol), 2-methyl-2,4,5,6-tetrahydrocyclopenta[c]pyrazol-3-amine (90 mg, 0.6 mmol), K$_3$PO$_4$ (212 mg, 1.0 mmol), and anhydrous toluene (4 mL). The mixture was heated at reflux for overnight before quenching with methanol. The reaction mixture was filtered through a pad of Celite® and the organic layer was collected, concentrated, and purified by HPLC to yield Cpd. No. 122 as a CF$_3$CO$_2$H salt in 38 mg. $^1$H NMR (300 MHz, MeOD-d4): 7.46 (s, 1H), 7.27 (s, 1H), 3.85 (s, 3H), 3.82 (s, 3H), 2.80-2.70 (m, 2H), 2.73 (s, 3H), 2.56-2.34 (m, 4H), 2.31 (s, 3H), 2.14 (s, 3H). ESI-MS calculated for C$_{24}$H$_{26}$N$_7$O$_2$ [M+H]$^+$=444.21, Observed: 444.42.

Example 73

Synthesis of 1-Methyl-1H-pyrazolo[4,3-b]pyridin-3-amine (CF55)

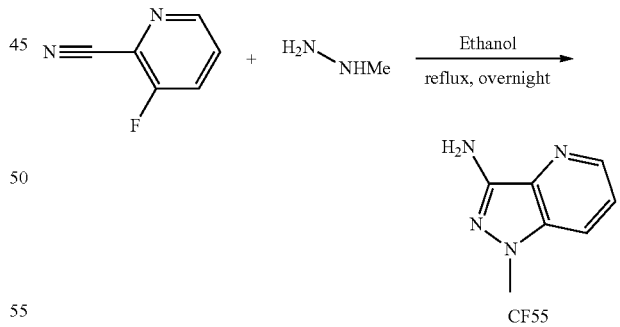

3-Fluoro-2-pyridinecarbonitrile (1.5 g, 12.3 mmol) was dissolved in ethanol (30 mL). Methyl hydrazine (2.63 mL, 50 mmol) was added and the mixture was heated at reflux for overnight. The mixture was concentrated on a rotary evaporator followed by addition of ethyl acetate and water. The aqueous layer was extracted with ethyl acetate and the organic layers were combined, dried, and concentrated on a rotary evaporator. The remaining residue (1.28 g) was used directly for the next step without further purification. $^1$H NMR (300 MHz, CDCl$_3$): 8.37 (d, J=4.33 Hz, 1H), 7.54 (d, J=8.56 Hz, 1H), 7.28-7.20 (m, 1H), 4.40 (br, 2H), NH$_2$), 3.84 (s, 3H). ESI-MS calculated for C$_7$H$_9$N$_4$ [M+H]$^+$=149.08, Observed: 149.08.

Synthesis of 7-(3,5-Dimethylisoxazol-4-yl)-6-methoxy-2-methyl-N-(1-methyl-1H-pyrazolo[4,3-b]pyridin-3-yl)-9H-pyrimido[4,5-b]indol-4-amine (Cpd. No. 123)

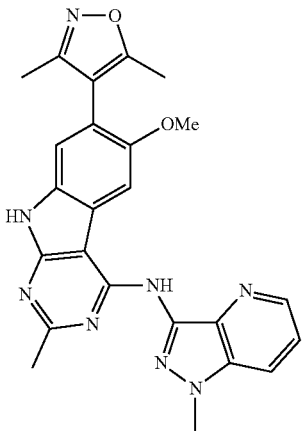 [SMILES: COc1cc2c(cc1-c1c(C)noc1C)[nH]c1nc(C)nc(Nc3nn(C)c4cccnc34)c12]

Pd$_2$(dba)$_3$ (27 mg, 0.03 mmol) and BINAP (37 mg, 0.06 mmol) were mixed in anhydrous toluene (5 mL). The mixture was heated at reflux for 3-4 minutes. This clear, orange-red color solution was transferred into a round-bottom flask containing S13 (102 mg, 0.3 mmol), 1-methyl-1H-pyrazolo[4,3-b]pyridin-3-amine (90 mg, 0.6 mmol), K$_3$PO$_4$ (212 mg, 1.0 mmol), and anhydrous toluene (5 mL). The mixture was heated at reflux for overnight before quenching with methanol. The reaction mixture was filtered through a pad of Celite® and the organic layer was collected, concentrated, and purified by HPLC to yield Cpd. No. 123 in 27.9 mg as a CF$_3$CO$_2$H salt. $^1$H NMR (300 MHz, MeOD-d4): 8.69 (d, J=3.63 Hz, 1H), 8.32 (dd, J=8.69, 0.79 Hz, 1H), 8.26 (s, 1H), 7.67 (dd, J=8.74, 4.41 Hz, 1H), 7.49 (s, 1H), 4.22 (s, 3H), 4.01 (s, 3H), 2.84 (s, 3H), 2.35 (s, 3H), 2.18 (s, 3H). ESI-MS calculated for C$_{24}$H$_{23}$N$_8$O$_2$ [M+H]$^+$=455.19, Observed: 455.42

Example 74

Synthesis of 1-Methyl-4,5,6,7-tetrahydro-1H-indazol-3-amine (CF58)

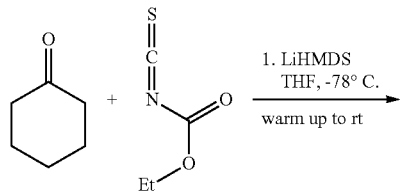

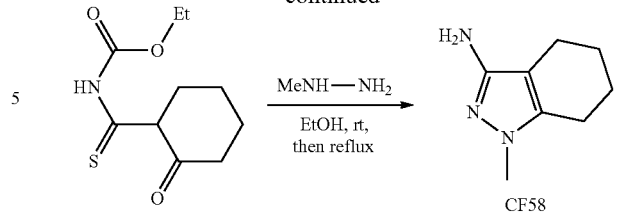

Step 1: LiHMDS (10 mL of 1.0 M in THF) was cooled to −78° C. for 10 min. Cyclohexanone (0.52 mL, 5.0 mmol) was added via a syringe and the mixture was stirred at −78° C. for 10 min. Ethoxycarbonylisothiocyanate (0.60 mL, 5.0 mmol) was added via a syringe and the reaction was allowed to stir at −78° C. for 3 h before warm up to ambient temperature overnight. Water was then added and the aqueous layer was extracted with ethyl acetate, and the organic layers were combined, dried, and concentrated on a rotary evaporator. The remaining residue was used without purification.

Step 2: The residue from step 1 was dissolved in ethanol and methyl hydrazine (0.8 mL, 16 mmol) was added via a syringe. The solution was stirred at ambient temperature for 6 h then heated at reflux for overnight. The reaction mixture was cooled to ambient temperature and the solvent was removed on a rotary evaporator. Ethyl acetate and water was added and the aqueous layer was extracted with ethyl acetate. The organic layers were combined, dried, and concentrated on a rotary evaporator. The remaining residue was purified by flash column chromatography and the desired product was obtained in 0.22 g. $^1$H NMR (300 MHz, CDCl$_3$): 3.50 (s, 3H), 2.43 (t, J=5.87 Hz, 2H), 2.26 (t, J=5.76 Hz, 2H), 1.80-1.60 (m, 4H). ESI-MS calculated for C$_8$H$_{14}$N$_3$ [M+H]$^+$=152.12, Observed: 152.50.

Synthesis of 7-(3,5-Dimethylisoxazol-4-yl)-6-methoxy-2-methyl-N-(1-methyl-4,5,6,7-tetrahydro-1H-indazol-3-yl)-9H-pyrimido[4,5-b]indol-4-amine (Cpd. No. 124)

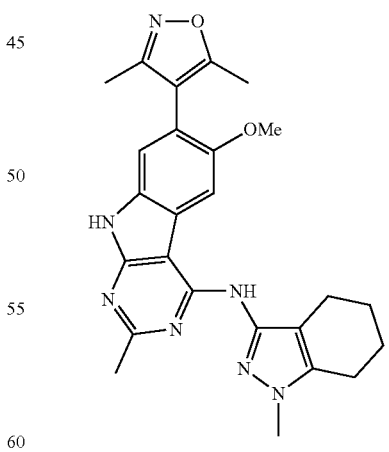

Pd$_2$(dba)$_3$ (64 mg, 0.07 mmol) and BINAP (88 mg, 0.14 mmol) were mixed in anhydrous toluene (5 mL). The mixture was heated at reflux for 3-4 minutes. This clear, orange-red color solution was transferred into a round-bottom flask containing S13 (240 mg, 0.7 mmol), 1-methyl-4,5,6,7-tetrahydro-1H-indazol-3-amine (220 mg, 1.4 mmol), K$_3$PO$_4$ (600 mg, 3.0 mmol), and anhydrous toluene (10 mL). The mixture was heated at reflux for overnight before quenching with methanol. The reaction mixture was filtered through a pad of Celite® and the organic layer was collected, concentrated, and purified by HPLC to yield Cpd. No. 124 in 100 mg as a CF$_3$CO$_2$H salt. $^1$H NMR (300 MHz, MeOD-d4): 7.71 (s, 1H), 7.45 (s, 1H), 3.90 (s, 3H), 3.81 (s, 3H), 2.77 (s, 3H), 2.71 (t, J=6.06 Hz, 2H), 2.53 (t, J=5.95 Hz, 2H), 2.32 (s, 3H), 2.15 (s, 3H), 1.98-1.84 (m, 2H), 1.84-1.70 (m, 2H). ESI-MS calculated for C$_{25}$H$_{28}$N$_7$O$_2$ [M+H]$^+$=458.23, Observed: 458.75.

Example 75

Synthesis of 2-Methyl-4,5,6,7-tetrahydro-2H-indazol-3-amine

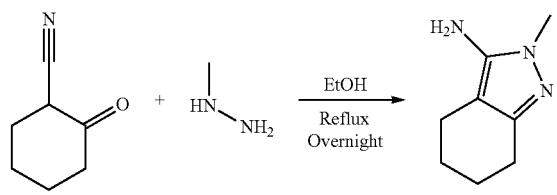

2-Oxocyclohexanecarbonitrile (2.0 g, 16 mmol) was dissolved in ethanol (40 mL). Methyl hydrazine (1.7 mL, 32 mmol) was added via a syringe and the reaction mixture was heated at reflux for overnight. The reaction mixture was cooled to ambient temperature and the solvent was removed on a rotary evaporator. Ethyl acetate and water was added and the aqueous layer was extracted with ethyl acetate. The organic layers were combined, dried, and concentrated on a rotary evaporator. The remaining residues were purified by flash column chromatography (the desired product was washed out at 40% methanol in ethyl acetate). The desired product was obtained in 1.58 g. $^1$H NMR (300 MHz, CDCl$_3$): 3.50 (s, 3H), 2.416 (t, J=5.54 Hz, 2H), 2.21 (t, J=5.49 Hz, 2H), 1.76-1.56n (m, 4H). $^{13}$C NMR (75 MHz, CDCl$_3$):147.63, 140.71, 99.76, 33.91, 23.49, 23.36, 23.32, 19.56.

Synthesis of 7-(3,5-Dimethylisoxazol-4-yl)-6-methoxy-2-methyl-N-(2-methyl-4,5,6,7-tetrahydro-2H-indazol-3-yl)-9H-pyrimido[4,5-b]indol-4-amine (Cpd. No. 125)

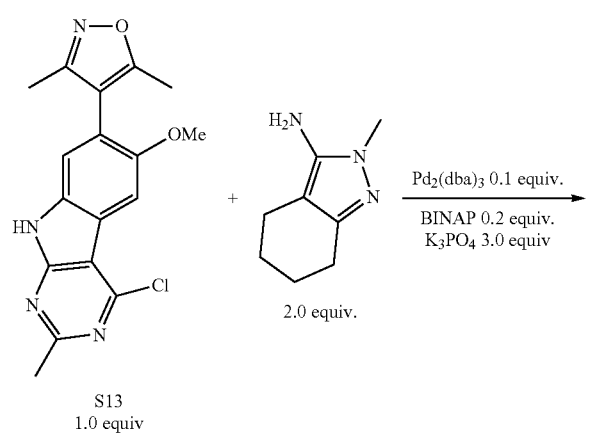

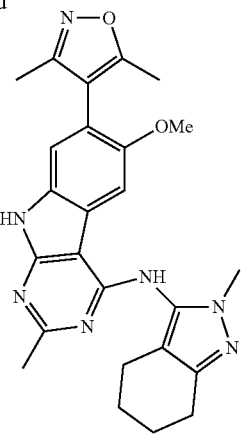

Pd$_2$(dba)$_3$ (37 mg, 0.04 mmol) and BINAP (50 mg, 0.08 mmol) were mixed in anhydrous toluene (5 mL). The mixture was heated at reflux for 3-4 minutes. This clear, orange-red color solution was transferred into a round-bottom flask containing S13 (136 mg, 0.4 mmol), 2-methyl-4,5,6,7-tetrahydro-2H-indazol-3-amine (144 mg, 1.0 mmol), K$_3$PO$_4$ (320 mg, 1.5 mmol), and anhydrous toluene (10 mL). The mixture was heated at reflux for overnight before quenching with methanol. The reaction mixture was filtered through a pad of Celite® and the organic layer was collected, concentrated, and purified by HPLC to yield Cpd. No. 125 as a CF$_2$CO$_2$H salt in 25 mg. $^1$H NMR (300 MHz, MeOD-d4): 7.45 (s, 1H), 7.14 (s, 1H), 3.83 (s, 3H), 3.80 (s, 3H), 2.80-2.60 (m, 2H), 2.71 (s, 3H), 2.40-2.20 (m, 2H), 2.31 (s, 3H), 2.13 (s, 3H), 1.90-1.76 (m, 2H), 1.76-1.60 (m, 2H). ESI-MS calculated for C$_{25}$H$_{28}$N$_7$O$_2$ [M+H]$^+$=458.23, Observed: 458.50.

Example 76

Synthesis of N-(3-(tert-Butyl)-1H-pyrazol-5-yl)-7-(3,5-dimethylisoxazol-4-yl)-6-methoxy-2-methyl-9H-pyrimido[4,5-b]indol-4-amine (Cpd. No. 126)

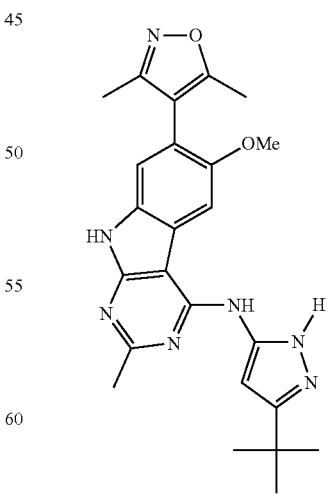

Pd$_2$(dba)$_3$ (27 mg, 0.03 mmol) and BINAP (37 mg, 0.06 mmol) were mixed in anhydrous toluene (5 mL). The mixture was heated at reflux for 3-4 minutes. This clear, orange-red color solution was transferred into a round-bottom flask containing S13 (102 mg, 0.3 mmol), 5-amino-3-tert-butylpyrazole (84 mg, 0.6 mmol), $K_3PO_4$ (212 mg, 1.0 mmol), and anhydrous toluene (5 mL). The mixture was heated at reflux for overnight before quenching with methanol. The reaction mixture was filtered through a pad of Celite® and the organic layer was collected, concentrated, and purified by HPLC to yield Cpd. No. 126 in 31 mg as a $CF_3CO_2H$ salt. $^1H$ NMR (300 MHz, MeOD-d4): 8.29 (s, 1H), 7.46 (s, 1H), 6.30 (s, 1H), 3.99 (s, 3H), 2.83 (s, 3H), 2.33 (s, 3H), 2.16 (s, 3H), 1.41 (s, 9H). ESI-MS calculated for $C_{24}H_{28}N_7O_2$ $[M+H]^+$=446.23, Observed: 446.42.

Example 77

Synthesis of 7-(3,5-Dimethylisoxazol-4-yl)-N-(5-fluoro-1-methyl-1H-indazol-3-yl)-6-methoxy-2-methyl-9H-pyrimido[4,5-b]indol-4-amine (Cpd. No. 127)

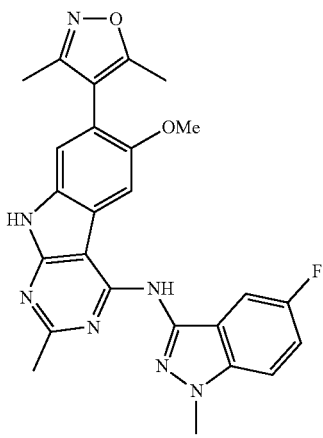 [SMILES: COc1cc2c(cc1-c1c(C)noc1C)[nH]c1nc(C)nc(Nc3nn(C)c4ccc(F)cc34)c12]

5-Fluoro-1-methyl-1H-indazol-3-ylamine (100 mg, 0.6 mol) and S13 (102 mg, 0.3 mmol) were mixed in anhydrous isopropanol (5 mL). Concentrated HCl (5 drops) was added via a glass pipette. The reaction was heated at reflux for overnight. The reaction was diluted with methanol and filter through a pad of Celite®. The solution was concentrated and subsequently purified on a reverse phase HPLC. The desired product Cpd. No. 127 was isolated in 17 mg as a salt of trifluoroacetic acid. $^1H$ NMR (300 MHz, MeOD-d4): 7.93 (s, 1H), 7.71 (dd, J=9.05, 3.80 Hz, 1H), 7.56 (dd, J=8.80, 2.24 Hz, 1H), 7.48 (s, 1H), 7.44-7.32 (m, 1H), 4.16 (s, 3H), 3.89 (s, 3H), 2.71 (s, 3H), 2.33 (s, 3H), 2.16 (s, 3H). ESI-MS calculated for $C_{25}H_{23}FN_7O_2[M+H]^+$=472.19, Observed: 472.42.

Example 78

Synthesis of 7-(3,5-Dimethylisoxazol-4-yl)-N-(6-fluoro-1-methyl-1H-indazol-3-yl)-6-methoxy-2-methyl-9H-pyrimido[4,5-b]indol-4-amine (Cpd. No. 59)

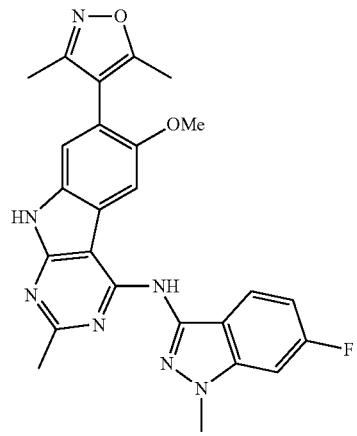 [SMILES: COc1cc2c(cc1-c1c(C)noc1C)[nH]c1nc(C)nc(Nc3nn(C)c4cc(F)ccc34)c12]

6-Fluoro-1-methyl-1H-indazol-3-ylamine (100 mg, 0.6 mol) and S13 (102 mg, 0.3 mmol) were mixed in anhydrous isopropanol (5 mL). Concentrated HCl (5 drops) was added via a glass pipette. The reaction was heated at reflux for overnight. The reaction was diluted with methanol and filter through a pad of Celite®. The solution was concentrated and subsequently purified on a reverse phase HPLC. The desired product Cpd. No. 59 was isolated in 77 mg as a salt of trifluoroacetic acid. $^1H$ NMR (300 MHz, MeOD-d4): 8.06 (s, 1H), 7.66 (t, J=7.97 Hz, 1H), 7.49 (s, 1H), 7.16-7.00 (m, 2H), 3.94 (s, 3H), 3.49 (s, 3H), 2.76 (s, 3H), 2.32 (s, 3H), 2.14 (s, 3H). ESI-MS calculated for $C_{25}H_{23}FN_7O_2$ $[M+H]^+$=472.19, Observed: 472.67.

Example 79

Synthesis of 7-(3,5-Dimethylisoxazol-4-yl)-N-(7-fluoro-1-methyl-1H-indazol-3-yl)-6-methoxy-2-methyl-9H-pyrimido[4,5-b]indol-4-amine (Cpd. No. 129)

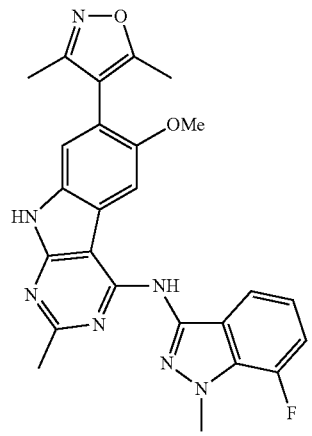 [SMILES: COc1cc2c(cc1-c1c(C)noc1C)[nH]c1nc(C)nc(Nc3nn(C)c4c(F)cccc34)c12]

7-Fluoro-1-methyl-1H-indazol-3-ylamine (100 mg, 0.6 mol) and S13 (102 mg, 0.3 mmol) were mixed in anhydrous isopropanol (5 mL). Concentrated HCl (5 drops) was added via a glass pipette. The reaction was heated at reflux for overnight. The reaction was diluted with methanol and filter through a pad of Celite®. The solution was concentrated and subsequently purified on a reverse phase HPLC. The desired product Cpd. No. 129 was isolated in 50 mg as a salt of trifluoroacetic acid. $^1$H NMR (300 MHz, MeOD-d4): 7.83 (s, 1H), 7.63 (d, J=7.94 Hz, 1H), 7.48 (s, 1H), 7.30-7.12 (m, 2H), 4.27 (s, 3H), 3.86 (s, 3H), 2.69 (s, 3H), 2.33 (s, 3H), 2.15 (s, 3H). ESI-MS calculated for $C_{25}H_{23}FN_7O_2$ $[M+H]^+$=472.19, Observed: 472.50.

Example 80

Synthesis of 7-(3,5-Dimethylisoxazol-4-yl)-N-(1H-indazol-3-yl)-6-methoxy-2-methyl-9H-pyrimido[4,5-b]indol-4-amine (Cpd. No. 58)

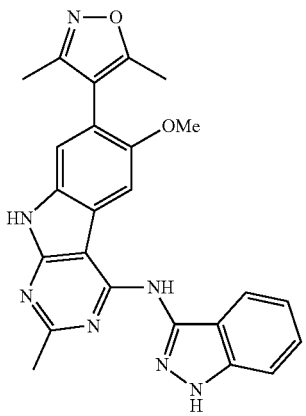 [SMILES: COc1cc2c(cc1-c1c(C)noc1C)[nH]c1nc(C)nc(Nc3n[nH]c4ccccc34)c12]

1H-indazol-3-ylamine (84 mg, 0.6 mol) and S13 (102 mg, 0.3 mmol) were mixed in anhydrous isopropanol (5 mL). Concentrated HCl (5 drops) was added via a glass pipette. The reaction was heated at reflux for overnight. The reaction was diluted with methanol and filter through a pad of Celite®. The solution was concentrated and subsequently purified on a reverse phase HPLC. The desired product Cpd. No. 58 was isolated in 27 mg as a salt of trifluoroacetic acid. $^1$H NMR (300 MHz, MeOD-d4): 7.92 (d, J=8.29 Hz, 1H), 7.74 (s, 1H), 7.64 (d, J=8.55 Hz, 1H), 7.57-7.50 (m, 1H), 7.47 (s, 1H), 7.32-7.25 (m, 1H), 3.84 (s, 3H), 2.76 (s, 3H), 2.32 (s, 3H), 2.15 (s, 3H). ESI-MS calculated for $C_{24}H_{22}N_7O_2$ $[M+H]^+$=440.18, Observed: 440.33.

Example 81

Synthesis of 2-(3-Amino-1H-indazol-1-yl)ethanol (CF40)

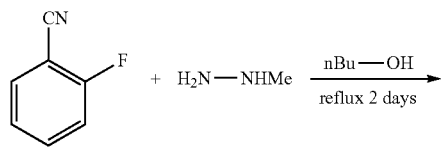

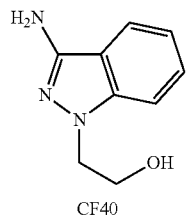

2-Fluorobenzonitrile (1 g, 8.25 mmol) was dissolved in n-butanol (30 mL). 2-Hydrazinoethanol (2.5 g, 33 mmol) was added and the mixture was heated at reflux for two days. The mixture was concentrated on a rotary evaporator followed by addition of ethyl acetate and water. The aqueous layer was extracted with ethyl acetate and the organic layers were combined, dried, and concentrated on a rotary evaporator. The remaining residue (1.11 g) was used directly for the next step without further purification. ESI-MS calculated for $C_9H_{12}N_3O$ $[M+H]^+$=178.10, Observed: 178.50.

Synthesis of 2-(3-((7-(3,5-Dimethylisoxazol-4-yl)-6-methoxy-2-methyl-9H-pyrimido[4,5-b]indol-4-yl)amino)-1H-indazol-1-yl)ethanol (Cpd. No. 131)

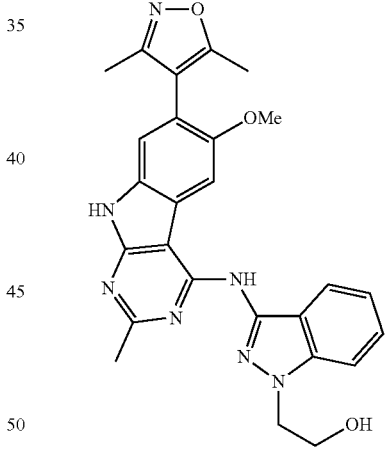

2-(3-Amino-1H-indazol-1-yl)ethanol (290 mg, 1.6 mol) and S13 (170 mg, 0.5 mmol) were mixed in anhydrous isopropanol (15 mL). Concentrated HCl (6 drops) was added via a glass pipette. The reaction was heated at reflux for overnight. The reaction was diluted with methanol and filter through a pad of Celite®. The solution was concentrated and subsequently purified on a reverse phase HPLC. The desired product Cpd. No. 131 was isolated in 107 mg as a salt of trifluoroacetic acid. $^1$H NMR (300 MHz, MeOD-d4): 7.91 (d, J=8.25 Hz, 1H), 7.84 (s, 1H), 7.70 (d, J=8.65 Hz, 1H), 7.54 (t, J=7.58 Hz, 1H), 7.47 (s, 1H), 7.27 (t, J=7.50 Hz, 1H), 4.57 (t, J=5.10 Hz, 2H), 4.05 (t, J=5.10 Hz, 2H), 3.83 (s, 3H), 2.71 (s, 3H), 2.32 (s, 3H), 2.15 (s, 3H). ESI-MS calculated for $C_{26}H_{26}N_7O_3$ $[M+H]^+$=484.21, Observed: 484.25.

Example 82

Synthesis of 7-(3,5-Dimethylisoxazol-4-yl)-N-(4-fluoro-1-methyl-1H-indazol-3-yl)-6-methoxy-2-methyl-9H-pyrimido[4,5-b]indol-4-amine (Cpd. No. 132)

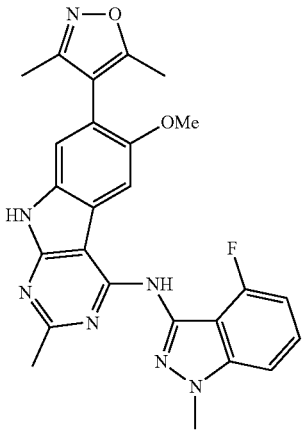 [SMILES: COc1cc2c(cc1-c1c(C)noc1C)[nH]c1nc(C)nc(Nc3nn(C)c4cccc(F)c34)c12]

4-Fluoro-1-methyl-1H-indazol-3-ylamine (102 mg, 0.6 mol) and S13 (102 mg, 0.3 mmol) were mixed in anhydrous isopropanol (5 mL). Concentrated HCl (5 drops) was added via a glass pipette. The reaction was heated at reflux for overnight. The reaction was diluted with methanol and filter through a pad of Celite®. The solution was concentrated and subsequently purified on a reverse phase HPLC. The desired product Cpd. No. 132 was isolated in 75 mg as a salt of trifluoroacetic acid. $^1$H NMR (300 MHz, MeOD-d4): 7.82 (s, 1H), 7.54-7.45 (m, 2H), 7.49 (s, 1H), 6.98-6.87 (m, 1H), 4.16 (s, 3H), 3.87 (s, 3H), 2.72 (s, 3H), 2.33 (s, 3H), 2.15 (s, 3H). ESI-MS calculated for $C_{25}H_{23}FN_7O_2$[M+H]$^+$=472.19, Observed: 472.33.

Example 83

Synthesis of 3-(tert-Butyl)-N-(7-(3,5-dimethylisoxazol-4-yl)-6-methoxy-2-methyl-9H-pyrimido[4,5-b]indol-4-yl)isothiazol-5-amine (Cpd. No. 133)

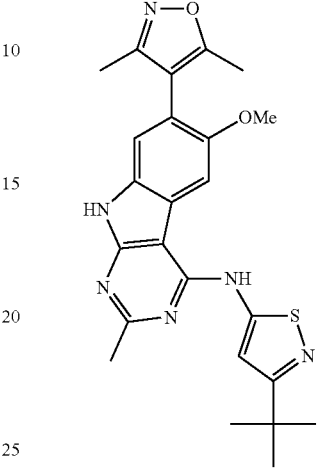

3-Tert-butylisothiazol-5-amine (90 mg, 0.6 mol) and S13 (102 mg, 0.3 mmol) were mixed in anhydrous isopropanol (5 mL). Concentrated HCl (5 drops) was added via a glass pipette. The reaction was heated at reflux for overnight. The reaction was diluted with methanol and filter through a pad of Celite®. The solution was concentrated and subsequently purified on a reverse phase HPLC. The desired product Cpd. No. 133 was isolated in 22 mg as a salt of trifluoroacetic acid. $^1$H NMR (300 MHz, MeOD-d4): 8.26 (s, 1H), 7.40 (s, 1H), 7.31 (s, 1H), 3.98 (s, 3H), 2.81 (s, 3H), 2.34 (s, 3H), 2.17 (s, 3H), 1.47 (s, 3H). ESI-MS calculated for $C_{24}H_{27}N_6O_2S$ [M+H]$^+$=463.19, Observed: 463.42.

Example 84

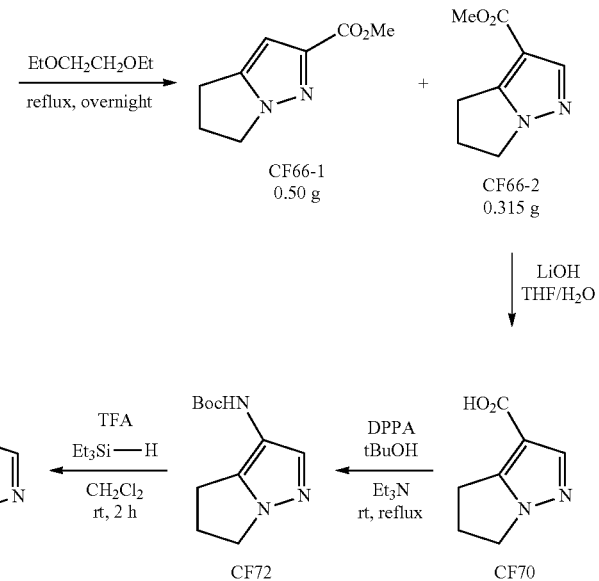

Step 1: Synthesis of methyl 5,6-dihydro-4H-pyrrolo[1,2-b]pyrazole-3-carboxylate (CF66-2)

3a,4,5,6-Tetrahydro-3-oxo-3H-pyrrolo[1,2-c][1,2,3]oxadiazol-7-ium ylide was prepared according to literature procedures (Organic Process Research & Development 2006, 10, 712-716). 3a,4,5,6-Tetrahydro-3-oxo-3H-pyrrolo[1,2-c][1,2,3]oxadiazol-7-ium ylide (21.6 mmol) was dissolved in 1,2-diethoxyethane (40 mL). The solution was heated at 120° C. Methyl propiolate (1.68 g, 20 mmol) was added via a syringe and the mixture was held at reflux overnight. The reaction mixture was concentrated on a rotary evaporator and the remaining residues were purified by flash column chromatography. CF66-2 was isolated in 315 mg and CF66-1 was isolated in 500 mg. $^1$H NMR (300 MHz, CDCl$_3$): 7.80 (s, 1H), 4.07 (t, J=7.32 Hz, 2H), 3.71 (s, 3H), 2.99 (t, J=7.34 Hz, 2H), 2.66-2.50 (m, 2H). $^{13}$C NMR (75 MHz, CDCl$_3$): 163.84, 149.91, 145.21, 107.69, 51.12, 48.20, 25.96, 23.84. ESI-MS calculated for $C_8H_{11}N_2O_2$ [M+H]$^+$=167.08, Observed: 167.25.

Step 2: Synthesis of 5,6-dihydro-4H-pyrrolo[1,2-b]pyrazole-3-carboxylic acid (CF70)

CF66-2 (315 mg) was dissolved in THF (5 mL). Water (5 mL) and LiOH—H$_2$O (2 g) were added subsequently and the solution was stirred at ambient temperature for overnight. The aqueous was extracted with diethyl ether and subsequently acidified with 1 N HCl. The aqueous layer was extracted with ethyl acetate. The organic layers were combined, dried, and concentrated on a rotary evaporator. The remaining residue containing CF70 (280 mg) was used without further purification. $^1$H NMR (300 MHz, MeOD-d4): 7.83 (s, 1H), 4.14 (t, J=7.30 Hz, 2H), 3.07 (t, J=7.38 Hz, 2H), 2.74-2.60 (m, 4H). $^{13}$C NMR (75 MHz, MeOD-d4): 164.99, 150.21, 144.61, 107.63, 47.51, 25.24, 23.08. ESI-MS calculated for $C_7H_9N_2O_2$[M+H]$^+$=153.07, Observed: 153.08.

Step 3: Synthesis of tert-butyl (5,6-dihydro-4H-pyrrolo[1,2-b]pyrazol-3-yl)carbamate (CF72)

CF70 (280 mg, 1.84 mmol) was mixed with tert-butanol (6 mL) and triethyl amine (0.8 mL, 4 mmol). Diphenyl phosphoryl azide (0.71 mL, 3.31 mmol) was added via a syringe and the mixture was stirred at ambient temperature for overnight. The solution was heated at reflux for 24 h. The volatile components were removed on a rotary evaporator and the residue was purified by flash column chromatography. CF72 was isolated in 224 mg. $^1$H NMR (300 MHz, CDCl$_3$): 7.36 (s, 1H), 6.24 (s, 1H), 4.05 (t, J=7.31 Hz, 2H), 2.98-2.82 (m, 2H), 2.60-2.44 (m, 4H), 1.46 (s, 9H). $^{13}$C NMR (75 MHz, CDCl$_3$): 153.76, 137.82, 137.01, 114.08, 80.10, 48.23, 28.48, 26.26, 23.63. ESI-MS calculated for $C_{11}H_{18}N_3O_2$ [M+H]$^+$=224.14, Observed: 224.58.

Step 4: Synthesis of 5,6-dihydro-4H-pyrrolo[1,2-b]pyrazol-3-amine

CF72 (224 mg, 1.0 mmol) was dissolved in CH$_2$Cl$_2$ (4 mL). Triethylsilane (0.05 mL) and trifluoroacetic acid (6 mL) was added via syringes. The reaction was stirred at ambient temperature for 2 h before concentrated on a rotary evaporator. The remaining residue containing 5,6-dihydro-4H-pyrrolo[1,2-b]pyrazol-3-amine was used for the next step without further purification. ESI-MS calculated for $C_6H_{10}N_3$ [M+H]$^+$=124.09, Observed: 124.42.

Synthesis of N-(5,6-Dihydro-4H-pyrrolo[1,2-b]pyrazol-3-yl)-7-(3,5-dimethylisoxazol-4-yl)-6-methoxy-2-methyl-9H-pyrimido[4,5-b]indol-4-amine (Cpd. No. 134)

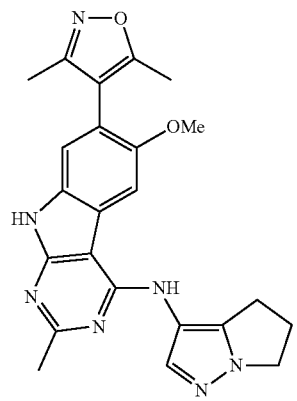 [SMILES: COc1cc2c(cc1-c1c(C)noc1C)[nH]c1nc(C)nc(Nc3cnn4c3CCC4)c12]

5,6-Dihydro-4H-pyrrolo[1,2-b]pyrazol-3-amine prepared for previous step 4 and S13 (342 mg, 1.0 mmol) were mixed in anhydrous isopropanol (10 mL). Concentrated HCl (6 drops) was added via a glass pipette. The reaction was heated at reflux for overnight. The reaction was diluted with methanol and filter through a pad of Celite®. The solution was concentrated and subsequently purified on a reverse phase HPLC. The desired product Cpd. No. 134 was isolated in 175 mg as a salt of trifluoroacetic acid. $^1$H NMR (300 MHz, MeOD-d4): 8.00 (s, 1H), 7.60 (s, 1H), 7.32 (s, 1H), 4.14 (t, J=7.26 Hz, 2H), 3.87 (s, 3H), 2.87 (t, J=7.20 Hz, 2H), 2.60-2.50 (m, 2H), 2.54)s, 3H), 2.28 (s, 3H), 2.08 (s, 3H). ESI-MS calculated for $G_3H_{24}N_7O_2$ [M+H]$^+$=430.20, Observed: 430.42.

Example 85

Synthesis of N-(1-Cyclopentyl-4-methyl-1H-pyrazol-5-yl)-7-(3,5-dimethylisoxazol-4-yl)-6-methoxy-2-methyl-9H-pyrimido[4,5-b]indol-4-amine (Cpd. No. 135)

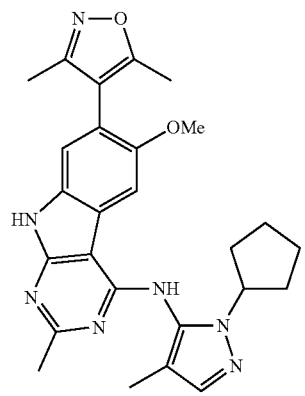 [SMILES: COc1cc2c(cc1-c1c(C)noc1C)[nH]c1nc(C)nc(Nc3c(C)cnn3C3CCCC3)c12]

Pd$_2$(dba)$_3$ (27 mg, 0.03 mmol) and BINAP (37 mg, 0.06 mmol) were mixed in anhydrous toluene (5 mL). The mixture was heated at reflux for 3-4 minutes. This clear, orange-red color solution was transferred into a round-bottom flask containing S13 (102 mg, 0.3 mmol), 1-cyclopentyl-4-methyl-1H-pyrazol-5-amine (100 mg, 0.6 mmol), tBuONa (120 mg, 1.2 mmol), and anhydrous toluene (5 mL). The mixture was heated at reflux for overnight before quenching with methanol. The reaction mixture was concentrated, filtered, and purified by HPLC to yield Cpd. No. 135 in 26 mg as a CF$_3$CO$_2$H salt. $^1$H NMR (300 MHz, MeOD-D4): 7.53 (s, 1H), 7.45 (s, 1H), 4.80-4.70 (m, 1H), 3.83 (s, 3H), 2.70 (s, 3H), 2.31 (s, 3H), 2.14 (s, 3H), 2.10-2.00 (m, 4H), 2.00-1.80 (m, 2H), 1.93 (s, 3H), 1.70-1.50 (m, 2H). ESI-MS calculated for G$_6$H$_{30}$N$_7$O$_2$ [M+H]$^+$=472.25; Observed: 472.58.

Example 86

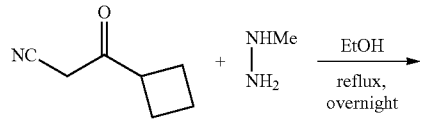

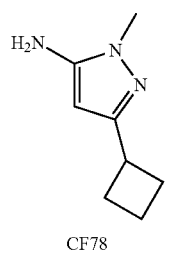

CF78

Synthesis of 3-Cyclobutyl-1-methyl-1H-pyrazol-5-amine (CF78)

3-Cyclobutyl-3-oxopropanenitrile (1.0 g, 8.1 mmol) and methyl hydrazine (0.90 mL, 17 mmol) were dissolved in ethanol, and the mixture was heated at reflux for overnight. The reaction mixture was cooled to room temperature and ethanol was removed on a rotary evaporator. Water was added and the aqueous layer was extracted with ethyl acetate. The combined organic layers were washed with brine, dried over anhydrous sodium sulfate, and concentrated on a rotary evaporator. The remaining residue was purified by flash column chromatography to yield CF78 in 0.986 g. $^1$H NMR (300 MHz, CDCl$_3$): 5.42 (s, 1H), 3.59 (s, 3H), 3.60-3.40 (br, 2H, NH), 3.50-3.30 (m, 1H), 2.34-2.20 (m, 2H), 2.20-2.04 (m, 2H), 2.041-1.90 (m, 1H), 1.90-1.74 (m, 1H). ESI-MS calculated for C$_8$H$_{14}$N$_3$[M+H]$^+$=152.12; Observed: 152.25.

Synthesis of N-(3-Cyclobutyl-1-methyl-1H-pyrazol-5-yl)-7-(3,5-dimethylisoxazol-4-yl)-6-methoxy-2-methyl-9H-pyrimido[4,5-b]indol-4-amine (Cpd. No. 136)

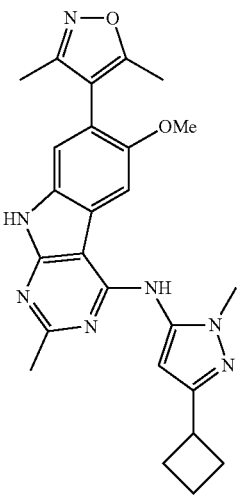

Pd$_2$(dba)$_3$ (27 mg, 0.03 mmol) and BINAP (37 mg, 0.06 mmol) were mixed in anhydrous toluene (5 mL). The mixture was heated at reflux for 3-4 minutes. This clear, orange-red color solution was transferred into a round-bottom flask containing S13 (102 mg, 0.3 mmol), 1-methyl-3-cyclobutyl-1H-pyrazol-5-amine (90 mg, 0.6 mmol), K$_3$PO$_4$ (212 mg, 1.0 mmol), and anhydrous toluene (5 mL). The mixture was heated at reflux for overnight before quenching with methanol. The reaction mixture was filtered through a pad of Celite® and the organic layer was collected, concentrated, and purified by HPLC to yield Cpd. No. 136 as a CF$_3$CO$_2$H salt in 49 mg. $^1$H NMR (300 MHz, MeOD-D4): 7.45 (s, 1H), 7.34 (s, 1H), 6.31 (s, 1H), 3.85 (s, 3H), 3.78 (s, 3H), 3.65-3.50 (m, 1H), 2.71 (s, 3H), 2.50-2.30 (m, 2H), 2.31 (s, 3H), 2.30-2.15 (m, 2H), 2.15-2.00 (m, 1H), 2.14 (s, 3H), 2.00-1.80 (m, 1H). ESI-MS calculated for C$_{25}$H$_{28}$N$_7$O$_2$ [M+H]$^+$=458.23; Observed: 458.50.

Example 87

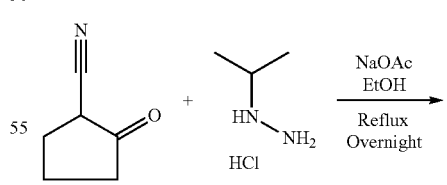

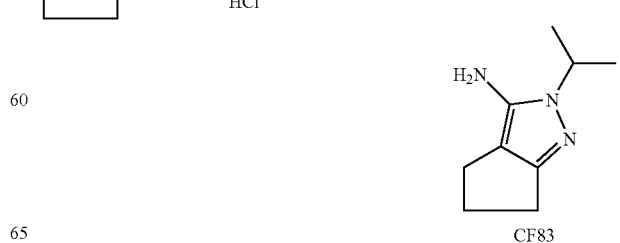

CF83

Synthesis of 2-Isopropyl-2,4,5,6-tetrahydrocyclopenta[c]pyrazol-3-amine (CF83)

2-Oxocyclopentanecarbonitrile (2.0 g, 18.3 mmol), sodium acetate (3.04 g, 37 mmol), and isopropyl hydrazine-HCl (2.5 g, 22 mmol) were mixed in ethanol, and the mixture was heated at reflux for overnight. The reaction mixture was cooled to room temperature and ethanol was removed on a rotary evaporator. Water was added and the aqueous layer was extracted with ethyl acetate. The combined organic layers were washed with brine, dried over anhydrous sodium sulfate, and concentrated on a rotary evaporator. The remaining residue was purified by flash column chromatography to yield CF83 in 2.60 g. $^1$H NMR (300 MHz, CDCl$_3$): 4.21 (septet, J=6.63 Hz, 1H), 2.60 (t, J=7.26 Hz, 2H), 2.40-2.38 (m, 2H), 2.38-2.20 (m, 2H), 1.39 (d, J=6.67 Hz, 6H). $^{13}$C NMR (75 MHz, CDCl$_3$): 159.89, 137.22, 109.30, 48.44, 30.01, 25.24, 22.59, 22.41. ESI-MS calculated for $C_9H_{16}N_3$[M+H]$^+$=166.13; Observed: 166.25.

Synthesis of 7-(3,5-Dimethylisoxazol-4-yl)-N-(2-isopropyl-2,4,5,6-tetrahydrocyclopenta[c]pyrazol-3-yl)-6-methoxy-2-methyl-9H-pyrimido[4,5-b]indol-4-amine (Cpd. No. 137)

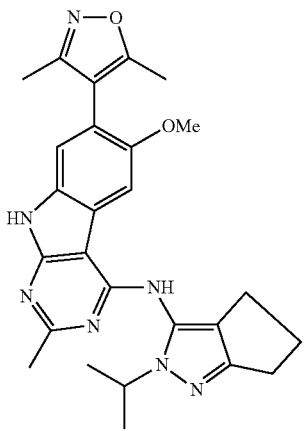 [SMILES: COc1cc2c(cc1-c1c(C)noc1C)[nH]c1nc(C)nc(Nc3c4c(nn3C(C)C)CCC4)c12]

Cpd. No. 137 was prepared from S13 (102 mg) and 2-isopropyl-2,4,5,6-tetrahydrocyclopenta[c]pyrazol-3-amine (107 mg) following the same procedure for preparation of Cpd. No. 135. Cpd. No. 137 was obtained in 27 mg as a salt of CF$_3$CO$_2$H. $^1$H NMR (300 MHz, MeOD-D4): 7.44 (s, 1H), 6.88 (s, 1H), 4.70-4.55 (m, 1H), 3.79 (s, 3H), 2.80-2.60 (m, 2H), 2.72 (s, 3H), 2.44-2.30 (m, 4H), 2.31 (s, 3H), 2.13 (s, 3H), 1.50 (d, J=6.65 Hz, 6H). ESI-MS calculated for $C_{26}H_{30}N_7O_2$ [M+H]$^+$=472.25; Observed: 472.83.

Example 88

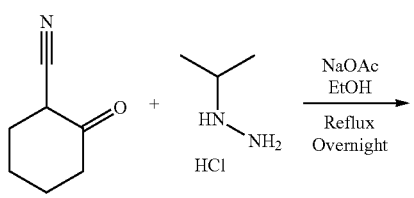

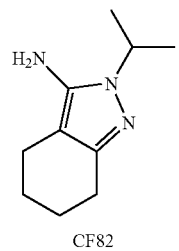

Synthesis of 2-Isopropyl-4,5,6,7-tetrahydro-2H-indazol-3-amine (CF82)

2-Oxocyclohexanecarbonitrile (2.0 g, 16.2 mmol), sodium acetate (2.7 g, 33 mmol), and isopropyl hydrazine-HCl (2.13 g, 19.4 mmol) were mixed in ethanol, and the mixture was heated at reflux for overnight. The reaction mixture was cooled to room temperature and ethanol was removed on a rotary evaporator. Water was added and the aqueous layer was extracted with ethyl acetate. The combined organic layers were washed with brine, dried over anhydrous sodium sulfate, and concentrated on a rotary evaporator. The remaining residue was purified by flash column chromatography to yield CF82 in 2.47 g. $^1$H NMR (300 MHz, CDCl$_3$): 4.32 (septet, J=6.69 Hz, 1H), 2.60 (t, J=5.80 Hz, 2H), 2.31 (t, J=5.59 Hz, 2H), 1.80-1.66 (m, 4H), 1.44 (d, J=6.69 Hz, 6H). ESI-MS calculated for $C_{10}H_{18}N_3$ [M+H]$^+$=180.15; Observed: 180.25.

Synthesis of 7-(3,5-Dimethylisoxazol-4-yl)-N-(2-isopropyl-4,5,6,7-tetrahydro-2H-indazol-3-yl)-6-methoxy-2-methyl-9H-pyrimido[4,5-b]indol-4-amine (Cpd. No. 138)

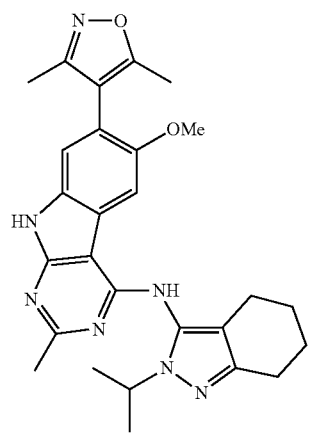 [SMILES: COc1cc2c(cc1-c1c(C)noc1C)[nH]c1nc(C)nc(Nc3c4c(nn3C(C)C)CCCC4)c12]

Cpd. No. 138 was prepared from S13 (102 mg) and 2-isopropyl-4,5,6,7-tetrahydro-2H-indazol-3-amine (115 mg) following the same procedure for preparation of Cpd. No. 135. Cpd. No. 138 was obtained in 42 mg as a salt of CF$_3$CO$_2$H. $^1$H NMR (300 MHz, MeOD-D4): 7.44 (s, 1H), 6.78 (s, 1H), 4.78-4.62 (m, 1H), 3.78 (s, 3H), 2.75-2.65 (m, 2H), 2.72 (s, 3H), 2.30 (s, 3H), 2.24-2.15 (m, 2H), 2.12 (s, 3H), 1.85-1.72 (m, 2H), 1.72-1.60 (m, 2H), 1.49 (d, J=6.65 Hz, 6H). ESI-MS calculated for $C_{27}H_{32}N_7O_2$ [M+H]$^+$=486.26; Observed: 486.42.

Example 89

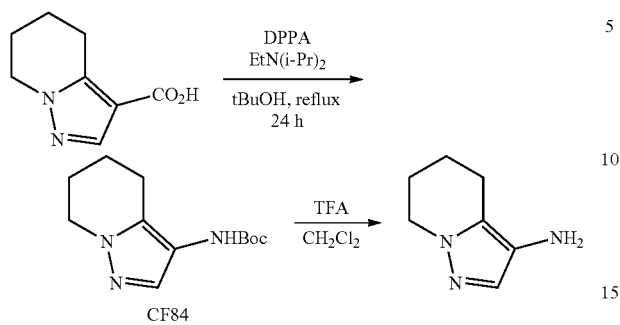

Synthesis of tert-Butyl (4,5,6,7-tetrahydropyrazolo[1,5-a]pyridin-3-yl)carbamate (CF84)

4,5,6,7-Tetrahydropyrazolo[1,5-a]pyridine-3-carboxylic acid (1.0 g, 6.0 mmol) and EtN(i-Pr)$_2$ (3 mL, 18 mmol) were mixed in t-BuOH (20 mL) at room temperature. Diphenyl phosphoryl azide (DPPA, 2.33 mL, 10.8 mmol) was added via a syringe and the mixture was stirred at room temperature for overnight followed by heating at reflux for 24 hours. The mixture was concentrated on a rotary evaporator and the remaining residue was purified by flash column chromatography to yield CF84 in 0.72 g. $^1$H NMR (300 MHz, CDCl$_3$): 7.43 (s, 1H), 5.99 (s, 1H), 4.10-4.00 (m, 2H), 2.70-2.55 (m, 2H), 2.05-1.90 (m, 2H), 1.90-1.75 (m, 2H), 1.46 (s, 9H). $^{13}$C NMR (75 MHz, CDCl$_3$): 154.09, 133.87, 129.79, 120.51, 80.11, 48.12, 28.44, 23.35, 21.09, 20.06. ESI-MS calculated for $C_{12}H_{20}N_3O_2$ [M+H]$^+$=238.16; Observed: 238.42.

Synthesis of 7-(3,5-Dimethylisoxazol-4-yl)-6-methoxy-2-methyl-N-(4,5,6,7-tetrahydropyrazolo[1,5-a]pyridin-3-yl)-9H-pyrimido[4,5-b]indol-4-amine (Cpd. No. 139)

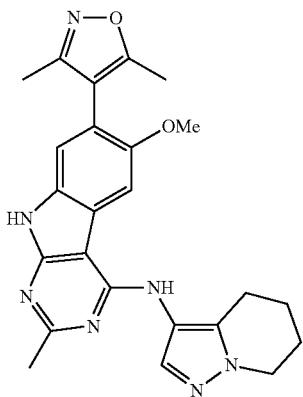 [SMILES: COc1cc2c(cc1-c1c(C)noc1C)[nH]c1nc(C)nc(Nc3cnn4c3CCCC4)c12]

Step 1: CF84 (100 mg) and TES-H (0.1 mL) were dissolved in dichloromethane (5 mL). TFA (5 mL) was added via a syringe and the mixture was stirred at ambient temperature for 1 hour. The volatile components were removed on a rotary evaporator and the remaining residue was used for the next step without further purification.

Step 2: 4,5,6,7-tetrahydropyrazolo[1,5-a]pyridin-3-amine obtained from step 1 and S13 (136 mg, 0.4 mmol) were mixed in anhydrous isopropanol (5 mL). Concentrated HCl (5 drops) was added via a glass pipette. The reaction was heated at reflux for overnight. The reaction was diluted with methanol and filter through a pad of Celite®. The solution was concentrated and subsequently purified on a reverse phase HPLC. The desired product Cpd. No. 139 was isolated in 90 mg as a salt of trifluoroacetic acid. $^1$H NMR (300 MHz, MeOD-D4): 8.00-7.50 (br, 1H), 7.67 (s, 1H), 7.45 (s, 1H), 4.20 (t, J=6.01 Hz, 2H), 3.89 (s, 3H), 2.78-2.68 (m, 2H), 2.68 (s, 3H), 2.31 (s, 3H), 2.18-2.05 (m, 2H), 2.14 (s, 3H), 1.98-1.85 (m, 2H). ESI-MS calculated for $C_{24}H_{26}N_7O_2$ [M+H]$^+$=444.21; Observed: 444.82.

Example 90

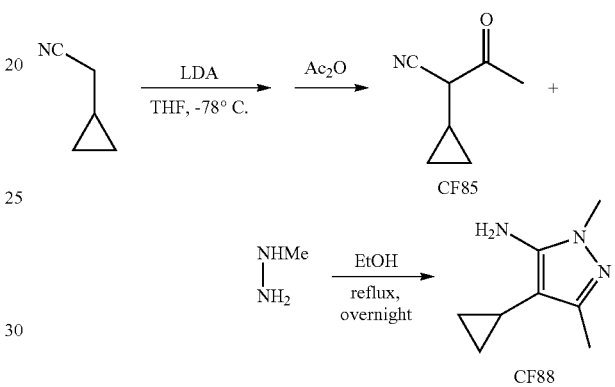

Synthesis of 2-Cyclopropyl-3-oxobutanenitrile (CF85)

Step 1: 2-Cyclopropylacetonitrile (4.86 g, 60 mmol) was dissolved in anhydrous THF (60 mL) and the solution was cooled to −78° C. LDA (96 mL, 1.0 M in THF, 96 mmol) was added via a syringe over 20 minutes and the mixture was stirred at −78° C. for 20 min. Acetic anhydride (2.83 mL, 30 mmol) was added dropwise via a syringe and the mixture was stirred at −78° C. for 20 minutes. The reaction was quenched with 1 N HCl and extracted with ethyl acetate. The combined organic layers were washed with brine, dried over anhydrous sodium sulfate, and concentrated on a rotary evaporator. The remaining residue was purified by flash column chromatography to yield CF85 in 0.98 g. $^1$H NMR (300 MHz, CDCl$_3$): 3.17 (d, J=7.63 Hz, 1H), 2.40 (s, 3H), 1.30-1.20 (m, 1H), 0.85-0.70 (m, 2H), 0.60-0.45 (m, 2H).

Synthesis of 4-Cyclopropyl-1,3-dimethyl-1H-pyrazol-5-amine (CF88)

Step 2: 2-Cyclopropyl-3-oxobutanenitrile (0.50 g, 4.1 mmol) and methyl hydrazine (0.42 mL, 8.2 mmol) were dissolved in ethanol, and the mixture was heated at reflux for overnight. The reaction mixture was cooled to room temperature and ethanol was removed on a rotary evaporator. Water was added and the aqueous layer was extracted with ethyl acetate. The combined organic layers were washed with brine, dried over anhydrous sodium sulfate, and concentrated on a rotary evaporator. The remaining residue was purified by flash column chromatography to yield CF88 in 0.47 g. $^1$H NMR (300 MHz, CDCl$_3$): 3.55 (s, 3H), 2.15 (s, 3H), 1.45-1.30 (m, 1H), 1.80-1.65 (m, 2H), 1.45-1.30 (m, 2H). ESI-MS calculated for $C_8H_{14}N_3[M+H]^+$=152.12; Observed: 152.42.

Synthesis of N-(4-Cyclopropyl-1,3-dimethyl-1H-pyrazol-5-yl)-7-(3,5-dimethylisoxazol-4-yl)-6-methoxy-2-methyl-9H-pyrimido[4,5-b]indol-4-amine (Cpd. No. 140)

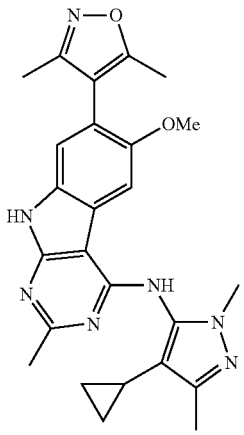

Cpd. No. 140 was prepared from S13 (102 mg) and 4-cyclopropyl-1,3-dimethyl-1H-pyrazol-5-amine (90 mg) following the same procedure for preparation of Cpd. No. 135. Cpd. No. 140 was obtained in 8 mg as a salt of $CF_3CO_2H$. $^1$H NMR (300 MHz, MeOD-D4): 7.46 (s, 1H), 7.30-7.00 (br, 1H), 3.84 (s, 3H), 3.76 (s, 3H), 2.72 (s, 3H), 2.32 (s, 3H), 2.29 (s, 3H), 2.14 (s, 3H), 1.40-1.20 (m, 1H), 0.70-0.50 (m, 2H), 0.50-0.30 (m, 2H). ESI-MS calculated for $C_{25}H_{28}N_7O_2$ [M+H]$^+$=458.23; Observed: 458.58.

Example 91

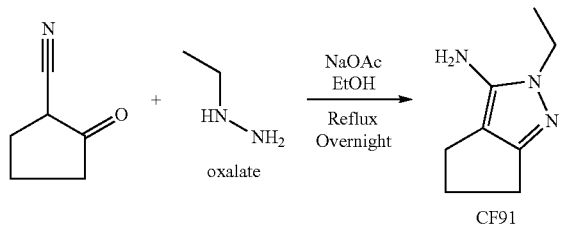

2-Ethyl-2,4,5,6-tetrahydrocyclopenta[c]pyrazol-3-amine (CF91)

2-Oxocyclopentanecarbonitrile (1.5 g, 14 mmol), sodium acetate (3.4 g, 42 mmol), and ethyl hydrazine-oxalate (4.2 g, 28 mmol) were mixed in ethanol, and the mixture was heated at reflux for overnight. The reaction mixture was cooled to room temperature and ethanol was removed on a rotary evaporator. Water was added and the aqueous layer was extracted with ethyl acetate. The combined organic layers were washed with brine, dried over anhydrous sodium sulfate, and concentrated on a rotary evaporator. The remaining residue was purified by flash column chromatography to yield CF91 in 1.03 g. $^1$H NMR (300 MHz, CDCl$_3$):

3.92 (q, J=7.23 Hz, 2H), 3.40-3.20 (m, 2H, NH), 2.62 (t, J=7.19 Hz, 2H), 2.54-2.44 (m, 2H), 2.40-2.28 (m, 2H), 1.38 (t, J=7.24 Hz, 3H). ESI-MS calculated for $C_8H_{14}N_3$ [M+H]$^+$=152.12; Observed: 152.33

Synthesis of 7-(3,5-Dimethylisoxazol-4-yl)-N-(2-ethyl-2,4,5,6-tetrahydrocyclopenta[c]pyrazol-3-yl)-6-methoxy-2-methyl-9H-pyrimido[4,5-b]indol-4-amine (Cpd. No. 141)

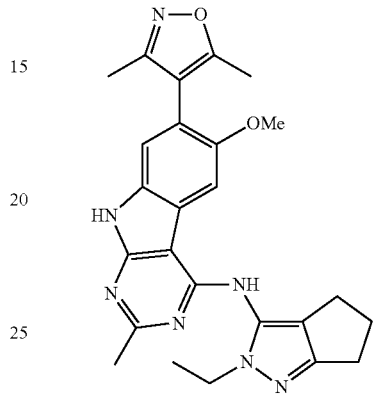

Cpd. No. 141 was prepared from S13 (102 mg) and 2-ethyl-2,4,5,6-tetrahydrocyclopenta[c]pyrazol-3-amine (90 mg) following the same procedure for preparation of Cpd. No. 135. Cpd. No. 141 was obtained in 39 mg as a salt of $CF_3CO_2H$. $^1$H NMR (300 MHz, MeOD-D4): 7.45 (s, 1H), 7.00 (s, 1H), 4.17 (q, J=7.16 Hz, 1H), 3.80 (s, 3H), 2.80-2.60 (m, 2H), 2.73 (s, 3H), 2.45-2.25 (m, 4H), 2.30 (s, 3H), 2.13 (s, 3H), 1.46 (t, J=7.19 Hz, 3H). ESI-MS calculated for $C_{25}H_{28}N_7O_2$ [M+H]$^+$=458.23; Observed: 458.75.

Example 92

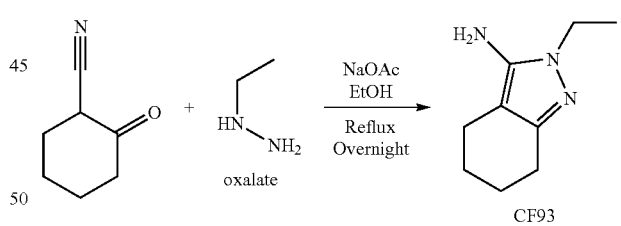

Synthesis of 2-Ethyl-4,5,6,7-tetrahydro-2H-indazol-3-amine (CF93)

2-Oxocyclohexanecarbonitrile (2.0 g, 16.2 mmol), sodium acetate (3.94 g, 48 mmol), and ethyl hydrazine-oxalate (4.8 g, 32 mmol) were mixed in ethanol, and the mixture was heated at reflux for overnight. The reaction mixture was cooled to room temperature and ethanol was removed on a rotary evaporator. Water was added and the aqueous layer was extracted with ethyl acetate. The combined organic layers were washed with brine, dried over anhydrous sodium sulfate, and concentrated on a rotary evaporator. The remaining residue was purified by flash column chromatography to yield CF93 in 3.94 g. $^1$H NMR (300 MHz, CDCl$_3$): 3.94 (q, J=7.26 Hz, 2H), 3.40-3.10 (m, 2H, NH), 2.58 (t, J=5.94 Hz, 2H), 2.31 (t, J=5.64 Hz, 2H), 1.80-1.60 (m, 4H), 1.39 (t, J=7.26 Hz, 3H). $^{13}$C NMR (75 MHz, CDCl$_3$): 147.94, 139.61, 100.67, 42.16, 23.80, 23.65, 23.57, 19.82, 15.27. ESI-MS calculated for C$_9$H$_{16}$N$_3$[M+H]$^+$=166.13; Observed: 166.33

Synthesis of 7-(3,5-Dimethylisoxazol-4-yl)-N-(2-ethyl-4,5,6,7-tetrahydro-2H-indazol-3-yl)-6-methoxy-2-methyl-9H-pyrimido[4,5-b]indol-4-amine (Cpd. No. 142)

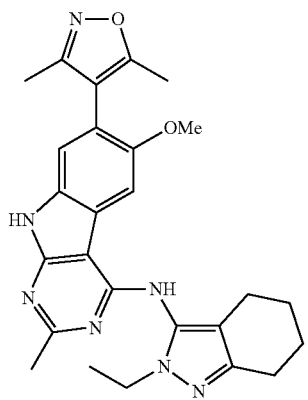 [SMILES: CCn1nc2c(c1Nc1nc(C)nc3[nH]c4cc(-c5c(C)noc5C)c(OC)cc4c13)CCCC2]

Cpd. No. 142 was prepared from S13 (102 mg) and 2-ethyl-4,5,6,7-tetrahydro-2H-indazol-3-amine (90 mg) following the same procedure for preparation of Cpd. No. 135. Cpd. No. 142 was obtained in 49 mg as a salt of CF$_3$CO$_2$H. $^1$H NMR (300 MHz, MeOD-D4): 7.44 (s, 1H), 6.90 (s, 1H), 4.17 (q, J=7.16 Hz, 2H), 3.80 (s, 3H), 2.80-2.60 (m, 2H), 2.72 (s, 3H), 2.30 (s, 3H), 2.25-2.15 (m, 2H), 2.13 (s, 3H), 1.90-1.70 (m, 2H), 1.70-1.50 (m, 2H), 1.45 (t, J=7.17 Hz, 3H). ESI-MS calculated for G$_6$H$_{30}$N$_7$O$_2$ [M+H]$^+$=472.25; Observed: 472.33.

Example 93

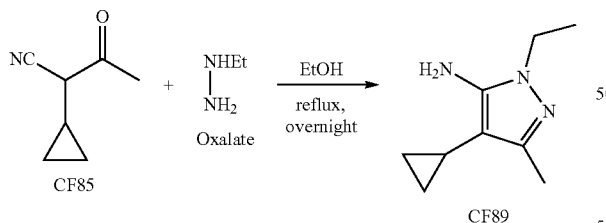

Synthesis of 4-Cyclopropyl-1-ethyl-3-methyl-1H-pyrazol-5-amine (CF89)

CF85 (0.50 g, 4.1 mmol), ethyl hydrazine-oxalate (1.35 g, 9 mmol), and sodium acetate (1 g, 12 mmol) were dissolved in ethanol, and the mixture was heated at reflux for overnight. The reaction mixture was cooled to room temperature and ethanol was removed on a rotary evaporator. Water was added and the aqueous layer was extracted with ethyl acetate. The combined organic layers were washed with brine, dried over anhydrous sodium sulfate, and concentrated on a rotary evaporator. The remaining residue was purified by flash column chromatography to yield CF89 in 171 mg. $^1$H NMR (300 MHz, CDCl$_3$): 3.88 (q, J=7.24 Hz, 2H), 3.60-3.40 (br, 2H, NH), 2.16 (s, 3H), 1.40-1.30 (m, 1H), 1.34 (t, J=7.22 Hz, 3H), 0.80-0.70 (m, 2H), 0.44-0.36 (m, 2H). ESI-MS calculated for C$_9$H$_{16}$N$_3$[M+H]$^+$=166.13; Observed: 166.17.

Synthesis of N-(4-Cyclopropyl-1-ethyl-3-methyl-1H-pyrazol-5-yl)-7-(3,5-dimethylisoxazol-4-yl)-6-methoxy-2-methyl-9H-pyrimido[4,5-b]indol-4-amine (Cpd. No. 143)

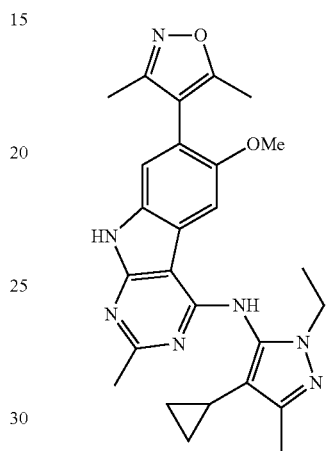

Cpd. No. 143 was prepared from S13 (170 mg) and 4-cyclopropyl-1-ethyl-3-methyl-1H-pyrazol-5-amine (170 mg) following the same procedure for preparation of Cpd. No. 135. Cpd. No. 143 was obtained in 76 mg as a salt of CF$_3$CO$_2$H. $^1$H NMR (300 MHz, MeOD-D4): 7.45 (s, 1H), 7.00-6.50 (br, 1H), 4.13 (q, J=7.15 Hz, 2H), 3.78 (s, 3H), 2.74 (s, 3H), 2.30 (s, 6H), 2.12 (s, 3H), 1.43 (t, J=7.19 Hz, 3H), 1.30-1.10 (m, 1H), 0.70-0.54 (m, 2H), 0.54-0.40 (m, 2H). ESI-MS calculated for G$_6$H$_{30}$N$_7$O$_2$ [M+H]$^+$=472.25; Observed: 472.33.

Example 94

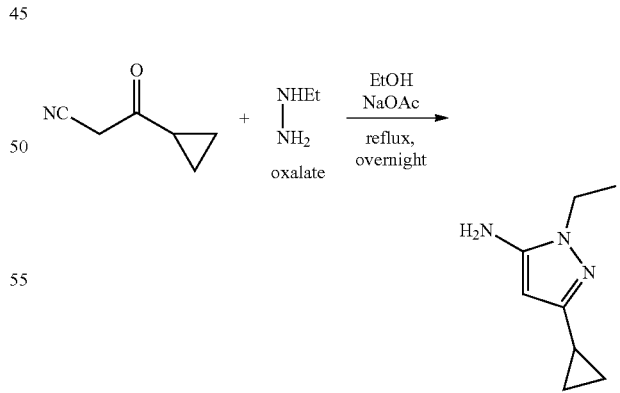

Synthesis of 3-Cyclopropyl-1-ethyl-1H-pyrazol-5-amine (CF96)

3-Cyclopropyl-3-oxopropanenitrile (2.0 g, 18.3 mmol), sodium acetate (5.4 g, 54 mmol), and ethyl hydrazine-oxalate (5.4 g, 36 mmol) were mixed in ethanol, and the mixture was heated at reflux for overnight. The reaction mixture was cooled to room temperature and ethanol was removed on a rotary evaporator. Water was added and the aqueous layer was extracted with ethyl acetate. The combined organic layers were washed with brine, dried over anhydrous sodium sulfate, and concentrated on a rotary evaporator. The remaining residue was purified by flash column chromatography to yield CF96 in 1.32 g. $^1$H NMR (300 MHz, CDCl$_3$): 5.17 (s, 1H), 3.91 (q, J=7.25 Hz, 2H), 3.50-3.30 (m, 2H, NH), 1.90-1.76 (m, 1H), 1.36 (t, J=7.20 Hz, 3H), 0.90-0.80 (m, 2H), 0.66-0.58 (m, 2H). ESI-MS calculated for C$_8$H$_{14}$N$_3$[M+H]$^+$=152.12; Observed: 152.17.

Synthesis of N-(3-Cyclopropyl-1-ethyl-1H-pyrazol-5-yl)-7-(3,5-dimethylisoxazol-4-yl)-6-methoxy-2-methyl-9H-pyrimido[4,5-b]indol-4-amine (Cpd. No. 144)

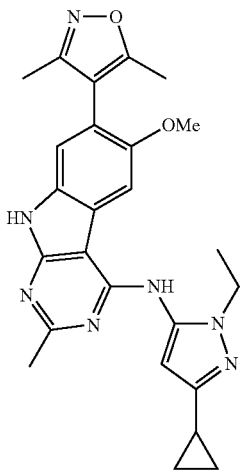 [SMILES: CCn1nc(C2CC2)cc1Nc1nc(C)nc2[nH]c3cc(-c4c(C)noc4C)c(OC)cc3c12]

Cpd. No. 144 was prepared from S13 (180 mg) and 3-cyclopropyl-1-ethyl-1H-pyrazol-5-amine (140 mg) following the similar procedure for preparation of Cpd. No. 135. Cpd. No. 144 was obtained in 83 mg as a salt of CF$_3$CO$_2$H. $^1$H NMR (300 MHz, MeOD-D4): 7.44 (s, 1H), 6.92 (s, 1H), 6.03 (s, 1H), 4.11 (q, J=7.20 Hz, 2H), 3.83 (s, 3H), 2.71 (s, 3H), 2.29 (s, 3H), 2.12 (s, 3H), 2.00-1.85 (m, 1H), 1.44 (t, J=7.20 Hz, 3H), 1.00-0.90 (m, 2H), 0.75-0.65 (m, 2H). ESI-MS calculated for C$_{25}$H$_{28}$N$_7$O$_2$ [M+H]$^+$=458.23; Observed: 458.33.

Example 95

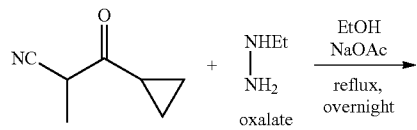

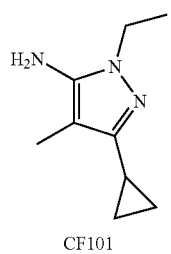

Synthesis of 3-Cyclopropyl-1-ethyl-4-methyl-1H-pyrazol-5-amine (CF101)

3-Cyclopropyl-2-methyl-3-oxopropanenitrile (2.0 g, 16 mmol), sodium acetate (2.62 g, 32 mmol), and ethyl hydrazine-oxalate (2.4 g, 16 mmol) were mixed in ethanol, and the mixture was heated at reflux for overnight. The reaction mixture was cooled to room temperature and ethanol was removed on a rotary evaporator. Water was added and the aqueous layer was extracted with ethyl acetate. The combined organic layers were washed with brine, dried over anhydrous sodium sulfate, and concentrated on a rotary evaporator. The remaining residue was purified by flash column chromatography to yield CF101 in 0.52 g. $^1$H NMR (300 MHz, CDCl$_3$): 3.93 (q, J=7.23 Hz, 2H), 3.60-3.00 (br, 2H, NH), 1.91 (s, 3H), 1.80-1.60 (m, 1H), 1.31 (t, J=7.24 Hz, 3H), 0.85-0.75 (m, 4H). ESI-MS calculated for CH$_{16}$N$_3$[M+H]$^+$=166.13; Observed: 166.33

Synthesis of N-(3-Cyclopropyl-1-ethyl-4-methyl-1H-pyrazol-5-yl)-7-(3,5-dimethylisoxazol-4-yl)-6-methoxy-2-methyl-9H-pyrimido[4,5-b]indol-4-amine (Cpd. No. 145)

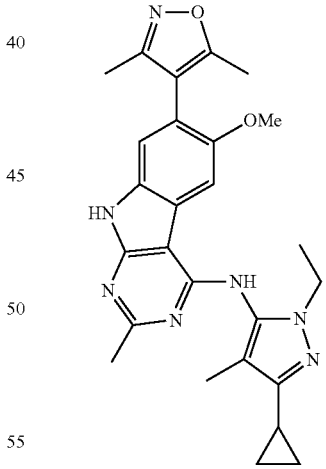

Cpd. No. 145 was prepared from S13 (202 mg) and 3-cyclopropyl-1-ethyl-4-methyl-1H-pyrazol-5-amine (132 mg) following the similar procedure for preparation of Cpd. No. 135. Cpd. No. 145 was obtained in 87 mg as a salt of CF$_3$CO$_2$H. $^1$H NMR (300 MHz, MeOD-D4): 7.45 (s, 1H), 7.20-6.80 (br, 1H), 4.09 (q, J=7.19 Hz, 2H), 3.82 (s, 3H), 2.72 (s, 3H), 2.31 (s, 3H), 2.13 (s, 3H), 1.90 (s, 3H), 2.00-1.80 (m, 1H), 1.38 (t, J=7.21 Hz, 3H), 1.00-0.80 (m, 4H). ESI-MS calculated for C$_{26}$H$_{30}$N$_7$O$_2$ [M+H]$^+$=472.25; Observed: 472.58.

Example 96

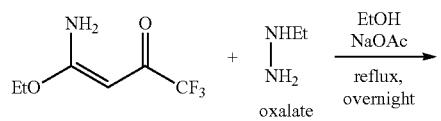

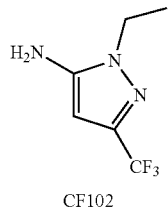

Synthesis of 1-Ethyl-3-(trifluoromethyl)-1H-pyrazol-5-amine (CF102)

(E)-4-Amino-4-ethoxy-1,1,1-trifluorobut-3-en-2-one (1.0 g, 5.5 mmol), sodium acetate (1.50 g, 18 mmol), and ethyl hydrazine-oxalate (1.7 g, 11 mmol) were mixed in ethanol, and the mixture was heated at reflux for overnight. The reaction mixture was cooled to room temperature and ethanol was removed on a rotary evaporator. Water was added and the aqueous layer was extracted with ethyl acetate. The combined organic layers were washed with brine, dried over anhydrous sodium sulfate, and concentrated on a rotary evaporator. The remaining residue was purified by flash column chromatography to yield CF102 in 0.51 g. $^1$H NMR (300 MHz, CDCl$_3$): 5.80 (s, 1H), 4.04 (q, J=7.42 Hz, 2H), 3.70-3.45 (br, 2H, NH), 1.42 (t, J=7.25 Hz, 3H). ESI-MS calculated for C$_6$H$_9$F$_3$N$_3$[M+H]$^+$=180.07; Observed: 180.33.

Synthesis of 7-(3,5-Dimethylisoxazol-4-yl)-N-(1-ethyl-3-(trifluoromethyl)-1H-pyrazol-5-yl)-6-methoxy-2-methyl-9H-pyrimido[4,5-b]indol-4-amine (Cpd. No. 146)

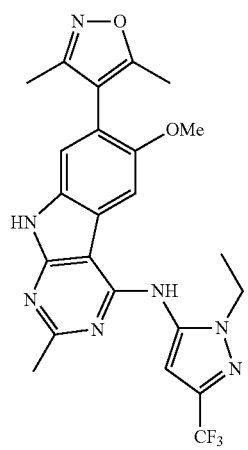 [SMILES: CCn1nc(C(F)(F)F)cc1Nc1nc(C)nc2[nH]c3cc(-c4c(C)noc4C)c(OC)cc3c12]

Cpd. No. 146 was prepared from S13 (136 mg) and 1-ethyl-3-(trifluoromethyl)-1H-pyrazol-5-amine (143 mg) following the similar procedure for preparation of Cpd. No. 135. Cpd. No. 146 was obtained in 26 mg as a salt of CF$_3$CO$_2$H. $^1$H NMR (300 MHz, MeOD-D4): 7.72 (s, 1H), 7.49 (s, 1H), 6.70 (s, 1H), 4.21 (q, J=7.17 Hz, 2H), 3.90 (s, 3H), 2.68 (s, 3H), 2.30 (s, 3H), 2.13 (s, 3H), 1.50 (t, J=7.20 Hz, 3H). ESI-MS calculated for C$_{23}$H$_{23}$F$_3$N$_7$O$_2$[M+H]$^+$=486.19; Observed: 486.33.

Example 97

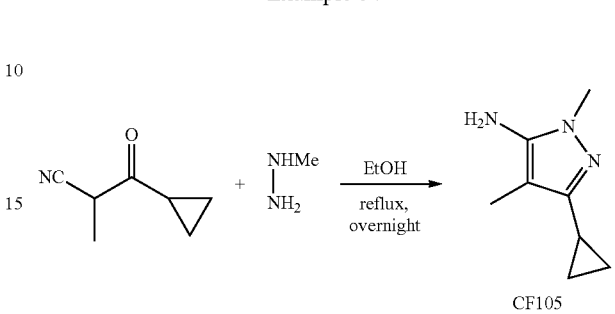

Synthesis of 3-Cyclopropyl-1,4-dimethyl-1H-pyrazol-5-amine (CF105)

3-Cyclopropyl-2-methyl-3-oxopropanenitrile (1.5 g, 12 mmol) and methyl hydrazine (1.26 mL, 24 mmol) were mixed in ethanol, and the mixture was heated at reflux for overnight. The reaction mixture was cooled to room temperature and ethanol was removed on a rotary evaporator. Water was added and the aqueous layer was extracted with ethyl acetate. The combined organic layers were washed with brine, dried over anhydrous sodium sulfate, and concentrated on a rotary evaporator. The remaining residue was purified by flash column chromatography to yield CF105 in 0.70 g. $^1$H NMR (300 MHz, CDCl$_3$): 3.58 (s, 3H), 3.40-3.10 (br, 2H, NH), 1.92 (s, 3H), 1.80-1.60 (m, 2H), 1.85-1.70 (m, 4H). ESI-MS calculated for C$_8$H$_{14}$N$_3$[M+H]$^+$=152.12; Observed: 152.25.

Synthesis of N-(3-Cyclopropyl-1,4-dimethyl-1H-pyrazol-5-yl)-7-(3,5-dimethylisoxazol-4-yl)-6-methoxy-2-methyl-9H-pyrimido[4,5-b]indol-4-amine (Cpd. No. 147)

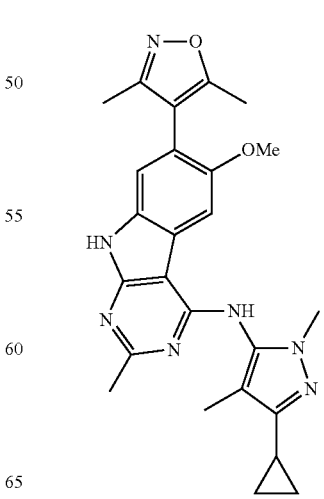

Cpd. No. 147 was prepared from S13 (136 mg) and 3-cyclopropyl-1,4-dimethyl-1H-pyrazol-5-amine (120 mg) following the similar procedure for preparation of Cpd. No. 135. Cpd. No. 147 was obtained in 16 mg as a salt of CF$_3$CO$_2$H. $^1$H NMR (300 MHz, MeOD-D4): 7.45 (s, 1H), 7.30-7.00 (br, 1H), 3.84 (s, 3H), 3.72 (s, 3H), 2.71 (s, 3H), 2.31 (s, 3H), 2.13 (s, 3H), 1.94 (s, 3H), 2.00-1.80 (m, 2H), 1.00-0.75 (m, 4H). ESI-MS calculated for C$_{25}$H$_{28}$N$_7$O$_2$ [M+H]$^+$=458.23; Observed: 458.50.

Example 98

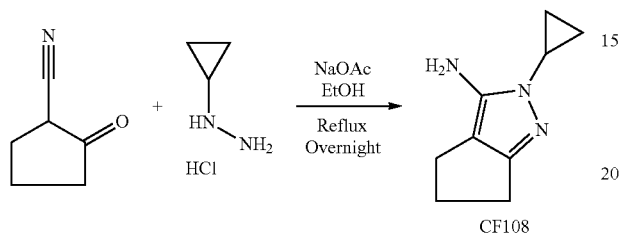

Synthesis of 2-Cyclopropyl-2,4,5,6-tetrahydrocyclopenta[c]pyrazol-3-amine (CF108)

2-Oxocyclopentanecarbonitrile (1.0 g, 9 mmol), sodium acetate (1.6 g, 20 mmol), and isopropyl hydrazine-HCl (1.0 g, 10 mmol) were mixed in ethanol, and the mixture was heated at reflux for overnight. The reaction mixture was cooled to room temperature and ethanol was removed on a rotary evaporator. Water was added and the aqueous layer was extracted with ethyl acetate. The combined organic layers were washed with brine, dried over anhydrous sodium sulfate, and concentrated on a rotary evaporator. The remaining residue was purified by flash column chromatography to yield CF108 in 0.56 g. $^1$H NMR (300 MHz, CDCl$_3$): 4.00-3.50 (br, 2H, NH), 3.20-3.00 (m, 1H), 2.70-2.50 (m, 2H), 2.50-2.35 (m, 2H), 2.35-2.20 (m, 2H), 1.20-0.90 (m, 4H). ESI-MS calculated for C$_9$H$_{14}$N$_3$[M+H]$^+$=164.12; Observed: 164.50

Synthesis of N-(2-Cyclopropyl-2,4,5,6-tetrahydrocyclopenta[c]pyrazol-3-yl)-7-(3,5-dimethylisoxazol-4-yl)-6-methoxy-2-methyl-9H-pyrimido[4,5-b]indol-4-amine (Cpd. No. 148)

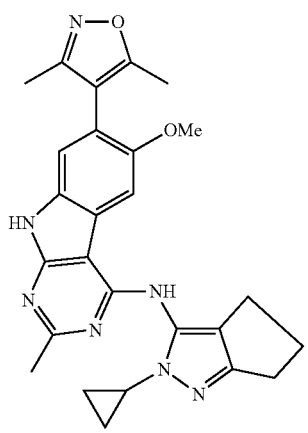 [SMILES: COc1cc2c(cc1-c1c(C)noc1C)[nH]c1nc(C)nc(Nc3c4c(nn3C3CC3)CCC4)c12]

Cpd. No. 148 was prepared from S13 (136 mg) and 2-cyclopropyl-2,4,5,6-tetrahydro-cyclopenta[c]pyrazol-3-amine (162 mg) following the similar procedure for preparation of Cpd. No. 135. Cpd. No. 148 was obtained in 84 mg as a salt of CF$_3$CO$_2$H. $^1$H NMR (300 MHz, MeOD-D4): 7.46 (s, 1H), 7.09 (s, 1H), 3.81 (s, 3H), 3.50-3.30 (m, 1H), 2.80-2.60 (m, 2H), 2.74 (s, 3H), 2.60-2.40 (m, 2H), 2.40-2.20 (m, 2H), 2.31 (s, 3H), 2.13 (s, 3H), 1.20-1.10 (m, 2H), 1.10-0.90 (m, 2H). ESI-MS calculated for C$_{26}$H$_{28}$N$_7$O$_2$ [M+H]$^+$=470.23; Observed: 470.50.

Example 99

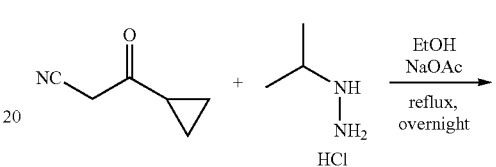

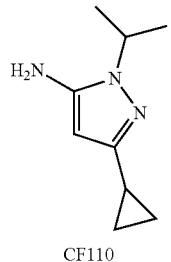

Synthesis of 3-Cyclopropyl-1-isopropyl-1H-pyrazol-5-amine (CF110)

3-Cyclopropyl-3-oxopropanenitrile (1.0 g, 9 mmol), sodium acetate (2.0 g, 20 mmol), and isopropyl hydrazine-HCl (1.6 g, 15 mmol) were mixed in ethanol, and the mixture was heated at reflux for overnight. The reaction mixture was cooled to room temperature and ethanol was removed on a rotary evaporator. Water was added and the aqueous layer was extracted with ethyl acetate. The combined organic layers were washed with brine, dried over anhydrous sodium sulfate, and concentrated on a rotary evaporator. The remaining residue was purified by flash column chromatography to yield CF110 in 1.27 g. $^1$H NMR (300 MHz, CDCl$_3$): 5.08 (s, 1H), 5.00-4.20 (br, 2H, NH), 4.35-4.10 (m, 1H), 1.94-1.80 (m, 1H), 1.42 (d, J=6.69 Hz, 6H), 0.90-0.80 (m, 2H), 0.62-0.52 (m, 2H). $^{13}$C NMR (75 MHz, CDCl$_3$): 154.07, 143.79, 86.80, 48.21, 22.05, 9.72, 7.99. ESI-MS calculated for C$_9$H$_{16}$N$_3$[M+H]$^+$=166.13; Observed: 166.17.

Synthesis of N-(3-Cyclopropyl-1-isopropyl-1H-pyrazol-5-yl)-7-(3,5-dimethylisoxazol-4-yl)-6-methoxy-2-methyl-9H-pyrimido[4,5-b]indol-4-amine (Cpd. No. 149)

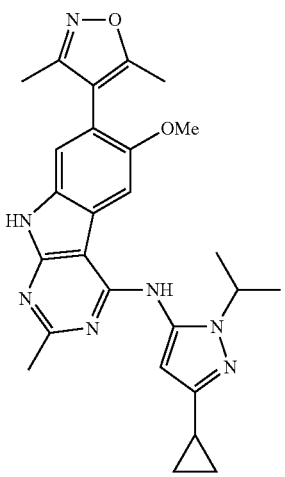 [SMILES: COc1cc2c(cc1-c1c(C)noc1C)[nH]c1nc(C)nc(Nc3cc(C4CC4)nn3C(C)C)c12]

Cpd. No. 149 was prepared from S13 (273 mg) and 3-cyclopropyl-1-isopropyl-1H-pyrazol-5-amine (320 mg) following the similar procedure for preparation of Cpd. No. 135. Cpd. No. 149 was obtained in 119 mg as a salt of $CF_3CO_2H$. $^1$H NMR (300 MHz, MeOD-D4): 7.43 (s, 1H), 6.86 (s, 1H), 5.95 (s, 1H), 4.70-4.50 (m, 1H), 3.82 (s, 3H), 2.71 (s, 3H), 2.30 (s, 3H), 2.13 (s, 3H), 2.10-1.90 (m, 1H), 1.47 (d, J=6.64 Hz, 6H), 1.10-0.90 (m, 2H), 0.80-0.60 (m, 2H). ESI-MS calculated for $C_{26}H_{30}N_7O_2$ [M+H]$^+$=472.25; Observed: 472.58

Example 100

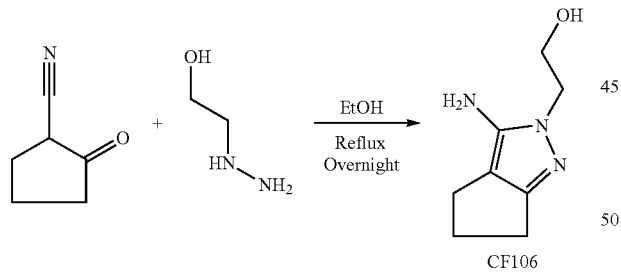

Synthesis of 2-(3-Amino-5,6-dihydrocyclopenta[c]pyrazol-2(4H)-yl)ethanol (CF106)

2-Oxocyclopentanecarbonitrile (1.0 g, 9 mmol) and 2-hydrazinylethanol (1.3 mL, 18 mmol) were mixed in ethanol, and the mixture was heated at reflux for overnight. The reaction mixture was cooled to room temperature and ethanol was removed on a rotary evaporator. Water was added and the aqueous layer was extracted with ethyl acetate. The combined organic layers were washed with brine, dried over anhydrous sodium sulfate, and concentrated on a rotary evaporator. The remaining residue was purified by flash column chromatography to yield CF106 in 0.347 g. $^1$H NMR (300 MHz, CDCl$_3$): 4.00-3.90 (m, 2H), 3.90-3.70 (m, 2H), 2.65-2.50 (m, 2H), 2.50-2.35 (m, 2H), 2.35-2.20 (m, 2H). ESI-MS calculated for $C_8H_{14}N_3O$ [M+H]$^+$=168.11; Observed: 168.33.

Synthesis of 2-(3-((7-(3,5-Dimethylisoxazol-4-yl)-6-methoxy-2-methyl-9H-pyrimido[4,5-b]indol-4-yl)amino)-5,6-dihydrocyclopenta[c]pyrazol-2(4H)-yl)ethanol (Cpd. No. 150)

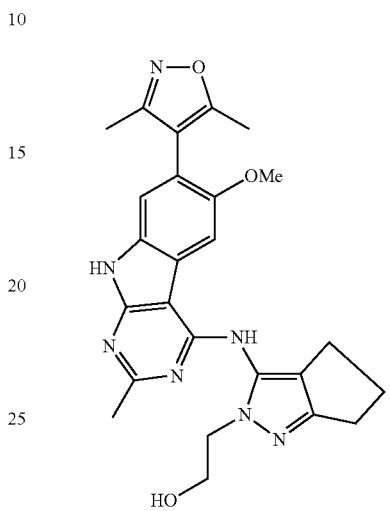

Cpd. No. 150 was prepared from S13 (136 mg) and 2-(3-amino-5,6-dihydrocyclopenta[c]pyrazol-2(4H)-yl)ethanol (120 g) following the similar procedure for preparation of Cpd. No. 135. Cpd. No. 150 was obtained in 106 mg as a salt of $CF_3CO_2H$. $^1$H NMR (300 MHz, MeOD-D4): 7.54 (s, 1H), 7.47 (s, 1H), 4.37 (t, J=4.53 Hz, 2H), 4.00 (t, J=4.51 Hz, 2H), 3.88 (s, 3H), 2.90-2.70 (m, 2H), 2.75 (s, 3H), 2.65-2.50 (m, 2H), 2.50-2.30 (m, 2H), 2.31 (s, 3H), 2.14 (s, 3H). ESI-MS calculated for $C_{25}H_{28}N_7O_3$ [M+H]$^+$=474.23; Observed: 474.92.

Example 101

Synthesis of 7-(3,5-Dimethylisoxazol-4-yl)-N-(2-(2-fluoroethyl)-2,4,5,6-tetrahydrocyclopenta[c]pyrazol-3-yl)-6-methoxy-2-methyl-9H-pyrimido[4,5-b]indol-4-amine (Cpd. No. 151)

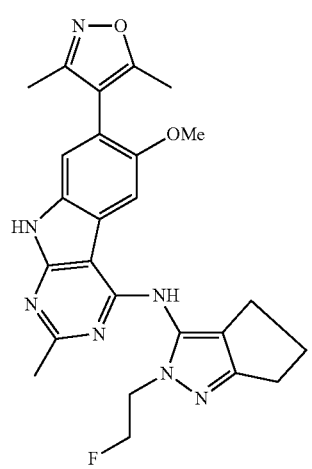 [SMILES: COc1cc2c(cc1-c1c(C)noc1C)[nH]c1nc(C)nc(Nc3c4c(nn3CCF)CCC4)c12]

Cpd. No. 150 (30 mg, 0.05 mmol) was mixed with anhydrous dichloromethane (4 mL) and the mixture was cooled to −78° C. for 10 minutes. A dichloromethane solution of DAST (40 mg, 0.25 mmol) was added via a syringe and the mixture was stirred at −78° C. for 20 minutes. The mixture was then warmed up to ambient temperature and stirred for 3 h before quenching with sodium bicarbonate saturated solution. Methanol was added and the mixture was concentrated on a rotary evaporator. The remaining residue was purified on reverse phase HPLC and Cpd. No. 151 was obtained in 21 mg as a salt of $CF_3CO_2H$. $^1$H NMR (300 MHz, MeOD-D4): 7.44 (s, 1H), 7.13 (s, 1H), 4.73 (t, J=4.65 Hz, 1H), 4.49 (t, J=4.64 Hz, 1H), 4.40 (t, J=4.54, 1H), 3.82 (s, 3H), 2.80-2.60 (m, 2H), 2.72 (s, 3H), 2.45-2.25 (m, 4H), 2.31 (s, 3H), 2.14 (s, 3H). ESI-MS calculated for $C_{25}H_{27}FN_7O_2[M+H]^+$=476.22; Observed: 476.58.

Example 102

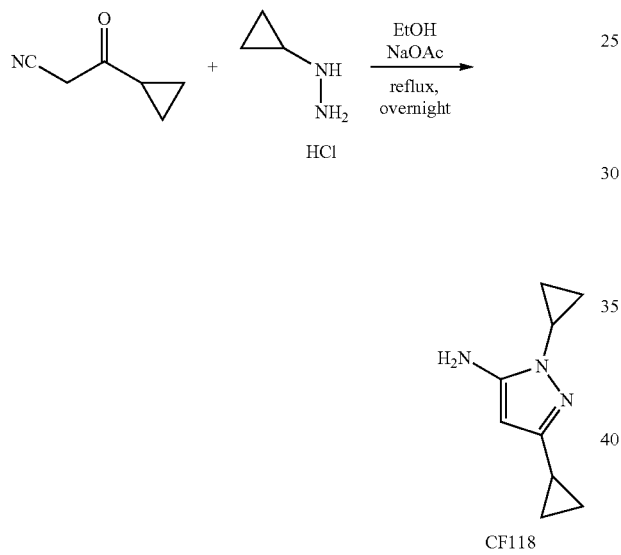

Synthesis of 1,3-Dicyclopropyl-1H-pyrazol-5-amine (CF118)

3-Cyclopropyl-3-oxopropanenitrile (1.0 g, 9 mmol), sodium acetate (1.6 g, 20 mmol), and cyclopropyl hydrazine-HCl (1.0 g, 9.2 mmol) were mixed in ethanol, and the mixture was heated at reflux for overnight. The reaction mixture was cooled to room temperature and ethanol was removed on a rotary evaporator. Water was added and the aqueous layer was extracted with ethyl acetate. The combined organic layers were washed with brine, dried over anhydrous sodium sulfate, and concentrated on a rotary evaporator. The remaining residue was purified by flash column chromatography to yield CF118 in 0.88 g. $^1$H NMR (300 MHz, CDCl$_3$): 5.05 (s, 1H), 3.80-3.70 (br, 2H, NH), 3.12-3.00 (m, 1H), 1.88-1.76 (m, 1H), 1.16-1.06 (m, 2H), 1.06-0.94 (m, 2H), 0.88-0.80 (m, 2H), 0.66-0.56 (m, 2H). ESI-MS calculated for $C_9H_{14}N_3$ [M+H]$^+$=164.12; Observed: 164.17.

Synthesis of N-(1,3-Dicyclopropyl-1H-pyrazol-5-yl)-7-(3,5-dimethylisoxazol-4-yl)-6-methoxy-2-methyl-9H-pyrimido[4,5-b]indol-4-amine (Cpd. No. 152)

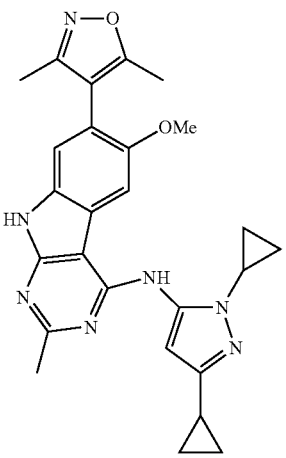 [SMILES: COc1cc2c(cc1-c1c(C)noc1C)[nH]c1nc(C)nc(Nc3cc(C4CC4)nn3C3CC3)c12]

Cpd. No. 152 was prepared from S13 (136 mg) and 1,3-dicyclopropyl-1H-pyrazol-5-amine (130 mg) following the similar procedure for preparation of Cpd. No. 135. Cpd. No. 152 was obtained in 140 mg as a salt of $CF_3CO_2H$. $^1$H NMR (300 MHz, MeOD-D4): 7.44 (s, 1H), 7.08 (s, 1H), 6.10 (s, 1H), 3.83 (s, 3H), 3.40-3.20 (m, 1H), 2.73 (s, 3H), 2.31 (s, 3H), 2.14 (s, 3H), 2.05-1.85 (m, 1H), 1.20-1.00 (m, 2H), 1.00-0.80 (m, 4H), 0.80-0.60 (m, 2H). ESI-MS calculated for $C_{26}H_{28}N_7O_2$ [M+H]$^+$=470.23; Observed: 470.58.

Example 103

Synthesis of N-(3-Cyclopropyl-1H-pyrazol-5-yl)-7-(3,5-dimethylisoxazol-4-yl)-6-methoxy-2-methyl-9H-pyrimido[4,5-b]indol-4-amine (Cpd. No. 153)

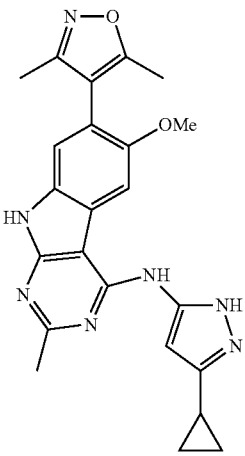 [SMILES: COc1cc2c(cc1-c1c(C)noc1C)[nH]c1nc(C)nc(Nc3cc(C4CC4)n[nH]3)c12]

Cpd. No. 153 was prepared from S13 (170 mg) and 3-cyclopropyl-1H-pyrazol-5-amine (162 mg) following the similar procedure for preparation of Cpd. No. 135. Cpd. No. 153 was obtained in 37.5 mg as a salt of $CF_3CO_2H$. $^1$H NMR (300 MHz, MeOD-D4): 8.21 (s, 1H), 7.45 (s, 1H), 6.12 (s, 1H), 3.97 (s, 3H), 2.81 (s, 3H), 2.33 (s, 3H), 2.16 (s, 3H), 2.10-1.95 (m, 1H), 1.80-1.00 (m, 2H), 0.90-0.70 (m, 2H). ESI-MS calculated for $C_{23}H_{24}N_7O_2$ $[M+H]^+$=430.20; Observed: 430.42.

Example 104

Synthesis of 1-(3-Cyclopropyl-5-((7-(3,5-dimethylisoxazol-4-yl)-6-methoxy-2-methyl-9H-pyrimido[4,5-b]indol-4-yl)amino)-1H-pyrazol-1-yl)ethanone (Cpd. No. 154)

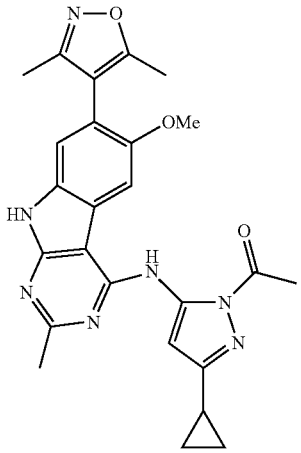 [SMILES: COc1cc2c(cc1-c1c(C)noc1C)[nH]c1nc(C)nc(Nc3cc(C4CC4)nn3C(C)=O)c12]

Cpd. No. 153 (20 mg) and NaHCO$_3$ (200 mg) were mixed with anhydrous THF (4 mL). Acetic chloride (0.2 mL) was added via a syringe and the mixture was stirred at ambient temperature for overnight. The reaction mixture was concentrated on a rotary evaporator and the remaining residue was purified by reverse phase HPLC. Cpd. No. 154 was obtained in 3 mg as a salt of CF$_3$CO$_2$H. ESI-MS calculated for $C_{25}H_{26}N_7O_3$ $[M+H]^+$=472.21; Observed: 472.33.

Example 105

Synthesis of Ethyl 3-cyclopropyl-5-((7-(3,5-dimethylisoxazol-4-yl)-6-methoxy-2-methyl-9H-pyrimido[4,5-b]indol-4-yl)amino)-1H-pyrazole-1-carboxylate (Cpd. No. 155)

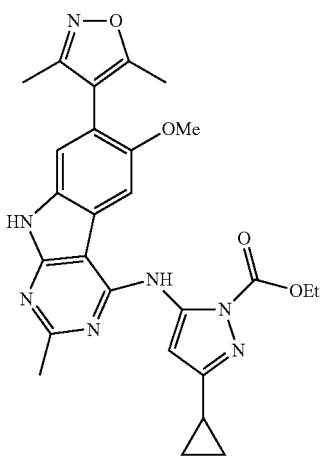 [SMILES: CCOC(=O)n1nc(C2CC2)cc1Nc1nc(C)nc2[nH]c3cc(-c4c(C)noc4C)c(OC)cc3c12]

Cpd. No. 153 (20 mg, 0.037 mmol) and NaHCO$_3$ (500 mg, excess) were mixed with anhydrous THF (5 mL). Ethyl chloroformate (0.2 mL, 2 mmol) was added via a syringe and the mixture was stirred at ambient temperature for overnight. The reaction mixture was concentrated on a rotary evaporator and the remaining residue was purified by reverse phase HPLC. Cpd. No. 155 was obtained in 10 mg as a salt of CF$_3$CO$_2$H. ESI-MS calculated for $C_{26}H_{28}N_7O_4$ $[M+H]^+$=502.22; Observed: 502.67.

Example 106

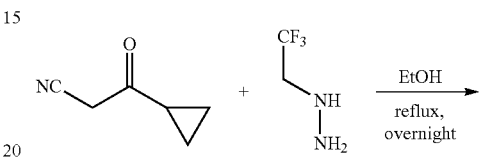

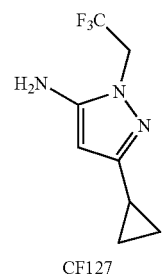

Synthesis of 3-Cyclopropyl-1-(2,2,2-trifluoroethyl)-1H-pyrazol-5-amine (CF127)

3-Cyclopropyl-3-oxopropanenitrile (1.0 g, 9.2 mmol) and (2,2,2-trifluoroethyl)hydrazine (2.9 mL, 70% in water, 23 mmol) were mixed in ethanol, and the mixture was heated at reflux for overnight. The reaction mixture was cooled to room temperature and ethanol was removed on a rotary evaporator. Water was added and the aqueous layer was extracted with ethyl acetate. The combined organic layers were washed with brine, dried over anhydrous sodium sulfate, and concentrated on a rotary evaporator. The remaining residue was purified by flash column chromatography to yield CF127 in 1.04 g. $^1$H NMR (300 MHz, CDCl$_3$): 5.27 (s, 1H), 4.51 (q, J=8.72 Hz, 2H), 3.55-3.40 (m, 2H, NH), 1.90-1.76 (m, 1H), 0.94-0.82 (m, 2H), 0.70-0.60 (m, 2H). ESI-MS calculated for $C_8H_{11}F_3N_3$ $[M+H]^+$=206.09; Observed: 206.50.

Synthesis of N-(3-Cyclopropyl-1-(2,2,2-trifluoro-ethyl)-1H-pyrazol-5-yl)-7-(3,5-dimethylisoxazol-4-yl)-6-methoxy-2-methyl-9H-pyrimido[4,5-b]indol-4-amine (Cpd. No. 156)

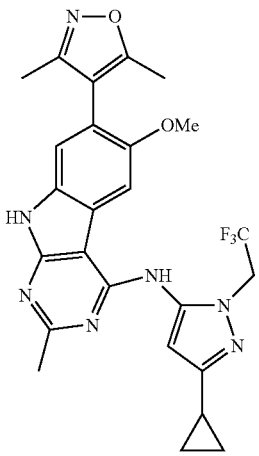 [SMILES: COc1cc2c(cc1-c1c(C)noc1C)[nH]c1nc(C)nc(Nc3cc(C4CC4)nn3CC(F)(F)F)c12]

Cpd. No. 156 was prepared from S13 (170 mg) and 3-cyclopropyl-1-(2,2,2-trifluoroethyl)-1H-pyrazol-5-amine (200 mg) following the similar procedure for preparation of Cpd. No. 135. Cpd. No. 156 was obtained in 30 mg as a salt of CF$_3$CO$_2$H. $^1$H NMR (300 MHz, MeOD-D4): 7.44 (s, 1H), 7.19 (s, 1H), 6.09 (s, 1H), 5.00-4.80 (m, 2H), 3.84 (s, 3H), 2.70 (s, 3H), 2.31 (s, 3H), 2.13 (s, 3H), 2.05-1.90 (m, 1H), 1.05-0.90 (m, 2H), 0.80-0.60 (m, 2H). ESI-MS calculated for C$_{25}$H$_{25}$F$_3$N$_7$O$_2$ [M+H]$^+$=512.20; Observed: 512.58.

Example 107

Synthesis of 7-(3,5-Dimethylisoxazol-4-yl)-6-methoxy-2-methyl-N-(2-(2,2,2-trifluoroethyl)-2,4,5,6-tetrahydrocyclopenta[c]pyrazol-3-yl)-9H-pyrimido[4,5-b]indol-4-amine (Cpd. No. 157)

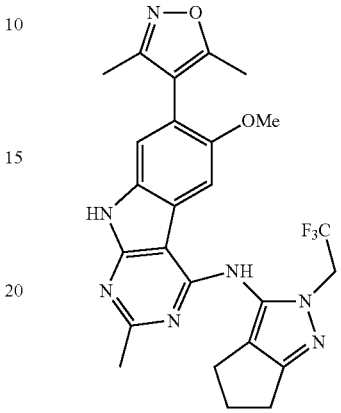

Cpd. No. 157 was prepared from S13 (170 mg) and 2-(2,2,2-Trifluoroethyl)-2,4,5,6-tetrahydro-cyclopenta[c]pyrazol-3-amine (200 mg) following the similar procedure for preparation of Cpd. No. 135. Cpd. No. 157 was obtained in 9 mg as a salt of CF$_3$CO$_2$H. $^1$H NMR (300 MHz, MeOD-D4): 7.44 (s, 1H), 7.28 (s, 1H), 3.83 (s, 3H), 2.80-2.70 (m, 2H), 2.70 (s, 3H), 2.50-2.30 (m, 4H), 2.32 (s, 3H), 2.14 (s, 3H). ESI-MS calculated for C$_{25}$H$_{25}$F$_3$N$_7$O$_2$ [M+H]$^+$=512.20; Observed: 512.83.

Example 108

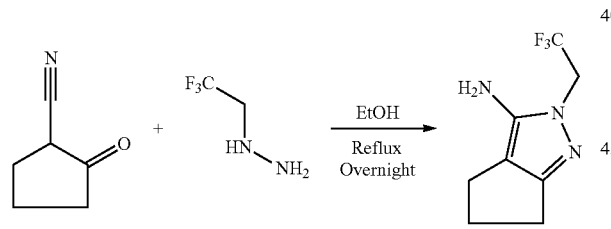

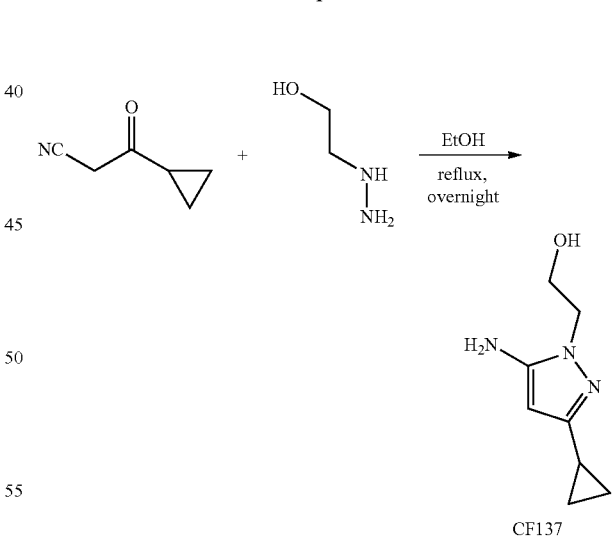

Synthesis of 2-(2,2,2-Trifluoroethyl)-2,4,5,6-tetrahydrocyclopenta[c]pyrazol-3-amine (CF128)

2-Oxocyclopentanecarbonitrile (1.0 g, 9.2 mmol) and (2,2,2-trifluoroethyl)hydrazine (2.9 mL, 70% in water, 23 mmol) were mixed in ethanol, and the mixture was heated at reflux for overnight. The reaction mixture was cooled to room temperature and ethanol was removed on a rotary evaporator. Water was added and the aqueous layer was extracted with ethyl acetate. The combined organic layers were washed with brine, dried over anhydrous sodium sulfate, and concentrated on a rotary evaporator. The remaining residue was purified by flash column chromatography to yield CF128 in 1.66 g. $^1$H NMR (300 MHz, CDCl$_3$): 4.53 (q, J=8.76 Hz, 2H), 3.40-3.30 (br, 2H, NH), 2.65 (t, J=7.27 Hz, 2H), 2.56-2.46 (m, 2H), 2.40-2.30 (m, 2H). ESI-MS calculated for C$_8$H$_{11}$F$_3$N$_3$ [M+H]$^+$=206.09; Observed: 206.33.

Synthesis of 2-(5-Amino-3-cyclopropyl-1H-pyrazol-1-yl)ethanol (CF137)

3-Cyclopropyl-3-oxopropanenitrile (5.0 g, 46 mmol) and 2-hydrazinylethanol (4.7 mL, 92 mmol) were mixed in ethanol, and the mixture was heated at reflux for overnight. The reaction mixture was cooled to room temperature and ethanol was removed on a rotary evaporator. Water was added and the aqueous layer was extracted with ethyl acetate. The combined organic layers were washed with brine, dried over anhydrous sodium sulfate, and concentrated on a rotary evaporator. The remaining residue was washed with dichloromethane and filtered to yield CF137 in 4.52 g as a white solid. $^1$H NMR (300 MHz, CDCl$_3$): 5.10 (s, 1H), 3.98-3.88 (m, 2H), 3.80 (t, J=4.95 Hz, 2H), 1.80-1.66 (m, 1H), 0.88-0.72 (m, 2H), 0.64-0.52 (m, 2H). ESI-MS calculated for C$_8$H$_{14}$N$_3$O [M+H]$^+$=168.11; Observed: 168.58.

Synthesis of 2-(3-Cyclopropyl-5-((7-(3,5-dimethyl-isoxazol-4-yl)-6-methoxy-2-methyl-9H-pyrimido[4,5-b]indol-4-yl)amino)-1H-pyrazol-1-yl)ethanol (Cpd. No. 158)

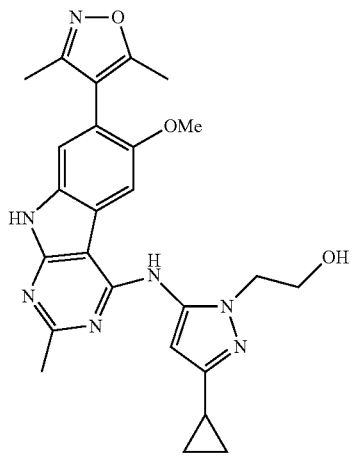 [SMILES: COc1cc2c(cc1-c1c(C)noc1C)[nH]c1nc(C)nc(Nc3cc(C4CC4)nn3CCO)c12]

Cpd. No. 158 was prepared from S13 (800 mg) and 2-(5-amino-3-cyclopropyl-1H-pyrazol-1-yl)ethanol (640 mg) following the similar procedure for preparation of Cpd. No. 135. Cpd. No. 158 was obtained in 253 mg as a salt of CF$_3$CO$_2$H. $^1$H NMR (300 MHz, MeOD-D4): 7.48 (s, 1H), 7.46 (s, 1H), 6.27 (s, 1H), 4.33 (t, J=4.61, 2H), 3.99 (t, J=4.67, 2H), 3.89 (s, 3H), 2.74 (s, 3H), 2.30 (s, 3H), 2.13 (s, 3H), 2.04-1.90 (s, 1H), 1.04-0.90 (m, 2H), 0.80-0.70 (m, 2H). ESI-MS calculated for C$_{25}$H$_{28}$N$_7$O$_3$ [M+H]$^+$=474.23; Observed: 474.50.

Example 109

Synthesis of N-(3-Cyclopropyl-1-(2-fluoroethyl)-1H-pyrazol-5-yl)-7-(3,5-dimethylisoxazol-4-yl)-6-methoxy-2-methyl-9H-pyrimido[4,5-b]indol-4-amine (Cpd. No. 159)

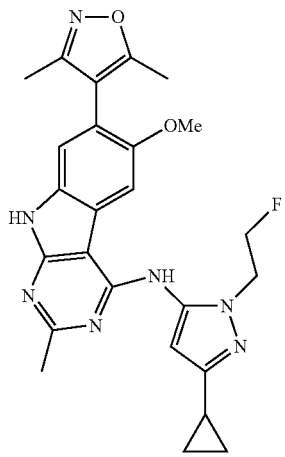 [SMILES: COc1cc2c(cc1-c1c(C)noc1C)[nH]c1nc(C)nc(Nc3cc(C4CC4)nn3CCF)c12]

Cpd. No. 158 (20 mg) was mixed with anhydrous dichloromethane (4 mL) and the mixture was cooled to −78° C. for 10 minutes. A dichloromethane solution of DAST (20 mg) was added via a syringe and the mixture was stirred at −78° C. for 20 minutes. The mixture was then warmed up to ambient temperature and stirred for 3 hours before quenching with sodium bicarbonate saturated solution. Methanol was added and the mixture was concentrated on a rotary evaporator. The remaining residue was purified on reverse phase HPLC and Cpd. No. 159 was obtained in 13 mg as a salt of CF$_3$CO$_2$H. $^1$H NMR (300 MHz, MeOD-D4): 7.44 (s, 1H), 7.12 (s, 1H), 6.08 (s, 1H), 4.87 (t, J=4.67 Hz, 1H), 4.71 (t, J=4.63 Hz, 1H), 4.44 (t, J=4.45 Hz, 1H), 4.35 (t, J=4.70 Hz, 1H), 3.84 (s, 1H), 2.72 (s, 1H), 2.31 (s, 1H), 2.14 (s, 1H), 2.24-1.90 (m, 1H), 1.04-0.90 (m, 2H), 0.80-0.66 (m, 2H). ESI-MS calculated for C$_{25}$H$_{27}$FN$_7$O$_2$[M+H]$^+$=476.22; Observed: 476.58.

Example 110

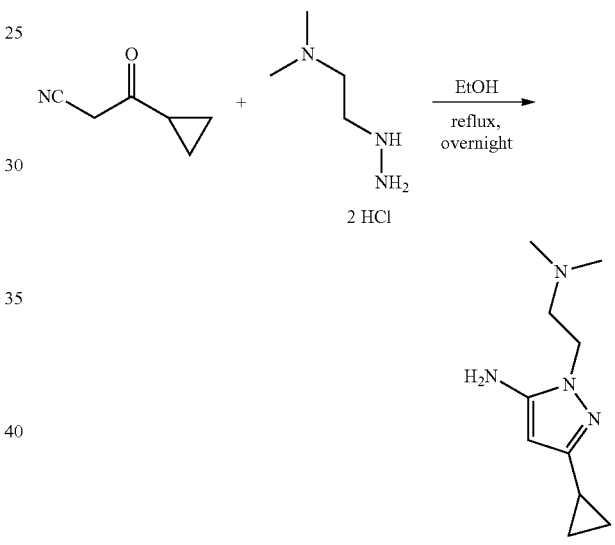

Synthesis of 3-Cyclopropyl-1-(2-(dimethylamino)ethyl)-1H-pyrazol-5-amine (CF148)

3-Cyclopropyl-3-oxopropanenitrile (1.0 g, 9.1 mmol) and 2-hydrazinyl-N,N-dimethylethanamine-2 HCl (1.76 g, 9.0 mmol) were mixed in ethanol, and the mixture was heated at reflux for overnight. The reaction mixture was cooled to room temperature and ethanol was removed on a rotary evaporator. Water was added and the aqueous layer was extracted with ethyl acetate. The combined organic layers were washed with brine, dried over anhydrous sodium sulfate, and concentrated on a rotary evaporator. The remaining residue (CF148, 2.50 g) was used for next step without further purification. $^1$H NMR (300 MHz, DMSO-D6): 5.40-5.30 (m, 1H), 4.50-4.35 (m, 2H), 3.50-3.40 (m, 2H), 2.79 (s, 6H), 1.90-1.80 (m, 1H), 1.05-0.90 (m, 2H), 0.90-0.75 (m, 2H). ESI-MS calculated for C$_{10}$H$_{19}$N$_4$[M+H]$^+$=195.16; Observed: 195.25.

Synthesis of N-(3-Cyclopropyl-1-(2-(dimethyl-amino)ethyl)-1H-pyrazol-5-yl)-7-(3,5-dimethylisoxazol-4-yl)-6-methoxy-2-methyl-9H-pyrimido[4,5-b]indol-4-amine (Cpd. No. 160)

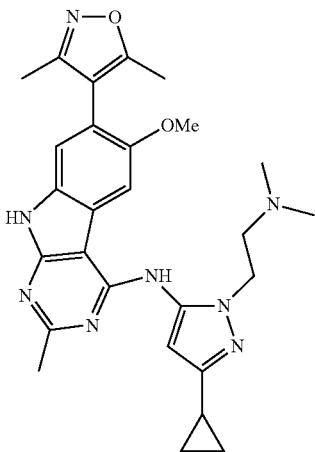

Cpd. No. 160 was prepared from S13 (100 mg) and 3-cyclopropyl-1-(2-(dimethylamino)ethyl)-1H-pyrazol-5-amine (160 mg) following the similar procedure for preparation of Cpd. No. 135. Cpd. No. 160 was obtained in 43 mg as a salt of $CF_3CO_2H$. $^1H$ NMR (300 MHz, MeOD-D4): 7.51 (s, 1H), 7.43 (s, 1H), 6.07 (s, 1H), 4.45 (t, J=5.47 Hz, 2H), 3.67 (t, J=5.57 Hz, 2H), 3.89 (s, 3H), 2.99 (s, 6H), 2.68 (s, 3H), 2.32 (s, 3H), 2.14 (s, 3H), 2.02-1.90 (m, 1H), 1.04-0.90 (m, 2H), 0.80-0.70 (m, 2H). ESI-MS calculated for $C_{27}H_{33}N_8O_2$ $[M+H]^+$=501.27; Observed: 501.67

Example 111

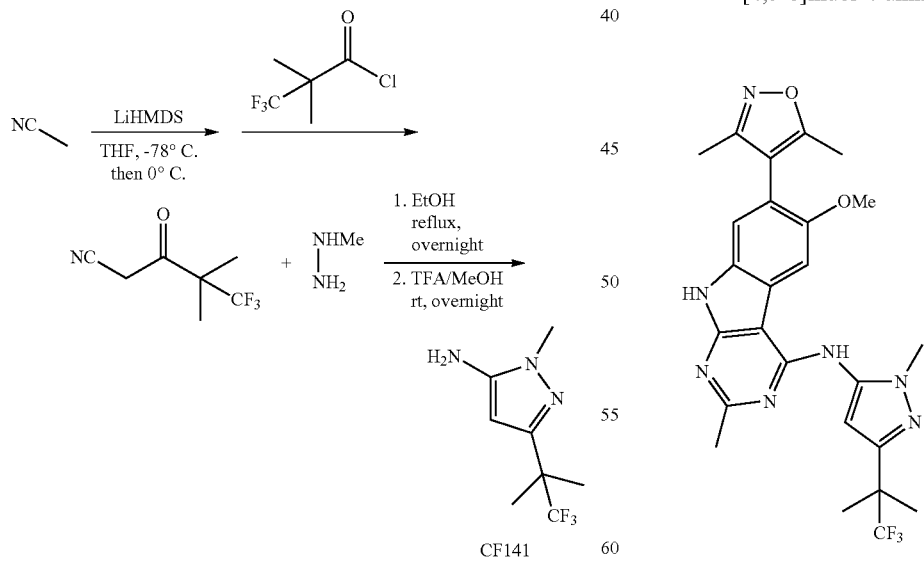

Synthesis of 1-Methyl-3-(1,1,1-trifluoro-2-methylpropan-2-yl)-1H-pyrazol-5-amine (CF141 TFA salt)

Step 1: 3,3,3-trifluoro-2,2-dimethylpropanoic acid (1.5 g, 10 mmol) and DMF (one drop) were dissolved in anhydrous dichloromethane (15 mL). Oxalyl chloride (1.0 mL, 12 mmol) was added via a syringe at ambient temperature and the mixture was stirred for overnight. Dichloromethane was removed on a rotary evaporator with 0° C. water bath. The remaining residues were used for next step without further purification.

Step 2: Acetonitrile (1.56 mL, 30 mmol) was dissolved in anhydrous THF (30 mL) and the solution was cooled to −78° C. LiHMDS (30 mL, 1.0 M in THF, 30 mmol) was added via a syringe over 10 minutes and the mixture was stirred at −78° C. for 20 min. THF solution of 3,3,3-trifluoro-2,2-dimethylpropanoyl chloride prepare from step 1 was added via a syringe and the mixture was stirred at −78° C. for 2 hours. The reaction was quenched with 1 N HCl and extracted with ethyl acetate. The combined organic layers were washed with brine, dried over anhydrous sodium sulfate, and concentrated on a rotary evaporator. The remaining residue was used for next step without further purification.

Step 3: 5,5,5-trifluoro-4,4-dimethyl-3-oxopentanenitrile prepared from step 2 was dissolved in ethanol (30 mL). Methyl hydrazine (1.1 mL, 20 mmol) was added via a syringe and the mixture was heated at reflux for overnight. The reaction mixture was cooled to room temperature and ethanol was removed on a rotary evaporator. Water was added and the aqueous layer was extracted with ethyl acetate. The combined organic layers were washed with brine, dried over anhydrous sodium sulfate, and concentrated on a rotary evaporator. The remaining residue was purified on flash chromatography to yield CF141 in 0.22 g. $^1H$ NMR (300 MHz, MeOD-d4): 5.54 (s, 1H), 3.61 (s, 3H), 3.60-3.40 (m, 2H, NH), 1.45 (s, 6H). ESI-MS calculated for $C_8H_{13}F_3N_3$ $[M+H]^+$=208.11; Observed: 208.25.

Synthesis of 7-(3,5-Dimethylisoxazol-4-yl)-6-methoxy-2-methyl-N-(1-methyl-3-(1,1,1-trifluoro-2-methylpropan-2-yl)-1H-pyrazol-5-yl)-9H-pyrimido[4,5-b]indol-4-amine (Cpd. No. 161)

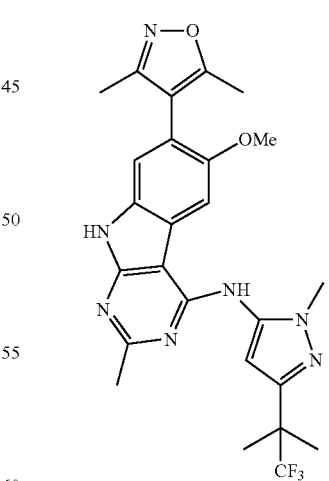

Cpd. No. 161 was prepared from S13 (102 mg) and 1-methyl-3-(1,1,1-trifluoro-2-methylpropan-2-yl)-1H-pyrazol-5-amine (120 mg) following the similar procedure for preparation of Cpd. No. 135. Cpd. No. 161 was obtained in 48 mg as a salt of $CF_3CO_2H$. $^1H$ NMR (300 MHz, MeOD-D4): 7.67 (s, 1H), 7.46 (s, 1H), 6.41 (s, 1H), 3.90 (s, 1H), 3.83 (s, 3H), 2.69 (s, 3H), 2.32 (s, 3H), 2.15 (s, 3H), 1.55 (s, 6H). ESI-MS calculated for C$_{25}$H$_{27}$F$_3$N$_7$O$_2$[M+H]$^+$=514.22; Observed: 514.67.

Example 112

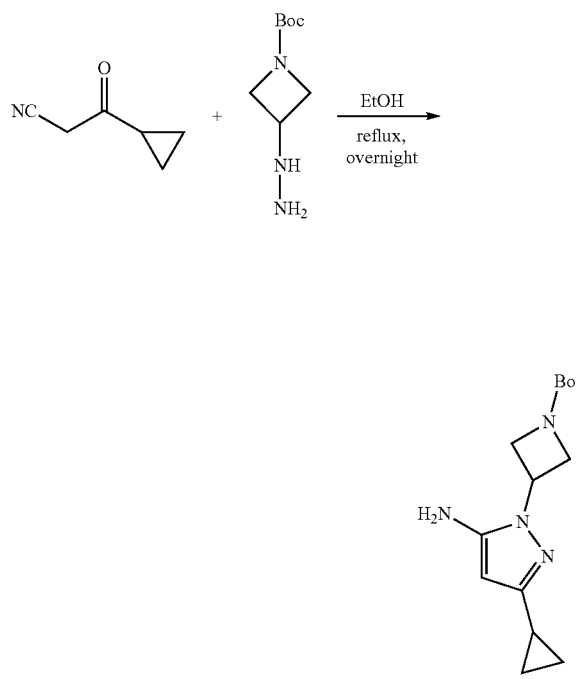

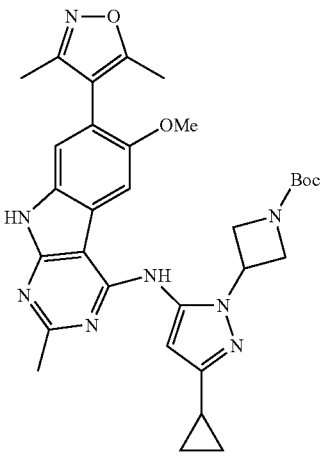 [SMILES: COc1cc2c(cc1-c1c(C)noc1C)[nH]c1nc(C)nc(Nc3cc(C4CC4)nn3C3CN(C(=O)OC(C)(C)C)C3)c12]

CF178

Synthesis of tert-butyl 3-(5-amino-3-cyclopropyl-1H-pyrazol-1-yl)azetidine-1-carboxylate (CF178)

3-Cyclopropyl-3-oxopropanenitrile (2.16 g, 20 mmol) and 1-Boc-3-hydrazinylazetidine-(3.83 g, 20.0 mmol, prepared according to WO 2012/004706 A2) were mixed in ethanol, and the mixture was heated at reflux for overnight. The reaction mixture was cooled to room temperature and ethanol was removed on a rotary evaporator. Water was added and the aqueous layer was extracted with ethyl acetate. The combined organic layers were washed with brine, dried over anhydrous sodium sulfate, and concentrated on a rotary evaporator. The remaining residue was washed with dichloromethane and filtered to yield CF178 in 2.67 g. $^1$H NMR (300 MHz, CDCl$_3$): 5.21 (s, 1H), 4.95-4.80 (m, 1H), 4.50-4.35 (m, 2H), 4.30-4.15 (m, 2H), 1.90-1.80 (m, 1H), 1.45 (s, 9H), 0.95-0.80 (m, 2H), 0.70-0.60 (m, 2H). ESI-MS calculated for C$_{14}$H$_{23}$N$_4$O$_2$ [M+H]$^+$=279.18; Observed: 279.58.

Synthesis of tert-butyl 3-(3-cyclopropyl-5-((7-(3,5-dimethylisoxazol-4-yl)-6-methoxy-2-methyl-9H-pyrimido[4,5-b]indol-4-yl)amino)-1H-pyrazol-1-yl)azetidine-1-carboxylate (Cpd. No. 162)

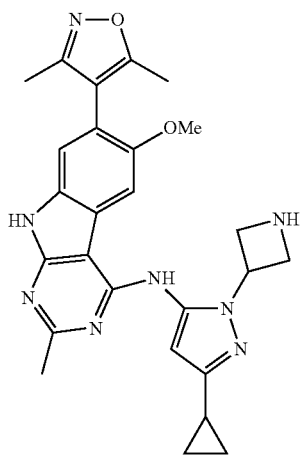 [SMILES: COc1cc2c(cc1-c1c(C)noc1C)[nH]c1nc(C)nc(Nc3cc(C4CC4)nn3C3CNC3)c12]

Cpd. No. 162 was prepared from S13 (205 mg) and tert-butyl 3-(5-amino-3-cyclopropyl-1H-pyrazol-1-yl)azetidine-1-carboxylate (348 mg) following the similar procedure for preparation of Cpd. No. 135. Cpd. No. 162 was used in the next reaction without purification.

Example 113

Synthesis of N-(1-(Azetidin-3-yl)-3-cyclopropyl-1H-pyrazol-5-yl)-7-(3,5-dimethylisoxazol-4-yl)-6-methoxy-2-methyl-9H-pyrimido[4,5-b]indol-4-amine (Cpd. No. 163)

Cpd. No. 162 (crude product) and triethylsilane (0.2 mL) were dissolved in CF$_3$CO$_2$H-dichloromethane (1:1, 12 mL) and the mixture was stirred at room temperature for 1 h. The reaction mixture was concentrated on a rotary evaporator and the remaining residue was purified on reverse HPLC to yield 126 mg of Cpd. No. 163 as a salt of CF$_3$CO$_2$H. $^1$H NMR (300 MHz, MeOD-D4): 7.54 (s, 1H), 7.46 (s, 1H), 6.09 (s, 1H), 5.40-5.20 (m, 1H), 5.70-5.50 (m, 2H), 5.50-

5.30 (m, 2H), 3.89 (s, 3H), 2.65 (s, 3H), 2.30 (s, 3H), 2.12 (s, 3H), 2.10-1.95 (m, 1H), 1.05-0.90 (m, 2H), 0.90-0.75 (m, 2H). ESI-MS calculated for $C_{26}H_{29}N_8O_2$ [M+H]$^+$=485.24; Observed: 485.67.

Example 114

Synthesis of N-(1-(tert-butyl)-3-methyl-1H-pyrazol-5-yl)-7-(3,5-dimethylisoxazol-4-yl)-6-methoxy-2-methyl-9H-pyrimido[4,5-b]indol-4-amine (Cpd. No. 62)

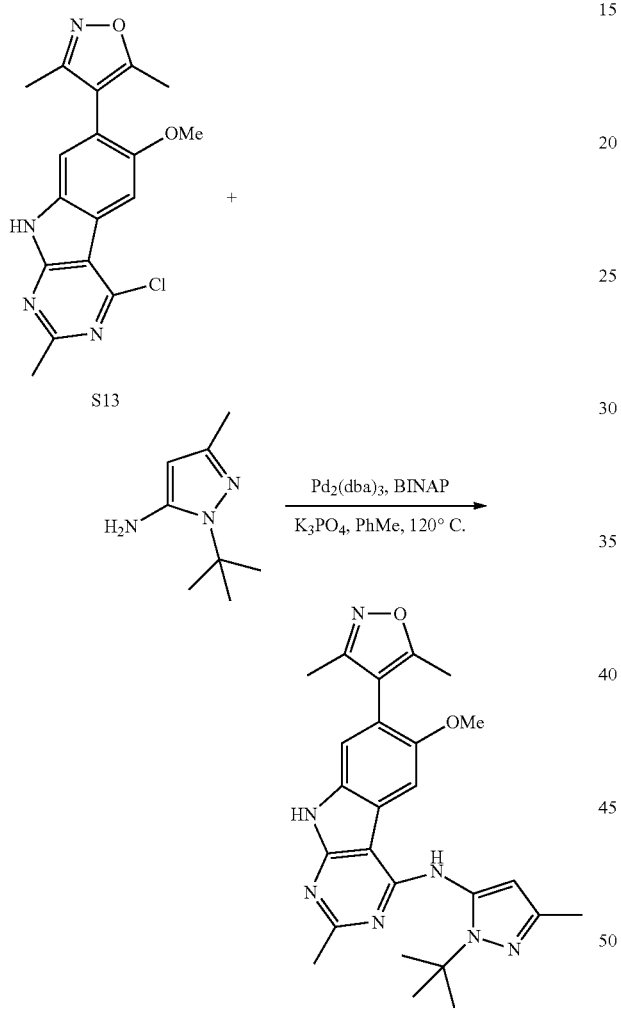

Pd$_2$(dba)$_3$ (18 mg) and BINAP (26 mg) were mixed in anhydrous toluene. And the mixture was heated at reflux for 3-4 minutes. This mixture was transferred into a round-bottom flask containing S13 (60 mg), 1-(tert-butyl)-3-methyl-1H-pyrazol-5-amine (84 mg), K$_3$PO$_4$ (130 mg), and toluene (2 mL). The mixture was heated at reflux for overnight before quenching with methanol. The reaction mixture was filtered and the mixture was purified by HPLC to yield Cpd. No. 62 as a CF$_3$CO$_2$H salt in 15 mg. ESI-MS calculated for $C_{25}H_{30}N_7O_2$ [M+H]$^+$=460.24; Observed: 460.55. $^1$H NMR (300 MHz, MeOD) δ 7.44 (s, 1H), 6.59 (s, 1H), 6.24 (s, 1H), 3.80 (s, 3H), 2.74 (s, 3H), 2.31 (s, 3H), 2.30 (s, 3H), 2.14 (s, 3H), 1.72 (s, 9H).

Example 115

Synthesis of 7-(3,5-dimethylisoxazol-4-yl)-6-methoxy-2-methyl-N-(1-methyl-1H-imidazol-4-yl)-9H-pyrimido[4,5-b]indol-4-amine (Cpd. No. 166)

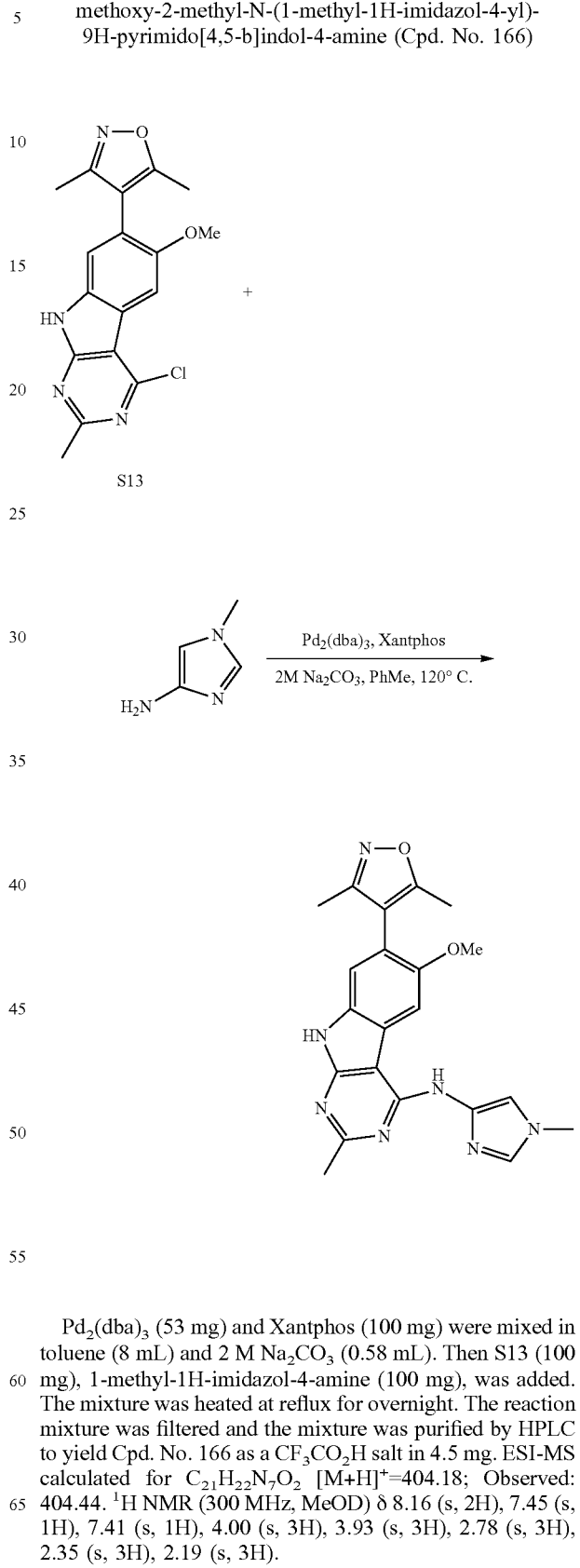

Pd$_2$(dba)$_3$ (53 mg) and Xantphos (100 mg) were mixed in toluene (8 mL) and 2 M Na$_2$CO$_3$ (0.58 mL). Then S13 (100 mg), 1-methyl-1H-imidazol-4-amine (100 mg), was added. The mixture was heated at reflux for overnight. The reaction mixture was filtered and the mixture was purified by HPLC to yield Cpd. No. 166 as a CF$_3$CO$_2$H salt in 4.5 mg. ESI-MS calculated for $C_{21}H_{22}N_7O_2$ [M+H]$^+$=404.18; Observed: 404.44. $^1$H NMR (300 MHz, MeOD) δ 8.16 (s, 2H), 7.45 (s, 1H), 7.41 (s, 1H), 4.00 (s, 3H), 3.93 (s, 3H), 2.78 (s, 3H), 2.35 (s, 3H), 2.19 (s, 3H).

Example 116

Synthesis of N-(1,4-dimethyl-1H-pyrazol-3-yl)-7-(3,5-dimethylisoxazol-4-yl)-6-methoxy-2-methyl-9H-pyrimido[4,5-b]indol-4-amine (Cpd. No. 77)

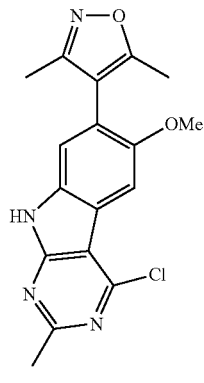

S13

+

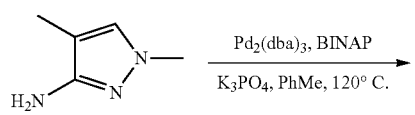

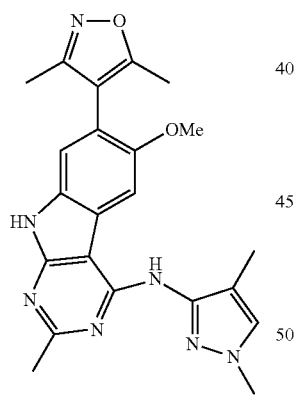

Pd$_2$(dba)$_3$ (18 mg) and BINAP (26 mg) were mixed in anhydrous toluene. And the mixture was heated at reflux for 3-4 minutes. This mixture was transferred into a round-bottom flask containing S13 (60 mg), 1,4-dimethyl-1H-pyrazol-3-amine (84 mg), K$_3$PO$_4$ (130 mg), and toluene (2 mL). The mixture was heated at reflux for overnight before quenching with methanol. The reaction mixture was filtered and the mixture was purified by HPLC to yield Cpd. No. 77 as a CF$_3$CO$_2$H salt in 20 mg. ESI-MS calculated for C$_{22}$H$_{24}$N$_7$O$_2$ [M+H]$^+$=418.19; Observed: 418.44. $^1$H NMR (300 MHz, MeOD) δ 7.65 (s, 1H), 7.62 (s, 1H), 7.47 (s, 1H), 3.93 (s, 3H), 3.91 (s, 3H), 2.75 (s, 3H), 2.35 (s, 3H), 2.17 (s, 3H), 2.12 (s, 3H).

Example 117

Synthesis of N-(1,4-dimethyl-1H-pyrazol-5-yl)-7-(3,5-dimethylisoxazol-4-yl)-6-methoxy-2-methyl-9H-pyrimido[4,5-b]indol-4-amine (Cpd. No. 76)

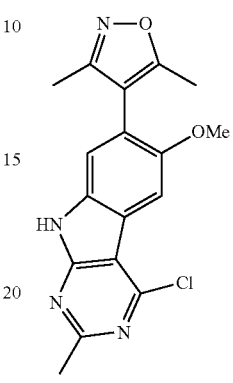

S13

+

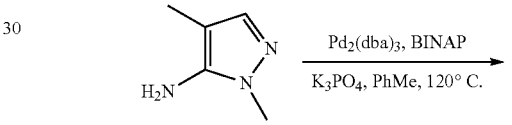

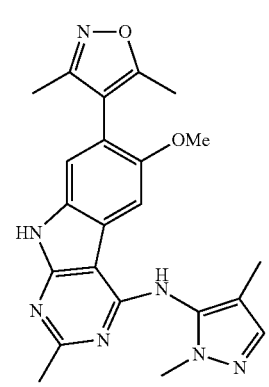

Pd$_2$(dba)$_3$ (18 mg) and BINAP (26 mg) were mixed in anhydrous toluene. And the mixture was heated at reflux for 3-4 minutes. This mixture was transferred into a round-bottom flask containing S13 (60 mg), 1,4-dimethyl-1H-pyrazol-5-amine (84 mg), K$_3$PO$_4$ (130 mg), and toluene (2 mL). The mixture was heated at reflux for overnight before quenching with methanol. The reaction mixture was filtered and the mixture was purified by HPLC to yield Cpd. No. 76 as a CF$_3$CO$_2$H salt in 20 mg. ESI-MS calculated for C$_{22}$H$_{24}$N$_7$O$_2$ [M+H]$^+$=418.19; Observed: 418.64. $^1$H NMR (300 MHz, MeOD) δ 7.52 (s, 1H), 7.48 (s, 1H), 7.37 (brs, 1H), 3.88 (s, 3H), 3.83 (s, 3H), 2.72 (s, 3H), 2.33 (s, 3H), 2.16 (s, 3H), 1.98 (s, 3H).

Example 118

Synthesis of 7-(3,5-dimethylisoxazol-4-yl)-N-(3-ethyl-1,4-dimethyl-1H-pyrazol-5-yl)-6-methoxy-2-methyl-9H-pyrimido[4,5-b]indol-4-amine (Cpd. No. 169)

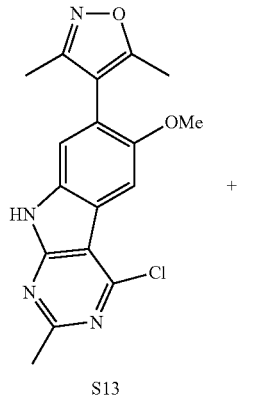

+

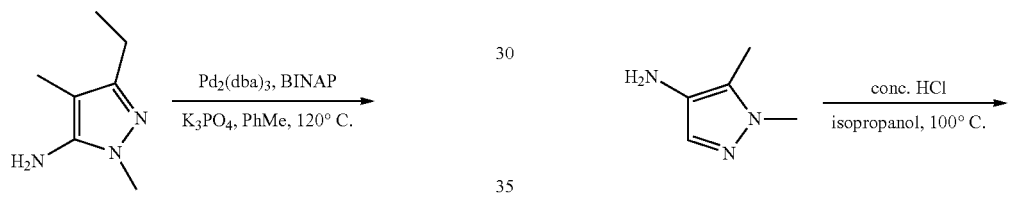

Example 119

Synthesis of N-(1,5-dimethyl-1H-pyrazol-4-yl)-7-(3,5-dimethylisoxazol-4-yl)-6-methoxy-2-methyl-9H-pyrimido[4,5-b]indol-4-amine (Cpd. No. 170)

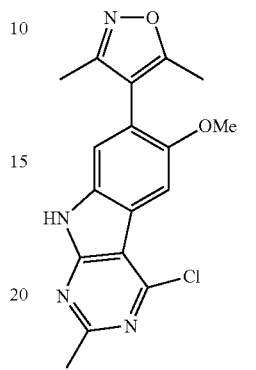

+

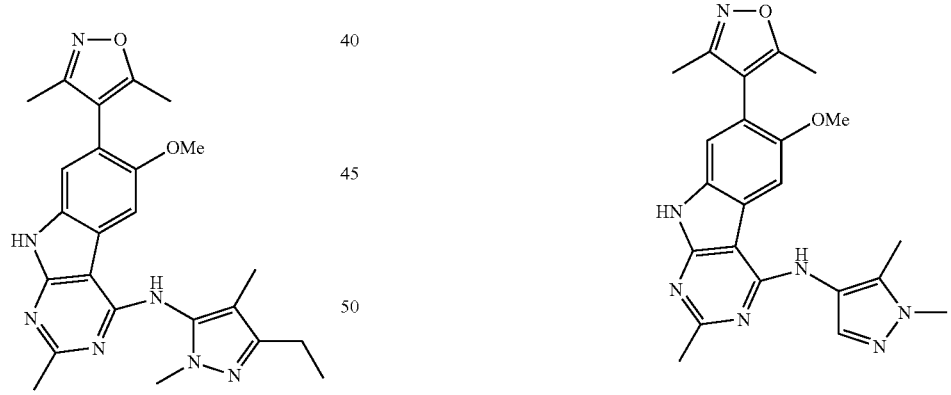

Pd$_2$(dba)$_3$ (18 mg) and BINAP (26 mg) were mixed in anhydrous toluene. And the mixture was heated at reflux for 3-4 minutes. This mixture was transferred into a round-bottom flask containing S13 (60 mg), 3-ethyl-1,4-dimethyl-1H-pyrazol-5-amine (84 mg), K$_3$PO$_4$ (130 mg), and toluene (2 mL). The mixture was heated at reflux for overnight before quenching with methanol. The reaction mixture was filtered and the mixture was purified by HPLC to yield Cpd. No. 169 as a CF$_3$CO$_2$H salt in 20 mg. ESI-MS calculated for C$_{24}$H$_{28}$N$_7$O$_2$ [M+H]$^+$=446.23; Observed: 446.67. $^1$H NMR (300 MHz, MeOD) δ 7.46 (s, 1H), 7.37 (brs, 1H), 3.88 (s, 3H), 3.78 (s, 3H), 2.74-2.60 (m, 5H), 2.34 (s, 3H), 2.17 (s, 3H), 1.89 (s, 3H), 1.27 (t, J=7.6 Hz, 3H).

S13 (70 mg) and 1,5-dimethyl-1H-pyrazol-4-amine (68 mg) were dissolved in isopropanol (5 mL). Four drops of concentrated HCl was added via a glass pipette. The mixture was heated at reflux for overnight. The reaction was concentrated on a rotary evaporator and the remaining residues were purified by HPLC to yield the desired product Cpd. No. 170 in 50 mg as a salt of trifluoroacetic acid. ESI-MS calculated for C$_{22}$H$_{24}$N$_7$O$_2$ [M+H]$^+$=418.19; Observed: 418.46. $^1$H NMR (300 MHz, MeOD) δ 7.95 (brs, 1H), 7.65 (s, 1H), 7.47 (s, 1H), 3.92 (s, 3H), 3.91 (s, 3H), 2.70 (s, 3H), 2.33 (s, 3H), 2.31 (s, 3H), 2.16 (s, 3H).

Example 120

Synthesis of N-(1,2-dimethyl-1H-imidazol-5-yl)-7-(3,5-dimethylisoxazol-4-yl)-6-methoxy-2-methyl-9H-pyrimido[4,5-b]indol-4-amine (Cpd. No. 171)

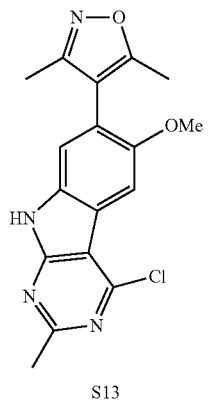

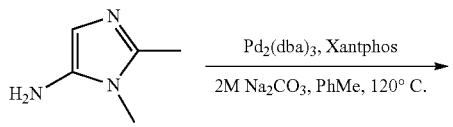

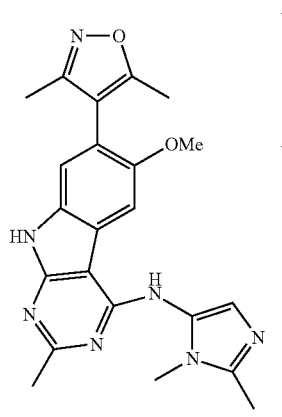

Pd$_2$(dba)$_3$ (53 mg) and Xantphos (100 mg) were mixed in toluene (8 mL) and 2 M Na$_2$CO$_3$ (0.58 mL). Then S13 (100 mg), 1,2-dimethyl-1H-imidazol-5-amine (100 mg), was added. The mixture was heated at reflux for overnight. The reaction mixture was filtered and the mixture was purified by HPLC to yield Cpd. No. 171 as a CF$_3$CO$_2$H salt in 7.5 mg. ESI-MS calculated for C$_{22}$H$_{24}$N$_7$O$_2$ [M+H]$^+$=418.19; Observed: 418.42. $^1$H NMR (300 MHz, MeOD) δ 8.10 (s, 1H), 7.60 (s, 1H), 7.47 (s, 1H), 3.98 (s, 3H), 3.70 (s, 3H), 2.77 (s, 3H), 2.63 (s, 3H), 2.36 (s, 3H), 2.19 (s, 3H).

Example 121

Synthesis of 7-(3,5-dimethylisoxazol-4-yl)-6-methoxy-2-methyl-N-(1-methyl-1H-pyrazol-5-yl)-9H-pyrimido[4,5-b]indol-4-amine (Cpd. No. 172)

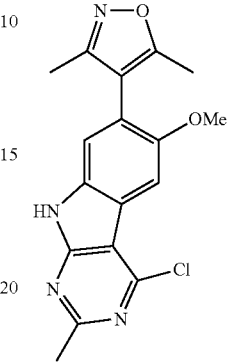

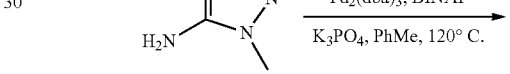

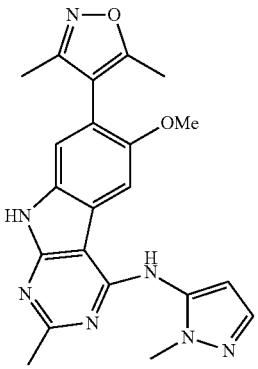

Pd$_2$(dba)$_3$ (18 mg) and BINAP (26 mg) were mixed in anhydrous toluene. And the mixture was heated at reflux for 3-4 minutes. This mixture was transferred into a round-bottom flask containing S13 (60 mg), 1-methyl-1H-pyrazol-5-amine (84 mg), K$_3$PO$_4$ (130 mg), and toluene (2 mL). The mixture was heated at reflux for overnight before quenching with methanol. The reaction mixture was filtered and the mixture was purified by HPLC to yield Cpd. No. 172 as a CF$_3$CO$_2$H salt in 22 mg. ESI-MS calculated for C$_{21}$H$_{22}$N$_7$O$_2$ [M+H]$^+$=404.18; Observed: 404.45. $^1$H NMR (300 MHz, MeOD) δ 7.63 (d, J=2.1 Hz, 1H), 7.49 (s, 1H), 7.48 (s, 1H), 6.43 (d, J=2.1 Hz, 1H), 3.90 (s, 3H), 3.85 (s, 3H), 2.71 (s, 3H), 2.33 (s, 3H), 2.15 (s, 3H).

Example 122

Synthesis of 7-(3,5-dimethylisoxazol-4-yl)-N-(1-ethyl-1H-pyrazol-5-yl)-6-methoxy-2-methyl-9H-pyrimido[4,5-b]indol-4-amine (Cpd. No. 173)

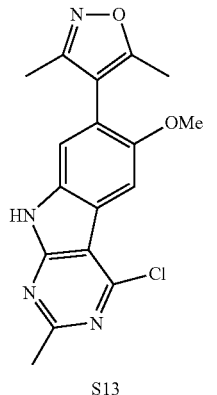

+

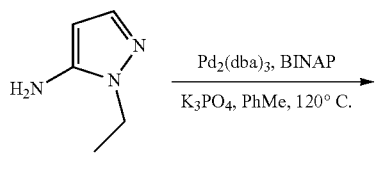

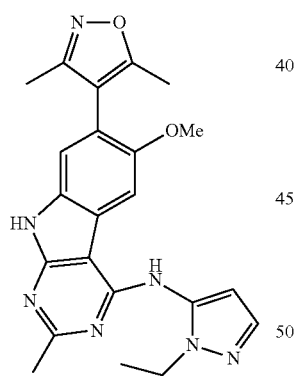

Pd₂(dba)₃ (18 mg) and BINAP (26 mg) were mixed in anhydrous toluene. And the mixture was heated at reflux for 3-4 minutes. This mixture was transferred into a round-bottom flask containing S13 (60 mg), 1-ethyl-1H-pyrazol-5-amine (84 mg), K₃PO₄ (130 mg), and toluene (2 mL). The mixture was heated at reflux for overnight before quenching with methanol. The reaction mixture was filtered and the mixture was purified by HPLC to yield Cpd. No. 173 as a CF₃CO₂H salt in 22 mg. ESI-MS calculated for $C_{22}H_{24}N_7O_2$ [M+H]⁺=418.19; Observed: 418.66. ¹H NMR (300 MHz, MeOD) δ 7.67 (d, J=2.0 Hz, 1H), 7.50 (s, 1H), 7.45 (s, 1H), 6.39 (d, J=2.0 Hz, 1H), 4.17 (q, J=7.3 Hz, 2H), 3.90 (s, 3H), 2.67 (s, 3H), 2.34 (s, 3H), 2.17 (s, 3H), 1.48 (t, J=7.2 Hz, 3H).

Example 123

Synthesis of 5-((7-(3,5-dimethylisoxazol-4-yl)-6-methoxy-2-methyl-9H-pyrimido[4,5-b]indol-4-yl)amino)-1-methyl-1H-pyrazole-4-carbonitrile (Cpd. No. 174)

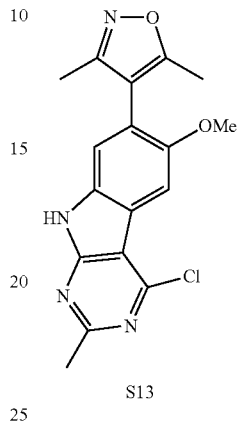

+

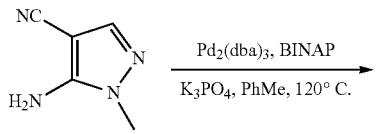

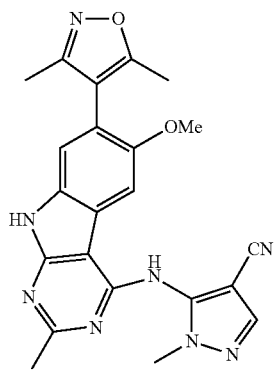

Pd₂(dba)₃ (18 mg) and BINAP (26 mg) were mixed in anhydrous toluene. And the mixture was heated at reflux for 3-4 minutes. This mixture was transferred into a round-bottom flask containing S13 (60 mg), 5-amino-1-methyl-1H-pyrazole-4-carbonitrile (84 mg), K₃PO₄ (130 mg), and toluene (2 mL). The mixture was heated at reflux for overnight before quenching with methanol. The reaction mixture was filtered and the mixture was purified by HPLC to yield Cpd. No. 174 as a CF₃CO₂H salt in 26 mg. ESI-MS calculated for $C_{22}H_{21}N_8O_2$ [M+H]⁺=429.17; Observed: 429.44. ¹H NMR (300 MHz, MeOD) δ 8.01 (s, 1H), 7.94 (s, 1H), 7.49 (s, 1H), 3.96 (s, 3H), 3.87 (s, 3H), 2.68 (s, 3H), 2.36 (s, 3H), 2.19 (s, 3H).

Example 124

Synthesis of 7-(3,5-dimethylisoxazol-4-yl)-N-(1-isopropyl-1H-pyrazol-5-yl)-6-methoxy-2-methyl-9H-pyrimido[4,5-b]indol-4-amine (Cpd. No. 175)

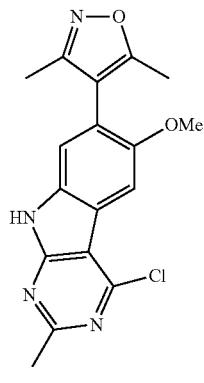

+

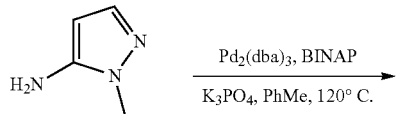

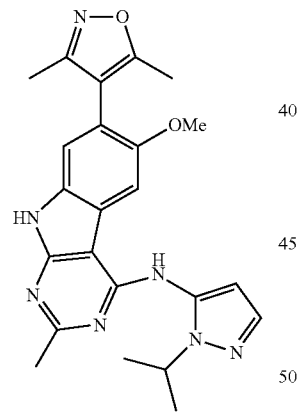

Pd$_2$(dba)$_3$ (18 mg) and BINAP (26 mg) were mixed in anhydrous toluene. And the mixture was heated at reflux for 3-4 minutes. This mixture was transferred into a round-bottom flask containing S13 (60 mg), 1-isopropyl-1H-pyrazol-5-amine (84 mg), K$_3$PO$_4$ (130 mg), and toluene (2 mL). The mixture was heated at reflux for overnight before quenching with methanol. The reaction mixture was filtered and the mixture was purified by HPLC to yield Cpd. No. 175 as a CF$_3$CO$_2$H salt in 22 mg. ESI-MS calculated for C$_{23}$H$_{26}$N$_7$O$_2$ [M+H]$^+$=432.21; Observed: 432.44. $^1$H NMR (300 MHz, MeOD) δ 7.69 (d, J=1.9 Hz, 1H), 7.46 (s, 1H), 7.28 (s, 1H), 6.37 (d, J=2.0 Hz, 1H), 4.65 (dq, J=13.2, 6.6 Hz, 1H), 3.87 (s, 3H), 2.70 (s, 3H), 2.32 (s, 3H), 2.15 (s, 3H), 1.51 (d, J=6.6 Hz, 6H).

Example 125

Synthesis of 7-(3,5-dimethylisoxazol-4-yl)-N-(1-ethyl-4-methyl-1H-pyrazol-5-yl)-6-methoxy-2-methyl-9H-pyrimido[4,5-b]indol-4-amine (Cpd. No. 176)

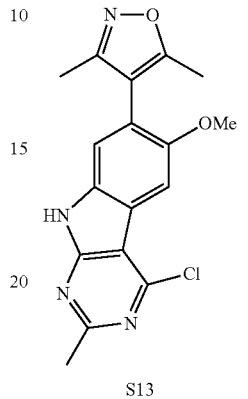

+

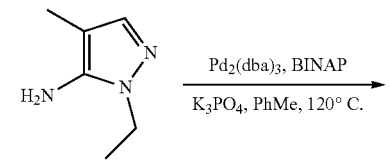

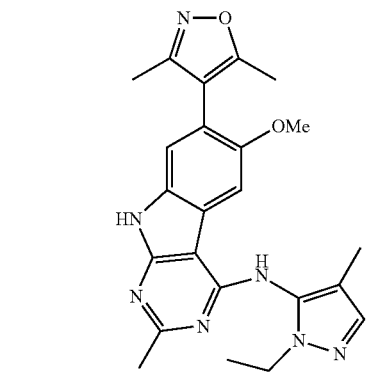

Pd$_2$(dba)$_3$ (18 mg) and BINAP (26 mg) were mixed in anhydrous toluene. And the mixture was heated at reflux for 3-4 minutes. This mixture was transferred into a round-bottom flask containing S13 (60 mg), 1-ethyl-4-methyl-1H-pyrazol-5-amine (84 mg), K$_3$PO$_4$ (130 mg), and toluene (2 mL). The mixture was heated at reflux for overnight before quenching with methanol. The reaction mixture was filtered and the mixture was purified by HPLC to yield Cpd. No. 176 as a CF$_3$CO$_2$H salt in 22 mg. ESI-MS calculated for C$_{23}$H$_{26}$N$_7$O$_2$ [M+H]$^+$=432.21; Observed: 432.48. $^1$H NMR (300 MHz, MeOD) δ 7.54 (s, 1H), 7.48 (s, 1H), 7.06 (brs, 1H), 4.18 (q, J=7.2 Hz, 2H), 3.85 (s, 3H), 2.73 (s, 3H), 2.32 (s, 3H), 2.14 (s, 3H), 1.95 (s, 3H), 1.45 (t/=7.2 Hz, 3H).

Example 126

Synthesis of N-(7-(3,5-dimethylisoxazol-4-yl)-6-methoxy-2-methyl-9H-pyrimido[4,5-b]indol-4-yl)-2,4-dimethylthiazol-5-amine (Cpd. No. 177)

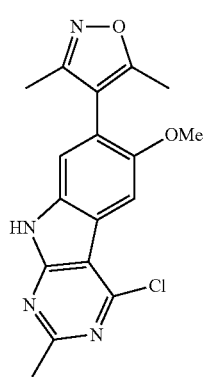

Pd$_2$(dba)$_3$ (18 mg) and BINAP (26 mg) were mixed in anhydrous toluene. And the mixture was heated at reflux for 3-4 minutes. This mixture was transferred into a round-bottom flask containing S13 (60 mg), 2,4-dimethylthiazol-5-amine (84 mg), K$_3$PO$_4$ (130 mg), and toluene (2 mL). The mixture was heated at reflux for overnight before quenching with methanol. The reaction mixture was filtered and the mixture was purified by HPLC to yield Cpd. No. 177 as a CF$_3$CO$_2$H salt in 14 mg. ESI-MS calculated for C$_{22}$H$_{23}$N$_6$O$_2$S [M+H]$^+$=435.16; Observed: 435.44. $^1$H NMR (300 MHz, MeOD) δ 7.98 (s, 1H), 7.48 (s, 1H), 3.97 (s, 3H), 2.78 (s, 3H), 2.73 (s, 3H), 2.41 (s, 3H), 2.35 (s, 3H), 2.18 (s, 3H).

Example 127

Synthesis of N-(1-cyclopentyl-1H-pyrazol-5-yl)-7-(3,5-dimethylisoxazol-4-yl)-6-methoxy-2-methyl-9H-pyrimido[4,5-b]indol-4-amine (Cpd. No. 178)

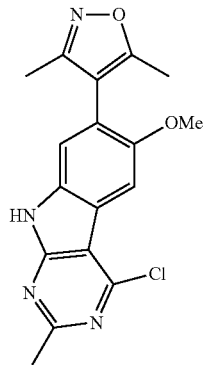

Pd$_2$(dba)$_3$ (18 mg) and BINAP (26 mg) were mixed in anhydrous toluene. And the mixture was heated at reflux for 3-4 minutes. This mixture was transferred into a round-bottom flask containing S13 (60 mg), 1-cyclopentyl-1H-pyrazol-5-amine (84 mg), K$_3$PO$_4$ (130 mg), and toluene (2 mL). The mixture was heated at reflux for overnight before quenching with methanol. The reaction mixture was filtered and the mixture was purified by HPLC to yield Cpd. No. 178 as a CF$_3$CO$_2$H salt in 20 mg. ESI-MS calculated for C$_{25}$H$_{28}$N$_7$O$_2$ [M+H]$^+$=458.23; Observed: 458.55. $^1$H NMR (300 MHz, MeOD) δ 7.67 (d, J=1.8 Hz, 1H), 7.45 (s, 1H), 7.35 (s, 1H), 6.37 (d, J=2.0 Hz, 1H), 4.78 (p, J=7.6 Hz, 1H), 3.87 (s, 3H), 2.68 (s, 3H), 2.33 (s, 3H), 2.16 (s, 3H), 2.14-2.04 (m, 4H), 2.00-1.86 (m, 2H), 1.72-1.57 (m, 2H).

Example 128

Synthesis of 7-(3,5-dimethylisoxazol-4-yl)-6-methoxy-2-methyl-N-(1-methyl-3-(trifluoromethyl)-1H-pyrazol-4-yl)-9H-pyrimido[4,5-b]indol-4-amine (Cpd. No. 179)

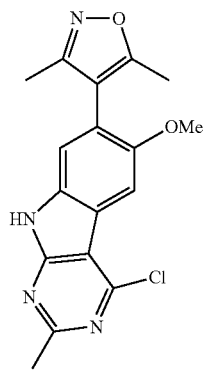

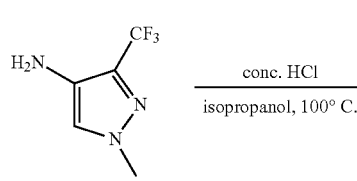

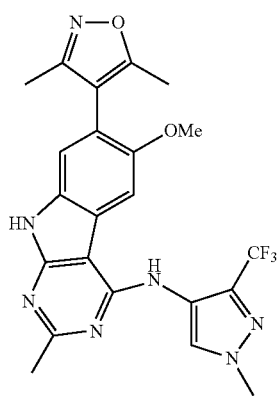

S13 (70 mg) and 1-methyl-3-(trifluoromethyl)-1H-pyrazol-4-amine (68 mg) were dissolved in isopropanol (5 mL). Four drops of concentrated HCl was added via a glass pipette. The mixture was heated at reflux for overnight. The reaction was concentrated on a rotary evaporator and the remaining residues were purified by HPLC to yield the desired product Cpd. No. 179 in 50 mg as a salt of trifluoroacetic acid. ESI-MS calculated for $C_{22}H_{21}F_3N_7O_2$ $[M+H]^+$=472.17; Observed: 472.44. $^1$H NMR (300 MHz, MeOD) δ 8.15 (s, 1H), 7.97 (s, 1H), 7.49 (s, 1H), 4.08 (s, 3H), 3.96 (s, 3H), 2.70 (s, 3H), 2.35 (s, 3H), 2.18 (s, 3H).

Example 129

Synthesis of 7-(3,5-dimethylisoxazol-4-yl)-6-methoxy-2-methyl-N-(1,3,4-trimethyl-1H-pyrazol-5-yl)-9H-pyrimido[4,5-b]indol-4-amine (Cpd. No. 80)

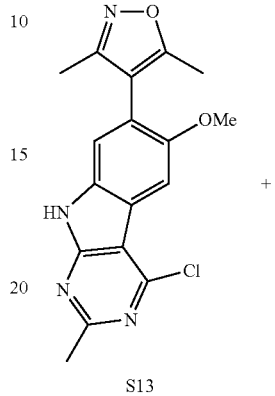

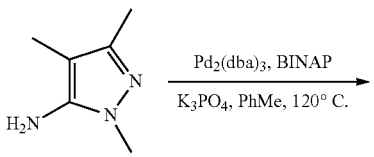

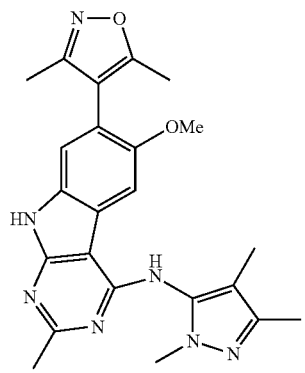

Pd$_2$(dba)$_3$ (18 mg) and BINAP (26 mg) were mixed in anhydrous toluene. And the mixture was heated at reflux for 3-4 minutes. This mixture was transferred into a round-bottom flask containing S13 (60 mg), 1,3,4-trimethyl-1H-pyrazol-5-amine (84 mg), K$_3$PO$_4$ (130 mg), and toluene (2 mL). The mixture was heated at reflux for overnight before quenching with methanol. The reaction mixture was filtered and the mixture was purified by HPLC to yield Cpd. No. 80 as a CF$_3$CO$_2$H salt in 20 mg. ESI-MS calculated for $C_{23}H_{26}N_7O_2$ $[M+H]^+$=432.21; Observed: 432.65. $^1$H NMR (300 MHz, MeOD) δ 7.47 (s, 1H), 7.29 (brs, 1H), 3.87 (s, 3H), 3.77 (s, 3H), 2.71 (s, 3H), 2.33 (s, 3H), 2.26 (s, 3H), 2.16 (s, 3H), 1.90 (s, 3H).

Example 130

Synthesis of 3-isopropyl-1-methyl-1H-pyrazol-4-amine (ZBB153)

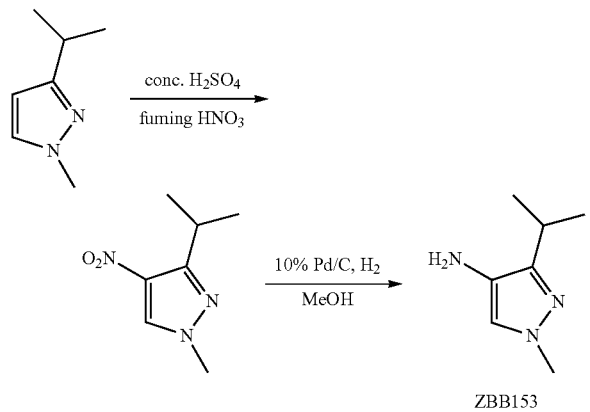

The mixture of 3-isopropyl-1-methyl-1H-pyrazole (500 mg), conc. H$_2$SO$_4$ (1 mL) and fuming HNO$_3$ (1 mL) was heated at 60° C. overnight. Then the mixture was poured into cooled aq. NaOH water solution and extracted with Ethyl acetate. The organic phase was concentrated on a rotary evaporator and was dissolved in MeOH (10 mL). 50 mg 10% Pd/C was added. the reaction mixture was degassed 2 times, each time replacing the vacuum with hydrogen, then stirred at room temperature under I-overnight. The mixture was filtered and concentrated on a rotary evaporator to give ZBB153 (300 mg). ESI-MS calculated for C$_7$H$_{14}$N$_3$ [M+H]$^+$=140.11; Observed: 140.44.

Synthesis of 7-(3,5-dimethylisoxazol-4-yl)-N-(3-isopropyl-1-methyl-1H-pyrazol-4-yl)-6-methoxy-2-methyl-9H-pyrimido[4,5-b]indol-4-amine (Cpd. No. 181)

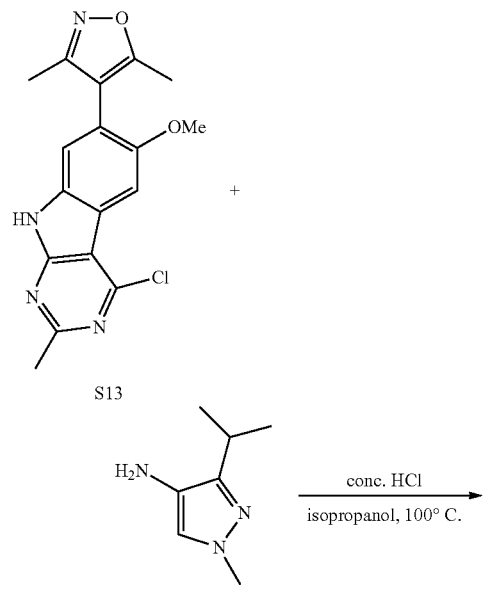

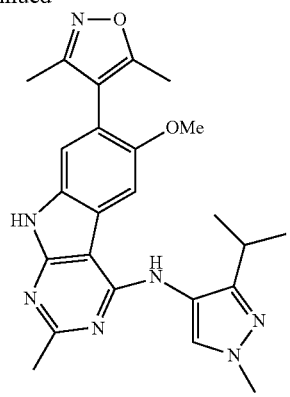

S13 (70 mg) and 3-isopropyl-1-methyl-1H-pyrazol-4-amine (68 mg) were dissolved in isopropanol (5 mL). Four drops of concentrated HCl was added via a glass pipette. The mixture was heated at reflux for overnight. The reaction was concentrated on a rotary evaporator and the remaining residues were purified by HPLC to yield the desired product Cpd. No. 181 in 45 mg as a salt of trifluoroacetic acid. ESI-MS calculated for C$_{24}$H$_{28}$N$_7$O$_2$ [M+H]$^+$=446.23; Observed: 446.44. $^1$H NMR (300 MHz, MeOD) δ 7.85 (s, 1H), 7.60 (brs, 1H), 7.47 (s, 1H), 3.95 (s, 3H), 3.89 (s, 3H), 3.02 (hept, J=6.7 Hz, 1H), 2.71 (s, 3H), 2.33 (s, 3H), 2.16 (s, 3H), 1.30 (d, J=7.0 Hz, 6H).

Example 131

Synthesis of 7-(3,5-dimethylisoxazol-4-yl)-N-(3-ethyl-1-methyl-1H-pyrazol-4-yl)-6-methoxy-2-methyl-9H-pyrimido[4,5-b]indol-4-amine (Cpd. No. 182)

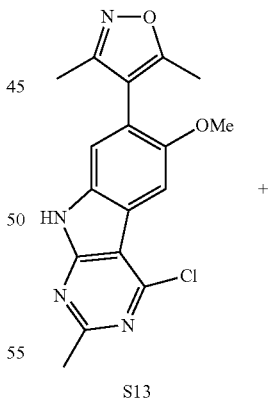

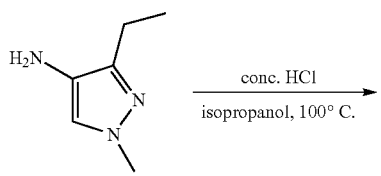

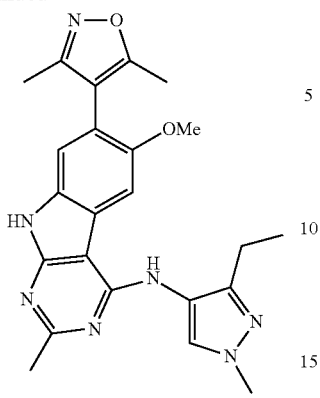

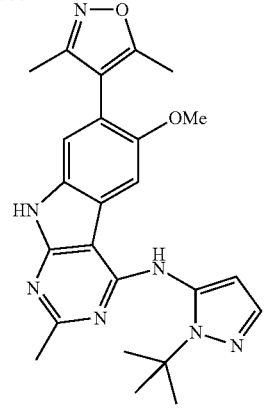

S13 (70 mg) and 3-ethyl-1-methyl-1H-pyrazol-4-amine (68 mg) were dissolved in isopropanol (5 mL). Four drops of concentrated HCl was added via a glass pipette. The mixture was heated at reflux for overnight. The reaction was concentrated on a rotary evaporator and the remaining residues were purified by HPLC to yield the desired product Cpd. No. 182 in 45 mg as a salt of trifluoroacetic acid. ESI-MS calculated for $C_{23}H_{26}N_7O_2$ $[M+H]^+=432.21$; Observed: 432.55.

Example 132

Synthesis of N-(1-(tert-butyl)-1H-pyrazol-5-yl)-7-(3,5-dimethylisoxazol-4-yl)-6-methoxy-2-methyl-9H-pyrimido[4,5-b]indol-4-amine (Cpd. No. 183)

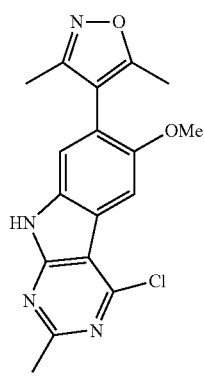

+

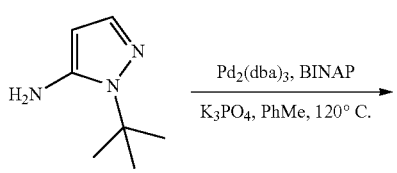

$Pd_2(dba)_3$ (18 mg) and BINAP (26 mg) were mixed in anhydrous toluene. And the mixture was heated at reflux for 3-4 minutes. This mixture was transferred into a round-bottom flask containing S13 (60 mg), 1-(tert-butyl)-1H-pyrazol-5-amine (84 mg), $K_3PO_4$ (130 mg), and toluene (2 mL). The mixture was heated at reflux for overnight before quenching with methanol. The reaction mixture was filtered and the mixture was purified by HPLC to yield Cpd. No. 183 as a $CF_3CO_2H$ salt in 20 mg. ESI-MS calculated for $C_{24}H_{28}N_7O_2$ $[M+H]^+=446.23$; Observed: 446.65.

Example 133

1-isopropyl-3,4-dimethyl-1H-pyrazol-5-amine (ZBB159)

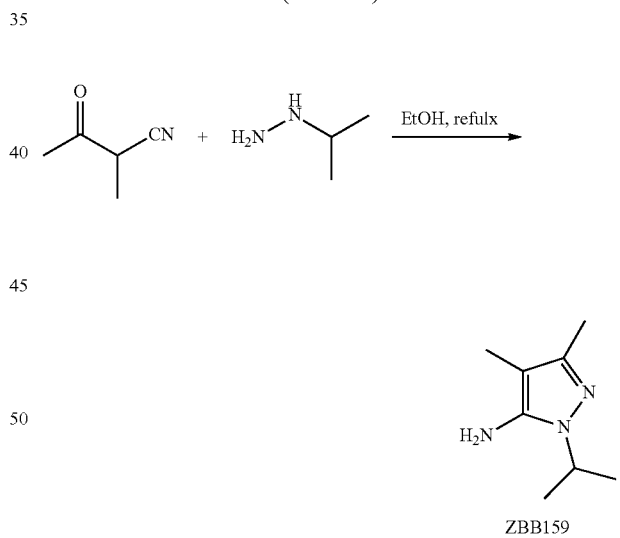

2-methyl-3-oxobutanenitrile (1 g) was dissolved in ethanol (30 mL). isopropylhydrazine. HCl salt (5 g) was added and the mixture was heated at reflux for overnight. The mixture was concentrated on a rotary evaporator followed by addition of ethyl acetate and aq. $NaHCO_3$. The aqueous layer was extracted with ethyl acetate and the organic layers were combined, dried, and concentrated on a rotary evaporator. The remaining residue was purified by flash column chromatography and the desired product was obtained in 1.3 g. ESI-MS calculated for $C_8H_{16}N_3[M+H]^+=154.13$; Observed: 154.66.

Example 134

Synthesis of 7-(3,5-dimethylisoxazol-4-yl)-N-(1-isopropyl-3,4-dimethyl-1H-pyrazol-5-yl)-6-methoxy-2-methyl-9H-pyrimido[4,5-b]indol-4-amine (Cpd. No. 81)

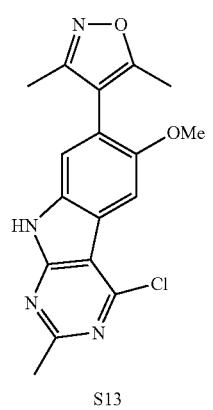

S13

+

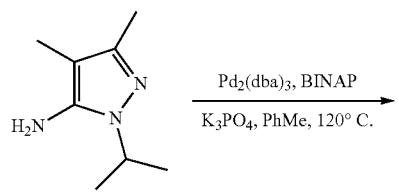

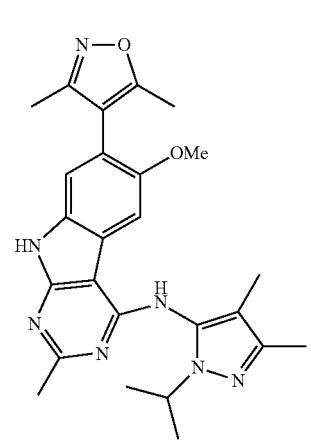

Pd$_2$(dba)$_3$ (18 mg) and BINAP (26 mg) were mixed in anhydrous toluene. And the mixture was heated at reflux for 3-4 minutes. This mixture was transferred into a round-bottom flask containing S13 (60 mg), 1-isopropyl-3,4-dimethyl-1H-pyrazol-5-amine (84 mg), K$_3$PO$_4$ (130 mg), and toluene (2 mL). The mixture was heated at reflux for overnight before quenching with methanol. The reaction mixture was filtered and the mixture was purified by HPLC to yield Cpd. No. 81 as a CF$_3$CO$_2$H salt in 20 mg. ESI-MS calculated for C$_{25}$H$_{30}$N$_7$O$_2$ [M+H]$^+$=460.24; Observed: 460.44.

Example 135

Synthesis of 1-(tert-butyl)-3,4-dimethyl-1H-pyrazol-5-amine (ZBB160)

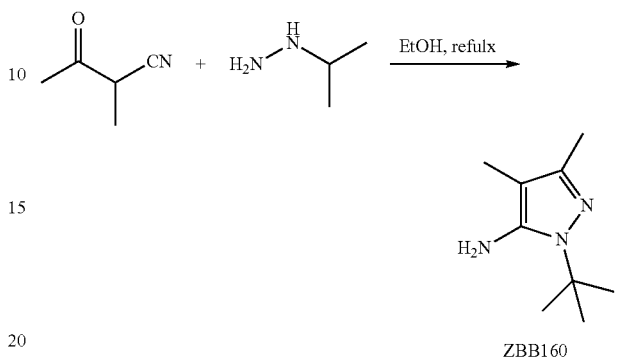

ZBB160

2-methyl-3-oxobutanenitrile (1 g) was dissolved in ethanol (30 mL). tert-butylhydrazine.HCl salt (5 g) was added and the mixture was heated at reflux for overnight. The mixture was concentrated on a rotary evaporator followed by addition of ethyl acetate and aq. NaHCO$_3$. The aqueous layer was extracted with ethyl acetate and the organic layers were combined, dried, and concentrated on a rotary evaporator. The remaining residue was purified by flash column chromatography and the desired product was obtained in 1.3 g. ESI-MS calculated for C$_9$H$_{18}$N$_3$[M+H]$^+$=168.15; Observed: 168.44.

Example 136

Synthesis of N-(1-(tert-butyl)-3,4-dimethyl-1H-pyrazol-5-yl)-7-(3,5-dimethylisoxazol-4-yl)-6-methoxy-2-methyl-9H-pyrimido[4,5-b]indol-4-amine (Cpd. No. 185)

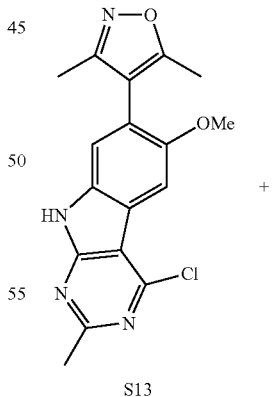

S13

+

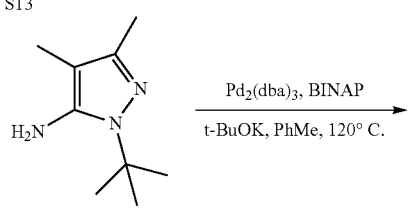

383

-continued

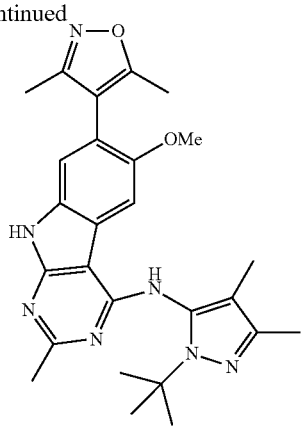

Pd$_2$(dba)$_3$ (18 mg) and BINAP (26 mg) were mixed in anhydrous toluene. And the mixture was heated at reflux for 3-4 minutes. This mixture was transferred into a round-bottom flask containing S13 (60 mg), 1-(tert-butyl)-3,4-dimethyl-1H-pyrazol-5-amine (84 mg), t-BuOK (100 mg), and toluene (2 mL). The mixture was heated at reflux for overnight before quenching with methanol. The reaction mixture was filtered and the mixture was purified by HPLC to yield Cpd. No. 185 as a CF$_3$CO$_2$H salt in 20 mg. ESI-MS calculated for C$_{26}$H$_{32}$N$_7$O$_2$ [M+H]$^+$=474.26; Observed: 474.44.

Example 137

Synthesis of 1-ethyl-3,4-dimethyl-1H-pyrazol-5-amine (ZBB164)

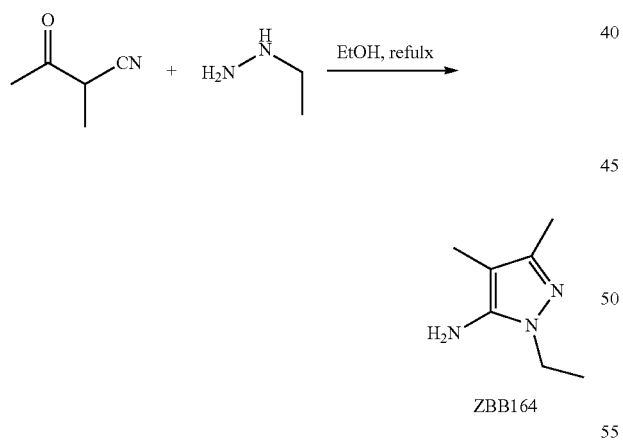

2-methyl-3-oxobutanenitrile (1 g) was dissolved in ethanol (30 mL). ethylhydrazine. HCl salt (5 g) was added and the mixture was heated at reflux for overnight. The mixture was concentrated on a rotary evaporator followed by addition of ethyl acetate and aq. NaHCO$_3$. The aqueous layer was extracted with ethyl acetate and the organic layers were combined, dried, and concentrated on a rotary evaporator. The remaining residue was purified by flash column chromatography and the desired product was obtained in 1.3 g. ESI-MS calculated for C$_7$H$_{14}$N$_3$[M+H]$^+$=140.11; Observed: 140.34.

384

Example 138

Synthesis of 7-(3,5-dimethylisoxazol-4-yl)-N-(1-ethyl-3,4-dimethyl-1H-pyrazol-5-yl)-6-methoxy-2-methyl-9H-pyrimido[4,5-b]indol-4-amine (Cpd. No. 186)

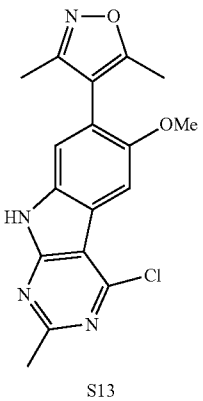

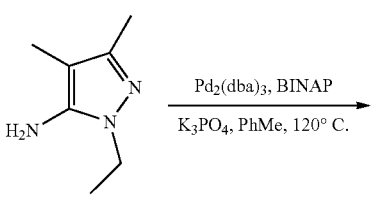

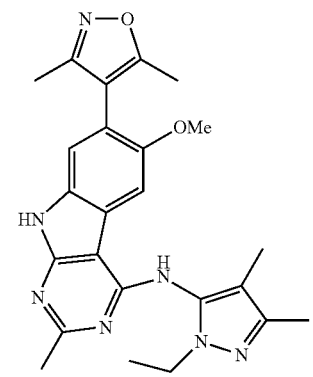

Pd$_2$(dba)$_3$ (18 mg) and BINAP (26 mg) were mixed in anhydrous toluene. And the mixture was heated at reflux for 3-4 minutes. This mixture was transferred into a round-bottom flask containing S13 (60 mg), 1-ethyl-3,4-dimethyl-1H-pyrazol-5-amine (84 mg), K$_3$PO$_4$ (130 mg), and toluene (2 mL). The mixture was heated at reflux for overnight before quenching with methanol. The reaction mixture was filtered and the mixture was purified by HPLC to yield Cpd. No. 186 as a CF$_3$CO$_2$H salt in 25 mg. ESI-MS calculated for C$_{24}$H$_{28}$N$_7$O$_2$ [M+H]$^+$=446.23; Observed: 446.36.

Example 139

Synthesis of 1-cyclobutyl-3,4-dimethyl-1H-pyrazol-5-amine (ZBB165)

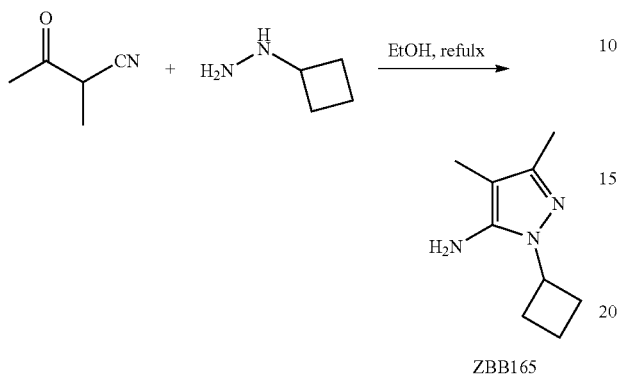

2-methyl-3-oxobutanenitrile (1 g) was dissolved in ethanol (30 mL). cyclobutylhydrazine. HCl salt (5 g) was added and the mixture was heated at reflux for overnight. The mixture was concentrated on a rotary evaporator followed by addition of ethyl acetate and aq. NaHCO$_3$. The aqueous layer was extracted with ethyl acetate and the organic layers were combined, dried, and concentrated on a rotary evaporator. The remaining residue was purified by flash column chromatography and the desired product was obtained in 1.3 g. ESI-MS calculated for C$_9$H$_{16}$N$_3$[M+H]$^+$=166.13; Observed: 166.64.

Synthesis of N-(1-cyclobutyl-3,4-dimethyl-1H-pyrazol-5-yl)-7-(3,5-dimethylisoxazol-4-yl)-6-methoxy-2-methyl-9H-pyrimido[4,5-b]indol-4-amine (Cpd. No. 187)

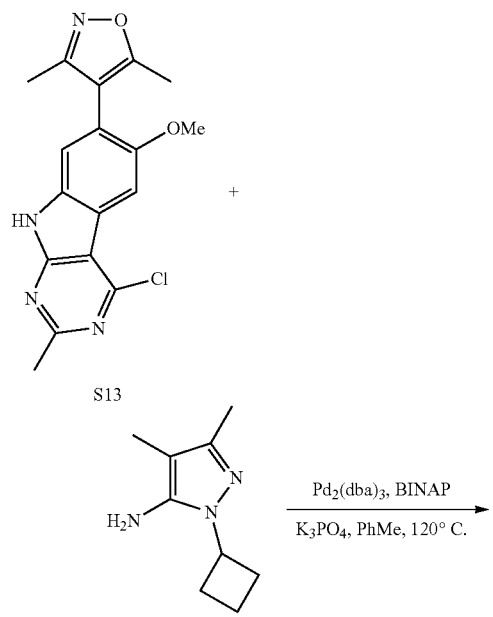

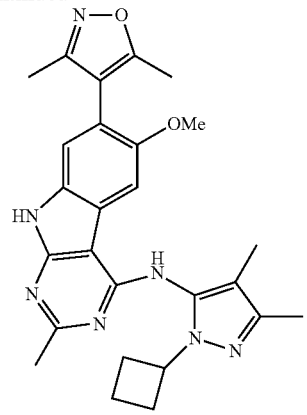

Pd$_2$(dba)$_3$ (18 mg) and BINAP (26 mg) were mixed in anhydrous toluene. And the mixture was heated at reflux for 3-4 minutes. This mixture was transferred into a round-bottom flask containing S13 (60 mg), 1-cyclobutyl-3,4-dimethyl-1H-pyrazol-5-amine (84 mg), K$_3$PO$_4$ (130 mg), and toluene (2 mL). The mixture was heated at reflux for overnight before quenching with methanol. The reaction mixture was filtered and the mixture was purified by HPLC to yield Cpd. No. 187 as a CF$_3$CO$_2$H salt in 30 mg. ESI-MS calculated for C$_{26}$H$_{30}$N$_7$O$_2$ [M+H]$^+$=472.24; Observed: 472.66.

Example 140

Synthesis of 1-cyclopropyl-3,4-dimethyl-1H-pyrazol-5-amine (ZBB170)

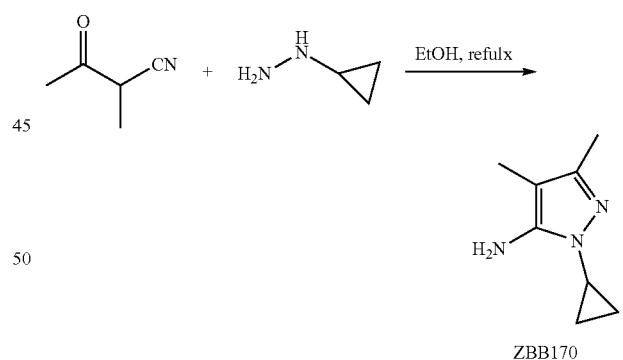

2-methyl-3-oxobutanenitrile (1 g) was dissolved in ethanol (30 mL). cyclopropylhydrazine. HCl salt (5 g) was added and the mixture was heated at reflux for overnight. The mixture was concentrated on a rotary evaporator followed by addition of ethyl acetate and aq. NaHCO$_3$. The aqueous layer was extracted with ethyl acetate and the organic layers were combined, dried, and concentrated on a rotary evaporator. The remaining residue was purified by flash column chromatography and the desired product was obtained in 1.3 g. ESI-MS calculated for C$_8$H$_{14}$N$_3$[M+H]$^+$=152.11; Observed: 152.44.

Example 141

Synthesis of N-(1-cyclopropyl-3,4-dimethyl-1H-pyrazol-5-yl)-7-(3,5-dimethylisoxazol-4-yl)-6-methoxy-2-methyl-9H-pyrimido[4,5-b]indol-4-amine (Cpd. No. 188)

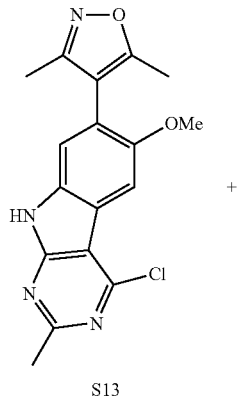

S13

+

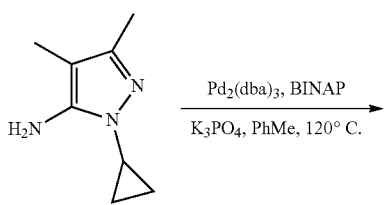

Pd$_2$(dba)$_3$, BINAP
K$_3$PO$_4$, PhMe, 120° C.

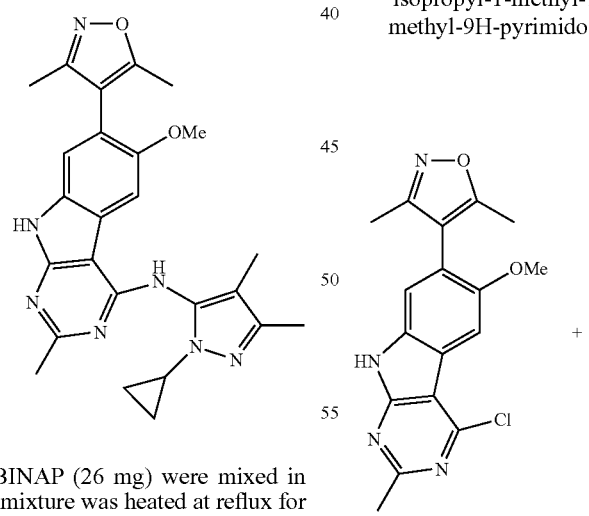

Pd$_2$(dba)$_3$ (18 mg) and BINAP (26 mg) were mixed in anhydrous toluene. And the mixture was heated at reflux for 3-4 minutes. This mixture was transferred into a round-bottom flask containing S13 (60 mg), 1-cyclopropyl-3,4-dimethyl-1H-pyrazol-5-amine (84 mg), K$_3$PO$_4$ (130 mg), and toluene (2 mL). The mixture was heated at reflux for overnight before quenching with methanol. The reaction mixture was filtered and the mixture was purified by HPLC to yield Cpd. No. 188 as a CF$_3$CO$_2$H salt in 25 mg. ESI-MS calculated for C$_{25}$H$_{28}$N$_7$O$_2$ [M+H]$^+$=458.23; Observed: 458.56.

Example 142

Synthesis of 4-isopropyl-1-methyl-1H-pyrazol-5-amine (ZBB171)

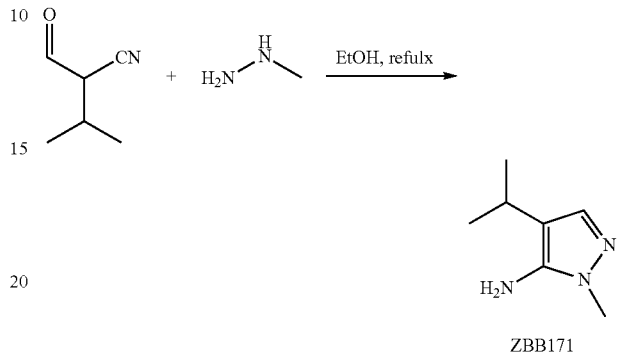

ZBB171

2-formyl-3-methylbutanenitrile (1 g) was dissolved in ethanol (30 mL). methylhydrazine (5 g) was added and the mixture was heated at reflux for overnight. The mixture was concentrated on a rotary evaporator followed by addition of ethyl acetate and aq. NaHCO$_3$. The aqueous layer was extracted with ethyl acetate and the organic layers were combined, dried, and concentrated on a rotary evaporator. The remaining residue was purified by flash column chromatography and the desired product was obtained in 0.4 g. ESI-MS calculated for C$_7$H$_{14}$N$_3$[M+H]$^+$=140.11; Observed: 140.43.

Synthesis of 7-(3,5-dimethylisoxazol-4-yl)-N-(4-isopropyl-1-methyl-1H-pyrazol-5-yl)-6-methoxy-2-methyl-9H-pyrimido[4,5-b]indol-4-amine (Cpd. No. 79)

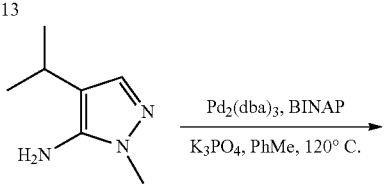

S13

+

Pd$_2$(dba)$_3$, BINAP
K$_3$PO$_4$, PhMe, 120° C.

389
-continued

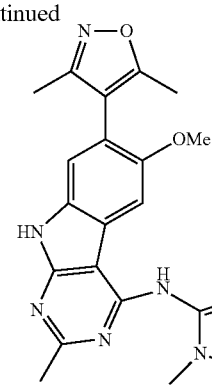

Pd₂(dba)₃ (18 mg) and BINAP (26 mg) were mixed in anhydrous toluene. And the mixture was heated at reflux for 3-4 minutes. This mixture was transferred into a round-bottom flask containing S13 (60 mg), 4-isopropyl-1-methyl-1H-pyrazol-5-amine (84 mg), K₃PO₄ (130 mg), and toluene (2 mL). The mixture was heated at reflux for overnight before quenching with methanol. The reaction mixture was filtered and the mixture was purified by HPLC to yield Cpd. No. 79 as a CF₃CO₂H salt in 12 mg. ESI-MS calculated for $C_{24}H_{28}N_7O_2$ $[M+H]^+$=446.23; Observed: 446.43. ¹H NMR (300 MHz, MeOD) δ 7.60 (s, 1H), 7.49 (s, 1H), 3.86 (s, 3H), 3.81 (s, 3H), 2.87-2.75 (m, 1H), 2.73 (s, 3H), 2.32 (s, 3H), 2.15 (s, 3H), 1.20 (d, J=6.9 Hz, 6H).

Example 143

Synthesis of 2-isopropyl-4-methylthiazol-5-amine (ZBB179)

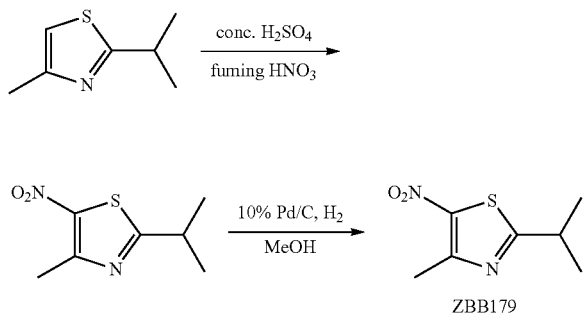

The mixture of 2-isopropyl-4-methylthiazole (500 mg), conc. H₂SO₄ (1 mL) and fuming HNO₃ (1 mL) was heated at 100° C. overnight. Then the mixture was poured into cooled aq. NaOH water solution and extracted with Ethyl acetate. The organic phase was concentrated on a rotary evaporator and was dissolved in MeOH (10 mL). 500 mg 10% Pd/C was added. the reaction mixture was degassed 2 times, each time replacing the vacuum with hydrogen, then stirred at room temperature under H₂ overnight. The mixture was filtered and concentrated on a rotary evaporator to give ZBB179 (300 mg). ESI-MS calculated for $C_7H_{13}N_2S$ $[M+H]^+$=157.07; Observed: 157.44. ¹H NMR (300 MHz, CDCl₃) δ 3.23 (hept, J=6.8 Hz, 1H), 2.79 (s, 3H), 1.40 (d, J=6.9 Hz, 6H).

390

Synthesis of N-(7-(3,5-dimethylisoxazol-4-yl)-6-methoxy-2-methyl-9H-pyrimido[4,5-b]indol-4-yl)-2-isopropyl-4-methylthiazol-5-amine (Cpd. No. 190)

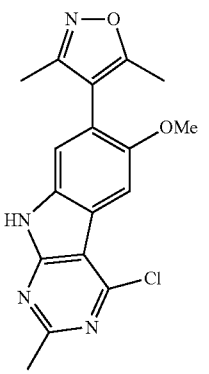

+

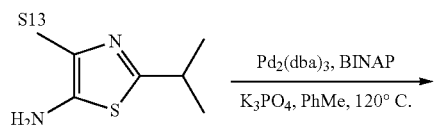

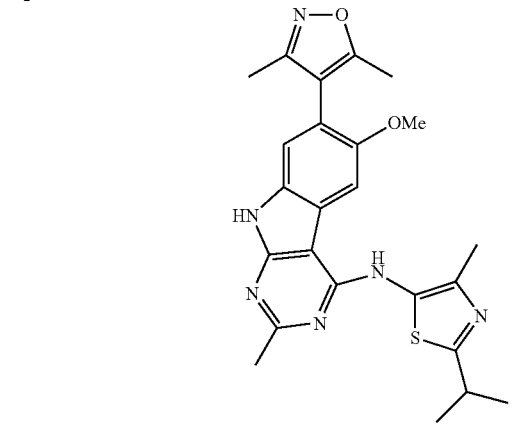

Pd₂(dba)₃ (18 mg) and BINAP (26 mg) were mixed in anhydrous toluene. And the mixture was heated at reflux for 3-4 minutes. This mixture was transferred into a round-bottom flask containing S13 (60 mg), 2-isopropyl-4-methylthiazol-5-amine (84 mg), K₃PO₄ (130 mg), and toluene (2 mL). The mixture was heated at reflux for overnight before quenching with methanol. The reaction mixture was filtered and the mixture was purified by HPLC to yield Cpd. No. 190 as a CF₃CO₂H salt in 35 mg. ESI-MS calculated for $C_{24}H_{27}N_6O_2S$ $[M+H]^+$=463.19; Observed: 463.44.

Example 144

Synthesis of 4-isopropyl-2-methylthiazol-5-amine (ZBB181)

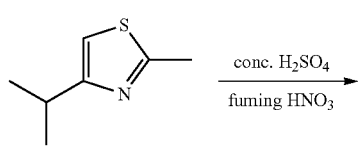

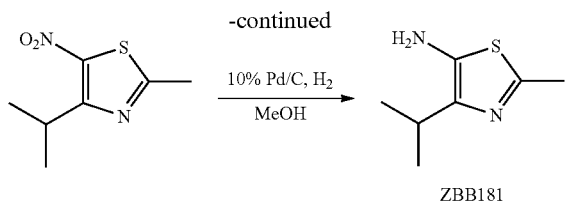

The mixture of 4-isopropyl-2-methylthiazole (500 mg), conc. H$_2$SO$_4$ (1 mL) and fuming HNO$_3$ (1 mL) was heated at 100° C. overnight. Then the mixture was poured into cooled aq. NaOH water solution and extracted with Ethyl acetate. The organic phase was concentrated on a rotary evaporator and was dissolved in MeOH (10 mL). 500 mg 10% Pd/C was added. the reaction mixture was degassed 2 times, each time replacing the vacuum with hydrogen, then stirred at room temperature under H$_2$ overnight. The mixture was filtered and concentrated on a rotary evaporator to give ZBB181 (400 mg). ESI-MS calculated for C$_7$H$_{13}$N$_2$S[M+H]$^+$=157.07; Observed: 157.34.

Synthesis of N-(7-(3,5-dimethylisoxazol-4-yl)-6-methoxy-2-methyl-9H-pyrimido[4,5-b]indol-4-yl)-4-isopropyl-2-methylthiazol-5-amine (Cpd. No. 84)

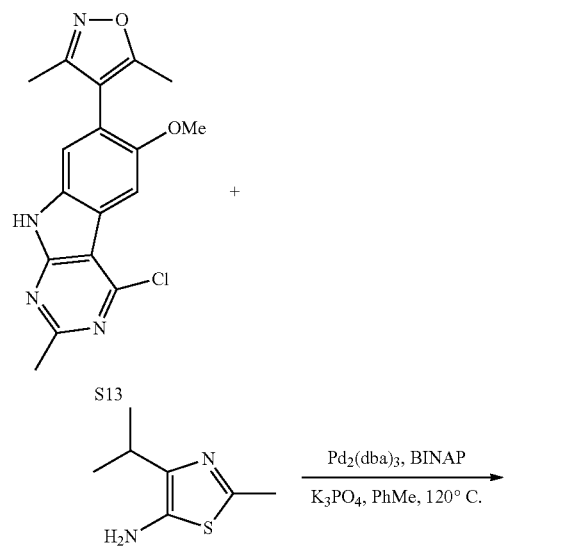

Pd$_2$(dba)$_3$ (18 mg) and BINAP (26 mg) were mixed in anhydrous toluene, and the mixture was heated at reflux for 3-4 minutes. This mixture was transferred into a round-bottom flask containing S13 (60 mg), 4-isopropyl-2-methylthiazol-5-amine (84 mg), K$_3$PO$_4$ (130 mg), and toluene (2 mL). The mixture was heated at reflux for overnight before quenching with methanol. The reaction mixture was filtered and the mixture was purified by HPLC to yield Cpd. No. 84 as a CF$_3$CO$_2$H salt in 35 mg. ESI-MS calculated for C$_{24}$H$_{27}$N$_6$O$_2$S [M+H]$^+$=463.19; Observed: 463.45. $^1$H NMR (300 MHz, MeOD) δ 7.84 (brs, 1H), 7.49 (s, 1H), 3.93 (s, 3H), 3.13 (dt, J=13.7, 6.8 Hz, 1H), 2.78 (s, 3H), 2.72 (s, 3H), 2.34 (s, 3H), 2.17 (s, 3H), 1.32 (d, J=6.9 Hz, 6H).

Example 145

Synthesis of 1-cyclopropyl-3-methyl-1H-pyrazol-5-amine (ZBB182)

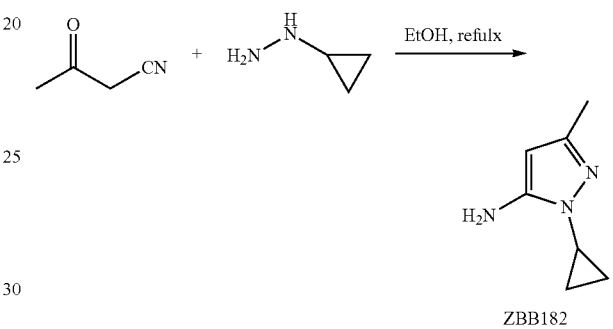

3-oxobutanenitrile (1 g) was dissolved in ethanol (30 mL). cyclopropylhydrazine (5 g) was added and the mixture was heated at reflux for overnight. The mixture was concentrated on a rotary evaporator followed by addition of ethyl acetate and aq. NaHCO$_3$. The aqueous layer was extracted with ethyl acetate and the organic layers were combined, dried, and concentrated on a rotary evaporator. The remaining residue was purified by flash column chromatography and the desired product was obtained in 0.4 g. ESI-MS calculated for C$_7$H$_{12}$N$_3$[M+H]$^+$=138.10; Observed: 138.33.

Synthesis of N-(1-cyclopropyl-3-methyl-1H-pyrazol-5-yl)-7-(3,5-dimethylisoxazol-4-yl)-6-methoxy-2-methyl-9H-pyrimido[4,5-b]indol-4-amine (Cpd. No. 192)

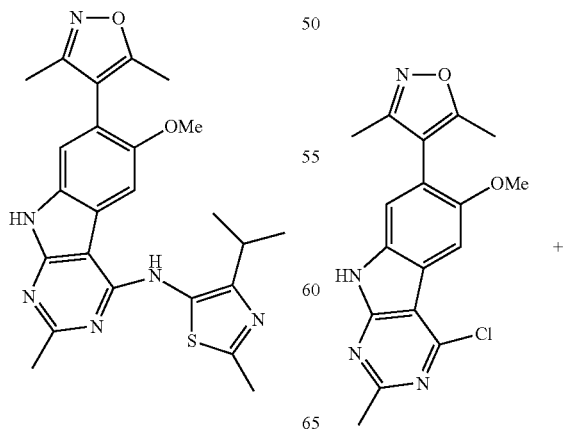

-continued

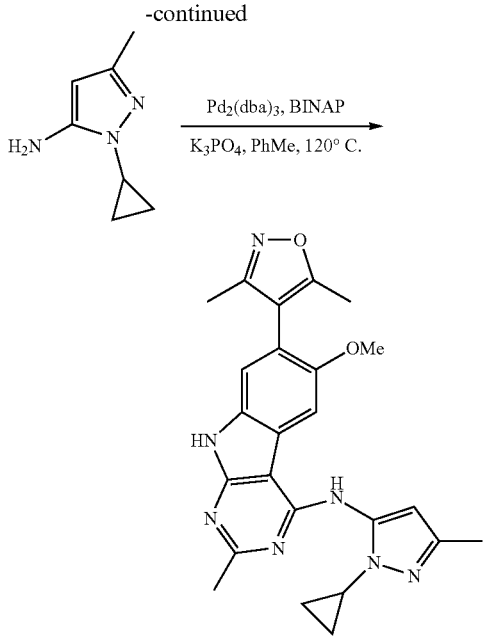

Pd$_2$(dba)$_3$ (18 mg) and BINAP (26 mg) were mixed in anhydrous toluene. And the mixture was heated at reflux for 3-4 minutes. This mixture was transferred into a round-bottom flask containing S13 (60 mg), 1-cyclopropyl-3-methyl-1H-pyrazol-5-amine (84 mg), K$_3$PO$_4$ (130 mg), and toluene (2 mL). The mixture was heated at reflux for overnight before quenching with methanol. The reaction mixture was filtered and the mixture was purified by HPLC to yield Cpd. No. 192 as a CF$_3$CO$_2$H salt in 30 mg. ESI-MS calculated for C$_{24}$H$_{26}$N$_7$O$_2$ [M+H]$^+$=444.21; Observed: 444.65.

Example 146

Synthesis of 3-(tert-butyl)-1-methyl-1H-pyrazol-4-amine (ZBB186)

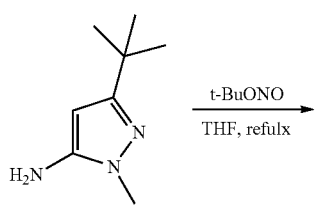

-continued

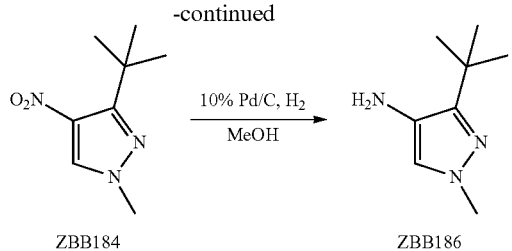

The mixture of 3-(tert-butyl)-1-methyl-1H-pyrazol-5-amine (500 g), t-BuONO (2 mL) in THF (10 mL) was heated at 90° C. for 3 h. Then the mixture was concentrated on a rotary evaporator and was dissolved in conc. H$_2$SO$_4$ (1 mL) and fuming HNO$_3$ (1 mL). And the mixture was heated at 60° C. overnight. Then the mixture was poured into cooled aq. NaOH water solution and extracted with Ethyl acetate. The organic phase was concentrated on a rotary evaporator. The remaining residue was purified by flash column chromatography to give ZBB184. $^1$H NMR (300 MHz, CDCl$_3$) δ 8.18 (s, 1H), 3.86 (s, 3H), 1.41 (s, 9H).

ZBB184 (200 mg) was dissolved in MeOH (10 mL). 50 mg 10% Pd/C was added. the reaction mixture was degassed 2 times, each time replacing the vacuum with hydrogen, then stirred at room temperature under H$_2$ overnight. The mixture was filtered and concentrated on a rotary evaporator to give ZBB186 (150 mg). ESI-MS calculated for C$_8$H$_{16}$N$_3$ [M+H]$^+$=154.13; Observed: 154.44.

Synthesis of N-(3-(tert-butyl)-1-methyl-1H-pyrazol-4-yl)-7-(3,5-dimethylisoxazol-4-yl)-6-methoxy-2-methyl-9H-pyrimido[4,5-b]indol-4-amine (Cpd. No. 193)

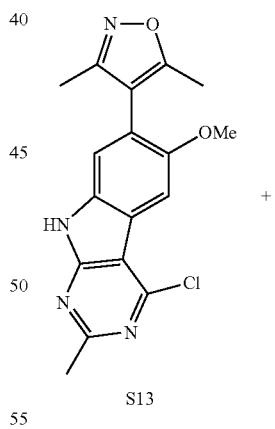

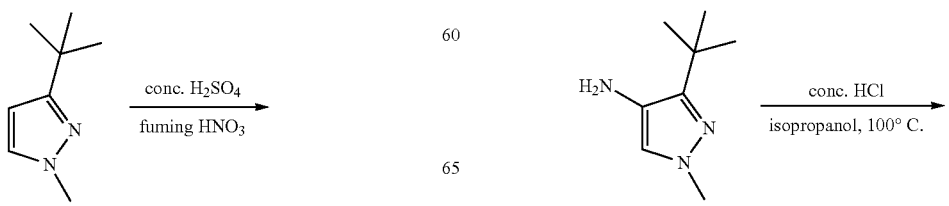

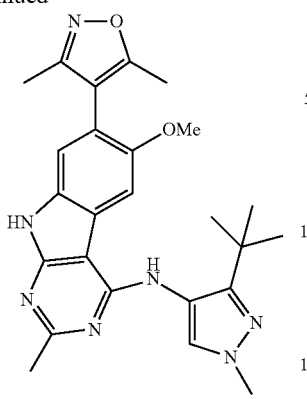

S13 (70 mg) and 3-(tert-butyl)-1-methyl-1H-pyrazol-4-amine (68 mg) were dissolved in isopropanol (5 mL). Four drops of concentrated HCl was added via a glass pipette. The mixture was heated at reflux for overnight. The reaction was concentrated on a rotary evaporator and the remaining residues were purified by HPLC to yield the desired product Cpd. No. 193 in 45 mg as a salt of trifluoroacetic acid. ESI-MS calculated for $C_{25}H_{30}N_7O_2$ [M+H]$^+$=460.24; Observed: 460.55. $^1$H NMR (300 MHz, MeOD) δ 7.85 (s, 1H), 7.46 (s, 1H), 3.94 (s, 3H), 3.88 (s, 3H), 2.71 (s, 3H), 2.34 (s, 3H), 2.17 (s, 3H), 1.38 (s, 9H).

Example 147

Synthesis of 3-isopropyl-1,5-dimethyl-1H-pyrazol-4-amine (ZBB192)

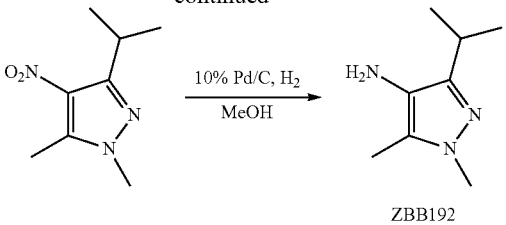

The mixture of 1-(1,5-dimethyl-1H-pyrazol-3-yl)ethan-1-one (1 g), t-BuOK (1.1 g) and CH$_3$PPh$_3$Br (3.9 g) in THF (10 mL) was stirred at room temperature for 5 h. Then aq. NaHCO$_3$ was added. The aqueous layer was extracted with ethyl acetate and the organic layers were combined, dried, and concentrated on a rotary evaporator. The remaining residue was purified by flash column chromatography and the desired product ZBB185 was obtained in 0.8 g.

ZBB185 (0.5 g) was dissolved in MeOH (10 mL). 50 mg 10% Pd/C was added. the reaction mixture was degassed 2 times, each time replacing the vacuum with hydrogen, then stirred at room temperature under H$_2$ overnight. The mixture was filtered and concentrated on a rotary evaporator to give a crude product which was dissolved in conc. H$_2$SO$_4$ (1 mL) and fuming HNO$_3$ (1 mL). And the mixture was heated at 60° C. overnight. Then the mixture was poured into cooled aq. NaOH water solution and extracted with Ethyl acetate. The organic phase was concentrated on a rotary evaporator to give the nitro intermediate which was dissolved in MeOH (10 mL). 50 mg 10% Pd/C was added. the reaction mixture was degassed 2 times, each time replacing the vacuum with hydrogen, then stirred at room temperature under H$_2$ overnight. The mixture was filtered and concentrated on a rotary evaporator to give ZBB192 (0.4 g). ESI-MS calculated for $C_8H_{16}N_3$[M+H]$^+$=154.13; Observed: 154.45.

Synthesis of 7-(3,5-dimethylisoxazol-4-yl)-N-(3-isopropyl-1,5-dimethyl-1H-pyrazol-4-yl)-6-methoxy-2-methyl-9H-pyrimido[4,5-b]indol-4-amine (Cpd. No. 194)

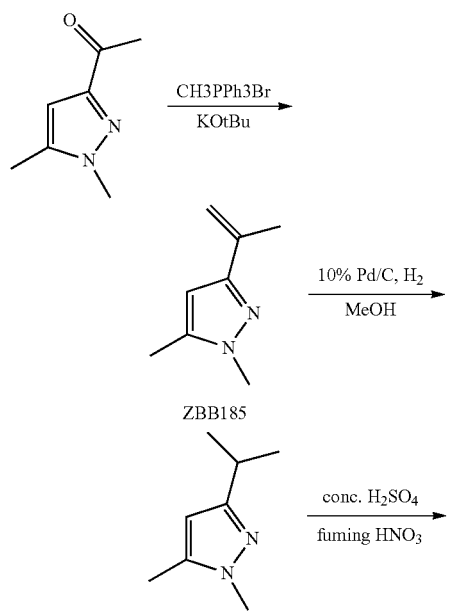

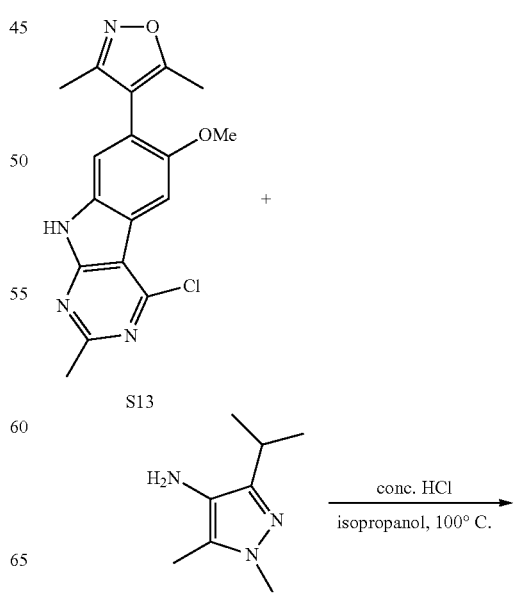

-continued

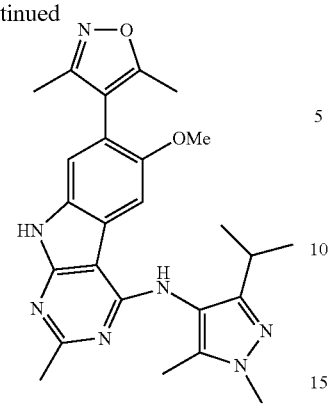

-continued

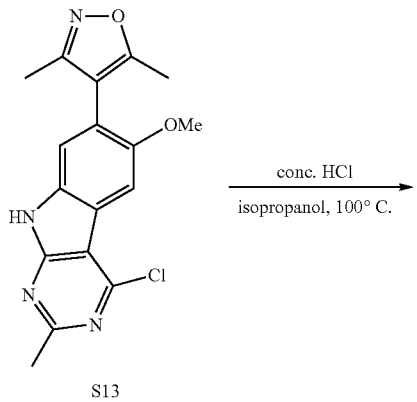

S13

S13 (70 mg) and 3-isopropyl-1,5-dimethyl-1H-pyrazol-4-amine (68 mg) were dissolved in isopropanol (5 mL). Four drops of concentrated HCl was added via a glass pipette. The mixture was heated at reflux for overnight. The reaction was concentrated on a rotary evaporator and the remaining residues were purified by HPLC to yield the desired product Cpd. No. 194 in 45 mg as a salt of trifluoroacetic acid. ESI-MS calculated for $C_{25}H_{30}N_7O_2$ $[M+H]^+=460.24$; Observed: 460.45.

Example 148

Synthesis of tert-butyl (3-cyclopropyl-1-methyl-1H-pyrazol-4-yl)carbamate (ZBB195)

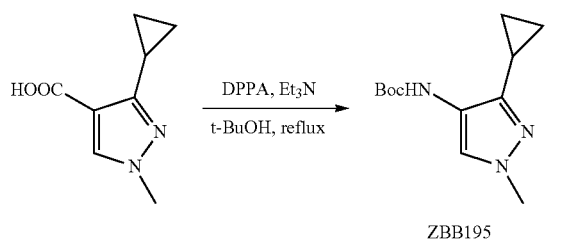

The mixture of 3-cyclopropyl-1-methyl-1H-pyrazole-4-carboxylic acid (0.5 g), DPPA (1.16 mL) and Et₃N (1.25 mL) in t-BuOH (10 mL) was stirred at room temperature for 3 h. Then the mixture was refluxed for 1 day and then concentrated on a rotary evaporator. The remaining residue was purified by flash column chromatography and the desired product ZBB195 was obtained in 0.3 g.

Synthesis of N-(3-cyclopropyl-1-methyl-1H-pyrazol-4-yl)-7-(3,5-dimethylisoxazol-4-yl)-6-methoxy-2-methyl-9H-pyrimido[4,5-b]indol-4-amine (Cpd. No. 195)

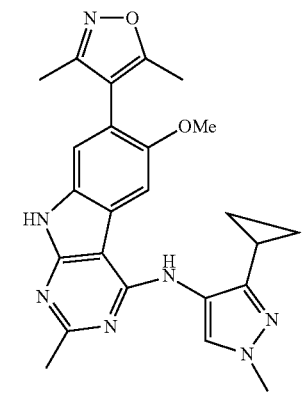

tert-butyl (3-cyclopropyl-1-methyl-1H-pyrazol-4-yl)carbamate (0.15 g) was dissolved in DCM/TFA (10 mL, 1:1) and the mixture was stirred at room temperature for 3 h. Then the mixture was concentrated on a rotary evaporator to give the crude amine which was dissolved in isopropanol (5 mL). Four drops of concentrated HCl and S13 (70 mg) was added via a glass pipette. The mixture was heated at reflux for overnight. The reaction was concentrated on a rotary evaporator and the remaining residues were purified by HPLC to yield the desired product Cpd. No. 195 in 47 mg as a salt of trifluoroacetic acid. ESI-MS calculated for $C_{24}H_{26}N_7O_2$ $[M+H]^+=444.21$; Observed: 444.34. ¹H NMR (300 MHz, MeOD) δ 8.0-7.7 (m, 2H), 7.47 (s, 1H), 3.92 (s, 3H), 3.91 (s, 3H), 2.72 (s, 3H), 2.34 (s, 3H), 2.17 (s, 3H), 1.79 (tt, J=7.9, 5.5 Hz, 1H), 0.95-0.79 (m, 4H).

Example 149

Synthesis of 1-(tert-butyl)-4-methyl-1H-pyrazol-5-amine (ZBB197)

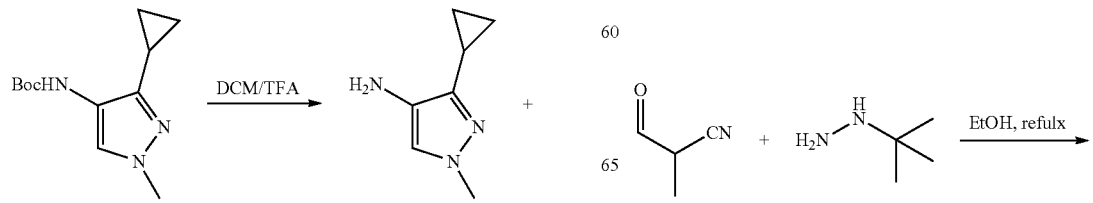

-continued

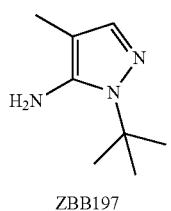

ZBB197

2-methyl-3-oxopropanenitrile (1 g) was dissolved in ethanol (30 mL). tert-butylhydrazine. HCl salt (5 g) was added and the mixture was heated at reflux for overnight. The mixture was concentrated on a rotary evaporator followed by addition of ethyl acetate and aq. NaHCO$_3$. The aqueous layer was extracted with ethyl acetate and the organic layers were combined, dried, and concentrated on a rotary evaporator. The remaining residue was purified by flash column chromatography and the desired product was obtained in 0.3 g. ESI-MS calculated for C$_8$H$_{16}$N$_3$[M+H]$^+$=154.13; Observed: 154.44. $^1$H NMR (300 MHz, CDCl$_3$) δ 7.12 (s, 1H), 3.29 (s, 2H), 1.90 (s, 3H), 1.64 (s, 9H).

Synthesis of N-(1-(tert-butyl)-4-methyl-1H-pyrazol-5-yl)-7-(3,5-dimethylisoxazol-4-yl)-6-methoxy-2-methyl-9H-pyrimido[4,5-b]indol-4-amine (Cpd. No. 196)

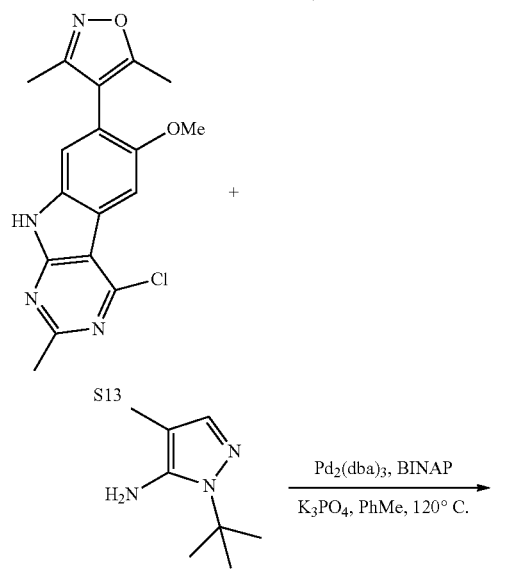

Pd$_2$(dba)$_3$ (18 mg) and BINAP (26 mg) were mixed in anhydrous toluene. And the mixture was heated at reflux for 3-4 minutes. This mixture was transferred into a round-bottom flask containing S13 (60 mg), 1-(tert-butyl)-4-methyl-1H-pyrazol-5-amine (84 mg), t-BuOK (130 mg), and toluene (2 mL). The mixture was heated at reflux for overnight before quenching with methanol. The reaction mixture was filtered and the mixture was purified by HPLC to yield Cpd. No. 196 as a CF$_3$CO$_2$H salt in 25 mg. ESI-MS calculated for C$_{25}$H$_{30}$N$_7$O$_2$ [M+H]$^+$=460.24; Observed: 460.44. $^1$H NMR (300 MHz, MeOD) δ 7.51 (s, 1H), 7.45 (s, 1H), 3.80 (s, 3H), 2.75 (s, 3H), 2.32 (s, 3H), 2.15 (s, 3H), 1.85 (s, 3H), 1.69 (s, 9H).

Example 150

Synthesis of 1-cyclopropyl-4-methyl-1H-pyrazol-5-amine (ZBB198)

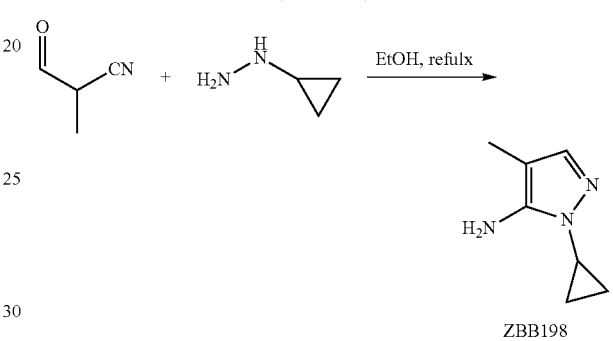

ZBB198

2-methyl-3-oxopropanenitrile (1 g) was dissolved in ethanol (30 mL). cyclopropylhydrazine. HCl salt (5 g) was added and the mixture was heated at reflux for overnight. The mixture was concentrated on a rotary evaporator followed by addition of ethyl acetate and aq. NaHCO$_3$. The aqueous layer was extracted with ethyl acetate and the organic layers were combined, dried, and concentrated on a rotary evaporator. The remaining residue was purified by flash column chromatography and the desired product was obtained in 0.3 g. ESI-MS calculated for C$_7$H$_{12}$N$_3$ [M+H]$^+$=138.10; Observed: 138.44.

Synthesis of N-(1-cyclopropyl-4-methyl-1H-pyrazol-5-yl)-7-(3,5-dimethylisoxazol-4-yl)-6-methoxy-2-methyl-9H-pyrimido[4,5-b]indol-4-amine (Cpd. No. 197)

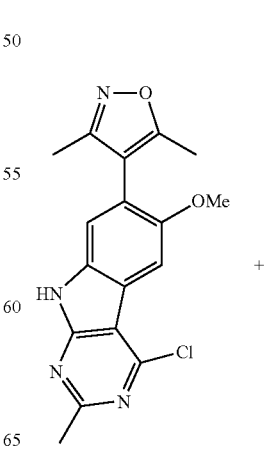

S13

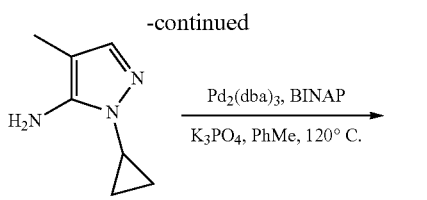

Pd₂(dba)₃ (18 mg) and BINAP (26 mg) were mixed in anhydrous toluene. And the mixture was heated at reflux for 3-4 minutes. This mixture was transferred into a round-bottom flask containing S13 (60 mg), 1-cyclopropyl-4-methyl-1H-pyrazol-5-amine (84 mg), K₃PO₄ (130 mg), and toluene (2 mL). The mixture was heated at reflux for overnight before quenching with methanol. The reaction mixture was filtered and the mixture was purified by HPLC to yield Cpd. No. 197 as a CF₃CO₂H salt in 25 mg. ESI-MS calculated for $C_{24}H_{26}N_7O_2$ [M+H]⁺=444.21; Observed: 444.54. ¹H NMR (300 MHz, MeOD) δ 7.73 (s, 1H), 7.49 (s, 1H), 7.47 (s, 1H), 3.89 (s, 3H), 3.77-3.62 (m, 1H), 2.77 (s, 3H), 2.34 (s, 3H), 2.17 (s, 3H), 2.14 (s, 3H), 1.17-0.96 (m, 4H).

Example 151

Synthesis of 1-cyclobutyl-4-methyl-1H-pyrazol-5-amine (ZBB200)

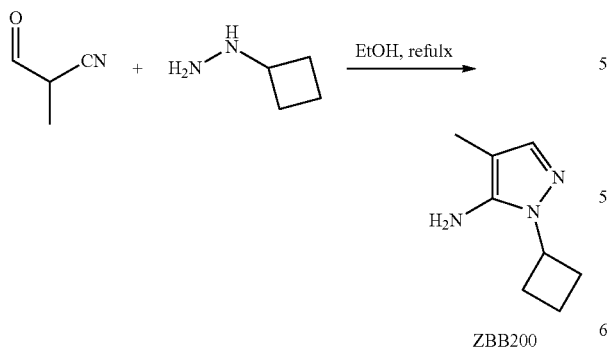

2-methyl-3-oxopropanenitrile (1 g) was dissolved in ethanol (30 mL). cyclobutylhydrazine. HCl salt (5 g) was added and the mixture was heated at reflux for overnight. The mixture was concentrated on a rotary evaporator followed by addition of ethyl acetate and aq. NaHCO₃. The aqueous layer was extracted with ethyl acetate and the organic layers were combined, dried, and concentrated on a rotary evaporator. The remaining residue was purified by flash column chromatography and the desired product was obtained in 0.3 g. ESI-MS calculated for $CH_{14}N_3$[M+H]⁺=152.11; Observed: 152.54. ¹H NMR (300 MHz, CDCl₃) δ 7.21 (s, 1H), 4.72-4.52 (m, 1H), 3.23 (brs, 2H), 2.76-2.58 (m, 2H), 2.45-2.28 (m, 2H), 2.03-1.67 (m, 5H).

Synthesis of N-(1-cyclobutyl-4-methyl-1H-pyrazol-5-yl)-7-(3,5-dimethylisoxazol-4-yl)-6-methoxy-2-methyl-9H-pyrimido[4,5-b]indol-4-amine (Cpd. No. 198)

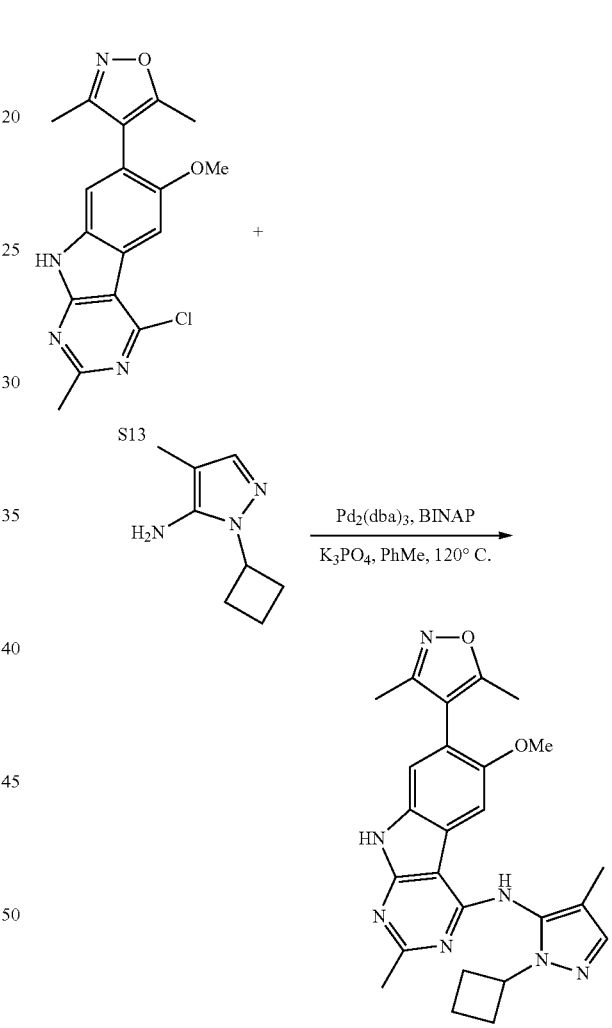

Pd₂(dba)₃ (18 mg) and BINAP (26 mg) were mixed in anhydrous toluene. And the mixture was heated at reflux for 3-4 minutes. This mixture was transferred into a round-bottom flask containing S13 (60 mg), 1-cyclobutyl-4-methyl-1H-pyrazol-5-amine (84 mg), K₃PO₄ (130 mg), and toluene (2 mL). The mixture was heated at reflux for overnight before quenching with methanol. The reaction mixture was filtered and the mixture was purified by HPLC to yield Cpd. No. 198 as a CF₃CO₂H salt in 25 mg. ESI-MS calculated for $C_{25}H_{28}N_7O_2$ [M+H]⁺=458.23; Observed: 458.55. ¹H NMR (300 MHz, MeOD) δ 7.60 (s, 1H), 7.48 (s, 1H), 4.98-4.79 (m, 1H), 3.86 (s, 3H), 2.81-2.57 (m, 5H), 2.40-2.25 (m, 5H), 2.16 (s, 3H), 1.97 (s, 3H), 1.90-1.70 (m, 2H).

Example 152

Synthesis of 7-(3,5-dimethylisoxazol-4-yl)-N-(1-ethyl-3-isopropyl-1H-pyrazol-4-yl)-6-methoxy-2-methyl-9H-pyrimido[4,5-b]indol-4-amine (Cpd. No. 199)

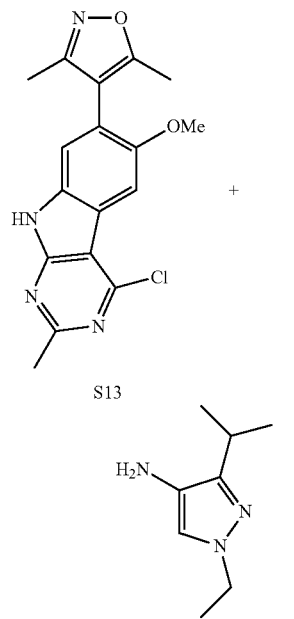

S13 (70 mg) and 1-ethyl-3-isopropyl-1H-pyrazol-4-amine (68 mg) were dissolved in isopropanol (5 mL). Four drops of concentrated HCl was added via a glass pipette. The mixture was heated at reflux for overnight. The reaction was concentrated on a rotary evaporator and the remaining residues were purified by HPLC to yield the desired product Cpd. No. 199 in 45 mg as a salt of trifluoroacetic acid. ESI-MS calculated for $C_{25}H_{30}N_7O_2$ $[M+H]^+$=460.24; Observed: 460.55.

Example 153

Synthesis of 3-cyclobutyl-1-methyl-1H-pyrazol-4-amine (ZBB214-1)

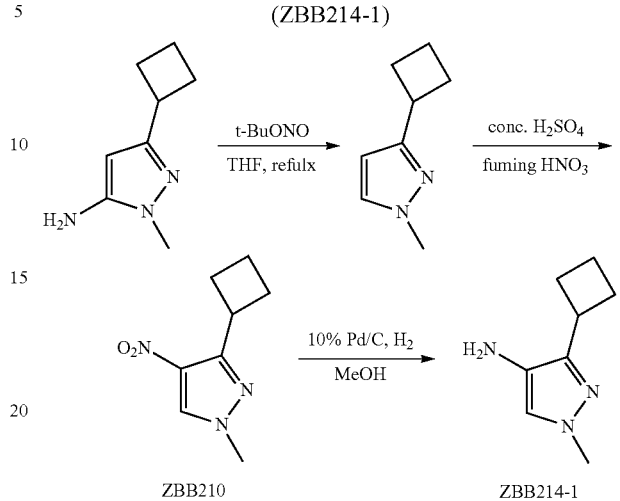

The mixture of 3-cyclobutyl-1-methyl-1H-pyrazol-5-amine (500 mg), t-BuONO (2 mL) in THF (10 mL) was heated at 90° C. for 3 h. Then the mixture was concentrated on a rotary evaporator and was dissolved in conc. $H_2SO_4$ (1 mL) and fuming $HNO_3$ (1 mL). And the mixture was heated at 60° C. overnight. Then the mixture was poured into cooled aq. NaOH water solution and extracted with Ethyl acetate. The organic phase was concentrated on a rotary evaporator. The remaining residue was purified by flash column chromatography to give ZBB210 (250 mg). $^1$H NMR (300 MHz, CDCl$_3$) δ 8.10 (s, 1H), 4.07-3.93 (m, 1H), 3.91 (s, 3H), 2.48-2.22 (m, 4H), 2.16-1.81 (m, 2H).

ZBB210 (200 mg) was dissolved in MeOH (10 mL). 50 mg 10% Pd/C was added. the reaction mixture was degassed 2 times, each time replacing the vacuum with hydrogen, then stirred at room temperature under H$_2$ overnight. The mixture was filtered and concentrated on a rotary evaporator to give ZBB214-1 (150 mg). ESI-MS calculated for $C_8H_{14}N_3[M+H]^+$=152.11; Observed: 152.34.

Synthesis of N-(3-cyclobutyl-1-methyl-1H-pyrazol-4-yl)-7-(3,5-dimethylisoxazol-4-yl)-6-methoxy-2-methyl-9H-pyrimido[4,5-b]indol-4-amine (Cpd No. 200)

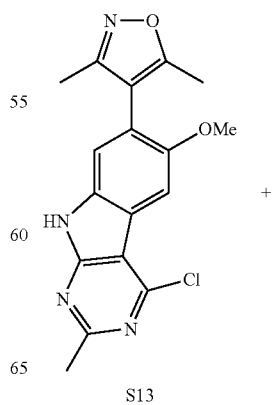

-continued

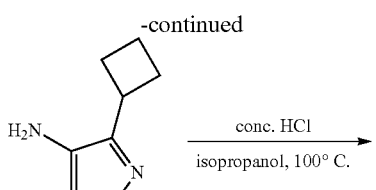

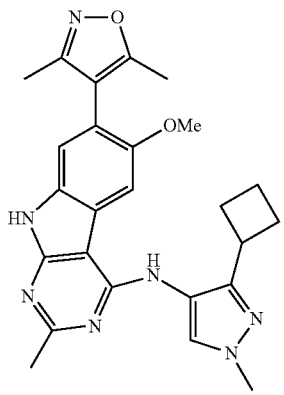

S13 (70 mg) and 3-cyclobutyl-1-methyl-1H-pyrazol-4-amine (68 mg) were dissolved in isopropanol (5 mL). Four drops of concentrated HCl was added via a glass pipette. The mixture was heated at reflux for overnight. The reaction was concentrated on a rotary evaporator and the remaining residues were purified by HPLC to yield the desired product Cpd. No. 200 in 40 mg as a salt of trifluoroacetic acid. ESI-MS calculated for $C_{25}H_{28}N_7O_2$ $[M+H]^+=458.23$; Observed: 458.66.

Example 154

Synthesis of 3-cyclobutyl-1-ethyl-1H-pyrazol-4-amine (ZBB221)

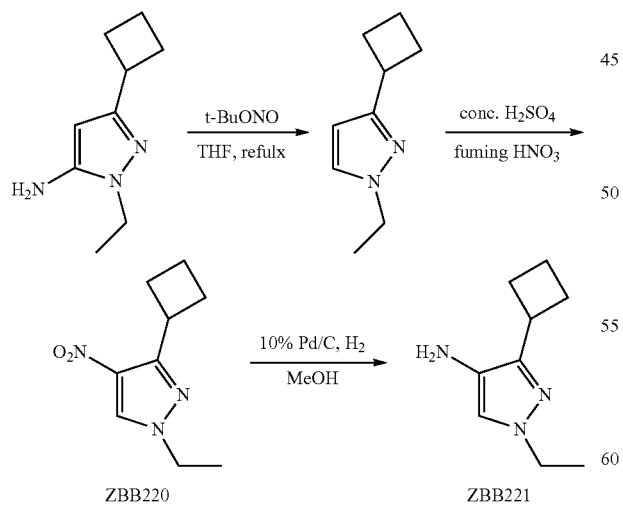

The mixture of 3-cyclobutyl-1-ethyl-1H-pyrazol-5-amine (500 mg), t-BuONO (2 mL) in THF (10 mL) was heated at 90° C. for 3 h. Then the mixture was concentrated on a rotary evaporator and was dissolved in conc. $H_2SO_4$ (1 mL) and fuming $HNO_3$ (1 mL). And the mixture was heated at 60° C. overnight. Then the mixture was poured into cooled aq. NaOH water solution and extracted with Ethyl acetate. The organic phase was concentrated on a rotary evaporator. The remaining residue was purified by flash column chromatography to give ZBB220.

ZBB220 (200 mg) was dissolved in MeOH (10 mL). 50 mg 10% Pd/C was added. the reaction mixture was degassed 2 times, each time replacing the vacuum with hydrogen, then stirred at room temperature under $H_2$ overnight. The mixture was filtered and concentrated on a rotary evaporator to give ZBB221 (150 mg). ESI-MS calculated for $C_9H_{16}N_3$ $[M+H]^+=166.13$; Observed: 166.55.

Synthesis of N-(3-cyclobutyl-1-ethyl-1H-pyrazol-4-yl)-7-(3,5-dimethylisoxazol-4-yl)-6-methoxy-2-methyl-9H-pyrimido[4,5-b]indol-4-amine (Cpd. No. 201)

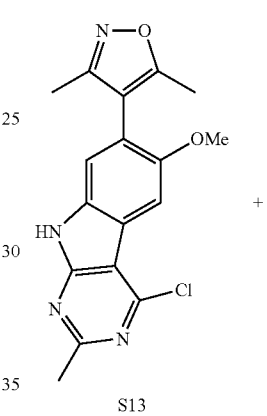

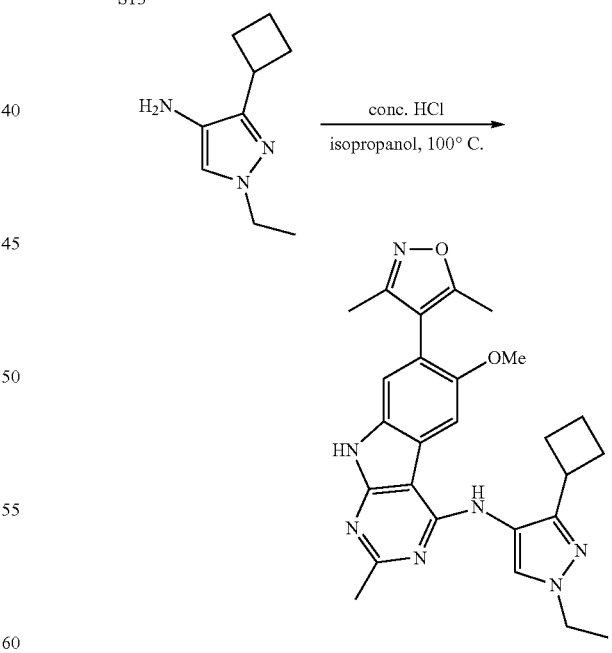

S13 (70 mg) and 3-cyclobutyl-1-ethyl-1H-pyrazol-4-amine (68 mg) were dissolved in isopropanol (5 mL). Four drops of concentrated HCl was added via a glass pipette. The mixture was heated at reflux for overnight. The reaction was concentrated on a rotary evaporator and the remaining residues were purified by HPLC to yield the desired product Cpd. No. 201 in 40 mg as a salt of trifluoroacetic acid. ESI-MS calculated for $C_{26}H_{30}N_7O_2$ [M+H]$^+$=472.24; Observed: 472.66.

Example 155

Synthesis of 2-(tert-butyl)-4-methylthiazol-5-amine (ZBB222-2)

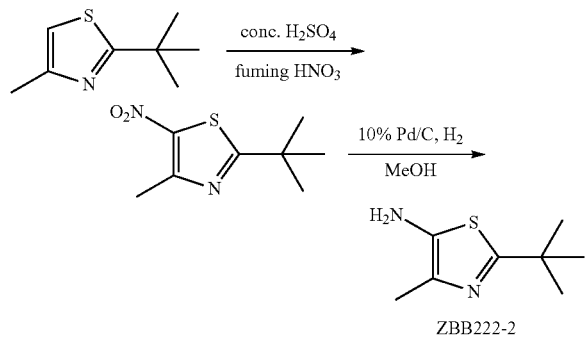

The mixture of 2-(tert-butyl)-4-methylthiazole (500 mg), conc. H$_2$SO$_4$ (1 mL) and fuming HNO$_3$ (1 mL) was heated at 100° C. overnight. Then the mixture was poured into cooled aq. NaOH water solution and extracted with Ethyl acetate. The organic phase was concentrated on a rotary evaporator and was dissolved in MeOH (10 mL). 500 mg 10% Pd/C was added. the reaction mixture was degassed 2 times, each time replacing the vacuum with hydrogen, then stirred at room temperature under H$_2$ overnight. The mixture was filtered and concentrated on a rotary evaporator to give ZBB222-2 (300 mg). ESI-MS calculated for $C_8H_{15}N_2S$[M+H]$^+$=171.09; Observed: 171.44.

Synthesis of 2-(tert-butyl)-N-(7-(3,5-dimethylisoxazol-4-yl)-6-methoxy-2-methyl-9H-pyrimido[4,5-b]indol-4-yl)-4-methylthiazol-5-amine (Cpd. No. 202)

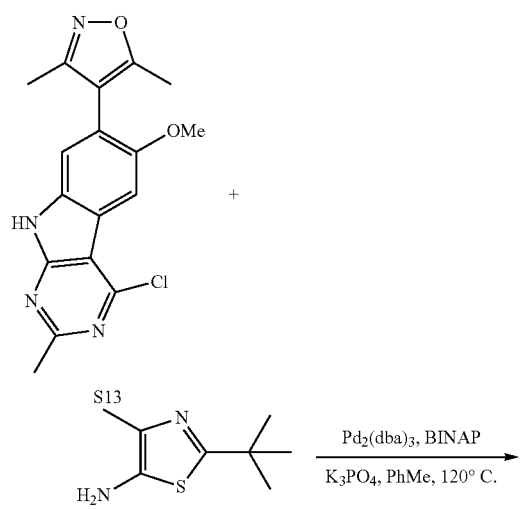

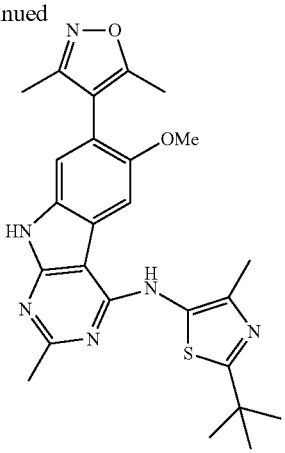

Pd$_2$(dba)$_3$ (18 mg) and BINAP (26 mg) were mixed in anhydrous toluene. And the mixture was heated at reflux for 3-4 minutes. This mixture was transferred into a round-bottom flask containing S13 (60 mg), 2-(tert-butyl)-4-methylthiazol-5-amine (84 mg), K$_3$PO$_4$ (130 mg), and toluene (2 mL). The mixture was heated at reflux for overnight before quenching with methanol. The reaction mixture was filtered and the mixture was purified by HPLC to yield Cpd. No. 202 as a CF$_3$CO$_2$H salt in 35 mg. ESI-MS calculated for $C_{25}H_{29}N_6O_2S$ [M+H]$^+$=477.20; Observed: 477.44. $^1$H NMR (300 MHz, MeOD) δ 8.02 (s, 1H), 7.49 (s, 1H), 3.96 (s, 3H), 2.73 (s, 3H), 2.40 (s, 3H), 2.35 (s, 3H), 2.18 (s, 3H), 1.51 (s, 9H).

Example 156

Synthesis of 1-ethyl-3-isopropyl-1H-pyrazol-5-amine (ZBB243)

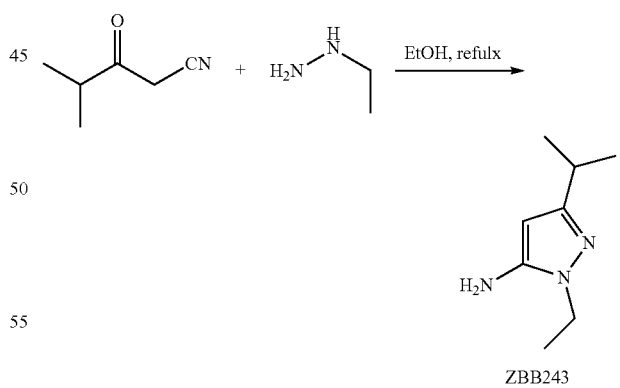

4-methyl-3-oxopentanenitrile (1 g) was dissolved in ethanol (30 mL). Ethylhydrazine. HCl salt (5 g) was added and the mixture was heated at reflux for overnight. The mixture was concentrated on a rotary evaporator followed by addition of ethyl acetate and aq. NaHCO$_3$. The aqueous layer was extracted with ethyl acetate and the organic layers were combined, dried, and concentrated on a rotary evaporator. The remaining residue was purified by flash column chromatography and the desired product was obtained in 0.9 g. ESI-MS calculated for $C_8H_{16}N_3[M+H]^+=154.13$; Observed: 154.44.

Synthesis of 7-(3,5-dimethylisoxazol-4-yl)-N-(1-ethyl-3-isopropyl-1H-pyrazol-5-yl)-6-methoxy-2-methyl-9H-pyrimido[4,5-b]indol-4-amine (Cpd. No. 203)

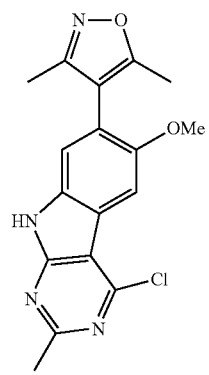

+

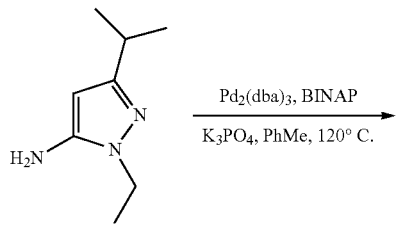

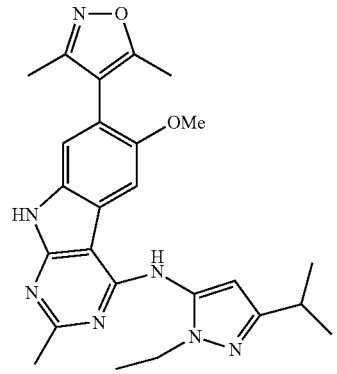

Pd$_2$(dba)$_3$ (18 mg) and BINAP (26 mg) were mixed in anhydrous toluene. And the mixture was heated at reflux for 3-4 minutes. This mixture was transferred into a round-bottom flask containing S13 (60 mg), 1-ethyl-3-isopropyl-1H-pyrazol-5-amine (84 mg), K$_3$PO$_4$ (130 mg), and toluene (2 mL). The mixture was heated at reflux for overnight before quenching with methanol. The reaction mixture was filtered and the mixture was purified by HPLC to yield Cpd. No. 203 as a CF$_3$CO$_2$H salt in 25 mg. ESI-MS calculated for $C_{25}H_{30}N_7O_2$ [M+H]$^+$=460.24; Observed: 460.66.

Example 157

Synthesis of 1,3-diisopropyl-1H-pyrazol-5-amine (ZBB246)

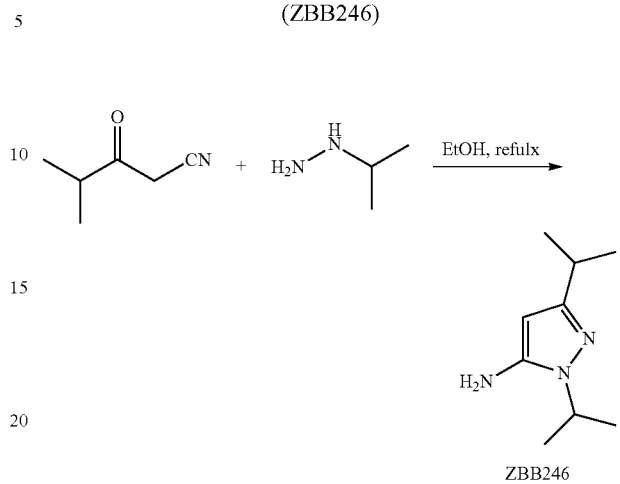

4-methyl-3-oxopentanenitrile (1 g) was dissolved in ethanol (30 mL). isopropylhydrazine. HCl salt (5 g) was added and the mixture was heated at reflux for overnight. The mixture was concentrated on a rotary evaporator followed by addition of ethyl acetate and aq. NaHCO$_3$. The aqueous layer was extracted with ethyl acetate and the organic layers were combined, dried, and concentrated on a rotary evaporator. The remaining residue was purified by flash column chromatography and the desired product was obtained in 0.9 g. ESI-MS calculated for $C_9H_{18}N_3[M+H]^+=168.15$; Observed: 168.44.

Synthesis of N-(1,3-diisopropyl-1H-pyrazol-5-yl)-7-(3,5-dimethylisoxazol-4-yl)-6-methoxy-2-methyl-9H-pyrimido[4,5-b]indol-4-amine (Cpd. No. 83)

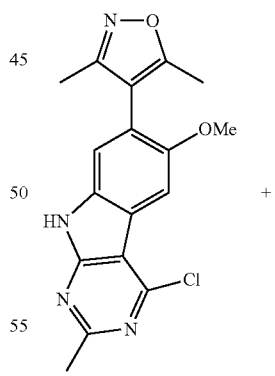

+

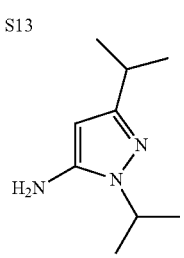

-continued

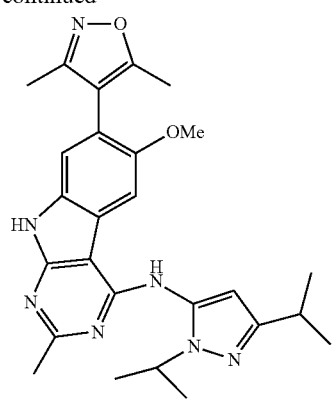

Pd$_2$(dba)$_3$ (18 mg) and BINAP (26 mg) were mixed in anhydrous toluene. And the mixture was heated at reflux for 3-4 minutes. This mixture was transferred into a round-bottom flask containing S13 (60 mg), 1,3-diisopropyl-1H-pyrazol-5-amine (84 mg), K$_3$PO$_4$ (130 mg), and toluene (2 mL). The mixture was heated at reflux for overnight before quenching with methanol. The reaction mixture was filtered and the mixture was purified by HPLC to yield Cpd. No. 83 as a CF$_3$CO$_2$H salt in 25 mg. ESI-MS calculated for C$_{26}$H$_{32}$N$_7$O$_2$ [M+H]$^+$=474.26; Observed: 474.44.

Example 158

Synthesis of 1-cyclopropyl-3-isopropyl-1H-pyrazol-5-amine (ZBB247)

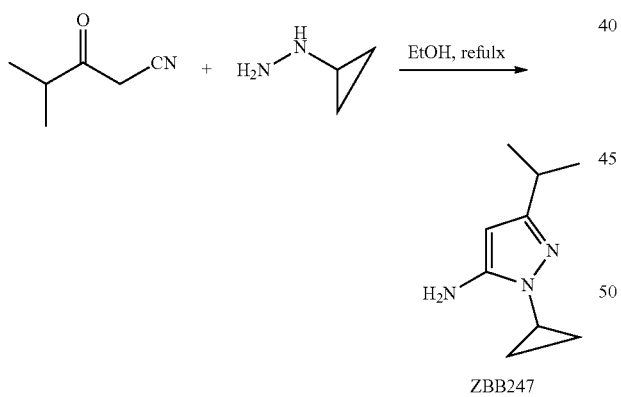

4-methyl-3-oxopentanenitrile (1 g) was dissolved in ethanol (30 mL). cyclopropylhydrazine. HCl salt (5 g) was added and the mixture was heated at reflux for overnight. The mixture was concentrated on a rotary evaporator followed by addition of ethyl acetate and aq. NaHCO$_3$. The aqueous layer was extracted with ethyl acetate and the organic layers were combined, dried, and concentrated on a rotary evaporator. The remaining residue was purified by flash column chromatography and the desired product was obtained in 0.9 g. ESI-MS calculated for C$_9$H$_{16}$N$_3$[M+H]$^+$=166.13; Observed: 166.56.

Synthesis of N-(1-cyclopropyl-3-isopropyl-1H-pyrazol-5-yl)-7-(3,5-dimethylisoxazol-4-yl)-6-methoxy-2-methyl-9H-pyrimido[4,5-b]indol-4-amine (Cpd. No. 205)

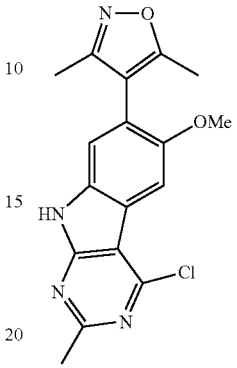

S13

+

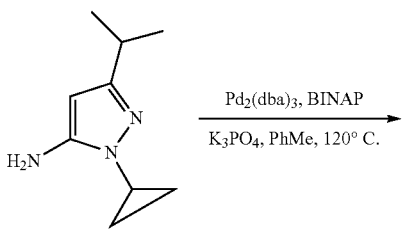

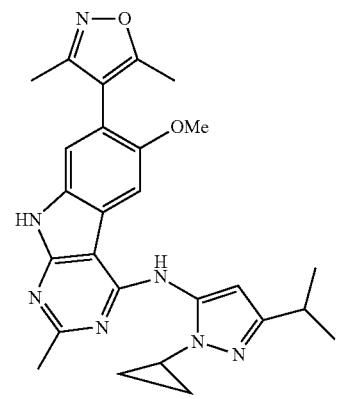

Pd$_2$(dba)$_3$ (18 mg) and BINAP (26 mg) were mixed in anhydrous toluene. And the mixture was heated at reflux for 3-4 minutes. This mixture was transferred into a round-bottom flask containing S13 (60 mg), 1-cyclopropyl-3-isopropyl-1H-pyrazol-5-amine (84 mg), K$_3$PO$_4$ (130 mg), and toluene (2 mL). The mixture was heated at reflux for overnight before quenching with methanol. The reaction mixture was filtered and the mixture was purified by HPLC to yield Cpd. No. 205 as a CF$_3$CO$_2$H salt in 25 mg. ESI-MS calculated for C$_{26}$H$_{30}$N$_7$O$_2$ [M+H]$^+$=472.24; Observed: 472.44.

Example 159

Synthesis of 2-amino-7-(3,5-dimethylisoxazol-4-yl)-6-methoxy-9H-pyrimido[4,5-b]indol-4-ol (ZBB251)

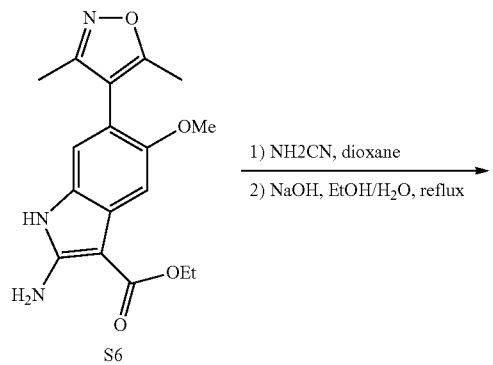

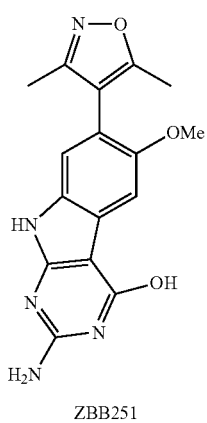

To a round-bottom flask, S6 (1 g), NH₂CN (0.2 g) conc. HCl (0.2 mL) and dioxane (30 ml) were added at room temperature. The reaction mixture was warmed up to reflux (ca, 90° C.) for 2 day. The reaction was then cooled to room temperature and the volatile components were removed on a rotary evaporator. To this crude mixture, 10% NaOH aqueous solution (20 mL) were added and the solution was heated at reflux for 8 h. The volatile components were then removed on a rotary evaporator and the aqueous residue was acidified with 2N HCl aqueous solution. The product ZBB251 was allowed to precipitate at 0° C. Filtration of the mixture furnished pure ZBB251 in 0.5 g. ESI-MS calculated for $C_{16}H_{16}N_5O_3$ [M+H]$^+$=326.12; Observed: 326.44. $^1$H NMR (300 MHz, DMSO) δ 11.31 (s, 1H), 10.64 (s, 1H), 7.39 (s, 1H), 7.04 (s, 1H), 6.66 (s, 2H), 3.78 (s, 3H), 2.27 (s, 3H), 2.07 (s, 3H).

Example 160

Synthesis of 4-chloro-7-(3,5-dimethylisoxazol-4-yl)-6-methoxy-9H-pyrimido[4,5-b]indol-2-amine (ZBB253)

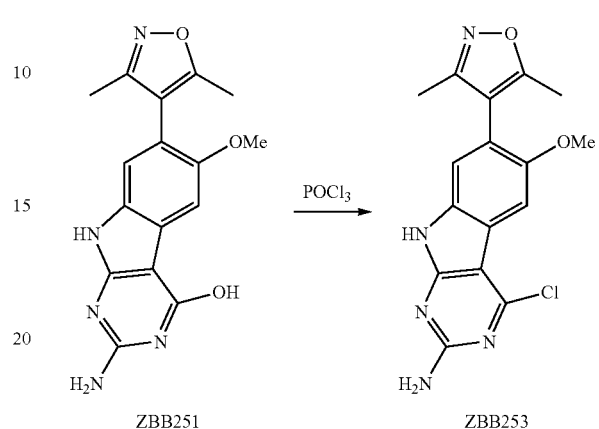

To a round-bottom flask, ZBB251 (0.278 g, 0.8 mmol) and POCl₃ (8 mL) were added. The mixture was heated at 90° C. for 6 h. The reaction mixture was cooled to room temperature and the volatile components were removed on a rotary evaporator. Water (20 mL) and ethyl acetate (20 mL) were added and the pH was adjusted to 8 using NaHCO₃ saturated aqueous solution. Filtration of the mixture furnished ZBB253 as a brown solid in 0.208 g. ESI-MS calculated for $C_6H_{15}ClN_5O_2$[M+H]$^+$=344.09; Observed: 344.44.

Example 161

Synthesis of N4-(3-cyclopropyl-1-methyl-1H-pyrazol-5-yl)-7-(3,5-dimethylisoxazol-4-yl)-6-methoxy-9H-pyrimido[4,5-b]indole-2,4-diamine (Cpd. No. 206)

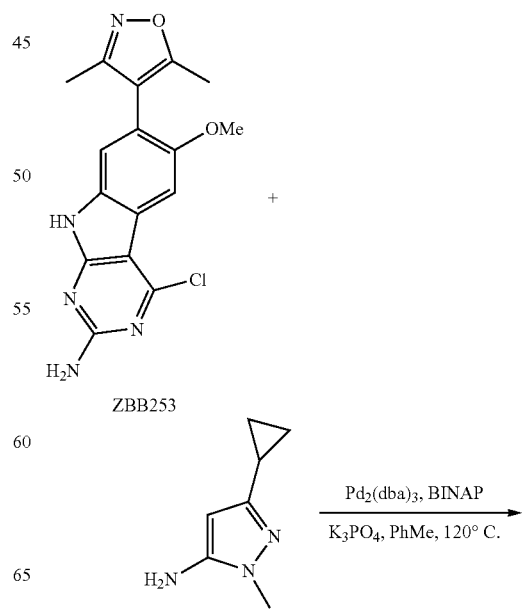

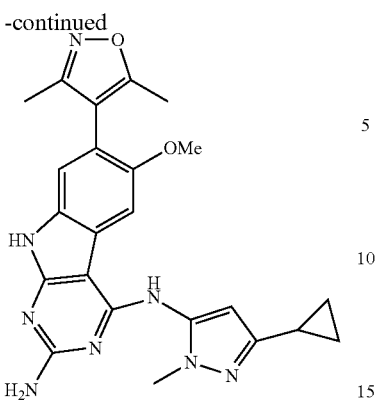

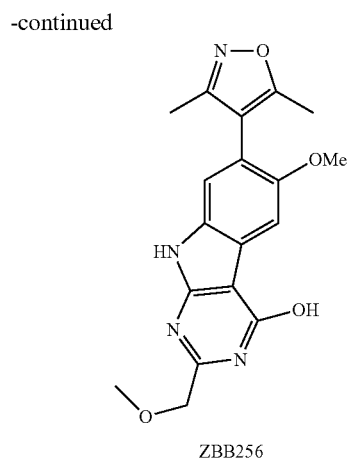

ZBB256

Pd₂(dba)₃ (18 mg) and BINAP (26 mg) were mixed in anhydrous toluene. And the mixture was heated at reflux for 3-4 minutes. This mixture was transferred into a round-bottom flask containing ZBB253 (60 mg), 3-cyclopropyl-1-methyl-1H-pyrazol-5-amine (84 mg), K₃PO₄ (130 mg), and toluene (2 mL). The mixture was heated at reflux for overnight before quenching with methanol. The reaction mixture was filtered and the mixture was purified by HPLC to yield Cpd. No. 206 as a CF₃CO₂H salt in 15 mg. ESI-MS calculated for $C_{23}H_{25}N_8O_2$ [M+H]⁺=445.21; Observed: 445.54. ¹H NMR (300 MHz, MeOD) δ 7.70 (s, 1H), 7.35 (s, 1H), 6.09 (s, 1H), 3.92 (s, 3H), 3.74 (s, 3H), 2.33 (s, 3H), 2.16 (s, 3H), 1.98-1.88 (m, 1H), 1.03-0.93 (m, 2H), 0.78-0.71 (m, 2H).

Example 162

Synthesis of 7-(3,5-dimethylisoxazol-4-yl)-6-methoxy-2-(methoxymethyl)-9H-pyrimido[4,5-b]indol-4-ol (ZBB256)

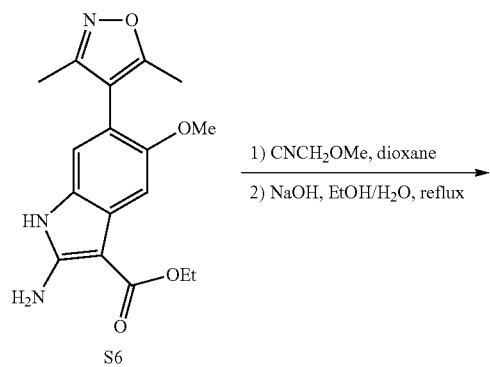

To a round-bottom flask, S6 (1 g), MeOCH₂CN (4 mL) and hydrogen chloride solution, 4 M in dioxane (4 mL) were added at room temperature. The reaction mixture was stirred overnight. The volatile components were removed on a rotary evaporator. To this crude mixture, 10% NaOH aqueous solution (10 mL) and EtOH (20 mL) were added and the solution was heated at reflux for 8 h. The volatile components were then removed on a rotary evaporator and the aqueous residue was acidified with 2 N HCl aqueous solution. The product ZBB256 was allowed to precipitate at 0° C. Filtration of the mixture furnished pure ZBB256 in 0.8 g. ESI-MS calculated for $C_{18}H_{19}N_4O_4$ [M+H]⁺=355.14; Observed: 355.44. ¹H NMR (300 MHz, DMSO) δ 12.15 (s, 1H), 12.09 (s, 1H), 7.59 (s, 1H), 7.26 (s, 1H), 4.39 (s, 2H), 3.84 (s, 3H), 3.38 (s, 3H), 2.29 (s, 3H), 2.09 (s, 3H).

Example 163

Synthesis of 4-(4-chloro-6-methoxy-2-(methoxymethyl)-9H-pyrimido[4,5-b]indol-7-yl)-3,5-dimethylisoxazole (ZBB257)

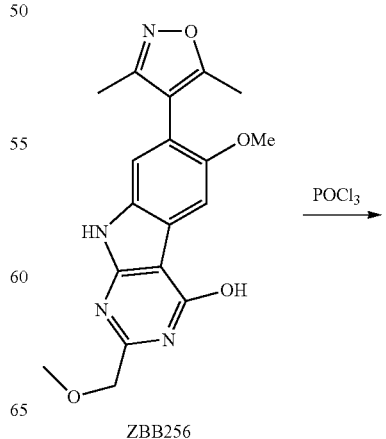

417

-continued

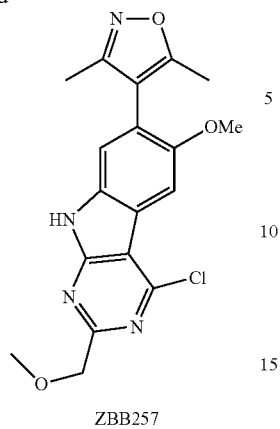

ZBB257

To a round-bottom flask, ZBB256 (0.278 g, 0.8 mmol) and POCl₃ (8 mL) were added. The mixture was heated at 90° C. for 6 h. The reaction mixture was cooled to room temperature and the volatile components were removed on a rotary evaporator. Water (20 mL) and ethyl acetate (20 mL) were added and the pH was adjusted to 8 using NaHCO₃ saturated aqueous solution. Filtration of the mixture furnished ZBB257 as a brown solid in 0.22 g. ESI-MS calculated for $C_{18}H_{18}ClN_4O_3[M+H]^+$=373.10; Observed: 373.44. ¹H NMR (300 MHz, DMSO) δ 7.83 (s, 1H), 7.48 (s, 1H), 4.62 (s, 2H), 3.90 (s, 3H), 3.42 (s, 3H), 2.32 (s, 3H), 2.12 (s, 3H).

Example 164

Synthesis of N-(3-cyclopropyl-1-methyl-1H-pyrazol-5-yl)-7-(3,5-dimethylisoxazol-4-yl)-6-methoxy-2-(methoxymethyl)-9H-pyrimido[4,5-b]indol-4-amine (Cpd. No. 207)

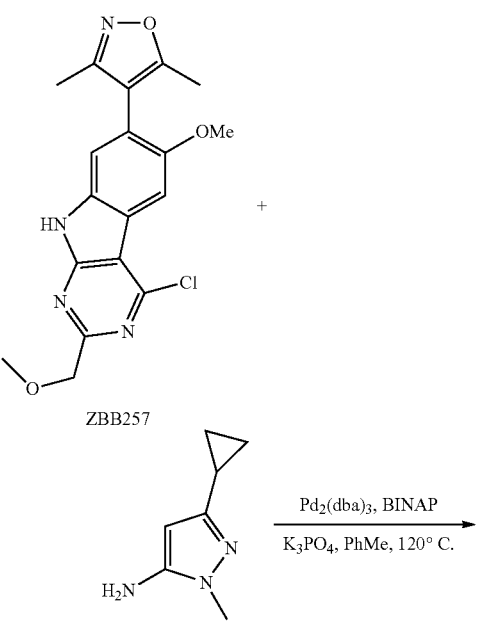

418

-continued

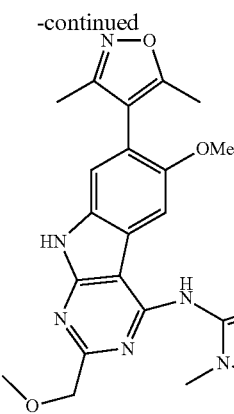

Pd₂(dba)₃ (18 mg) and BINAP (26 mg) were mixed in anhydrous toluene. And the mixture was heated at reflux for 3-4 minutes. This mixture was transferred into a round-bottom flask containing ZBB257 (60 mg), 3-cyclopropyl-1-methyl-1H-pyrazol-5-amine (84 mg), K₃PO₄ (130 mg), and toluene (2 mL). The mixture was heated at reflux for overnight before quenching with methanol. The reaction mixture was filtered and the mixture was purified by HPLC to yield ZBB259 as a CF₃CO₂H salt in 15 mg. ESI-MS calculated for $C_{25}H_{28}N_7O_3$ $[M+H]^+$=474.22; Observed: 474.67. ¹H NMR (300 MHz, MeOD) δ 7.50 (s, 1H), 7.38 (s, 1H), 6.11 (s, 1H), 4.69 (s, 2H), 3.90 (s, 3H), 3.76 (s, 3H), 3.59 (s, 3H), 2.34 (s, 3H), 2.17 (s, 3H), 2.05-1.86 (m, 1H), 1.04-0.95 (m, 2H), 0.78-0.72 (m, 2H).

Example 165

The following compounds were prepared as described for Cpd. No. 97 in EXAMPLE 51:

N-(3-chloro-4-fluorophenyl)-7-(3,5-dimethylisoxazol-4-yl)-6-methoxy-2-methyl-9H-pyrimido[4,5-b]indol-4-amine (Cpd. No. 107)

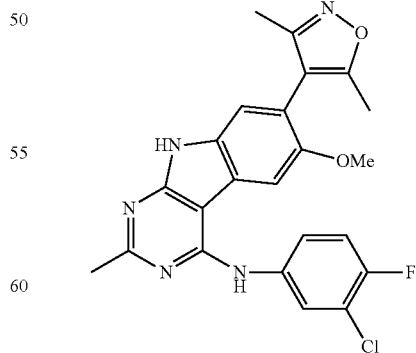

¹H-NMR (300 MHz, CD₃OD) ppm 7.85-7.77 (m, 2H), 7.62-7.54 (m, 1H), 7.47-7.36 (m, 2H), 3.90 (s, 3H), 2.68 (s, 3H), 2.33 (s, 3H), 2.16 (d, 3H);

7-(3,5-dimethylisoxazol-4-yl)-6-methoxy-2-methyl-N-(5-methylpyridin-3-yl)-9H-pyrimido[4,5-b]indol-4-amine (Cpd. No. 108)

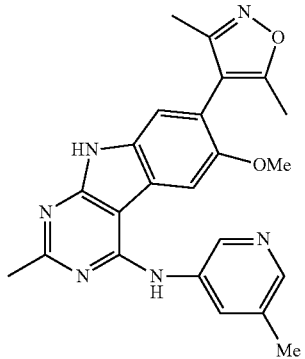

$^1$H-NMR (300 MHz, CD$_3$OD) δ ppm 9.47 (s, 1H), 8.56 (s, 1H), 8.42 (s, 1H), 8.04 (s, 1H), 7.41 (s, 1H), 3.98 (s, 3H), 2.70 (s, 3H), 2.60 (s, 3H), 2.34 (s, 3H), 2.18 (s, 3H);

7-(3,5-dimethylisoxazol-4-yl)-6-methoxy-2-methyl-N-(quinolin-8-yl)-9H-pyrimido[4,5-b]indol-4-amine (Cpd. No. 210)

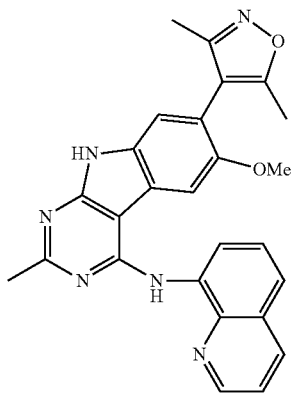

$^1$H-NMR (300 MHz, CDCl$_3$) δ ppm 13.36 (s, 1H), 11.10 (s, 1H), 9.19 (dd, J=2.25, 6.67 Hz, 1H), 8.93 (dd, J=1.51, 4.24 Hz, 1H), 8.34 (dd, J=1.38, 8.22 Hz, 1H), 8.11 (s, 1H), 7.78-7.66 (m, 2H), 7.65-7.54 (m, 2H), 4.17 (s, 3H), 2.98 (s, 3H), 2.39 (s, 3H), 2.25 (s, 3H);

7-(3,5-dimethylisoxazol-4-yl)-6-methoxy-2-methyl-N-(quinolin-5-yl)-9H-pyrimido[4,5-b]indol-4-amine (Cpd. No. 211)

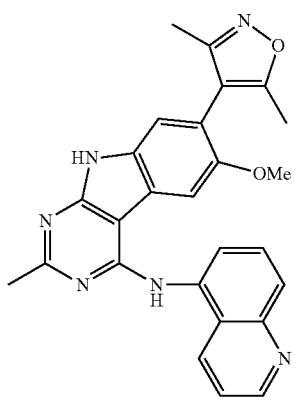

$^1$H-NMR (300 MHz, CD$_3$OD) δ ppm 9.14-9.05 (m, 1H), 8.80 (d, J=7.79 Hz, 1H), 8.25 (d, J=8.65 Hz, 1H), 8.06 (t, J=7.96 Hz, 1H), 7.90 (d, J=7.15 Hz, 1H), 7.84-7.73 (m, 2H), 7.48 (s, 1H), 3.78 (s, 3H), 2.54 (s, 3H), 2.33 (s, 3H), 2.16 (s, 3H); 7-(3,5-dimethylisoxazol-4-yl)-6-methoxy-2-methyl-N-m-tolyl-9H-pyrimido[4,5-b]indol-4-amine (Cpd. No. 212)

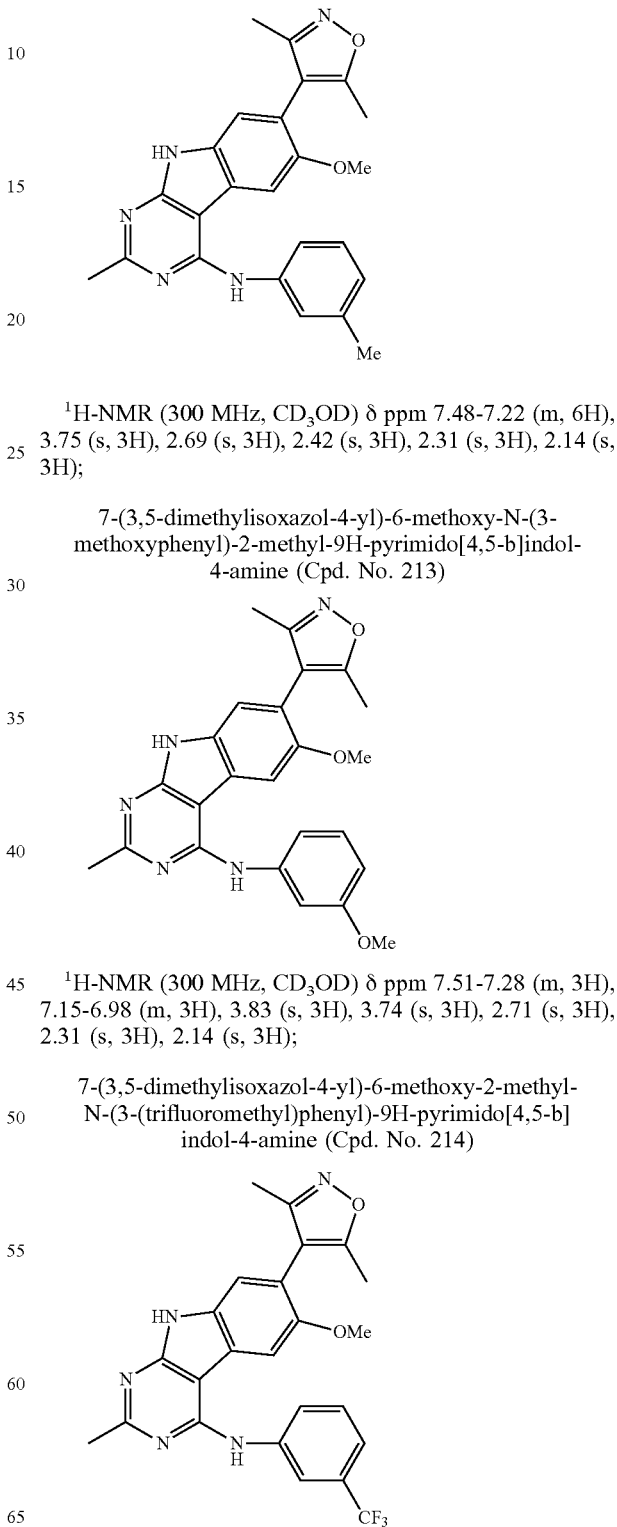

$^1$H-NMR (300 MHz, CD$_3$OD) δ ppm 7.48-7.22 (m, 6H), 3.75 (s, 3H), 2.69 (s, 3H), 2.42 (s, 3H), 2.31 (s, 3H), 2.14 (s, 3H);

7-(3,5-dimethylisoxazol-4-yl)-6-methoxy-N-(3-methoxyphenyl)-2-methyl-9H-pyrimido[4,5-b]indol-4-amine (Cpd. No. 213)

$^1$H-NMR (300 MHz, CD$_3$OD) δ ppm 7.51-7.28 (m, 3H), 7.15-6.98 (m, 3H), 3.83 (s, 3H), 3.74 (s, 3H), 2.71 (s, 3H), 2.31 (s, 3H), 2.14 (s, 3H);

7-(3,5-dimethylisoxazol-4-yl)-6-methoxy-2-methyl-N-(3-(trifluoromethyl)phenyl)-9H-pyrimido[4,5-b]indol-4-amine (Cpd. No. 214)

¹H-NMR (300 MHz, CD₃OD) δ ppm 7.97 (s, 1H), 7.87 (d, J=7.56 Hz, 1H), 7.75-7.61 (m, 3H), 7.45 (s, 1H), 3.85 (s, 3H), 2.69 (s, 3H), 2.33 (s, 3H), 2.15 (s, 3H).

N-(7-(3,5-dimethylisoxazol-4-yl)-6-methoxy-2-methyl-9H-pyrimido[4,5-b]indol-4-yl)-3,5-dimethyl-isoxazol-4-amine (Cpd. No. 215)

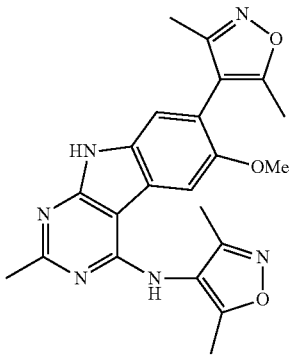

¹H-NMR (300 MHz, CD₃OD) δ ppm 8.02 (s, 1H), 7.49 (s, 1H), 3.96 (s, 3H), 2.69 (s, 3H), 2.44 (s, 3H), 2.34 (s, 3H), 2.26 (s, 3H), 2.16 (s, 3H);

7-(3,5-dimethylisoxazol-4-yl)-N-(3-ethylphenyl)-6-methoxy-2-methyl-9H-pyrimido[4,5-b]indol-4-amine (Cpd. No. 216)

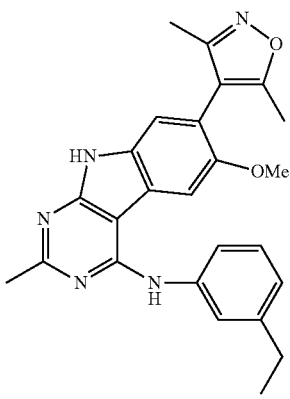

¹H-NMR (300 MHz, CD₃OD) δ ppm 7.52-7.40 (m, 2H), 7.37-7.27 (m, 3H), 7.16 (s, 1H), 3.69 (s, 3H), 2.78-2.64 (m, 5H), 2.30 (s, 3H), 2.13 (s, 3H), 1.21 (t, J=7.59 Hz, 3H);

N-(3-chloro-2-fluorophenyl)-7-(3,5-dimethylisoxazol-4-yl)-6-methoxy-2-methyl-9H-pyrimido[4,5-b]indol-4-amine (Cpd. No. 217)

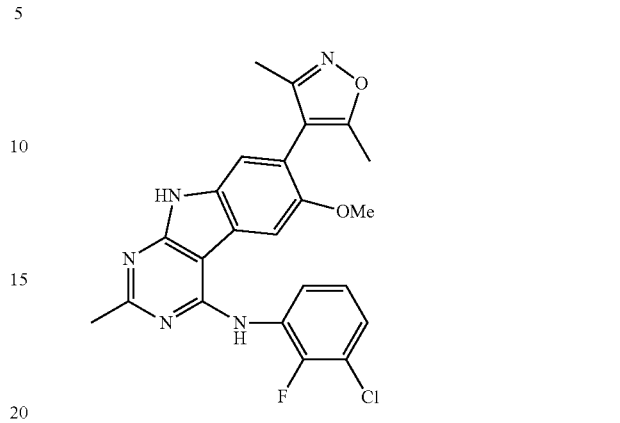

¹H-NMR (300 MHz, CD₃OD) δ ppm 7.92 (s, 1H), 7.61-7.53 (m, 2H), 7.46 (s, 1H), 7.37-7.29 (m, 1H) 3.91 (s, 3H), 2.67 (s, 3H), 2.34 (s, 3H), 2.17 (s, 3H);

7-(3,5-dimethylisoxazol-4-yl)-6-methoxy-N-(3-methoxy-5-methylphenyl)-2-methyl-9H-pyrimido[4,5-b]indol-4-amine (Cpd. No. 218)

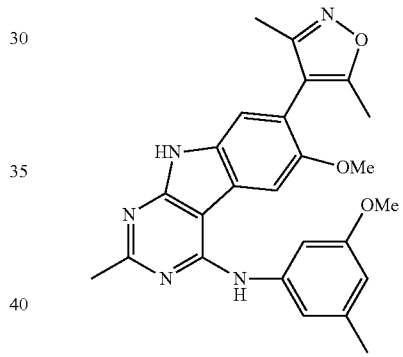

¹H-NMR (300 MHz, CD₃OD) δ ppm 7.40 (s, 1H), 7.14 (s, 1H), 6.92-6.81 (m, 3H), 3.79 (s, 3H), 3.70 (s, 3H), 2.71 (s, 3H), 2.36 (s, 3H), 2.31 (s, 3H), 2.13 (s, 3H);

N-(7-(3,5-dimethylisoxazol-4-yl)-6-methoxy-2-methyl-9H-pyrimido[4,5-b]indol-4-yl)-3,4-dimethyl-isoxazol-5-amine (Cpd. No. 219)

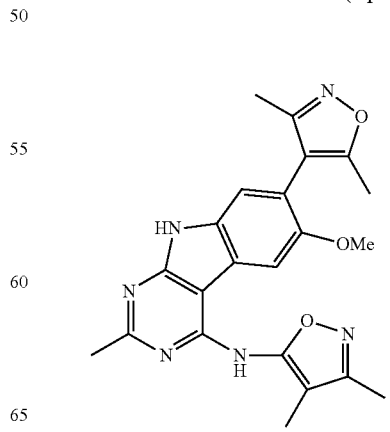

423

¹H-NMR (300 MHz, CD₃OD) δ ppm 7.74 (s, 1H), 7.40 (s, 1H), 3.90 (s, 3H), 2.64 (s, 3H), 2.33 (s, 3H), 2.30 (s, 3H), 2.16 (s, 3H), 1.92 (s, 3H);

7-(3,5-dimethylisoxazol-4-yl)-N-(1H-indol-4-yl)-6-methoxy-2-methyl-9H-pyrimido[4,5-b]indol-4-amine (Cpd. No. 220)

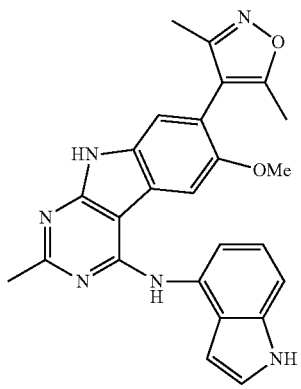

¹H-NMR (300 MHz, CD₃OD) δ ppm 7.57 (d, J=8.13 Hz, 1H), 7.39 (s, 1H), 7.37 (d, J=3.18 Hz, 1H), 7.29 (t, J=7.82 Hz, 1H), 7.18 (d, J=6.85 Hz, 1H), 7.12 (br. s., 1H), 6.40 (dd, J=0.78, 3.20 Hz, 1H), 3.57 (s, 3H), 2.64 (s, 3H), 2.29 (s, 3H), 2.11 (s, 3H);

7-(3,5-dimethylisoxazol-4-yl)-N-(isoquinolin-5-yl)-6-methoxy-2-methyl-9H-pyrimido[4,5-b]indol-4-amine (Cpd. No. 221)

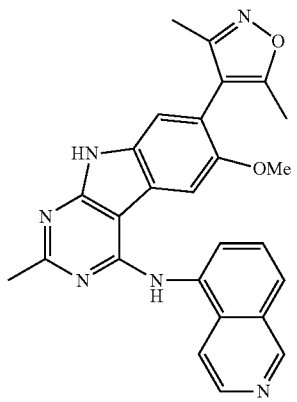

¹H-NMR (300 MHz, CD₃OD) δ ppm 9.66 (s, 1H), 8.60-8.52 (m, 1H), 8.43 (d, J=8.60 Hz, 1H), 8.31-8.13 (m, 2H), 8.02 (t, J=7.87 Hz, 1H), 7.92 (s, 1H), 7.47 (s, 1H), 3.84 (s, 3H), 2.48 (s, 3H), 2.34 (s, 3H), 2.17 (s, 3H);

424

N-(7-(3,5-dimethylisoxazol-4-yl)-6-methoxy-2-methyl-9H-pyrimido[4,5-b]indol-4-yl)-4,5-dimethyl-isoxazol-3-amine (Cpd. No. 222)

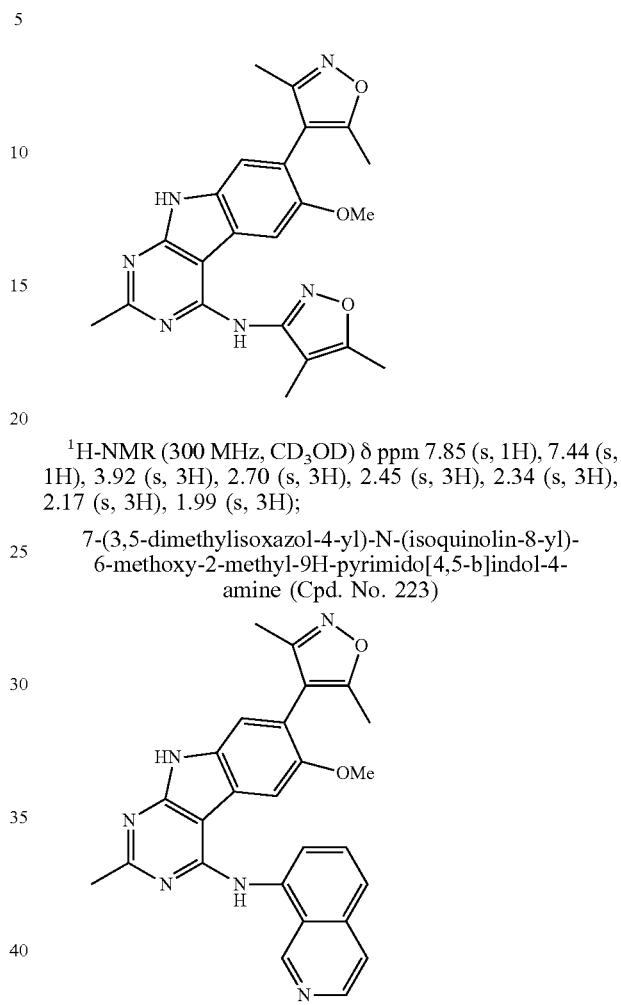

¹H-NMR (300 MHz, CD₃OD) δ ppm 7.85 (s, 1H), 7.44 (s, 1H), 3.92 (s, 3H), 2.70 (s, 3H), 2.45 (s, 3H), 2.34 (s, 3H), 2.17 (s, 3H), 1.99 (s, 3H);

7-(3,5-dimethylisoxazol-4-yl)-N-(isoquinolin-8-yl)-6-methoxy-2-methyl-9H-pyrimido[4,5-b]indol-4-amine (Cpd. No. 223)

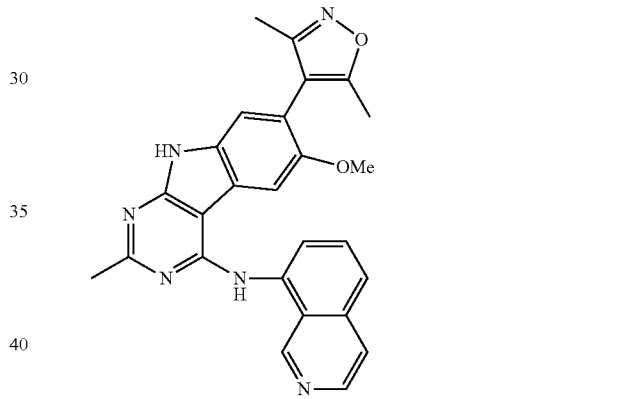

¹H-NMR (300 MHz, CD₃OD) δ ppm 9.75 (s, 1H), 8.68-8.58 (m, 1H), 8.40 (d, J=6.43 Hz, 1H), 8.28-8.14 (m, 2H), 8.01 (d, J=6.82 Hz, 1H), 7.80 (s, 1H), 7.46 (s, 1H), 3.80 (s, 3H), 2.51 (s, 3H), 2.34 (s, 3H), 2.16 (s, 3H);

N-(5-chloro-2-fluorophenyl)-7-(3,5-dimethylisoxazol-4-yl)-6-methoxy-2-methyl-9H-pyrimido[4,5-b]indol-4-amine (Cpd. No. 224)

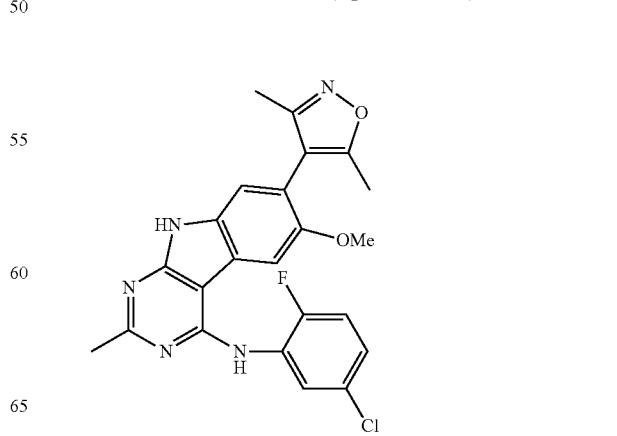

¹H-NMR (300 MHz, CD₃OD) δ ppm 7.88 (s, 1H), 7.84-7.78 (m, 1H), 7.49-7.30 (m, 3H), 3.91 (s, 3H), 2.66 (s, 3H), 2.34 (s, 3H), 2.17 (s, 3H);

N-(3-chloro-5-fluorophenyl)-7-(3,5-dimethylisoxazol-4-yl)-6-methoxy-2-methyl-9H-pyrimido[4,5-b]indol-4-amine (Cpd. No. 225)

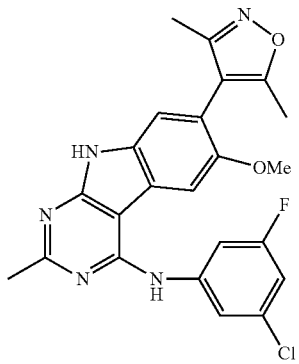

¹H-NMR (300 MHz, CD₃OD) δ ppm 7.82 (s, 1H), 7.57 (s, 1H), 7.51 (d, J=10.68 Hz, 1H), 7.43 (s, 1H), 7.15 (d, J=7.91 Hz, 1H), 3.91 (s, 3H), 2.71 (s, 3H), 2.33 (s, 3H), 2.16 (s, 3H);

7-(3,5-dimethylisoxazol-4-yl)-6-methoxy-2-methyl-N-phenyl-9H-pyrimido[4,5-b]indol-4-amine (Cpd. No. 226)

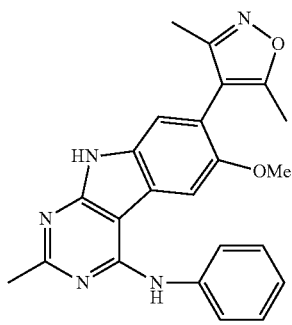

¹H-NMR (300 MHz, CD₃OD) δ ppm 7.60-7.51 (m, 4H), 7.48-7.37 (m, 3H), 3.75 (s, 3H), 2.69 (s, 3H), 2.31 (s, 3H), 2.14 (s, 3H);

7-(3,5-dimethylisoxazol-4-yl)-6-methoxy-2-methyl-N-(1-methyl-H-pyrrolo[2,3-b]pyridin-3-yl)-9H-pyrimido[4,5-b]indol-4-amine (Cpd. No. 227)

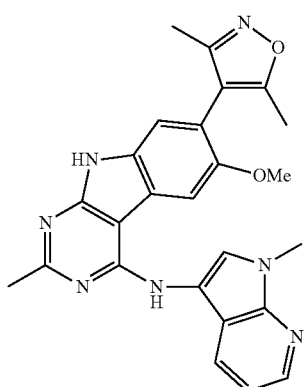

¹H-NMR (300 MHz, CD₃OD) δ ppm 8.43 (dd, J=1.42, 4.83 Hz, 1H), 8.07 (dd, J=1.44, 7.95 Hz, 1H), 7.93 (br. s., 1H), 7.79 (s, 1H), 7.47 (s, 1H), 7.27 (dd, J=4.82, 7.93 Hz, 1H), 4.02 (s, 3H), 3.86 (s, 3H), 2.60 (s, 3H), 2.33 (s, 3H), 2.16 (s, 3H);

7-(3,5-dimethylisoxazol-4-yl)-6-methoxy-2-methyl-N-(2-methylquinolin-5-yl)-9H-pyrimido[4,5-b]indol-4-amine (Cpd. No. 228)

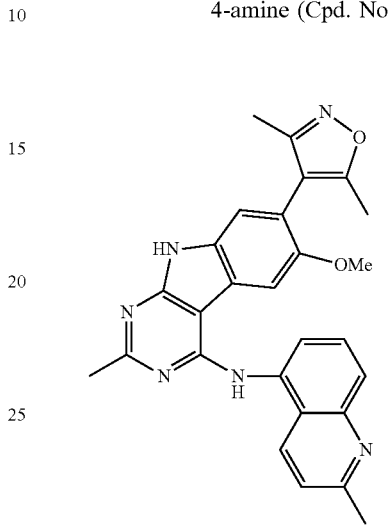

¹H-NMR (300 MHz, CD₃OD) δ ppm 8.93 (d, J=8.71 Hz, 1H), 8.21-8.11 (m, 2H), 7.95 (dd, J=2.17, 6.41 Hz, 1H), 7.89 (s, 1H), 7.83 (d, J=8.81 Hz, 1H), 7.47 (s, 1H), 3.84 (s, 3H), 2.98 (s, 3H), 2.49 (s, 3H), 2.34 (s, 3H), 2.17 (s, 3H);

N-(7-(3,5-dimethylisoxazol-4-yl)-6-methoxy-2-methyl-9H-pyrimido[4,5-b]indol-4-yl)benzo[d]thiazol-7-amine (Cpd. No. 229)

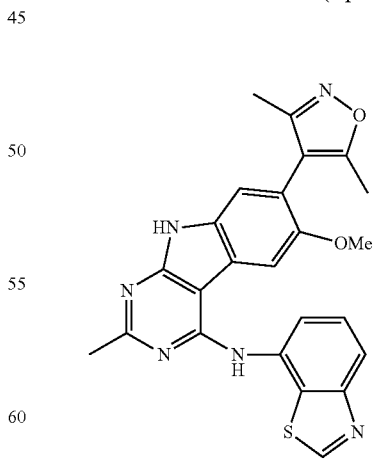

¹H-NMR (300 MHz, CD₃OD) δ ppm 9.31 (s, 1H), 8.19 (dd, J=1.11, 8.04 Hz, 1H), 7.75 (t, J=7.88 Hz, 1H), 7.67 (d, J=7.69 Hz, 1H), 7.54 (s, 1H), 7.46 (s, 1H), 3.74 (s, 3H), 2.62 (s, 3H), 2.32 (s, 3H), 2.14 (s, 3H);

427

N1-(7-(3,5-dimethylisoxazol-4-yl)-6-methoxy-2-methyl-9H-pyrimido[4,5-b]indol-4-yl)-N3,N3-dimethylbenzene-1,3-diamine (Cpd. No. 230)

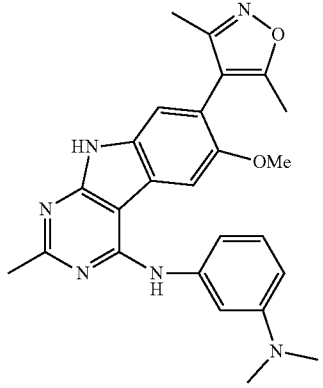

¹H-NMR (300 MHz, CD₃OD) δ ppm 7.44 (m, 2H), 7.20 (s, 1H), 7.03-6.87 (m, 3H), 3.70 (s, 3H), 3.01 (s, 3H), 2.71 (s, 3H), 2.31 (s, 3H), 2.13 (s, 3H);

7-(3,5-dimethylisoxazol-4-yl)-N-(indolin-4-yl)-6-methoxy-2-methyl-9H-pyrimido[4,5-b]indol-4-amine (Cpd. No. 231)

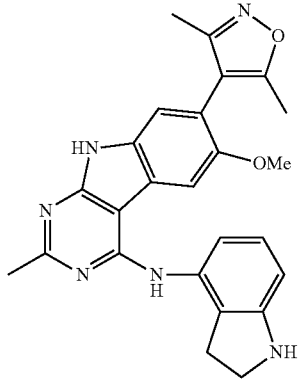

¹H-NMR (300 MHz, CD₃OD) δ ppm 7.45 (br. s., 1H), 7.43 (s, 1H), 7.38 (t, J=7.93 Hz, 1H), 7.17 (d, J=7.56 Hz, 1H), 7.11 (d, J=7.72 Hz, 1H), 3.79 (s, 3H), 3.71 (t, J=8.04 Hz, 2H), 3.09 (t, J=7.89 Hz, 2H), 2.68 (s, 3H), 2.32 (s, 3H), 2.14 (s, 3H);

7-(3,5-dimethylisoxazol-4-yl)-6-methoxy-2-methyl-N-(1-methylindolin-6-yl)-9H-pyrimido[4,5-b]indol-4-amine (Cpd. No. 232)

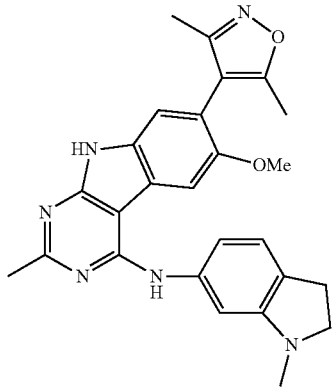 [SMILES: COc1cc2c(cc1-c1c(C)noc1C)[nH]c1nc(C)nc(Nc3ccc4c(c3)N(C)CC4)c12]

ESI-MS m/z 455.83 (M+H)⁺;

428

7-(3,5-dimethylisoxazol-4-yl)-N-(1H-indol-6-yl)-6-methoxy-2-methyl-9H-pyrimido[4,5-b]indol-4-amine (Cpd. No. 233)

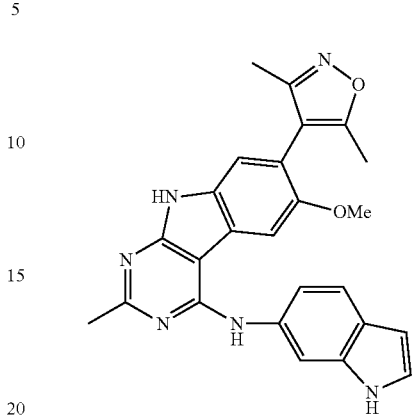

¹H-NMR (300 MHz, CD₃OD) δ ppm 7.74 (d, J=8.40 Hz, 1H), 7.57 (s, 1H), 7.40 (d, J=3.17 Hz, 1H), 7.36 (s, 1H), 7.18 (dd, J=1.93, 8.37 Hz, 1H), 6.70 (br. s., 1H), 6.58 (dd, J=0.85, 3.17 Hz, 1H), 3.29 (s, 3H), 2.69 (s, 3H), 2.27 (s, 3H), 2.08 (s, 3H);

N-(2,3-dihydrobenzofuran-4-yl)-7-(3,5-dimethylisoxazol-4-yl)-6-methoxy-2-methyl-9H-pyrimido[4,5-b]indol-4-amine (Cpd. No. 234)

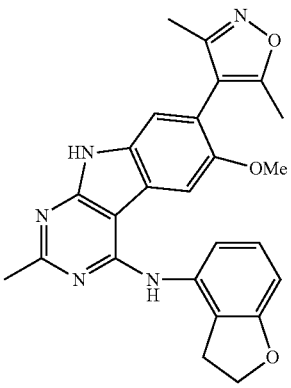

¹H-NMR (300 MHz, CD₃OD) δ ppm 7.43 (s, 1H), 7.28 (t, J=8.02 Hz, 1H), 7.25 (s, 1H), 6.96 (dd, J=0.68, 7.95 Hz, 1H), 6.86 (d, J=7.74 Hz, 1H), 4.60 (t, J=8.67 Hz, 2H), 3.73 (s, 3H), 3.15 (t, J=8.66 Hz, 2H), 2.71 (s, 3H), 2.31 (s, 3H), 2.13 (s, 3H);

7-(3,5-dimethylisoxazol-4-yl)-6-methoxy-2-methyl-
N-(1-methyl-1H-indazol-4-yl)-9H-pyrimido[4,5-b]
indol-4-amine (Cpd. No. 235)

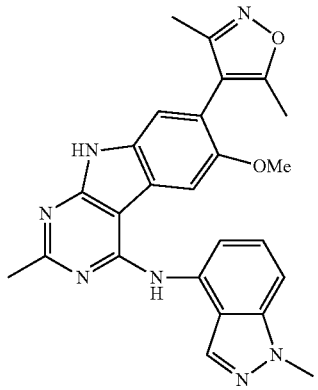

¹H-NMR (300 MHz, CD₃OD) δ ppm 8.02 (d, J=0.82 Hz, 1H), 7.68 (d, J=8.53 Hz, 1H), 7.57 (dd, J=7.30, 8.48 Hz, 1H), 7.43 (s, 1H), 7.34 (s, 1H), 7.29 (dd, J=0.47, 7.17 Hz, 1H), 4.15 (s, 3H), 3.65 (s, 3H), 2.65 (s, 3H), 2.30 (s, 3H), 2.13 (s, 3H);

7-(3,5-dimethylisoxazol-4-yl)-6-methoxy-2-methyl-
N-(1-methyl-1H-indol-4-yl)-9H-pyrimido[4,5-b]
indol-4-amine (Cpd. No. 236)

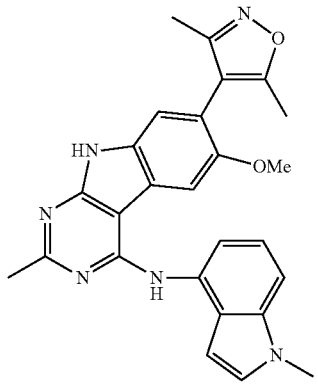

¹H-NMR (300 MHz, CD₃OD) δ ppm 7.58 (d, J=8.22 Hz, 1H), 7.40 (s, 1H), 7.40-7.28 (m, 2H), 7.22 (dd, J=0.57, 7.48 Hz, 1H), 7.17 (br. s., 1H), 6.39 (dd, J=0.73, 3.19 Hz, 1H), 3.90 (s, 3H), 3.58 (s, 3H), 2.63 (s, 3H), 2.30 (s, 3H), 2.12 (s, 3H);

7-(3,5-dimethylisoxazol-4-yl)-N-(3,5-dimethylphenyl)-6-methoxy-2-methyl-9H-pyrimido[4,5-b]indol-4-amine (Cpd. No. 237)

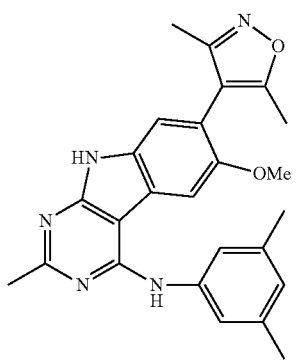

¹H-NMR (300 MHz, CD₃OD) δ ppm 7.42 (s, 1H), 7.21-7.09 (m, 4H), 3.70 (s, 3H), 2.70 (s, 3H), 2.37 (s, 3H), 2.31 (s, 3H), 2.13 (s, 3H);

7-(3,5-dimethylisoxazol-4-yl)-N-(2,5-dimethylphenyl)-6-methoxy-2-methyl-9H-pyrimido[4,5-b]indol-4-amine (Cpd. No. 238)

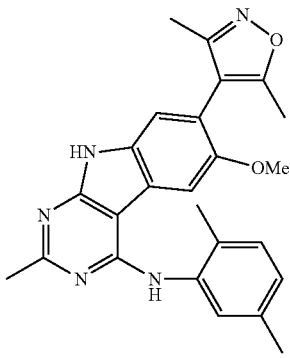

¹H-NMR (300 MHz, CD₃OD) δ ppm 7.43 (s, 1H), 7.38 (d, J=8.12 Hz, 1H), 7.34-7.23 (m, 3H), 3.74 (s, 3H), 2.67 (s, 3H), 2.36 (s, 3H), 2.31 (s, 3H), 2.14 (s, 3H);

N-(3,5-dicyclopropyl-1-methyl-1H-pyrazol-4-yl)-7-(3,5-dimethylisoxazol-4-yl)-6-methoxy-2-methyl-9H-pyrimido[4,5-b]indol-4-amine (Cpd. No. 239)

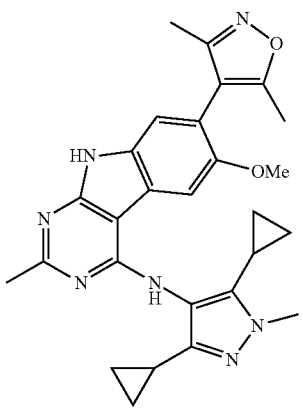

¹H-NMR (300 MHz, CD₃OD) δ ppm 8.18 (br. s., 1H), 7.47 (s, 1H), 3.96 (br. s., 3H), 3.90 (s, 3H), 2.70 (s, 3H), 2.33 (s, 3H), 2.16 (s, 3H), 1.84-1.67 (m, 2H), 1.01-0.67 (m, 8H);

431

N-(3,5-diethyl-1-methyl-1H-pyrazol-4-yl)-7-(3,5-dimethylisoxazol-4-yl)-6-methoxy-2-methyl-9H-pyrimido[4,5-b]indol-4-amine (Cpd. No. 240)

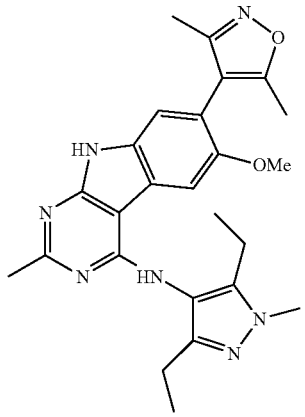

$^1$H-NMR (300 MHz, CD$_3$OD) δ ppm 8.17 (s, 1H), 7.47 (s, 1H), 3.96 (br. s., 3H), 3.88 (s, 3H), 2.82-2.49 (m, 7H), 2.32 (s, 3H), 2.15 (s, 3H), 1.36-1.01 (m, 6H);

7-(3,5-dimethylisoxazol-4-yl)-6-methoxy-2-methyl-N-(1,3,5-triethyl-1H-pyrazol-4-yl)-9H-pyrimido[4,5-b]indol-4-amine (Cpd. No. 241)

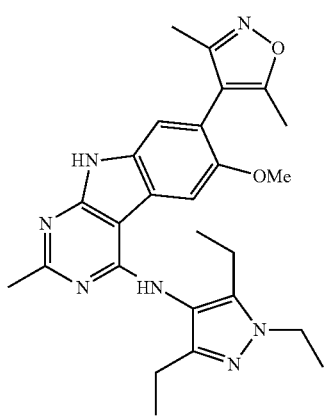 [SMILES: CCc1nn(CC)c(CC)c1Nc1nc(C)nc2[nH]c3cc(-c4c(C)noc4C)c(OC)cc3c12]

$^1$H-NMR (300 MHz, CD$_3$OD) δ ppm 8.16 (s, 1H), 7.47 (s, 1H), 4.28-4.12 (m, 2H), 3.96 (s, 3H), 2.85-2.52 (m, 7H), 2.33 (s, 3H), 2.15 (s, 3H), 1.57-1.38 (m, 3H), 1.34-0.96 (m, 6H);

432

N-(3,5-diisopropyl-1-methyl-1H-pyrazol-4-yl)-7-(3,5-dimethylisoxazol-4-yl)-6-methoxy-2-methyl-9H-pyrimido[4,5-b]indol-4-amine (Cpd. No. 242)

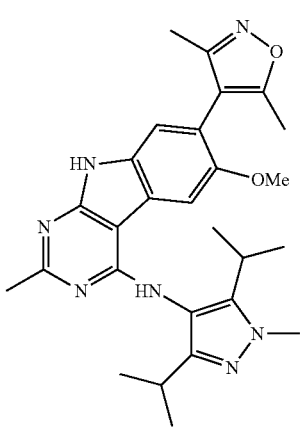

ESI-MS m/z 488.67 (M+H)$^+$; and 7-(3,5-dimethylisoxazol-4-yl)-N-(2-isopropylphenyl)-6-methoxy-2-methyl-9H-pyrimido[4,5-b]indol-4-amine (Cpd. No. 243)

$^1$H-NMR (300 MHz, CD$_3$OD) δ ppm 7.63 (d, J=7.83 Hz, 1H), 7.56-7.47 (m, 1H), 7.45-7.39 (m, 3H), 6.89 (br. s., 1H), 3.64 (s, 3H), 2.69 (s, 3H), 2.29 (s, 3H), 2.12 (s, 3H), 1.31 (d, J=6.82 Hz, 6H).

Example 166

Synthesis of 7-(3,5-dimethylisoxazol-4-yl)-6-methoxy-2-methyl-N-(4-methylpyridin-3-yl)-9H-pyrimido[4,5-b]indol-4-amine (Cpd. No. 109)

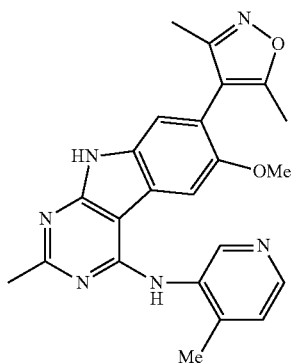

A solution of Pd$_2$(dba)$_3$ (18.3 mg, 0.02 mmol) and BINAP (25 mg, 0.04 mmol) in anhydrous toluene were refluxed for 5 minutes in a pre-heated oil bath (temp. 120° C.). After briefly cooling, the mixture was transferred to a round bottom flask containing S13 (68 mg, 0.2 mmol), 4-methylpyridin-3-amine (43 mg, 0.4 mmol), K$_3$PO$_4$ (127 mg, 0.6 mmol), and toluene (1 mL) and the mixture was refluxed. After refluxing overnight the reaction was cooled to RT, quenched with methanol, and concentrated to dryness. The crude solid was re-dissolved in 3:1 methanol:water, acidified, filtered and purified by HPLC to yield the title compound as its TFA salt. $^1$H-NMR (300 MHz, CD$_3$OD) δ ppm 9.12 (s, 1H), 8.63 (d, J=4.92 Hz, 1H), 8.00-7.92 (m, 2H), 7.46 (s, 1H), 3.95 (s, 3H), 2.64 (s, 3H), 2.62 (s, 3H), 2.34 (s, 3H), 2.17 (s, 3H).

Example 167

The following compounds were prepares as described for Cpd. No. 109 in EXAMPLE 166. In some cases, NaOt-Bu was used instead of K$_3$PO$_4$.

7-(3,5-dimethylisoxazol-4-yl)-6-methoxy-2-methyl-N-(4-methylpyridin-2-yl)-9H-pyrimido[4,5-b]indol-4-amine (Cpd. No. 110)

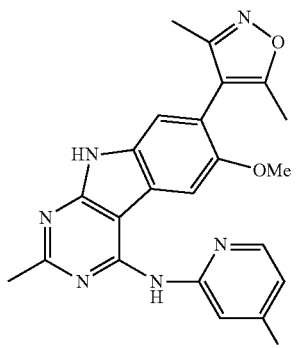

$^1$H-NMR (300 MHz, CD$_3$OD) δ ppm 8.42 (d, J=5.53 Hz, 1H), 8.22 (s, 1H), 7.58 (s, 1H), 7.46 (s, 1H), 7.29 (d, J=5.67 Hz, 1H), 4.02 (s, 3H), 2.88 (s, 3H), 2.56 (s, 3H), 2.35 (s, 3H), 2.18 (s, 3H);

7-(3,5-dimethylisoxazol-4-yl)-6-methoxy-2-methyl-N-(6-methylpyridin-2-yl)-9H-pyrimido[4,5-b]indol-4-amine (Cpd. No. 111)

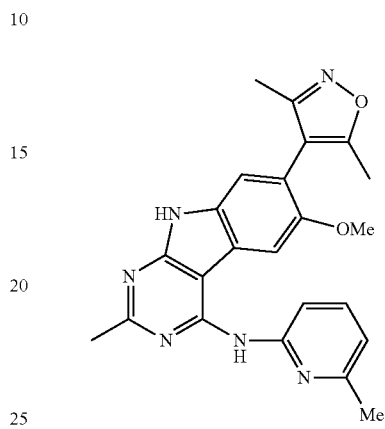

$^1$H-NMR (300 MHz, CD$_3$OD) δ ppm 8.25 (s, 1H), 8.02 (t, J=8.02 Hz, 1H), 7.53 (d, J=8.28 Hz, 1H), 7.48 (s, 1H), 7.28 (d, J=7.67 Hz, 1H), 4.01 (s, 3H), 2.90 (s, 3H), 2.74 (s, 3H), 2.35 (s, 3H), 2.18 (s, 3H);

7-(3,5-dimethylisoxazol-4-yl)-6-methoxy-2-methyl-N-(quinolin-4-yl)-9H-pyrimido[4,5-b]indol-4-amine (Cpd. No. 247)

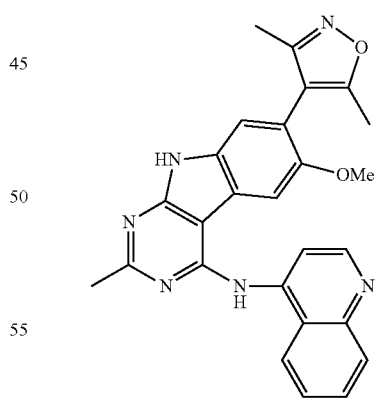

$^1$H-NMR (300 MHz, CD$_3$OD) δ ppm 8.74 (d, J=7.83 Hz, 1H), 8.30-8.23 (m 1H), 8.03-7.71 (m, 3H), 7.41 (s, 1H), 6.95-6.75 (m, 2H), 3.41 (s, 3H), 2.77 (s, 3H), 2.29 (s, 3H), 2.11 (s, 3H);

435

7-(3,5-dimethylisoxazol-4-yl)-6-methoxy-2-methyl-N-(2-methylpyridin-4-yl)-9H-pyrimido[4,5-b]indol-4-amine (Cpd. No. 248)

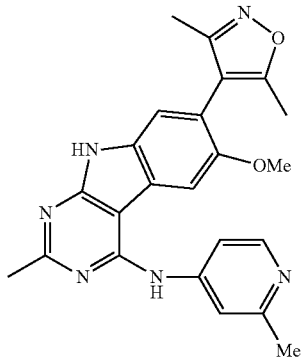

$^1$H-NMR (300 MHz, CD$_3$OD) δ ppm 8.39 (d, J=7.07 Hz, 1H), 8.20 (dd, J=2.39, 7.03 Hz, 1H), 8.05 (d, J=2.16 Hz, 1H), 7.89 (s, 1H), 7.40 (s, 1H), 3.95 (s, 3H), 2.76 (s, 3H), 2.71 (s, 3H), 2.34 (s, 3H), 2.17 (s, 3H);

N-(3-cyclopropyl-4-fluoro-1-methyl-1H-pyrazol-5-yl)-7-(3,5-dimethylisoxazol-4-yl)-6-methoxy-2-methyl-9H-pyrimido[4,5-b]indol-4-amine (Cpd. No. 249)

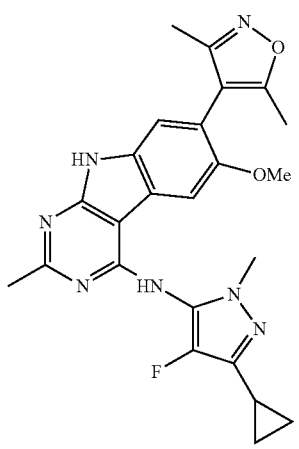 [SMILES: COc1cc2c(cc1-c1c(C)noc1C)[nH]c1nc(C)nc(Nc3c(F)c(C4CC4)nn3C)c12]

$^1$H-NMR (300 MHz, CD$_3$OD) δ ppm 7.96 (s, 1H), 7.45 (s, 1H), 3.94 (s, 6H), 2.71 (s, 3H), 2.34 (s, 3H), 2.17 (s, 3H), 1.96-1.80 (m, 1H), 1.18-1.03 (m, 2H), 0.99-0.84 (m, 2H);

436

N-(3-cyclopropyl-1-ethyl-4-fluoro-1H-pyrazol-5-yl)-7-(3,5-dimethylisoxazol-4-yl)-6-methoxy-2-methyl-9H-pyrimido[4,5-b]indol-4-amine (Cpd. No. 250)

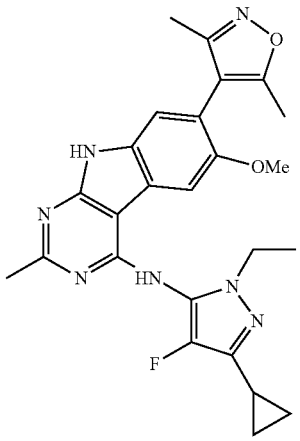 [SMILES: CCn1nc(C2CC2)c(F)c1Nc1nc(C)nc2[nH]c3cc(-c4c(C)noc4C)c(OC)cc3c12]

$^1$H-NMR (300 MHz, CD$_3$OD) δ ppm 7.66 (br. s., 1H), 7.44 (s, 1H), 4.01 (q, J=7.07 Hz, 2H), 3.91 (s, 3H), 2.65 (s, 3H), 2.33 (s, 3H), 2.16 (s, 3H), 2.01-1.86 (m, 1H), 1.39 (t, J=7.19 Hz, 3H), 1.05-0.83 (m, 4H);

7-(3,5-dimethylisoxazol-4-yl)-6-methoxy-2-methyl-N-(1-methyl-3-(1-methylcyclopropyl)-1H-pyrazol-5-yl)-9H-pyrimido[4,5-b]indol-4-amine (Cpd. No. 251)

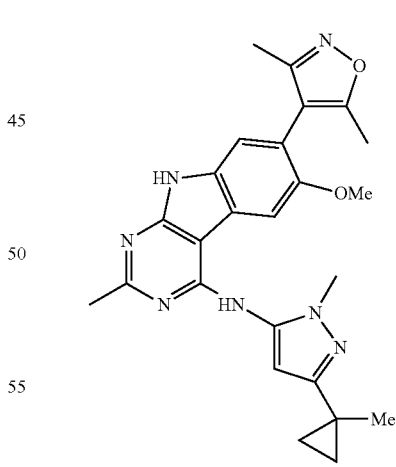

$^1$H-NMR (300 MHz, CD$_3$OD) δ ppm 7.44 (s, 1H), 7.38 (br. s., 1H), 6.14 (s, 1H), 3.88 (s, 3H), 3.75 (s, 3H), 2.69 (s, 3H), 2.32 (s, 3H), 2.15 (s, 3H), 1.45 (s, 3H), 0.99-0.90 (m, 2H), 0.84-0.72 (m, 2H);

437

7-(3,5-dimethylisoxazol-4-yl)-N-(1-ethyl-3-(1-methylcyclopropyl)-1H-pyrazol-5-yl)-6-methoxy-2-methyl-9H-pyrimido[4,5-b]indol-4-amine (Cpd. No. 252)

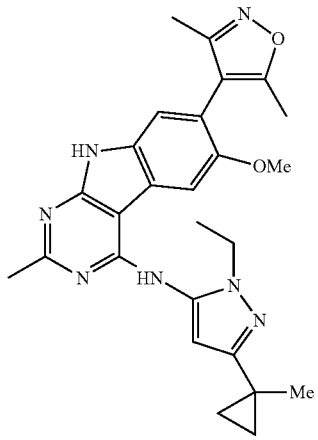 [SMILES: CCn1nc(C2(C)CC2)cc1Nc1nc(C)nc2[nH]c3cc(-c4c(C)noc4C)c(OC)cc3c12]

$^1$H-NMR (300 MHz, CD$_3$OD) δ ppm 7.43 (s, 1H), 7.12 (br. s., 1H), 6.10 (s, 1H), 4.12 (q, J=7.22 Hz, 2H), 3.84 (s, 3H), 2.70 (s, 3H), 2.32 (s, 3H), 2.14 (s, 3H), 1.50-1.38 (m, 6H), 0.99-0.91 (m, 2H), 0.81-0.74 (m, 2H);

7-(3,5-dimethylisoxazol-4-yl)-N-(1-isopropyl-3-(1-methylcyclopropyl)-1H-pyrazol-5-yl)-6-methoxy-2-methyl-9H-pyrimido[4,5-b]indol-4-amine (Cpd. No. 253)

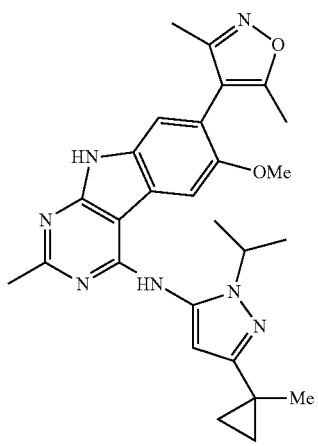 [SMILES: COc1cc2c(cc1-c1c(C)noc1C)[nH]c1nc(C)nc(Nc3cc(C4(C)CC4)nn3C(C)C)c12]

$^1$H-NMR (300 MHz, CD$_3$OD) δ ppm 7.40 (s, 1H), 7.09 (br. s., 1H), 6.03 (s, 1H), 4.62-4.43 (m, 1H), 3.84 (s, 3H), 2.66 (s, 3H), 2.32 (s, 3H), 2.14 (s, 3H), 1.47 (d, J=6.79 Hz, 6H), 1.44 (s, 3H), 0.99-0.88 (m, 2H), 0.79-0.68 (m, 2H); and

438

N-(3-cyclopropyl-4-fluoro-1-isopropyl-1H-pyrazol-5-yl)-7-(3,5-dimethylisoxazol-4-yl)-6-methoxy-2-methyl-9H-pyrimido[4,5-b]indol-4-amine (Cpd. No. 254)

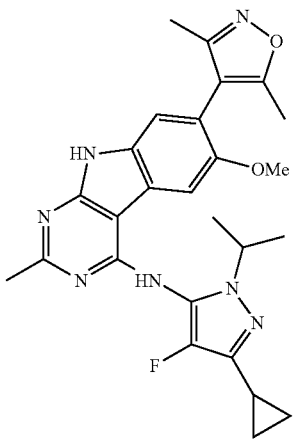 [SMILES: COc1cc2c(cc1-c1c(C)noc1C)[nH]c1nc(C)nc(Nc3c(F)c(C4CC4)nn3C(C)C)c12]

$^1$H-NMR (300 MHz, CD$_3$OD) δ ppm 7.60 (br. s., 1H), 7.44 (s, 1H), 4.52-4.38 (m, 1H), 3.91 (s, 3H), 2.65 (s, 3H), 2.33 (s, 3H), 2.16 (s, 3H), 1.99-1.88 (m, 1H), 1.44 (d, J=6.57 Hz, 6H), 1.01-0.85 (m, 4H).

7-(3,5-dimethylisoxazol-4-yl)-6-methoxy-N-(3-(1-methoxycyclopropyl)-1-methyl-1H-pyrazol-5-yl)-2-methyl-9H-pyrimido[4,5-b]indol-4-amine (Cpd. No. 260)

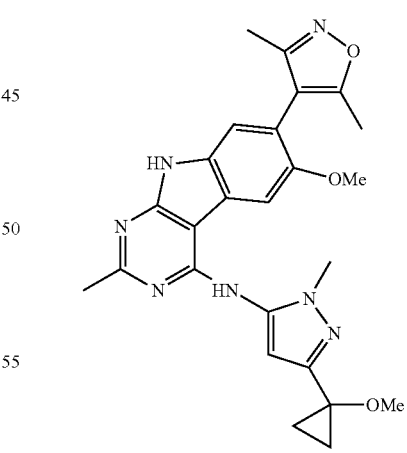

$^1$H-NMR (300 MHz, CD$_3$OD) δ ppm 7.60 (s, 1H), 7.43 (s, 1H), 6.33 (s, 1H), 3.90 (s, 3H), 3.79 (s, 3H), 3.34 (s, 3H), 2.66 (s, 3H), 2.33 (s, 3H), 2.15 (s, 3H), 1.22-1.11 (m, 2H), 1.11-1.01 (m, 2H).

439

7-(3,5-dimethylisoxazol-4-yl)-6-methoxy-2-methyl-N-(1-methyl-3-(1-(trifluoromethyl)cyclopropyl)-1H-pyrazol-5-yl)-9H-pyrimido[4,5-b]indol-4-amine (Cpd. No. 261)

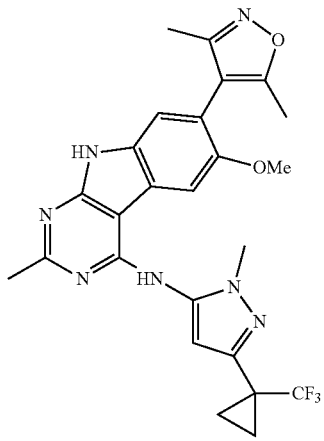 [SMILES: COc1cc2c(cc1-c1c(C)noc1C)[nH]c1nc(C)nc(Nc3cc(C4(C(F)(F)F)CC4)nn3C)c12]

¹H-NMR (300 MHz, CD₃OD) δ ppm 7.72 (s, 1H), 7.43 (s, 1H), 6.43 (s, 1H), 3.91 (s, 3H), 3.78 (s, 3H), 2.65 (s, 3H), 2.33 (s, 3H), 2.16 (s, 3H), 1.41-1.25 (m, 4H)

2-(3-cyclopropyl-5-(7-(3,5-dimethylisoxazol-4-yl)-6-methoxy-2-methyl-9H-pyrimido[4,5-b]indol-4-ylamino)-1H-pyrazol-1-yl)-N-ethylacetamide (Cpd. No. 262)

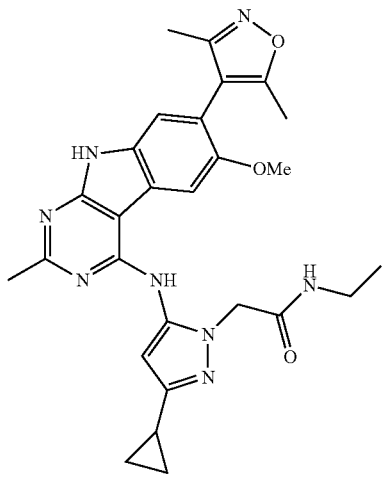 [SMILES: CCNC(=O)Cn1nc(C2CC2)cc1Nc1nc(C)nc2[nH]c3cc(-c4c(C)noc4C)c(OC)cc3c12]

¹H-NMR (300 MHz, CD₃OD) δ ppm 7.86 (s, 1H), 7.44 (s, 1H), 6.28 (s, 1H), 4.95-4.84 (m, 2H), 3.95 (s, 3H), 3.30-3.21 (m, 2H), 2.72 (s, 3H), 2.33 (s, 3H), 2.16 (s, 3H), 2.01-1.88 (m, 1H), 1.14 (t, J=7.30 Hz, 3H), 1.02-0.92 (m, 2H), 0.80-0.71 (m, 2H)

440

N-(3-cyclopropyl-1-(piperidin-4-yl)-1H-pyrazol-5-yl)-7-(3,5-dimethylisoxazol-4-yl)-6-methoxy-2-methyl-9H-pyrimido[4,5-b]indol-4-amine (Cpd. No. 263)

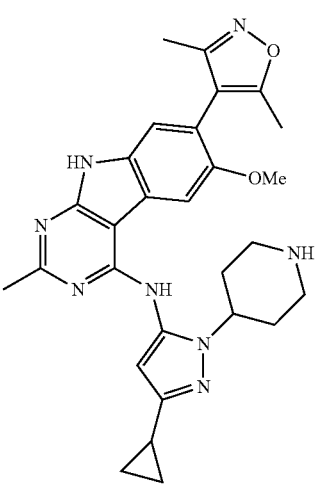 [SMILES: COc1cc2c(cc1-c1c(C)noc1C)[nH]c1nc(C)nc(Nc3cc(C4CC4)nn3C3CCNCC3)c12]

¹H-NMR (300 MHz, CD₃OD) δ ppm 7.39 (s, 1H), 7.33 (s, 1H), 5.93 (s, 1H), 4.59-4.41 (m, 1H), 3.87 (s, 3H), 3.62-3.48 (m, 2H), 3.16-3.00 (m, 2H), 2.61 (s, 3H), 2.48-2.19 (m, 7H), 2.15 (s, 3H), 2.03-1.88 (m, 1H), 1.00-0.91 (m, 2H), 0.74-0.66 (m, 2H)

N-(3-cyclopropyl-1-(1-ethylpiperidin-4-yl)-1H-pyrazol-5-yl)-7-(3,5-dimethylisoxazol-4-yl)-6-methoxy-2-methyl-9H-pyrimido[4,5-b]indol-4-amine (Cpd. No. 264)

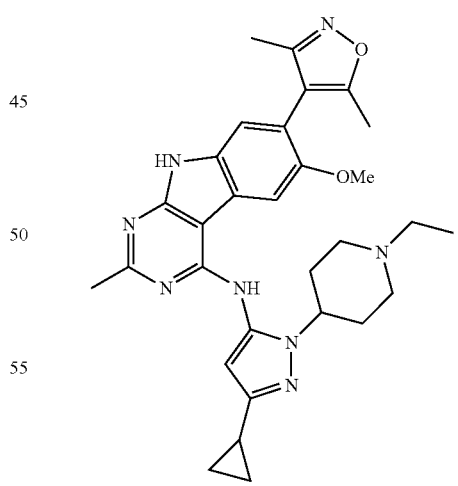

¹H-NMR (300 MHz, CD₃OD) δ ppm 7.40 (s, 1H), 7.31 (s, 1H), 5.94 (s, 1H), 4.59-4.40 (m, 1H), 3.86 (s, 3H), 3.76-3.61 (m, 2H), 3.15 (q, J=7.34 Hz, 2H), 3.10-2.94 (m, 2H), 2.62 (s, 3H), 2.55-2.23 (m, 7H), 2.15 (s, 3H), 2.03-1.87 (m, 1H), 1.33 (t, J=7.32 Hz, 3H), 1.01-0.88 (m, 2H), 0.76-0.64 (m, 2H)

441

1-(4-(3-cyclopropyl-5-(7-(3,5-dimethylisoxazol-4-yl)-6-methoxy-2-methyl-9H-pyrimido[4,5-b]indol-4-ylamino)-1H-pyrazol-1-yl)piperidin-1-yl)ethanone (Cpd. No. 265)

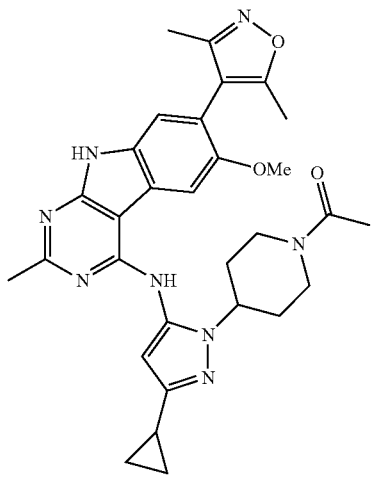 [SMILES: COc1cc2c(cc1-c1c(C)noc1C)[nH]c1nc(C)nc(Nc3cc(C4CC4)nn3C3CCN(C(C)=O)CC3)c12]

¹H-NMR (300 MHz, CD₃OD) δ ppm 7.39 (s, 1H), 7.25 (s, 1H), 5.90 (s, 1H), 4.66-4.55 (m, 1H), 4.50-4.33 (m, 1H), 4.10-3.98 (m, 1H), 3.86 (s, 3H), 3.24-3.01 (m, 2H), 2.62 (s, 3H), 2.32 (s, 3H), 2.23-1.87 (m, 11H), 0.99-0.86 (m, 2H), 0.73-0.62 (m, 2H); ESI-MS m/z 555.58 (M+H)⁺;

(2S)-4-(3-cyclopropyl-5-(7-(3,5-dimethylisoxazol-4-yl)-6-methoxy-2-methyl-9H-pyrimido[4,5-b]indol-4-ylamino)-1H-pyrazol-1-yl)butane-1,2-diol (Cpd. No. 280)

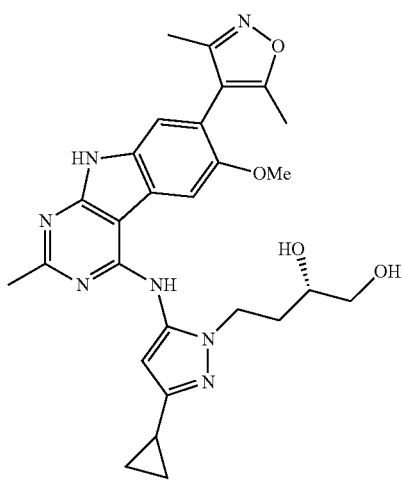 [SMILES: COc1cc2c(cc1-c1c(C)noc1C)[nH]c1nc(C)nc(Nc3cc(C4CC4)nn3CC[C@H](O)CO)c12]

¹H-NMR (300 MHz, CD₃OD) δ ppm 7.53 (s, 1H), 7.44 (s, 1H), 6.12 (s, 1H), 4.31-4.18 (m, 2H), 3.91 (s, 3H), 3.57-3.34 (m, 3H), 2.70 (s, 3H), 2.32 (s, 3H), 2.15 (s, 3H), 2.04-1.76 (m, 3H), 1.05-0.91 (m, 2H), 0.80-0.68 (m, 2H);

442

(S)-3-(3-cyclopropyl-5-((7-(3,5-dimethylisoxazol-4-yl)-6-methoxy-2-methyl-9H-pyrimido[4,5-b]indol-4-yl)amino)-1H-pyrazol-1-yl)propane-1,2-diol (Cpd. No. 281)

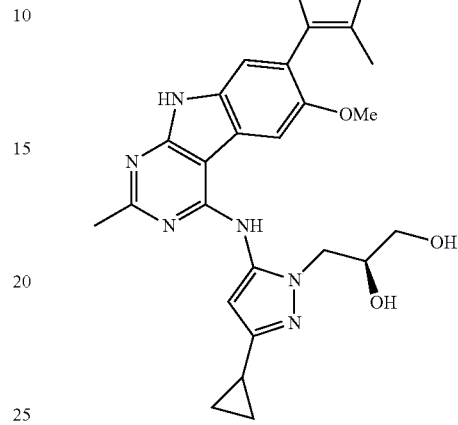

¹H-NMR (300 MHz, CD₃OD) δ ppm 7.62 (s, 1H), 7.46 (s, 1H), 6.34 (s, 1H), 4.44-4.23 (m, 2H), 4.19-4.04 (m, 1H), 3.93 (s, 3H), 3.68-3.52 (m, 2H), 2.75 (s, 3H), 2.33 (s, 3H), 2.15 (s, 3H), 2.03-1.90 (m, 1H), 1.04-0.93 (m, 2H), 0.81-0.68 (m, 2H);

N-(1-((1,4-dioxan-2-yl)methyl)-3-cyclopropyl-1H-pyrazol-5-yl)-7-(3,5-dimethylisoxazol-4-yl)-6-methoxy-2-methyl-9H-pyrimido[4,5-b]indol-4-amine (Cpd. No. 282)

¹H-NMR (300 MHz, CD₃OD) δ ppm 7.43 (s, 1H), 7.00 (s, 1H), 6.12 (s, 1H), 4.25-4.17 (m, 2H), 4.07-3.95 (m, 1H), 3.89-3.79 (m, 4H), 3.71-3.39 (m, 5H), 2.73 (s, 3H), 2.32 (s, 3H), 2.15 (s, 3H), 2.03-1.89 (m, 1H), 1.02-0.93 (m, 2H), 0.74-0.65 (m, 2H);

443

N-(3-cyclopropyl-1-(tetrahydro-2H-pyran-4-yl)-1H-pyrazol-5-yl)-7-(3,5-dimethylisoxazol-4-yl)-6-methoxy-2-methyl-9H-pyrimido[4,5-b]indol-4-amine (Cpd. No. 283)

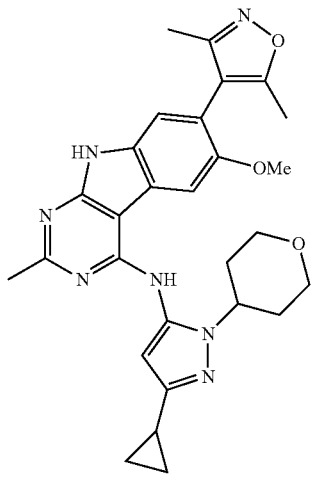 [SMILES: COc1cc2c(cc1-c1c(C)noc1C)[nH]c1nc(C)nc(Nc3cc(C4CC4)nn3C3CCOCC3)c12]

$^1$H-NMR (300 MHz, CD$_3$OD) δ ppm 7.43 (s, 1H), 7.06 (s, 1H), 5.96 (s, 1H), 4.50-4.35 (m, 1H), 4.02 (dd, J=3.96, 11.84 Hz, 2H), 3.85 (s, 3H), 3.52-3.38 (m, 2H), 2.69 (s, 3H), 2.38-2.19 (m, 5H), 2.14 (s, 3H), 2.06-1.83 (m, 3H), 1.01-0.90 (m, 2H), 0.73-0.63 (m, 2H);

N-(3-cyclopropyl-1-(2-morpholinoethyl)-1H-pyrazol-5-yl)-7-(3,5-dimethylisoxazol-4-yl)-6-methoxy-2-methyl-9H-pyrimido[4,5-b]indol-4-amine (Cpd. No. 284)

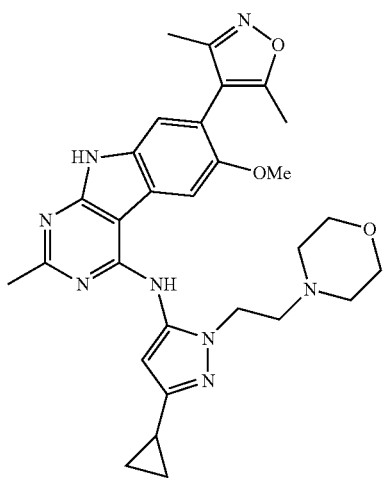 [SMILES: COc1cc2c(cc1-c1c(C)noc1C)[nH]c1nc(C)nc(Nc3cc(C4CC4)nn3CCN3CCOCC3)c12]

444

$^1$H-NMR (300 MHz, CD$_3$OD) δ ppm 7.56 (s, 1H), 7.44 (s, 1H), 6.11 (s, 1H), 4.50 (t, J=6.03 Hz, 2H), 4.01-3.87 (m, 7H), 3.70 (t, J=6.03 Hz, 2H), 3.52-3.36 (m, 4H), 2.69 (s, 3H), 2.32 (s, 3H), 2.15 (s, 3H), 2.05-1.91 (m, 1H), 1.04-0.91 (m, 2H), 0.82-0.70 (m, 2H);

Example 168

Synthesis of N-(3-cyclopropyl-1-methyl-1H-pyrazol-5-yl)-7-(3,5-dimethylisoxazol-4-yl)-8-methoxy-5H-pyrido[4,3-b]indol-1-amine (Cpd. No. 255)

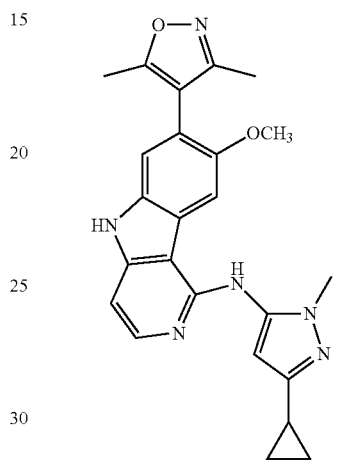

In a round bottom flask, 4-(1-chloro-8-methoxy-5H-pyrido[4,3-b]indol-7-yl)-3,5-dimethylisoxazole (10 mg, 0.03 mmol), 3-cyclopropyl-1-methyl-1H-pyrazol-5-amine (9.06 mg, 0.06 mmol) and sodium tert-butoxide (11.5 mg, 0.12 mmol) were dissolved in dry toluene (10 mL). A solution of Pd$_2$(dba)$_3$ (10.8 mg, 0.012 mmol) and Dave Phos (9.4 mg, 0.024 mmol) in dry toluene (5 mL) was heated to reflux for 5 mins in a two-neck container before it was transferred into the round bottom flask by needle syringe. The resulting mixture was vacuumed and protected with nitrogen balloon, and heated to reflux overnight. As the reaction reach completion, the system were acidified with trifluoroacetic acid and concentrated in vacuum. The residue were dissolved in MeOH/H$_2$O (3:1) system, filtered and purified by prep-HPLC. The product was lyophilized to give the title compound as a color-less powder (2.4 mg, yield 18.7%). $^1$HNMR (300 MHz, MeOD-d$_4$) δ 8.01 (s, 1H), 7.80 (d, 1H, J=7.2 Hz), 7.56 (s, 1H), 7.37 (d, 1H, J=7.2 Hz), 6.24 (s, 1H), 3.98 (s, 3H), 3.80 (s, 3H), 2.36 (s, 3H), 2.19 (s, 3H), 2.00 (m, 1H), 1.00 (m, 2H), 0.81 (m, 2H). ESIMS m/z [M+H]$^+$ calcd.=429.49; found=430.17.

The following compounds were prepared in similar fashion:

445

N-(3-cyclopropyl-1-ethyl-1H-pyrazol-5-yl)-7-(3,5-dimethylisoxazol-4-yl)-8-methoxy-5H-pyrido[4,3-b]indol-1-amine (Cpd. No. 285)

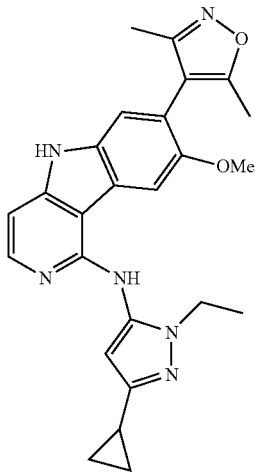 [SMILES: CCn1nc(C2CC2)cc1Nc1nccc2[nH]c3cc(-c4c(C)noc4C)c(OC)cc3c12]

¹H-NMR (300 MHz, CD₃OD) δ ppm 7.90 (s, 1H), 7.08 (d, J=7.03 Hz, 1H), 7.55 (s, 1H), 7.37 (d, J=7.05 Hz, 1H), 6.17 (s, 1H), 4.14 (q, J=7.23 Hz, 2H), 3.94 (s, 3H), 2.33 (s, 3H), 2.16 (s, 3H), 2.05-1.91 (m, 1H), 1.43 (t, J=7.23 Hz, 3H), 1.04-0.93 (m, 2H), 0.83-0.72 (m, 2H); and 7-(3,5-dimethylisoxazol-4-yl)-N-(2-isopropyl-2,4,5,6-tetrahydrocyclopenta[c]pyrazol-3-yl)-8-methoxy-5H-pyrido[4,3-b]indol-1-amine (Cpd. No. 286)

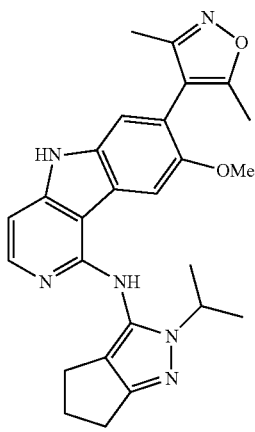 [SMILES: COc1cc2c(cc1-c1c(C)noc1C)[nH]c1ccnc(Nc3c4c(nn3C(C)C)CCC4)c12]

¹H-NMR (300 MHz, CD₃OD) δ ppm 7.93 (s, 1H), 7.81 (d, J=7.04 Hz, 1H), 7.56 (s, 1H), 7.37 (d, J=7.03 Hz, 1H), 4.61 (hept., J=6.55 Hz, 1H), 3.94 (s, 3H), 2.81 (t, J=7.19 Hz, 2H), 2.63-2.39 (m, 4H), 2.34 (s, 3H), 2.17 (s, 3H), 1.49 (d, J=6.65 Hz, 6H).

Example 169

The following compounds were prepared as described for Cpd. No. 255 in EXAMPLE 168.

446

N-(1-cyclopentyl-3-methyl-1H-pyrazol-5-yl)-7-(3,5-dimethylisoxazol-4-yl)-8-methoxy-5H-pyrido[4,3-b]indol-1-amine (Cpd. No. 256)

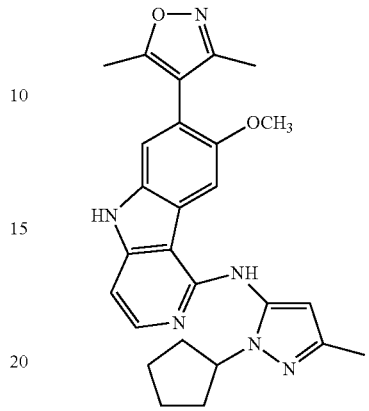

¹HNMR (300 MHz, MeOD-d₄) δ 8.08 (s, 1H), 7.78 (d, 1H, J=7.2 Hz), 7.57 (s, 1H), 7.36 (d, 1H, J=7.2 Hz), 6.34 (s, 1H), 3.98 (s, 3H), 2.38 (s, 3H), 2.36 (s, 3H), 2.19 (s, 3H), 2.07 (m, 4H), 1.95 (m, 2H), 1.66 (m, 2H), missing one proton. ESIMS m/z [M+H]⁺ calcd.=457.55; found=457.83;

7-(3,5-dimethylisoxazol-4-yl)-8-methoxy-N-(1-methyl-1H-pyrazolo[3,4-b]pyridin-3-yl)-5H-pyrido[4,3-b]indol-1-amine (Cpd. No. 257)

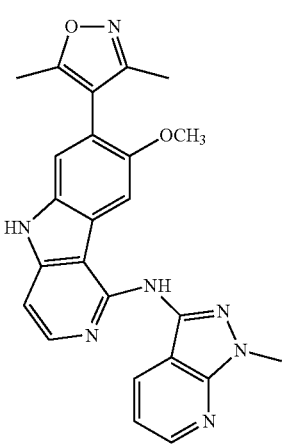

¹HNMR (300 MHz, MeOD-d₄) δ 8.73 (d, 1H, J=3.9 Hz), 8.46 (d, 1H, J=8.4 Hz), 8.21 (s, 1H), 8.05 (d, 1H, J=6.6 Hz), 7.59 (s, 1H), 7.46 (d, J=7.2 Hz), 7.39 (m, 1H), 4.25 (s, 3H), 4.05 (s, 3H), 2.38 (s, 3H), 2.21 (s, 3H). ESIMS m/z [M+H]⁺ calcd.=440.48; found=440.50;

N-(3-Cyclopropyl-1-(1-methylazetidin-3-yl)-1H-pyrazol-5-yl)-7-(3,5-dimethyl-isoxazol-4-yl)-6-methoxy-N,2,9-trimethyl-9H-pyrimido[4,5-b]indol-4-amine (Cpd No. 258)

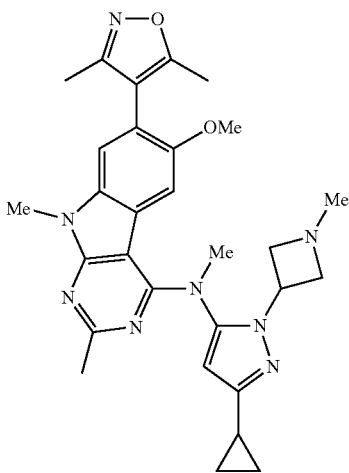 [SMILES: COc1cc2c3c(N(C)c4cc(C5CC5)nn4C4CN(C)C4)nc(C)nc3n(C)c2cc1-c1c(C)noc1C]

In a round-bottom flask, compound No. 163 (13 mg) was added. Paraformaldehyde (30 mg), NaBH(OAc)$_3$ (212 mg), and 1,2-dichloromethane (5 mL) were added followed by addition of acetic acid (0.1 mL) via a syringe. The reaction mixture was stirred at room temperature for overnight followed by purification using reverse phase HPLC to yield the titled compound Cpd 258 in 2 mg as a salt of trifluoroacetic acid. ESI-MS calculated for $C_{29}H_{35}N_8O_2$ [M+H]$^+$=527.29; Observed: 527.67;

N-(3-Cyclopropyl-1-(2-methoxyethyl)-1H-pyrazol-5-yl)-7-(3,5-dimethylisoxazol-4-yl)-6-methoxy-2-methyl-9H-pyrimido[4,5-b]indol-4-amine (Cpd No. 266)

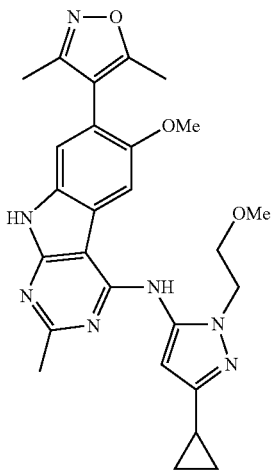 [SMILES: COCCn1nc(C2CC2)cc1Nc1nc(C)nc2[nH]c3cc(-c4c(C)noc4C)c(OC)cc3c12]

Step 1: 3-Cyclopropyl-3-oxopropanenitrile (1.4 g, 8 mmol) and 2-methoxyethyl hydrazine-HCl (1.0 g, 8.0 mmol) were mixed in ethanol (20 mL) and heated at reflux for overnight. The reaction mixture was cooled to room temperature and ethanol was removed on a rotary evaporator. Water was added and the aqueous layer was extracted with ethyl acetate. The combined organic layers were washed with brine, dried over anhydrous sodium sulfate, and concentrated on a rotary evaporator. The remaining residue was purified by flash column chromatography to yield 3-cyclopropyl-1-(2-methoxyethyl)-1H-pyrazol-5-amine in 0.89 g (4.92 mmol, 62% yield). $^1$H NMR (CDCl$_3$, 300 MHz): 5.12 (s, 1H), 4.12-4.06 (m, 2H), 3.95 (s, 2H), 3.70-3.64 (m, 2H), 3.32 (s, 3H), 1.95-1.70 (m, 1H), 0.90-0.80 (m, 2H), 0.70-0.60 (m, 2H). ESI-MS calculated for $C_9H_{16}N_3O$ [M+H]$^+$=182.13, Observed: 182.50.

Step 2: Cpd. No. 266 was prepared from S13 (444 mg) and 3-cyclopropyl-1-(2-methoxyethyl)-1H-pyrazol-5-amine (456 mg, 2.51 mmol) following the similar procedure for preparation of Cpd. No. 135. Cpd. No. 266 was obtained in 241 mg as a salt of CF$_3$CO$_2$H. $^1$H NMR (MeOD-d4, 300 MHz): 7.44 (s, 1H), 6.90 (s, 1H), 6.11 (s, 1H), 4.34 (t, J=4.62 Hz, 2H), 3.83 (s, 3H), 3.78 (t, J=4.81 Hz, 2H), 3.23 (s, 3H), 2.74 (s, 3H), 2.30 (s, 3H), 2.12 (s, 3H), 2.00-1.85 (m, 1H), 1.00-0.90 (m, 2H), 0.75-0.65 (m, 2H). ESI-MS calculated for $C_{26}H_{30}N_7O_3$ [M+H]$^+$=488.24; Observed: 488.58;

N-(3-Cyclopropyl-1-(1-methylpiperidin-4-yl)-1H-pyrazol-5-yl)-7-(3,5-dimethyl-isoxazol-4-yl)-6-methoxy-2-methyl-9H-pyrimido[4,5-b]indol-4-amine (Cpd No. 267)

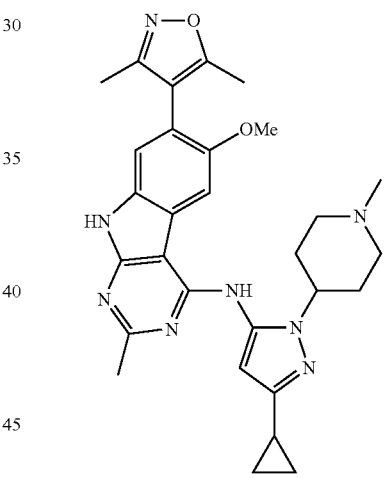

Step 1: 3-Cyclopropyl-3-oxopropanenitrile (900 mg, 5 mmol) and 4-hydrazinyl-1-methyl-piperidine-HCl (1.0 g, 4.9 mmol) were mixed in ethanol (20 mL) and heated at reflux for overnight. The reaction mixture was cooled to room temperature and ethanol was removed on a rotary evaporator. Water was added and the aqueous layer was extracted with ethyl acetate. The combined organic layers were washed with brine, dried over anhydrous sodium sulfate, and concentrated on a rotary evaporator. The remaining residue was purified by flash column chromatography to yield 3-cyclopropyl-1-(1-methylpiperidin-4-yl)-1H-pyrazol-5-amine in 0.81 g (74% yield). $^1$H NMR (CDCl$_3$, 300 MHz): 5.11 (s, 1H), 3.90-3.40 (m, 1H), 3.60 (s, 2H), 3.10-2.85 (m, 2H), 2.40-2.20 (m, 2H), 2.28 (s, 3H), 2.20-2.00 (m, 2H), 1.95-1.70 (m, 3H), 0.90-0.80 (m, 2H), 0.70-0.50 (m, 2H). ESI-MS calculated for $C_{12}H_{21}N_4$ [M+H]$^+$=221.18, Observed: 221.50.

Step 2: Cpd. No. 267 was prepared from S13 (650 mg) and 3-cyclopropyl-1-(1-methylpiperidin-4-yl)-1H-pyrazol- 5-amine (810 mg, 3.67 mmol) following the similar procedure for preparation of Cpd. No. 135. Cpd. No. 267 was obtained in 414 mg as a salt of $CF_3CO_2H$. $^1H$ NMR (MeOD-d4, 300 MHz): 7.44 (s, 1H), 6.90 (s, 1H), 5.98 (s, 1H), 5.70-5.50 (m, 1H), 3.82 (s, 3H), 3.70-3.65 (m, 2H), 3.20-3.00 (m, 2H), 2.86 (s, 3H), 2.71 (s, 3H), 2.60-2.40 (m, 2H), 2.30 (s, 3H), 2.30-2.20 (m, 2H), 2.12 (s, 3H), 2.00-1.85 (m, 1H), 1.00-0.90 (m, 2H), 0.80-0.60 (m, 2H). ESI-MS calculated for $C_{29}H_{35}N_8O_2$ $[M+H]^+=527.29$; Observed: 527.50;

1-(3-(3-Cyclopropyl-5-((7-(3,5-dimethylisoxazol-4-yl)-6-methoxy-2-methyl-9H-pyrimido[4,5-b]indol-4-yl)amino)-1H-pyrazol-1-yl)azetidin-1-yl)ethan-1-one (Cpd No. 277)

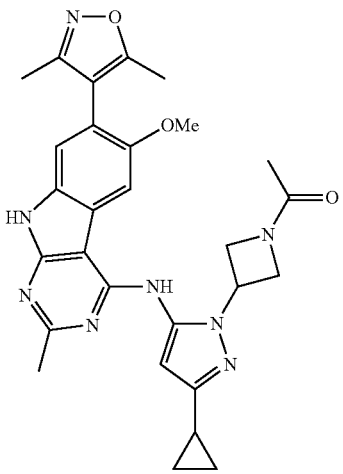 [SMILES: COc1cc2c(cc1-c1c(C)noc1C)[nH]c1nc(C)nc(Nc3cc(C4CC4)nn3C3CN(C(C)=O)C3)c12]

In a round-bottom flask, compound No. 163 (40 mg) was added. Triethyl amine (0.3 mL) and THF (5 mL) were added followed by addition of acetic anhydride (0.1 mL). The reaction mixture was stirred at room temperature for overnight and the mixture was purified using reverse phase HPLC to yield Cpd. No. 277 in 19 mg as a salt of $CF_3CO_2H$. $^1H$ NMR (MeOD-d4, 300 MHz): 7.50 (s, 1H), 7.46 (s, 1H), 6.06 (s, 1H), 5.20-5.05 (m, 1H), 4.63 (dd, J=9.00, 5.36 Hz, 1H), 4.51 (t, J=8.69 Hz, 1H), 4.33 (dd, J=9.98, 5.53 Hz, 1H), 4.25 (t, J=9.07 Hz, 1H), 3.89 (s, 3H), 2.68 (s, 3H), 2.31 (s, 3H), 2.14 (s, 3H), 2.10-1.96 (m, 1H), 1.91 (s, 3H), 1.05-0.95 (m, 2H), 0.80-0.70 (m, 2H). ESI-MS calculated for $C_{28}H_{31}N_8O_3$ $[M+H]^+=527.25$; Observed: 527.50.

Methyl 3-(3-cyclopropyl-5-((7-(3,5-dimethylisoxazol-4-yl)-6-methoxy-2-methyl-9H-pyrimido-[4,5-b]indol-4-yl)amino)-1H-pyrazol-1-yl)azetidine-1-carboxylate (Cpd No. 278)

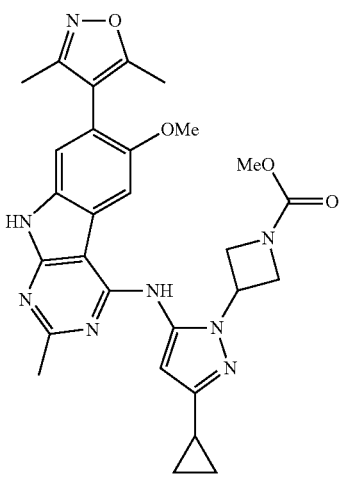 [SMILES: COC(=O)N1CC(n2nc(C3CC3)cc2Nc2nc(C)nc3[nH]c4cc(-c5c(C)noc5C)c(OC)cc4c23)C1]

In a round-bottom flask, compound No. 163 (30 mg) was added. Triethyl amine (0.3 mL) and THF (5 mL) were added followed by addition of methyl carbonochloridate (0.1 mL). The reaction mixture was stirred at room temperature for overnight and the mixture was purified using reverse phase HPLC to yield Cpd. No. 278 in 6 mg as a salt of $CF_3CO_2H$. $^1H$ NMR (MeOD-d4, 300 MHz): 7.52 (s, 1H), 7.46 (s, 1H), 6.05 (s, 1H), 5.15-5.05 (m, 1H), 4.50-4.35 (m, 1H), 4.35-4.20 (m, 1H), 3.89 (s, 3H), 3.66 (s, 3H), 2.66 (s, 3H), 2.32 (s, 3H), 2.15 (s, 3H), 2.10-2.00 (m, 1H), 2.03 (s, 3H), 1.05-0.95 (m, 2H), 0.80-0.70 (m, 2H). ESI-MS calculated for $C_{28}H_{31}N_8O_4$ $[M+H]^+=543.25$; Observed: 543.67; and N-(3-Cyclopropyl-1-(1-ethyl azetidin-3-yl)-1H-pyrazol-5-yl)-7-(3,5-dimethylisoxazol-4-yl)-6-methoxy-2-methyl-9H-pyrimido[4,5-b]indol-4-amine (Cpd No. 279)

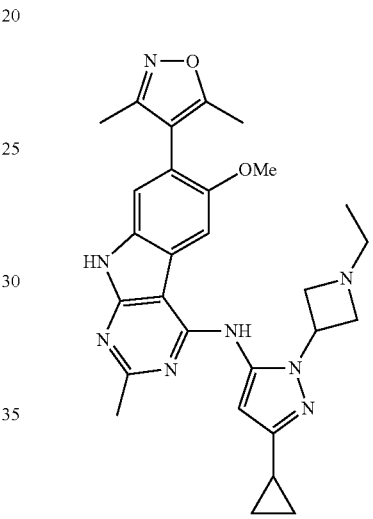

In a round-bottom flask, compound No. 163 (40 mg) was added. Acetaldehyde (0.1 mL), NaBH(OAc)$_3$ (424 mg) and 1,2-dichloroethane (5 mL) were added followed by addition of acetic acid (0.05 mL) via a syringe. The reaction mixture was stirred at room temperature for overnight and the mixture was purified using reverse phase HPLC to yield Cpd. No. 279 in 40 mg as a salt of $CF_3CO_2H$. $^1H$ NMR (MeOD-d4, 300 MHz): 7.66 (s, 1H), 7.47 (s, 1H), 6.08 (s, 1H), 5.50-5.30 (m, 1H), 4.80-4.60 (m, 2H), 4.55-4.30 (m, 2H), 3.90 (s, 3H), 3.54 (q, J=7.43 Hz, 2H), 2.66 (s, 3H), 2.31 (s, 3H), 2.14 (s, 3H), 2.10-2.00 (m, 1H), 1.28 (t, J=7.43 Hz, 3H), 1.05-0.95 (m, 2H), 0.85-0.75 (m, 2H). ESI-MS calculated for $C_{28}H_{33}N_8O_2$ $[M+H]^+=513.27$; Observed: 513.58.

Example 170

Scheme 1

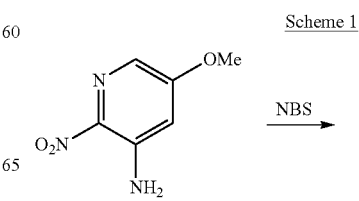

-continued

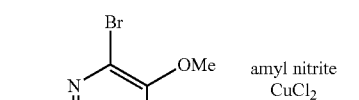

YH1

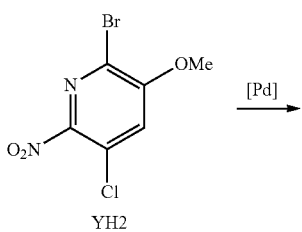

YH2

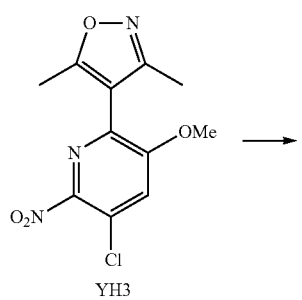

YH3

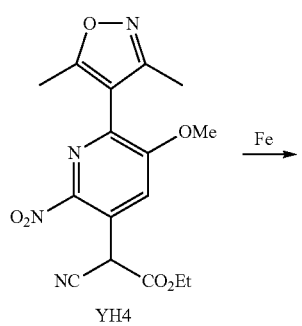

YH4

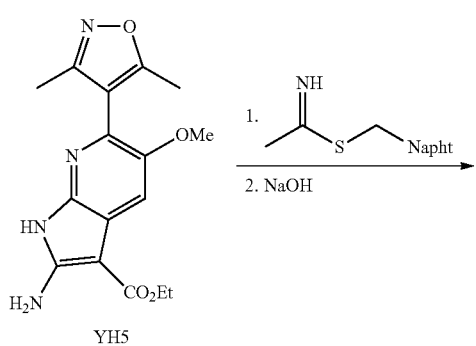

YH5

-continued

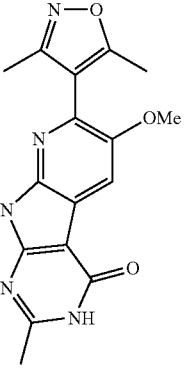

YH6

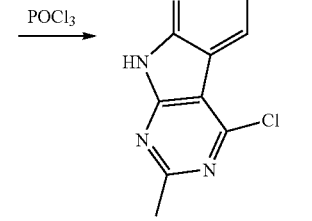

YH7

Step 1: Synthesis of 6-bromo-5-methoxy-2-nitropyridin-3-amine

To a stirred solution of 5-methoxy-2-nitropyridin-3-amine (1.32 g, 7.8 mmol) in DMF (15 mL) at r.t. was added NBS (1.46 g, 8.2 mmol) in portions. The resulting mixture was stirred for 1 h at r.t. Water (30 mL) was added. The yellow precipitate was filtered, washed with water, and dried to give title compound (1.9 g, 90%). $^1$H NMR (300 MHz, DMSO): 7.60 (s, 2H), 7.00 (s, 1H), 3.91 (s, 3H); ESI-MS calculated for $[M+H]^+$=248.0, observed: 248.1.

Step 2: Synthesis of 2-bromo-5-chloro-3-methoxy-6-nitropyridine

A solution of amyl nitrite (7.5 mmol, 1 mL) and CuCl2 (0.8 g, 6 mmol) in CH3CN (20 mL) was warmed to 55° C. Solid 6-bromo-5-methoxy-2-nitropyridin-3-amine (1.35 g, 5.5 mmol) was slowly added to the reaction mixture with the observance of the gas evolution. Once the addition was complete, the reaction temperature was raised to 65° C. and stirred for another 1 h. The reaction mixture was cooled to r.t. and the solvent was removed under vacuum. The residue was diluted with water and EtOAc. The organic layer was separated, dried over $Na_2SO_4$, and concentrated under vacuum. The residue was purified through column chromatography (eluent: hexanes/EtOAc=1/1) to afford YH2 as solid (1.2 g, 79%). $^1$H NMR (300 MHz, $CDCl_3$ ppm) 7.30 (s, 1H), 4.02 (s, 3H).

Step 3: Synthesis of 4-(5-chloro-3-methoxy-6-nitro-pyridin-2-yl)-3,5-dimethylisoxazole To a round-bottom flask was charged with YH2 (1.2 g, 4.3 mmol), 3,5-dimethyl-4-(4,4,5,5-tetramethyl-1,3,2-dioxaborolan-2-yl)isoxazole (1.45 g, 6.5 mmol), Pd(dppf)CH$_2$Cl$_2$ (175 mg, 0.2 mmol), dioxane (20 mL) and Na2CO3 (2 M, 5 mL). The reaction mixture was heated up under N at 100° C. for 12 h. The solution was cooled prior to being extracted with EtOAc (2×100 mL). The organic layers were combined and washed with brine (50 mL). The organic layer was separated, dried over $Na_2SO_4$, and concentrated under vacuum. The residue was purified through column chromatography (eluent: DCM/EtOAc=15:1) to afford YH3 as a solid (610 mg, 50%). $^1$H NMR (300 MHz, CDCl$_3$) 7.47 (s, 1H), 4.01 (s, 3H), 2.43 (s, 3H), 2.30 (s, 3H).

Step 4: Synthesis of ethyl 2-cyano-2-(6-(3,5-dimethylisoxazol-4-yl)-5-methoxy-2-nitropyridin-3-yl)acetate To a suspension of NaH (60% in mineral oil, 176 mg, 4.4 mmol) in DMF (8 mL) at 0° C. was added ethyl cyanoacetate (452 mg, 4 mmol) dropwise. The solution was allowed to warm to r.t. and stirred for 15 minutes. Then the reaction mixture was cooled back to 0° C. prior to the dropwise addition of a solution of YH3 (530 mg, 1.9 mmol) in THF/DMF (2 mL/2 mL). The reaction was stirred for 1 h at r.t. prior to being neutralized by 1 M HCl. The reaction mixture was extracted with EtOAc (2×20 mL). The organic layers were combined and washed with brine (3×20 mL). The organic layer was separated, dried over Na$_2$SO$_4$, and concentrated under vacuum. The residue was purified through column chromatography (eluent: hexanes/EtOAc=1/1) to afford YH4 as oil (648 mg, 95%). $^1$H NMR (300 MHz, CDCl$_3$): 7.67 (s, 1H), 5.80 (s, 1H), 4.38 (q, J=7.1 Hz, 2H), 4.09 (s, 3H), 2.47 (s, 3H), 2.35 (s, 3H), 1.39 (t, J=7.1 Hz, 3H).

Step 5: Synthesis of ethyl 2-amino-6-(3,5-dimethylisoxazol-4-yl)-5-methoxy-1H-pyrrolo[2,3-b]pyridine-3-carboxylate To a solution of YH4 (648 mg, 1.8 mmol) in acetic acid (10 mL) was added iron powder (360 mg, 6.4 mmol). The reaction was stirred at r.t for 6 h prior to the addition of DCM/MeOH (4:1, 20 mL) and the suspension was filtered. The filtrate was evaporated under vacuum and the residue was treated with EtOAc (100 mL) and water (100 mL). The organic layer was separated, washed successively with NaHCO$_3$ and brine. The organic layer was separated, dried over Na$_2$SO$_4$, and concentrated under vacuum. The residue was purified through column chromatography (eluent: DCM/MeOH=9/1) to afford YH5 as a solid (430 mg, 72%). $^1$H NMR (300 MHz, CDCl$_3$): 12.50 (s, 1H), 7.74 (s, 1H), 5.72-4.79 (m, 2H), 4.40 (q, J=7.0 Hz, 2H), 3.89 (s, 3H), 2.40 (s, 3H), 2.29 (s, 3H), 1.45 (t, J=7.0 Hz, 3H).

Step 6: Synthesis of 7-(3,5-dimethylisoxazol-4-yl)-6-methoxy-2-methyl-3,9-dihydro-4H-pyrido[3',2':4,5]pyrrolo[2,3-d]pyrimidin-4-one Naphthalen-2-ylmethyl ethanimidothioate hydrobromide (3.55 g, 12 mmol) was added to a vigorously stirred solution of K$_2$CO$_3$ (1.6 g, 12 mmol) in water (10 mL) and DCM (10 mL). After 10 minutes, the organic layer was separated and dried over Mg$_2$SO$_4$. The clear solution was decanted to a flask where it contained YH5 (400 mg, 1.2 mmol). To this solution was added acetic acid (0.34 mL, 6 mmol) and the reaction mixture was stirred for 12 h. The solution was evaporated to give a crude oil. A solution of NaOH (1 M, 10 mL) was added to the crude oil followed by the addition of ethanol (30 mL). The reaction mixture was heated up to 80° C. for 2 h. After the solution was cooled, the ethanol was evaporated under vacuum and the aqueous solution was cooled to 0° C. and 1 M HCl was added slowly until PH=4. The mixture was extracted with ethyl acetate. The organic layer was separated, dried over Na$_2$SO$_4$, and concentrated under vacuum. The residue was purified through column chromatography (eluent: DCM/MeOH=9/1) to afford YH6 as a solid (34 mg, 8%). $^1$H NMR (300 MHz, DMSO): 12.56 (s, 1H), 7.90 (s, 1H), 3.90 (s, 3H), 2.43 (s, 3H), 2.35 (s, 3H), 2.20 (s, 3H).

Step 7: Synthesis of 4-(4-chloro-6-methoxy-2-methyl-9H-pyrido[3',2':4,5]pyrrolo[2,3-d]pyrimidin-7-yl)-3,5-dimethylisoxazole A suspension of YH6 (34 mg, 0.1 mmol) in POCl$_3$ (4 mL) was heated at 90° C. for 1 h prior to the removal of the volatile under vacuum. The residue was taken up by the ethyl acetate (4 mL) and a saturated solution of NaHCO$_3$ was added until pH=9. The precipitate was filtered and washed with water and ethyl acetate to give title compound (30 mg, 88%). ESI-MS calculated for [M+H]$^+$=344.1, observed: 344.4.

Synthesis of N-(3-cyclopropyl-1-methyl-1H-pyrazol-5-yl)-7-(3,5-dimethylisoxazol-4-yl)-6-methoxy-9H-pyrido[3',2':4,5]pyrrolo[2,3-d]pyrimidin-4-amine (Cpd. No. 304)

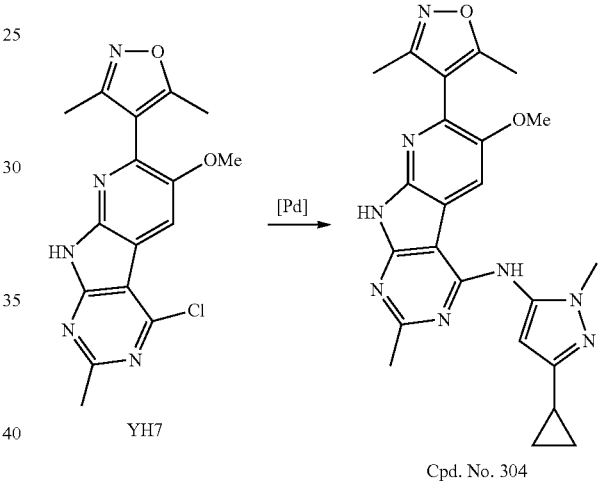

YH7

Cpd. No. 304

YH7 (12 mg), 3-cyclopropyl-1-methyl-1H-pyrazol-5-amine (20 mg), Pd$_2$(dba)$_3$ (5 mg), binap (6 mg), K3PO4 (30 mg), and anhydrous toluene (2 mL) were mixed and the reaction mixture was heated at reflux for 12 h. The crude mixture was diluted with EtOAc and the organic layer was washed with water. The solvent was removed and the residue was purified via reverse phase HPLC to yield the titled compound in 3 mg. $^1$H NMR (300 MHz, CD3OD): 7.40 (s, 1H), 6.09 (s, 1H), 3.93 (s, 3H), 3.76 (s, 3H), 2.70 (s, 3H), 2.41 (s, 3H), 2.29 (s, 3H), 2.02-1.90 (m, 1H), 1.08-0.92 (m, 2H), 0.85-0.70 (m, 2H).

Scheme 2

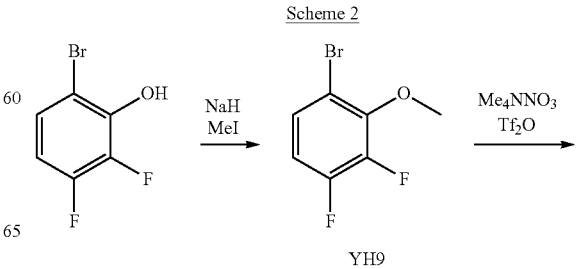

YH9

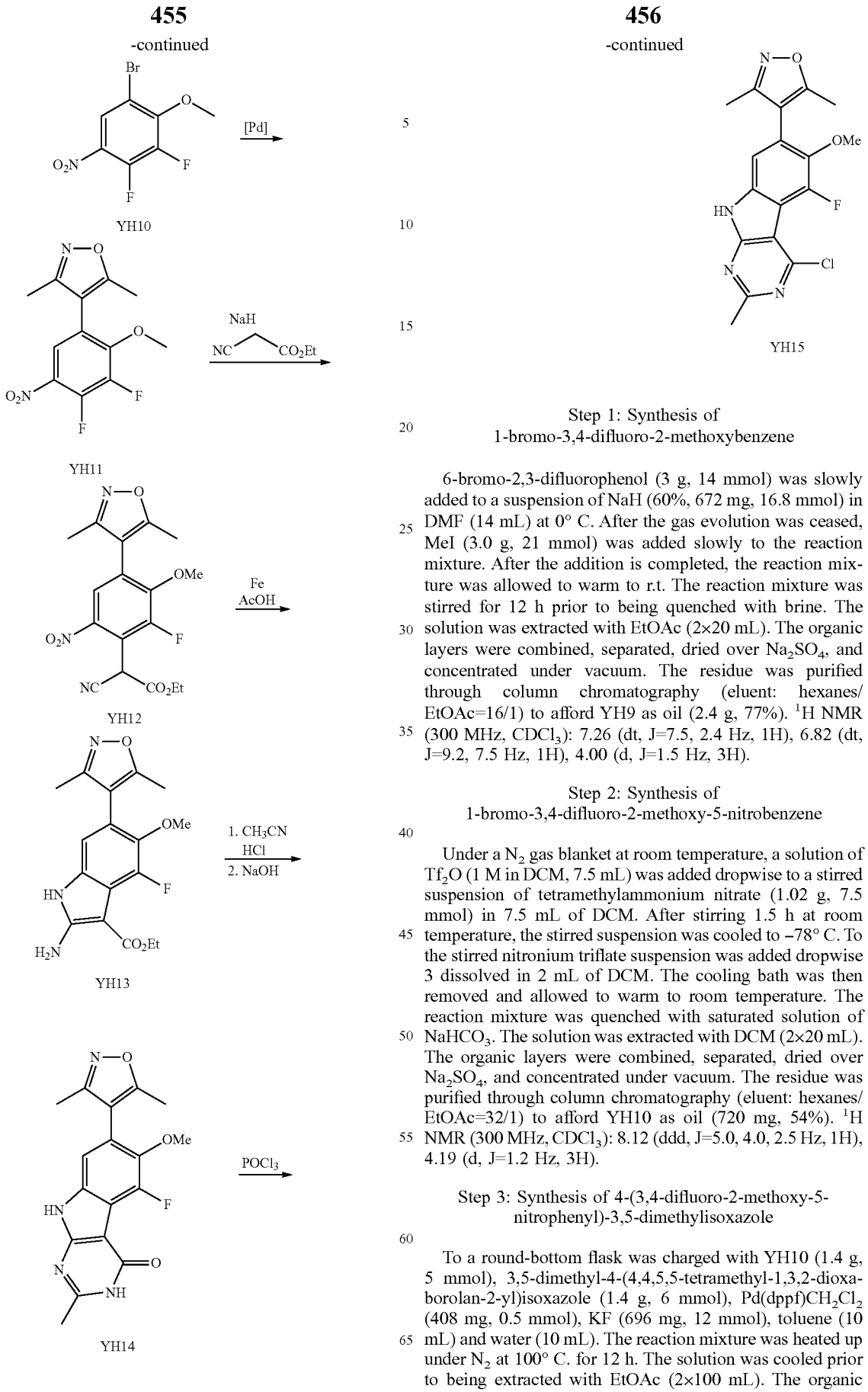

Step 1: Synthesis of 1-bromo-3,4-difluoro-2-methoxybenzene 6-bromo-2,3-difluorophenol (3 g, 14 mmol) was slowly added to a suspension of NaH (60%, 672 mg, 16.8 mmol) in DMF (14 mL) at 0° C. After the gas evolution was ceased, MeI (3.0 g, 21 mmol) was added slowly to the reaction mixture. After the addition is completed, the reaction mixture was allowed to warm to r.t. The reaction mixture was stirred for 12 h prior to being quenched with brine. The solution was extracted with EtOAc (2×20 mL). The organic layers were combined, separated, dried over $Na_2SO_4$, and concentrated under vacuum. The residue was purified through column chromatography (eluent: hexanes/EtOAc=16/1) to afford YH9 as oil (2.4 g, 77%). $^1$H NMR (300 MHz, $CDCl_3$): 7.26 (dt, J=7.5, 2.4 Hz, 1H), 6.82 (dt, J=9.2, 7.5 Hz, 1H), 4.00 (d, J=1.5 Hz, 3H).

Step 2: Synthesis of 1-bromo-3,4-difluoro-2-methoxy-5-nitrobenzene

Under a $N_2$ gas blanket at room temperature, a solution of $Tf_2O$ (1 M in DCM, 7.5 mL) was added dropwise to a stirred suspension of tetramethylammonium nitrate (1.02 g, 7.5 mmol) in 7.5 mL of DCM. After stirring 1.5 h at room temperature, the stirred suspension was cooled to −78° C. To the stirred nitronium triflate suspension was added dropwise 3 dissolved in 2 mL of DCM. The cooling bath was then removed and allowed to warm to room temperature. The reaction mixture was quenched with saturated solution of $NaHCO_3$. The solution was extracted with DCM (2×20 mL). The organic layers were combined, separated, dried over $Na_2SO_4$, and concentrated under vacuum. The residue was purified through column chromatography (eluent: hexanes/EtOAc=32/1) to afford YH10 as oil (720 mg, 54%). $^1$H NMR (300 MHz, $CDCl_3$): 8.12 (ddd, J=5.0, 4.0, 2.5 Hz, 1H), 4.19 (d, J=1.2 Hz, 3H).

Step 3: Synthesis of 4-(3,4-difluoro-2-methoxy-5-nitrophenyl)-3,5-dimethylisoxazole To a round-bottom flask was charged with YH10 (1.4 g, 5 mmol), 3,5-dimethyl-4-(4,4,5,5-tetramethyl-1,3,2-dioxaborolan-2-yl)isoxazole (1.4 g, 6 mmol), Pd(dppf)$CH_2Cl_2$ (408 mg, 0.5 mmol), KF (696 mg, 12 mmol), toluene (10 mL) and water (10 mL). The reaction mixture was heated up under $N_2$ at 100° C. for 12 h. The solution was cooled prior to being extracted with EtOAc (2×100 mL). The organic layers were combined and washed with brine (50 mL). The organic layer was separated, dried over $Na_2SO_4$, and concentrated under vacuum. The residue was purified through column chromatography (eluent: hexanes/EtOAc=4/1 to 2:1) to afford YH11 as a red solid, which was triturated with diethyl ether, followed by filtration to give YH11 as a yellow solid (1.0 g, 70%). $^1$H NMR (300 MHz, $CDCl_3$): 7.80-7.64 (m, 1H), 4.05 (s, 3H), 2.35 (s, 3H), 2.18 (s, 3H).

Step 4: Synthesis of ethyl 2-cyano-2-(4-(3,5-dimethylisoxazol-4-yl)-2-fluoro-3-methoxy-6-nitrophenyl)acetate To a suspension of NaH (60% in mineral oil, 88 mg, 2.2 mmol) in DMF (4 mL) at 0° C. was added ethyl cyanoacetate (226 mg, 2 mmol) dropwise. The solution was allowed to warm to r.t. and stirred for 15 minutes. Then the reaction mixture was cooled back to 0° C. prior to the dropwise addition of a solution of YH11 (284 mg, 1 mmol) in DMF (1 mL). The reaction was stirred for 1 h at 0° C. prior to being neutralized by 1 M HCl. The reaction mixture was extracted with EtOAc (2×20 mL). The organic layers were combined and washed with brine (3×10 mL). The organic layer was separated, dried over $Na_2SO_4$, and concentrated under vacuum. The residue was purified through column chromatography (eluent: hexanes/EtOAc=4/1, then 2/1) to afford YH12 as oil (377 mg, 99%). $^1$H NMR (300 MHz, $CDCl_3$): 7.94 (d, J=1.7 Hz, 1H), 5.62 (d, J=1.9 Hz, 1H), 4.45-4.25 (m, 2H), 4.00 (s, 3H), 2.37 (s, 3H), 2.21 (s, 3H), 1.39 (q, J=7.2 Hz, 3H).

Step 5: Synthesis of ethyl 2-amino-6-(3,5-dimethylisoxazol-4-yl)-4-fluoro-5-methoxy-1H-indole-3-carboxylate To a solution of YH12 (614 mg, 1.6 mmol) in acetic acid (6 mL) was added iron powder (537 mg, 9.6 mmol). The reaction mixture was stirred for 4 h prior to being filtered and washed with acetic acid (2 mL) and solvent (DCM/Methanol 9:1). The volatiles were removed under vacuum and the residue was treated with solvent (DCM/Methanol 9:1) and water (10 mL). The mixture was extracted with EtOAc and the organic layer was separated, washed successively with NaOH (1 M, 5 mL), $NaHCO_3$, and brine. The organic layer was separated, dried over $Na_2SO_4$, and concentrated under vacuum. The residue was triturated in EtOAc and filtered to afford YH13 as a solid (360 mg, 63%). $^1$H NMR (300 MHz, DMSO): 10.92 (m, 1H), 6.94 (s, 1H), 6.78 (s, 1H), 4.20 (q, J=7.1 Hz, 2H), 3.49 (s, 3H), 2.29 (s, 3H), 2.10 (s, 3H), 1.29 (t, J=7.1 Hz, 3H); %). ESI-MS calculated for [M+H]$^+$=348.1, observed: 348.2.

Step 6: Synthesis of 7-(3,5-dimethylisoxazol-4-yl)-5-fluoro-6-methoxy-2-methyl-3,9-dihydro-4H-pyrimido[4,5-b]indol-4-one HCl gas was bubbled into a solution of YH13 (35 mg, 0.1 mmol) in $CH_3CN$ (10 mL) for 5 min. The reaction mixture was heated up to 80° C. for 1 h. After the solution was cooled, the volatile was evaporated under vacuum and a solution of NaOH (1 M, 3 mL) was added followed by ethanol (9 mL). The solution was refluxed for 2 h prior to the removal of ethanol. To the residue was added 1 M HCl at 0° C. until the pH=4. The precipitate was filtered, washed with water (2 mL), ethyl acetate (2 mL). The solid was dried under vacuum and weighed crude 30 mg (88%). $^1$H NMR (300 MHz, $CD_3OD$): 7.06 (s, 1H), 3.61 (s, 3H), 2.41 (s, 3H), 2.32 (s, 3H), 2.13 (s, 3H); ESI-MS calculated for [M+H]$^+$=343.1, observed: 343.5.

Step 7: Synthesis of 4-(4-chloro-5-fluoro-6-methoxy-2-methyl-9H-pyrimido[4,5-b]indol-7-yl)-3,5-dimethylisoxazole A suspension of YH14 (30 mg, 0.09 mmol in $POCl_3$ (2 mL) was heated at 90° C. for 6 h prior to the removal of the volatile under vacuum. The residue was taken up by the ethyl acetate (4 mL) and a saturated solution of $NaHCO_3$ was added until pH=9. The precipitate was filtered and washed with water and ethyl acetate. $^1$H NMR (300 MHz, CD3OD): 12.97 (s, 1H), 7.44 (s, 1H), 3.48 (s, 3H), 2.68 (s, 2H), 2.37 (s, 3H), 2.16 (s, 3H); ESI-MS calculated for [M+H]$^+$=361.1, observed: 361.3.

N-(3-cyclopropyl-1-methyl-1H-pyrazol-5-yl)-7-(3,5-dimethylisoxazol-4-yl)-5-fluoro-6-methoxy-9H-pyrimido[4,5-b]indol-4-amine (Cpd. No. 305)

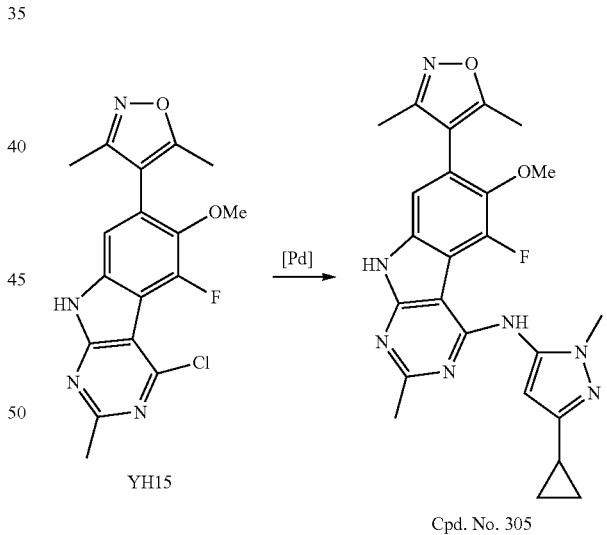

Cpd. No. 305 was synthesized following the same procedure as Cpd. No. 304. $^1$H NMR (300 MHz, CD3OD): 7.31 (s, 1H), 6.40 (s, 1H), 3.84 (s, 3H), 3.76 (s, 3H), 2.69 (s, 3H), 2.40 (s, 3H), 2.23 (s, 3H), 2.08-1.92 (m, 1H), 1.14-0.97 (m, 2H), 0.92-0.78 (m, 2H); ESI-MS calculated for [M+H]$^+$=462.20, observed: 462.50.

459
Synthesis of N-(3-cyclopropyl-1-methyl-1H-pyrazol-5-yl)-7-(3,5-dimethylisoxazol-4-yl)-5-fluoro-6-methoxy-N,2-dimethyl-9H-pyrimido[4,5-b]indol-4-amine (Cpd. No. 306)

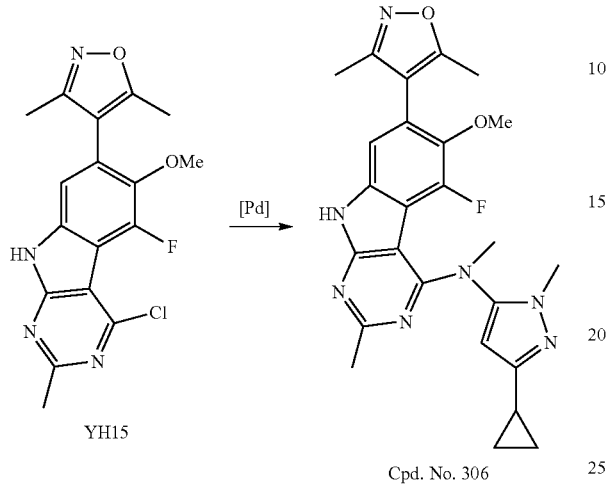

YH15 (36 g), 3-cyclopropyl-1-methyl-1H-pyrazol-5-amine (30 g), Pd(OAc)2 (2 mg), PCy3 (6 mg), Cs2CO3 (130 mg), and anhydrous THF (2 mL) were mixed and the reaction mixture was heated at reflux for 12 h. The crude mixture was diluted with EtOAc and the organic layer was washed with water. The solvent was removed and the residue was purified via reverse phase HPLC to yield the titled compound in 6 mg. $^1$H NMR (300 MHz, CD3OD): 6.03 (s, 1H), 5.41 (s, 1H), 3.75 (s, 3H), 3.73 (s, 3H), 3.71 (s, 3H), 2.79 (s, 3H), 2.27 (s, 3H), 2.10 (s, 3H), 1.99-1.80 (m, 1H), 1.03-0.84 (m, 2H), 0.74-0.54 (m, 2H); ESI-MS calculated for [M+H]$^+$=476.2, observed: 476.3.

Scheme 3

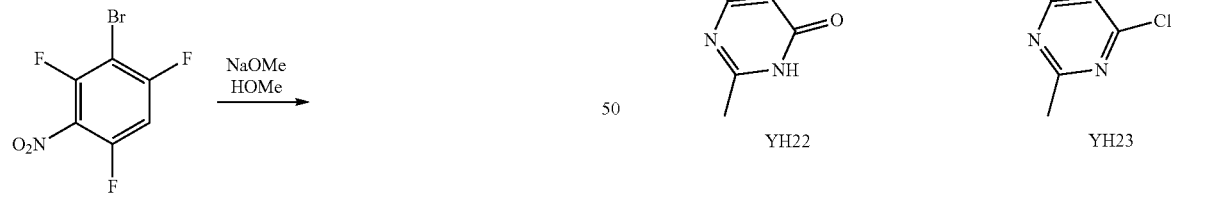

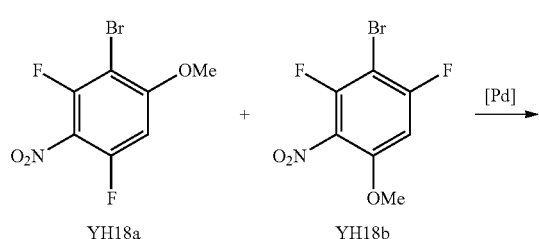

460

Step 1: Synthesis of 2-bromo-3,5-difluoro-1-methoxy-4-nitrobenzene

A solution of 2-bromo-1,3,5-trifluoro-4-nitrobenzene (4.48 g, 17.6 mmol) in methanol (35 mL) was cooled to −30° C. prior to dropwise addition of a solution of NaOMe in methanol (3.8 g, 25% wt). After the addition was completed, the reaction mixture was maintained at the temperature for 1 h prior to being allowed to warm to r.t. The solvent was removed under vacuum and the residue was diluted in EtOAc and water. The solution was extracted with EtOAc (2×50 mL). The organic layers were combined, separated, dried over Na$_2$SO$_4$, and concentrated under vacuum. The residue was purified through column chromatography (eluent: hexanes/EtOAc=8/1) to afford a mixture of YH18a and YH18b (3 g, 64%, ratio YH18a: YH18b=4:1). $^1$H NMR (300 MHz, CDCl$_3$): 6.69-6.59 (m, 1H), 3.99 (s, 3H).

Step 2: Synthesis of 4-(2,4-difluoro-6-methoxy-3-nitrophenyl)-3,5-dimethylisoxazole To a round-bottom flask was charged with a mixture of YH18a and YH18b (3 g, 11 mmol), 3,5-dimethyl-4-(4,4,5,5-tetramethyl-1,3,2-dioxaborolan-2-yl)isoxazole (3 g, 13 mmol), Pd(dppf) CH$_2$Cl$_2$ (898 mg, 1.1 mmol), KF (1.4 g, 24 mmol), toluene (22 mL) and water (22 mL). The reaction mixture was heated up under N$_2$ at 100° C. for 12 h. The solution was cooled prior to being extracted with EtOAc (2×100 mL). The organic layers were combined and washed with brine (50 mL). The organic layer was separated, dried over Na$_2$SO$_4$, and concentrated under vacuum. The residue was purified through column chromatography (eluent: hexanes/EtOAc=2:1) to afford YH19 as a solid (370 mg, 12%). $^1$H NMR (300 MHz, CDCl$_3$): 6.68 (dd, J=11.7, 1.8 Hz, 1H), 3.90 (s, 3H), 2.28 (s, 3H), 2.15 (s, 3H); ESI-MS calculated for [M+H]$^+$=285.1, observed: 285.1.

Step 3: Synthesis of ethyl 2-cyano-2-(4-(3,5-dimethylisoxazol-4-yl)-3-fluoro-5-methoxy-2-nitrophenyl)acetate To a suspension of NaH (60% in mineral oil, 114 mg, 2.9 mmol) in DMF (6 mL) at 0° C. was added ethyl cyanoacetate (294 mg, 2.6 mmol) dropwise. The solution was allowed to warm to r.t. and stirred for 15 minutes. Then the reaction mixture was cooled back to 0° C. prior to the dropwise addition of a solution of YH19 (370 mg, 1.3 mmol) in DMF (1 mL). The reaction was stirred for 1 h at 0° C. prior to being neutralized by 1 M HCl. The reaction mixture was extracted with EtOAc (2×20 mL). The organic layers were combined and washed with brine (3×10 mL). The organic layer was separated, dried over Na$_2$SO$_4$, and concentrated under vacuum. The residue was purified through column chromatography (eluent: hexanes/EtOAc=1/1) to afford YH20 as oil (476 mg, 97%). $^1$H NMR (300 MHz, CDCl$_3$): 7.08 (s, 1H), 5.49 (s, 1H), 4.40-4.20 (m, 2H), 3.96 (s, 3H), 2.26 (s, 3H), 2.13 (s, 3H), 1.32 (t, J=7.1 Hz, 3H); ESI-MS calculated for [M+H]$^+$=378.1, observed: 378.2.

Step 4: Synthesis of ethyl 2-amino-6-(3,5-dimethylisoxazol-4-yl)-7-fluoro-5-methoxy-1H-indole-3-carboxylate To a solution of YH20 (476 mg, 1.26 mmol) in acetic acid (4 mL) was added iron powder (424 mg, 7.6 mmol). The reaction was stirred for 12 h prior to being diluted with EtOAc (10 mL) and the suspension was filtered. The volatiles were removed under vacuum and the residue was treated with EtOAc (50 mL) and water (10 mL). The organic layer was separated, washed successively with NaOH (1 M, 5 mL), NaHCO$_3$, and brine. The organic layer was separated, dried over Na$_2$SO$_4$, and concentrated under vacuum. The residue was purified through column chromatography (eluent: DCM/EtOAc=4/1) to afford YH21 as a solid (240 mg, 55%). $^1$H NMR (300 MHz, CDCl$_3$): 9.81 (s, 1H), 7.25 (s, 1H), 6.13 (s, 1H), 4.41 (q, J 7.0 Hz, 2H), 3.81 (s, 3H), 2.27 (s, 3H), 2.16 (s, 3H), 1.46 (t, J=7.0 Hz, 3H); ESI-MS calculated for [M+H]$^+$=348.1, observed: 348.5.

Step 5: Synthesis of 7-(3,5-dimethylisoxazol-4-yl)-8-fluoro-6-methoxy-2-methyl-3,9-dihydro-4H-pyrimido[4,5-b]indol-4-one HCl gas was bubbled into a solution of YH21 (240 mg, 0.7 mmol) in CH$_3$CN (10 mL) for 10 min. The reaction mixture was heated up to 80° C. for 1 h. After the solution was cooled, the volatile was evaporated under vacuum and a solution of NaOH (1 M, 6 mL) was added followed by ethanol (18 mL). The solution was refluxed for 2 h prior to the removal of ethanol. To the residue was added 1 M HCl at 0° C. until the pH=4. The precipitate was filtered, washed with water (2 mL), ethyl acetate (2 mL). The solid was dried under vacuum and weighed crude 200 mg (83%) $^1$H NMR (300 MHz, CD$_3$OD): 12.40 (s, 1H), 7.40 (s, 1H), 3.85 (s, 3H), 2.43 (s, 3H), 2.26 (s, 3H), 2.07 (s, 3H ESI-MS calculated for [M+H]$^+$=343.1, observed: 343.3;

Step 6: Synthesis of 4-(4-chloro-8-fluoro-6-methoxy-2-methyl-9H-pyrimido[4,5-b]indol-7-yl)-3,5-dimethylisoxazole A suspension of YH22 (100 mg, 0.3 mmol in POCl$_3$ (4 mL) was refluxed for 4 h prior to the removal of the volatile under vacuum. The residue was taken up by the ethyl acetate (4 mL) and a saturated solution of NaHCO$_3$ was added until pH=9. The precipitate was filtered and washed with water and ethyl acetate to give YH23 (100 mg, 95%). $^1$H NMR (300 MHz, CD3OD): 7.65 (s, 1H), 3.92 (s, 3H), 2.70 (s, 3H), 2.29 (s, 3H), 2.10 (s, 3H); ESI-MS calculated for [M+H]$^+$=361.1, observed: 361.2.

N-(3-cyclopropyl-1-methyl-1H-pyrazol-5-yl)-7-(3,5-dimethylisoxazol-4-yl)-8-fluoro-6-methoxy-2-methyl-9H-pyrimido[4,5-b]indol-4-amine (Cpd. No. 307)

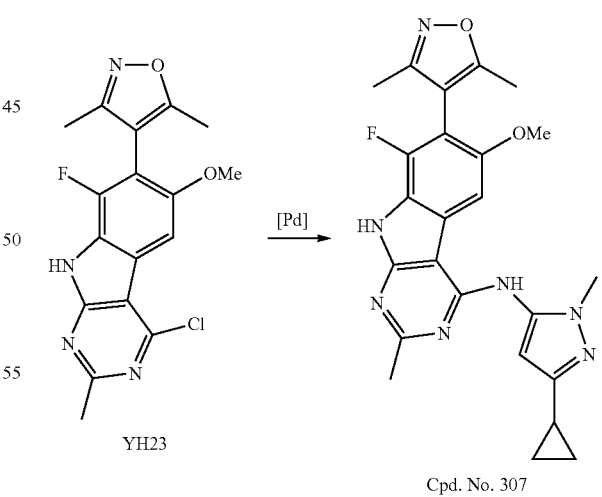

Cpd. No. 307 was synthesized following the same procedure as Cpd. No. 304. $^1$H NMR (300 MHz, CD3OD): 7.20 (s, 1H), 6.05 (s, 1H), 3.91 (s, 3H), 3.74 (s, 3H), 2.65 (s, 3H), 2.31 (s, 3H), 2.15 (s, 3H), 2.04-1.85 (m, 1H), 1.14-0.83 (m, 2H), 0.85-0.74 (m, 2H); ESI-MS calculated for [M+H]$^+$=462.2, observed: 462.4.

463

N-(3-cyclopropyl-1-methyl-1H-pyrazol-5-yl)-7-(3,5-dimethylisoxazol-4-yl)-8-fluoro-6-methoxy-N,2-dimethyl-9H-pyrimido[4,5-b]indol-4-amine (Cpd. No. 308)

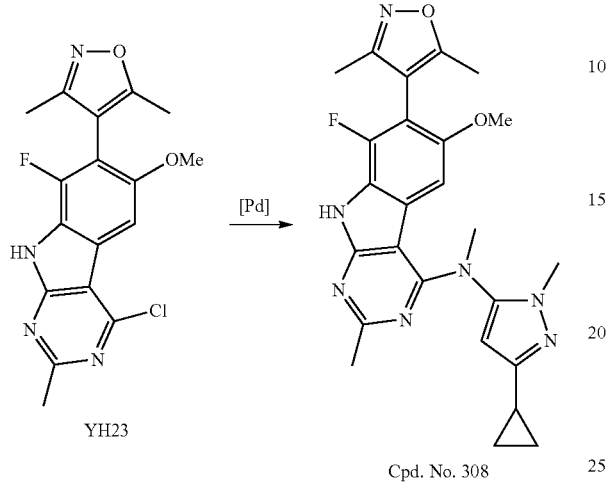

Cpd. No. 308 was synthesized following the same procedure as Cpd. No. 306. $^1$H NMR (300 MHz, CD3OD): 6.03 (s, 1H), 5.41 (s, 1H), 3.75 (s, 3H), 3.73 (s, 3H), 3.71 (s, 3H), 2.79 (s, 3H), 2.27 (s, 3H), 2.10 (s, 3H), 1.99-1.80 (m, 1H), 1.03-0.84 (m, 2H), 0.74-0.54 (m, 2H); ESI-MS calculated for [M+H]$^+$=476.2, observed: 476.3.

Scheme 4

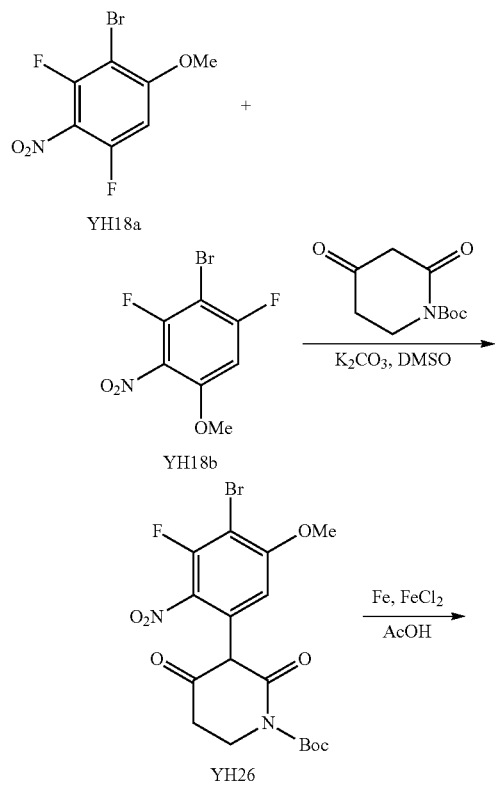

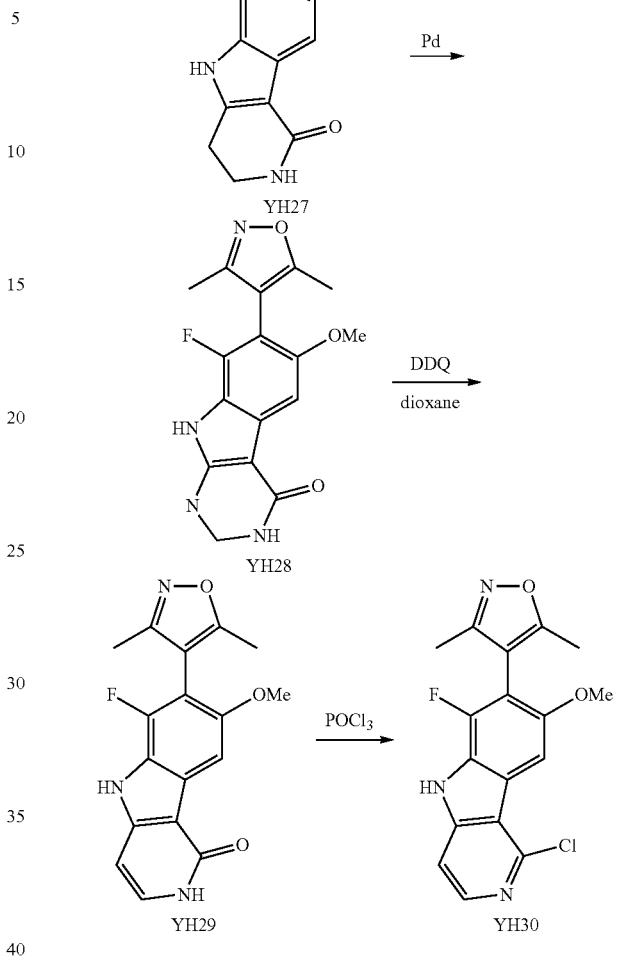

Step 1: Synthesis of tert-butyl 3-(4-bromo-3-fluoro-5-methoxy-2-nitrophenyl)-2,4-dioxopiperidine-1-carboxylate To a round-bottom flask was charged with tert-butyl 2,4-dioxopiperidine-1-carboxylate (2.13 g, 10 mmol), K$_2$CO$_3$ (2.07 g, 15 mmol), DMSO (15 mL). The reaction mixture was stirred for 10 minutes prior to the addition of a mixture of YH18a and YH18b (1.4 g, 5 mmol). The reaction mixture was heated up under N at 60° C. for 2 h. The solution was cooled prior to being diluted with water and EtOAc (100 mL). The organic layer was separated and washed with water and brine (50 mL). The organic layer was separated, dried over Na$_2$SO$_4$, and concentrated under vacuum. The residue was purified through column chromatography (eluent: hexanes/EtOAc=1:1) to afford YH26 as a solid (820 mg, 45%). $^1$H NMR (300 MHz, CDCl$_3$ □□□ ppm 6.65 (d, J=1.2 Hz, 1H), 4.00-3.92 (m, 2H), 3.94 (s, 3H), 2.71-2.53 (m, 2H), 1.55 (s, 9H); ESI-MS (M+H): 461.0 calculated, 461.1 observed.

Step 2: Synthesis of 7-bromo-6-fluoro-8-methoxy-2,3,4,5-tetrahydro-1H-pyrido[4,3-b]indol-1-one To a solution of YH26 (820 mg, 1.7 mmol) in ethanol (10 mL) was added iron powder (952 mg, 17 mmol), FeCl$_2$ (324 mg, 2.6 mmol) and acetic acid (0.48 mL, 8.5 mmol). The reaction mixture was heated up to reflux for 12 h prior to being cooled down to r.t. The reaction mixture was diluted with EtOAc (10 mL) and the suspension was filtered. The volatiles were removed under vacuum and the residue was treated with EtOAc (50 mL) and water (10 mL). The organic layer was separated, washed successively with NaHCO$_3$ and brine. The organic layer was separated, dried over Na$_2$SO$_4$, and concentrated under vacuum. The residue was purified through column chromatography (eluent: DCM/MeOH=9/1) to afford YH27 as a solid (310 mg, 59%). ESI-MS (M+H): 313.0 calculated, 313.2 observed.

Step 3: Synthesis of 7-(3,5-dimethylisoxazol-4-yl)-6-fluoro-8-methoxy-2,3,4,5-tetrahydro-1H-pyrido[4,3-b]indol-1-one To a round-bottom flask was charged with YH27 (150 mg, 0.5 mmol), 3,5-dimethyl-4-(4,4,5,5-tetramethyl-1,3,2-dioxaborolan-2-yl)isoxazole (223 mg, 1 mmol), Pd(dppf)CH$_2$Cl$_2$ (20 mg, 0.025 mmol), dioxane (4 mL) and Na$_2$CO$_3$ solution (2 M, 1 mL). The reaction mixture was heated up under N at 100° C. for 12 h. The solution was cooled prior to being extracted with EtOAc (2×10 mL). The organic layer was separated and concentrated under vacuum. The residue was purified through HPLC to afford YH28 as a solid (50 mg, 30%). $^1$H NMR (300 MHz, CD$_3$OD□□□ 7.43 (s, 1H), 3.84 (s, 3H), 3.65 (d, J=5.8 Hz, 2H), 3.07 (t, J=6.2 Hz, 2H), 2.26 (s, 3H), 2.11 (s, 3H); ESI-MS (M+H): 330.12 calculated, 330.33 observed.

Step 4: Synthesis of 7-(3,5-dimethylisoxazol-4-yl)-6-fluoro-8-methoxy-2,5-dihydro-1H-pyrido[4,3-b]indol-1-one To a solution of YH28 (50 mg, 0.15 mmol) in dioxane (4 mL) was added DDQ (69 mg, 0.3 mmol). The reaction mixture was refluxed for 6 h. After the solution was cooled, the reaction was diluted with water (2 mL) and ethyl acetate (10 mL). The organic layer was separated, dried over Na$_2$SO$_4$, and concentrated under vacuum. The residue was purified through column chromatography (eluent: DCM/MeOH=9/1) to afford YH29 as a solid (41 mg, 87%). $^1$H NMR (300 MHz, CD$_3$OD) δ ppm 7.67 (s, 1H), 7.39 (d, J=6.9 Hz, 1H), 6.66 (d, J=6.9 Hz, 1H), 3.92 (s, 3H), 2.32 (s, 3H), 2.16 (s, 3H); ESI-MS (M+H): 328.10 calculated, 328.20 observed.

Step 5: Synthesis of 4-(1-chloro-6-fluoro-8-methoxy-5H-pyrido[4,3-b]indol-7-yl)-3,5-dimethylisoxazole A suspension of 18 (41 mg, 0.13 mmol) in POCl$_3$ (3 mL) was refluxed for 4 h prior to the removal of the volatile under vacuum. The residue was taken up by the ethyl acetate (4 mL) and a saturated solution of NaHCO$_3$ was added until pH=9. The precipitate was filtered and washed with water and ethyl acetate to give 19 (12 mg, 29%). $^1$H NMR (300 MHz, DMSO) δ ppm 12.77 (s, 1H), 8.27 (d, J=5.6 Hz, 1H), 7.81 (s, 1H), 7.53 (d, J=5.6 Hz, 1H), 3.93 (s, 3H), 2.30 (s, 3H), 2.10 (s, 3H); ESI-MS (M+H): 346.1 calculated, 346.2 observed.

N-(3-cyclopropyl-1-methyl-1H-pyrazol-5-yl)-7-(3,5-dimethylisoxazol-4-yl)-6-fluoro-8-methoxy-5H-pyrido[4,3-b]indol-1-amine (Cpd. No. 309)

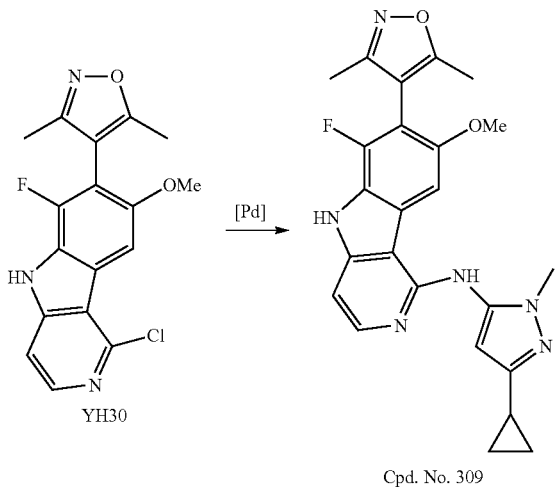

Cpd. No. 309 was synthesized following the same procedure as Cpd. No. 304. $^1$H NMR (300 MHz, CD$_3$OD) δ ppm 7.86 (s, 1H), 7.85 (d, J 7.2 Hz, 1H), 7.37 (d, J=7.1 Hz, 1H), 6.24 (s, 1H), 3.99 (s, 3H), 3.81 (s, 3H), 2.34 (s, 3H), 2.17 (s, 3H), 2.01-1.91 (m, 1H), 1.00-0.95 (m, 2H), 0.87-0.73 (m, 2H); ESI-MS (M+H): 447.2 calculated, 447.3 observed.

Scheme 5

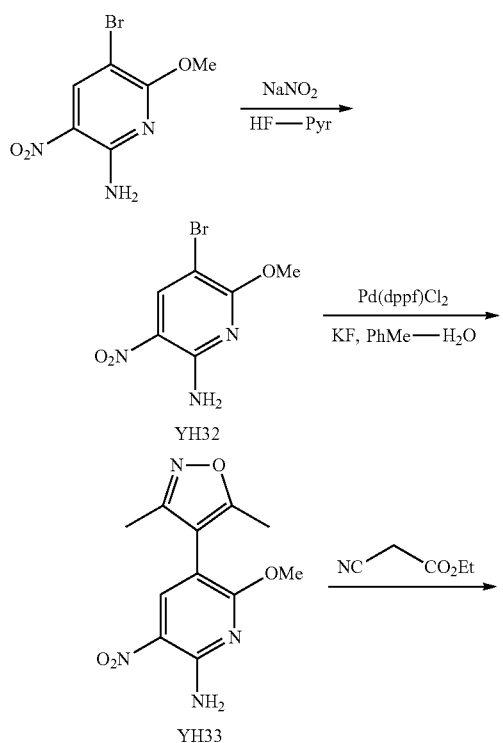

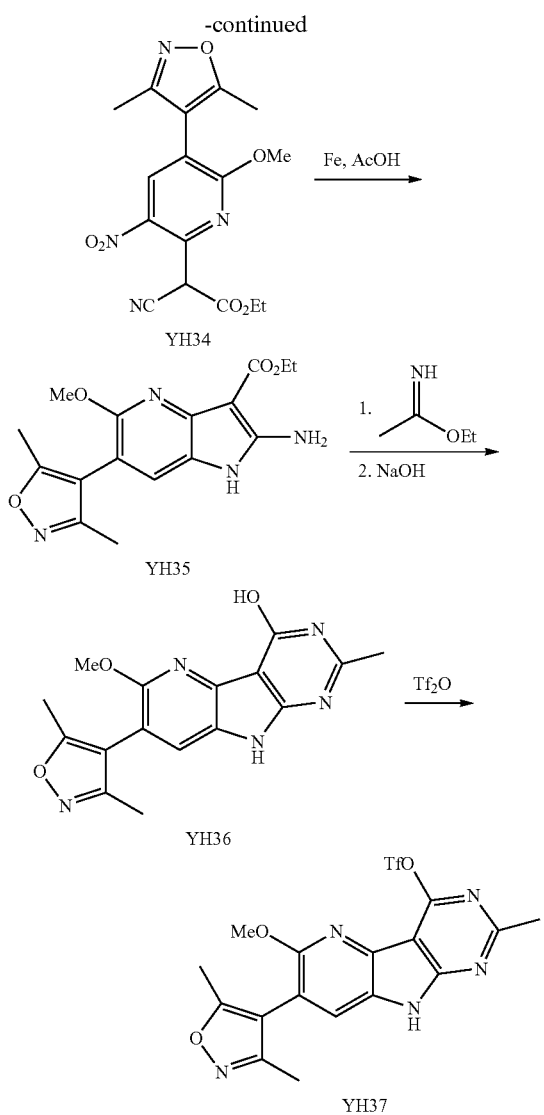

Step 2: Synthesis of 4-(6-fluoro-2-methoxy-5-nitro-pyridin-3-yl)-3,5-dimethylisoxazole To a round-bottom flask was charged with YH32 (3.8 g, 15 mmol), 3,5-dimethyl-4-(4,4,5,5-tetramethyl-1,3,2-dioxaborolan-2-yl)isoxazole (3.7 g, 16.5 mmol), Pd(dppf)CH$_2$Cl$_2$ (612 mg, 0.75 mmol), KF (1.9 g, 33 mmol), toluene (40 mL) and water (40 mL). The reaction mixture was heated up under N$_2$ at 100° C. for 12 h. The solution was cooled prior to being extracted with EtOAc (2×100 mL). The organic layers were combined and washed with brine (50 mL). The organic layer was separated, dried over Na$_2$SO$_4$, and concentrated under vacuum. The residue was purified through column chromatography (eluent: hexanes/EtOAc=4/1 to 2:1) to afford YH33 as a red solid, which was triturated with diethyl ether, followed by filtration to give YH33 as a yellow solid (2.2 g, 55%) $^1$H NMR (300 MHz, CDCl$_3$) δ ppm 8.30 (d, J=8.6 Hz, 1H), 4.06 (s, 3H), 2.33 (s, 3H), 2.17 (s, 3H).

Step 3: Synthesis of ethyl 2-cyano-2-(5-(3,5-dimethylisoxazol-4-yl)-6-methoxy-3-nitropyridin-2-yl)acetate To a suspension of NaH (60% in mineral oil, 2.5 g, 63 mmol) in DMF (114 mL) at 0° C. was added ethyl cyanoacetate (6.4 g, 57 mmol) dropwise. The solution was allowed to warm to r.t. and stirred for 15 minutes. Then the reaction mixture was cooled back to 0° C. prior to the dropwise addition of a solution of YH33 (7.6 g, 28.5 mmol) in THF (8 mL). The reaction was stirred for 1 h at 0° C. prior to being neutralized by 2 M HCl. The reaction mixture was extracted with EtOAc (2×200 mL). The organic layers were combined and washed with brine (3×100 mL). The organic layer was separated, dried over Na$_2$SO$_4$, and concentrated under vacuum. The residue was purified through column chromatography (eluent: hexanes/EtOAc=4/1, then DCM) to afford YH34 as oil (10 g, 98%). $^1$H NMR (300 MHz, CDCl$_3$) δ ppm 8.32 (s, 1H), 5.87 (s, 1H), 4.36 (q, J=7.1 Hz, 2H), 4.14 (s, 3H), 2.37 (s, 3H), 2.22 (s, 3H), 1.37 (t, J=7.1 Hz, 3H).

Step 4: Synthesis of ethyl 2-amino-6-(3,5-dimethyl-isoxazol-4-yl)-5-methoxy-1H-pyrrolo[3,2-b]pyridine-3-carboxylate To a solution of YH34 (10.1 g, 28.5 mmol) in acetic acid (99 mL) was added iron powder (9.6 g, 171 mmol). The reaction was stirred and the temperature of the solution rose as the reaction progressed. After the temperature fell back to r.t, the reaction mixture was diluted with EtOAc (100 mL) and the suspension was filtered. The volatiles were removed under vacuum and the residue was treated with EtOAc (500 mL) and water (100 mL). The organic layer was separated, washed successively with NaOH (1 M, 50 mL), NaHCO$_3$, and brine. The organic layer was separated, dried over Na$_2$SO$_4$, and concentrated under vacuum. The residue was purified through column chromatography (eluent: hexanes/EtOAc=2/1, then EtOAc) to afford YH35 as a solid (7 g, 76%). $^1$H NMR (300 MHz, CDCl$_3$) δ ppm 10.19 (s, 1H), 6.72 (s, 1H), 6.52 (s, 2H), 4.40 (q, J=6.8 Hz, 2H), 3.89 (s, 3H), 2.05 (s, 3H), 1.91 (s, 3H), 1.44 (t, J=6.8 Hz, 3H).

Step 5: Synthesis of 7-(3,5-dimethylisoxazol-4-yl)-6-methoxy-2-methyl-9H-pyrido[2',3':4,5]pyrrolo[2,3-d]pyrimidin-4-ol Ethyl acetimidate hydrochloride (22.2 g, 180 mmol) was added to a vigorously stirred solution of K$_2$CO$_3$ (24.8 g, 180

Step 1: Synthesis of 3-bromo-6-fluoro-2-methoxy-5-nitropyridine 5-bromo-6-methoxy-3-nitropyridin-2-amine (19 g, 80 mmol) was slowly added to a solution of HF/pyridine (70% HF, 30% pyridine 77 mL) at 0° C. NaNO$_2$ (5.8 g, 84 mmol) was added slowly portion wise to the reaction mixture. After the addition is completed, the reaction mixture was allowed to warm to r.t. The reaction mixture became very hot as the reaction progressed and occasional cooling was applied to keep the temperature from overheating. The reaction mixture was stirred for another 1 h prior to being poured into ice. The solution was extracted with Et$_2$O (2×200 mL). The organic layers were combined and washed successively with NaOH (1 M, 2×500 mL), saturated NaHCO$_3$ (100 mL), and brine (100 mL). The organic layer was separated, dried over Na$_2$SO$_4$, and concentrated under vacuum. The residue was purified through column chromatography (eluent: hexanes/EtOAc=8/1) to afford YH32 as white solid (16 g, 82%). $^1$H NMR (300 MHz, CDCl$_3$) δ ppm 8.67 (d, J=8.2 Hz, 1H), 4.12 (s, 3H).

mmol) in water (200 mL) and DCM (200 mL). After 10 minutes, the organic layer was separated and dried over MgSO₄. The clear solution was decanted to a flask where it contained YH35 (2.0 g, 6 mmol). To this solution was added acetic acid (3.4 mL, 60 mmol) and the reaction mixture was stirred for 12 h during which time precipitate occurred. The solution was filtered and the filtrate was evaporated to give a crude oil. A solution of NaOH (2.5 M, 36 mL) was added to the crude oil followed by the addition of ethanol (80 mL). The reaction mixture was heated up to 80° C. for 4 h. After the solution was cooled, the ethanol was evaporated under vacuum and the aqueous solution was cooled to 0° C. and 1 M HCl was added slowly until PH=4. The precipitate was filtered, washed with water (50 mL), ethyl acetate (50 mL), and DCM (50 mL). The white solid was dried under vacuum and weighed 1.0 g (50%). ¹H NMR (300 MHz, CD₃OD) δ ppm 7.67 (s, 1H), 4.08 (s, 3H), 2.53 (s, 2H), 2.35 (s, 3H), 2.18 (s, 3H); ESI-MS (M+H): 323.2 calculated, 323.4 observed.

Step 6: Synthesis of 7-(3,5-dimethylisoxazol-4-yl)-6-methoxy-2-methyl-9H-pyrido[2',3':4,5]pyrrolo[2,3-d]pyrimidin-4-yl trifluoromethanesulfonate To a suspension of YH36 (2.2 g, 6.8 mmol) and 2-chloropyridine (2.55 mL, 27.2 mmol) in THF (200 mL) and DCM (100 mL) at −78° C. was added dropwise a solution of Tf₂O in DCM (1 M, 13.6 mL). The reaction mixture was stirred for 10 min, and TLC indicated that some starting material remained. 2-Chloropyridine (2.55 mL, 27.2 mmol) was added followed by dropwise addition of a solution of Tf₂O in DCM (1 M, 13.6 mL). After addition, the reaction mixture was quenched by saturated NaHCO₃ (20 mL). The organic layer was separated, and the aqueous layer was extracted with EtOAc. The organic layers were combined, dried over Na₂SO₄, and concentrated under vacuum. The crude solid was triturated in DCM, and the white solid was filtered to afford YH37 (1.3 g). The filtrate was concentrated and purified through column chromatography (eluent: DCM/EtOAc=3/1, then EtOAc) to afford another batch of YH37 (0.7 g, total yield 64%). ¹H NMR (300 MHz, CD3OD) δ ppm 7.87 (s, 1H), 4.09 (s, 3H), 2.80 (s, 3H), 2.39 (s, 3H), 2.22 (s, 3H). ESI-MS (M+H): 458.1 calculated, 458.5 observed.

Synthesis of Cpd. No. 310 and Related Analogs

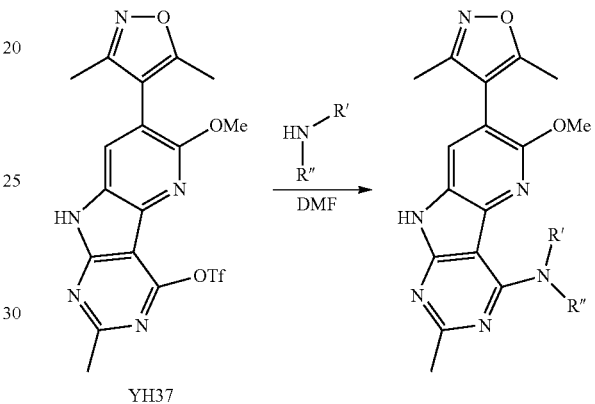

YH37

YH37 (0.1 mmol), amine (0.2 mmol), and anhydrous DMF (1 mL) were mixed and the reaction mixture was heated at 80° C. for 12 h. Solvent DMF was removed and the residue was purified via reverse phase HPLC to yield the following compounds:

| Cpd. No. | Structure | Characterization |
|---|---|---|
| 310 | (structure) | 1H NMR (300 MHz, CD3OD) δ ppm 7.87 (s, 1H), 4.09 (s, 3H), 2.70 (s, 3H), 2.37 (s, 3H), 2.33 (s, 3H), 2.20 (s, 3H), 1.75 (s, 9H), ESI-MS (M + H): 461.54; UPLC(10 to 100% CH₃CN: H₂O 10 min): 4.15 min |

| Cpd. No. | Structure | Characterization |
| --- | --- | --- |
| 311 | 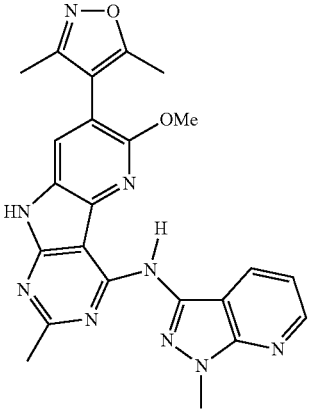 [SMILES: COc1nc2c(cc1-c1c(C)noc1C)[nH]c1nc(C)nc(Nc3nn(C)c4ncccc34)c12] | 1H NMR (300 MHz, DMSO) δ ppm 12.06 (s, 1H), 9.01 (s, 1H), 8.70-8.50 (m, 2H), 7.81 (s, 1H), 7.24 (dd, J = 7.7, 4.8 Hz, 1H), 4.04 (s, 3H), 4.01 (s, 3H), 2.54 (s, 3H), 2.34 (s, 3H), 2.14 (s, 3H); ESI-MS (M + H): 456.80; UPLC(10 to 100% CH$_3$CN: H$_2$O 10 min): 3.80 min |
| 312 | 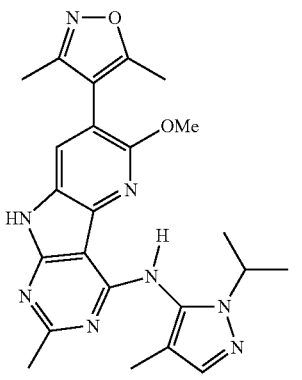 | 1H NMR (300 MHz, CD3OD) δ ppm 7.86 (s, 1H), 7.52 (s, 1H), 4.70-4.60 (m, 1H), 4.13 (s, 3H), 2.65 (s, 3H), 2.38 (s, 3H), 2.21 (s, 3H), 2.14 (m, 3H), 1.51 (d, J = 6.7 Hz, 6H); ); ESI-MS (M + H): 447.68; UPLC(10 to 100% CH$_3$CN: H$_2$O 10 min): 3.99 min |
| 313 | 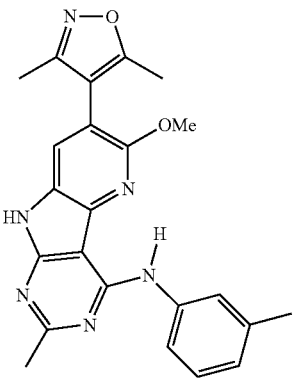 | 1H NMR (300 MHz, DMSO) δ ppm 12.23 (s, 1H), 8.85 (d, J = 0.8 Hz, 1H), 7.84 (s, 1H), 7.77 (d, J = 8.1 Hz, 1H), 7.70 (s, 1H), 7.32 (t, J = 7.7 Hz, 1H), 6.97 (d, J = 7.5 Hz, 1H), 4.10 (s, 3H), 2.63 (s, 3H), 2.37 (s, 3H), 2.34 (s, 3H), 2.14 (s, 3H); ESI-MS (M + H): 415.52; UPLC(10 to 100% CH$_3$CN: H$_2$O 10 min): 4.99 min |

| Cpd. No. | Structure | Characterization |
|---|---|---|
| 314 | 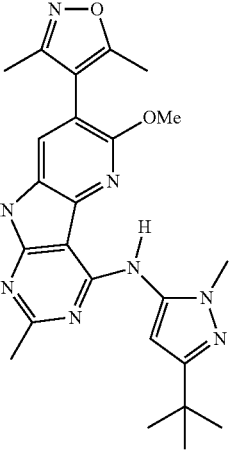 | 1H NMR (300 MHz, DMSO) δ ppm 12.02 (s, 1H), 8.63 (s, 1H), 7.79 (s, 1H), 6.42 (s, 1H), 4.07 (s, 3H), 3.75 (s, 3H), 2.55 (s, 3H), 2.32 (s, 3H), 2.13 (s, 3H), 1.20 (s, 9H); ESI-MS (M + H): 461.25; UPLC(10 to 100% CH$_3$CN: H$_2$O 10 min): 4.64 min |
| 315 | 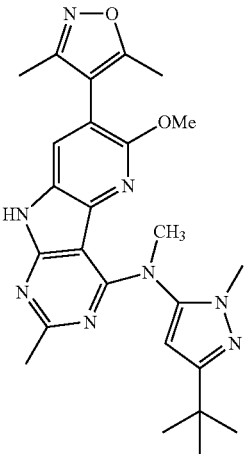 | 1H NMR (300 MHz, CD3OD) δ ppm 7.74 (s, 1H), 5.93 (s, 1H), 3.99 (s, 3H), 3.93 (s, 3H), 3.83 (s, 3H), 2.66 (s, 3H), 2.33 (s, 3H), 2.16 (s, 3H), 1.24 (s, 9H); ESI-MS (M + H): 475.57; UPLC(10 to 100% CH$_3$CN: H$_2$O 10 min): 4.77 min |
| 316 | 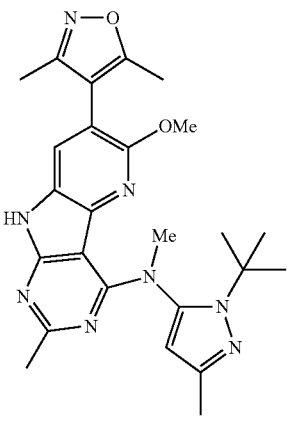 [SMILES: COc1nc2c(cc1-c1c(C)noc1C)[nH]c1nc(C)nc(N(C)c3cc(C)nn3C(C)(C)C)c12] | 1H NMR (300 MHz, CD3OD) δ ppm 7.92 (s, 1H), 5.98 (s, 1H), 4.44 (s, 3H), 3.98 (s, 3H), 2.65 (s, 3H), 2.38 (s, 6H), 2.24 (s, 3H), 1.61 (s, 9H); ESI-MS (M + H): 475.50; UPLC(10 to 100% CH$_3$CN: H$_2$O 10 min): 4.70 min |

| Cpd. No. | Structure | Characterization |
|---|---|---|
| 317 | 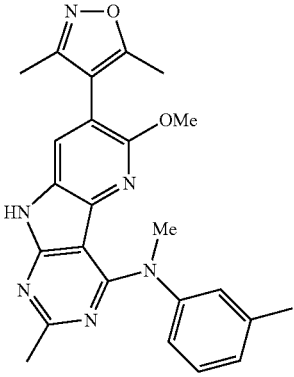 | 1H NMR (300 MHz, DMSO) δ ppm 7.64 (s, 1H), 7.19-7.04 (m, 2H), 6.99-6.85 (m, 2H), 3.82 (s, 3H), 3.45 (s, 3H), 2.27 (s, 3H), 2.24 (s, 3H), 2.05 (s, 3H); ESI-MS (M + H): 429.67; |
| 318 | 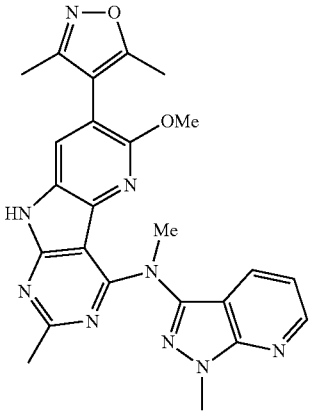 [SMILES: COc1nc2c(cc1-c1c(C)noc1C)[nH]c1nc(C)nc(N(C)c3nn(C)c4ncccc34)c12] | 1H NMR (300 MHz, CD3OD) δ ppm 8.53 (dd, J = 4.6, 1.4 Hz, 1H), 7.83 (dd, J = 8.2, 1.4 Hz, 1H), 7.71 (s, 1H), 7.08 (dd, J = 8.2, 4.5 Hz, 1H), 4.20 (s, 3H), 4.04 (s, 3H), 2.69 (s, 3H), 2.28 (s, 3H), 2.09 (s, 3H); ESI-MS (M + H): 470.42; UPLC(10 to 100% CH3CN: H2O 10 min): 3.86 min |
| 319 | 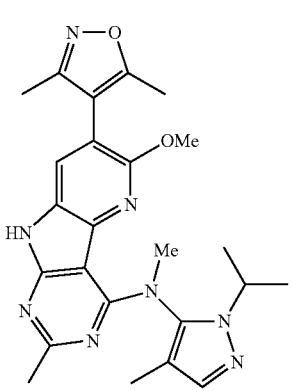 | 1H NMR (300 MHz, CDCl3) δ ppm 7.89 (s, 1H), 7.67 (s, 1H), 4.47 (s, 3H), 4.26-4.20 (m, 1H), 3.99 (s, 3H), 2.61 (s, 3H), 2.37 (s, 3H), 2.23 (s, 3H), 1.97 (s, 3H), 1.53 (d, J = 6.7 Hz, 3H), 1.44 (d, J = 6.6 Hz, 3H); ESI-MS (M + H): 461.50; UPLC(10 to 100% CH3CN: H2O 10 min): 4.31 min |

| Cpd. No. | Structure | Characterization |
|---|---|---|
| 320 | 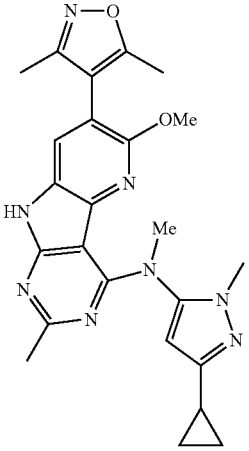 | 1H NMR (300 MHz, CD3OD) δ ppm 7.85 (s, 1H), 5.97 (s, 1H), 4.19 (s, 3H), 3.95 (s, 3H), 3.71 (s, 3H), 2.68 (s, 3H), 2.35 (s, 3H), 2.18 (s, 3H), 1.93-1.87 (m, 1H), 1.04-0.84 (m, 2H), 0.79-0.59 (m, 2H); ESI-MS (M + H): 459.68; UPLC(10 to 100% CH$_3$CN: H$_2$O 10 min): 4.24 min |
| 321 | 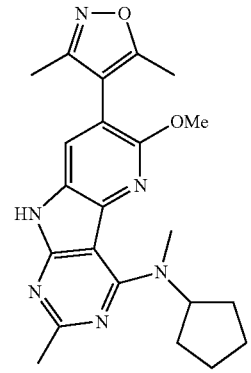 [SMILES: COc1nc2c(cc1-c1c(C)noc1C)[nH]c1nc(C)nc(N(C)C3CCCC3)c12] | 1H NMR (300 MHz, DMSO) δ ppm 7.67 (s, 1H), 6.30 (s, 1H), 3.94 (s, 3H), 3.31 (s, 3H), 2.44 (s, 3H), 2.31 (s, 3H), 2.12 (s, 3H), 2.05-1.86 (m, 2H), 1.85-1.68 (m, 4H), 1.68-1.44 (m, 2H); ); ESI-MS (M + H): 407.50; UPLC(10 to 100% CH$_3$CN: H$_2$O 10 min): 4.84 min |
| 322 | 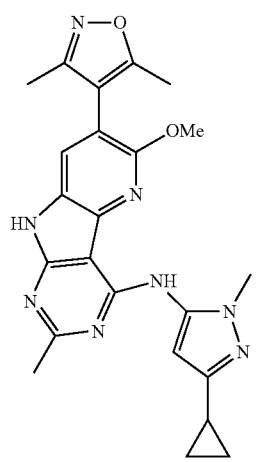 | 1H NMR (300 MHz, DMSO) δ ppm 12.2 (s, 1H), 8.74 (s, 1H), 7.81 (s, 1H), 6.28 (s, 1H), 4.06 (s, 3H), 3.71 (s, 3H), 2.32 (s, 3H), 2.13 (s, 3H), 1.94-1.77 (m, 1H), 0.99-0.79 (m, 2H), 0.79-0.53 (m, 2H), ; ESI-MS (M + H): 445.4; UPLC(10 to 100% CH$_3$CN: H$_2$O 10 min): 4.09 min, 97% purity |

Synthesis of Cpd. No. 325 and Related Analogs

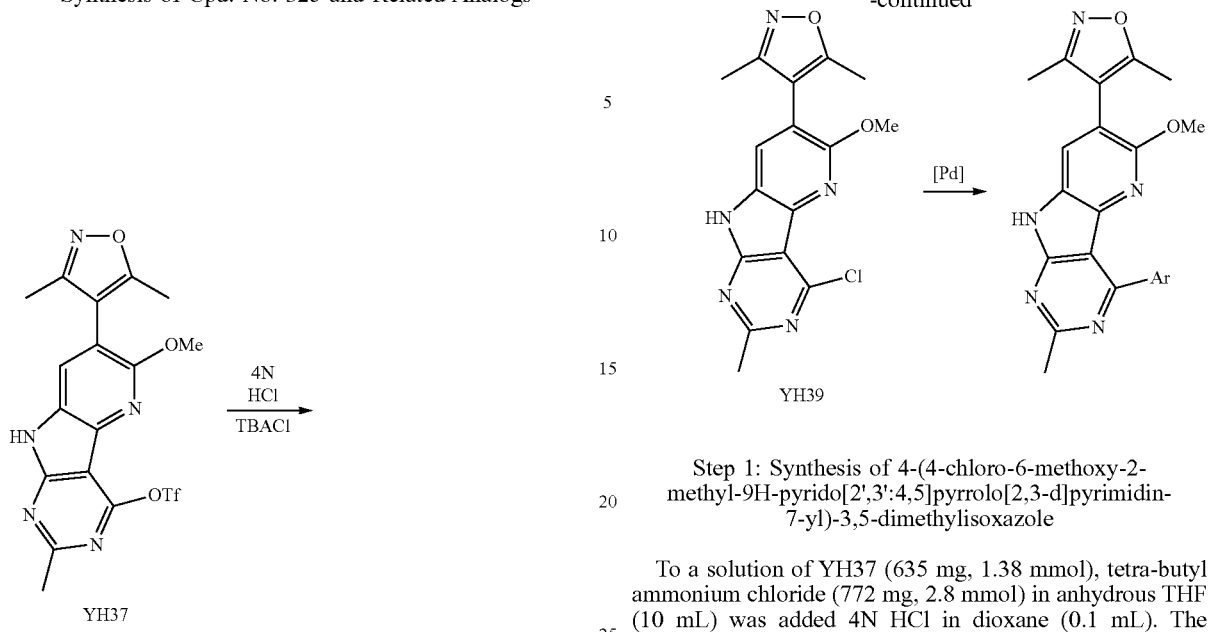

Step 1: Synthesis of 4-(4-chloro-6-methoxy-2-methyl-9H-pyrido[2',3':4,5]pyrrolo[2,3-d]pyrimidin-7-yl)-3,5-dimethylisoxazole To a solution of YH37 (635 mg, 1.38 mmol), tetra-butyl ammonium chloride (772 mg, 2.8 mmol) in anhydrous THF (10 mL) was added 4N HCl in dioxane (0.1 mL). The reaction mixture was stirred for 12 h prior to the removal of solvent under vacuum. The residue was diluted with DCM, filtered, and washed with water to provide YH39 as white solid (398 mg, 84% yield).

Step 2: YH39 (0.1 mmol), borate ester (0.1 mmol), Pd(dppf)Cl2 (8 mg), KF (19 mg) and dioxane/H2O (1 mL/0.5 mL) were mixed and the reaction mixture was heated at reflux for 12 h. The crude mixture was diluted with EtOAc and the organic layer was washed with water. The solvent was removed and the residue was purified via reverse phase HPLC to yield the following compounds:

| Cpd. No. | Structure | Characterization |
| --- | --- | --- |
| 325 | (structure shown) | 1H NMR (300 MHz, CDCl3): 9.36 (d, J = 4.8 Hz, 1H), 8.36 (d, J = 8.4 Hz, 1H), 8.26 (d, J = 5.1 Hz, 1H), 8.12 (d, J = 7.8 Hz, 2H), 7.90 (s, 1H), 7.81 (d, J = 7.5 Hz, 1H), 3.18 (s, 3H), 3.01 (s, 3H), 2.30 (s, 3H), 2.11 (s, 3H); ESI-MS (M + H): 437.57; UPLC(10 to 100% CH3CN: H2O 10 min): 2.88 min |

-continued

| Cpd. No. | Structure | Characterization |
|---|---|---|
| 326 | 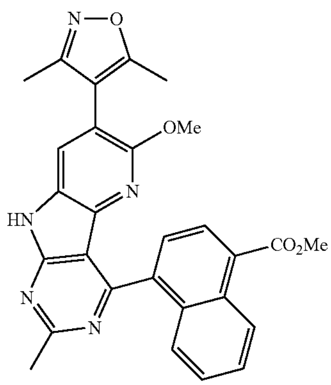 [SMILES: COC(=O)c1ccc(-c2nc(C)nc3[nH]c4cc(-c5c(C)noc5C)c(OC)nc4c23)c2ccccc12] | 1H NMR (300 MHz, CDCl3): 9.90 (s, 1H), 9.01 (d, J = 8.6 Hz, 1H), 8.33 (d, J = 7.6 Hz, 1H), 7.93 (d, J = 7.7 Hz, 2H), 7.58 (s, 2H), 7.49-7.38 (m, 1H), 4.03 (s, 3H), 3.18 (s, 3H), 3.04 (s, 3H), 2.29 (s, 3H), 2.13 (s, 3H); ESI-MS (M + H): 494.50; UPLC(10 to 100% CH$_3$CN: H$_2$O 10 min): 4.29 min |
| 327 | 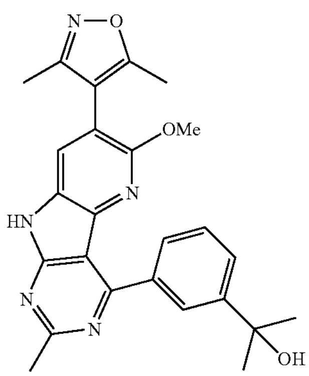 [SMILES: COc1nc2c(cc1-c1c(C)noc1C)[nH]c1nc(C)nc(-c3cccc(C(C)(C)O)c3)c12] | 1H NMR (300 MHz, CDCl3) δ ppm 8.74-8.52 (m, 1H), 8.47 (s, 1H), 7.82 (s, 1H), 7.76-7.63 (m, 1H), 7.53 (s, 1H), 3.96 (s, 3H), 3.56 (s, 1H), 3.04 (s, 3H), 2.33 (s, 3H), 2.18 (s, 3H), 1.65 (s, 6H); ESI-MS (M + H): 444.42; UPLC(10 to 100% CH$_3$CN: H$_2$O 10 min): 3.61 min |
| 328 | 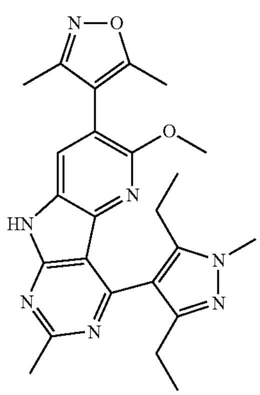 | 1H NMR (300 MHz, CD3OD) δ ppm 7.99 (s, 1H), 3.97 (s, 3H), 3.86 (s, 3H), 2.98 (s, 3H), 2.93-2.80 (m, 2H), 2.80-2.70 (m, 2H), 2.37 (s, 3H), 2.19 (s, 3H), 1.10 (d, J = 8.5 Hz, 3H), 1.07 (d, J = 8.5 Hz, 3H); ESI-MS (M + H): 446.83; UPLC(10 to 100% CH$_3$CN: H$_2$O 10 min): 3.2 min, 98% purity |
| 329 | 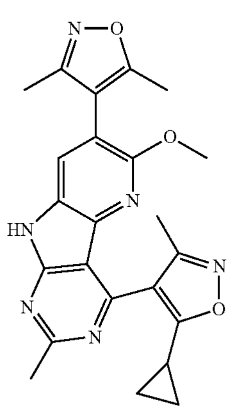 [SMILES: COc1nc2c(cc1-c1c(C)noc1C)[nH]c1nc(C)nc(-c3c(C)noc3C3CC3)c12] | 1H NMR (300 MHz, CD3OD) δ ppm 7.96 (s, 1H), 3.93 (s, 3H), 2.96 (s, 3H), 2.37 (s, 3H), 2.36 (s, 3H), 2.19 (s, 3H), 2.25-2.11 (m, 1H), 1.14-1.04 (m, 4H); ESI-MS (M + H): 431.58; UPLC(10 to 100% CH$_3$CN: H$_2$O 10 min): 3.8 min, 99% purity |

-continued

| Cpd. No. | Structure | Characterization |
|---|---|---|
| 330 | 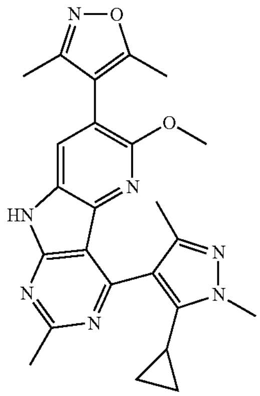 | 1H NMR (300 MHz, CD3OD) δ ppm 7.93 (s, 1H), 4.03 (s, 3H), 3.90 (s, 3H), 2.97 (s, 3H), 2.37 (s, 3H), 2.31 (s, 3H), 2.19 (s, 3H), 2.13-2.07 (m, 1H), 1.03-0.72 (m, 4H); ESI-MS (M + H): 444.42; UPLC(10 to 100% CH₃CN: H₂O 10 min): 3.2 min, 95% purity |
| 331 | 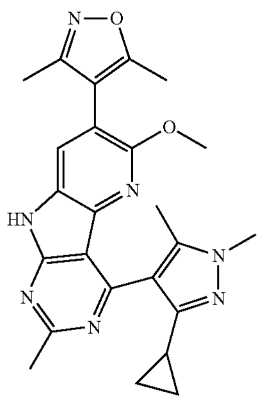 | 1H NMR (300 MHz, CD3OD) δ ppm 7.98 (s, 1H), 3.93 (s, 3H), 3.89 (s, 3H), 2.99 (s, 3H), 2.40 (s, 3H), 2.37 (s, 3H), 2.19 (s, 3H), 2.05-1.84 (m, 1H), 0.93-0.75 (m, 4H), ESI-MS (M + H): 444.42; UPLC(10 to 100% CH₃CN: H₂O 10 min): 3.3 min, 99% purity |

Example 171

Synthesis of 7-(3,5-dimethylisoxazol-4-yl)-6-methoxy-2-(2-methoxyethyl)-9H-pyrimido[4,5-b]indol-4-ol (ZBB261)

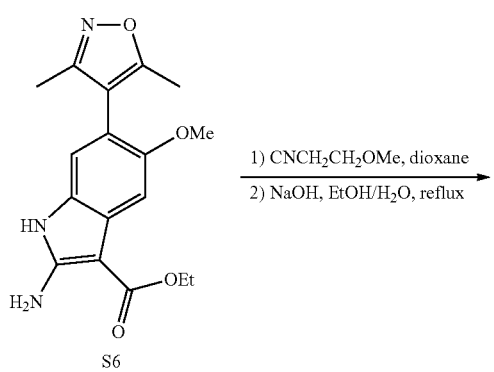

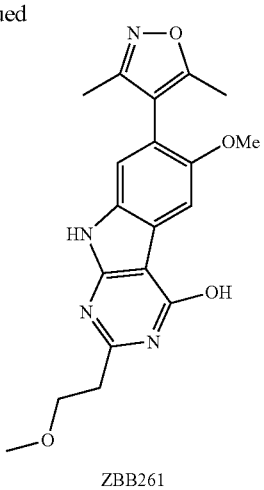

ZBB261

To a round-bottom flask, S6 (1 g), MeOCH₂CH₂CN (4 mL) and hydrogen chloride solution, 4 M in dioxane (4 mL) were added at room temperature. The reaction mixture was stirred overnight. The volatile components were removed on a rotary evaporator. To this crude mixture, 10% NaOH aqueous solution (10 mL) and EtOH (20 mL) were added and the solution was heated at reflux for 8 h. The volatile components were then removed on a rotary evaporator and the aqueous residue was acidified with 2 N HCl aqueous solution. The product ZBB261 was allowed to precipitate at 0° C. Filtration of the mixture furnished crude ZBB261 which was purified by HPLC to yield the desired product as a $CF_3CO_2H$ salt in 0.15 g. ESI-MS calculated for $C_{19}H_{21}N_4O_4$ $[M+H]^+$=369.15; Observed: 369.74. $^1H$ NMR (300 MHz, MeOD) δ 7.80 (s, 1H), 7.30 (s, 1H), 3.98-3.79 (m, 5H), 3.40 (s, 3H), 3.03 (t, J=6.2 Hz, 2H), 2.33 (s, 3H), 2.17 (s, 3H).

Synthesis of 4-(4-chloro-6-methoxy-2-(2-methoxyethyl)-9H-pyrimido[4,5-b]indol-7-yl)-3,5-dimethylisoxazole (ZBB264)

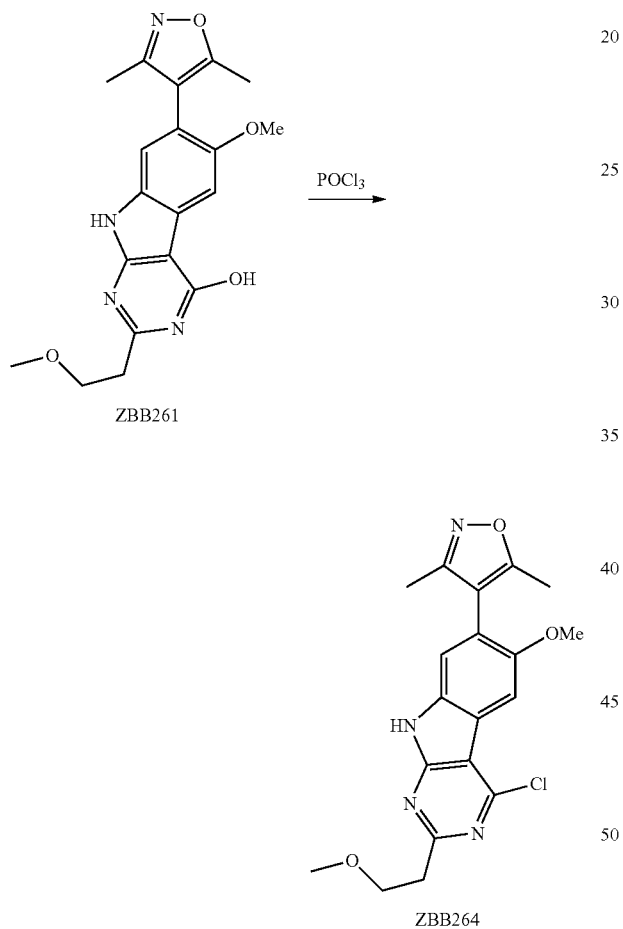

To a round-bottom flask, ZBB261 (0.278 g, 0.8 mmol) and $POCl_3$ (8 mL) were added. The mixture was heated at 90° C. for 6 h. The reaction mixture was cooled to room temperature and the volatile components were removed on a rotary evaporator. Water (20 mL) and ethyl acetate (20 mL) were added and the pH was adjusted to 8 using $NaHCO_3$ saturated aqueous solution. Filtration of the mixture furnished ZBB264 as a brown solid in 0.24 g. ESI-MS calculated for $C_{19}H_{20}ClN_4O_3[M+H]^+$=387.12; Observed: 387.44. $^1H$ NMR (300 MHz, DMSO) δ 12.56 (s, 1H), 7.82 (s, 1H), 7.43 (s, 1H), 3.94-3.84 (m, 5H), 3.27 (s, 3H), 3.18 (t, J=6.4 Hz, 2H), 2.32 (s, 3H), 2.12 (s, 3H).

Synthesis of N-(3-cyclopropyl-1-methyl-1H-pyrazol-5-yl)-7-(3,5-dimethylisoxazol-4-yl)-6-methoxy-2-(2-methoxyethyl)-9H-pyrimido[4,5-b]indol-4-amine (Cpd. No. 287)

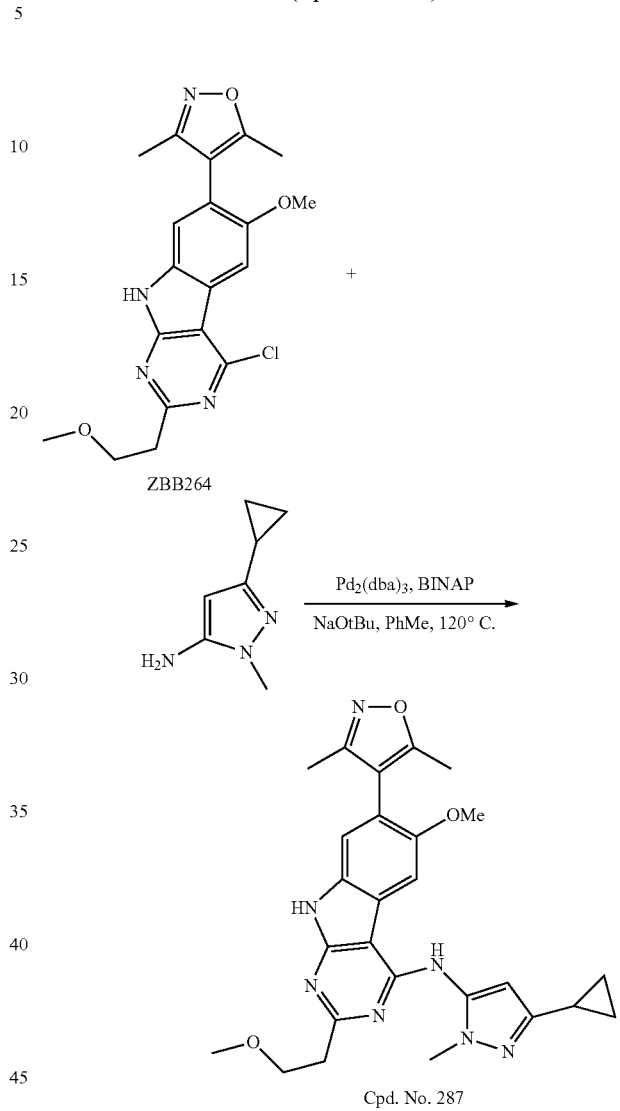

$Pd_2(dba)_3$ (18 mg) and BINAP (26 mg) were mixed in anhydrous toluene. And the mixture was heated at reflux for 3-4 minutes. This mixture was transferred into a round-bottom flask containing ZBB264 (60 mg), 3-cyclopropyl-1-methyl-1H-pyrazol-5-amine (84 mg), NaOtBu (100 mg), and toluene (4 mL). The mixture was heated at reflux for overnight before quenching with methanol. The reaction mixture was filtered and the mixture was purified by HPLC to yield Cpd. No. 287 as a $CF_3CO_2H$ salt in 25 mg. ESI-MS calculated for $C_{25}H_{28}N_7O_3$ $[M+H]^+$=488.24; Observed: 488.76. $^1H$ NMR (300 MHz, MeOD) δ 7.49 (s, 1H), 7.46 (s, 1H), 6.14 (s, 1H), 3.91 (s, 3H), 3.87 (t, J=5.9 Hz, 2H), 3.78 (s, 3H), 3.36 (s, 3H), 3.22 (t, J=5.9 Hz, 2H), 2.34 (s, 3H), 2.17 (s, 3H), 2.02-1.89 (m, 1H), 1.04-0.94 (m, 2H), 0.81-0.69 (m, 2H).

487

Synthesis of 7-(3,5-dimethylisoxazol-4-yl)-6-methoxy-2-((2-methoxyethoxy)methyl)-9H-pyrimido[4,5-b]indol-4-ol (ZBB266)

488

Synthesis of 4-(4-chloro-6-methoxy-2-((2-methoxyethoxy)methyl)-9H-pyrimido[4,5-b]indol-7-yl)-3,5-dimethylisoxazole (ZBB267)

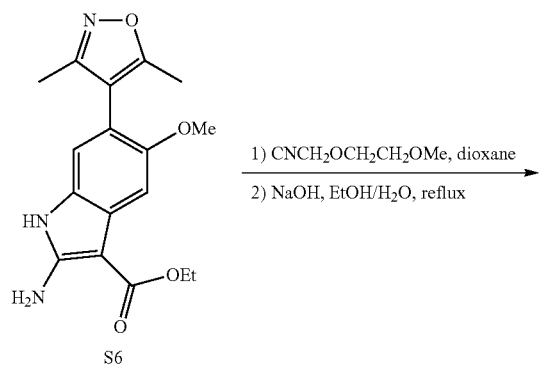

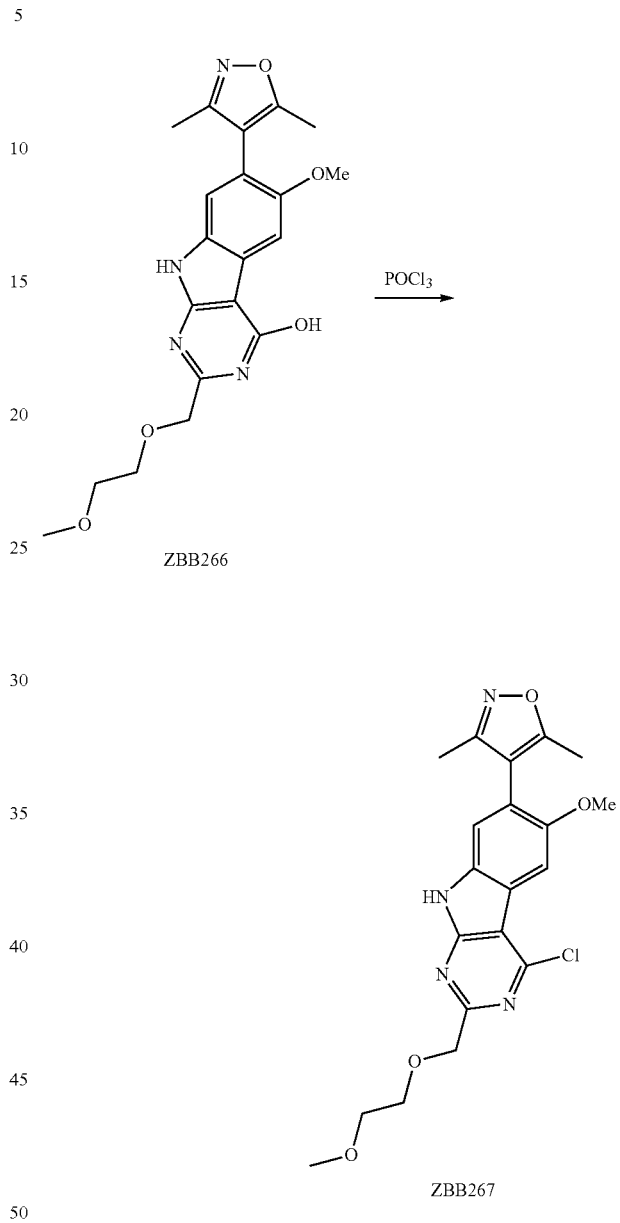

To a round-bottom flask, S6 (1 g), MeOCH$_2$CH$_2$OCH$_2$CN (4 mL) and hydrogen chloride solution, 4 M in dioxane (4 mL) were added at room temperature. The reaction mixture was stirred overnight. The volatile components were removed on a rotary evaporator. To this crude mixture, 10% NaOH aqueous solution (10 mL) and EtOH (20 mL) were added and the solution was heated at reflux for 8 h. The volatile components were then removed on a rotary evaporator and the aqueous residue was acidified with 2 N HCl aqueous solution. The product ZBB266 was allowed to precipitate at 0° C. Filtration of the mixture furnished crude ZBB266 in 0.7 g. ESI-MS calculated for C$_{20}$H$_{23}$N$_4$O$_5$ [M+H]$^+$=399.16; Observed: 399.44. $^1$H NMR (300 MHz, DMSO) δ 12.12 (s, 1H), 12.04 (s, 1H), 7.59 (s, 1H), 7.26 (s, 1H), 4.49 (s, 2H), 3.84 (s, 3H), 3.76-3.65 (m, 2H), 3.53 (dd, J=5.6, 3.7 Hz, 2H), 3.28 (s, 3H), 2.29 (s, 3H), 2.09 (s, 3H).

To a round-bottom flask, ZBB266 (0.278 g, 0.8 mmol) and POCl$_3$ (8 mL) were added. The mixture was heated at 90° C. for 6 h. The reaction mixture was cooled to room temperature and the volatile components were removed on a rotary evaporator. Water (20 mL) and ethyl acetate (20 mL) were added and the pH was adjusted to 8 using NaHCO$_3$ saturated aqueous solution. Filtration of the mixture furnished ZBB267 as a brown solid in 0.25 g. ESI-MS calculated for C$_{20}$H$_{22}$ClN$_4$O$_4$[M+H]$^+$=417.13; Observed: 417.65.

489

Synthesis of N-(3-cyclopropyl-1-methyl-1H-pyrazol-5-yl)-7-(3,5-dimethylisoxazol-4-yl)-6-methoxy-2-((2-methoxyethoxy)methyl)-9H-pyrimido[4,5-b]indol-4-amine (Cpd. No. 288)

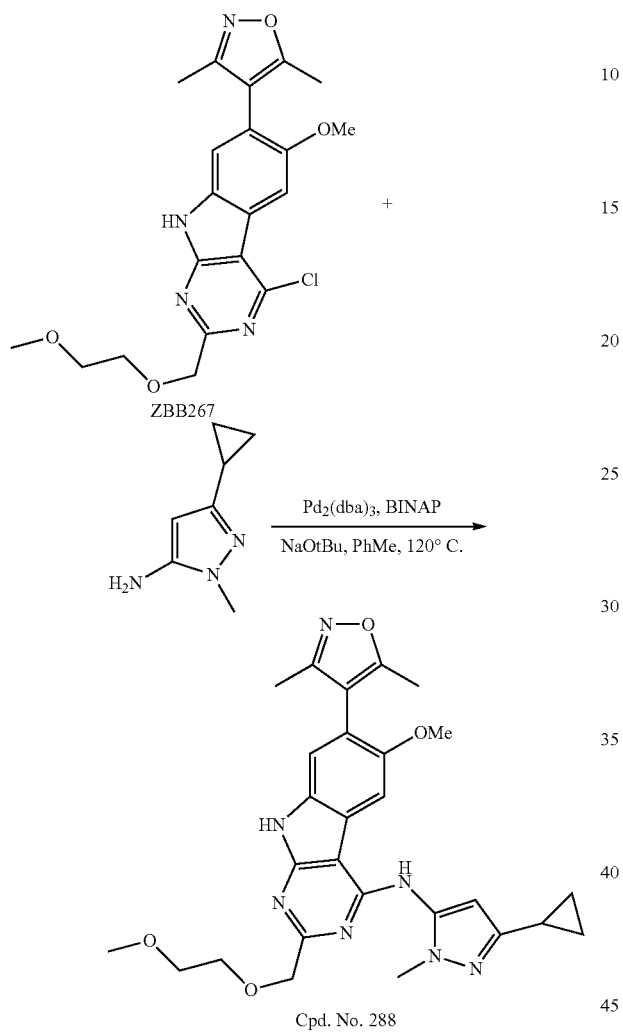

Pd$_2$(dba)$_3$ (18 mg) and BINAP (26 mg) were mixed in anhydrous toluene. And the mixture was heated at reflux for 3-4 minutes. This mixture was transferred into a round-bottom flask containing ZBB267 (60 mg), 3-cyclopropyl-1-methyl-1H-pyrazol-5-amine (84 mg), NaOtBu (100 mg), and toluene (4 mL). The mixture was heated at reflux for overnight before quenching with methanol. The reaction mixture was filtered and the mixture was purified by HPLC to yield Cpd. No. 288 as a CF$_3$CO$_2$H salt in 23 mg. ESI-MS calculated for C$_{27}$H$_{32}$N$_7$O$_4$ [M+H]$^+$=518.25; Observed: 518.44. $^1$H NMR (300 MHz, MeOD) δ 7.50 (s, 1H), 7.43 (s, 1H), 6.12 (s, 1H), 4.79 (s, 2H), 3.91 (s, 3H), 3.86 (dd, J=4.1, 2.0 Hz, 2H), 3.76 (s, 3H), 3.69-3.64 (m, 2H), 3.39 (s, 3H), 2.32 (s, 3H), 2.15 (s, 3H), 1.95 (tt, J=8.4, 5.1 Hz, 1H), 1.04-0.94 (m, 2H), 0.79-0.71 (m, 2H).

490

Synthesis of 7-(3,5-dimethylisoxazol-4-yl)-6-methoxy-2-((methyl sulfonyl)methyl)-9H-pyrimido[4,5-b]indol-4-ol (ZBB271)

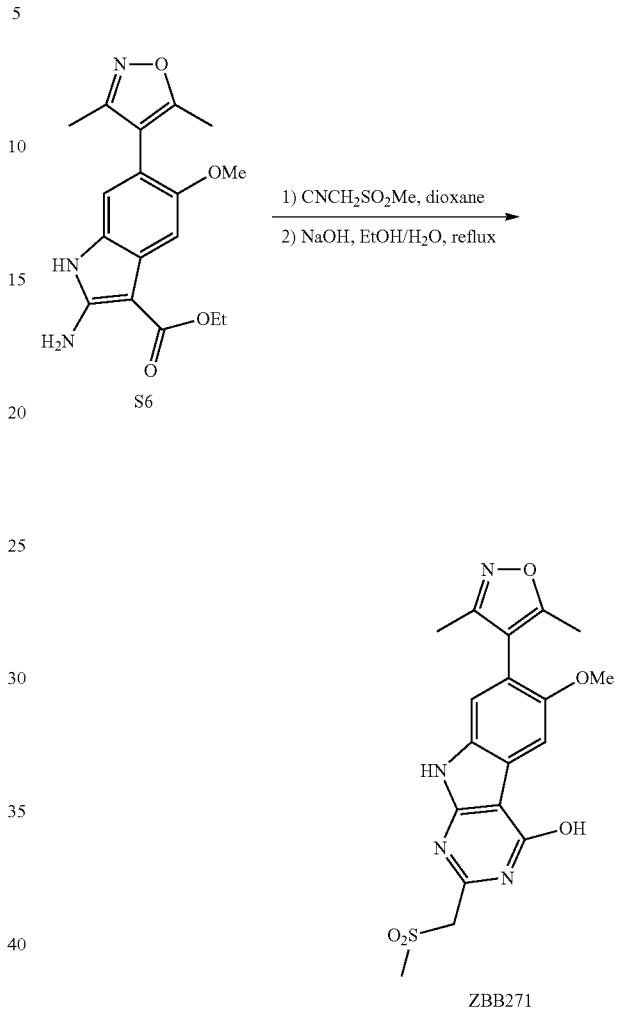

To a round-bottom flask, S6 (1 g), MeSO$_2$CH$_2$CN (4 mL) and hydrogen chloride solution, 4 M in dioxane (4 mL) were added at room temperature. The reaction mixture was stirred overnight. The volatile components were removed on a rotary evaporator. To this crude mixture, 10% NaOH aqueous solution (10 mL) and EtOH (20 mL) were added and the solution was heated at reflux for 8 h. The volatile components were then removed on a rotary evaporator and the aqueous residue was acidified with 2 6dN HCl aqueous solution. The product ZBB271 was allowed to precipitate at 0° C. Filtration of the mixture furnished crude ZBB271 in 0.8 g. ESI-MS calculated for C$_{18}$H$_{19}$N$_4$O$_5$S [M+H]$^+$=403.10; Observed: 403.55. $^1$H NMR (300 MHz, MeOD) δ 7.82 (s, 1H), 7.34 (s, 1H), 4.62 (s, 2H), 3.91 (s, 3H), 3.25 (s, 3H), 2.33 (s, 3H), 2.17 (s, 3H).

491

Synthesis of 4-(4-chloro-6-methoxy-2-((methylsulfonyl)methyl)-9H-pyrimido[4,5-b]indol-7-yl)-3,5-dimethylisoxazole (ZBB273)

492

Synthesis of N-(3-cyclopropyl-1-methyl-1H-pyrazol-5-yl)-7-(3,5-dimethylisoxazol-4-yl)-6-methoxy-2-((methylsulfonyl)methyl)-9H-pyrimido[4,5-b]indol-4-amine (Cpd. No. 289)

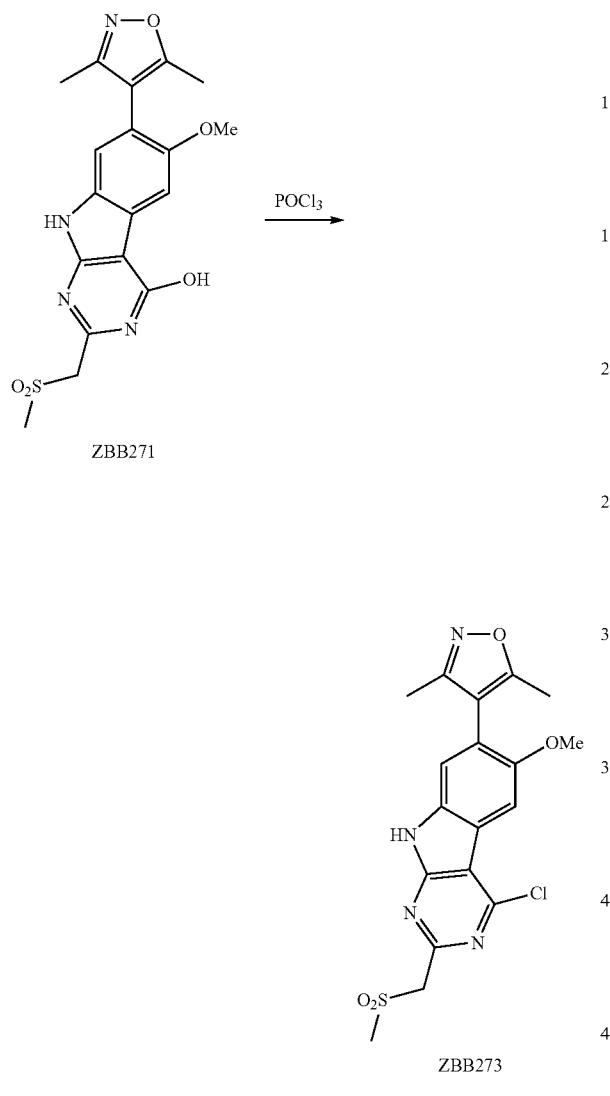

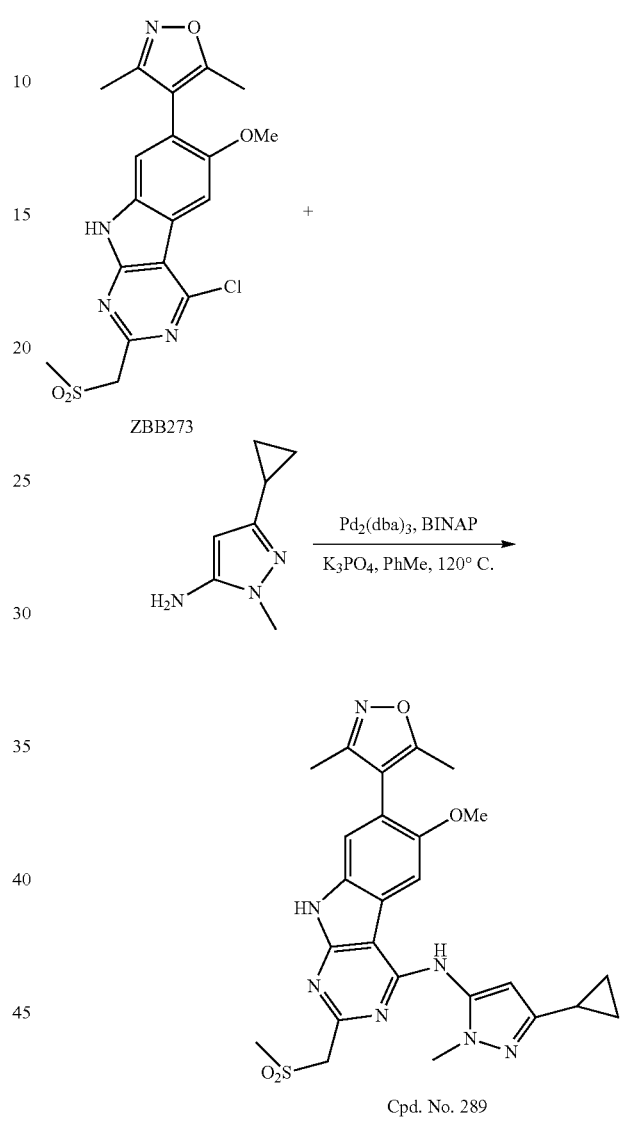

To a round-bottom flask, ZBB271 (0.278 g, 0.8 mmol) and POCl$_3$ (8 mL) were added. The mixture was heated at 90° C. for 6 h. The reaction mixture was cooled to room temperature and the volatile components were removed on a rotary evaporator. Water (20 mL) and ethyl acetate (20 mL) were added and the pH was adjusted to 8 using NaHCO$_3$ saturated aqueous solution. Filtration of the mixture furnished ZBB273 as a brown solid in 0.21 g. ESI-MS calculated for C$_{18}$H$_{18}$ClN$_4$O$_4$S [M+H]$^+$=421.07; Observed: 421.44.

Pd$_2$(dba)$_3$ (18 mg) and BINAP (26 mg) were mixed in anhydrous toluene. And the mixture was heated at reflux for 3-4 minutes. This mixture was transferred into a round-bottom flask containing ZBB273 (60 mg), 3-cyclopropyl-1-methyl-1H-pyrazol-5-amine (84 mg), K$_3$PO$_4$ (130 mg), and toluene (4 mL). The mixture was heated at reflux for overnight before quenching with methanol. The reaction mixture was filtered and the mixture was purified by HPLC to yield Cpd. No. 289 as a CF$_3$CO$_2$H salt in 27 mg. ESI-MS calculated for C$_{25}$H$_{28}$N$_7$O$_4$S [M+H]$^+$=522.19; Observed: 522.44.

493

Synthesis of N4-(3-cyclopropyl-1-ethyl-1H-pyrazol-5-yl)-7-(3,5-dimethylisoxazol-4-yl)-6-methoxy-9H-pyrimido[4,5-b]indole-2,4-diamine (Cpd. No. 290)

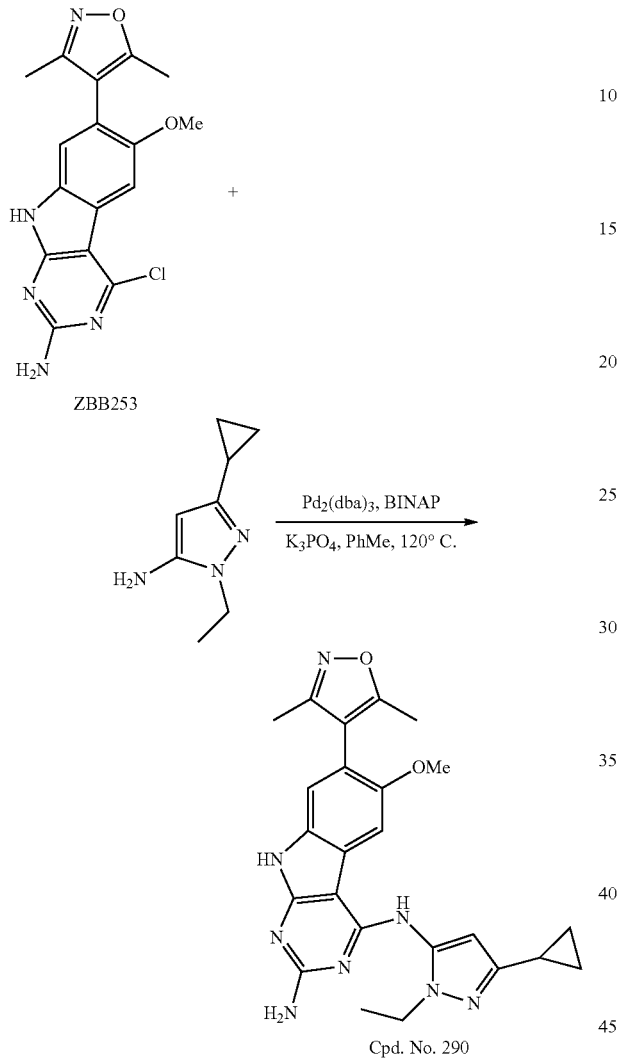

494

Synthesis of N4-(1,3-dicyclopropyl-1H-pyrazol-5-yl)-7-(3,5-dimethylisoxazol-4-yl)-6-methoxy-9H-pyrimido[4,5-b]indole-2,4-diamine (Cpd. No. 291)

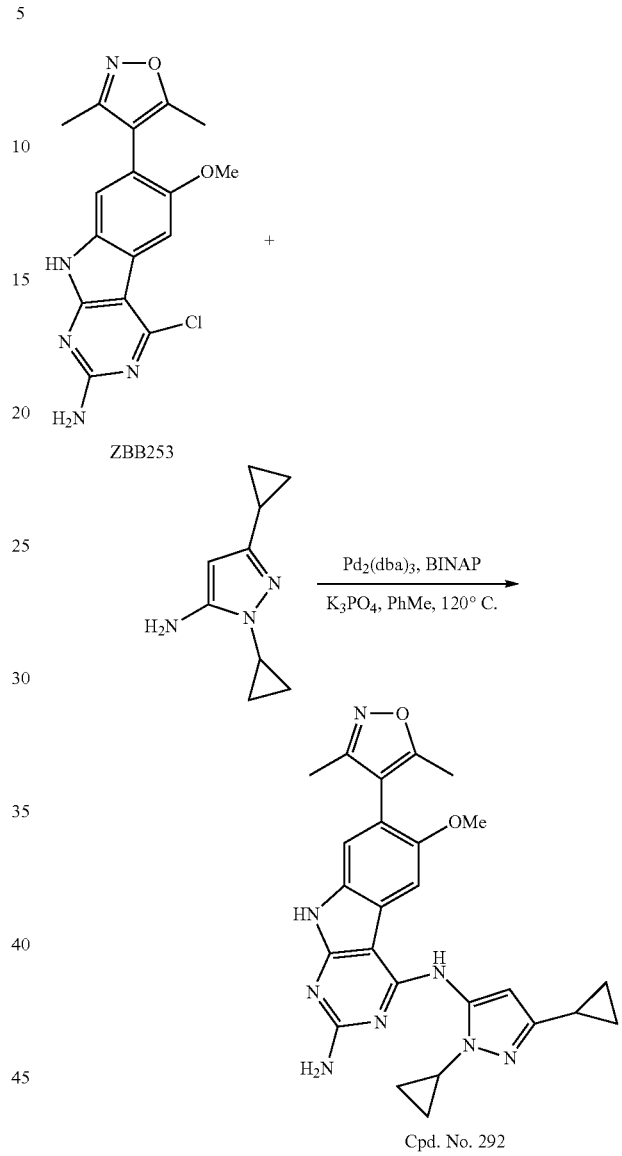

Pd$_2$(dba)$_3$ (18 mg) and BINAP (26 mg) were mixed in anhydrous toluene. And the mixture was heated at reflux for 3-4 minutes. This mixture was transferred into a round-bottom flask containing ZBB253 (60 mg), 3-cyclopropyl-1-ethyl-1H-pyrazol-5-amine (84 mg), K$_3$PO$_4$ (130 mg), and toluene (4 mL). The mixture was heated at reflux for overnight before quenching with methanol. The reaction mixture was filtered and the mixture was purified by HPLC to yield Cpd. No. 290 as a CF$_3$CO$_2$H salt in 20 mg. ESI-MS calculated for C$_{24}$H$_{27}$N$_8$O$_2$ [M+H]$^+$=459.22; Observed: 459.67. $^1$H NMR (300 MHz, MeOD) δ 7.56 (s, 1H), 7.34 (s, 1H), 6.04 (s, 1H), 4.07 (q, J=7.2 Hz, 2H), 3.90 (s, 3H), 2.32 (s, 3H), 2.15 (s, 3H), 1.95 (ddd, J=13.3, 8.4, 5.0 Hz, 1H), 1.44 (t, J=7.2 Hz, 3H), 1.03-0.91 (m, 2H), 0.79-0.65 (m, 2H).

Pd$_2$(dba)$_3$ (18 mg) and BINAP (26 mg) were mixed in anhydrous toluene. And the mixture was heated at reflux for 3-4 minutes. This mixture was transferred into a round-bottom flask containing ZBB253 (60 mg), 1,3-dicyclopropyl-1H-pyrazol-5-amine (88 mg), K$_3$PO$_4$ (130 mg), and toluene (4 mL). The mixture was heated at reflux for overnight before quenching with methanol. The reaction mixture was filtered and the mixture was purified by HPLC to yield Cpd. No. 291 as a CF$_3$CO$_2$H salt in 24 mg. ESI-MS calculated for C$_{25}$H$_{27}$N$_8$O$_2$ [M+H]$^+$=471.22; Observed: 471.33. $^1$H NMR (300 MHz, MeOD) δ 7.59 (s, 1H), 7.35 (s, 1H), 6.10 (s, 1H), 3.90 (s, 3H), 3.44-3.34 (m, 1H), 2.33 (s, 3H), 2.16 (s, 3H), 1.92 (td, J=8.4, 4.4 Hz, 1H), 1.16-1.08 (m, 2H), 1.00-0.92 (m, 4H), 0.77-0.71 (m, 2H).

Synthesis of 7-(3,5-dimethylisoxazol-4-yl)-N4-(2-isopropyl-2,4,5,6-tetrahydrocyclopenta[c]pyrazol-3-yl)-6-methoxy-9H-pyrimido[4,5-b]indole-2,4-diamine (Cpd. No. 292)

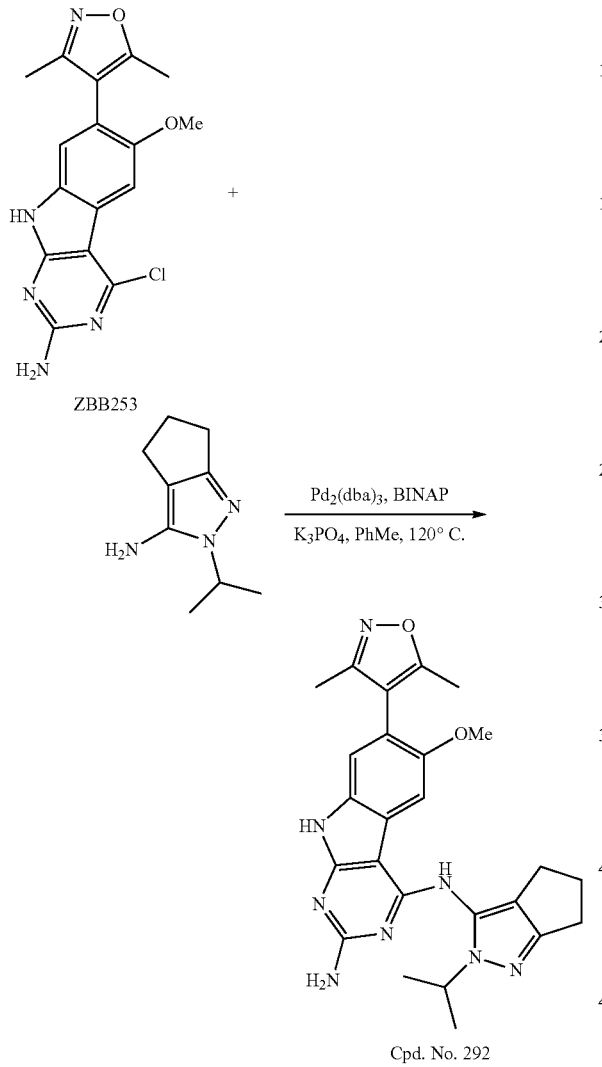

Cpd. No. 292

Pd$_2$(dba)$_3$ (18 mg) and BINAP (26 mg) were mixed in anhydrous toluene. And the mixture was heated at reflux for 3-4 minutes. This mixture was transferred into a round-bottom flask containing ZBB253 (60 g), 2-isopropyl-2,4,5,6-tetrahydrocyclopenta[c]pyrazol-3-amine (88 mg), K$_3$PO$_4$ (130 mg), and toluene (4 mL). The mixture was heated at reflux for overnight before quenching with methanol. The reaction mixture was filtered and the mixture was purified by HPLC to yield Cpd. No. 292) as a CF$_3$CO$_2$H salt in 24 mg. ESI-MS calculated for C$_{25}$H$_{29}$N$_8$O$_2$ [M+H]$^+$=473.24; Observed: 473.56. $^1$H NMR (300 MHz, CDCl$_3$) δ 7.47 (s, 1H), 7.35 (s, 1H), 4.65-4.45 (m, 1H), 3.87 (s, 3H), 2.77 (t, J=7.2 Hz, 2H), 2.58 (t, J=6.9 Hz, 2H), 2.49-2.36 (m, 2H), 2.31 (s, 3H), 2.13 (s, 3H), 1.51 (d, J=6.7 Hz, 6H).

Synthesis of 3-(3-Cyclopropyl-5-((7-(3,5-dimethylisoxazol-4-yl)-6-methoxy-2-methyl-9H-pyrimido[4,5-b]-indol-4-yl)amino)-1H-pyrazol-1-yl)azetidine-1-carbaldehyde (Cpd. No. 293)

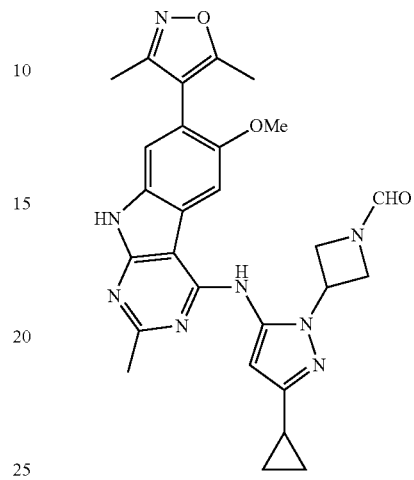

Cpd. No. 163 (50 mg), formic acid (13.8 mg), EDCI-HCl (76 mg), and HOBt (54 mg) were dissolved in anhydrous DMF (3 mL). EtN(i-Pr)$_2$ (0.1 mL) was added via a syringe and the reaction mixture was stirred at room temperature for overnight. The reaction mixture was the purified by reverse phase HPLC to yield the titled compound in 24 mg as a salt of CF$_3$CO$_2$H. $^1$H NMR (300 MHz, MeOD): 8.01 (s, 1H), 7.47 (s, 1H), 6.07 (s, 1H), 5.30-5.15 (m, 1H), 4.70-4.50 (m, 2H), 4.40-4.20 (m, 2H), 3.89 (s, 3H), 2.68 (s, 3H), 2.31 (s, 3H), 2.13 (s, 3H), 2.10-1.90 (m, 1H), 1.10-0.90 (m, 2H), 1.80-1.70 (m, 2H). ESI-MS calculated for C$_{27}$H$_{29}$NO$_3$ [M+H]$^+$=513.24, observed: 513.67.

Synthesis of N-(3-Cyclopropyl-1-(oxetan-3-ylmethyl)-1H-pyrazol-5-yl)-7-(3,5-dimethylisoxazol-4-yl)-6-methoxy-2-methyl-9H-pyrimido[4,5-b]indol-4-amine (Cpd. No. 294)

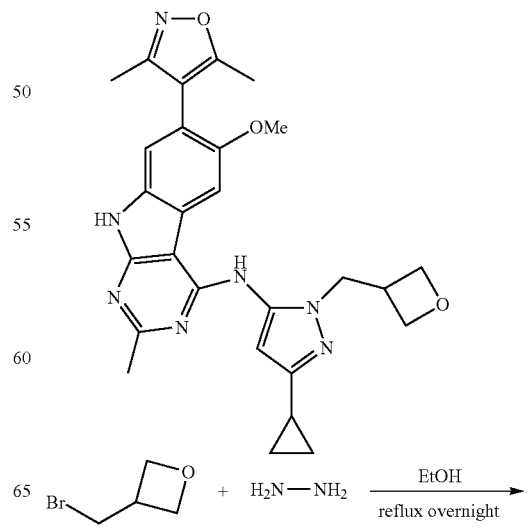

-continued

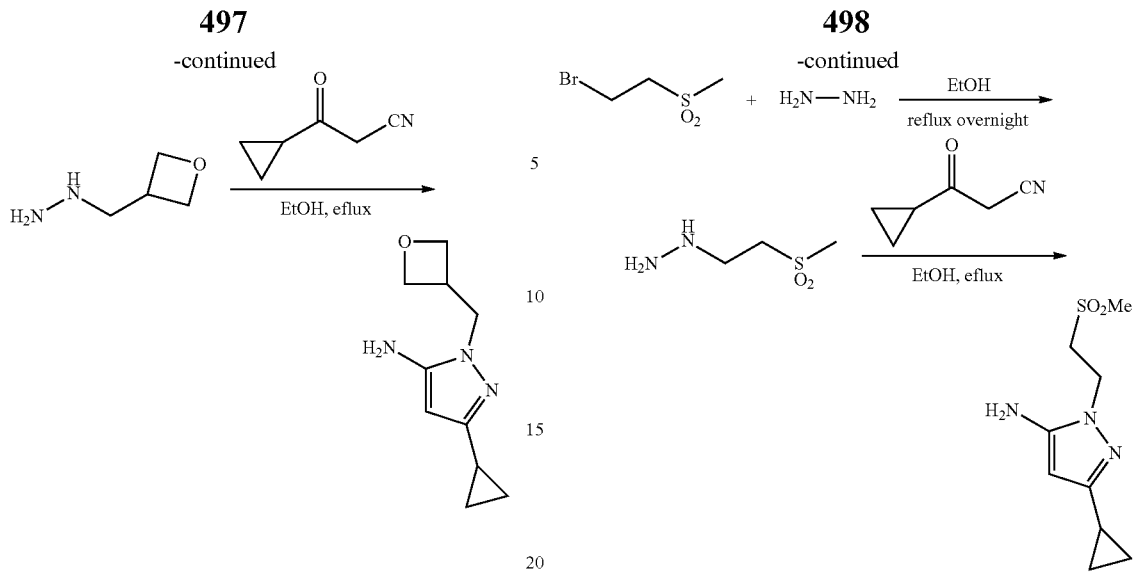

Step 1: 3-Cyclopropyl-1-(oxetan-3-ylmethyl)-1H-pyrazol-5-amine 3-(Bromomethyl)oxetane (0.5 g, 3.3 mmol) and hydrazine (250 mg, 5.0 mmol) were dissolved in ethanol (20 mL) and the mixture was heated at reflux for overnight. To the reaction mixture, 3-cyclopropyl-3-oxopropanenitrile (540 mg) was added and the reaction was heated at reflux for 12 h. The mixture was purified by reverse phase HPLC to yield the titled compound in 198 mg. ESI-MS calculated for $C_{10}H_{16}N_3O$ $[M+H]^+$=194.13, Observed: 194.58.

Step 2

The titled compound was prepared from S13 (180 mg) and 3-cyclopropyl-1-(oxetan-3-ylmethyl)-1H-pyrazol-5-amine (198 mg) following the similar procedure for preparation of Cpd. No. 135. The titled compound was obtained in 15 mg as a salt of $CF_3CO_2H$. $^1H$ NMR (300 MHz, MeOD): 8.00 (s, 1H), 7.46 (s, 1H), 6.41 (s, 1H), 4.80-4.70 (m, 1H), 4.65-4.45 (m, 2H), 4.45-4.30 (m, 1H), 3.94 (s, 3H), 3.85-3.75 (m, 2H), 3.65-3.50 (m, 1H), 2.73 (s, 3H), 2.32 (s, 3H), 2.15 (s, 3H). 2.20-2.05 (m, 1H), 1.40-1.25 (m, 2H), 1.10-0.90 (m, 2H). ESI-MS calculated for $C_{27}H_{30}N_7O_3$ $[M+H]^+$=500.24, observed: 500.50.

Synthesis of N-(3-cyclopropyl-1-(2-(methylsulfonyl)ethyl)-1H-pyrazol-5-yl)-7-(3,5-dimethylisoxazol-4-yl)-6-methoxy-2-methyl-9H-pyrimido[4,5-b]indol-4-amine (Cpd. No. 295)

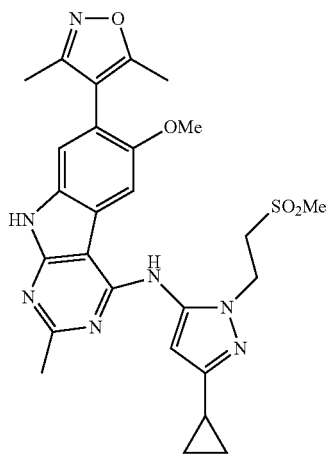

-continued

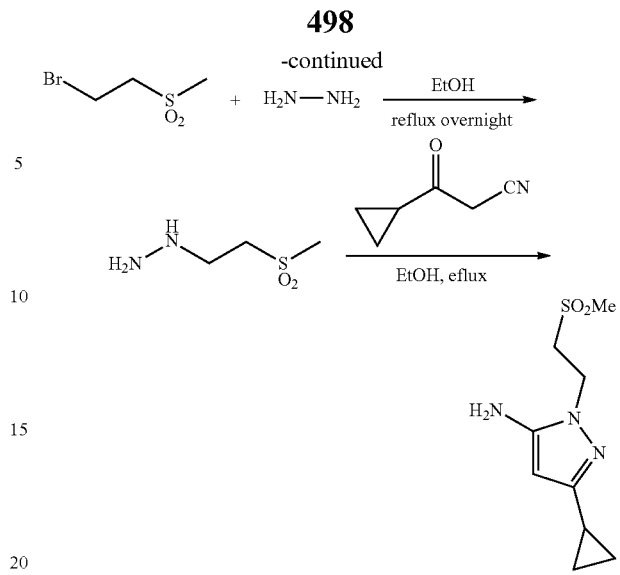

Step 1: 3-Cyclopropyl-1-(2-(methylsulfonyl)ethyl)-1H-pyrazol-5-amine

1-Bromo-2-(methylsulfonyl)ethane (1.87 g, 10 mmol) and hydrazine (4.8 mL, 10 mmol) were dissolved in ethanol (50 mL) and the mixture was heated at reflux for overnight. To the mixture, 3-cyclopropyl-3-oxopropanenitrile (810 mg) was added and the reaction was heated at reflux for 12 h. Ethanol was then removed and the mixture was neutralized with 2 N NaOH aq. solution. The aq. phase was extracted with ethyl acetate and the product was purified by flash column chromatography to yield the titled compound in 733 mg. ESI-MS calculated for $C_9H_{16}N_3O_2S$ $[M+H]^+$=230.10, Observed: 230.67.

Step 2

The titled compound was prepared from S13 (547 mg) and 3-cyclopropyl-1-(2-(methyl sulfonyl)ethyl)-1H-pyrazol-5-amine (773 mg) following the similar procedure for preparation of Cpd. No. 135. The titled compound was obtained in 90 mg as a salt of $CF_3CO_2H$. $^1H$ NMR (300 MHz, MeOD): 7.63 (s, 1H), 7.47 (s, 1H), 6.17 (s, 1H), 4.54 (t, J=6.14 Hz, 2H), 3.75 (t, J=5.98 Hz, 2H), 3.92 (s, 3H), 2.84 (s, 3H), 2.71 (s, 3H), 2.32 (s, 3H), 2.15 (s, 3H), 2.00-1.90 (m, 1H), 1.00-0.90 (m, 2H), 0.80-0.70 (m, 2H). ESI-MS calculated for $C_{26}H_{30}N_7O_4S$ $[M+H]^+$=536.21, observed: 535.83.

Synthesis of 4-(4-chloro-6-methoxy-9H-pyrido[3,4-b]indol-7-yl)-3,5-dimethylisoxazole

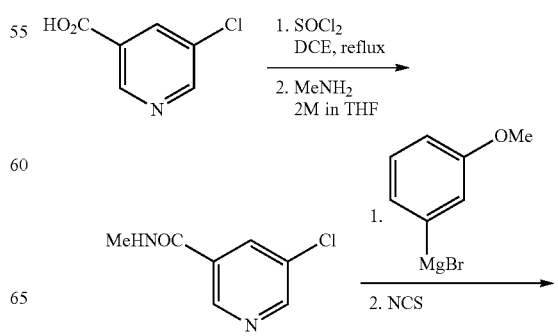

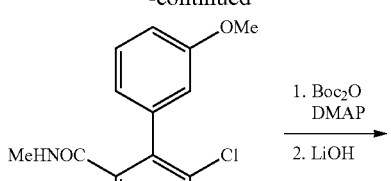

YJ3

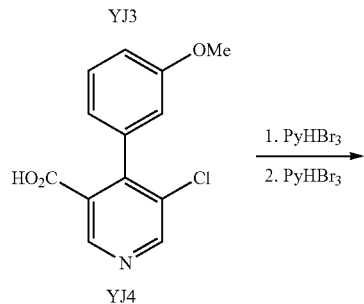

YJ4

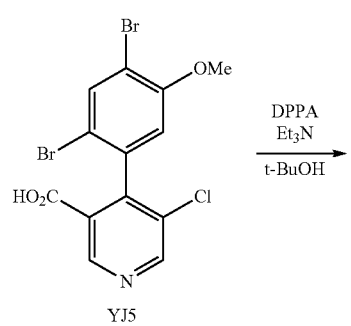

YJ5

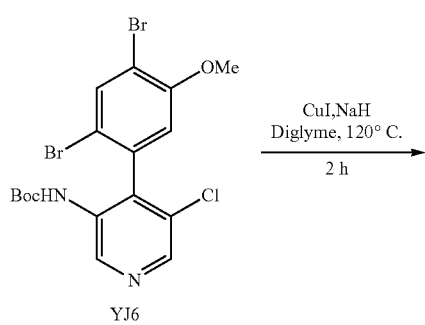

YJ6

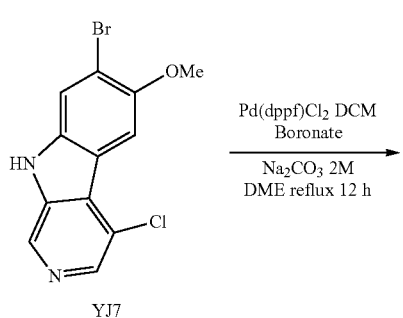

YJ7

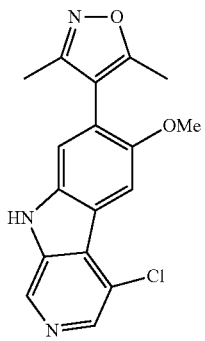

YJ8

Step 1: synthesis of 5-chloro-N-methylnicotinamide. 5-chloronicotinic acid (25 g) and anhydrous DMF (0.1 mL) was dissolved in anhydrous 1,2-dichloroethane (250 mL). SOCl$_2$ (34.8 mL) was added via a syringe and the reaction mixture was heated at reflux for 5 h. The volatile components were removed on a rotary evaporator. Dichloromethane (200 mL) was added and the volatile components were removed on a rotary evaporator. This process was repeated twice and the remaining solid was dissolvent in anhydrous THF (250 mL). Me-NH$_2$ solution in THF (2 M, 240 mL) was added at 0° C. via a dropping funnel and the reaction mixture was stirred at ambient temperature for overnight. Water was added and the aqueous phase was extracted with ethyl acetate. The combined organic layers were combined, dried over anhydrous sodium sulfate, and concentrated on a rotary evaporator. The solid was dried under vacuum for overnight affording 5-chloro-N-methylnicotinamide as dry powder in 25.73 g. ESI-MS calculated for $C_7H_8{}^{35}ClN_2O$ [M+H]$^+$=171.0, Observed: 171.1.

Step 2: synthesis of 5-chloro-4-(3-methoxyphenyl)-N-methylnicotinamide (YJ3). Dry 5-chloro-N-methylnicotinamide (6.8 g, 40 mmol) was dissolved in anhydrous THF (100 mL). (3-Methoxyphenyl)magnesium bromide (1.0 M in THF, 200 mL) was added via a dropping funnel while the reaction flask was cooled with a water bath. The reaction was stirred at ambient temperature for 8 h. Methanol (11.4 mL, 280 mmol) was added at 0° C. via a syringe followed by addition of NCS (6.91 g, 52 mmol) in small portions. The reaction was stirred at ambient temperature for overnight. The reaction was then quenched with NIH aqueous solution (15%). The aqueous phase was extracted with ethyl acetate and the combined organic layers were combined and dried over anhydrous sodium sulfate. The solvent was removed on a rotary evaporator and the remaining residues was purified by flash column chromatography. The titled compound (YJ3) was isolated in 8.0 g. ESI-MS calculated for $C_{14}H_{14}{}^{37}ClN_2O_2$[M+H]$^+$=279.07, Observed: 279.42.

Step 3: synthesis of 5-chloro-4-(3-methoxyphenyl)nicotinic acid (YJ4). YJ3 (8.0 g), Boc$_2$O (9.8 g), and Et$_3$N (10 mL) were dissolved in anhydrous THF (40 mL). DMAP (366 mg) was added in small portions and the mixture was stirred at ambient temperature for 6 h. The mixture was concentrated on a rotary evaporator and the residue was dissolved in THF (40 mL) and water (40 mL). LiOH—H$_2$O (7.14 g, 170 mmol) was added and the mixture was stirred at ambient temperature for overnight. t-BuOMe (150 mL) was added and the organic layer was extracted with NaOH (0.5 M, 3×40 mL). The aqueous layers were combined and acidified with 10% citric acid. The aqueous layer was then extracted with ethyl acetate/THF (2:1, 7×40 mL). The combined organic layer was dried over anhydrous sodium sulfate and concentrated on a rotary evaporator to yield the titled compound (YJ4) in 7.03 g. The crude was used without further purification. ESI-MS calculated for $C_{13}H_{11}{}^{35}ClNO_3$ [M+H]$^+$=264.04, Observed: 263.83.

Step 4: synthesis of 5-chloro-4-(2,4-dibromo-5-methoxyphenyl)nicotinic acid (YJ5). YJ4 (7.03 g) was dissolved in AcOH/H$_2$O (30 mL: 20 mL). PyHBr$_3$ (15.5 g, 1.8 equiv.) was added in small portions. The reaction mixture was stirred at ambient temperature for 4 h. The reaction mixture was quenched with NaHSO$_3$ (gas evolve) and filter through a pad of Celite®. The Celite® was washed with methanol and all the solvents were removed on a rotary evaporator. Water (100 mL) was added and the mixture was extracted with ethyl acetate (3×100 mL). The organic layers were combined and dried over anhydrous sodium sulfate. The solvents were removed on a rotary evaporator to yield 4-(2-bromo-5-methoxyphenyl)-5-chloronicotinic acid. The crude material was dissolved in AcOH/water (50 mL/33 mL). PyHBr$_3$ (12.8 g, 40 mmol) was added in small portions. The mixture was stirred at ambient temperature for overnight. The reaction was then extracted with ethyl acetate (3×100 mL). The organic layers were combined and dried over anhydrous sodium sulfate. The remaining residues were purified by reverse phase HPLC to yield the titled compound (YJ5) in 1.03 g. $^1$H NMR (300 MHz, MeOD-d4): 9.10 (s, 1H), 8.91 (s, 1H), 7.76 (s, 1H), 6.66 (s, 1H), 3.82 (s, 3H). ESI-MS calculated for $C_{13}H_9{}^{79}Br_2{}^{35}ClNO_3$ [M+H]$^+$=421.86, Observed: 422.33.

Step 5: synthesis of tert-butyl (5-chloro-4-(2,4-dibromo-5-methoxyphenyl)pyridin-3-yl)carbamate (YJ6). YJ5 (1.03 g, 2.5 mmol) and EN (1 mL, 7.17 mmol) were dissolved in t-BuOH (20 mL). DPPA was added via a syringe at ambient temperature and the mixture was stir for 4 h at ambient temperature before heated at reflux for overnight. Solvent was removed on a rotary evaporator and residues was purified by flash column chromatography to yield the titled compound (YJ6) in 673 mg. $^1$H NMR (300 MHz, CDCl$_3$): 9.28 (s, 1H), 8.53 (s, 1H), 7.90 (s, 1H), 6.68 (s, 1H), 3.88 (s, 3H), 1.46 (s, 9H). ESI-MS calculated for $C_7H_{18}{}^{79}Br_2{}^{35}ClN_2O_3$ [M+H]$^+$=492.94; Observed: 493.25.

Step 6: synthesis of 7-bromo-4-chloro-6-methoxy-9H-pyrido[3,4-b]indole (YJ7). YJ6 (673 mg), NaH (60% in mineral oil, 109 mg), and CuI (400 mg) were weighted into a dry round-bottom flask. Anhydrous diglyme (5 mL) was added and the system was degassed and refilled with nitrogen. The reaction heated at 120° C. for 2 h. The reaction mixture was then pour into 5% NH$_3$ aqueous solution and the aqueous layer was then extracted with ethyl acetate. The solvent was removed on a rotary evaporator and the remaining residues was purified by flash column chromatography to yield the titled compound (YJ7) in 347 mg. $^1$H NMR (300 MHz, DMSO-d6): 11.92 (s, 1H), 8.89 (s, 1H), 8.41 (s, 1H), 8.10 (s, 1H), 7.94 (s, 1H), 3.95 (s, 3H).

Step 7: synthesis of 4-(4-chloro-6-methoxy-9H-pyrido[3,4-b]indol-7-yl)-3,5-dimethylisoxazole (YJ8). YJ7 (135 mg, 0.44 mmol) and 3,5-dimethyl-4-(4,4,5,5-tetramethyl-1,3,2-dioxaborolan-2-yl)isoxazole (196 mg, 0.88 mmol) were mixed with DME (6 mL) followed by addition of Na$_2$CO$_3$ (2 M aqueous solution, 3 mL). The system was degassed and refilled with nitrogen. Pd(dppf)Cl$_2$-DCM (33 mg) was added and the system was degassed and refilled with nitrogen. The reaction mixture was then heated at reflux for overnight. The aqueous layer was then extracted with ethyl acetates and the combined organic layers were dried and concentrated on a rotary evaporator. The remaining residues were purified by flash column chromatography to yield the titled compound (YJ8) in 40 mg. $^1$H NMR (300 MHz, CDCl$_3$): 9.83 (s, 1H), 8.83 (s, 1H), 8.41 (s, 1H), 8.09 (s, 1H), 7.32 (s, 1H), 3.95 (s, 3H), 2.35 (s, 3H), 2.22 (s, 3H). ESI-MS calculated for $C_{17}H_{15}{}^{35}ClN_3O_2$[M+H]$^+$=328.09, observed: 328.42

Synthesis of N-(3-Cyclopropyl-1-methyl-1H-pyrazol-5-yl)-7-(3,5-dimethylisoxazol-4-yl)-6-methoxy-9H-pyrido[3,4-b]indol-4-amine (Cpd. No. 323)

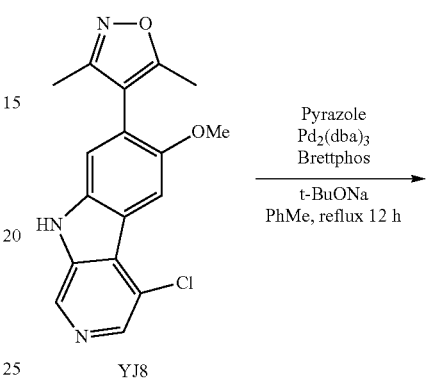

Pd$_2$(dba)$_3$ (45 mg) and BrettPhos (sigma-aldrich, 107 mg) were mixed in anhydrous toluene. The mixture was heated at reflux for 10 min. The preformed catalyst solution was cooled and transferred into a degassed and nitrogen-filled flask containing YJ8 (80 mg), 3-cyclopropyl-1-methyl-1H-pyrazol-5-amine (83 mg), t-BuONa (100 mg), and anhydrous toluene (10 mL). The reaction mixture was heated at reflux for overnight. The crude mixture was quenched with methanol, acidified, and purified by reverse phase HPLC to yield the titled compound in 3 mg as a salt of CF$_3$CO$_2$H. $^1$H NMR (300 MHz, MeOD): 8.74 (s, 1H), 7.69 (s, 1H), 7.62 (s, 1H), 7.58 (s, 1H), 5.78 (s, 1H), 3.88 (s, 3H), 3.79 (s, 3H), 2.35 (s, 3H), 2.17 (s, 3H), 2.00-1.80 (m, 1H), 1.00-0.80 (m, 2H), 0.70-0.50 (m, 2H). ESI-MS calculated for $C_{24}H_{25}N_6O_2$ [M+H]$^+$=429.20, observed: 429.75.

503
Alternate Route to Prepare N-(3-cyclopropyl-1-methyl-1H-pyrazol-5-yl)-7-(3,5-dimethyl-isoxazol-4-yl)-6-methoxy-9H-pyrido[3,4-b]indol-4-amine (Cpd. No. 323)
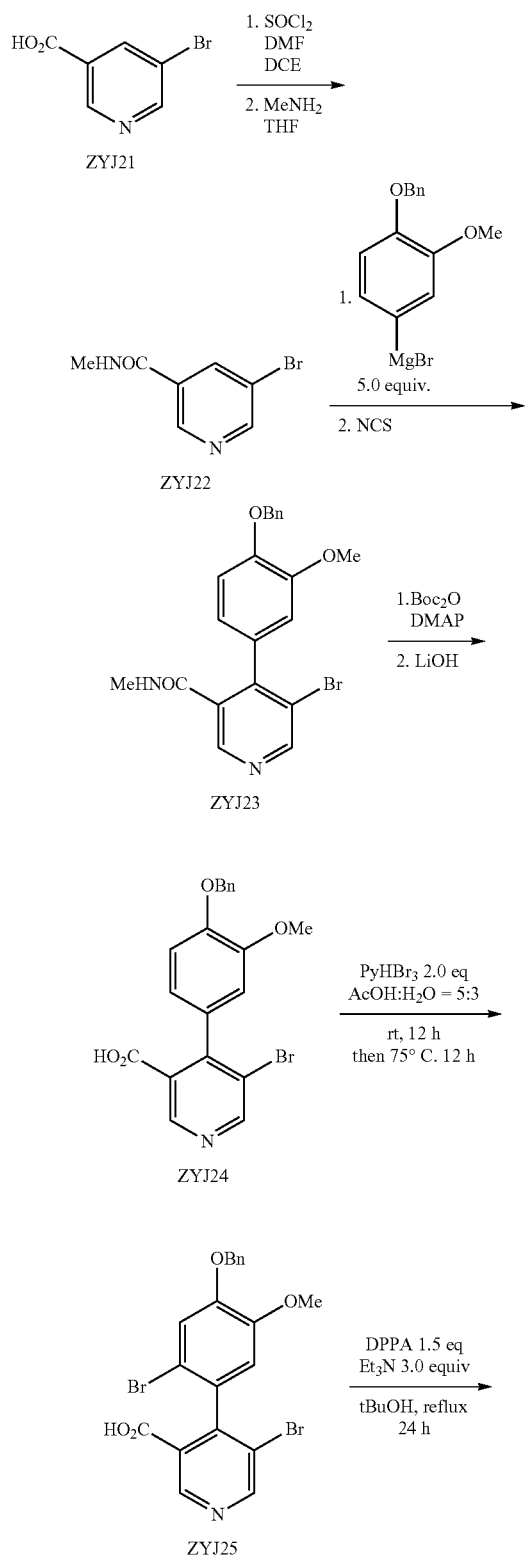
504
-continued
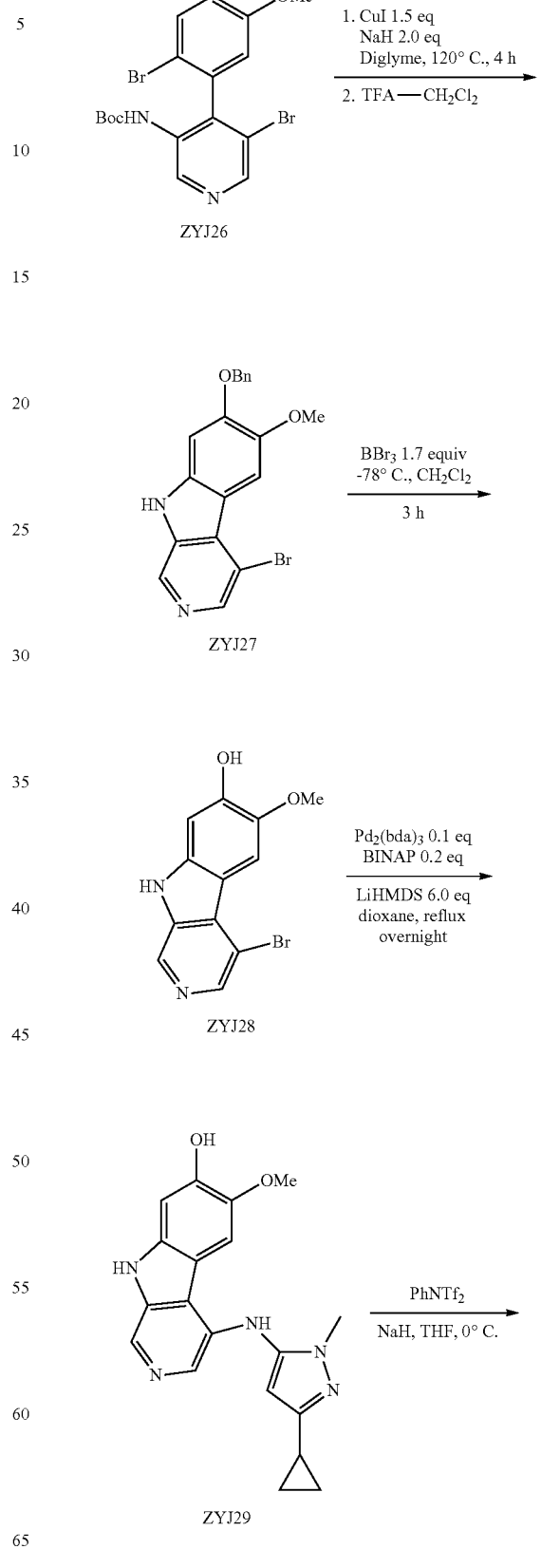

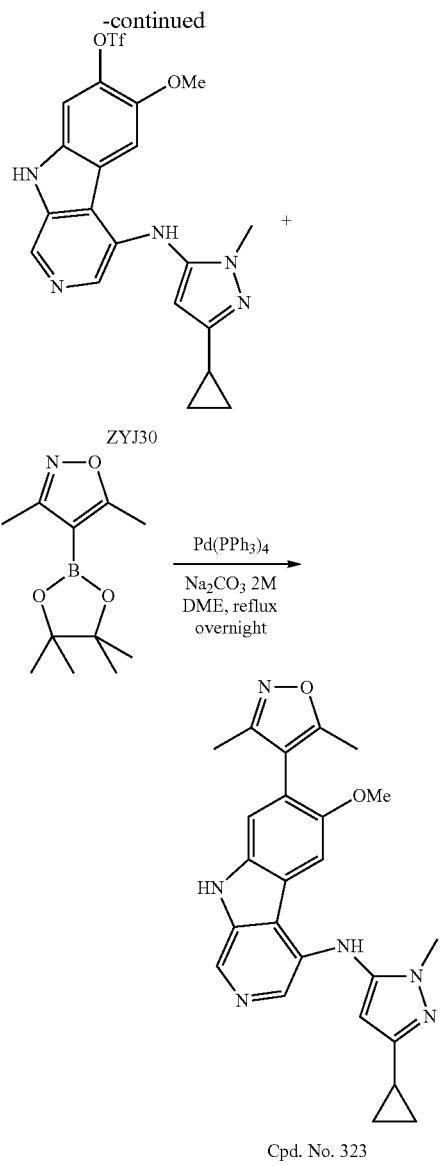

Step 1: 5-Bromonicotinic acid (25 g, 124 mmol) was dissolved in 1,2-dichloroethane (200 mL). SOCl$_2$ (27 mL, 371 mmol) was added at 0° C. followed by anhydrous DMF (0.2 mL) to initiate the reaction. The reaction mixture was heated at reflux for 5 h then concentrated on a rotary evaporator. CH$_2$Cl$_2$ (100 mL) was added and removed on a rotary evaporator and this process was repeated once. The remaining residues were dissolved in THF (100 mL) and methyl amine (124 mL, 2 M in THF) was added. Volatile components were removed on a rotary evaporator and the remaining residues were dissolved in ethyl acetate followed by addition of water. The aqueous layer was extracted with ethyl acetate, the combined organic layers were washed with brine, then dried over anhydrous Na$_2$SO$_4$. The ethyl acetate was removed on a rotary evaporator affording ZYJ22 as a solid in 25.3 g. $^1$H NMR (300 MHz, DMSO-d6): 8.94 (d, J=1.73 Hz, 1H), 8.83 (d, J=2.17 Hz, 1H), 8.72 (br, 1H), 8.37 (t, J=1.93 Hz, 1H), 2.79 (s, 1.5H), 2.78 (s, 1.5H). ESI-MS calculated for C$_7$H$_8$$^{79}$BrN$_2$O [M+H]$^+$=214.98; Observed: 215.0.

Step 2: 1-(Benzyloxy)-4-bromo-2-methoxybenzene (30.5 g, 104 mmol) in anhydrous THF (100 mL) reacted with magnesium turning (3.0 g, 125 mmol) in the presence of catalytic iodine provided the corresponding Grignard reagents. The Grignard reagents was transferred into a THF solution of ZYJ22 (5.09 g, 49 mmol) and the reaction was stirred at ambient temperature for overnight. The reaction was then quenched with methanol (5.9 mL, 146 mmol) at 0° C. After 20 min, NCS (6.5 g, 49 mmol) was added in small portions. The reaction was stirred at ambient temperature for overnight and then quenched with 7% ammonia solution. Ethyl acetate was added to aqueous solution and the solid was collected affording the desired ZYJ23 (2.06 g). The aqueous layer was extracted with ethyl acetate, the combined organic layers were washed with brine, then dried over anhydrous Na$_2$SO$_4$. The ethyl acetate was removed on a rotary evaporator and the remaining solid was mixed with diethyl ether. Filtration provided another portion of ZYJ23 in 4.57 g. $^1$H NMR (300 MHz, DMSO-d6): 8.85 (s, 1H), 8.51 (s, 1H), 8.34-8.22 (m, 1H), 7.54-7.30 (m, 5H), 7.12-7.08 (m, 1H), 6.89 (s, 1H), 6.82-6.72 (m, 1H), 5.10 (s, 2H), 3.72 (s, 3H), 2.52 (d, J=4.50 3H). ESI-MS calculated for C$_{21}$H$_{20}$$^{79}$BrN$_2$O$_3$[M+H]$^+$=427.07; Observed: 427.17.

Step 3: ZYJ23 (6.63 g, 15.5 mmol) and Boc$_2$O (7.0 g, 32 mmol) was dissolved in anhydrous THF (40 mL). DMAP (1.95 g, 16 mmol) was added in small portions. The reaction was stirred at ambient temperature for overnight. LiOH—H$_2$O (6.72 g, 160 mmol) and water (40 mL) were added to the reaction mixture and it was stirred for overnight. Water (100 mL) was added and the aqueous layers were extracted with diethyl ether (100 mL×2). The aqueous layer was acidified with citric acid and extracted with THF/ethyl acetate (4:1, 5×50 mL). The combined organic layers were dried over anhydrous sodium sulfate and concentrated on a rotary evaporator affording ZYJ24 in 6.60 g. $^1$H NMR (400 MHz, DMSO-d6): 8.95 (s, 1H), 8.83 (s, 1H), 7.52-7.46 (m, 2H), 7.46-7.40 (m, 2H), 7.40-7.34 (m, 1H), 7.14 (d, J=8.30 Hz, 1H), 6.90 (d, J=1.83 Hz, 1H), 6.78 (dd, J=8.22, 1.86 Hz, 1H), 5.13 (s, 2H), 4.09 (br, 1H), 3.76 (s, 3H), 3.32 (br, 1H).

Step 4: ZYJ24 (6.60 g, 16 mmol) was mixed with AcOH-water (200 mL, 6:4). PyHBr$_3$ (5.12 g, 16 mmol) was added in small portions and the mixture was stirred at ambient temperature for overnight. Additional 5 g of PyHBr$_3$ was added and the reaction was heated at 75° C. until conversion completed (>6 h). The reaction mixture was diluted with water (400 mL) and cool with ice-water bath for 15 min. The solid was collected by filtration and washed with cool ether (40 mL) affording the desired product ZYJ25 in 5.90 g. $^1$H NMR (400 MHz, DMSO-d6): 9.04 (s, 1H), 9.02 (s, 1H), 7.54-7.48 (m, 2H), 7.48-7.40 (m, 2H), 7.40-7.36 (m, 1H), 7.36 (s, 1H), 6.91 (s, 1H), 5.15 (s, 2H), 3.72 (s, 3H). ESI-MS calculated for C$_{20}$H$_{16}$$^{79}$Br$_2$NO$_4$ [M+H]$^+$=491.94; Observed: 492.0.

Step 5: ZYJ 25 (5.90 g, 12 mmol) was mixed with t-BuOH (30 mL). EN (4.3 mL, 30 mmol) was added via a syringe, followed by addition of diphenylphosphoryl azide (4.13 mL, 19.2 mmol) via a syringe. The mixture was stirred at ambient temperature for 3 h then heated at reflux for 24 h. The reaction was cooled to ambient temperature for 6 h and diluted with MeOH (200 mL). The solid was collected by filtration to give ZYJ26 in 5.60 g. The mother liquid was concentrated and purified by flash column chromatography to give ZYJ26 in 0.33 g. $^1$H NMR (400 MHz, MeOD-d4): 8.56 (s, 1H), 7.56-7.34 (m, 5H), 7.28 (s, 1H), 6.68 (s, 1H), 5.96 (s, 1H), 5.21 (s, 2H), 3.89 (s, 3H), 1.50 (s, 9H). ESI-MS calculated for C$_{24}$H$_{25}$$^{79}$Br$^{81}$BrN$_2$O$_4$[M+H]$^+$=565.02; Observed: 565.42

Step 6: ZYJ26 (5.93 g, 10.5 mmol) was mixed with anhydrous diglyme (40 mL). NaH (840 mg, 21 mmol, 60% in mineral oil) was added in small portions followed by addition of CuI (3.04 g, 16 mmol). The system was degased and refilled with nitrogen, followed by heating at reflux for 4 h. The reaction was quenched with 50 mL concentrated ammonia and 150 mL water. The solid was collected by filtration and dissolved in $CH_2Cl_2$ (40 mL) and $CF_3CO_2H$ (15 mL) following stirring at ambient temperature for 2 h. The desired product ZYJ27 was collected by filtration as a green solid, which is 4.23 g after drying in high vacuum overnight. $^1H$ NMR (400 MHz, DMSO-d6): 12.32 (s, 1H), 8.03 (s, 1H), 7.56-7.50 (m, 2H), 7.48-7.40 (m, 2H), 7.40-7.36 (m, 1H), 7.35 (s, 1H), 5.31 (s, 2H), 3.92 (s, 3H). ESI-MS calculated for $C_{19}H_{16}{}^{79}BrN_2O_2[M+H]^+$=383.04; Observed: 383.50.

Step 7: ZYJ27 (2.0 g, 4.5 mmol) mixed with anhydrous $CH_2Cl_2$ and the mixture was cooled to −78° C. $BBr_3$ (7.65 mL, 1.0 M in $CH_2Cl_2$) was added via a syringe and the reaction was monitored by HPLC and completed in about 3 h. The reaction was quenched with MeOH (20 mL) at −78° C. and then water was added at room temperature. Solid was collected and washed with diethyl ether to provided ZYJ28 as a solid in 1.41 g. $^1H$ NMR (400 MHz, DMSO-d6): 12.47 (s, 1H), 9.09 (s, 1H), 8.68 (s, 1H), 8.02 (s, 1H), 7.19 (s, 1H), 3.94 (s, 3H). ESI-MS calculated for $C_{12}H_{10}{}^{79}BrN_2O_2$ $[M+H]^+$=292.99; Observed: 292.25.

Step 8: $Pd_2(dba)_3$ (184 mg, 0.2 mmol) and BINAP (248 mg, 0.4 mmol) were mixed in anhydrous 1,4-dioxane (10 mL). The mixture was heated at reflux for 5 minutes. This clear, orange-red color solution was transferred into a round-bottom flask containing ZYJ28 (620 mg, 2.2 mmol), 3-cyclopropyl-1-methyl-1H-pyrazol-5-amine (602 mg, 4.4 mmol), LiHMDS (13.2 mL, 1.0 M in toluene), and anhydrous 1,4-dioxane (20 mL). The mixture was heated at reflux for overnight before quenching with methanol. The reaction mixture was concentrated, filtered, and purified by HPLC to yield ZYJ29 in 340 mg as a $CF_3CO_2H$ salt. $^1H$ NMR (400 MHz, MeOH-d4): 8.65 (s, 1H), 7.84 (s, 1H), 7.15 (s, 1H), 7.06 (s, 1H), 5.65 (s, 1H), 3.88 (s, 3H), 3.87 (s, 3H), 1.95-1.83 (m, 1H), 1.00-0.90 (m, 2H), 0.70-0.62 (m, 2H). ESI-MS calculated for $C_{19}H_{20}N_5O_2$ $[M+H]^+$=350.16; Observed: 350.25.

Step 9: ZYJ29 (287 mg, 0.62 mmol) was dissolved in anhydrous THF (10 mL). NaH (180 mg, 3.0 mmol, 60% in mineral oil) was added in small portions at 0° C. followed by addition of $PhN(Tf)_2$ (428 mg, 1.2 mmol) in one portion. The reaction warmed up to ambient temperature over 4 h before quenching with water. The aqueous layer was extracted with ethyl acetate, the combined organic layers were washed with brine, then dried over anhydrous $Na_2SO_4$. The ethyl acetate was removed on a rotary evaporator and the remaining residues containing ZYJ30 were used for Suzuki coupling without further purification.

Step 10: The crude ZYJ30 and 3,5-dimethyl-4-(4,4,5,5-tetramethyl-1,3,2-dioxaborolan-2-yl)isoxazole (401 mg, 1.8 mmol) were dissolved in DME (9 mL) followed by addition of $Na_2CO_3$ (2 M aqueous, 6 mL). The system was degased followed by addition of $Pd(PPh_3)_4$ (80 mg, 0.06 mmol) and the reaction was heated at reflux for overnight. The aqueous layer was extracted with ethyl acetate, the combined organic layers were washed with brine, then dried over anhydrous $Na_2SO_4$. The ethyl acetate was removed on a rotary evaporator and the remaining residues were purified by reverse phase HPLC to yield Cpd. No. 323 in 60 mg as a salt of $CF_3CO_2H$.

Example 172

Competitive Fluorescence-Polarization (FP) Assays

Fluorescence Polarization (FP) competitive binding studies were carried out using a FAM labeled fluorescent probe (ZBA248 or BRD-1F) to determine binding affinities of representative Compounds of the Disclosure for recombinant BRD4 BD1 and BRD4 BD2 proteins. For example, equilibrium dissociation constants ($K_d$) values of ZBA248 to these six proteins were determined from protein saturation experiments by monitoring the total fluorescence polarization of mixtures composed with the fluorescent probe at a fixed concentration and proteins with increasing concentrations up to full saturation. Serial dilutions of testing protein were mixed with ZBA248 to a final volume of 200 μl in the assay buffer. In order to achieve large dynamic rages, particularly for BD1 bromodomains, 100 mM phosphate buffer (pH=6.5, 0.01% Triton X-100 (Sigma, 282103) being added right before assays) was used as the assay buffer. Final ZBA248 concentration was 1.5 nM for all proteins. Plates were incubated at room temperature for 30 minutes with gentle shaking to assure equilibrium. FP values in millipolarization units (mP) were measured using the Infinite M-1000 plate reader (Tecan U.S., Research Triangle Park, N.C.) in Microfluor 1 96-well, black, round-bottom plates (Thermo Scientific, Waltham, Mass.) at an excitation wavelength of 485 nm and an emission wavelength of 530 nm. IQ values of ZBA248 were calculated by fitting the sigmoidal dose-dependent FP increases as a function of protein concentrations using Graphpad Prism 6.0 software (Graphpad Software, San Diego, Calif.).

The $IC_{50}$ and $K_i$ values of representative Compounds of the Disclosure were determined in a competitive binding experiment as described above. Mixtures of 10 μl of the tested compounds in assay buffer with 40% Ethylene Glycol and 190 μl of preincubated protein/probe complex solution in the assay buffer (100 mM potassium phosphate, pH 6.5, 0.01% Triton X-100) were added into assay plates which were incubated at room temperature for 30 minutes with gentle shaking. Final concentrations of proteins were 10 and 6 nM in assays for BD1 and BD2 of BRD4, respectively. Final probe concentration is 1.5 nM in all assays. Negative controls containing protein/probe complex only (equivalent to 0% inhibition), and positive controls containing only free probes (equivalent to 100% inhibition), were included in each assay plate. FP values were measured as described above. $IC_{50}$ values were determined by nonlinear regression fitting of the competition curves. Instead of being calculated from $IC_{50}$ values as described before, K, values of competitive inhibitors were obtained directly by nonlinear regression fitting as well, based upon the $K_d$ values of the probe to different proteins, and concentrations of the proteins and probes in the competitive assays (Wang, FEBS Lett. 360; 111 (1995); Zhang et al., Analytical Biochemistry, 331; 138 (2004)).

Binding affinities of representative Compounds of the Disclosure to BRD4 BD1 and BRD4 BD2 proteins in competitive, fluorescence-polarization assays are presented in Table 2.

TABLE 2

| | $IC_{50}$ (nM) | |
|---|---|---|
| Cpd. No. | BRD4 BD1 | BRD4 BD2 |
| 1 | na | 21.8 |
| 2 | na | 41.9 |

TABLE 2-continued

| Cpd. No. | IC$_{50}$ (nM) | |
|---|---|---|
| | BRD4 BD1 | BRD4 BD2 |
| 3 | 540 | 183 |
| 4 | 52.9 | 21.7 |
| 5 | 340 | 381 |
| 7 | 365 | 198 |
| 8 | 9.7 | 8.0 |
| 9 | 6.1 | 6.3 |
| 10 | 21.5 | 43.3 |
| 11 | 240 | 235 |
| 12 | na | 28.2 |
| 13 | >1000 | >1000 |
| 14 | 14.6 | 22.6 |
| 15 | 10.1 | 18.8 |
| 16 | 248 | 194 |
| 17 | 16.7 | 82.3 |
| 18 | 211 | 1159 |
| 19 | 200 | 613 |
| 21 | 13.3 | 34.6 |
| 22 | 49.1 | 40.6 |
| 23 | >1000 | >1000 |
| 24 | >1000 | >1000 |
| 25 | >1000 | >1000 |
| 26 | >1000 | >1000 |
| 27 | >1000 | >1000 |
| 29 | >1000 | >1000 |
| 32 | 26.5 | 39.4 |
| 33 | 24.5 | 21.5 |
| 34 | 30.2 | 28.7 |
| 35 | 20.4 | 42.9 |
| 36 | 68.5 | 92.6 |
| 37 | 12.1 | 6.5 |
| 58 | 11 | 22.6 |
| 59 | 90.5 | 174 |
| 63 | 15.7 | 8.6 |
| 65 | 6.1 | 4.1 |
| 76 | 29.4 | 23.7 |
| 77 | 64.4 | 168 |
| 78 | 16 | 63.5 |
| 79 | 9.3 | 1.8 |
| 80 | 6.5 | 18.5 |
| 81 | 5.1 | 19.6 |
| 82 | 4.6 | 3.3 |
| 95 | >1000 | >1000 |
| 96 | 864 | 379 |
| 97 | 34 | 8 |
| 98 | 76 | 13 |
| 99 | 47 | 87 |
| 100 | 99 | 89 |
| 101 | 978 | 786 |
| 102 | 18 | 17 |
| 103 | 29 | 38 |
| 104 | >1000 | 810 |
| 105 | >1000 | 868 |
| 106 | 1414 | 619 |
| 107 | 92 | 33 |
| 108 | 58 | 21 |
| 109 | 284 | 253 |
| 110 | 73 | 33 |
| 111 | 312 | 218 |
| 112 | 460 | 395 |
| 113 | 582 | 564 |
| 115 | 23.2 | 136 |
| 116 | 14 | 9.6 |
| 117 | 62.4 | na |
| 118 | 4.2 | 3.4 |
| 119 | 11.4 | 10.6 |
| 120 | 9.6 | 5.8 |
| 121 | 1.6 | 3.2 |
| 122 | 4.3 | 2.3 |
| 123 | 257 | 483 |
| 124 | 5 | 29.5 |
| 125 | 4.4 | 2 |
| 126 | 11 | 32.8 |
| 127 | 24.5, 55 | 133, >1000 |
| 129 | 105 | 202 |
| 131 | 9.6 | 51.4 |
| 132 | 68.6 | 718 |

TABLE 2-continued

| Cpd. No. | IC$_{50}$ (nM) | |
|---|---|---|
| | BRD4 BD1 | BRD4 BD2 |
| 133 | >1000 | >1000 |
| 134 | 40.2 | 30.5 |
| 135 | 5.6 | 1.3 |
| 136 | 10.5 | 6.9 |
| 137 | 4.5 | 1.2 |
| 138 | 4.2 | 1.2 |
| 139 | 16.3 | 16.5 |
| 140 | 39.3 | 95 |
| 141 | 4.6 | 1.1 |
| 142 | 4.5 | 0.5 |
| 143 | 27.9 | 57.7 |
| 144 | 2.1 | 0.7 |
| 145 | 18.9 | 56.9 |
| 146 | 13.7 | 7.7 |
| 147 | 59.9 | 93.7 |
| 148 | 7.9 | 5 |
| 149 | 6.8 | 5.4 |
| 150 | 9.6 | 7.2 |
| 152 | 10.6 | 5.6 |
| 160 | 14.1 | na |
| 163 | 8.8 | na |
| 166 | 119 | 161 |
| 169 | 14.3 | 23 |
| 170 | 44.9 | 56.5 |
| 171 | 153 | 79.5 |
| 172 | 57.2 | 49.5 |
| 173 | 31.7 | 25.1 |
| 174 | 142 | 117 |
| 175 | 28.7 | 6.9 |
| 176 | 13.7 | 10.3 |
| 177 | 7.9 | 13.2 |
| 178 | 9 | 0.6 |
| 179 | 166 | 116 |
| 181 | 4.4 | 10.2 |
| 182 | 15.6 | 23.6 |
| 183 | 9.6 | 6.1 |
| 185 | 4.9 | 12.3 |
| 186 | 33.9 | 55.1 |
| 187 | 10.5 | 10.9 |
| 188 | 2.1 | 3.7 |
| 192 | 30.1 | 114 |
| 193 | 3.6 | 2.7 |
| 194 | 10.1 | 14.2 |
| 195 | 16.6 | 14.4 |
| 196 | 10 | 7.5 |
| 197 | 70.1 | 69.9 |
| 198 | 6.9 | 3.6 |
| 199 | 13.3 | 14.5 |
| 200 | 10.9 | 5.9 |
| 206 | 5.6 | na |
| 207 | 2.9 | 1.3 |
| 210 | >1000.0 | >1000.0 |
| 211 | 16 | 17 |
| 212 | 18 | 8 |
| 213 | 54 | 28 |
| 214 | 855 | 348 |
| 215 | 128 | 57 |
| 216 | 19 | 35 |
| 217 | 165 | 68 |
| 218 | 17 | 15 |
| 219 | 219 | 365 |
| 220 | 17 | 9 |
| 221 | 49 | 57 |
| 222 | 183 | 276 |
| 223 | 47 | 55 |
| 224 | 105 | 33 |
| 225 | 213 | 108 |
| 226 | 21 | 20 |
| 227 | 14 | 22 |
| 228 | 25 | 26 |
| 229 | 24 | 22 |
| 230 | 13 | 8 |
| 231 | 35 | 44 |
| 232 | 29 | 52 |
| 233 | 69 | 38 |
| 234 | 25 | 25 |

TABLE 2-continued

| Cpd. No. | IC$_{50}$ (nM) BRD4 BD1 | BRD4 BD2 |
|---|---|---|
| 235 | 41 | 52 |
| 236 | 14 | 59 |
| 237 | 10 | 5 |
| 238 | 5 | 3 |
| 239 | 19 | 28 |
| 240 | 13 | 20 |
| 241 | 16 | 29 |
| 242 | 9 | 12 |
| 243 | 15 | 14 |
| 247 | 165 | 121 |
| 248 | 70 | 79 |
| 249 | 29 | 99 |
| 250 | 12 | 14 |
| 251 | 9 | 5.5 |
| 255 | 10.5 | 8.5 |
| 258 | 8.1 | 2.8 |
| 266 | 10.3 | 3.1 |
| 269 | 21.9 | 35.1 |

Binding affinities to BRD2 BD1 and BD2, BRD3 BD1 and BD2, and BRD4 BD1 and BD2 can also be determined by a label free binding assay using the OctetRED label free biolayer interferometry (BLI) binding assay.

Example 173

Cell Growth Inhibition

Cell growth inhibitory activity of representative Compounds of the Disclosure was determined using CellTiter-Glo® Luminescent Cell Viability Assay. For leukemia cell lines MV-4-11 (ATCC, Manassas, Va.) and MOLM-13 (DSMZ, Germany), cells were seeded in 96-well white opaque cell culture plates at a density of 10,000 cells/well with serially diluted compounds and incubated at 37° C. in an atmosphere of 95% air and 5% CO2 for 4 days. Cell viability was determined using the CellTiter-Glo® Luminescent Cell Viability Assay Kit (Promega, Madison, Wis.) according to the manufacture's instruction. Briefly, a volume of CellTiter-Glo® Reagent equal to the volume of cell culture medium was added to each well, and then the plates were incubated at room temperature for 10-20 minutes. The luminescent signal was measured using a Tecan Infinite M1000 multimode microplate reader (Tecan, Morrisville, N.C.). The half maximal inhibitory concentration (IC50) was calculated using the GraphPad Prism 5 software (GraphPad Software, La Jolla, Calif.).

For breast cancer cell lines, cells were seeded in 96-well cell culture plates at a density of 5,000-10,000 cells/well with serially diluted compounds and incubated at 37° C. in an atmosphere of 95% air and 5% CO2 for 4 days. All the breast cancer cell lines were obtained from the ATCC. Cell viability was determined using the WST-8 (2-(2-methoxy-4-nitrophenyl)-3-(4-nitrophenyl)-5-(2,4-disulfophenyl)-2H-tetrazolium, monosodium salt) based Cell Counting-8 Kit (Dojindo Molecular Technologies, Inc., Rockville, Md.) according to the manufacture's instruction. Briefly, WST-8 was added to each well at a final concentration of 10% (v/v), and then the plates were incubated at 37° C. for 1-2 hours for color development. The absorbance was measured at 450 nm using a SPECTRAmax PLUS plate reader (Molecular Devices, Sunnyvale, Calif.). The IC$_{50}$ was calculated using the GraphPad Prism 5 software.

For prostate cancer cell lines, VCaP prostate cancer cells were grown in DMEM with Glutamax (Gibco) supplemented with 10% FBS (Invitrogen) in 5% CO2 cell culture incubator. All cell lines were tested and found to be free of mycoplasma contamination. Cells were seeded in 96-well plates at 2,000-10,000 cells per well (optimum density for growth) in a total volume of 100 ml media containing 10% FBS. Serially diluted compounds in 100 ml media were added to the cells 12 h later. After 96 h incubation, cell viability was assessed by Cell-Titer GLO (Promega). The values were normalized and IC$_{50}$ was calculated using GraphPad Prism software.

Cell growth inhibition of representative Compounds of the Disclosure in MOLM13 leukemia and MDA-MB-436 breast cancer cell lines are presented in Table 3, and in VCaP prostate cancer cell lines presented in Table 4.

TABLE 3

| | IC$_{50}$ (nM) | |
|---|---|---|
| Cpd. No. | MOLM-13 Cell Line (CellTiter-Glo assay) | MDA-MB-436 Cell Line (WST assay) |
| 1 | 29.8 | 148.0 |
| 2 | 68.0 | 246.0 |
| 3 | 38.4 | 386 |
| 4 | 69.3 | 249 |
| 5 | 475 | 719 |
| 6 | 52.6 | 1522.0 |
| 7 | 56.3 | 142.0 |
| 8 | 10.3 | 55.1 |
| 9 | 5.0 | 29.6 |
| 10 | 45.6 | 138 |
| 11 | 23.9 | 398.0 |
| 12 | 15.2 | 59.6 |
| 13 | 107.8 | 1077.0 |
| 14 | 23.7 | 83.3 |
| 15 | 5.1 | 33.7 |
| 16 | 14.6 | 529.0 |
| 17 | 28.4 | 51.0 |
| 18 | 86.2 | 140.6 |
| 19 | 108.6 | 323.3 |
| 21 | 21.9 | 52.7 |
| 22 | 77.5 | 84.8 |
| 29 | 82.1 | 1106.0 |
| 32 | 40.9 | 155.2 |
| 33 | 2419.0 | 302.7 |
| 34 | 32.7 | 97.6 |
| 35 | 38.9 | 88.9 |
| 36 | 103.3 | 236.2 |
| 37 | 54.1 | 56.2 |
| 58 | 32.0 | 54.6 |
| 59 | 401.0 | 535.0 |
| 63 | 22.8 | 46.1 |
| 65 | 11.7 | 26.0 |
| 76 | 117.1 | 155.9 |
| 77 | 242.1 | 350.6 |
| 78 | 97.4 | 271.0 |
| 79 | 43.9 | 121.3 |
| 80 | 26.1 | 55.2 |
| 81 | 22.9 | 67.0 |
| 82 | 10.5 | 13.8 |
| 97 | 43.0 | 180.0 |
| 98 | 171.0 | 380.0 |
| 99 | 206.0 | 307.0 |
| 100 | 147.0 | 235.0 |
| 101 | 266.0 | 811.0 |
| 102 | 510.0 | 363.0 |
| 103 | 39.0 | 120.0 |
| 104 | 603 | 3.4 |
| 105 | 371 | 885 |
| 106 | 56.0 | 618.0 |
| 107 | 8.0 | 229.0 |
| 108 | 19.0 | 181.0 |
| 109 | 12.0 | 679.0 |
| 110 | 16.0 | 354.0 |
| 111 | 7.0 | 1100.0 |
| 112 | 15050.0 | 2429.0 |
| 113 | 853.0 | 1100.0 |

TABLE 3-continued

| Cpd. No. | MOLM-13 Cell Line (CellTiter-Glo assay) IC$_{50}$ (nM) | MDA-MB-436 Cell Line (WST assay) IC$_{50}$ (nM) |
|---|---|---|
| 115 | 30.7 | 81.1 |
| 116 | 15.4 | 26.3 |
| 117 | 90.9 | 177.0 |
| 118 | 17.7 | 25.0 |
| 119 | 38.8 | 26.0 |
| 120 | 23.0 | 23.5 |
| 121 | 11.7 | 11.2 |
| 122 | 6.0 | 7.8 |
| 123 | 759.0 | 1420.0 |
| 124 | 41.9 | 58.3 |
| 125 | 11.3 | 17.5 |
| 126 | 65.3 | 140.0 |
| 127 | 178.0 | 508.0 |
| 129 | 144.0 | 201.0 |
| 131 | 32.7 | 97.6 |
| 132 | 97.5 | 224.0 |
| 133 | 433.0 | 47870.0 |
| 134 | 32.0 | 128.0 |
| 135 | 30.2 | 57.6 |
| 136 | 26.6 | 63.2 |
| 137 | 4.3 | 11.3 |
| 138 | 5.7 | 30.3 |
| 139 | 49.2 | 110.2 |
| 140 | 120.0 | 210.0 |
| 141 | 1.6 | 13.6 |
| 142 | 1.1 | 7.3 |
| 143 | 98.0 | 175.0 |
| 144 | 3.0 | 14.5 |
| 145 | 69.5 | 170.0 |
| 146 | 26.0 | 39.2 |
| 147 | 201.0 | 319.0 |
| 148 | 3.4 | 20.4 |
| 149 | 7.2 | 14.2 |
| 150 | 7.2 | 29.8 |
| 152 | 19.0 | 34.0 |
| 166 | 503.5 | 1425.0 |
| 169 | 63.3 | 93.9 |
| 170 | 131.2 | 222.0 |
| 171 | 609.0 | 1533.0 |
| 172 | 453.2 | 634.0 |
| 173 | 121.3 | 197.6 |
| 174 | 108.2 | 118.0 |
| 175 | 40.5 | 71.0 |
| 176 | 52.9 | 83.3 |
| 177 | 78.6 | 109.6 |
| 178 | 22.5 | 52.9 |
| 179 | 2083.0 | 329.5 |
| 181 | 22.2 | 22.9 |
| 182 | 34.8 | 98.0 |
| 183 | 29.7 | 83.7 |
| 185 | 17.0 | 71.0 |
| 186 | 27.1 | 132.3 |
| 187 | 38.8 | 121.4 |
| 188 | 3.2 | 12.8 |
| 192 | 114.0 | 422.0 |
| 193 | 8.1 | 47.5 |
| 194 | 13.2 | 59.6 |
| 195 | 29.1 | 75.1 |
| 196 | 32.7 | 52.5 |
| 197 | 357.0 | 511.0 |
| 198 | 25.7 | 58.7 |
| 199 | 30.5 | 67.9 |
| 200 | 25.4 | 40.0 |
| 210 | 1130.0 | na |
| 211 | 76.0 | 57.0 |
| 212 | 103.0 | 112.0 |
| 213 | 103.0 | 211.0 |
| 214 | 208.0 | 249.0 |
| 215 | 318.0 | 360.0 |
| 216 | 220.0 | 292.0 |
| 217 | 498.0 | 1930.0 |
| 218 | 9340.0 | na |
| 219 | 912.0 | 849.0 |
| 220 | 37.0 | 72.0 |
| 221 | 189.0 | 209.0 |
| 222 | 629.0 | 731.0 |
| 223 | 115.0 | 152.0 |
| 224 | 192.0 | 740.0 |
| 225 | 189.0 | 315.0 |
| 226 | 94.0 | 91.0 |
| 227 | 31.0 | 62.0 |
| 228 | 87.0 | 129.0 |
| 229 | 69.0 | 88.0 |
| 230 | 71.0 | 123.0 |
| 231 | 28.0 | 79.0 |
| 232 | 62.0 | 238.0 |
| 233 | 101.0 | 222.0 |
| 234 | 34.0 | 139.0 |
| 235 | 74.0 | 146.0 |
| 236 | 49.0 | 117.0 |
| 237 | 41.0 | 72.0 |
| 238 | 39.0 | 61.0 |
| 239 | 22.0 | 43.0 |
| 240 | 20.0 | 46.0 |
| 241 | 33.0 | 76.0 |
| 242 | 24.0 | 47.0 |
| 243 | 61.0 | 162.0 |
| 247 | 113.0 | 115.0 |
| 249 | 159.0 | 302.0 |
| 250 | 21.0 | 67.0 |
| 251 | 11.0 | 23.0 |
| 255 | 12.0 | 26.0 |
| 269 | 97.4 | 154.4 |

TABLE 4

| Cpd. No. | VCaP Cell Line (CellTiter-Glo assay) IC$_{50}$ (nM) |
|---|---|
| 137 | 23.4 |
| 141 | 19.3 |
| 144 | 53.8 |
| 185 | 64.7 |

Additional biological data from the assays described above are provided in Table 5.

TABLE 5

| Cpd. No. | Binding affinities (FP) BRD4BD1 IC50 (nM) | BRD4BD1 K$_i$ (nM) | BRD4BD2 IC50 (nM) | BRD4BD2 K$_i$ (nM) | Cellular data (nM) MDA-MB-436 IC$_{50}$ (nM) | LNCaP IC$_{50}$ (nM) |
|---|---|---|---|---|---|---|
| 281 | 6.1 | 2.0 | 3.6 | 5.7 | 351 | 116 |
| 282 | 6.1 | 1.3 | 0.5 | 1.0 | 33 | 22 |
| 283 | 4.5 | 0.6 | 5.0 | 0.9 | 19 | 12 |
| 284 | 10 | 3.0 | 10.6 | 2.6 | 268 | 105 |
| 285 | 18.9 | 3.7 | 9.8 | 2.1 | | |
| 286 | 28.7 | 5.1 | 18.5 | 4.6 | | |
| 287 | 3.1 | <1 | 1.4 | <1 | 58 | 81 |
| 288 | 4.9 | <1 | 1.6 | <1 | 13 | 37 |
| 289 | 2.4 | <1 | 2.2 | <1 | 57 | 130 |
| 290 | 4.8 | <1 | 4.5 | <1 | 19 | 12 |
| 291 | 5.2 | 1.5 | 4.9 | 1.0 | 37 | 20 |
| 292 | 2.0 | <1 | 2.3 | <1 | 12 | 7 |
| 304 | 63 | 15 | 318 | 94 | N/A | N/A |
| 305 | >5000 | N/A | 850 | 342 | 1193 | 1165 |
| 306 | 129 | 30 | 43 | 10 | 67 | 534 |
| 307 | 16 | 3.8 | 18 | 4.3 | 130 | 59 |
| 308 | 23 | 5.0 | 25 | 5.3 | 181 | 106 |

TABLE 5-continued

| | Binding affinities (FP) | | | | Cellular data (nM) | |
| --- | --- | --- | --- | --- | --- | --- |
| | BRD4BD1 | | BRD4BD2 | | MDA-MB-436 | LNCaP |
| Cpd. No. | IC50 (nM) | $K_i$ (nM) | IC50 (nM) | $K_i$ (nM) | $IC_{50}$ (nM) | $IC_{50}$ (nM) |
| 309 | 18 | 4.1 | 40 | 13 | 141 | 136 |
| 310 | 378 | 143 | 313 | 113 | 1280 | N/A |
| 311 | 1087 | 602 | >1000 | N/A | 1100 | N/A |
| 312 | 378 | 140 | 346 | 101 | 1055 | N/A |
| 313 | 4067 | 1198 | 4073 | 1144 | >2000 | N/A |
| 314 | 457 | 146 | 986 | 209 | >2000 | N/A |
| 315 | 28 | 7.8 | 16 | 4.7 | 164 | N/A |
| 316 | 317 | 106 | 311 | 106 | 1018 | N/A |
| 317 | 74 | 27 | 139 | 44 | 1138 | N/A |
| 318 | 35 | 12 | 108 | 34 | 299 | N/A |
| 319 | 102 | 38 | 92 | 27 | 646 | N/A |
| 320 | 10.2 | 1.8 | 7 | 1.3 | 85 | N/A |
| 321 | 482 | 171 | 796 | 239 | 4428 | N/A |
| 322 | 199 | 68 | 214 | 67 | 646 | 674 |
| 323 | 11.8 | 1.6 | 5.9 | 1.2 | 15 | 21 |

Example 174

AR Signaling is Blocked by BET Bromodomain Inhibitors

Figure 3:
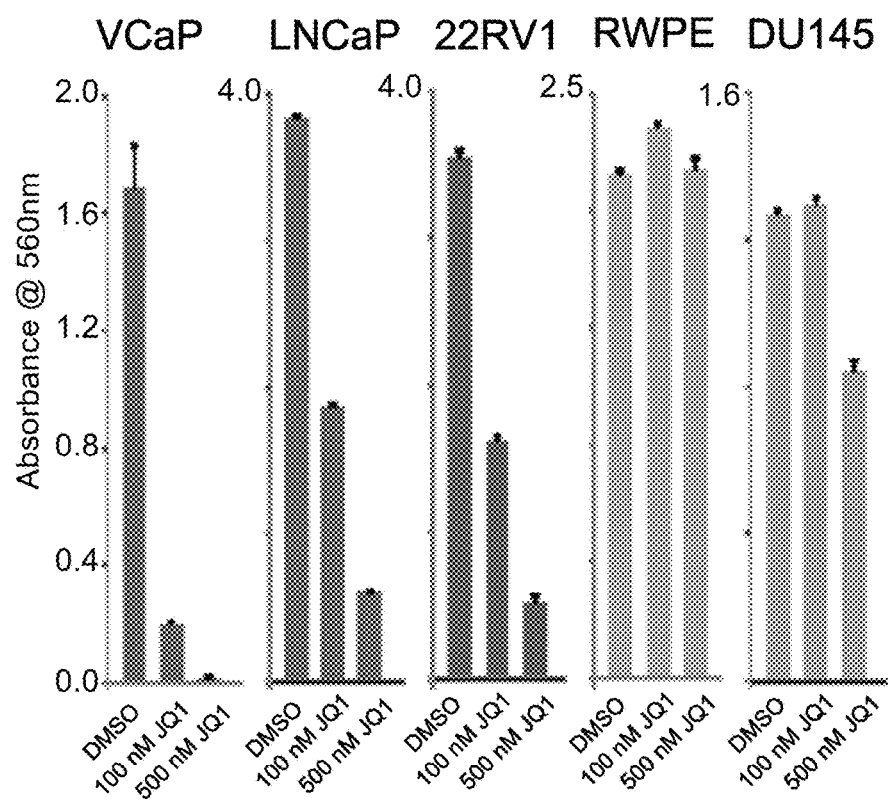
FIG. 3 is a bar graph showing colony formation assays of prostate cell lines. Cells were cultured in the presence or absence of 100 and 500 nM of JQ1 for 12 days, followed by staining and quantification.
Figure 4:
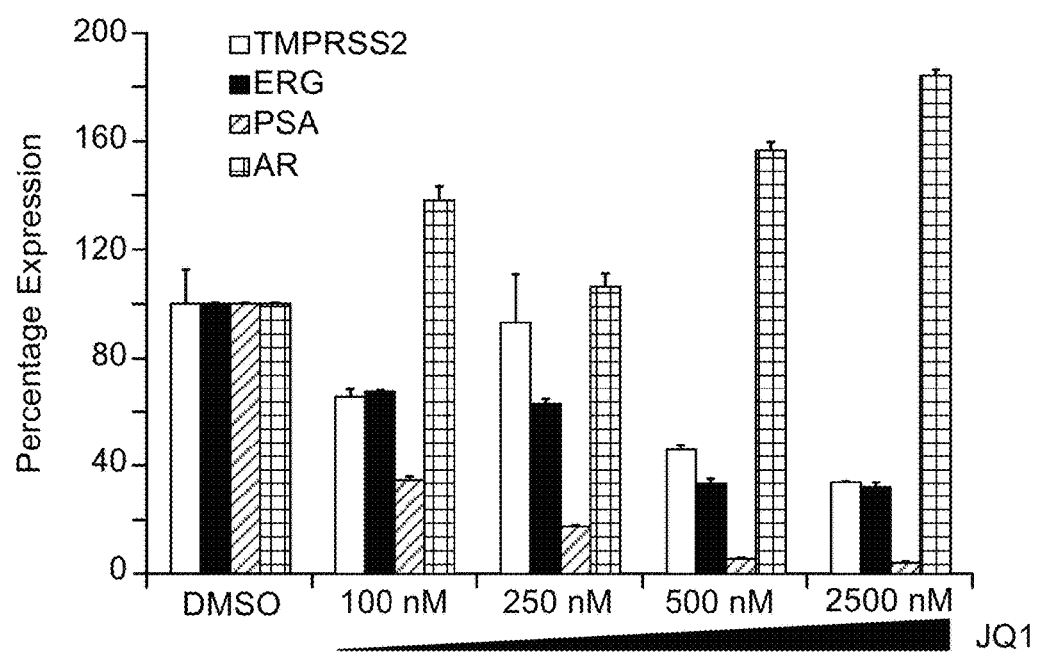
FIG. 4 is a bar graph showing QRT-PCR analysis of indicated genes in VCaP treated with different concentrations of JQ1 for 24 h.
Figure 5:
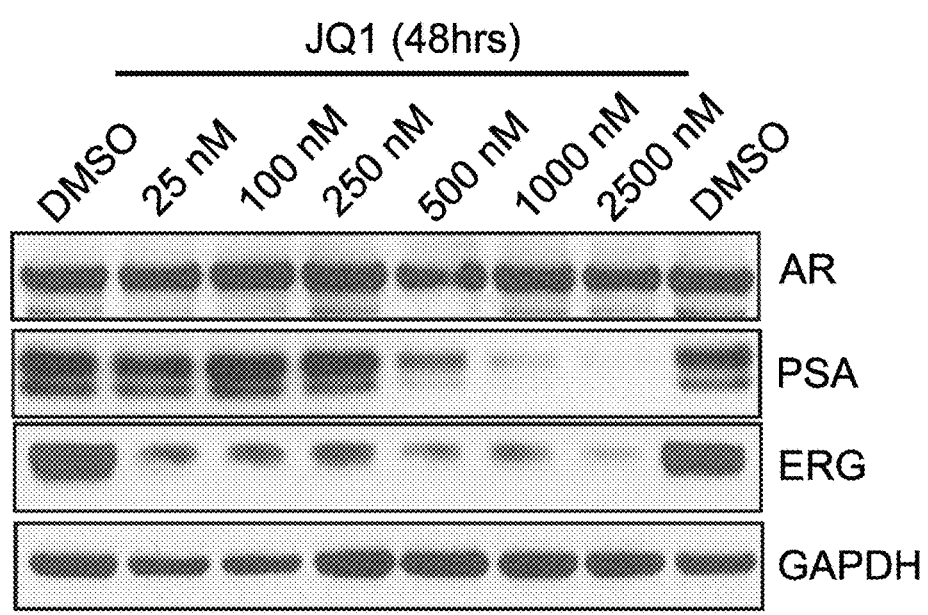
FIG. 5 is an illustration showing immunoblot analyses of AR, PSA and ERG levels in VCaP treated with JQ1.
Figure 6:
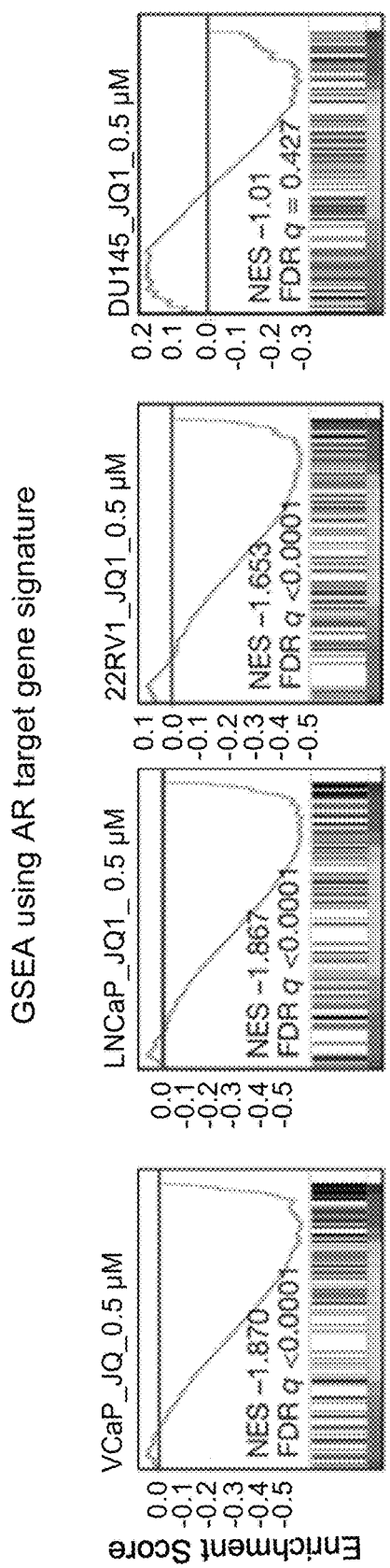
FIG. 6 is four illustrations showing GSEA of the AR target gene signature in VCaP, LNCaP, 22RV1, and DU145 cells. NS, not-significant, *P≤0.05, **P≤0.005 by t-test.

A panel of 5 prostate cancer and 1 benign prostate cell line was treated with the JQ1. Three of the AR-signaling positive cells were found to be sensitive to JQ1, though all six cell lines express high levels of its target proteins (FIG. 1). Next, knockdown of BRD2/3/4 (data not shown) showed significant inhibition of cell proliferation/invasion, phenocopying JQ1-treatment (data not shown). Further, JQ1-treatment induced $G_0$-$G_1$ arrest, apoptosis and associated transcriptional downregulation of the anti-apoptotic BCL-x1 protein in AR-positive cells (FIG. 2) (Filippakopoulos, P. et al., Nature 468:1067-1073 (2010); Mertz, J. A. et al., Proc Natl Acad Sci USA 108:16669-16674 (2011)). Similar to BCL2 down-regulation by the BET-inhibitor, I-BET151, in leukemia (Dawson, M. A. et al., Nature 478:529-533 (2011)); reduction in BCL-x1 by JQ1 could in part be explained by the observation of loss of BRD2/3/4 recruitment to its promoter region (data not shown). Even at 100 nM, long term colony-formation of AR-positive cells were severely inhibited with JQ1 (FIG. 3) with no apparent effect on JQ1 target proteins (data not shown). As AR-positive cells were preferentially sensitive to JQ1, it was examined whether JQ1 has an effect on AR-target genes. VCaP cells, which harbor the TMPRSS2-ERG gene fusion and AR amplification (Tomlins, S. A. et al., Science 310:644-648 (2005)), displayed a dose-dependent decrease in PSA and ERG-both at the mRNA and protein level (FIGS. 4 and 5). Similar effects of JQ1-treatment were seen in LNCaP and 22RV1 cells (data not shown). Furthermore, bortezomib did not reverse the JQ1-mediated PSA and ERG protein loss, indicating that these genes are regulated at the transcriptional level (data not shown). Microarray analysis was performed to examine changes in global gene expression upon JQ1-treatment. Gene Set Enrichment Analysis (GSEA) using the AR-gene signature (Table 6), revealed these genes were significantly repressed in AR-positive cells (FIG. 6) suggesting BET-protein regulation of AR-mediated transcription. Additionally, a loss of the MYC associated gene signature was observed in AR-positive cell lines upon JQ1-treatment (Table 7). MYC is a known transcriptional target of BET-inhibition in hematological cancers (Delmore, J. E. et al., Cell 146:904-917 (2011); Mertz, J. A. et al., Proc Natl Acad Sci USA 108:16669-16674 (2011)). MYC levels were attenuated by JQ1 in cells which are AR-positive and sensitive to JQ1 inhibition, but not in AR-negative cells (data not shown). Thus, high expression of MYC per se (data not shown) does not confer sensitivity to JQ1 in prostate cancer cells. Time-course experiments with JQ1 demonstrated loss of MYC (data not shown), and cyclohexamide had no additional effect on MYC protein (data not shown), ruling out a post-translational mode of JQ1 action on MYC proteins. Phenotypically, knockdown of MYC did not affect cell invasion (data not shown), while JQ1-treatment inhibited invasion (data not shown). Additionally, exogenous expression of MYC did not result in a rescue of JQ1-mediated inhibition of cell growth (data not shown). Thus, while MYC levels may be repressed by JQ1 in AR-positive cells, and may have a role in proliferation, MYC does not appear to be the primary target for the anti-neoplastic effects of JQ1.

Figure 7:
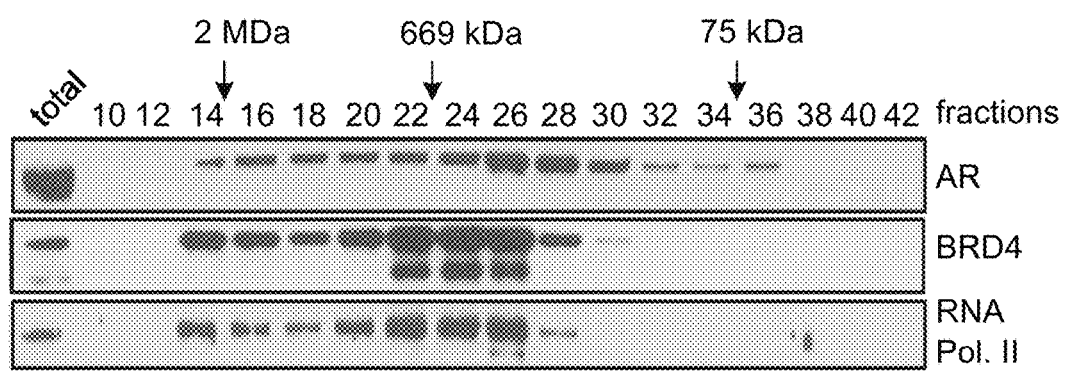
FIG. 7 is an illustration showing VCaP nuclear extracts fractionated on a Superose-6 column and AR, BRD4 and RNA PolII and analysis by immunoblotting.
Figure 8:
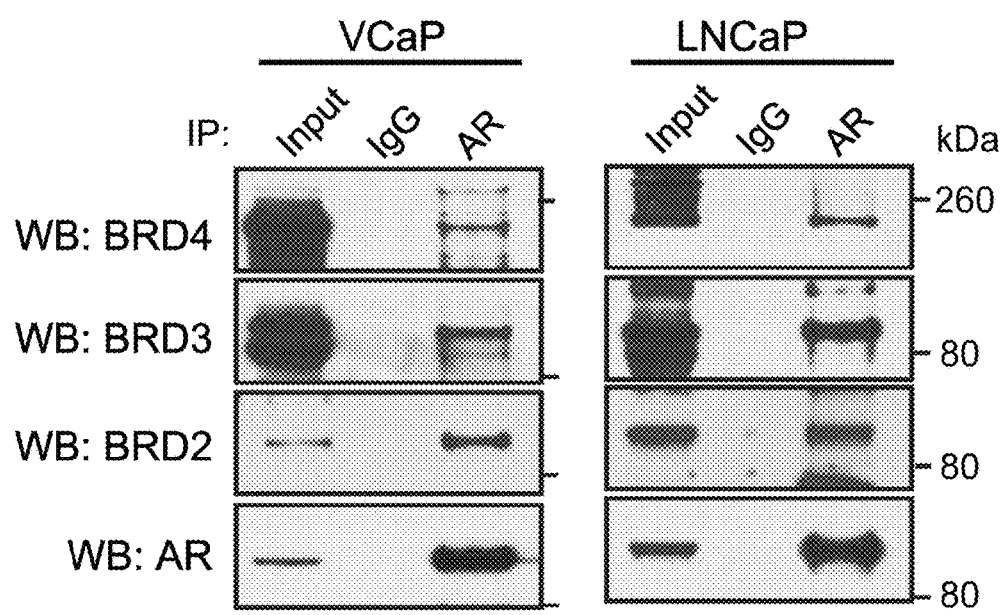
FIG. 8 is two illustrations showing endogenous association of AR and BRD2/3/4. VCaP and LNCaP nuclear extracts were subjected to immunoprecipation using an anti-AR antibody. Immunoprecipitates were analyzed for the presence of BRD2/3/4 by immunoblotting (upper panel). The immunoblot was stripped and reprobed for AR (lower panel). 5% total lysate was used as input control.
Figure 9:
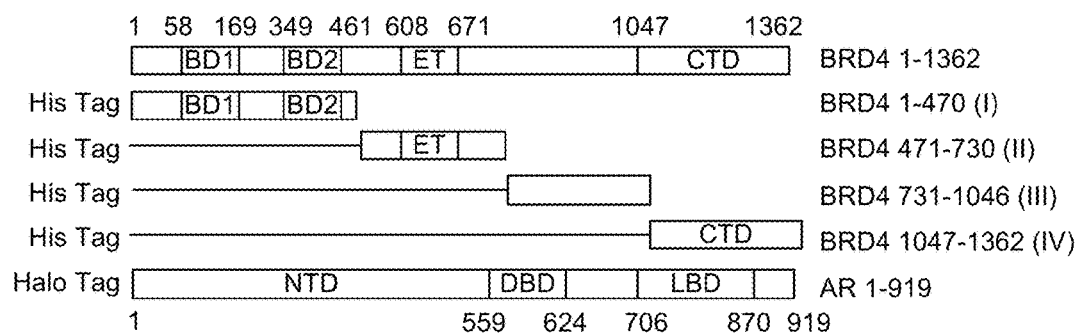
FIG. 9 is a schematic of BRD4 and AR constructs used for co-immunoprecipitation experiments (BD1, bromodomain 1; BD2, bromodomain 2; ET, Extraterminal domain. CTD; C-terminal domain; NTD, N-terminal domain; DBD, DNA-binding domain; and LBD, ligand-binding domain).
Figure 10:
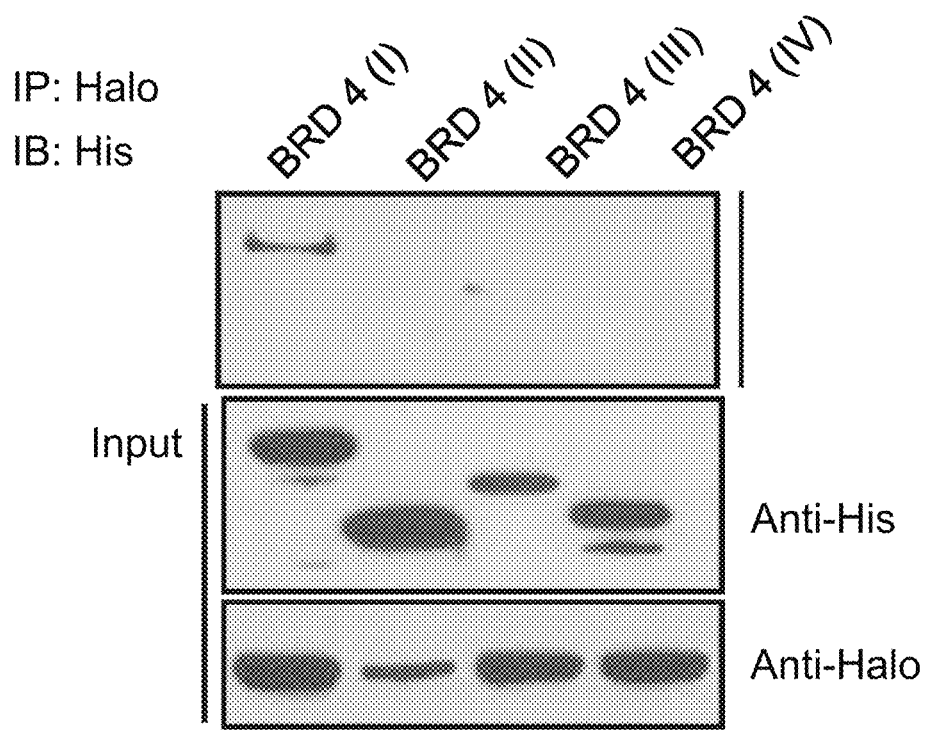
FIG. 10 is an illustration showing the N-terminal domain of BRD4 interacts with AR. Proteins from 293T cells co-transfected with different His-tag-BRD4 deletion and Halo-tag-AR constructs were subjected to immunoprecipitation with Halo-beads followed by immunoblotting with His-tag antibody. Inputs are shown in the bottom panel.
Figure 11:
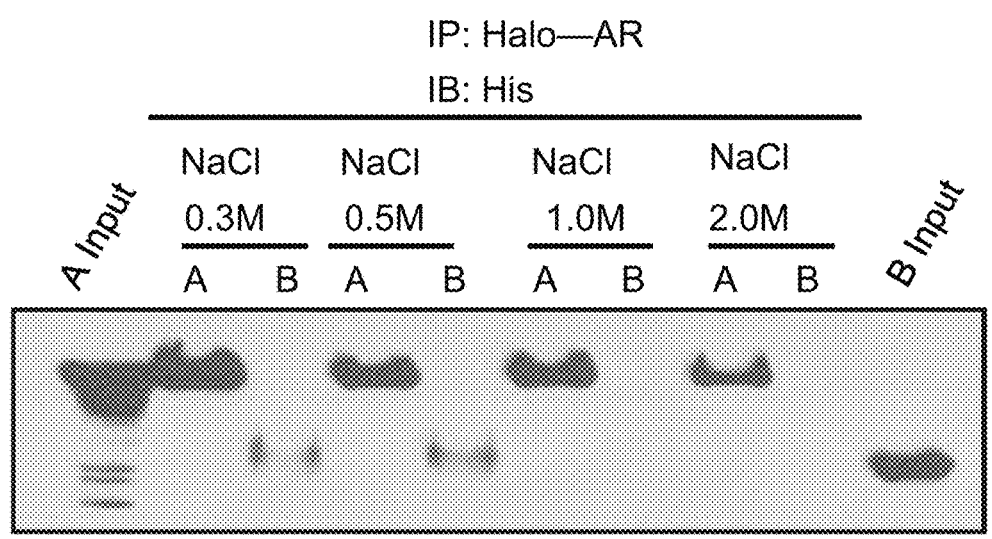
FIG. 11 is an illustration as in FIG. 10 but with the indicated salt concentrations.
Figure 12:
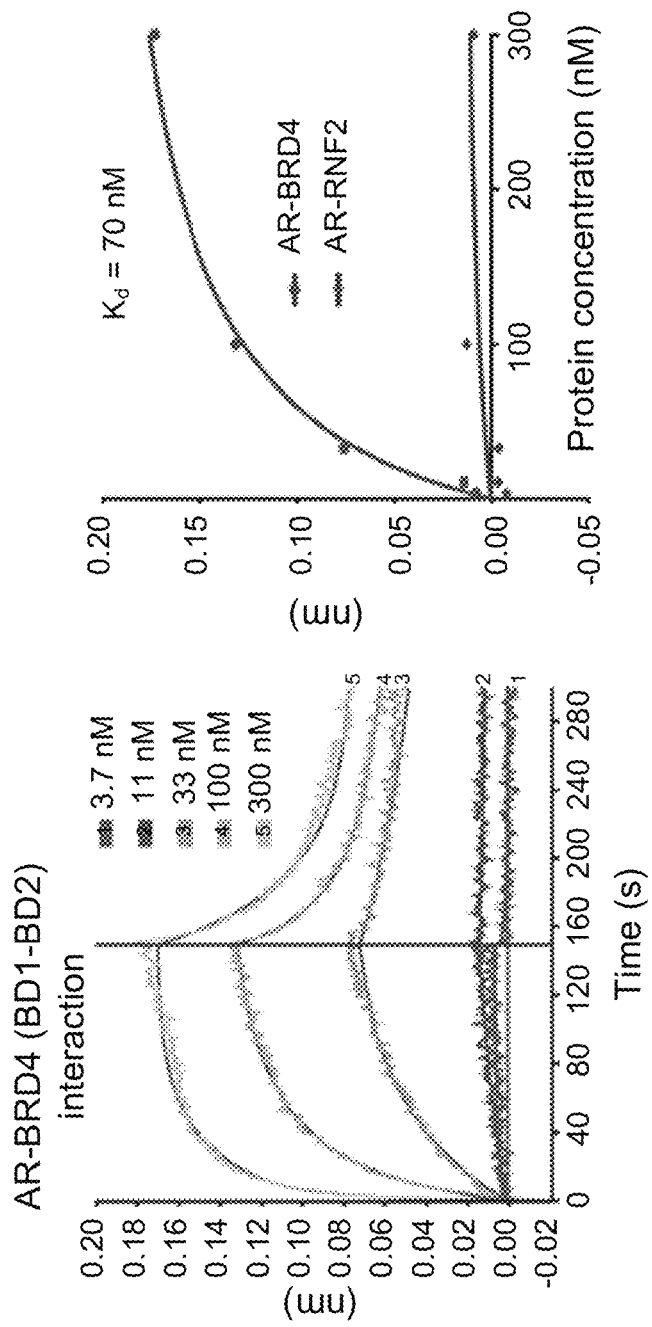
FIG. 12 is an illustration showing representative sensorgrams for AR:BRD4 (BD1-BD2) by an OctetRED biolayer interferometry showing direct interaction. Real-time binding was measured by immobilizing biotinylated AR protein on the super streptavidin biosensor and subsequent interaction with different concentrations of BRD4 (BD1-BD2) protein. The plots show the response versus protein concentration curves derived from the raw binding data. Right, Dissociation constant (Kd) represents the BRD4 (BD1-BD2) concentration yielding half-maximal binding to AR. Protein RNF2 was used as negative control.
Figure 13:
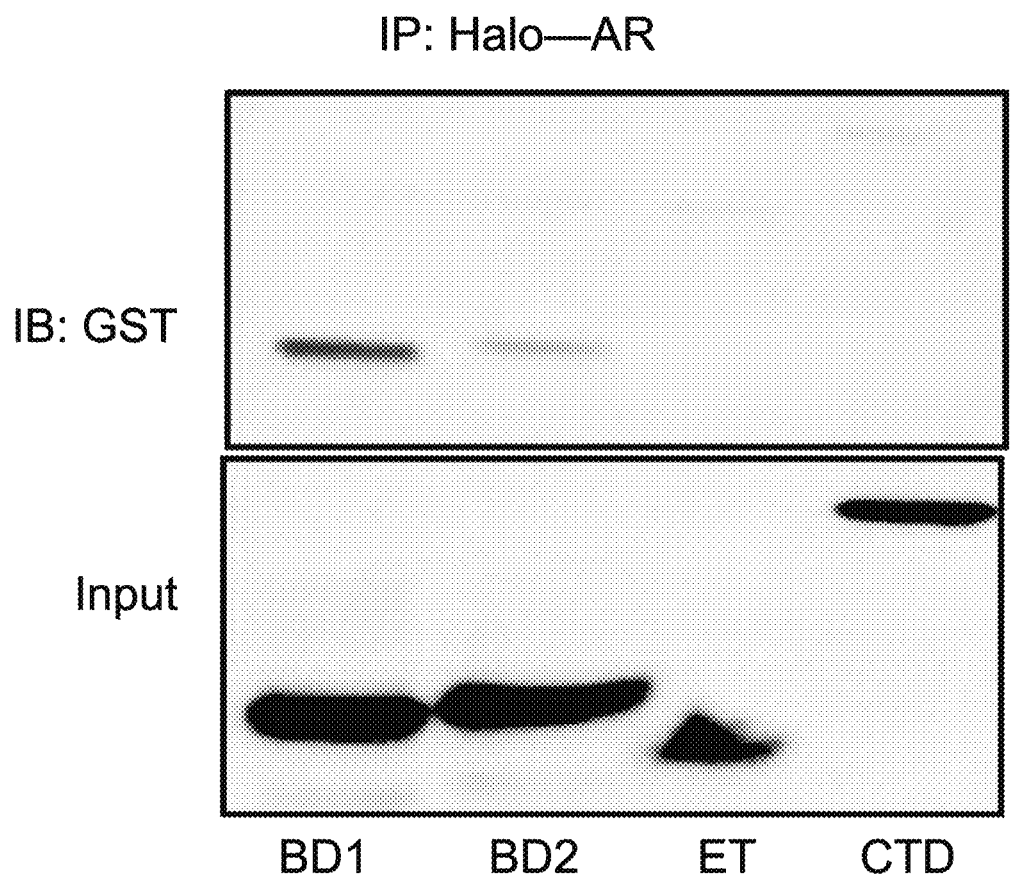
FIG. 13 is an illustration showing in vitro binding analysis of AR and indicated domains of BRD4. Equal amounts of in vitro translated full-length Halo-tag-AR protein and GST-tag-BRD4 domains were combined and immunoprecipitated using Halo beads followed by immunoblot analysis with anti-GST antibody.
Figure 14:
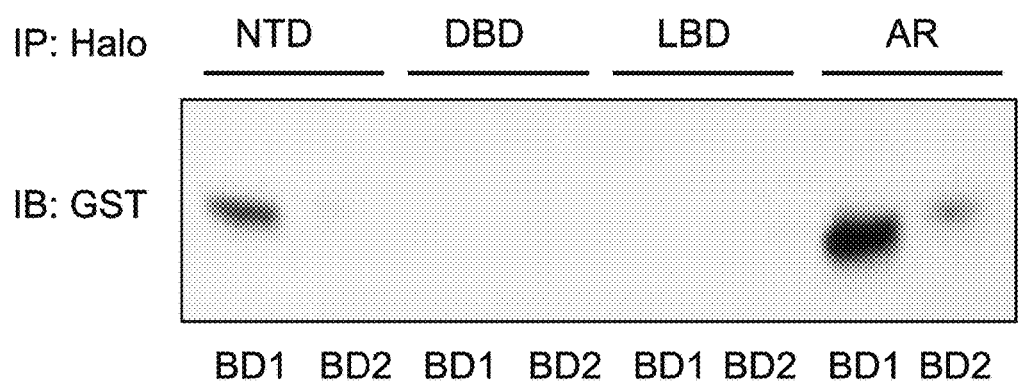
FIG. 14 is an illustration showing the NTD domain of AR interacts with BD1 of BRD4. As in FIG. 8, immunoprecipitation with different domains of Halo-AR followed by immunoblot analysis with anti-GST antibody.
Figure 15:
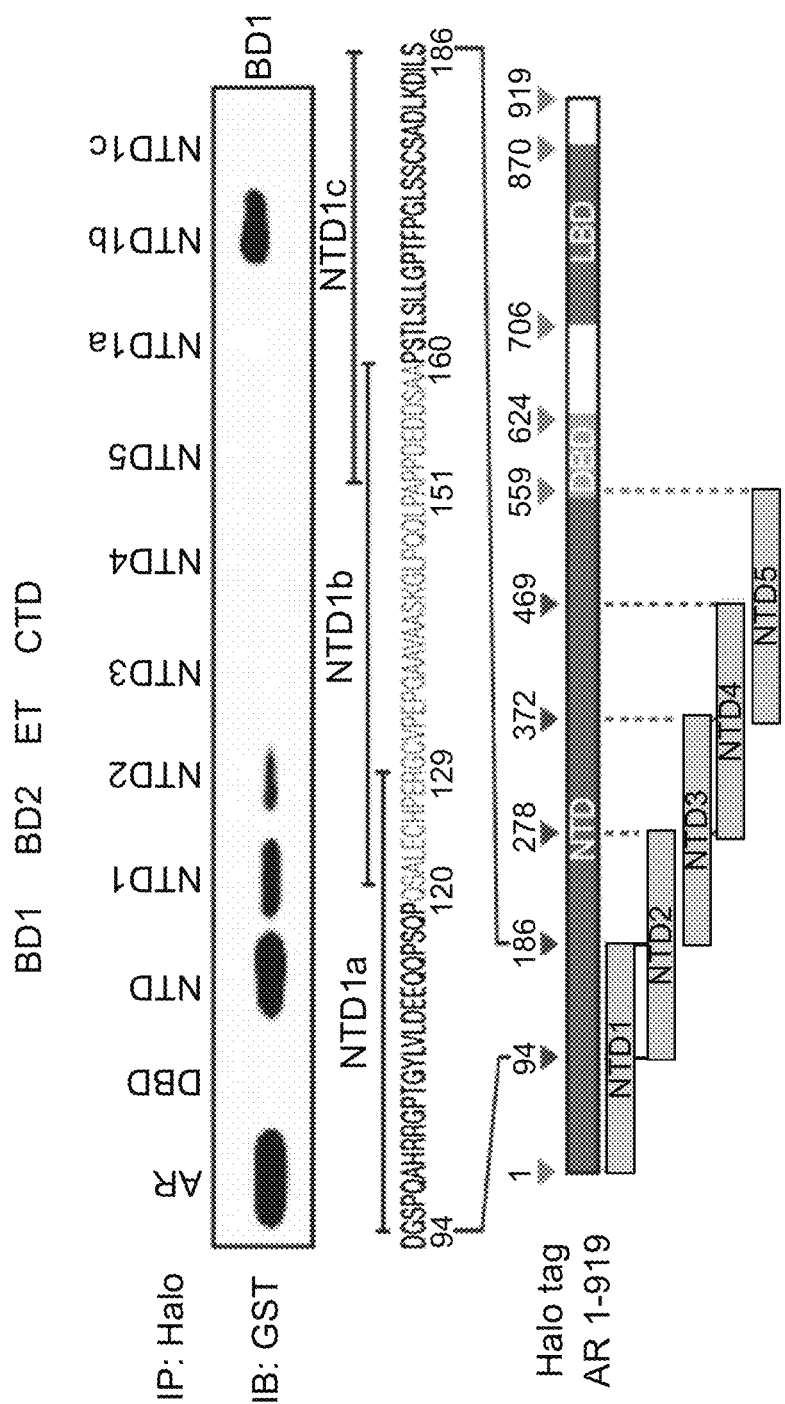
FIG. 15 is an illustration showing the NTD domain of AR interacts with BD1 of BRD4. As in FIG. 8, immunoprecipitation with different domains of Halo-AR followed by immunoblot analysis with anti-GST antibody.
Figure 16:
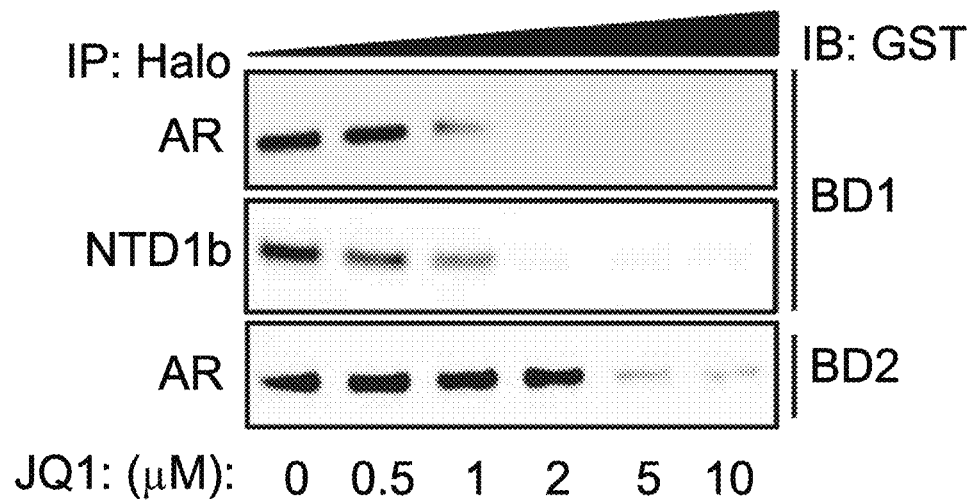
FIG. 16 is an illustration showing JQ1 disrupts AR-BD1 interactions. Varying concentrations of JQ1 were incubated to the AR-BD1, NTD1b-BD1, and AR-BD2 complex prior to immunoprecipitation followed by immunoblot analysis.

JQ1 block or AR target gene transcription (FIGS. 4-6) suggested that AR may interact with BRD4 which is known to engage sequence-specific DNA binding proteins (Wu, S. Y. et al., Mol Cell 49:843-857 (2013)). Gel-filtration-chromatography were performed and it was found that AR and BRD4 predominantly eluted together in a high-molecular weight complex (FIG. 7). Moreover, RNA PolII which was reported as a target for phosphorylation by BRD4 (Devaiah, B. N. et al., Proc Natl Acad Sci USA 109:6927-6932 (2012)) also co-eluted in the same complex, suggestive of the existence of a large multi-protein complex consisting of AR, BRD4 and RNA PolII. Immunoprecipitation experiments further confirmed an endogenous association between AR and BRD4 (FIG. 8). Additionally, an interaction between AR and BRD2/3 (FIG. 8) was observed, implying a common region in BRD2/3/4 proteins responsible for AR interaction. In order to map the region mediating this interaction, the ability of different deletion variants of BRD4 to pull-down AR in 293T cells (FIG. 9) was tested. It was found that truncated version of BRD4 which comprised BD1-BD2 domains maintained the ability to pull-down AR even at high salt concentrations (FIGS. 10 and 11). To determine whether the BD1-BD2 domains directly interact with AR, quantitative assessment of the binding affinity using the Octet-RED system was carried out. Varying concentrations of BD1-BD2 protein were applied to biosensors with immobilized AR, and it was found that BRD4 interacts with AR in a concentration dependent fashion, with an estimated Kd of 70 nM, supporting a high affinity interaction (FIG. 12). This interaction was fine-mapped to create a series of Halo-AR and GST-BRD4 constructs for in vitro pull-down studies that demonstrated that the BD1, and to a lesser extent the BD2, of BRD4 bind directly to NTD-domain of AR, which was further mapped to a 38 amino acid region NTD1b of AR (FIGS. 13-15). Subsequently, the disruption of BD1-AR and BD1-NTD1b interactions by JQ1 (FIG. 16) was observed. Likewise, JQ1 treated VCaP displayed loss of the endogenous BRD4-AR interaction (data not shown). Together, these data suggest that BET protein inhibition leads to disruption of the AR-BRD4 interaction and may account for the preferential activity of JQ1 in AR-positive prostate cancer cells.

Ubiquitously expressed BRD2/3/4 proteins are suggested to have overlapping functions (Dawson, M. A. et al., Nature 478:529-533 (2011); Filippakopoulos, P. et al., Nature 468: 1067-1073 (2010); Belkina, A. C. and Denis, G. V., Nat Rev Cancer 12:465-477 (2012) and consistent with this, AR interaction with BRD2/3/4 was observed. BET-inhibitors such as JQ1 and I-BET762 are known for their high affinity binding toward BD1/BD2 domain of BRD2/3/4 proteins (Dawson, M. A. et al., *Nature* 478:529-533 (2011); Delmore, J. E. et al., *Cell* 146:904-917 (2011); Filippakopoulos, P. et al., *Nature* 468:1067-1073 (2010)). This suggests that BET-inhibitors might affect genome-wide recruitment of all the three BET-proteins. Towards this end, ChIP-seq with antibodies against BRD2/3/4 in VCaP cells treated with JQ1 or I-BET762 (Table 8) was performed. A high genome-wide overlap between BRD2/3/4 (62-86% peak overlap) was observed (data not shown). JQ1 or I-BET762 treatment led to a reduction in the recruitment of all three proteins to the chromatin (data not shown). Moreover, this reduced BRD2/3/4 recruitment was equally distributed for regions with or without AR (data not shown).

Figure 17:
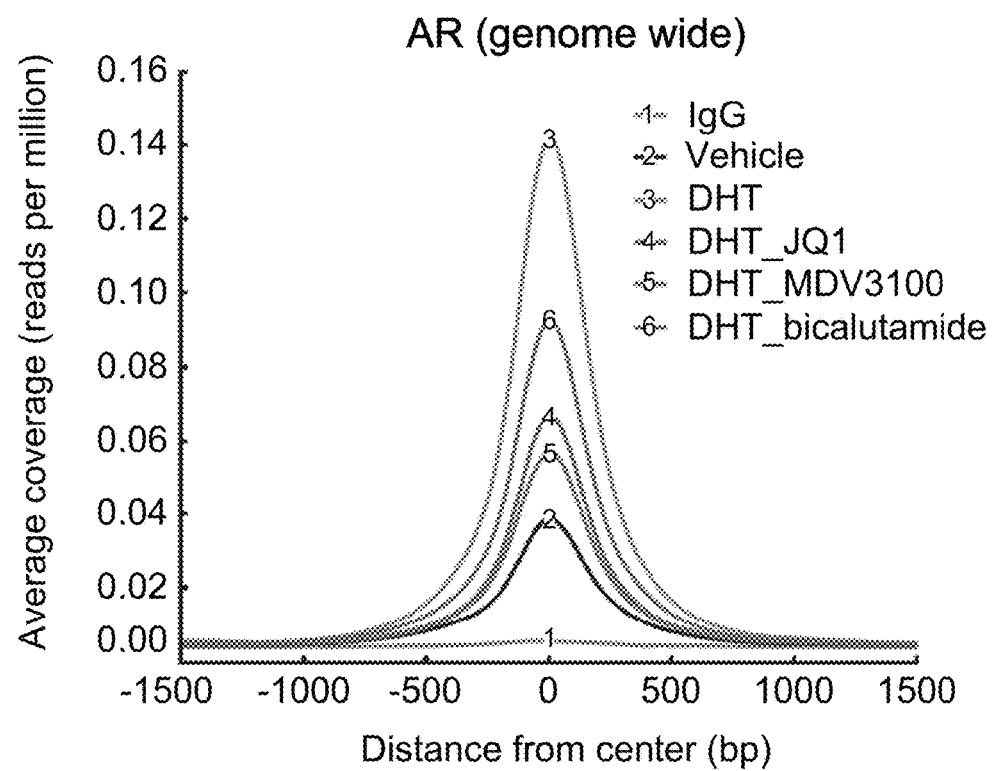
FIG. 17 is an illustration showing AR ChIP-seq in VCaP cells treated for 12 h with vehicle, DHT (10 nM), DHT+JQ1 (500 nM), DHT+MDV3100 (10M) or DHT+Bicalutamide (25 μM). Summary plot of AR enrichment (average coverage) across ARBs (AR Binding sites) in different treatment groups is shown.
Figure 18:
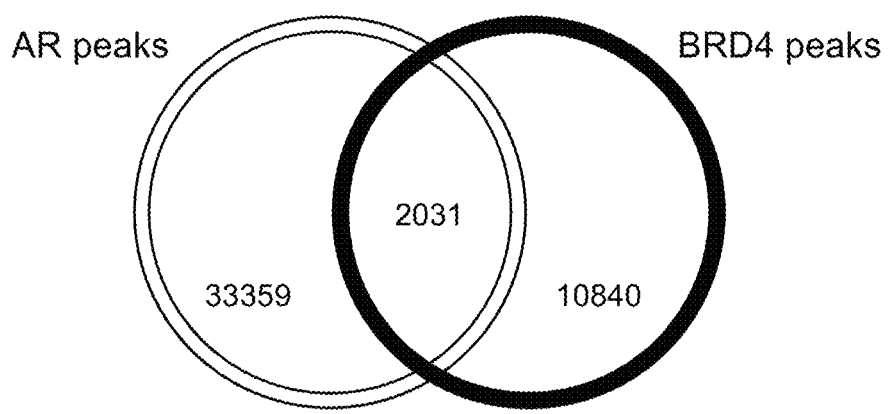
FIG. 18 is a Venn diagram illustrating the overlap of AR and BRD4 enriched peaks in DHT treated sample.
Figure 19:
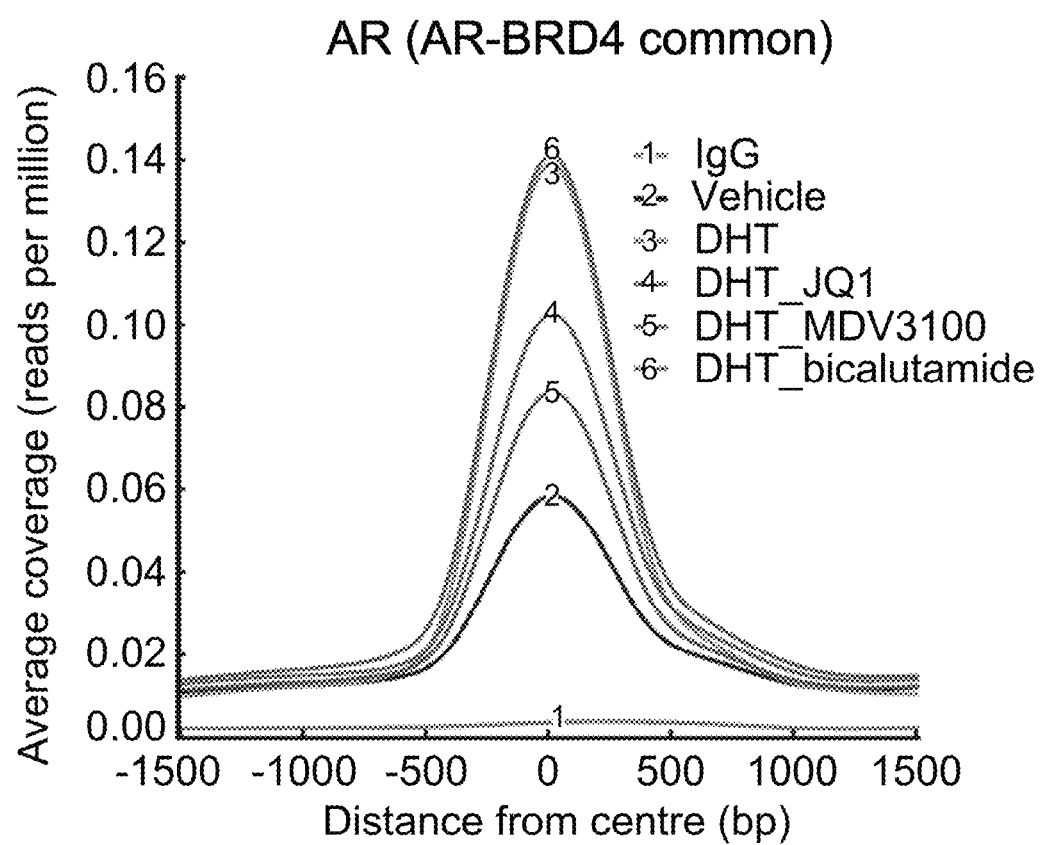
FIG. 19 is an illustration showing AR and BRD4 enrichment for the AR-BRD4 overlapping (2031) regions.
Figure 20:
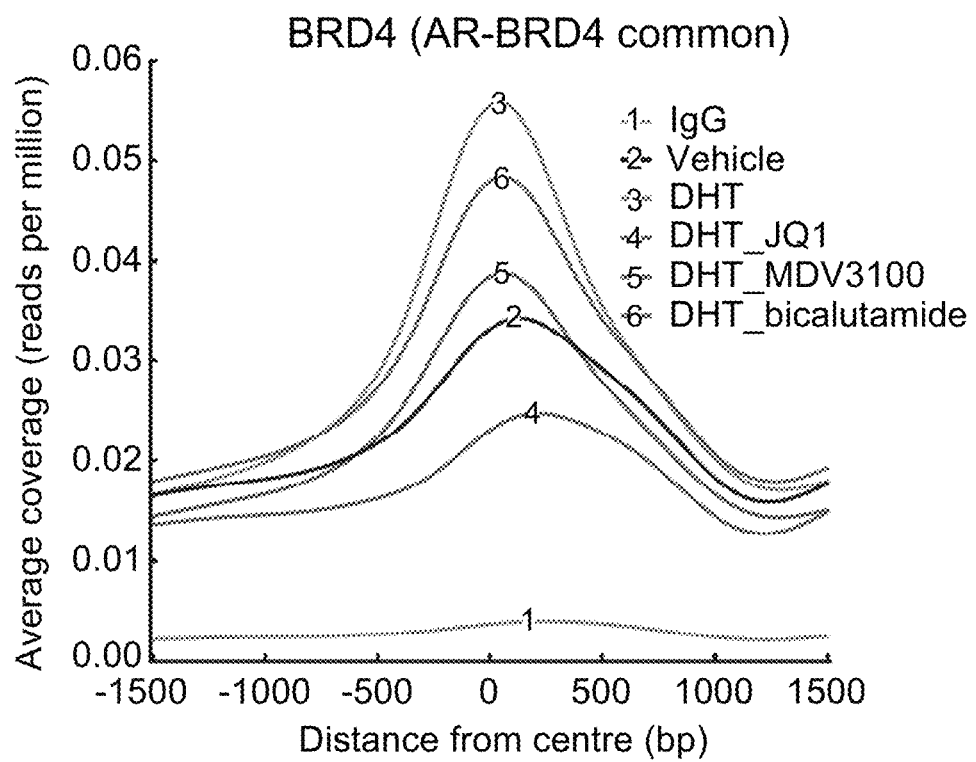
FIG. 20 is an illustration showing AR and BRD4 enrichment for the AR-BRD4 overlapping (2031) regions.
Figure 21:
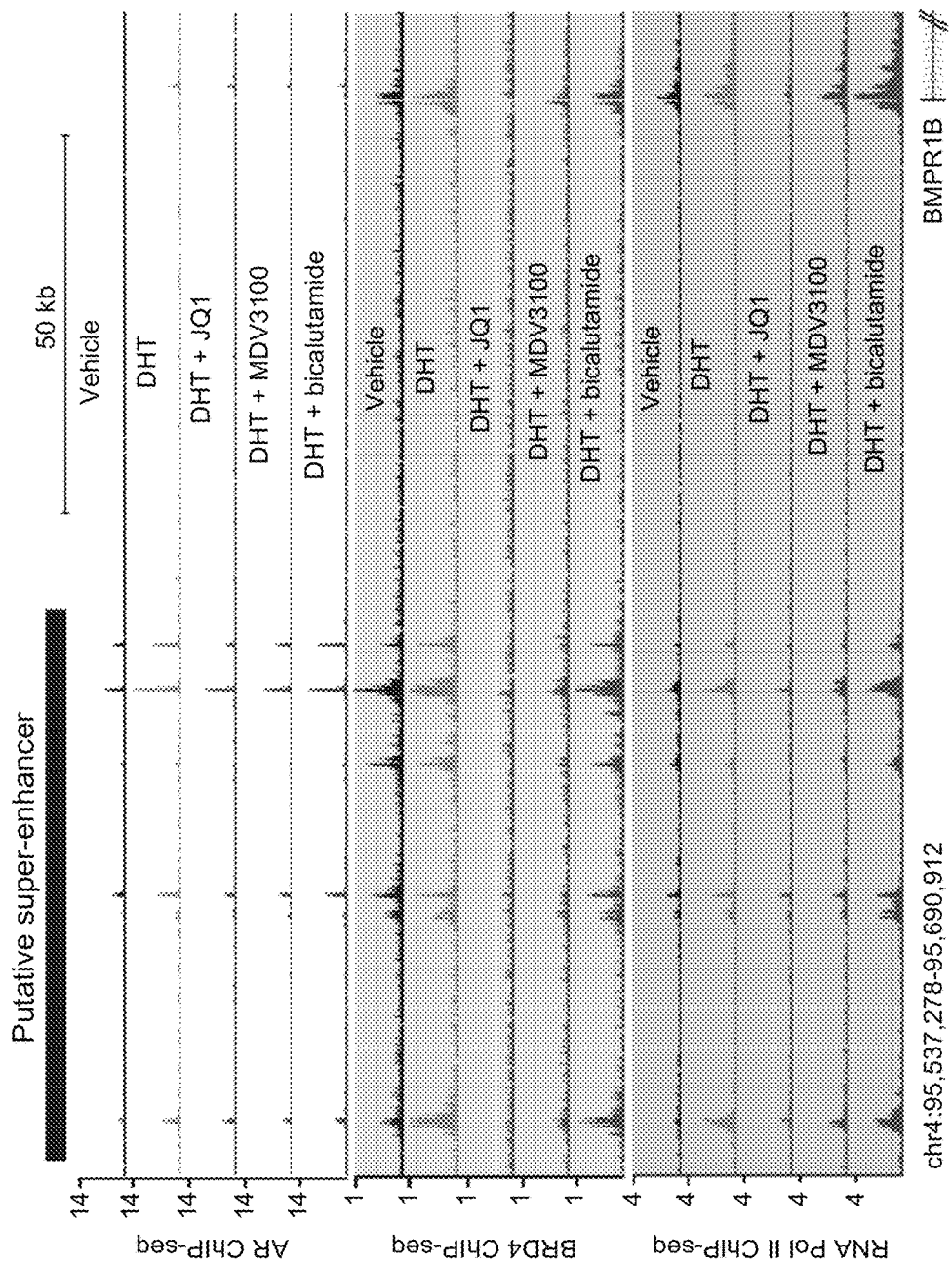
FIG. 21 is an illustration showing a genome browser representation of AR, BRD4 and RNA PolII binding events on a putative "super-enhancer" of the AR-regulated BMPR1B gene. They-axis denotes reads per million per base pair (rpm/bp). The x-axis denotes the genomic position with a scale bar on top right. The putative super-enhancer region enriched for AR, BRD4 and RNA PolII is depicted with a black bar on the top left.

Binding of androgen (DHT) to AR leads to its activation/translocation from the cytoplasm to the nucleus where it binds to regions of DNA comprising AREs and results in subsequent recruitment of proteins involved in transcriptional activation or suppression in a gene-specific manner. BRD4 interacts with acetylated histones as well as DNA binding transcription factors, leading to context-dependent transcriptional activation or inhibition of target genes (Jang, M. K. et al., *Mol Cell* 19:523-534 (2005); Wu, S. Y. et al., *Mol Cell* 49:843-857 (2013); Belkina, A. C. and Denis, G. V., *Nat Rev Cancer* 12:465-477 (2012)). Since the AR-BRD4 interaction is disrupted by JQ1 (FIGS. 7-16), it was explored whether this affects AR localization in a genome-wide context. ChIP-seq with antibodies against AR, BRD4, and RNA PolII in cells that were either starved, treated with DHT, or DHT plus JQ1 (Table 8) were performed. Two anti-androgens, bicalutamide and MDV3100 were used for comparison. The average ChIP-seq signal for AR was highly enriched in DHT-treated cells (FIG. 17). Recruitment of AR to target loci was markedly attenuated by MDV3100 and less so by bicalutamide. JQ1 could block AR recruitment to a level almost equivalent to MDV3100 (FIG. 17). Furthermore, a co-recruitment of AR and BRD4 at 2031 sites was observed. The strongest association is observed within promoters of AR-regulated genes (502 promoters, p=4e-49), and for the highest AR peaks (1112 sites, p=1e-38) (FIG. 18). Limiting the evaluation to AR and BRD4 coincident peaks, it was observed that DHT can mediate AR recruitment to these loci which was inhibited by MDV3100 and to a lesser extent by JQ1 (FIG. 19). By contrast, JQ1 almost completely abrogated DHT induced BRD4 recruitment to the AR-BRD4 shared loci (FIG. 20). Examples of gene tracks for AR and BRD4 associated genomic regions such as enhancers and super-enhancers (Loven, J. et al., *Cell* 153: 320-334 (2013)) and the effects of different treatments on their levels are shown in FIG. 21. In corroboration with the ChIP-seq data, gene expression analysis in VCaP and LNCaP cells displayed efficient repression of DHT-induced AR-target genes by JQ1 than MDV3100 or bicalutamide (data not shown).

Next, the oncogenic ERG expression in VCaP cells was explored since JQ1-treatment had a marked effect on its expression (FIGS. 4 and 5). The attenuation of DHT induced ERG expression by JQ1 was due to de-recruitment of RNA PolII from ERG gene body and reduced binding of AR and BRD4 on the TMPRSS2 promoter/enhancer (data not shown). This efficient ERG downregulation by JQ1 is compelling considering that the TMPRSS2-ERG gene fusion product is a key oncogenic driver in 50% of prostate cancers (Tomlins, S. A. et al., *Science* 310:644-648 (2005); Chen, Y. et al., *Nat Med* 19:1023-1029 (2013)). Next, the effect of JQ1 on ERG mediated transcription was investigated. Towards this, ERG ChIP-seq in cells treated with JQ1 for 12 h was performed; a time window where ERG protein levels were still unaffected by JQ1 (data not shown). A significant loss in the -top 4% ERG enriched peaks was observed (data not shown). Next, the functional consequence of ERG de-recruitment by testing the expression of several of its target genes after JQ1-treatment was determined (data not shown). The ERG activated genes were down-regulated and ERG repressed genes were de-repressed by JQ1 (data not shown). To confirm the BET-inhibitors role in blocking ERG mediated oncogenic function in an isogenic setting, RWPE and PC3 cells overexpressing ERG were tested (data not shown). Treatment of JQ1 or I-BET762 led to attenuation of ERG-mediated invasion (data not shown) and GSEA demonstrated a highly significant negative enrichment for ERG target genes in these cells upon BET-inhibitor treatment (data not shown). Next, it was investigated whether ERG is involved in the transcriptional regulation of MYC. ERG was found to be highly enriched on the known distal-enhancer of MYC; but was reduced upon JQ1-treatment (data not shown). Likewise, ETV1 occupies the same distal-enhancer region in ETV1 fusion positive LNCaP (Chen, Y. et al., *Nat Med* 19:1023-1029 (2013). Knockdown of ERG and ETV1 along with AR led to MYC down-regulation, implicating ETS transcription factors in the regulation of MYC in fusion-positive prostate cancer cells (data not shown). ChIP-seq analysis of AR and RNA PolII enrichment at the MYC locus presented an interesting pattern where DHT treatment led to increased AR and reduced RNA PolII binding on the MYC distal-enhancer and gene body respectively, that was reinstated in the presence of MDV3100 or bicalutamide but not by JQ1 (data not shown), and this result was supported by the observed concomitant reduction in MYC expression upon DHT treatment that was de-repressed in the presence of MDV3100 but not by JQ1 (data not shown). Lack of de-repression of MYC by JQ1 in this setting could be explained by the fact that both AR and ERG are absent from the MYC distal-enhancer leading to net loss of MYC expression. This data also suggests a mechanism by which CRPC may become resistant to anti-androgen therapy by maintaining expression of the MYC oncogene.

Figure 22:
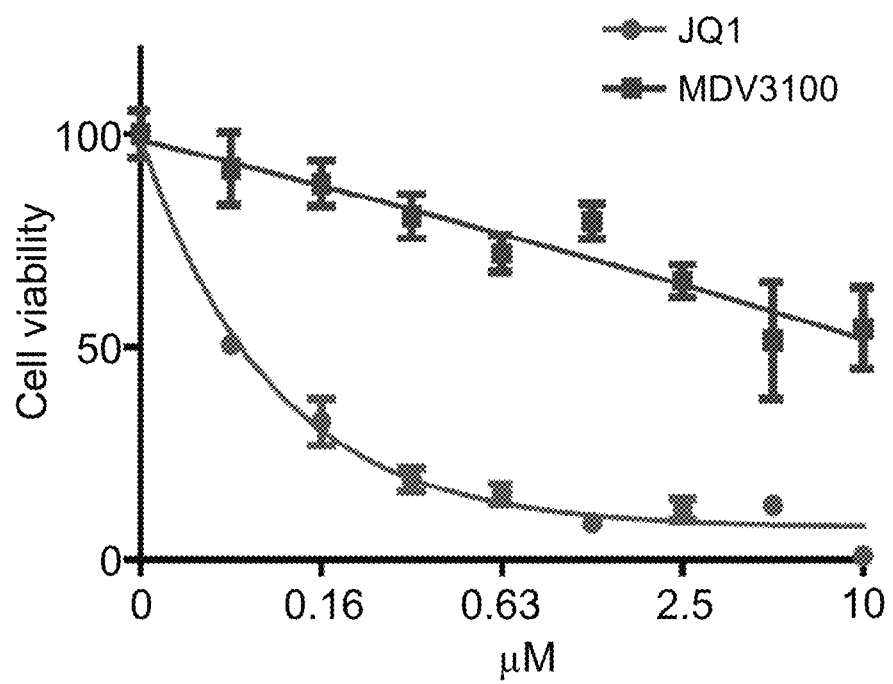
FIG. 22 is a line graph comparison of JQ1 and MDV3100 treatment on VCaP cell viability in vitro. VCaP cells were treated with MDV3100 or JQ1 for 8 days and assayed for viability with Cell-titerGLO.
Figure 23:
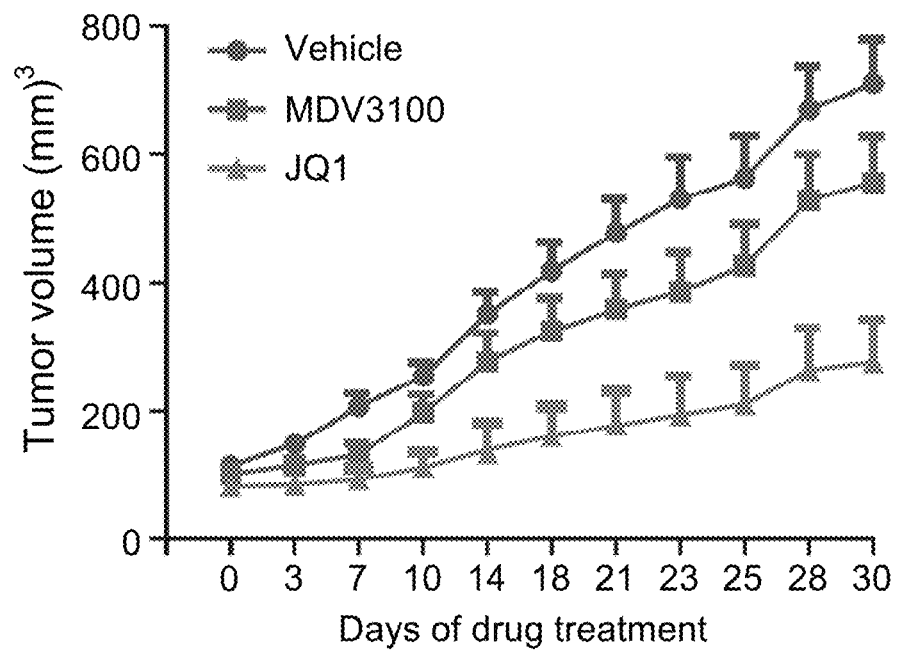
FIG. 23 is a line graph comparison of JQ1 and MDV3100VCaP. Cells were implanted subcutaneously in mice and grown until tumors reached the size of approximately 100 mm$^3$. Xenografted mice were randomized and then received vehicle or 50 mg/kg JQ1 or 10 mg/kg MDV3100 as indicated 5 days/week. Caliper measurements were taken bi-weekly. Mean tumor volume±SEM is shown.
Figure 24:
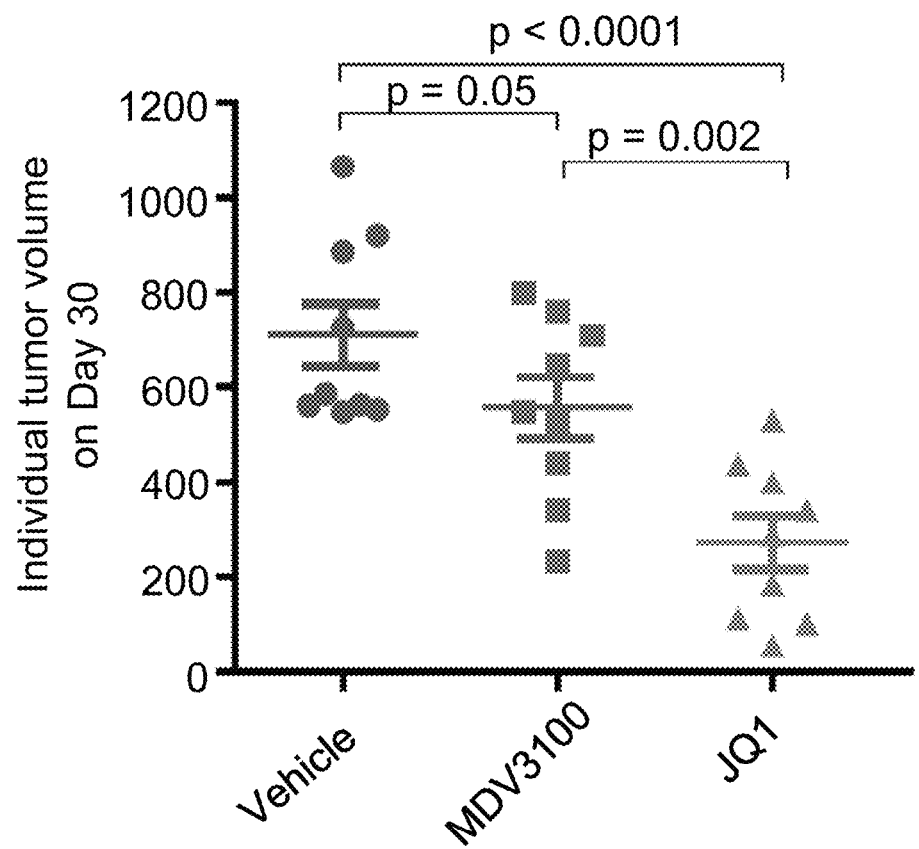
FIG. 24 is an illustration of individual tumor volume and weight from different treatment groups with p-values is shown.
Figure 25:
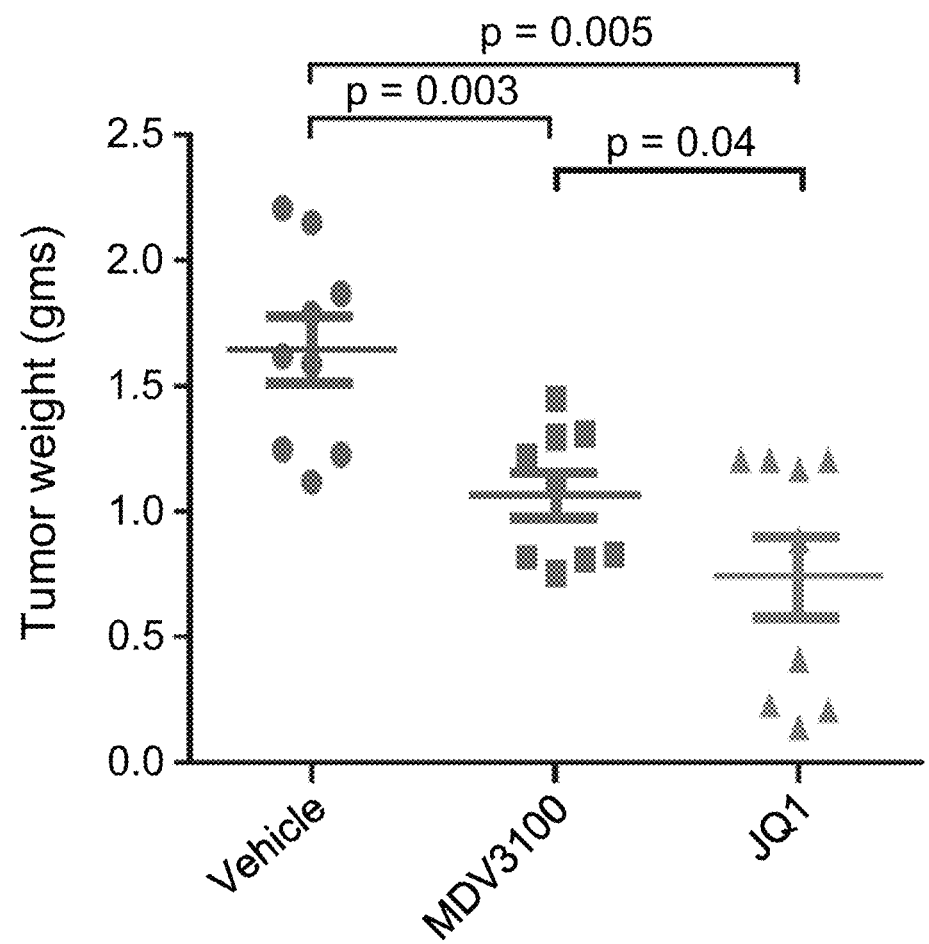
FIG. 25 is an illustration of individual tumor volume and weight from different treatment groups with p-values is shown.
Figure 26:
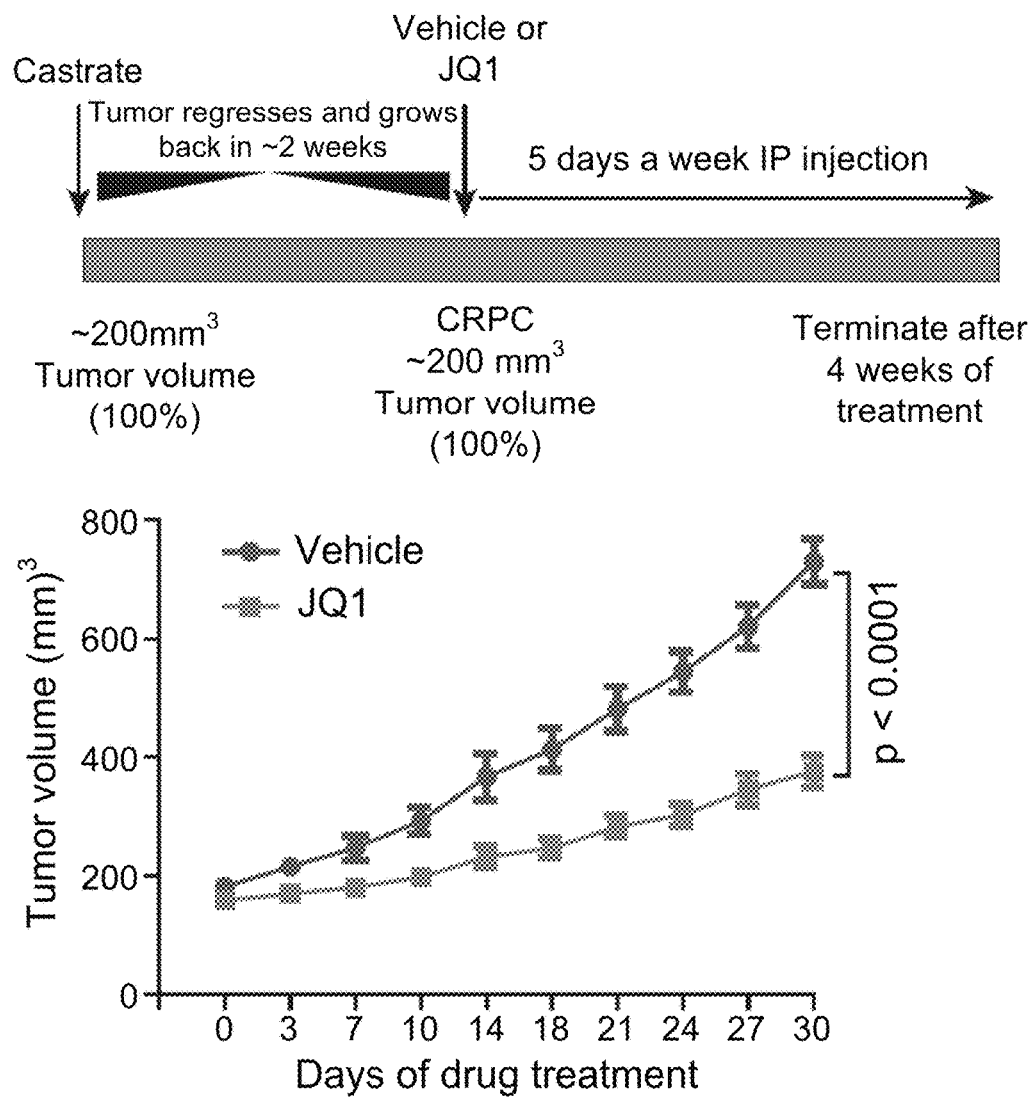
FIG. 26 is a schematic illustrating the VCaP CRPC mouse xenograft experimental design (top panel). Castrated mice bearing VCaP CRPC xenograft received vehicle or 50 mg/kg JQ1 as indicated 5 days/week (bottom panel).

JQ1 efficacy in comparison to MDV3100, a direct AR antagonist used clinically for advanced CRPC, was studied (Scher, H. I. et al., *N Engl J Med* 367:1187-1197 (2012)). Before embarking on the in vivo experiment, JQ1 and MDV3100 were tested on VCaP cells in vitro for 8 days. Marginal cell death for MDV3100 versus suppression of cell growth at sub-micromolar concentrations by JQ1 was observed (FIG. 22). No effect on physiologic androgen-regulated processes was found suggesting that JQl does not act a generic anti-androgen However, JQ1 reduced testes size in mice as reported earlier (Lin, T. H. et al., *Cell Death Dis* 4:e764 (2013)). (data not shown). Treatment of VCaP tumor-bearing mice with JQ1 led to significant reduction in tumor volume/weight (FIGS. 23-25). However, MDV3100 had a less pronounced effect. Recently, several studies described the pro-metastatic effects of MDV3100 in pre-clinical models (Lin, T. H. et al., *Cell Death Dis* 4:e764 (2013)). Whether MDV3100 treatment leads to spontaneous metastasis in the VCaP xenograft model was tested. Towards this, femur, liver and spleen from MDV3100 treated mice were isolated, and evidence of metastases in femur and liver was observed (data not shown). By contrast, JQ1 treated mice displayed no evidence of metastasis (data not shown). Taken together, these pre-clinical studies suggest that the use of MDV3100 in clinically localized prostate cancer may potentiate the formation of micro-metastases, which would not be the case with BET-inhibitors. Consistent with previous reports JQ1 and MDV3100 were well tolerated by mice (data not shown). Although VCaP cells were originally derived from a patient with CRPC, VCaP tumor xenograft respond to castration in mouse models. Whether JQ1 would still have a growth inhibitory effect in castration-resistant VCaP tumor xenografts was studied, and a 50% reduction in these castration-resistant tumors by JQ1-treatment was observed (FIG. 26).

Figure 27:
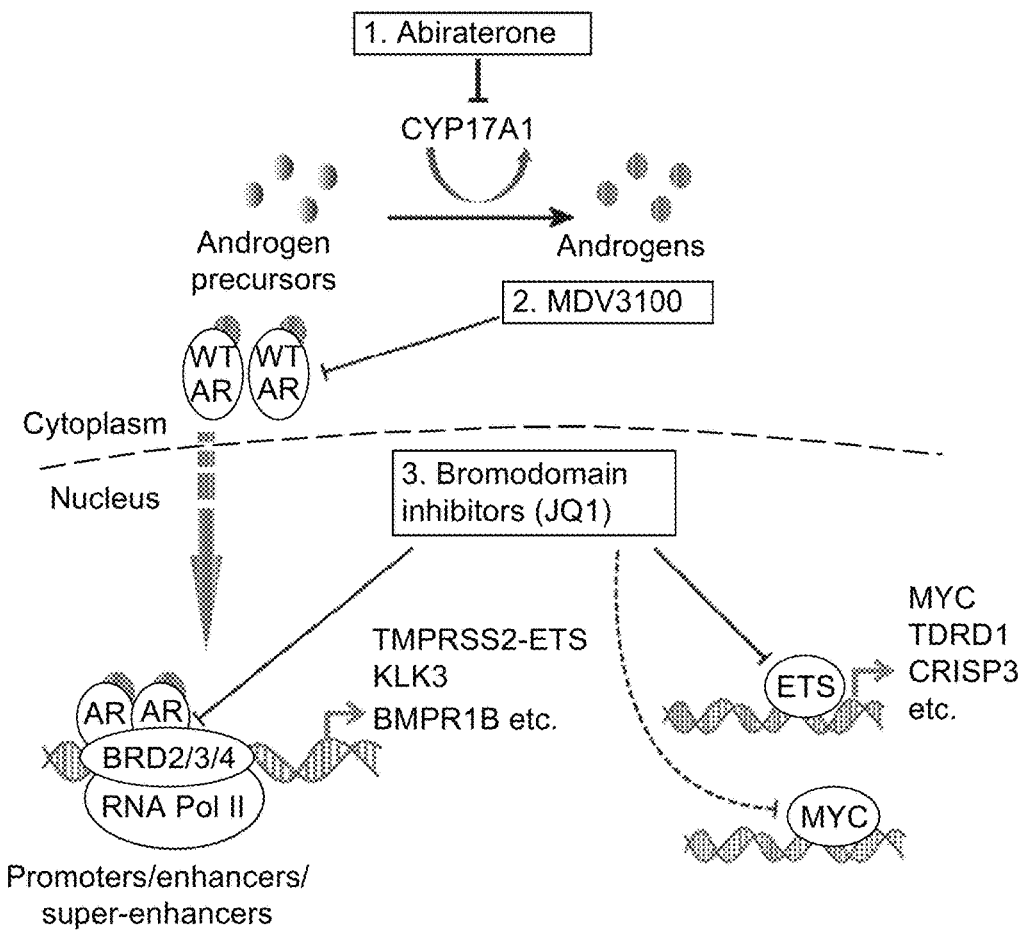
FIG. 27 is a schematic depicting varying mechanisms to block AR-signaling in CRPC. 1) Abiraterone inhibits androgen biosynthesis by blocking the enzyme CYP17A1. 2) MDV3100 competitively antagonizes androgen binding to AR preventing nuclear translocation and recruitment to target gene loci. 3) JQ1 (or BET-inhibitors) blocks AR and BRD2/3/4 interaction and co-recruitment to target gene loci as well as the functional activity and/or expression of ETS and MYC.

Maintenance of AR signaling has been identified as the most common resistance mechanism that patients with advanced prostate cancer develop after conventional hormonal treatments (Harris, W. P. et al., *Nat Clin Pract Urol* 6:76-85 (2009)). AR amplification, mutation, and alternative splicing have all been suggested as potential resistance mechanisms to anti-androgen treatments (Chen, C. D. et al., *Nat Med* 10:33-39 (2004); Taplin, M. E. et al., *Cancer Res* 59:2511-2515 (1999); Sun, S. et al., *J Cln Invest* 120:2715-2730 (2010)). Over half of CRPC patients have at least one of these aberrations in the AR pathway (Grasso, C. S. et al., *Nature* 487:239-243 (2012). As BET-inhibitors function "downstream" of AR itself (FIG. 27), these data suggest that these compounds may be effective in the context of AR directed resistance mechanisms including compensatory mechanisms involving related steroid hormone receptors which are also likely to require BET bromodomain function. By functioning downstream of AR, BET-inhibition is less likely to be affected by acquired resistance associated with AR antagonists, including the recently identified F876L mutation of AR (Balbas, M. D. et al., *Elife* 2:e00499 (2013)). While both MDV3100 and JQ1 block AR recruitment to target loci on a genome-wide scale (the "AR cistrome"), it was found that JQ1 likely has an enhanced effect by fully abrogating co-recruitment of BRD4, which is required for mobilization of the transcriptional machinery (Jang, M. K. et al., *Mol Cell* 19:523-534 (2005); Yang, Z. et al., *Mol Cell* 19:535-545 (2005)). A recent study demonstrated that BET-inhibition leads to preferential loss of BRD4 at "super-enhancers" and consequent transcriptional elongation defects (Loven, J et al. *Cell* 153:320-334 (2013)). These super-enhancers were often associated with key oncogenic drivers in a variety of cancers. Tumor cells are thought to become addicted to selected oncogenes, and become unusually reliant on their high expression which may explain the preferential sensitivity of BET-inhibition in cancer versus normal tissues. While MYC and its association with multiple myeloma was highlighted as a super-enhancer dependent cancer (Loven, J. et al. *Cell* 153:320-334 (2013)), this framework likely applies to key transcription factors involved in the development of CRPC including AR, ETS, and MYC (FIG. 27). Taken together, these data strongly suggest the clinical evaluation of BET-inhibitors is warranted in CRPC, either as monotherapy or in combination with second generation anti-androgens.

Methods

Cell Culture

VCaP prostate cancer cells were grown in DMEM with Glutamax (Gibco), LNCaP, 22RV1, DU145 and PC3 prostate cancer cell lines were grown in RPMI 1640, all were supplemented with 10% FBS (Invitrogen) in 5% $CO_2$ cell culture incubator. The immortalized benign prostate cell line RWPE-1 was grown in keratinocyte media with supplements (Lonza). All cell lines were tested and found to be free of mycoplasma contamination.

Cell Viability Assay

Cells were seeded in 96-well plates at 2000-10,000 cells/well (optimum density for growth) in a total volume of 100 μl media containing 10% FBS. Serially diluted compounds in 100 μl media were added to the cells 12 h later. Following 96 h. incubation, cell viability was assessed by Cell-Titer GLO (Promega). The values were normalized and IC50 was calculated using GraphPad Prism software. For long-term colony formation assay, 10,000-50,000 cells/well were seeded in six-well plates and treated with either 100 nM or 500 nM of JQ1 or DMSO. After 12 days cells were fixed with methanol, stained with crystal violet and photographed. For colorimetric assays, the stained wells were treated with 500 μl 10% acetic acid and the absorbance was measured at 560 nm using a spectrophotometer.

Cell Cycle Analysis

Cells were grown in 6 well plates and treated with varying concentrations of JQ1. For cell cycle analysis, cells were washed 48 h post-treatment with PBS and fixed in 70% ethanol overnight. The cells were washed again with PBS, stained with propidium iodide and analyzed by flow cytometry.

RNA Interference

For knockdown experiments, cells were seeded in six-well plates and transfected with 100 nM ON-TARGETplus SMARTpool siRNA (ThemoScientific) targeting BRD2, BRD3, BRD4, MYC or non-targeting control using oligofectamine (Invitrogen) according to the manufacturer's instructions. Cells were trypsinized 24 h post-transfection and used in cell proliferation and matrigel invasion assays as well as for RNA extractions to determine the knockdown efficiency. AR, ERG and ETV1 knockdown was achieved by transfecting 100 nM specific ON-TARGETplus SMART-pool siRNA using oligofectamine.

Cell Proliferation Assay

For cell proliferation assays post siRNA knockdown, 20,000 cells/well were seeded in 24-well plates (n=3), and cells were harvested and counted at the indicated time points by Coultercounter (Beckman Coulter, Fullerton, Calif.).

VCaP, LNcaP and 22RV1 cells were transduced with either Ad-c-MYC (Vector Biolabs, cat. No. 1285) or LacZ control Adeno viral particles. 24 h post infection; equal number of cells were seeded in 24 well plates and treated with vehicle, JQ1 or I-BET762 at 500 nM concentration. Cells were counted at the indicated time points by Coulter Counter.

Matrigel Invasion Assays

Twenty-four hours post-infection with siRNA or 500 nM JQ1 treatment, $0.2 \times 10^6$ VCaP or $0.1 \times 10^6$ LNCaP cells were seeded in a transwell chamber pre-coated with Matrigel (BD Biosciences). Medium containing 10% FBS in the lower chamber served as chemoattractant. In the case of JQ1, 500 nM compound was added to both upper and lower chambers. After 48 h, the non-invading cells and EC matrix were gently removed with a cotton swab and invasive cells located on the lower side of the chamber were stained with crystal violet, air dried, photographed and counted.

PC3 and RWPE cells were treated with JQ1 or I-BET762 at 500 nM concentration along with DMSO control for 24 h prior to seeding 50,000 cells/well in a transwell chamber pre-coated with Matrigel along with the corresponding drugs used for treatment. Medium containing 10% FBS in the lower chamber served as chemoattractant. After 48 h, the non-invading cells and EC matrix were gently removed with a cotton swab and invasive cells located on the lower side of the chamber were stained with crystal violet, air dried and photographed. For colorimetric assays, the inserts were treated with 150 µl of 10% acetic acid and the absorbance measured at 560 nm using a spectrophotometer (GE Healthcare).

RNA Isolation and Quantitative Real-Time PCR

Total RNA was isolated from cells using RNeasy Mini Kit (Qiagen) and cDNA was synthesized from 1,000 ng total RNA using SuperScript III First-Strand Synthesis SuperMix (Invitrogen). QPCRs were performed in duplicate or triplicate using Taqman assays (Applied Biosystems) or standard SYBR green reagents and protocols on a StepOnePlus Real-Time PCR system (Applied Biosystems). The target mRNA expression was quantified using $\Delta\Delta Ct$ method and normalized to GAPDH expression. All primers were designed using Primer 3 (http://frodo.wi.mit.edu/primer3/) and synthesized by Integrated DNA Technologies (Coralville, Iowa). The primer sequences for the SYBR green and catalogue numbers for TaqMan assays used are provided in Table 9.

Antibodies and Immunoblot Analyses

Antibodies used in the study are listed in Table 10. All antibodies were employed at dilutions suggested by the manufacturers. For Western blot analysis, 200 ug total protein extract was boiled in sample buffer and 10-20 g aliquots were separated by SDS-PAGE and transferred onto Polyvinylidene Difluoride membrane (GE Healthcare). The membrane was incubated for one hour in blocking buffer [Tris-buffered saline, 0.1% Tween (TBS-T), 5% nonfat dry milk] followed by incubation overnight at 4° C. with the primary antibody. Following a wash with TBS-T, the blot was incubated with horseradish peroxidase-conjugated secondary antibody and signals were visualized by enhanced chemiluminescence system as per manufacturer's protocol (GE Healthcare).

Immunoprecipitations

For endogenous immunoprecipitation experiments, nuclear extracts were obtained from VCaP and LNCaP cells using NE-PER nuclear extraction kit (Thermo Scientific). Nuclear pellet was then lysed in IP buffer (20 mM Tris pH7.5, 150 mM NaCl, 1% Triton-X 100, Protease Inhibitor) by sonication. Nuclear lysates (0.5-1.0 mg) were pre-cleaned by incubation with protein G Dynabeads (Life Technologies) for 1 h. on a rotator at 4° C. 5 µg antibody was added to the pre-cleared lysates and incubated on a rotator at 4° C. overnight prior to the addition of protein G Dynabeads for 1 h. Beads were washed thrice in IP buffer and resuspended in 40 µL of 2x loading buffer and boiled at 90° C. for 10 minutes for separation of the protein and beads. Samples were then analyzed by SDS-PAGE and western blotting as described above. For endogenous competitive assays, the VCaP cells were incubated with 5 or 25 µM JQ1 for 6 h prior to nuclear protein extractions.

For co-immunonoprecipitation experiments in 293T cells, plasmids encoding different deletions of BRD4 in pCDNA4c, (Addgene) and full length AR in pFN21 plasmid (Promega) were transfected using Fugene 6.0 HD (Roche) according to the manufacturer's instruction. Twenty four h post transfection; total proteins were extracted using IP buffer supplemented with protease inhibitor cocktail mix (Sigma), and checked for the expressions of the corresponding proteins by immunoblotting. Immunoprecipitation using Halo-beads followed by immunoblotting with anti-His antibody were performed as described above.

Cell Free Protein-Protein Interaction Studies

In vitro protein expression was carried out by cloning the desired expression cassettes downstream of a Halo- or GST-tag to create fusion proteins. Briefly, AR and its sub-domains were cloned into the pFN2K vector containing N-terminal GST sequence (Cat.# G1891, Promega); BRD4 and its sub-domains were cloned into the pFN19A vector containing N-terminal Halo sequence (Cat.# C8461, Promega). After cloning, the fusion proteins were expressed using the cell-free transcription and translation system (Cat.# L5030, Promega) following the manufacturer's protocol. For each reaction, protein expression was confirmed by Western blot.

A total of 10 µl cell-free reaction containing halo- and GST-tag fusion proteins were incubated in PBST (0.1% tween) at 4° C. overnight. Ten microliter HaloLink beads (Cat.# G931, Promega) were blocked in BSA at 4° C. for overnight. After washes with PBS, the beads were mixed with AR-BRD4 mixture and incubated at RT for 1 h. Halolink beads were then washed with PBST for 4 times and eluted in SDS loading buffer. Proteins were separated on SDS gel and blotted with anti-GST Ab (GE healthcare). For competitive assay, AR-BD1, NTD1b-BD1 and AR-BD2 mixture was incubated in the presence of different dose of JQ1.

AR:BRD4 Direct Interaction Assays by OctetRED

The binding affinity between AR and BRD4 was determined by biolayer interferometry technology using the OctetRED system (ForteBio). Recombinant AR protein (Cat.# AR-8486H, Creative Biomart) was biotinylated by EZ-Link NHS-PEG4 Biotinylation Kit (Cat.#21329, Thermo Scientific) following the manufacturer's protocol and any unincorporated biotin was removed from the reactions with Zeba 2 ml desalt columns. Biotinylated proteins (5 µg/ml) were then incubated with super streptavidin biosensors (Cat.#18-5057, ForteBio) in binding buffer (20 mM HEPES pH 7.4, 150 mM NaCl) and washed three times in binding buffer. BRD4 (BD1-BD2) protein (Cat.#31047, BPS Biosciences) was serially diluted in binding buffer, and the AR:BRD4 association/dissociation was monitored by OctetRED for 10 min at 25° C. Non-specific binding was controlled by subtracting the signal obtained from AR:RNF2 interactions from that of AR:BRD4 interactions and baseline signal drift was controlled by monitoring immobilized AR without BRD4. OctetRED analysis software was used to analyze the data.

Gene Expression Array Analysis

VCaP, LNCaP, 22RV1 and DU145 cells were treated with 500 nM JQ1 for 24 h and total RNA extracted using RNeasy Mini Kit (Qiagen) for gene expression array analysis. For anti-androgen comparative study, VCaP and LNCaP cells were grown in media containing 10% charcoal-striped serum for 48 h followed by pre-treatment with 500 nM JQ1, 10 µM MDV3100 or 25 µM Bicalutamide for 6 h and stimulated with 10 nM DHT (androgen) for 18 h. Cells treated with only vehicle or 10 nM DHT served as controls. For the effect of BET inhibitors in isogenic ERG system, RWPE-ERG and PC3-ERG cells were treated with 500 nM JQ1 or I-BET762 for 24 h. Expression profiling was performed using the Agilent Whole Human Genome Oligo Microarray (SantaClara, Calif.) according to the manufacturer's protocol. All samples were run in technical duplicates or quadruplets against control. Over- and under-expressed gene sets were generated by filtering to include only 2-fold average over- or underexpression (Log ratio with $p<0.001$) in all hybridizations. Gene Set Enrichment Analysis (GSEA) was performed using the JAVA program (http://www.broadinstitute.org/gsea) as described in Subramanian, A. et al., *Proc Natl Acad Sci USA* 102:15545-15550 (2005).

The AR target gene signature used in GSEA analysis was generated from common up-regulated genes in VCaP and LNCaP upon DHT treatment and the gene list is provided in Table 6.

The ERG gene signature was generated by extracting 2-fold up genes from RWPE and PC3 cells stably expressing ERG compared to respective LacZ expressing cells. GSEA was performed using this gene set on gene expression data obtained from the JQ1 and I-BET762 treated RWPE and PC3 cells. GSEA using gene set that were not changed upon expression of ERG to exclude the possibility that treatment with JQ1 and I-BET762 may change gene expression in a non-specific fashion was also tested.

Chromatin Immunoprecipitation (ChIP) and ChIP-Seq

The ChIP assays for BRD2, BRD3, BRD4, AR, RNA PolII, ERG and H3K27ac were performed using HighCell ChIP kit (Diagenode) according to manufacturer's protocol. For BRD2/3/4 ChIP-seq experiments with BET inhibitors, VCaP cells were treated with 500 nM JQ1 or I-BET762 for 12 h. For AR signaling ChIP-seq experiments, VCaP cells were grown in charcoal-stripped serum containing media for 48 h followed by 6 h pre-treatment with vehicle or 500 nM JQ1 or 10 M MDV3100 or 25 µM Bicalutamide and then stimulated with 10 nM DHT for 12 h. For ERG ChIP-seq studies, VCaP cells were treated with 500 nM JQ1 or vehicle for 12 h. Next, cells were cross-linked for 10 min. with 1% formaldehyde. Cross-linking was terminated by the addition of $\frac{1}{10}$ volume 1.25 M glycine for 5 min. at room temperature followed by cell lysis and sonication (Bioruptor, Diagenode), resulting in an average chromatin fragment size of 200 bp. Chromatin equivalent to $5 \times 10^6$ cells were used for ChIP using different antibodies. ChIP DNA was isolated (IPure Kit, Diagenode) from samples by incubation with the antibody at 4° C. overnight followed by wash and reversal of cross-linking. The ChIP-seq sample preparation for sequencing was performed according to the manufacturer's instructions (Illumina). ChIP-enriched DNA samples (1-10 ng) were converted to blunt-ended fragments using T4 DNA polymerase, *E. coli* DNA polymerase I large fragment (Klenow polymerase) and T4 polynuleotide kinase (New England BioLabs, NEB). A single A-base was added to fragment ends by Klenow fragment (3' to 5' exo minus; NEB) followed by ligation of Illumina adaptors (Quick ligase, NEB). The adaptor-modified DNA fragments were enriched by PCR using the Illumina Barcode primers and Phusion DNA polymerase (NEB). PCR products were size selected using 3% NuSieve agarose gels (Lonza) followed by gel extraction using QIAEX II reagents (QIAGEN). Libraries were quantified with the Bioanalyzer 2100 (Agilent) and sequenced on the Illumina HiSeq 2000 Sequencer (100 nucleotide read length).

ChIP-Seq Analysis

ChIP-Seq Enrichment Levels:

ChIP enrichment levels within a peak (or site) were calculated from the sequencing data as follows: (1) reads were aligned to the HG19 reference genome using Bowtie2 (Langmead, B. and Salzberg, S. L., *Nat Methods* 9:357-359 (2012)) with all default settings. (2) Aligned reads were sorted using NovoSort and exact duplicates were removed using Samtools (Li, H. et al., *Bioinformatics* 25:2078-2079 (2009)). (3) For each peak (site) overlapping reads were counted and this count was divided by the length of the peak or site. (4) To correct for differences in sequencing depth and alignment coverage the values are further normalized by the number of aligned reads per million.

ChIP-Seq Reproducibility Plots:

To assess the biological variability of AR and ERG ChIP-seq experiments, the enrichment levels of their respective replicates were compared. For each replicate peaks were called using MACS with all default setting against an IgG control. Peaks within genomic regions prone to technical-artifacts were exclude (Pickrell, J. K. et al., *Bioinformatics* 27:2144-2146 (2011)). For each replicate pair, a set of concordant peaks as those overlapping in both replicates was defined. For each concordant peak, enrichment levels within the union of the two overlapping peaks were calculated. The scatter plots include all peaks with enrichment levels up-to the 99th percentile.

Overlaps of Bromodomain Proteins:

The genome-wide distribution of BRD2, BRD3, and BRD4 peaks in DMSO treated VcaP cells was compared. First, peaks for each of the proteins using MACS with all default settings and IgG control were called. A moderately stringent significance cut-off (MACS score >100) was used. Next, all genomic regions that were enriched for at least one of the proteins were identified. Specifically, all stringent peaks were "reduced" using GenomicRanges (Lawrence, M et al., *PLoS Comput Biol* 9:e1003118 (2013)). For each of those regions, it was established which of the Bromodomain proteins were enriched to count the number of overlaps.

Drug-Induced Changes of Bromodomain Protein Enrichment Levels

For each protein (BRD2, BRD3, BRD4), quantitative changes in their respective enrichment levels upon drug treatment (I-BET762, JQ1) relative to the levels in the DMSO control were assessed. First, for all conditions and proteins, peaks were called as in Overlaps of bromodomain proteins were called. Next, for each protein separately, genomic that were enriched in any (union) of the treatment conditions (DMSO, I-BET762, or JQ1) were identified. Within those regions enrichment levels as described in (ChIP-seq enrichment levels) were quantified. Since enrichment levels of different proteins are not directly comparable, all enrichments to the median level of the (DMSO) control were normalized.

Differential AR-BRD4 Enrichment and AR-BRD4 Overlap:

HPeak, a Hidden Markov model (HMM)-based peak-calling software (Qin, Z. S. et al., *BMC Bioinformatics* 11:369 (2010)) designed for the identification of protein-interactive genomic regions, was employed for ChIP-seq peak determination. For enrichment plots shown in FIGS. 17, 19 and 20, identified peaks for each sample are centered by peak summit and average coverage per million was counted within 1500 bp relative to the peak center. The overlap of AR and BRD4 enriched regions were calculated by BEDtools (Quinlan, A. R. and Hall, I. M., *Bioinformatics* 26:841-842 (2010)) The significance of overlap between AR and BRD4 binding was calculated using hypergeometric test based on the derived number of associated genes. The heatmap for AR peak enrichment was generated using python-based script on raw data and visualized using Java-TreeView (Saldanha, A. J., *Bioinformatics* 20:3246-3248 (2004)).

Differential ERG Enrichment:

Sites with significant differences in ERG levels between DMSO and JQ1 treated cells were identified. First, concordant peaks (see ChIP-seq reproducibility plots) that were overlapping or in the +/−5 kbp proximity of annotated gene loci were identified. A gene locus was defined as the union of all of its known transcripts (Ensembl Genes 73). DESeq2 was used to assess the statistical significance of differences in ERG enrichment levels. Although DESeq2 was originally developed for RNA-seq its statistical model is well-suited to count data in general. The tools' default multiple hypothesis correction method and report peaks with significant differences in ERG levels (adjusted P-value <0.1) was used. To assess quantitative differences in ERG levels at significantly "gained" (positive difference in ERG levels upon JQ1 treatment) and "lost" (negative difference in ERG levels upon JQ1 treatment) the same procedure as in ChIP-seq enrichment levels was followed.

Murine Prostate Tumor Xenograft Model

Four week-old male SCID C.B17 mice were procured from a breeding colony at University of Michigan. All procedures involving mice were approved by the University Committee on Use and Care of Animals (UCUCA) at the University of Michigan and conform to all regulatory standards. Mice were anesthetized using 2% Isoflurane (inhalation) and $2 \times 10^6$ VCaP prostate cancer cells suspended in 100 µl of PBS with 50% Matrigel (BD Biosciences) were implanted subcutaneously into the dorsal flank on both sides of the mice. Once the tumors reached a palpable stage (100 mm$^3$), the animals were randomized and treated with either 10 mg/kg body weight MDV3100 or 50 mg/kg body weight (doses previously used in mouse prostate cancer and multiple myeloma models) (Delmore, J. E. et al., Cell 146:904-917 (2011); Tran, C. et al., Science 324:787-790 (2009)) by oral gavage or intraperitonially respectively for five days a week. Growth in tumor volume was recorded using digital calipers and tumor volumes were estimated using the formula $(\pi/6) (L \times W^2)$, where L=length of tumor and W=width. Loss of body weight during the course of the study was also monitored. At the end of the studies mice were sacrificed and tumors extracted and weighed. Additionally, femur bone marrow, liver and spleen were harvested to examine spontaneous metastasis by detecting human-Alu sequence. Briefly, genomic DNA from femur bone marrow, liver and spleen were prepared using Puregene DNA purification system (Qiagen), followed by quantification of human ALU sequence by human Alu specific Fluorogenic TaqMan qPCR probes as described (Tran, C. et al., Science 324:787-790 (2009); van der Horst, E. H. et al., Biotechniques 37:940-942, 944, 946 (2004)). For CRPC experiment, VCaP tumor bearing mice were castrated when the tumors were approximately 200 mm$^3$ in size and randomized later once the tumor grew back to the pre-castration size and treated with JQ1 or vehicle (D5W) control. All procedures involving mice were approved by the University Committee on Use and Care of Animals (UCUCA) at the University of Michigan and conform to all regulatory standards.

Prostate Histology and Hormone Measurement

Four to five weeks old male SCID C.B17 mice were administered vehicle, 10 mg/kg MDV3100 or 50 mg/kg JQ1, by oral gavage or intraperitonially, respectively for five days a week. Highly hormone responsive seminal vesicles attached to prostate were harvested from mice after four weeks of injection. Prostate were fixed in formalin solution and processed for sectioning. Standard H&E staining was achieved on the formalin fixed sections and were used to image the different lobes of the gland. To determine the testosterone levels, blood samples were collected by cardiac puncture from mice anesthetized with isoflurane. The serum was separated from the blood and stored at −80° C. until assayed. Serum testosterone levels were measured by the Ligand Assay at University of Michigan-ULAM Pathology Cores for Animal Research.

TABLE 6

AR target gene list: Common upregulated genes upon DHT stimulation in VCaP and LNCaP cells used for GSEA analysis shown in FIG. 6.

| | | | | | | |
|---|---|---|---|---|---|---|
| ABCC4 | B3GAT1 | ChGn | FRK | LOX | PER1 | STEAP4 |
| ABHD2 | BC039021 | CHIA | FZD5 | LRCH1 | PFKFB2 | STK17B |
| ACSL3 | BC041926 | CHKA | GADD45G | LRIG1 | PGC | TACC1 |
| ADARB2 | BC041955 | CHST2 | GIPR | LSS | PHACTR3 | TBRG1 |
| AF349445 | BC055421 | CLDN12 | GREB1 | MAF | PNPLAB | TBX15 |
| AFF4 | BC062780 | CLDN14 | GSR | MAK | PPP2CB | TG |
| AI089002 | BG462058 | CLDN8 | HERC3 | MALT1 | RAB27A | TGFB2 |
| AI207522 | BG618474 | CTBP1 | HLA-DRB3 | MAP1B | RAB4A | TIPARP |
| AI570240 | BI710972 | CUTL2 | HOMER2 | MAP7D1 | RASD1 | TLOC1 |
| AK023880 | BM469851 | CXorf9 | HPGD | MBOAT2 | RHOU | TMCC3 |
| AK025380 | BMPR1B | CYP1A1 | HS3ST4 | MFSD2 | RUNX1 | TMPRSS2 |
| AK055915 | BQ017638 | CYP2U1 | HSD17B2 | MICAL1 | S100A5 | TNFAIP3 |
| AK057576 | BQ706282 | DDR2 | IFI6 | MLPH | SCRG1 | TPD52 |
| AK074291 | BRP44 | DHCR24 | IGF1 | MOGAT2 | SGK | TRIM36 |
| AK092594 | BU567141 | DKFZp761P0 | IGF1R | MPZL1 | SHROOM3 | TRIM63 |
| AK093002 | BU753102 | DNAJB9 | IL20RA | MTMR9 | SLC16A6 | TTN |
| AK098478 | BX099483 | DOCK11 | IMPAD1 | NANOGP1 | SLC26A2 | TUBA3D |
| AK124281 | C10orf114 | DOCK8 | INPP4B | NAT1 | SLC26A3 | WIPI1 |
| AK124426 | C14orf162 | EAF2 | KCNMA1 | NCAPD3 | SLC2A14 | WNT7B |
| AL533190 | C16orf30 | EDG7 | KLF15 | NDFIP2 | SLC2A3 | WWTR1 |
| AL713762 | C18orf1 | ELL2 | KLK3 | NDRG1 | SLC38A4 | X03757 |
| ALDH1A3 | C1orf108 | ELOVL5 | KLK4 | NEBL | SLC41A1 | ZBTB1 |
| AMAC1L2 | C1orf113 | ELOVL7 | KLK5 | NEK10 | SLC45A3 | ZBTB16 |
| ANKRD37 | C1orf26 | EMP1 | KRT18 | NFKBIA | SLITRK6 | ZBTB24 |
| ANXA2 | C20orf112 | ENDOD1 | KRT19 | NNMT | SMC4 | |
| ARSG | C6orf81 | ENST000003 | KRT72 | NR4A1 | SMOC1 | |
| ASRGL1 | CA314451 | ERN1 | LAMA1 | NY-REN-7 | SNAI2 | |
| ATP10A | CA414006 | ERRFI1 | LDLR | ODC1 | SNTG2 | |
| ATP1A1 | CBLL1 | F2RL1 | LIFR | OLAH | SOCS2 | |
| ATP1A4 | CCDC4 | FAM13A1OS | LOC205251 | ORM1 | SPDEF | |
| ATRNL1 | CDC14B | FER1L3 | LOC401708 | ORM2 | SPDYA | |
| AUTS2 | CDC14C | FGD4 | LOC641467 | OTUD7B | SPINK5L3 | |
| AW029229 | CDYL2 | FKBP5 | LOC646282 | PACS1 | SPOCK1 | |

TABLE 6-continued

AR target gene list: Common upregulated genes upon DHT stimulation in
VCaP and LNCaP cells used for GSEA analysis shown in FIG. 6.

| AW389914 | CEBPD | FLJ31568 | LOC730498 | PDLIM5 | SPTB |
| AZGP1 | CENPN | FLJ39502 | LONRF1 | PECI | ST6GALNAC1 |

TABLE 7

GSEA showing loss of MYC signature (4 gene set) in AR-positive cells but
not AR-negative DU145 cells after JQ1 treatment.

| Sample | Gene set | Size | NES | P-value | FDR-q value |
|---|---|---|---|---|---|
| VCaP | MYC_UP.V1_UP | 113 | −2.265 | 0 | 0 |
| | SCHUHMACHER_MYC_TARGETS_UP | 70 | −2.275 | 0 | 0 |
| | SCHLOSSER_MYC_TARGETS_AND_SERUM_RESPONSE_UP | 39 | −1.824 | 0 | 0.028 |
| | SCHLOSSER_MYC_AND_SERUM_RESPONSE_SYNERGY | 28 | −1.818 | 0 | 0.029 |
| LNCaP | MYC_UP.V1_UP | 113 | −2.068 | 0 | 0.001 |
| | SCHUHMACHER_MYC_TARGETS_UP | 70 | −2.403 | 0 | 0 |
| | SCHLOSSER_MYC_TARGETS_AND_SERUM_RESPONSE_UP | 39 | −1.957 | 0 | 0.005 |
| | SCHLOSSER_MYC_AND_SERUM_RESPONSE_SYNERGY | 28 | −1.751 | 0 | 0.026 |
| 22RV1 | MYC_UP.V1_UP | 113 | −1.712 | 0 | 0.011 |
| | SCHUHMACHER_MYC_TARGETS_UP | 70 | −1.851 | 0 | 0.079 |
| | SCHLOSSER_MYC_TARGETS_AND_SERUM_RESPONSE_UP | 39 | −1.353 | 0.066 | 0.278 |
| | SCHLOSSER_MYC_AND_SERUM_RESPONSE_SYNERGY | 28 | −1.521 | 0.025 | 0.195 |
| DU145 | MYC_UP.V1_UP | 113 | −0.952 | 0.574 | 0.753 |
| | SCHUHMACHER_MYC_TARGETS_UP | 70 | −1.086 | 0.285 | 0.521 |
| | SCHLOSSER_MYC_TARGETS_AND_SERUM_RESPONSE_UP | 39 | −0.734 | 0.898 | 0.988 |
| | SCHLOSSER_MYC_AND_SERUM_RESPONSE_SYNERGY | 28 | −1.085 | 0.319 | 0.523 | size—number of genes in each set;
NES—normalized enrichment score;
p- and FDRq, test of statistical significance.

TABLE 8

High-throughput sequencing read information for ChIP libraries of
BRD2, BRD3, BRD4, AR, RNA Pol.II, ERG, H3K27ac and IgG.

| # | ChIP-seq sample | Total reads (millions) | Mapped reads (millions) | unique reads (millions) | % unique |
|---|---|---|---|---|---|
| 1 | BRD2_VEH | 57.15 | 51.32 | 50.78 | 88.86 |
| 2 | BRD2_JQ1 | 83.56 | 75.03 | 74.10 | 88.68 |
| 3 | BRD2_I-BET762 | 72.05 | 64.55 | 63.91 | 88.70 |
| 4 | BRD3_VEH | 50.59 | 46.55 | 46.11 | 91.14 |
| 5 | BRD3_JQ1 | 62.88 | 57.24 | 56.66 | 90.11 |
| 6 | BRD3_I-BET762 | 64.46 | 58.68 | 58.12 | 90.17 |
| 7 | BRD4_VEH | 68.56 | 66.93 | 64.24 | 93.69 |
| 8 | BRD4_JQ1 | 50.21 | 46.21 | 45.74 | 91.08 |
| 9 | BRD4_I-BET762 | 61.21 | 56.28 | 55.56 | 90.78 |
| 10 | AR_VEH_Exp.1 | 73.98 | 68.90 | 57.52 | 77.75 |
| 11 | AR_VEH_Exp.2 | 84.69 | 73.54 | 41.45 | 48.94 |
| 12 | AR_VEH_DHT_Exp.1 | 69.98 | 65.52 | 44.71 | 63.89 |
| 13 | AR_VEH_DHT_Exp.2 | 57.58 | 53.14 | 38.40 | 66.69 |
| 14 | AR_DHT_JQ1_Exp.1 | 73.86 | 69.74 | 64.23 | 86.97 |
| 15 | AR_DHT_JQ1_Exp.2 | 57.51 | 53.64 | 40.42 | 70.29 |
| 16 | AR_DHT_MDV3100_Exp.1 | 79.23 | 74.48 | 58.89 | 74.33 |
| 17 | AR_DHT_MDV3100_Exp.2 | 71.52 | 60.62 | 37.44 | 52.35 |
| 18 | AR_DHT_Bicalutamide_Exp.1 | 82.22 | 76.46 | 64.46 | 78.40 |
| 19 | AR_DHT_Bicalutamide_Exp.2 | 112.46 | 97.64 | 48.51 | 43.13 |
| 20 | BRD4_VEH | 34.31 | 32.50 | 30.60 | 89.20 |
| 21 | BRD4_DHT | 35.37 | 33.47 | 31.59 | 89.30 |
| 22 | BRD4_DHT_JQ1 | 36.16 | 34.07 | 32.81 | 90.75 |
| 23 | BRD4_DHT_MDV3100 | 41.23 | 38.29 | 37.25 | 90.34 |
| 24 | BRD4_DHT_Bicalutamide | 40.83 | 37.75 | 36.35 | 89.03 |
| 25 | RNA Pol II_VEH | 72.24 | 67.17 | 65.32 | 90.43 |
| 26 | RNA Pol II_DHT | 65.89 | 61.97 | 59.18 | 89.83 |
| 27 | RNA Pol II_DHT_JQ1 | 64.11 | 60.53 | 59.23 | 92.39 |
| 28 | RNA Pol II_DHT_MDV3100 | 65.18 | 62.01 | 60.60 | 92.97 |
| 29 | RNA Pol II_DHT_Bicalutamide | 69.77 | 65.88 | 63.96 | 91.67 |

TABLE 8-continued

High-throughput sequencing read information for ChIP libraries of BRD2, BRD3, BRD4, AR, RNA Pol.II, ERG, H3K27ac and IgG.

| # | ChIP-seq sample | Total reads (millions) | Mapped reads (millions) | unique reads (millions) | % unique |
|---|---|---|---|---|---|
| 30 | ERG_VEH_Exp.1 | 59.42 | 56.18 | 38.54 | 64.86 |
| 31 | ERG_VEH_Exp.2 | 50.79 | 49.20 | 45.53 | 89.64 |
| 32 | ERG_JQ1_Exp.1 | 62.22 | 59.81 | 50.07 | 80.48 |
| 33 | ERG_JQ1_Exp.2 | 55.83 | 52.71 | 38.56 | 69.07 |
| 34 | H3K27ac | 59.31 | 57.99 | 56.26 | 94.85 |
| 35 | IgG | 64.80 | 49.27 | 12.98 | 20.03 |

TABLE 9

PCR primers.

SYBR QPCR primers
BRD2_Fwd
BRD2_Rev
BRD3_Fwd
BRD3_Rev
BRD4_Fwd
BRD4_Rev
ERG_Fwd
ERG_Rev
PSA_Fwd
PSA_Rev
TMPRSS2_Fwd
TMPRSS2_Rev
FKBP5_Fwd
FKBP5_Rev
SLC45A3_Fwd
SLC45A3_Rev
MYC_Fwd
MYC_Rev
AR_Fwd
AR_Rev
ETV1_Fwd
ETV1_Rev
GAPDH_Fwd
GAPDH_Rev
gMYC dis.Enh_Fwd
gMYC dis.Enh_Rev
gMYC upstream_Fwd
gMYC upstream_Rev
TaqMan QPCR probe
TDRD1
CACNA1D
ARHGDIB
NDRG1
VCL
KRT8
MALAT1
BCL-XL
WNT2
CRISP3

TABLE 10

| Antibody | Use | Supplier | Cat. No. |
|---|---|---|---|
| AR_PG-21 | ChIP-seq | Millipore | 06-680 |
| AR | IP, IB | Abcam | ab74272 |
| RNA Pol II | IB, ChIP-seq | Abcam | ab5408 |
| BRD2 | IB | Abnova | PAB3245 |
| BRD2 | IB, ChIP-seq | Bethyl | A302-583A |
| BRD3 | IB | Santa Cruz | sc-81202 |
| BRD3 | IB, ChIP-seq | Bethyl | A302-368A |
| BRD4 | IB, ChIP-seq | Bethyl | A301-985A |
| ERG | IB | Epitomics | 2805-1 |
| MYC | IB | Sigma | M5546 |
| PSA | IB | Dako | A0562 |
| GST | IB | GE Life Science | 27-4577-01 |
| Halo | IP, IB | Promega | G9281 |
| Poly Histidine | IP, IB | Sigma | H1029 |
| BCL-X1 | IB | Cell Signaling | 2762 |
| cPARP | IB | Cell Signaling | 9541 |
| GAPDH(14C10) | IB | Cell Signaling | 3683S |

IP—Immunoprecipitation
IB—Immunoblot analysis
ChIP-seq—Chromatin Immunoprecipitation followed by sequencing

Having now fully described the methods, compounds, and compositions of matter provided herein, it will be understood by those of skill in the art that the same can be performed within a wide and equivalent range of conditions, formulations, and other parameters without affecting the scope of the methods, compounds, and compositions provided herein or any embodiment thereof. All patents, patent applications and publications cited herein are fully incorporated by reference herein in their entirety.

What is claimed is:

1. A method of treating a patient comprising administering to the patient a therapeutically effective amount of the compound having Formula I:

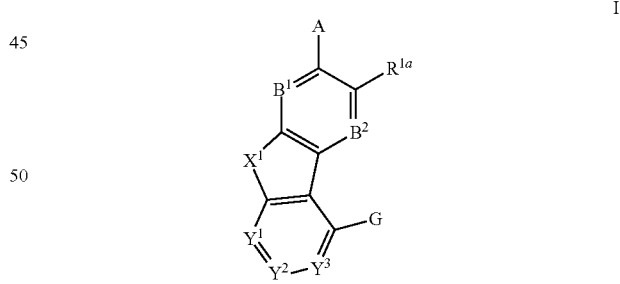

or a pharmaceutically acceptable salt, hydrate, or solvate thereof,
wherein:
$B^1$ is —C($R^{1b}$)—;
$B^2$ is —C($R^{1c}$)—;
$Y^1$ is selected from the group consisting of —C($R^{2a}$)= and —N=;
$Y^2$ is —C($R^{2b}$)=;
$Y^3$ is selected from the group consisting of —C($R^{2c}$)= and —N=;
G is —Z—$R^3$;
$R^{1a}$ is alkoxy;

$R^{1b}$ is selected from the group consisting of hydrogen and halo;

$R^{1c}$ is selected from the group consisting of hydrogen and fluoro;

$R^{2a}$ and $R^{2c}$ are hydrogen;

$R^{2b}$ is selected from the group consisting of hydrogen, amino, optionally substituted alkyl, hydroxyalkyl, alkoxyalkyl, heteroalkyl, (heterocyclo)alkyl, (amino)alkyl, optionally substituted cycloalkyl, optionally substituted heterocyclo, and carboxamido;

$R^3$ is selected from the group consisting of optionally substituted cycloalkyl, optionally substituted aryl, optionally substituted heteroaryl, and optionally substituted heterocyclo;

A is selected from the group consisting of

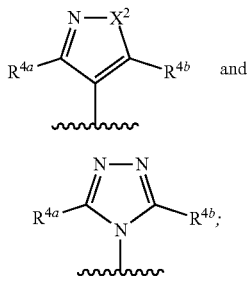

$X^2$ is selected from the group consisting of —O—, —S—, and —N($R^{5c1}$)—;

$R^{5c1}$ is selected from the group consisting of hydrogen and alkyl;

$R^{4a}$ and $R^{4b}$ are independently selected from the group consisting of hydrogen, halo, haloalkyl, and alkyl;

$X^1$ is —N($R^{5a1}$)—;

Z is selected from the group consisting of —C(=O)—, —O—, —S—, —SO$_2$—, and —N($R^{5b1}$)—;

$R^{5a1}$ is hydrogen; and $R^{5b1}$ is selected from the group consisting of hydrogen and alkyl, with the proviso:

at least one of $Y^1$ and $Y^3$ is —N=;

wherein the patient has a cancer selected from the group consisting of breast cancer, carcinoma, cervical cancer, colorectal cancer, esophageal cancer, glioblastoma multiforme, leukemia, lung cancer, lymphoma, multiple myeloma, neuroblastoma, ovarian cancer, and prostate cancer.

2. The method of claim 1, wherein the cancer is selected from the group consisting of acute monocytic leukemia, acute myelogenous leukemia, chronic myelogenous leukemia, chronic lymphocytic leukemia mixed lineage leukemia, NUT-midline carcinoma, multiple myeloma, small cell lung cancer, neuroblastoma, Burkitt's lymphoma, cervical cancer, esophageal cancer, ovarian cancer, colorectal cancer, prostate cancer, and breast cancer.

3. The method of claim 1, wherein the cancer is breast cancer having active androgen receptor signaling.

4. The method of claim 1, wherein the cancer is prostate cancer having active androgen receptor signaling.

5. The method of claim 1 further comprising administering a therapeutically effective amount of a second therapeutic agent useful in the treatment of breast cancer, carcinoma, cervical cancer, colorectal cancer, esophageal cancer, glioblastoma multiforme, leukemia, lung cancer, lymphoma, multiple myeloma, neuroblastoma, ovarian cancer, or prostate cancer.

6. The method of claim 1, wherein $X^2$ is —N($R^{5c1}$)—.

7. The method of claim 1, wherein Z is —NH—.

8. The method of claim 1, wherein $R^{2b}$ is alkyl.

9. The method of claim 1, wherein $Y^1$ is —N=.

10. The method of claim 7, wherein $R^3$ is optionally substituted heteroaryl.

11. The method of claim 1, wherein said compound having Formula I is selected from the group consisting of:
- 7-(3,5-dimethylisoxazol-4-yl)-6-methoxy-2-methyl-N-(3-methyl-1-phenyl-1H-pyrazol-5-yl)-9H-pyrimido[4,5-b]indol-4-amine;
- 7-(3,5-dimethylisoxazol-4-yl)-6-methoxy-2-methyl-N-(3-phenyl-1H-pyrazol-4-yl)-9H-pyrimido[4,5-b]indol-4-amine;
- 4-(4-((4-Isopropyl-5-methyl-4H-1,2,4-triazol-3-yl)thio)-6-methoxy-2-methyl-9H-pyrimido[4,5-b]indol-7-yl)-3,5-dimethylisoxazole;
- 7-(3,5-dimethylisoxazol-4-yl)-N-(1-isopropyl-5-methyl-3-phenyl-1H-pyrazol-4-yl)-6-methoxy-2-methyl-9H-pyrimido[4,5-b]indol-4-amine;
- 7-(3,5-dimethylisoxazol-4-yl)-6-methoxy-2-methyl-N-(5-methyl-4-phenyl-1H-pyrazol-3-yl)-9H-pyrimido[4,5-b]indol-4-amine;
- N-(7-(3,5-dimethylisoxazol-4-yl)-6-methoxy-2-methyl-9H-pyrimido[4,5-b]indol-4-yl)-2-(oxazol-2-yl)-4-phenylthiazol-5-amine;
- N-(1-(3-chlorophenyl)-3-methyl-1H-pyrazol-5-yl)-7-(3,5-dimethylisoxazol-4-yl)-6-methoxy-2-methyl-9H-pyrimido[4,5-b]indol-4-amine;
- N-(1,3-dimethyl-1H-pyrazol-5-yl)-7-(3,5-dimethylisoxazol-4-yl)-6-methoxy-2-methyl-9H-pyrimido[4,5-b]indol-4-amine;
- 7-(3,5-dimethylisoxazol-4-yl)-N-(1-isopropyl-3-methyl-1H-pyrazol-5-yl)-6-methoxy-2-methyl-9H-pyrimido[4,5-b]indol-4-amine;
- 7-(3,5-dimethylisoxazol-4-yl)-6-methoxy-2-methyl-N-(1-methyl-1H-pyrazolo[3,4-b]pyridin-3-yl)-9H-pyrimido[4,5-b]indol-4-amine;
- 7-(3,5-dimethylisoxazol-4-yl)-6-methoxy-2-methyl-N-(1-methyl-1H-pyrazolo[4,3-c]pyridin-3-yl)-9H-pyrimido[4,5-b]indol-4-amine;
- 7-(3,5-dimethylisoxazol-4-yl)-6-methoxy-2-methyl-N-(1-methyl-1H-indazol-3-yl)-9H-pyrimido[4,5-b]indol-4-amine;
- N-(5-chloro-1-methyl-1H-indazol-3-yl)-7-(3,5-dimethylisoxazol-4-yl)-6-methoxy-2-methyl-9H-pyrimido[4,5-b]indol-4-amine;
- 7-(3,5-dimethylisoxazol-4-yl)-6-methoxy-2-methyl-N-(pyrazolo[1,5-a]pyridin-3-yl)-9H-pyrimido[4,5-b]indol-4-amine;
- 7-(3,5-dimethylisoxazol-4-yl)-6-methoxy-2-methyl-N-(2-methylpyrazolo[i 5-a]pyridin-3-yl)-9H-pyrimido[4,5-b]indol-4-amine;
- 7-(3,5-dimethylisoxazol-4-yl)-6-methoxy-2-methyl-N-(pyrazolo[1,5-a]pyrimidin-3-yl)-9H-pyrimido[4,5-b]indol-4-amine;
- 7-(3,5-dimethylisoxazol-4-yl)-6-methoxy-N-(1-methyl-1H-indazol-3-yl)-9H-pyrimido[4,5-b]indol-4-amine;
- 7-(3,5-dimethylisoxazol-4-yl)-2-isopropyl-6-methoxy-N-(1-methyl-1H-indazol-3-yl)-9H-pyrimido[4,5-b]indol-4-amine;
- 7-(3,5-dimethylisoxazol-4-yl)-6-methoxy-N-(6-methoxy-1-methyl-1H-indazol-3-yl)-2-methyl-9H-pyrimido[4,5-b]indol-4-amine;

7-(3,5-dimethylisoxazol-4-yl)-6-methoxy-N-(1-methyl-1H-indazol-3-yl)-2-(tetrahydro-2H-pyran-4-yl)-9H-pyrimido[4,5-b]indol-4-amine;

7-(3,5-dimethylisoxazol-4-yl)-6-methoxy-2-methyl-N-(1-methyl-3-(trifluoromethyl)-1H-pyrazol-5-yl)-9H-pyrimido[4,5-b]indol-4-amine;

7-(3,5-dimethylisoxazol-4-yl)-N-(1-isopropyl-3-(trifluoromethyl)-1H-pyrazol-5-yl)-6-methoxy-2-methyl-9H-pyrimido[4,5-b]indol-4-amine;

4-(4-((2-chlorophenyl)thio)-6-methoxy-2-methyl-9H-pyrimido[4,5-b]indol-7-yl)-3,5-dimethylisoxazole;

4-(4-((3-chlorophenyl)thio)-6-methoxy-2-methyl-9H-pyrimido[4,5-b]indol-7-yl)-3,5-dimethylisoxazole;

4-(4-((2-isopropylphenyl)thio)-6-methoxy-2-methyl-9H-pyrimido[4,5-b]indol-7-yl)-3,5-dimethylisoxazole;

4-(4-((1H-indol-3-yl)thio)-6-methoxy-2-methyl-9H-pyrimido[4,5-b]indol-7-yl)-3,5-dimethylisoxazole;

4-(4-((3-(tert-butyl)phenyl)thio)-6-methoxy-2-methyl-9H-pyrimido[4,5-b]indol-7-yl)-3,5-dimethylisoxazole;

(R)—N-(chroman-4-yl)-7-(3,5-dimethylisoxazol-4-yl)-6-methoxy-2-methyl-9H-pyrimido[4,5-b]indol-4-amine;

7-(3,5-dimethylisoxazol-4-yl)-N-(1-isopropyl-1H-1,2,4-triazol-5-yl)-6-methoxy-2-methyl-9H-pyrimido[4,5-b]indol-4-amine;

N-(3-(tert-butyl)-1,5-dimethyl-1H-pyrazol-4-yl)-7-(3,5-dimethylisoxazol-4-yl)-6-methoxy-2-methyl-9H-pyrimido[4,5-b]indol-4-amine;

N-(5-(tert-butyl)-1,3-dimethyl-1H-pyrazol-4-yl)-7-(3,5-dimethylisoxazol-4-yl)-6-methoxy-2-methyl-9H-pyrimido[4,5-b]indol-4-amine;

7-(3,5-dimethylisoxazol-4-yl)-N-(4-isopropyl-1H-pyrazol-5-yl)-6-methoxy-2-methyl-9H-pyrimido[4,5-b]indol-4-amine;

4-(tert-butyl)-N-(7-(3,5-dimethylisoxazol-4-yl)-6-methoxy-2-methyl-9H-pyrimido[4,5-b]indol-4-yl)thiazol-5-amine;

N-(1,3-dimethyl-1H-pyrazol-4-yl)-7-(3,5-dimethylisoxazol-4-yl)-6-methoxy-2-methyl-9H-pyrimido[4,5-b]indol-4-amine;

7-(3,5-dimethylisoxazol-4-yl)-6-methoxy-2-methyl-N-(1,3,5-trimethyl-1H-pyrazol-4-yl)-9H-pyrimido[4,5-b]indol-4-amine;

7-(3,5-dimethylisoxazol-4-yl)-N-(1-isopropyl-3,5-dimethyl-1H-pyrazol-4-yl)-6-methoxy-2-methyl-9H-pyrimido[4,5-b]indol-4-amine;

7-(3,5-dimethylisoxazol-4-yl)-N-(1-isopropyl-4-methyl-1H-pyrazol-5-yl)-6-methoxy-2-methyl-9H-pyrimido[4,5-b]indol-4-amine;

3-(4-chlorophenyl)-N-(7-(3,5-dimethylisoxazol-4-yl)-6-methoxy-2-methyl-9H-pyrimido[4,5-b]indol-4-yl)-5-methylisoxazol-4-amine;

3-(3-chlorophenyl)-N-(7-(3,5-dimethylisoxazol-4-yl)-6-methoxy-2-methyl-9H-pyrimido[4,5-b]indol-4-yl)-5-methylisoxazol-4-amine;

4-(3-chlorophenyl)-N-(7-(3,5-dimethylisoxazol-4-yl)-6-methoxy-2-methyl-9H-pyrimido[4,5-b]indol-4-yl)-2-(oxazol-2-yl)thiazol-5-amine;

4-(4-chlorophenyl)-N-(7-(3,5-dimethylisoxazol-4-yl)-6-methoxy-2-methyl-9H-pyrimido[4,5-b]indol-4-yl)-2-(oxazol-2-yl)thiazol-5-amine;

7-(3,5-dimethylisoxazol-4-yl)-N-(1H-indol-3-yl)-6-methoxy-2-methyl-9H-pyrimido[4,5-b]indol-4-amine;

N-(7-(3,5-dimethylisoxazol-4-yl)-6-methoxy-2-methyl-9H-pyrimido[4,5-b]indol-4-yl)-2-isopropyl-4-phenylthiazol-5-amine;

7-(3,5-dimethylisoxazol-4-yl)-6-methoxy-2-methyl-N-(5-methyl-2-phenyl-1H-pyrrol-3-yl)-9H-pyrimido[4,5-b]indol-4-amine;

N-(2-(3-chlorophenyl)-5-methyl-1H-pyrrol-3-yl)-7-(3,5-dimethylisoxazol-4-yl)-6-methoxy-2-methyl-9H-pyrimido[4,5-b]indol-4-amine;

4-((7-(3,5-dimethylisoxazol-4-yl)-6-methoxy-2-methyl-9H-pyrimido[4,5-b]indol-4-yl)amino)-N,2-dimethyl-5-phenyl-1H-pyrrole-3-carboxamide;

(4-((7-(3,5-dimethylisoxazol-4-yl)-6-methoxy-2-methyl-9H-pyrimido[4,5-b]indol-4-yl)amino)-2-methyl-5-phenyl-1H-pyrrol-3-yl)(morpholino)methanone;

7-(3,5-dimethylisoxazol-4-yl)-6-methoxy-N-(5-methoxy-[1,1'-biphenyl]-2-yl)-2-methyl-9H-pyrimido[4,5-b]indol-4-amine;

N-(4'-chloro-5-methoxy-[1,1'-biphenyl]-2-yl)-7-(3,5-dimethylisoxazol-4-yl)-6-methoxy-2-methyl-9H-pyrimido[4,5-b]indol-4-amine;

N-(4-((dimethylamino)methyl)-5-methoxy-[1,1'-biphenyl]-2-yl)-7-(3,5-dimethylisoxazol-4-yl)-6-methoxy-2-methyl-9H-pyrimido[4,5-b]indol-4-amine;

7-(3,5-dimethylisoxazol-4-yl)-6-methoxy-2-methyl-N-(7-phenyl-2,3-dihydrobenzo[b][1,4]dioxin-6-yl)-9H-pyrimido[4,5-b]indol-4-amine;

N-(7-(3,5-dimethylisoxazol-4-yl)-6-methoxy-2-methyl-9H-pyrimido[4,5-b]indol-4-yl)-4-methyl-7-phenyl-3,4-dihydro-2H-benzo[b][1,4]oxazin-6-amine;

7-(3,5-dimethylisoxazol-4-yl)-6-methoxy-N-(6-methoxy-4-phenylpyridin-3-yl)-2-methyl-9H-pyrimido[4,5-b]indol-4-amine;

7-(3,5-dimethylisoxazol-4-yl)-6-methoxy-N-(4-methoxy-2-(pyridin-2-yl)phenyl)-2-methyl-9H-pyrimido[4,5-b]indol-4-amine;

7-(3,5-dimethylisoxazol-4-yl)-6-methoxy-N-(4-methoxy-2-(pyridin-4-yl)phenyl)-2-methyl-9H-pyrimido[4,5-b]indol-4-amine;

7-(3,5-dimethylisoxazol-4-yl)-6-methoxy-N-(4-methoxy-2-(oxazol-2-yl)phenyl)-2-methyl-9H-pyrimido[4,5-b]indol-4-amine;

7-(3,5-dimethylisoxazol-4-yl)-N-(4-ethoxynaphthalen-1-yl)-6-methoxy-2-methyl-9H-pyrimido[4,5-b]indol-4-amine 7-(3,5-dimethylisoxazol-4-yl)-N-(1H-indazol-3-yl)-6-methoxy-2-methyl-9H-pyrimido[4,5-b]indol-4-amine;

7-(3,5-dimethylisoxazol-4-yl)-N-(6-fluoro-1-methyl-1H-indazol-3-yl)-6-methoxy-2-methyl-9H-pyrimido[4,5-b]indol-4-amine;

7-(3,5-dimethylisoxazol-4-yl)-6-methoxy-N-(5-methoxy-1-methyl-1H-indazol-3-yl)-2-methyl-9H-pyrimido[4,5-b]indol-4-amine;

7-(3,5-dimethylisoxazol-4-yl)-N-(1H-indol-3-yl)-2-isopropyl-6-methoxy-9H-pyrimido[4,5-b]indol-4-amine;

N-(1-(tert-butyl)-3-methyl-1H-pyrazol-5-yl)-7-(3,5-dimethylisoxazol-4-yl)-6-methoxy-2-methyl-9H-pyrimido[4,5-b]indol-4-amine;

7-(3,5-dimethylisoxazol-4-yl)-2-isopropyl-N-(1-isopropyl-3-(trifluoromethyl)-1H-pyrazol-5-yl)-6-methoxy-9H-pyrimido[4,5-b]indol-4-amine;

7-(3,5-dimethylisoxazol-4-yl)-N-(3-isopropyl-1-methyl-1H-pyrazol-5-yl)-6-methoxy-2-methyl-9H-pyrimido[4,5-b]indol-4-amine;

2-(5-((7-(3,5-dimethylisoxazol-4-yl)-6-methoxy-2-methyl-9H-pyrimido[4,5-b]indol-4-yl)amino)-3-methyl-1H-pyrazol-1-yl)ethan-1-ol;

7-(3,5-dimethylisoxazol-4-yl)-6-methoxy-2-methyl-N-(3-methyl-1-(pyridin-4-yl)-1H-pyrazol-5-yl)-9H-pyrimido[4,5-b]indol-4-amine;

N-(1,3-dimethyl-1H-pyrazol-5-yl)-7-(3,5-dimethyl-4H-1,2,4-triazol-4-yl)-6-methoxy-2-methyl-9H-pyrimido[4,5-b]indol-4-amine;

7-(3,5-dimethyl-4H-1,2,4-triazol-4-yl)-6-methoxy-2-methyl-N-(1-methyl-1H-indazol-3-yl)-9H-pyrimido[4,5-b]indol-4-amine;

7-(3,5-dimethyl-4H-1,2,4-triazol-4-yl)-6-methoxy-2-methyl-N-(pyrazolo[1,5-a]pyridin-3-yl)-9H-pyrimido[4,5-b]indol-4-amine;

7-(3,5-dimethyl-1H-pyrazol-4-yl)-N-(1,3-dimethyl-1H-pyrazol-5-yl)-6-methoxy-2-methyl-9H-pyrimido[4,5-b]indol-4-amine;

7-(3,5-dimethylisoxazol-4-yl)-N-(1-isopropyl-3-methyl-1H-pyrazol-5-yl)-8-methoxy-5H-pyrido[4,3-b]indol-1-amine;

7-(3,5-dimethylisoxazol-4-yl)-2-isopropyl-N-(1-isopropyl-3-methyl-1H-pyrazol-5-yl)-6-methoxy-9H-pyrimido[4,5-b]indol-4-amine;

7-(3,5-dimethylisoxazol-4-yl)-N-(1-isopropyl-3-methyl-1H-pyrazol-5-yl)-6-methoxy-2-(tetrahydro-2H-pyran-4-yl)-9H-pyrimido[4,5-b]indol-4-amine;

7-(3,5-dimethylisoxazol-4-yl)-N-(1-isopropyl-3-methyl-1H-pyrazol-5-yl)-6-methoxy-9H-pyrimido[4,5-b]indol-4-amine;

N-(1,4-dimethyl-1H-pyrazol-5-yl)-7-(3,5-dimethylisoxazol-4-yl)-6-methoxy-2-methyl-9H-pyrimido[4,5-b]indol-4-amine;

N-(1,4-dimethyl-1H-pyrazol-3-yl)-7-(3,5-dimethylisoxazol-4-yl)-6-methoxy-2-methyl-9H-pyrimido[4,5-b]indol-4-amine;

7-(3,5-dimethylisoxazol-4-yl)-N-(4-isopropyl-1-methyl-1H-pyrazol-3-yl)-6-methoxy-2-methyl-9H-pyrimido[4,5-b]indol-4-amine;

7-(3,5-dimethylisoxazol-4-yl)-N-(4-isopropyl-1-methyl-1H-pyrazol-5-yl)-6-methoxy-2-methyl-9H-pyrimido[4,5-b]indol-4-amine;

7-(3,5-dimethylisoxazol-4-yl)-6-methoxy-2-methyl-N-(1,3,4-trimethyl-1H-pyrazol-5-yl)-9H-pyrimido[4,5-b]indol-4-amine;

7-(3,5-dimethylisoxazol-4-yl)-N-(1-isopropyl-3,4-dimethyl-1H-pyrazol-5-yl)-6-methoxy-2-methyl-9H-pyrimido[4,5-b]indol-4-amine;

N-(1,3-diisopropyl-1H-pyrazol-5-yl)-7-(3,5-dimethylisoxazol-4-yl)-6-methoxy-2-methyl-9H-pyrimido[4,5-b]indol-4-amine;

N-(7-(3,5-dimethylisoxazol-4-yl)-6-methoxy-2-methyl-9H-pyrimido[4,5-b]indol-4-yl)-4-isopropyl-2-methylthiazol-5-amine;

N-(7-(3,5-dimethylisoxazol-4-yl)-6-methoxy-2-methyl-9H-pyrimido[4,5-b]indol-4-yl)-4-methylthiazol-2-amine;

N-(7-(3,5-dimethylisoxazol-4-yl)-6-methoxy-2-methyl-9H-pyrimido[4,5-b]indol-4-yl)-5-methylthiazol-2-amine;

7-(3,5-dimethylisoxazol-4-yl)-N-(1-isopropyl-5-methyl-1H-imidazol-2-yl)-6-methoxy-2-methyl-9H-pyrimido[4,5-b]indol-4-amine;

7-(3,5-dimethylisoxazol-4-yl)-N-(1-isopropyl-4-methyl-1H-imidazol-2-yl)-6-methoxy-2-methyl-9H-pyrimido[4,5-b]indol-4-amine;

7-(3,5-dimethylisoxazol-4-yl)-N-(1-isopropyl-1H-imidazol-5-yl)-6-methoxy-2-methyl-9H-pyrimido[4,5-b]indol-4-amine;

N-(7-(3,5-dimethylisoxazol-4-yl)-6-methoxy-2-methyl-9H-pyrimido[4,5-b]indol-4-yl)-5-isopropyl-3-methylisoxazol-4-amine;

N-(7-(3,5-dimethylisoxazol-4-yl)-6-methoxy-2-methyl-9H-pyrimido[4,5-b]indol-4-yl)-3-isopropyl-5-methylisoxazol-4-amine;

N-(7-(3,5-dimethylisoxazol-4-yl)-6-methoxy-2-methyl-9H-pyrimido[4,5-b]indol-4-yl)-4-isopropyl-2-methyloxazol-5-amine;

4-(4-((3-chlorophenyl)sulfonyl)-6-methoxy-2-methyl-9H-pyrimido[4,5-b]indol-7-yl)-3,5-dimethylisoxazole;

4-(4-((4-isopropyl-4H-1,2,4-triazol-3-yl)sulfonyl)-6-methoxy-2-methyl-9H-pyrimido[4,5-b]indol-7-yl)-3,5-dimethylisoxazole;

4-(4-(3-chlorophenoxy)-6-methoxy-2-methyl-9H-pyrimido[4,5-b]indol-7-yl)-3,5-dimethylisoxazole;

4-(6-methoxy-2-methyl-4-(pyridin-3-yloxy)-9H-pyrimido[4,5-b]indol-7-yl)-3,5-dimethylisoxazole;

N-(3-chlorophenyl)-7-(3,5-dimethylisoxazol-4-yl)-6-methoxy-2-methyl-9H-pyrimido[4,5-b]indol-4-amine;

N-(7-(3,5-dimethylisoxazol-4-yl)-6-methoxy-2-methyl-9H-pyrimido[4,5-b]indol-4-yl)-5-methyl-3-phenylisoxazol-4-amine;

7-(3,5-dimethylisoxazol-4-yl)-N-(imidazo[1,2-a]pyridin-3-yl)-6-methoxy-2-methyl-9H-pyrimido[4,5-b]indol-4-amine;

7-(3,5-dimethylisoxazol-4-yl)-6-methoxy-N-(4-methoxynaphthalen-1-yl)-2-methyl-9H-pyrimido[4,5-b]indol-4-amine;

N-([1,2,4]triazolo[4,3-a]pyridin-3-yl)-7-(3,5-dimethylisoxazol-4-yl)-6-methoxy-2-methyl-9H-pyrimido[4,5-b]indol-4-amine;

7-(3,5-dimethylisoxazol-4-yl)-6-methoxy-2-methyl-N-(1H-pyrrolo[2,3-b]pyridin-3-yl)-9H-pyrimido[4,5-b]indol-4-amine;

N-(7-(3,5-dimethylisoxazol-4-yl)-6-methoxy-2-methyl-9H-pyrimido[4,5-b]indol-4-yl)thieno[2,3-b]pyridin-3-amine;

4-(6-methoxy-2-methyl-4-(quinolin-4-yloxy)-9H-pyrimido[4,5-b]indol-7-yl)-3,5-dimethylisoxazole;

4-(4-((5-bromopyridin-3-yl)oxy)-6-methoxy-2-methyl-9H-pyrimido[4,5-b]indol-7-yl)-3,5-dimethylisoxazole;

N-(5-chloropyridin-3-yl)-7-(3,5-dimethylisoxazol-4-yl)-6-methoxy-2-methyl-9H-pyrimido[4,5-b]indol-4-amine;

N-(3-chloro-4-fluorophenyl)-7-(3,5-dimethylisoxazol-4-yl)-6-methoxy-2-methyl-9H-pyrimido[4,5-b]indol-4-amine;

7-(3,5-dimethylisoxazol-4-yl)-6-methoxy-2-methyl-N-(5-methylpyridin-3-yl)-9H-pyrimido[4,5-b]indol-4-amine;

7-(3,5-dimethylisoxazol-4-yl)-6-methoxy-2-methyl-N-(4-methylpyridin-3-yl)-9H-pyrimido[4,5-b]indol-4-amine;

7-(3,5-dimethylisoxazol-4-yl)-6-methoxy-2-methyl-N-(4-methylpyridin-2-yl)-9H-pyrimido[4,5-b]indol-4-amine;

7-(3,5-dimethylisoxazol-4-yl)-6-methoxy-2-methyl-N-(6-methylpyridin-2-yl)-9H-pyrimido[4,5-b]indol-4-amine;

N-cyclohexyl-7-(3,5-dimethylisoxazol-4-yl)-6-methoxy-2-methyl-9H-pyrimido[4,5-b]indol-4-amine;

N-cyclopentyl-7-(3,5-dimethylisoxazol-4-yl)-6-methoxy-2-methyl-9H-pyrimido[4,5-b]indol-4-amine;

N-(1,5-dimethyl-1H-pyrazol-3-yl)-7-(3,5-dimethylisoxazol-4-yl)-6-methoxy-2-methyl-9H-pyrimido[4,5-b]indol-4-amine;

7-(3,5-dimethylisoxazol-4-yl)-N-(1-ethyl-3-methyl-1H-pyrazol-5-yl)-6-methoxy-2-methyl-9H-pyrimido[4,5-b]indol-4-amine;

N-(1-(tert-Butyl)-3-(trifluoromethyl)-1H-pyrazol-5-yl)-7-(3,5-dimethylisoxazol-4-yl)-6-methoxy-2-methyl-9H-pyrimido[4,5-b]indol-4-amine;

N-(1-cyclopentyl-3-methyl-1H-pyrazol-5-yl)-7-(3,5-dimethylisoxazol-4-yl)-6-methoxy-2-methyl-9H-pyrimido[4,5-b]indol-4-amine;

N-(1-cyclobutyl-3-methyl-1H-pyrazol-5-yl)-7-(3,5-dimethylisoxazol-4-yl)-6-methoxy-2-methyl-9H-pyrimido[4,5-b]indol-4-amine;

N-(3-tert-butyl-1-methyl-1H-pyrazol-5-yl)-7-(3,5-dimethylisoxazol-4-yl)-6-methoxy-2-methyl-9H-pyrimido[4,5-b]indol-4-amine;

N-(3-cyclopropyl-1-methyl-1H-pyrazol-5-yl)-7-(3,5-dimethylisoxazol-4-yl)-6-methoxy-2-methyl-9H-pyrimido[4,5-b]indol-4-amine;

7-(3,5-dimethylisoxazol-4-yl)-6-methoxy-2-methyl-N-(2-methyl-2,4,5,6-tetrahydrocyclopenta-[c]pyrazol-3-yl)-9H-pyrimido[4,5-b]indol-4-amine;

7-(3,5-dimethylisoxazol-4-yl)-6-methoxy-2-methyl-N-(1-methyl-1H-pyrazolo[4,3-b]pyridin-3-yl)-9H-pyrimido[4,5-b]indol-4-amine;

7-(3,5-dimethylisoxazol-4-yl)-6-methoxy-2-methyl-N-(1-methyl-4,5,6,7-tetrahydro-1H-indazol-3-yl)-9H-pyrimido[4,5-b]indol-4-amine;

7-(3,5-dimethylisoxazol-4-yl)-6-methoxy-2-methyl-N-(2-methyl-4,5,6,7-tetrahydro-2H-indazol-3-yl)-9H-pyrimido[4,5-b]indol-4-amine;

N-(3-(tert-butyl)-1H-pyrazol-5-yl)-7-(3,5-dimethylisoxazol-4-yl)-6-methoxy-2-methyl-9H-pyrimido[4,5-b]indol-4-amine;

7-(3,5-dimethylisoxazol-4-yl)-N-(5-fluoro-1-methyl-1H-indazol-3-yl)-6-methoxy-2-methyl-9H-pyrimido[4,5-b]indol-4-amine;

7-(3,5-dimethylisoxazol-4-yl)-N-(7-fluoro-1-methyl-1H-indazol-3-yl)-6-methoxy-2-methyl-9H-pyrimido[4,5-b]indol-4-amine;

2-(3-((7-(3,5-dimethylisoxazol-4-yl)-6-methoxy-2-methyl-9H-pyrimido[4,5-b]indol-4-yl)amino)-1H-indazol-1-yl)ethanol;

7-(3,5-dimethylisoxazol-4-yl)-N-(4-fluoro-1-methyl-1H-indazol-3-yl)-6-methoxy-2-methyl-9H-pyrimido[4,5-b]indol-4-amine;

3-(tert-butyl)-N-(7-(3,5-dimethylisoxazol-4-yl)-6-methoxy-2-methyl-9H-pyrimido[4,5-b]indol-4-yl)isothiazol-5-amine;

N-(5,6-dihydro-4H-pyrrolo[1,2-b]pyrazol-3-yl)-7-(3,5-dimethylisoxazol-4-yl)-6-methoxy-2-methyl-9H-pyrimido[4,5-b]indol-4-amine;

N-(1-cyclopentyl-4-methyl-1H-pyrazol-5-yl)-7-(3,5-dimethylisoxazol-4-yl)-6-methoxy-2-methyl-9H-pyrimido[4,5-b]indol-4-amine;

N-(3-cyclobutyl-1-methyl-1H-pyrazol-5-yl)-7-(3,5-dimethylisoxazol-4-yl)-6-methoxy-2-methyl-9H-pyrimido[4,5-b]indol-4-amine;

7-(3,5-dimethylisoxazol-4-yl)-N-(2-isopropyl-2,4,5,6-tetrahydrocyclopenta[c]pyrazol-3-yl)-6-methoxy-2-methyl-9H-pyrimido[4,5-b]indol-4-amine;

7-(3,5-dimethylisoxazol-4-yl)-N-(2-isopropyl-4,5,6,7-tetrahydro-2H-indazol-3-yl)-6-methoxy-2-methyl-9H-pyrimido[4,5-b]indol-4-amine;

7-(3,5-dimethylisoxazol-4-yl)-6-methoxy-2-methyl-N-(4,5,6,7-tetrahydropyrazolo[1,5-a]pyridin-3-yl)-9H-pyrimido[4,5-b]indol-4-amine;

N-(4-cyclopropyl-1,3-dimethyl-1H-pyrazol-5-yl)-7-(3,5-dimethylisoxazol-4-yl)-6-methoxy-2-methyl-9H-pyrimido[4,5-b]indol-4-amine;

7-(3,5-dimethylisoxazol-4-yl)-N-(2-ethyl-2,4,5,6-tetrahydrocyclopenta[c]pyrazol-3-yl)-6-methoxy-2-methyl-9H-pyrimido[4,5-b]indol-4-amine;

7-(3,5-dimethylisoxazol-4-yl)-N-(2-ethyl-4,5,6,7-tetrahydro-2H-indazol-3-yl)-6-methoxy-2-methyl-9H-pyrimido[4,5-b]indol-4-amine;

N-(4-cyclopropyl-1-ethyl-3-methyl-1H-pyrazol-5-yl)-7-(3,5-dimethylisoxazol-4-yl)-6-methoxy-2-methyl-9H-pyrimido[4,5-b]indol-4-amine;

N-(3-cyclopropyl-1-ethyl-1H-pyrazol-5-yl)-7-(3,5-dimethylisoxazol-4-yl)-6-methoxy-2-methyl-9H-pyrimido[4,5-b]indol-4-amine;

N-(3-cyclopropyl-1-ethyl-4-methyl-1H-pyrazol-5-yl)-7-(3,5-dimethylisoxazol-4-yl)-6-methoxy-2-methyl-9H-pyrimido[4,5-b]indol-4-amine;

7-(3,5-dimethylisoxazol-4-yl)-N-(1-ethyl-3-(trifluoromethyl)-1H-pyrazol-5-yl)-6-methoxy-2-methyl-9H-pyrimido[4,5-b]indol-4-amine;

N-(3-cyclopropyl-1,4-dimethyl-1H-pyrazol-5-yl)-7-(3,5-dimethylisoxazol-4-yl)-6-methoxy-2-methyl-9H-pyrimido[4,5-b]indol-4-amine;

N-(2-cyclopropyl-2,4,5,6-tetrahydrocyclopenta[c]pyrazol-3-yl)-7-(3,5-dimethylisoxazol-4-yl)-6-methoxy-2-methyl-9H-pyrimido[4,5-b]indol-4-amine;

N-(3-cyclopropyl-1-isopropyl-1H-pyrazol-5-yl)-7-(3,5-dimethylisoxazol-4-yl)-6-methoxy-2-methyl-9H-pyrimido[4,5-b]indol-4-amine;

2-(3-((7-(3,5-dimethylisoxazol-4-yl)-6-methoxy-2-methyl-9H-pyrimido[4,5-b]indol-4-yl)amino)-5,6-dihydrocyclopenta[c]pyrazol-2(4H)-yl)ethanol;

7-(3,5-dimethylisoxazol-4-yl)-N-(2-(2-fluoroethyl)-2,4,5,6-tetrahydrocyclopenta[c]pyrazol-3-yl)-6-methoxy-2-methyl-9H-pyrimido[4,5-b]indol-4-amine;

N-(1,3-dicyclopropyl-1H-pyrazol-5-yl)-7-(3,5-dimethylisoxazol-4-yl)-6-methoxy-2-methyl-9H-pyrimido[4,5-b]indol-4-amine;

N-(3-cyclopropyl-1H-pyrazol-5-yl)-7-(3,5-dimethylisoxazol-4-yl)-6-methoxy-2-methyl-9H-pyrimido[4,5-b]indol-4-amine;

1-(3-cyclopropyl-5-((7-(3,5-dimethylisoxazol-4-yl)-6-methoxy-2-methyl-9H-pyrimido[4,5-b]indol-4-yl)amino)-1H-pyrazol-1-yl)ethanone;

ethyl 3-cyclopropyl-5-((7-(3,5-dimethylisoxazol-4-yl)-6-methoxy-2-methyl-9H-pyrimido[4,5-b]indol-4-yl)amino)-1H-pyrazole-1-carboxylate;

N-(3-cyclopropyl-1-(2,2,2-trifluoroethyl)-1H-pyrazol-5-yl)-7-(3,5-dimethylisoxazol-4-yl)-6-methoxy-2-methyl-9H-pyrimido[4,5-b]indol-4-amine;

7-(3,5-dimethylisoxazol-4-yl)-6-methoxy-2-methyl-N-(2-(2,2,2-trifluoroethyl)-2,4,5,6-tetrahydrocyclopenta[c]pyrazol-3-yl)-9H-pyrimido[4,5-b]indol-4-amine;

2-(3-cyclopropyl-5-((7-(3,5-dimethylisoxazol-4-yl)-6-methoxy-2-methyl-9H-pyrimido[4,5-b]indol-4-yl)amino)-1H-pyrazol-1-yl)ethanol;

N-(3-cyclopropyl-1-(2-fluoroethyl)-1H-pyrazol-5-yl)-7-(3,5-dimethylisoxazol-4-yl)-6-methoxy-2-methyl-9H-pyrimido[4,5-b]indol-4-amine;

N-(3-cyclopropyl-1-(2-(dimethylamino)ethyl)-1H-pyrazol-5-yl)-7-(3,5-dimethylisoxazol-4-yl)-6-methoxy-2-methyl-9H-pyrimido[4,5-b]indol-4-amine;

7-(3,5-dimethylisoxazol-4-yl)-6-methoxy-2-methyl-N-(1-methyl-3-(1,1,1-trifluoro-2-methylpropan-2-yl)-1H-pyrazol-5-yl)-9H-pyrimido[4,5-b]indol-4-amine;

tert-butyl 3-(3-cyclopropyl-5-((7-(3,5-dimethylisoxazol-4-yl)-6-methoxy-2-methyl-9H-pyrimido[4,5-b]indol-4-yl)amino)-1H-pyrazol-1-yl)azetidine-1-carboxylate;

N-(1-(azetidin-3-yl)-3-cyclopropyl-1H-pyrazol-5-yl)-7-(3,5-dimethylisoxazol-4-yl)-6-methoxy-2-methyl-9H-pyrimido[4,5-b]indol-4-amine;

7-(3,5-dimethylisoxazol-4-yl)-6-methoxy-2-methyl-N-(1-methyl-1H-imidazol-4-yl)-9H-pyrimido[4,5-b]indol-4-amine;

7-(3,5-dimethylisoxazol-4-yl)-N-(3-ethyl-1,4-dimethyl-1H-pyrazol-5-yl)-6-methoxy-2-methyl-9H-pyrimido[4,5-b]indol-4-amine;

N-(1,5-dimethyl-1H-pyrazol-4-yl)-7-(3,5-dimethylisoxazol-4-yl)-6-methoxy-2-methyl-9H-pyrimido[4,5-b]indol-4-amine;

N-(1,2-dimethyl-1H-imidazol-5-yl)-7-(3,5-dimethylisoxazol-4-yl)-6-methoxy-2-methyl-9H-pyrimido[4,5-b]indol-4-amine;

7-(3,5-dimethylisoxazol-4-yl)-6-methoxy-2-methyl-N-(1-methyl-1H-pyrazol-5-yl)-9H-pyrimido[4,5-b]indol-4-amine;

7-(3,5-dimethylisoxazol-4-yl)-N-(1-ethyl-1H-pyrazol-5-yl)-6-methoxy-2-methyl-9H-pyrimido[4,5-b]indol-4-amine;

5-((7-(3,5-dimethylisoxazol-4-yl)-6-methoxy-2-methyl-9H-pyrimido[4,5-b]indol-4-yl)amino)-1-methyl-1H-pyrazole-4-carbonitrile;

7-(3,5-dimethylisoxazol-4-yl)-N-(1-isopropyl-1H-pyrazol-5-yl)-6-methoxy-2-methyl-9H-pyrimido[4,5-b]indol-4-amine;

7-(3,5-dimethylisoxazol-4-yl)-N-(1-ethyl-4-methyl-1H-pyrazol-5-yl)-6-methoxy-2-methyl-9H-pyrimido[4,5-b]indol-4-amine;

N-(7-(3,5-dimethylisoxazol-4-yl)-6-methoxy-2-methyl-9H-pyrimido[4,5-b]indol-4-yl)-2,4-dimethylthiazol-5-amine;

N-(1-cyclopentyl-1H-pyrazol-5-yl)-7-(3,5-dimethylisoxazol-4-yl)-6-methoxy-2-methyl-9H-pyrimido[4,5-b]indol-4-amine;

7-(3,5-dimethylisoxazol-4-yl)-6-methoxy-2-methyl-N-(1-methyl-3-(trifluoromethyl)-1H-pyrazol-4-yl)-9H-pyrimido[4,5-b]indol-4-amine;

7-(3,5-dimethylisoxazol-4-yl)-N-(3-isopropyl-1-methyl-1H-pyrazol-4-yl)-6-methoxy-2-methyl-9H-pyrimido[4,5-b]indol-4-amine;

7-(3,5-dimethylisoxazol-4-yl)-N-(3-ethyl-1-methyl-1H-pyrazol-4-yl)-6-methoxy-2-methyl-9H-pyrimido[4,5-b]indol-4-amine;

N-(1-(tert-butyl)-1H-pyrazol-5-yl)-7-(3,5-dimethylisoxazol-4-yl)-6-methoxy-2-methyl-9H-pyrimido[4,5-b]indol-4-amine;

N-(1-(tert-butyl)-3,4-dimethyl-1H-pyrazol-5-yl)-7-(3,5-dimethylisoxazol-4-yl)-6-methoxy-2-methyl-9H-pyrimido[4,5-b]indol-4-amine;

7-(3,5-dimethylisoxazol-4-yl)-N-(1-ethyl-3,4-dimethyl-1H-pyrazol-5-yl)-6-methoxy-2-methyl-9H-pyrimido[4,5-b]indol-4-amine;

N-(1-cyclobutyl-3,4-dimethyl-1H-pyrazol-5-yl)-7-(3,5-dimethylisoxazol-4-yl)-6-methoxy-2-methyl-9H-pyrimido[4,5-b]indol-4-amine;

N-(1-cyclopropyl-3,4-dimethyl-1H-pyrazol-5-yl)-7-(3,5-dimethylisoxazol-4-yl)-6-methoxy-2-methyl-9H-pyrimido[4,5-b]indol-4-amine;

N-(7-(3,5-dimethylisoxazol-4-yl)-6-methoxy-2-methyl-9H-pyrimido[4,5-b]indol-4-yl)-2-isopropyl-4-methylthiazol-5-amine;

N-(1-cyclopropyl-3-methyl-1H-pyrazol-5-yl)-7-(3,5-dimethylisoxazol-4-yl)-6-methoxy-2-methyl-9H-pyrimido[4,5-b]indol-4-amine;

N-(3-(tert-butyl)-1-methyl-1H-pyrazol-4-yl)-7-(3,5-dimethylisoxazol-4-yl)-6-methoxy-2-methyl-9H-pyrimido[4,5-b]indol-4-amine;

7-(3,5-dimethylisoxazol-4-yl)-N-(3-isopropyl-1,5-dimethyl-1H-pyrazol-4-yl)-6-methoxy-2-methyl-9H-pyrimido[4,5-b]indol-4-amine;

N-(3-cyclopropyl-1-methyl-1H-pyrazol-4-yl)-7-(3,5-dimethylisoxazol-4-yl)-6-methoxy-2-methyl-9H-pyrimido[4,5-b]indol-4-amine;

N-(1-(tert-butyl)-4-methyl-1H-pyrazol-5-yl)-7-(3,5-dimethylisoxazol-4-yl)-6-methoxy-2-methyl-9H-pyrimido[4,5-b]indol-4-amine;

N-(1-cyclopropyl-4-methyl-1H-pyrazol-5-yl)-7-(3,5-dimethylisoxazol-4-yl)-6-methoxy-2-methyl-9H-pyrimido[4,5-b]indol-4-amine;

N-(1-cyclobutyl-4-methyl-1H-pyrazol-5-yl)-7-(3,5-dimethylisoxazol-4-yl)-6-methoxy-2-methyl-9H-pyrimido[4,5-b]indol-4-amine;

7-(3,5-dimethylisoxazol-4-yl)-N-(1-ethyl-3-isopropyl-1H-pyrazol-4-yl)-6-methoxy-2-methyl-9H-pyrimido[4,5-b]indol-4-amine;

N-(3-cyclobutyl-1-methyl-1H-pyrazol-4-yl)-7-(3,5-dimethylisoxazol-4-yl)-6-methoxy-2-methyl-9H-pyrimido[4,5-b]indol-4-amine;

N-(3-cyclobutyl-1-ethyl-1H-pyrazol-4-yl)-7-(3,5-dimethylisoxazol-4-yl)-6-methoxy-2-methyl-9H-pyrimido[4,5-b]indol-4-amine;

2-(tert-butyl)-N-(7-(3,5-dimethylisoxazol-4-yl)-6-methoxy-2-methyl-9H-pyrimido[4,5-b]indol-4-yl)-4-methylthiazol-5-amine;

7-(3,5-dimethylisoxazol-4-yl)-N-(1-ethyl-3-isopropyl-1H-pyrazol-5-yl)-6-methoxy-2-methyl-9H-pyrimido[4,5-b]indol-4-amine;

N-(1-cyclopropyl-3-isopropyl-1H-pyrazol-5-yl)-7-(3,5-dimethylisoxazol-4-yl)-6-methoxy-2-methyl-9H-pyrimido[4,5-b]indol-4-amine;

N4-(3-cyclopropyl-1-methyl-1H-pyrazol-5-yl)-7-(3,5-dimethylisoxazol-4-yl)-6-methoxy-9H-pyrimido[4,5-b]indole-2,4-diamine;

N-(3-cyclopropyl-1-methyl-1H-pyrazol-5-yl)-7-(3,5-dimethylisoxazol-4-yl)-6-methoxy-2-(methoxymethyl)-9H-pyrimido[4,5-b]indol-4-amine;

7-(3,5-dimethylisoxazol-4-yl)-6-methoxy-2-methyl-N-(quinolin-8-yl)-9H-pyrimido[4,5-b]indol-4-amine;

7-(3,5-dimethylisoxazol-4-yl)-6-methoxy-2-methyl-N-(quinolin-5-yl)-9H-pyrimido[4,5-b]indol-4-amine;

7-(3,5-dimethylisoxazol-4-yl)-6-methoxy-2-methyl-N-m-tolyl-9H-pyrimido[4,5-b]indol-4-amine;

7-(3,5-dimethylisoxazol-4-yl)-6-methoxy-N-(3-methoxyphenyl)-2-methyl-9H-pyrimido[4,5-b] in do l-4-amine;

7-(3,5-dimethylisoxazol-4-yl)-6-methoxy-2-methyl-N-(3-(trifluoromethyl)phenyl)-9H-pyrimido[4,5-b]indol-4-amine;

N-(7-(3,5-dimethylisoxazol-4-yl)-6-methoxy-2-methyl-9H-pyrimido[4,5-b]indol-4-yl)-3,5-dimethylisoxazol-4-amine;

7-(3,5-dimethylisoxazol-4-yl)-N-(3-ethylphenyl)-6-methoxy-2-methyl-9H-pyrimido[4,5-b]indol-4-amine;

N-(3-chloro-2-fluorophenyl)-7-(3,5-dimethylisoxazol-4-yl)-6-methoxy-2-methyl-9H-pyrimido[4,5-b]indol-4-amine;

7-(3,5-dimethylisoxazol-4-yl)-6-methoxy-N-(3-methoxy-5-methylphenyl)-2-methyl-9H-pyrimido[4,5-b]indol-4-amine;

N-(7-(3,5-dimethylisoxazol-4-yl)-6-methoxy-2-methyl-9H-pyrimido[4,5-b]indol-4-yl)-3,4-dimethylisoxazol-5-amine;

7-(3,5-dimethylisoxazol-4-yl)-N-(1H-indol-4-yl)-6-methoxy-2-methyl-9H-pyrimido[4,5-b]indol-4-amine;

7-(3,5-dimethylisoxazol-4-yl)-N-(isoquinolin-5-yl)-6-methoxy-2-methyl-9H-pyrimido[4,5-b]indol-4-amine;

N-(7-(3,5-dimethylisoxazol-4-yl)-6-methoxy-2-methyl-9H-pyrimido[4,5-b]indol-4-yl)-4,5-dimethylisoxazol-3-amine;

7-(3,5-dimethylisoxazol-4-yl)-N-(isoquinolin-8-yl)-6-methoxy-2-methyl-9H-pyrimido[4,5-b]indol-4-amine;

N-(5-chloro-2-fluorophenyl)-7-(3,5-dimethylisoxazol-4-yl)-6-methoxy-2-methyl-9H-pyrimido[4,5-b]indol-4-amine;

N-(3-chloro-5-fluorophenyl)-7-(3,5-dimethylisoxazol-4-yl)-6-methoxy-2-methyl-9H-pyrimido[4,5-b]indol-4-amine;

7-(3,5-dimethylisoxazol-4-yl)-6-methoxy-2-methyl-N-phenyl-9H-pyrimido[4,5-b]indol-4-amine;

7-(3,5-dimethylisoxazol-4-yl)-6-methoxy-2-methyl-N-(1-methyl-1H-pyrrolo[2,3-b]pyridin-3-yl)-9H-pyrimido[4,5-b]indol-4-amine;

7-(3,5-dimethylisoxazol-4-yl)-6-methoxy-2-methyl-N-(2-methylquinolin-5-yl)-9H-pyrimido[4,5-b]indol-4-amine;

N-(7-(3,5-dimethylisoxazol-4-yl)-6-methoxy-2-methyl-9H-pyrimido[4,5-b]indol-4-yl)benzo[d]thiazol-7-amine;

N1-(7-(3,5-dimethylisoxazol-4-yl)-6-methoxy-2-methyl-9H-pyrimido[4,5-b]indol-4-yl)-N3,N3-dimethylbenzene-1,3-diamine;

7-(3,5-dimethylisoxazol-4-yl)-N-(indolin-4-yl)-6-methoxy-2-methyl-9H-pyrimido[4,5-b]indol-4-amine;

7-(3,5-dimethylisoxazol-4-yl)-6-methoxy-2-methyl-N-(1-methylindolin-6-yl)-9H-pyrimido[4,5-b]indol-4-amine;

7-(3,5-dimethylisoxazol-4-yl)-N-(11H-indol-6-yl)-6-methoxy-2-methyl-9H-pyrimido[4,5-b]indol-4-amine;

N-(2,3-dihydrobenzofuran-4-yl)-7-(3,5-dimethylisoxazol-4-yl)-6-methoxy-2-methyl-9H-pyrimido[4,5-b]indol-4-amine;

7-(3,5-dimethylisoxazol-4-yl)-6-methoxy-2-methyl-N-(1-methyl-1H-indazol-4-yl)-9H-pyrimido[4,5-b]indol-4-amine;

7-(3,5-dimethylisoxazol-4-yl)-6-methoxy-2-methyl-N-(1-methyl-1H-indol-4-yl)-9H-pyrimido[4,5-b]indol-4-amine;

7-(3,5-dimethylisoxazol-4-yl)-N-(3,5-dimethylphenyl)-6-methoxy-2-methyl-9H-pyrimido[4,5-b]indol-4-amine;

7-(3,5-dimethylisoxazol-4-yl)-N-(2,5-dimethylphenyl)-6-methoxy-2-methyl-9H-pyrimido[4,5-b]indol-4-amine;

N-(3,5-dicyclopropyl-1-methyl-1H-pyrazol-4-yl)-7-(3,5-dimethylisoxazol-4-yl)-6-methoxy-2-methyl-9H-pyrimido[4,5-b]indol-4-amine;

N-(3,5-diethyl-1-methyl-1H-pyrazol-4-yl)-7-(3,5-dimethylisoxazol-4-yl)-6-methoxy-2-methyl-9H-pyrimido[4,5-b]indol-4-amine;

7-(3,5-dimethylisoxazol-4-yl)-6-methoxy-2-methyl-N-(1,3,5-methyl-1H-pyrazol-4-yl)-9H-pyrimido[4,5-b]indol-4-amine;

N-(3,5-diisopropyl-1-methyl-1H-pyrazol-4-yl)-7-(3,5-dimethylisoxazol-4-yl)-6-methoxy-2-methyl-9H-pyrimido[4,5-b]indol-4-amine;

7-(3,5-dimethylisoxazol-4-yl)-N-(2-isopropylphenyl)-6-methoxy-2-methyl-9H-pyrimido[4,5-b]indol-4-amine;

7-(3,5-dimethylisoxazol-4-yl)-6-methoxy-2-methyl-N-(quinolin-4-yl)-9H-pyrimido[4,5-b]indol-4-amine;

7-(3,5-dimethylisoxazol-4-yl)-6-methoxy-2-methyl-N-(2-methylpyridin-4-yl)-9H-pyrimido[4,5-b]indol-4-amine;

N-(3-cyclopropyl-4-fluoro-1-methyl-1H-pyrazol-5-yl)-7-(3,5-dimethylisoxazol-4-yl)-6-methoxy-2-methyl-9H-pyrimido[4,5-b]indol-4-amine;

N-(3-cyclopropyl-1-ethyl-4-fluoro-1H-pyrazol-5-yl)-7-(3,5-dimethylisoxazol-4-yl)-6-methoxy-2-methyl-9H-pyrimido[4,5-b]indol-4-amine;

7-(3,5-dimethylisoxazol-4-yl)-6-methoxy-2-methyl-N-(1-methyl-3-(1-methylcyclopropyl)-1H-pyrazol-5-yl)-9H-pyrimido[4,5-b]indol-4-amine;

7-(3,5-dimethylisoxazol-4-yl)-N-(1-ethyl-3-(1-methylcyclopropyl)-1H-pyrazol-5-yl)-6-methoxy-2-methyl-9H-pyrimido[4,5-b]indol-4-amine;

7-(3,5-dimethylisoxazol-4-yl)-N-(1-isopropyl-3-(1-methylcyclopropyl)-1H-pyrazol-5-yl)-6-methoxy-2-methyl-9H-pyrimido[4,5-b]indol-4-amine;

N-(3-cyclopropyl-4-fluoro-1-isopropyl-1H-pyrazol-5-yl)-7-(3,5-dimethylisoxazol-4-yl)-6-methoxy-2-methyl-9H-pyrimido[4,5-b]indol-4-amine;

N-(3-cyclopropyl-1-methyl-1H-pyrazol-5-yl)-7-(3,5-dimethylisoxazol-4-yl)-8-methoxy-5H-pyrido[4,3-b]indol-1-amine;

N-(1-cyclopentyl-3-methyl-1H-pyrazol-5-yl)-7-(3,5-dimethylisoxazol-4-yl)-8-methoxy-5H-pyrido[4,3-b]indol-1-amine;

7-(3,5-dimethylisoxazol-4-yl)-8-methoxy-N-(1-methyl-1H-pyrazolo[3,4-b]pyridin-3-yl)-5H-pyrido[4,3-b]indol-1-amine;

N-(3-cyclopropyl-1-(1-methylazetidin-3-yl)-1H-pyrazol-5-yl)-7-(3,5-dimethylisoxazol-4-yl)-6-methoxy-N,2,9-trimethyl-9H-pyrimido[4,5-b]indol-4-amine;

7-(3,5-dimethylisoxazol-4-yl)-6-methoxy-2-methyl-N-(1H-pyrrolo[2,3-c]pyridin-3-yl)-9H-pyrimido[4,5-b]indol-4-amine;

7-(3,5-dimethylisoxazol-4-yl)-6-methoxy-N-(3-(1-methoxycyclopropyl)-1-methyl-1H-pyrazol-5-yl)-2-methyl-9H-pyrimido[4,5-b]indol-4-amine;

7-(3,5-dimethylisoxazol-4-yl)-6-methoxy-2-methyl-N-(1-methyl-3-(1-(trifluoromethyl)cyclopropyl)-1H-pyrazol-5-yl)-9H-pyrimido[4,5-b]indol-4-amine;

2-(3-cyclopropyl-5-((7-(3,5-dimethylisoxazol-4-yl)-6-methoxy-2-methyl-9H-pyrimido[4,5-b]indol-4-yl)amino)-1H-pyrazol-1-yl)-N-ethylacetamide;

N-(3-cyclopropyl-1-(piperidin-4-yl)-1H-pyrazol-5-yl)-7-(3,5-dimethylisoxazol-4-yl)-6-methoxy-2-methyl-9H-pyrimido[4,5-b]indol-4-amine;

N-(3-cyclopropyl-1-(1-ethylpiperidin-4-yl)-1H-pyrazol-5-yl)-7-(3,5-dimethylisoxazol-4-yl)-6-methoxy-2-methyl-9H-pyrimido[4,5-b]indol-4-amine;

1-(4-(3-cyclopropyl-5-(7-(3,5-dimethylisoxazol-4-yl)-6-methoxy-2-methyl-9H-pyrimido[4,5-b]indol-4-ylamino)-1H-pyrazol-1-yl)piperidin-1-yl)ethanone;

N-(3-cyclopropyl-1-(2-methoxyethyl)-1H-pyrazol-5-yl)-7-(3,5-dimethylisoxazol-4-yl)-6-methoxy-2-methyl-9H-pyrimido[4,5-b]indol-4-amine;

N-(3-cyclopropyl-1-(1-methylpiperidin-4-yl)-1H-pyrazol-5-yl)-7-(3,5-dimethylisoxazol-4-yl)-6-methoxy-2-methyl-9H-pyrimido[4,5-b]indol-4-amine;

1-(4-(7-(3,5-dimethylisoxazol-4-yl)-6-methoxy-2-methyl-9H-pyrimido[4,5-b]indol-4-ylamino)-1-methyl-1H-pyrazol-3-yl)ethanone;

2-(4-(7-(3,5-dimethylisoxazol-4-yl)-6-methoxy-2-methyl-9H-pyrimido[4,5-b]indol-4-ylamino)-1-methyl-1H-pyrazol-3-yl)propan-2-ol;

N-(3-tert-butyl-1,5-dimethyl-1H-pyrazol-4-yl)-7-(3,5-dimethylisoxazol-4-yl)-6-methoxy-2-methyl-9H-pyrimido[4,5-b]indol-4-amine;

methyl 5-(7-(3,5-dimethylisoxazol-4-yl)-6-methoxy-2-methyl-9H-pyrimido[4,5-b]indol-4-ylamino)-1-methyl-1H-pyrazole-3-carboxylate;

7-(3,5-dimethylisoxazol-4-yl)-6-methoxy-2-methyl-N-(1-methyl-3-(prop-1-en-2-yl)-1H-pyrazol-5-yl)-9H-pyrimido[4,5-b]indol-4-amine;

N-(3-cyclopropyl-1-methyl-1H-pyrazol-5-yl)-7-(3,5-dimethylisoxazol-4-yl)-6-methoxy-2-(2-methoxyethyl)-9H-pyrimido[4,5-b]indol-4-amine;

N-(3-cyclopropyl-1-methyl-1H-pyrazol-5-yl)-7-(3,5-dimethylisoxazol-4-yl)-6-methoxy-2-((2-methoxyethoxy)methyl)-9H-pyrimido[4,5-b]indol-4-amine;

1-(3-(3-cyclopropyl-5-(7-(3,5-dimethylisoxazol-4-yl)-6-methoxy-2-methyl-9H-pyrimido[4,5-b]indol-4-ylamino)-1H-pyrazol-1-yl)azetidin-1-yl)ethanone;

methyl 3-(3-cyclopropyl-5-(7-(3,5-dimethylisoxazol-4-yl)-6-methoxy-2-methyl-9H-pyrimido[4,5-b]indol-4-ylamino)-1H-pyrazol-1-yl)azetidine-1-carboxylate;

N-(3-cyclopropyl-1-(1-ethylazetidin-3-yl)-1H-pyrazol-5-yl)-7-(3,5-dimethylisoxazol-4-yl)-6-methoxy-2-methyl-9H-pyrimido[4,5-b]indol-4-amine;

(2S)-4-(3-cyclopropyl-5-(7-(3,5-dimethylisoxazol-4-yl)-6-methoxy-2-methyl-9H-pyrimido[4,5-b]indol-4-ylamino)-1H-pyrazol-1-yl)butane-1,2-diol;

(S)-3-(3-cyclopropyl-5-((7-(3,5-dimethylisoxazol-4-yl)-6-methoxy-2-methyl-9H-pyrimido[4,5-b]indol-4-yl)amino)-1H-pyrazol-1-yl)propane-1,2-diol;

N-(1-((1,4-dioxan-2-yl)methyl)-3-cyclopropyl-1H-pyrazol-5-yl)-7-(3,5-dimethylisoxazol-4-yl)-6-methoxy-2-methyl-9H-pyrimido[4,5-b]indol-4-amine;

N-(3-cyclopropyl-1-(tetrahydro-2H-pyran-4-yl)-1H-pyrazol-5-yl)-7-(3,5-dimethylisoxazol-4-yl)-6-methoxy-2-methyl-9H-pyrimido[4,5-b]indol-4-amine;

N-(3-cyclopropyl-1-(2-morpholinoethyl)-1H-pyrazol-5-yl)-7-(3,5-dimethylisoxazol-4-yl)-6-methoxy-2-methyl-9H-pyrimido[4,5-b]indol-4-amine;

N-(3-cyclopropyl-1-ethyl-1H-pyrazol-5-yl)-7-(3,5-dimethylisoxazol-4-yl)-8-methoxy-5H-pyrido[4,3-b]indol-1-amine;

7-(3,5-dimethylisoxazol-4-yl)-N-(2-isopropyl-2,4,5,6-tetrahydrocyclopenta[c]pyrazol-3-yl)-8-methoxy-5H-pyrido[4,3-b]indol-1-amine;

N-(3-cyclopropyl-1-methyl-1H-pyrazol-5-yl)-7-(3,5-dimethylisoxazol-4-yl)-6-methoxy-2-(2-methoxyethyl)-9H-pyrimido[4,5-b]indol-4-amine;

N-(3-cyclopropyl-1-methyl-1H-pyrazol-5-yl)-7-(3,5-dimethylisoxazol-4-yl)-6-methoxy-2-((2-methoxyethoxy)methyl)-9H-pyrimido[4,5-b]indol-4-amine;

N-(3-cyclopropyl-1-methyl-1H-pyrazol-5-yl)-7-(3,5-dimethylisoxazol-4-yl)-6-methoxy-2-((methylsulfonyl)methyl)-9H-pyrimido[4,5-b]indol-4-amine;

N4-(3-cyclopropyl-1-ethyl-1H-pyrazol-5-yl)-7-(3,5-dimethylisoxazol-4-yl)-6-methoxy-9H-pyrimido[4,5-b]indole-2,4-diamine;

N4-(1,3-dicyclopropyl-1H-pyrazol-5-yl)-7-(3,5-dimethylisoxazol-4-yl)-6-methoxy-9H-pyrimido[4,5-b]indole-2,4-diamine;

7-(3,5-dimethylisoxazol-4-yl)-N4-(2-isopropyl-2,4,5,6-tetrahydrocyclopenta[c]pyrazol-3-yl)-6-methoxy-9H-pyrimido[4,5-b]indole-2,4-diamine;

3-(3-cyclopropyl-5-((7-(3,5-dimethylisoxazol-4-yl)-6-methoxy-2-methyl-9H-pyrimido[4,5-b]indol-4-yl)amino)-1H-pyrazol-1-yl)azetidine-1-carbaldehyde;

N-(3-cyclopropyl-1-(oxetan-3-ylmethyl)-1H-pyrazol-5-yl)-7-(3,5-dimethylisoxazol-4-yl)-6-methoxy-2-methyl-9H-pyrimido[4,5-b]indol-4-amine;

N-(3-cyclopropyl-1-(2-(methylsulfonyl)ethyl)-1H-pyrazol-5-yl)-7-(3,5-dimethylisoxazol-4-yl)-6-methoxy-2-methyl-9H-pyrimido[4,5-b]indol-4-amine;

N-(3-cyclopropyl-1-methyl-1H-pyrazol-5-yl)-7-(3,5-dimethylisoxazol-4-yl)-6-methoxy-2-methyl-9H-pyrido[3',2':4,5]pyrrolo[2,3-d]pyrimidin-4-amine;

N-(3-cyclopropyl-1-methyl-1H-pyrazol-5-yl)-7-(3,5-dimethylisoxazol-4-yl)-5-fluoro-6-methoxy-2-methyl-9H-pyrimido[4,5-b]indol-4-amine;

N-(3-cyclopropyl-1-methyl-1H-pyrazol-5-yl)-7-(3,5-dimethylisoxazol-4-yl)-5-fluoro-6-methoxy-N,2-dimethyl-9H-pyrimido[4,5-b]indol-4-amine;

N-(3-cyclopropyl-1-methyl-1H-pyrazol-5-yl)-7-(3,5-dimethylisoxazol-4-yl)-8-fluoro-6-methoxy-2-methyl-9H-pyrimido[4,5-b]indol-4-amine;

N-(3-cyclopropyl-1-methyl-1H-pyrazol-5-yl)-7-(3,5-dimethylisoxazol-4-yl)-8-fluoro-6-methoxy-N,2-dimethyl-9H-pyrimido[4,5-b]indol-4-amine;

N-(3-cyclopropyl-1-methyl-1H-pyrazol-5-yl)-7-(3,5-dimethylisoxazol-4-yl)-6-fluoro-8-methoxy-5H-pyrido[4,3-b]indol-1-amine;

N-(1-(tert-butyl)-3-methyl-11H-pyrazol-5-yl)-7-(3,5-dimethylisoxazol-4-yl)-6-methoxy-2-methyl-9H-pyrido[2',3':4,5]pyrrolo[2,3-d]pyrimidin-4-amine;

7-(3,5-dimethylisoxazol-4-yl)-6-methoxy-2-methyl-N-(1-methyl-1H-pyrazolo[3,4-b]pyridin-3-yl)-9H-pyrido[2',3':4,5]pyrrolo[2,3-d]pyrimidin-4-amine;

7-(3,5-dimethylisoxazol-4-yl)-N-(1-isopropyl-4-methyl-1H-pyrazol-5-yl)-6-methoxy-2-methyl-9H-pyrido[2',3':4,5]pyrrolo[2,3-d]pyrimidin-4-amine;

7-(3,5-dimethylisoxazol-4-yl)-6-methoxy-2-methyl-N-(m-tolyl)-9H-pyrido[2',3':4,5]pyrrolo[2,3-d]pyrimidin-4-amine;

N-(3-(tert-butyl)-1-methyl-1H-pyrazol-5-yl)-7-(3,5-dimethylisoxazol-4-yl)-6-methoxy-2-methyl-9H-pyrido[2',3':4,5]pyrrolo[2,3-d]pyrimidin-4-amine;

N-(3-(tert-butyl)-1-methyl-1H-pyrazol-5-yl)-7-(3,5-dimethylisoxazol-4-yl)-6-methoxy-N,2-dimethyl-9H-pyrido[2',3':4,5]pyrrolo[2,3-d]pyrimidin-4-amine;

N-(1-(tert-butyl)-3-methyl-11H-pyrazol-5-yl)-7-(3,5-dimethylisoxazol-4-yl)-6-methoxy-N,2-dimethyl-9H-pyrido[2',3':4,5]pyrrolo[2,3-d]pyrimidin-4-amine;

7-(3,5-dimethylisoxazol-4-yl)-6-methoxy-N,2-dimethyl-N-(m-tolyl)-9H-pyrido[2',3':4,5]pyrrolo[2,3-d]pyrimidin-4-amine;

7-(3,5-dimethylisoxazol-4-yl)-6-methoxy-N,2-dimethyl-N-(1-methyl-1H-pyrazolo[3,4-b]pyridin-3-yl)-9H-pyrido[2',3':4,5]pyrrolo[2,3-d]pyrimidin-4-amine;

7-(3,5-dimethylisoxazol-4-yl)-N-(1-isopropyl-4-methyl-1H-pyrazol-5-yl)-6-methoxy-N,2-dimethyl-9H-pyrido[2',3':4,5]pyrrolo[2,3-d]pyrimidin-4-amine;

N-(3-cyclopropyl-1-methyl-1H-pyrazol-5-yl)-7-(3,5-dimethylisoxazol-4-yl)-6-methoxy-N,2-dimethyl-9H-pyrido[2',3':4,5]pyrrolo[2,3-d]pyrimidin-4-amine;

N-cyclopentyl-7-(3,5-dimethylisoxazol-4-yl)-6-methoxy-N,2-dimethyl-9H-pyrido[2',3':4,5]pyrrolo[2,3-d]pyrimidin-4-amine;

N-(3-cyclopropyl-1-methyl-1H-pyrazol-5-yl)-7-(3,5-dimethylisoxazol-4-yl)-6-methoxy-2-methyl-9H-pyrido[2',3':4,5]pyrrolo[2,3-d]pyrimidin-4-amine;

N-(3-cyclopropyl-1-methyl-1H-pyrazol-5-yl)-7-(3,5-dimethylisoxazol-4-yl)-6-methoxy-9H-pyrido[2,3-b]indol-4-amine; and N-(3-cyclopropyl-1-methyl-1H-pyrazol-5-yl)-6-methoxy-2-methyl-7-(1,3,5-trimethyl-1H-pyrazol-4-yl)-9H-pyrimido[4,5-b]indol-4-amine.

12. The method of claim 1, wherein the cancer is selected from the group consisting of breast cancer, leukemia, and prostate cancer.

13. The method of claim 11, wherein the cancer is selected from the group consisting of breast cancer, leukemia, and prostate cancer.

14. The method of claim 13, wherein the cancer is prostate cancer.

* * * * *

UNITED STATES PATENT AND TRADEMARK OFFICE
CERTIFICATE OF CORRECTION

PATENT NO. : 10,253,044 B2
APPLICATION NO. : 15/443336
DATED : April 9, 2019
INVENTOR(S) : Shaomeng Wang et al.

Page 1 of 1

It is certified that error appears in the above-identified patent and that said Letters Patent is hereby corrected as shown below:

In the Claims

At Column 531, Line 44, "proviso:" should be -- proviso --.

At Column 532, Line 55, "[i 5-a]" should be -- [1,5-a] --.

At Column 534, Line 42, "amine" should be -- amine; --.

At Column 541, Line 37, "7-(3,5-dimethylisoxazol-4-yl)-N-(11H-indol-6-yl)" should be -- 7-(3,5-dimethylisoxazol-4-yl)-N-(1H-indol-6-yl) --.

At Column 541, Line 59, "3,5-methyl-1H-pyrazol-4-yl)" should be -- 3,5-triethyl-1H-pyrazol-4-yl) --.

Signed and Sealed this
Twenty-fourth Day of September, 2019

Andrei Iancu
*Director of the United States Patent and Trademark Office*